US012611211B2

(12) United States Patent
Bakos et al.

(10) Patent No.: US 12,611,211 B2
(45) Date of Patent: Apr. 28, 2026

(54) METHOD OF OPERATING A SURGICAL INSTRUMENT

(71) Applicant: Cilag GmbH International, Zug (CH)

(72) Inventors: Gregory J. Bakos, Mason, OH (US); Darryl A. Parks, Mason, OH (US); Benjamin D. Dickerson, San Francisco, CA (US); Steven G. Hall, Cincinnati, OH (US); Robert J. Simms, Liberty Township, OH (US); Spencer J. Witte, Los Altos, CA (US); Taylor W. Aronhalt, Loveland, OH (US); Paul Moubarak, West Chester, OH (US); William C. Ryle, Covington, KY (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/536,451

(22) Filed: Dec. 12, 2023

(65) Prior Publication Data

US 2024/0108332 A1      Apr. 4, 2024

Related U.S. Application Data

(63) Continuation of application No. 17/360,199, filed on Jun. 28, 2021, now Pat. No. 11,883,024.
(Continued)

(51) Int. Cl.
*A61B 17/072*      (2006.01)
*A61B 17/00*      (2006.01)
(Continued)

(52) U.S. Cl.
CPC .... *A61B 17/0686* (2013.01); *A61B 17/00234* (2013.01); *A61B 17/068* (2013.01);
(Continued)

(58) Field of Classification Search
CPC . A61B 17/0686; A61B 17/072; A61B 17/068;
A61B 2034/301;
(Continued)

(56) References Cited

U.S. PATENT DOCUMENTS

| | | |
|---|---|---|
| 5,403,312 A | 4/1995 | Yates et al. |
| 7,000,818 B2 | 2/2006 | Shelton, IV et al. |

(Continued)

FOREIGN PATENT DOCUMENTS

| | | |
|---|---|---|
| EP | 3178413 A1 | 6/2017 |

OTHER PUBLICATIONS

International Search Report and Written Opinion dated Jan. 11, 2022, for International Application No. PCT/IB2021/056742, 18 pages.
(Continued)

*Primary Examiner* — Nathaniel C Chukwurah
(74) *Attorney, Agent, or Firm* — FBT Gibbons LLP

(57) ABSTRACT

A method of operating an articulatable surgical instrument. The method includes providing a rotary drive motion to a rotary drive member of a surgical end effector and converting the rotary drive motion to an upper axial motion and a lower axial motion at locations that are distal to the articulation joint. The method further includes applying the upper axial motion to an upper portion of a firing member and applying the lower axial motion to a lower portion of the firing member such that the upper axial motion and lower axial motion drives the firing member distally through the surgical end effector from a starting position to an ending position.

20 Claims, 167 Drawing Sheets

Related U.S. Application Data

(60) Provisional application No. 63/057,430, filed on Jul. 28, 2020, provisional application No. 63/057,432, filed on Jul. 28, 2020.

(51) Int. Cl.

| | |
|---|---|
| *A61B 17/068* | (2006.01) |
| *A61B 17/29* | (2006.01) |
| *A61B 17/32* | (2006.01) |
| *A61B 34/30* | (2016.01) |

(52) U.S. Cl.

CPC ...... *A61B 17/072* (2013.01); *A61B 17/07207* (2013.01); *A61B 17/29* (2013.01); *A61B 17/320092* (2013.01); *A61B 34/30* (2016.02); *A61B 2017/00314* (2013.01); *A61B 2017/00323* (2013.01); *A61B 2017/00336* (2013.01); *A61B 2017/00367* (2013.01); *A61B 2017/00389* (2013.01); *A61B 2017/00398* (2013.01); *A61B 2017/00477* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2017/320071* (2017.08); *A61B 2017/320093* (2017.08); *A61B 2017/320094* (2017.08); *A61B 2017/320095* (2017.08); *A61B 2017/320097* (2017.08); *A61B 2034/301* (2016.02)

(58) Field of Classification Search

CPC ....... A61B 2017/320097; A61B 2017/320071; A61B 2017/00323; A61B 2017/07214; A61B 2017/07257

USPC ........................................... 227/175.1–180.1

See application file for complete search history.

(56)  References Cited

U.S. PATENT DOCUMENTS

| | | | |
|---|---|---|---|
| 7,422,139 | B2 | 9/2008 | Shelton, IV et al. |
| 7,464,849 | B2 | 12/2008 | Shelton, IV et al. |
| 7,670,334 | B2 | 3/2010 | Hueil et al. |
| 7,753,245 | B2 | 7/2010 | Boudreaux et al. |
| 7,845,537 | B2 | 12/2010 | Shelton, IV et al. |
| 7,980,443 | B2 | 7/2011 | Scheib et al. |
| 8,210,411 | B2 | 7/2012 | Yates et al. |
| 8,220,688 | B2 | 7/2012 | Laurent et al. |
| 8,308,040 | B2 | 11/2012 | Huang et al. |
| 8,393,514 | B2 | 3/2013 | Shelton, IV et al. |
| 8,561,870 | B2 | 10/2013 | Baxter, III et al. |
| 8,573,465 | B2 | 11/2013 | Shelton, IV |
| 8,608,045 | B2 | 12/2013 | Smith et al. |
| 8,733,613 | B2 | 5/2014 | Huitema et al. |
| 9,050,083 | B2 | 6/2015 | Yates et al. |
| 9,072,535 | B2 | 7/2015 | Shelton, IV et al. |
| 9,101,358 | B2 | 8/2015 | Kerr et al. |
| 9,345,481 | B2 | 5/2016 | Hall et al. |
| 11,317,917 | B2 | 5/2022 | Shelton, IV et al. |
| 11,638,582 | B2 | 5/2023 | Bakos et al. |
| 11,660,090 | B2 | 5/2023 | Bakos et al. |
| 11,737,748 | B2 | 8/2023 | Witte |
| 11,826,013 | B2 | 11/2023 | Parks |
| 11,857,182 | B2 | 1/2024 | Witte |
| 11,864,756 | B2 | 1/2024 | Witte et al. |
| 11,871,925 | B2 | 1/2024 | Hall et al. |
| 11,883,024 | B2 | 1/2024 | Bakos et al. |
| 2004/0199147 | A1 | 10/2004 | Nishizawa et al. |
| 2007/0175955 | A1 | 8/2007 | Shelton et al. |
| 2010/0320252 | A1* | 12/2010 | Viola ................... A61B 17/068 227/176.1 |
| 2014/0263552 | A1 | 9/2014 | Hall et al. |
| 2015/0090759 | A1 | 4/2015 | Spivey et al. |
| 2015/0173756 | A1 | 6/2015 | Baxter, III |
| 2016/0015390 | A1 | 1/2016 | Timm et al. |
| 2017/0056118 | A1 | 3/2017 | Cooper et al. |
| 2018/0168649 | A1 | 6/2018 | Shelton, IV et al. |
| 2018/0168651 | A1 | 6/2018 | Shelton, IV et al. |
| 2019/0059986 | A1 | 2/2019 | Shelton, IV et al. |
| 2020/0305865 | A1* | 10/2020 | Shelton, IV ......... A61B 17/072 |
| 2020/0305868 | A1 | 10/2020 | Shelton, IV et al. |
| 2022/0031315 | A1 | 2/2022 | Bakos et al. |
| 2022/0031320 | A1 | 2/2022 | Hall et al. |
| 2022/0031346 | A1 | 2/2022 | Parks |
| 2022/0031350 | A1 | 2/2022 | Witte |
| 2022/0031351 | A1 | 2/2022 | Moubarak et al. |
| 2023/0190268 | A1 | 6/2023 | Bakos et al. |

OTHER PUBLICATIONS

International Search Report and Written Opinion dated Oct. 29, 2022, for International Application No. PCT/IB2021/056759, 12 pages.

U.S. Appl. No. 12/031,573, entitled "Surgical Cutting and Fastening Instrument Having RF Electrodes," filed Feb. 14, 2008.

* cited by examiner

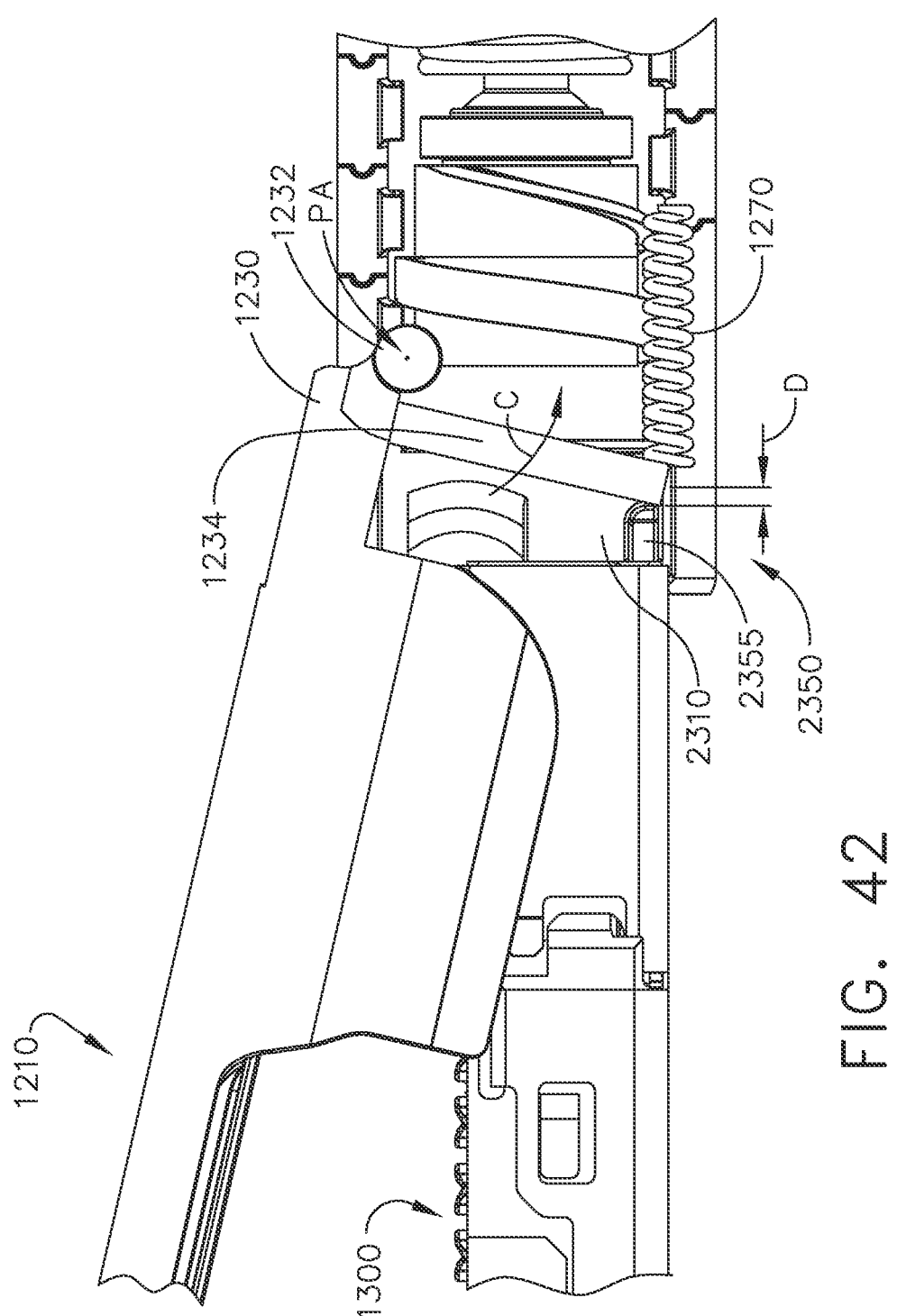
F I G. 42

7350

7340

7360

METHOD OF OPERATING A SURGICAL INSTRUMENT

PRIORITY

This application is a continuation of U.S. patent application Ser. No. 17/360,199, entitled "Method of Operating a Surgical Instrument," filed Jun. 28, 2021, issued as U.S. Pat. No. 11,883,024 on Jun. 28, 2021, which claims the benefit of U.S. Prov. Pat. App. No. 63/057,430, entitled "Surgical Instruments With Torsion Spine Drive Arrangements," filed Jul. 28, 2020, and U.S. Prov. Pat. App. No. 63/057,432, entitled "Articulation Joint Arrangements for Surgical Instruments," filed Jul. 28, 2020, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings in which:

FIG. 42 is a partial side elevational view of the surgical end effector of FIG. 19 with portions thereof omitted for clarity to illustrate the anvil opening springs applying an opening motion to the anvil and with the firing member in a home or starting position;

FIG. 119 is an exploded assembly perspective view of a portion of the surgical instrument of FIG. 115;

FIG. 120 is a bottom cross sectional view of an articulation joint and portions of the anvil of the surgical instrument of FIG. 115;

FIG. 121 is an exploded assembly view of the articulation joint of FIG. 120;

FIG. 122 is a side view of an annular disc member of the articulation joint of FIG. 121;

FIG. 123 is a perspective view of the annular disc member of FIG. 122;

FIG. 124 is a view of a distal face of the annular disc member of FIG. 122;

FIG. 125 is a view of a proximal face of the annular disc member of FIG. 122;

FIG. 126 is a top view of a pulley unit of the surgical instrument of FIG. 115;

FIG. 127 is a perspective view of a portion of the articulation joint and elongate shaft assembly of the surgical instrument of FIG. 115, with an outer shaft tube omitted for clarity;

FIG. 128 is a side elevational view of the pulley unit of FIG. 126;

FIG. 129 is another side elevational view of the pulley unit of FIG. 126;

FIG. 130 is a perspective view of the pulley unit of FIG. 126 and a continuum shaft of the articulation joint of the surgical instrument of FIG. 115;

Figure 115:
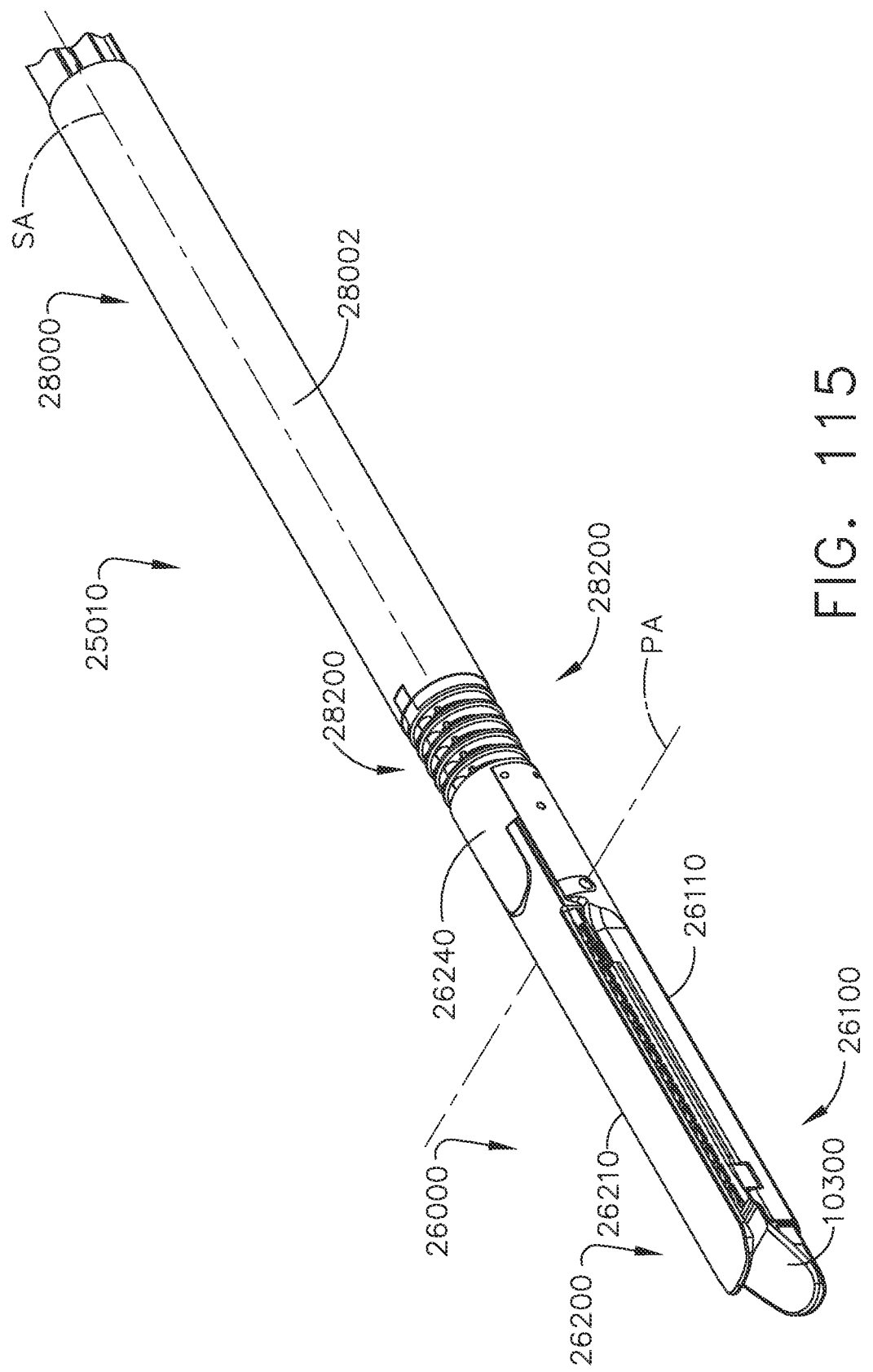
FIG. 115 is a perspective view of a portion of another surgical instrument embodiment.
Figure 116:
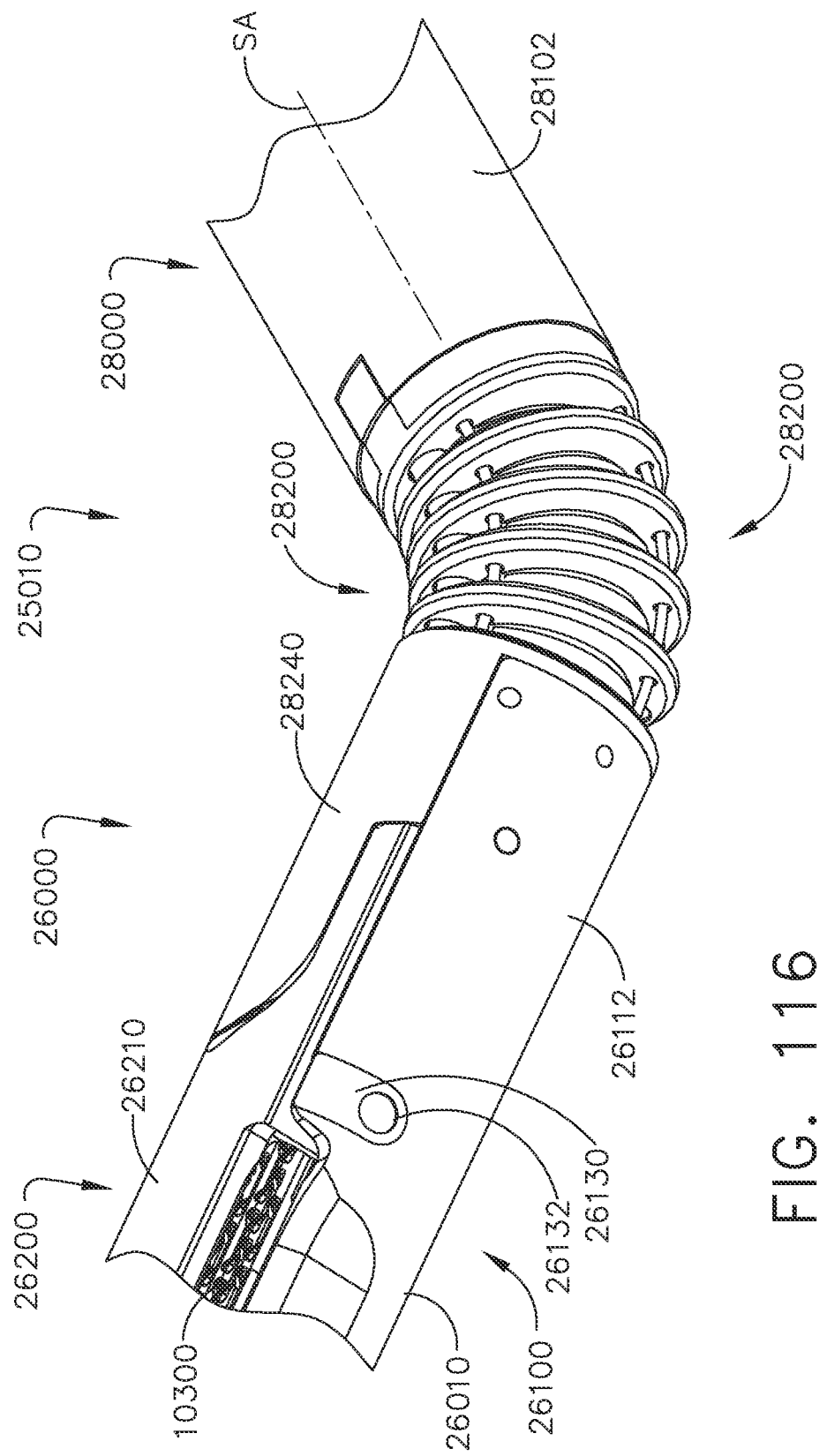
FIG. 116 is a perspective view of a portion of the surgical instrument of FIG. 115 with a surgical end effector portion thereof in an articulated position relative to an elongate shaft portion thereof.
Figures 117, 118:
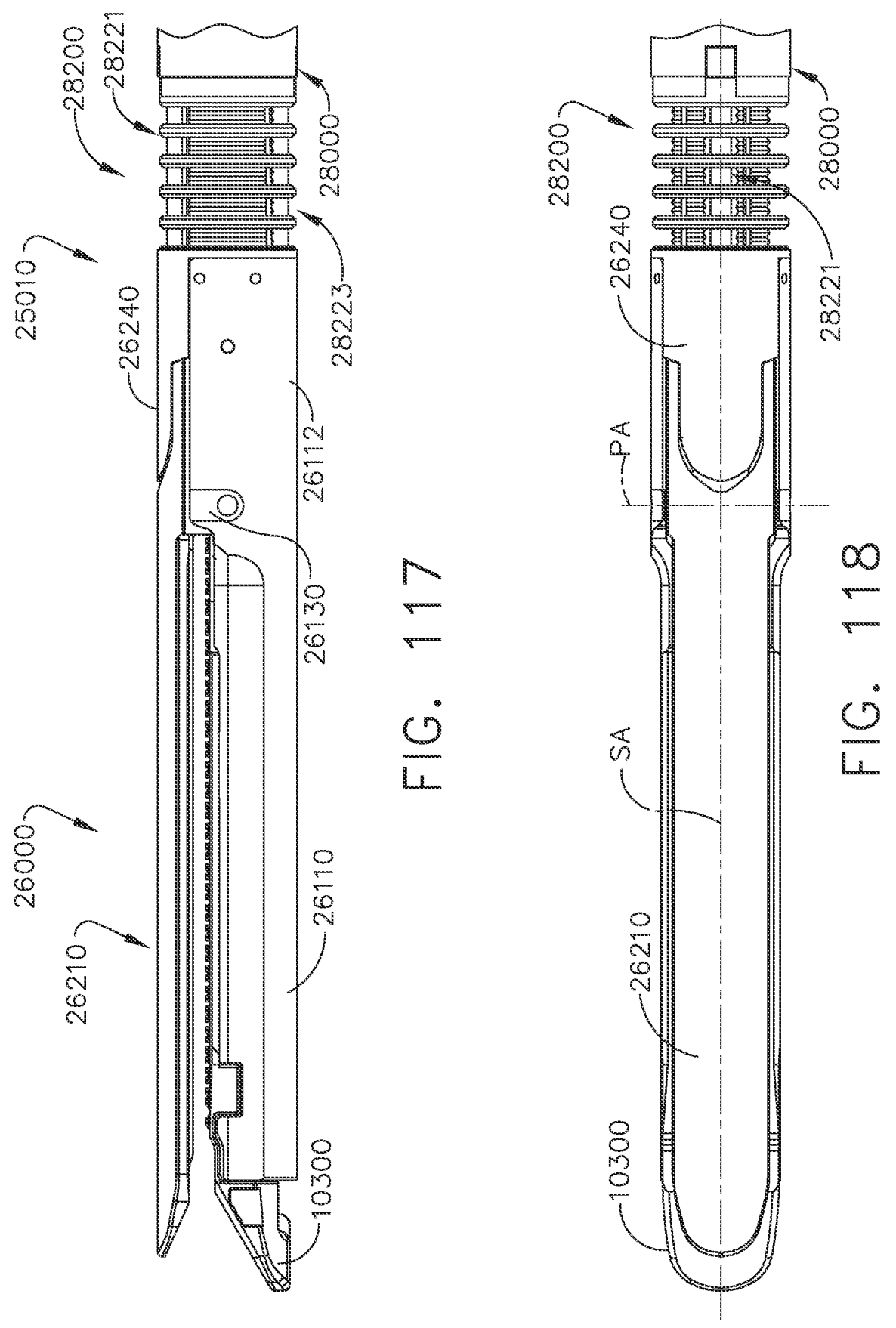
FIG. 117 is a side elevational view of the surgical end effector of FIG. 116, with an anvil thereof in a closed position.
FIG. 118 is a top view of the surgical end effector of FIG. 117.
Figure 126:
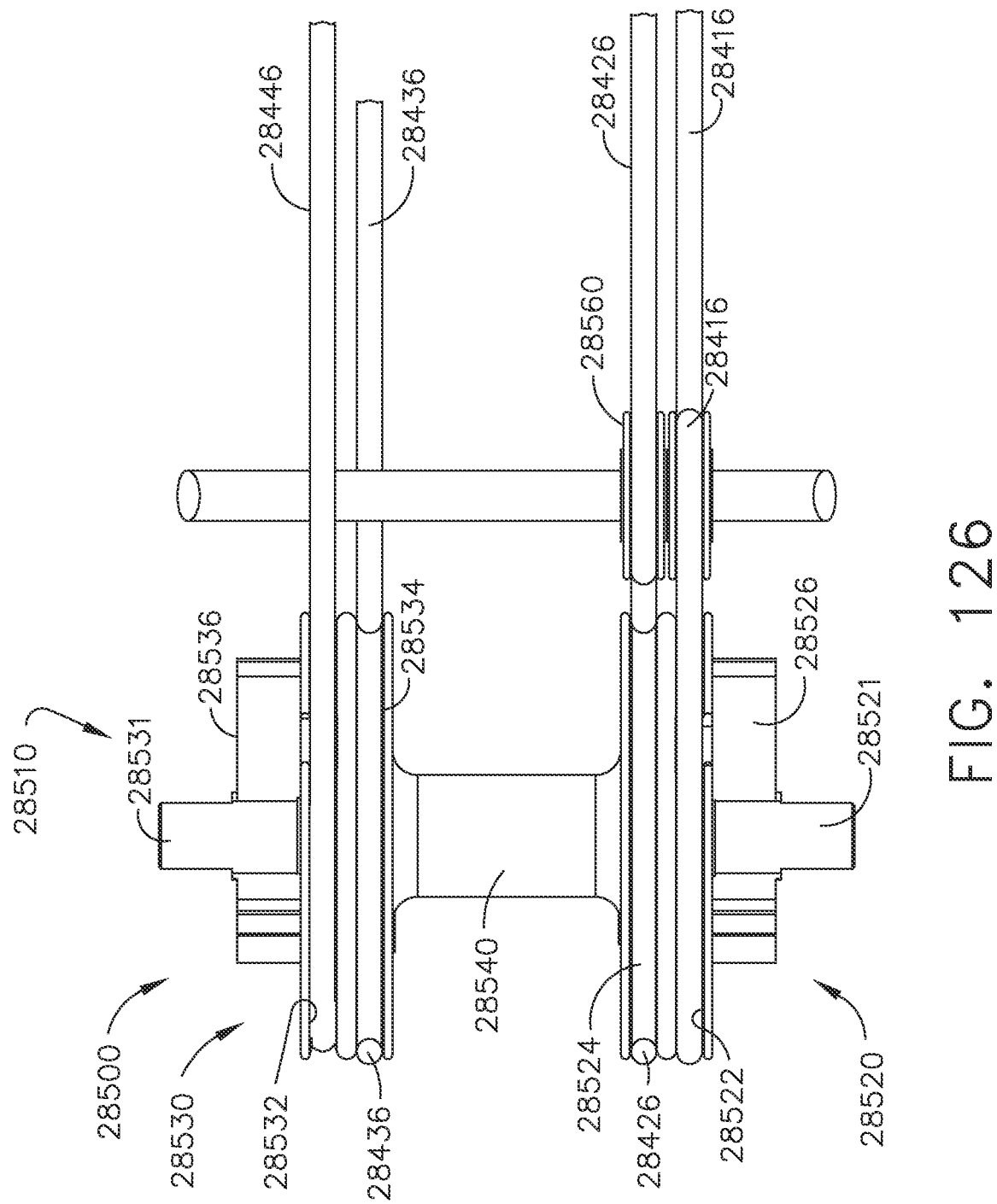
Figure 131:
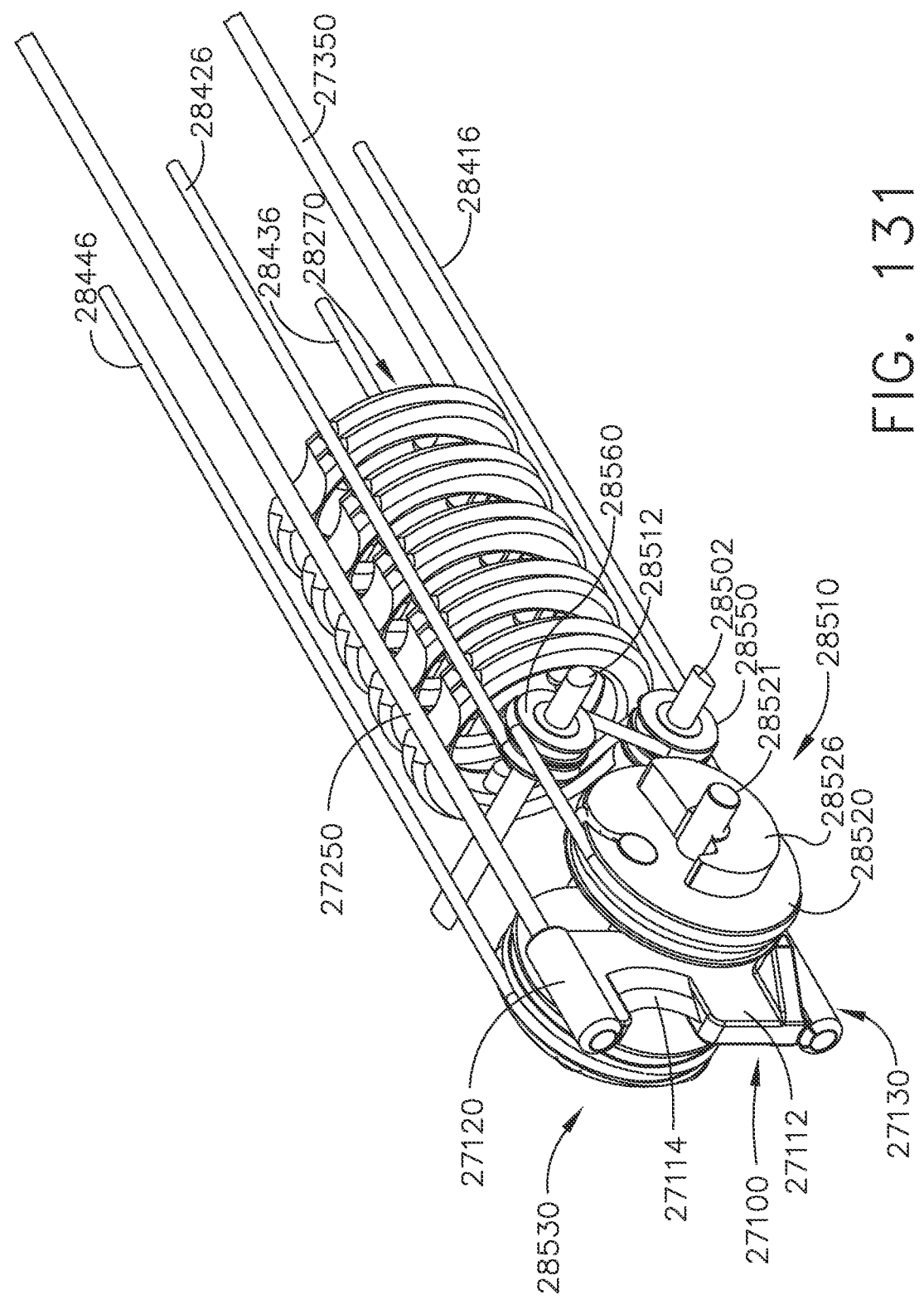
Figure 132:
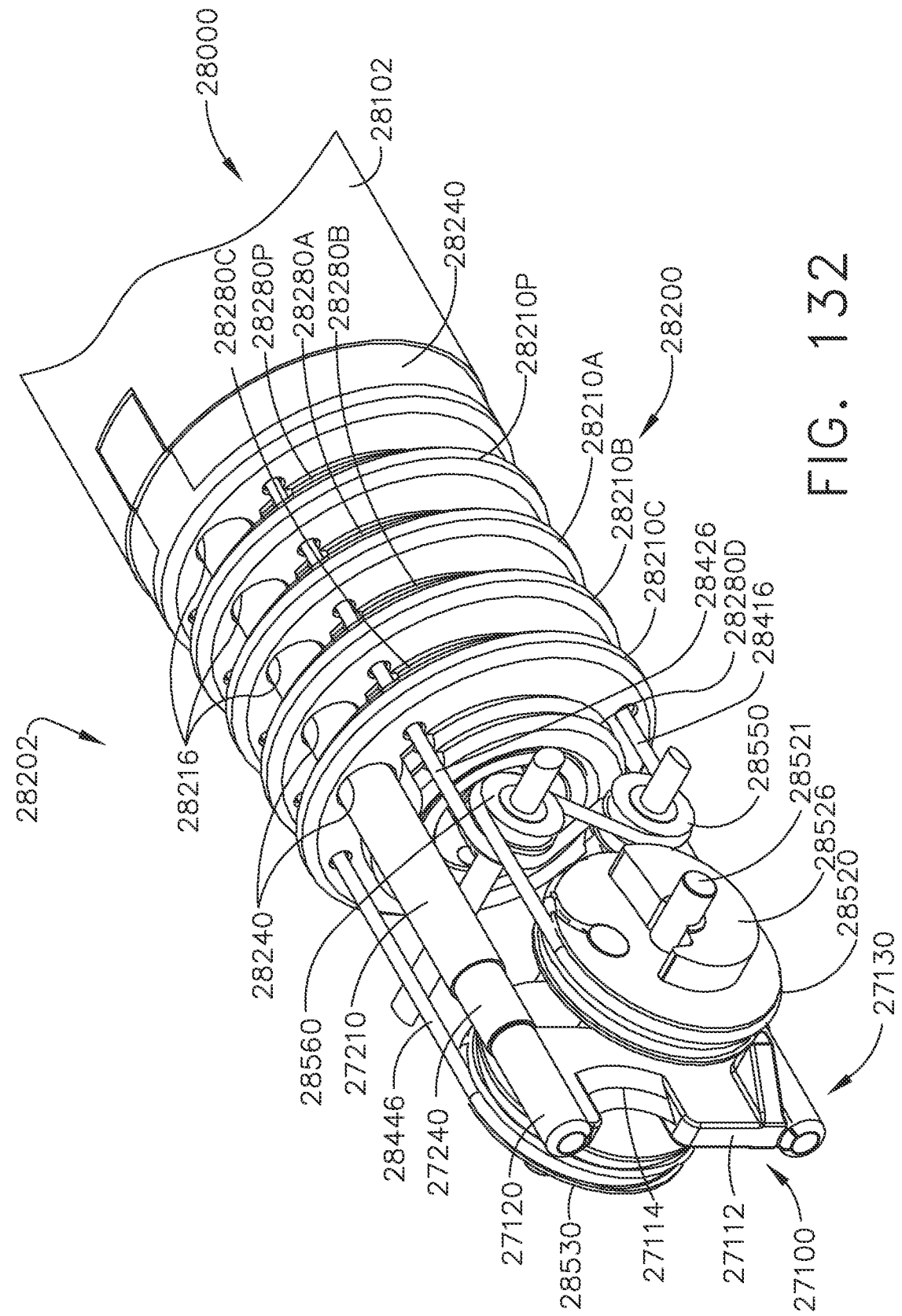
Figure 133:
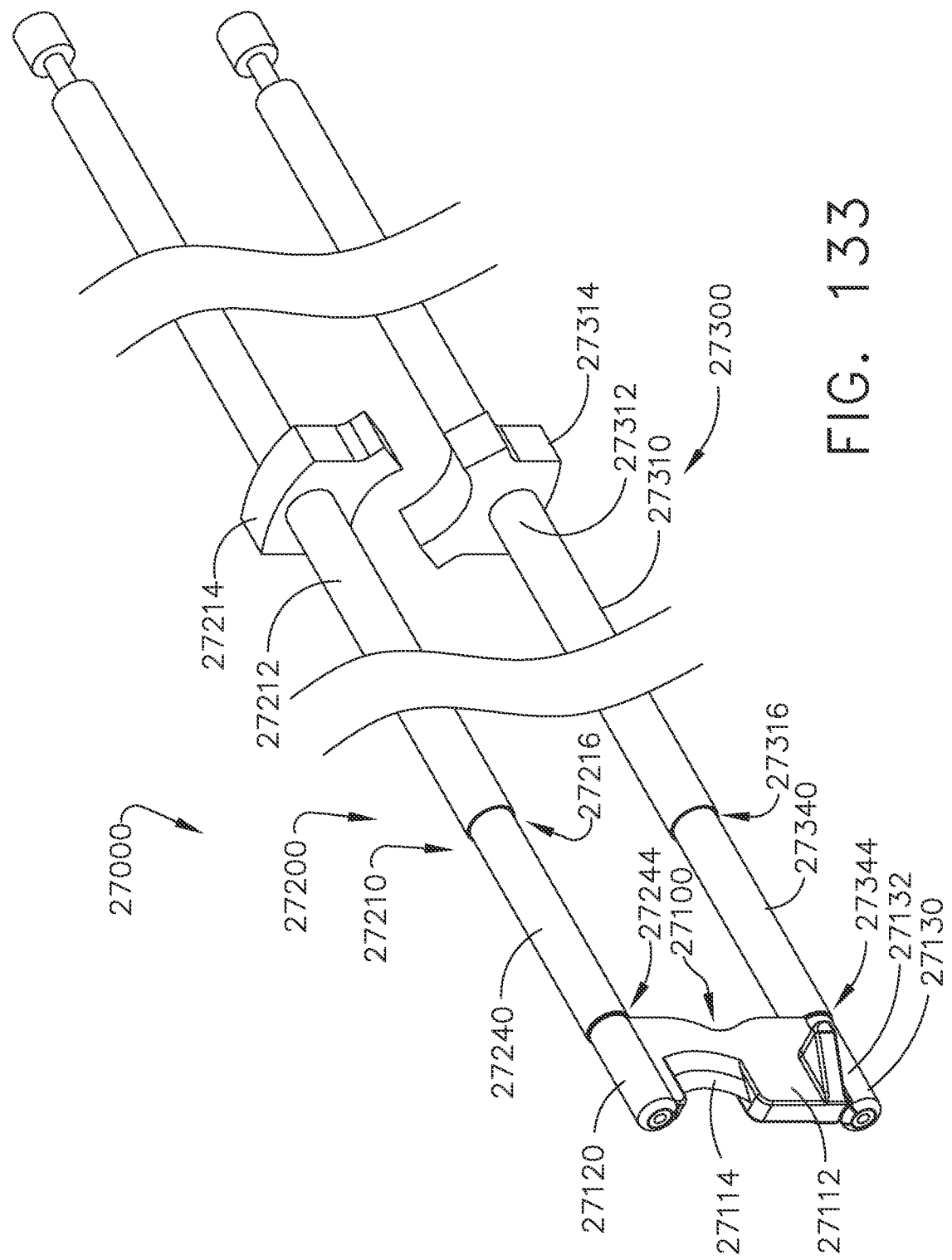
Figure 134:
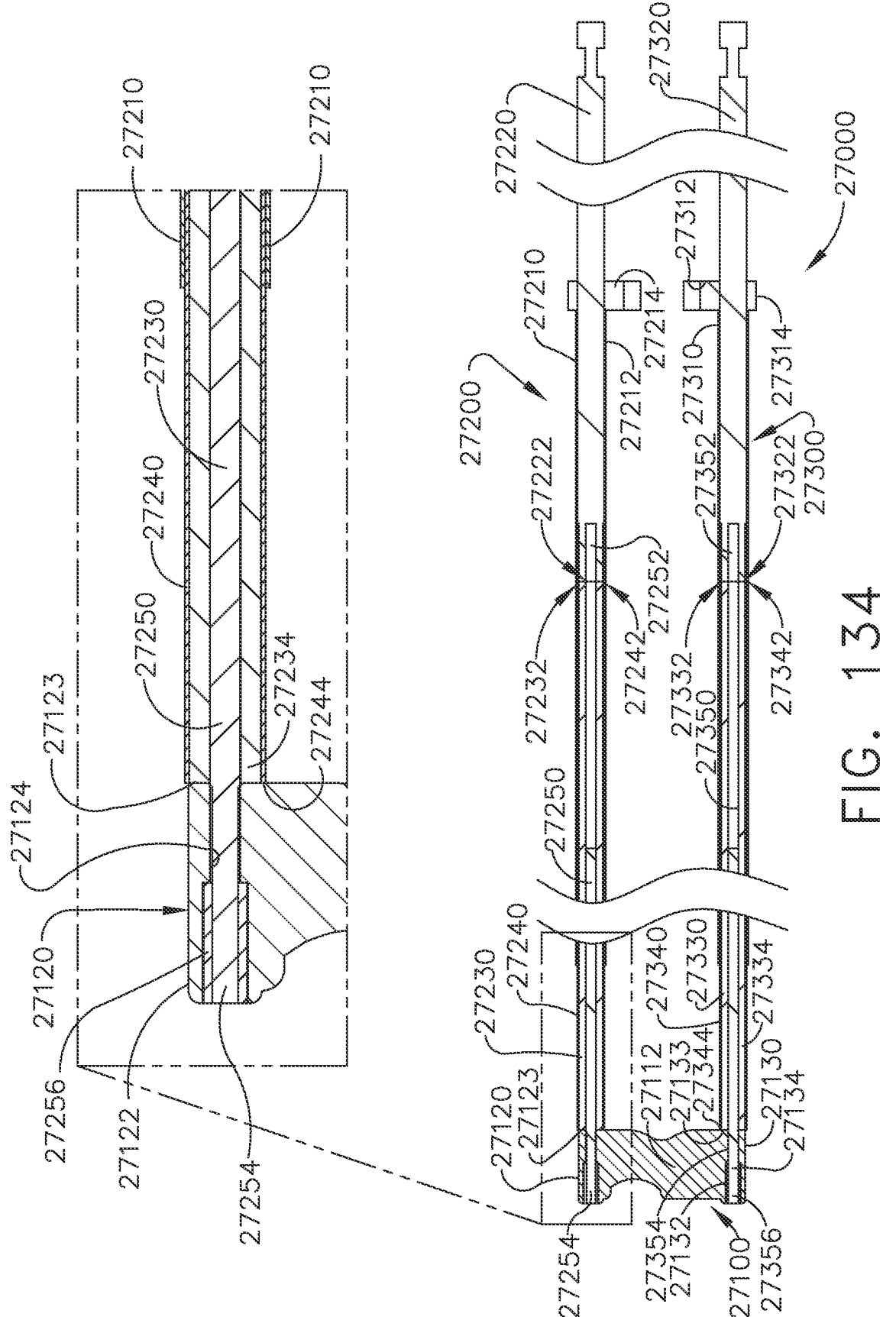
Figure 135:
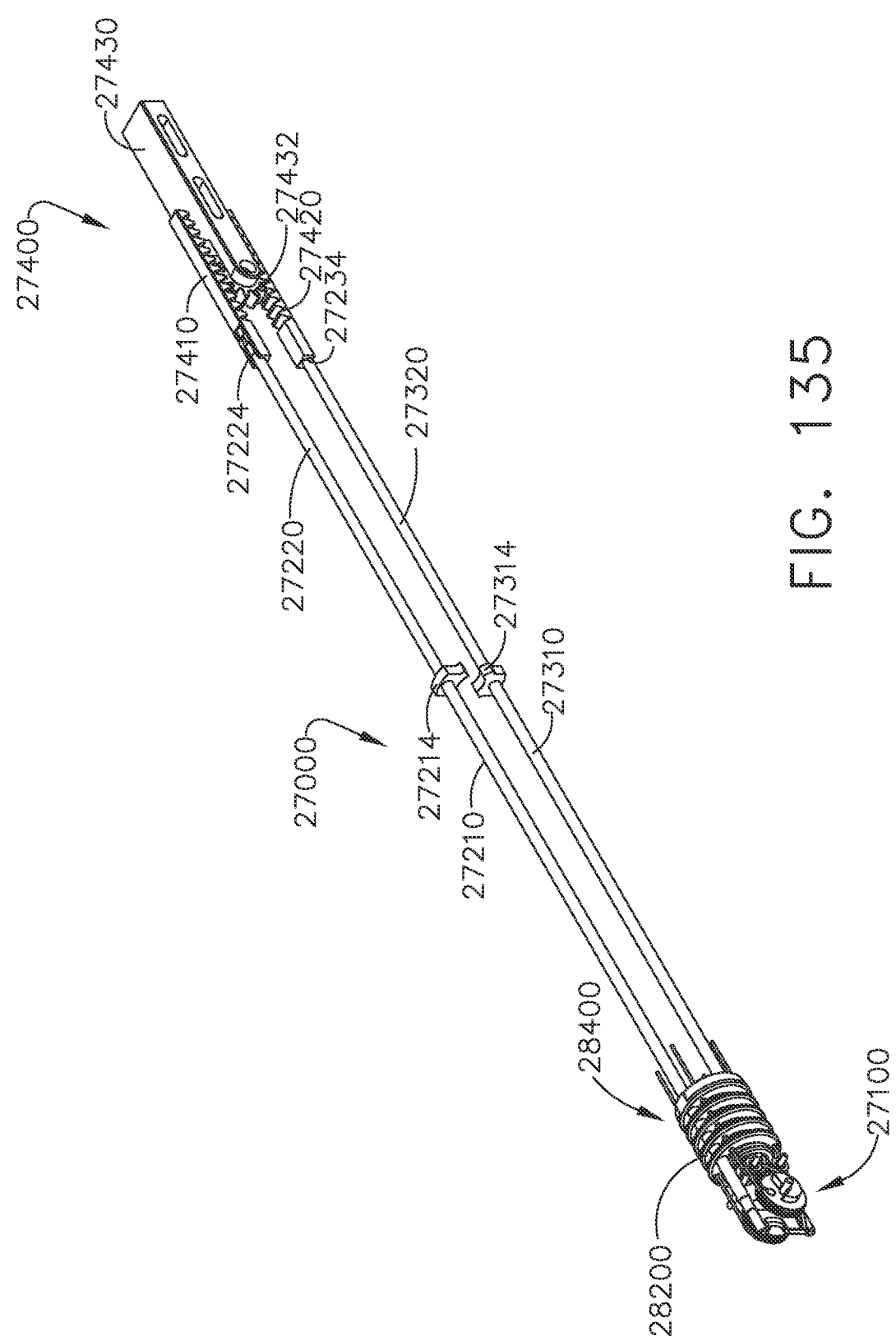
Figure 136:
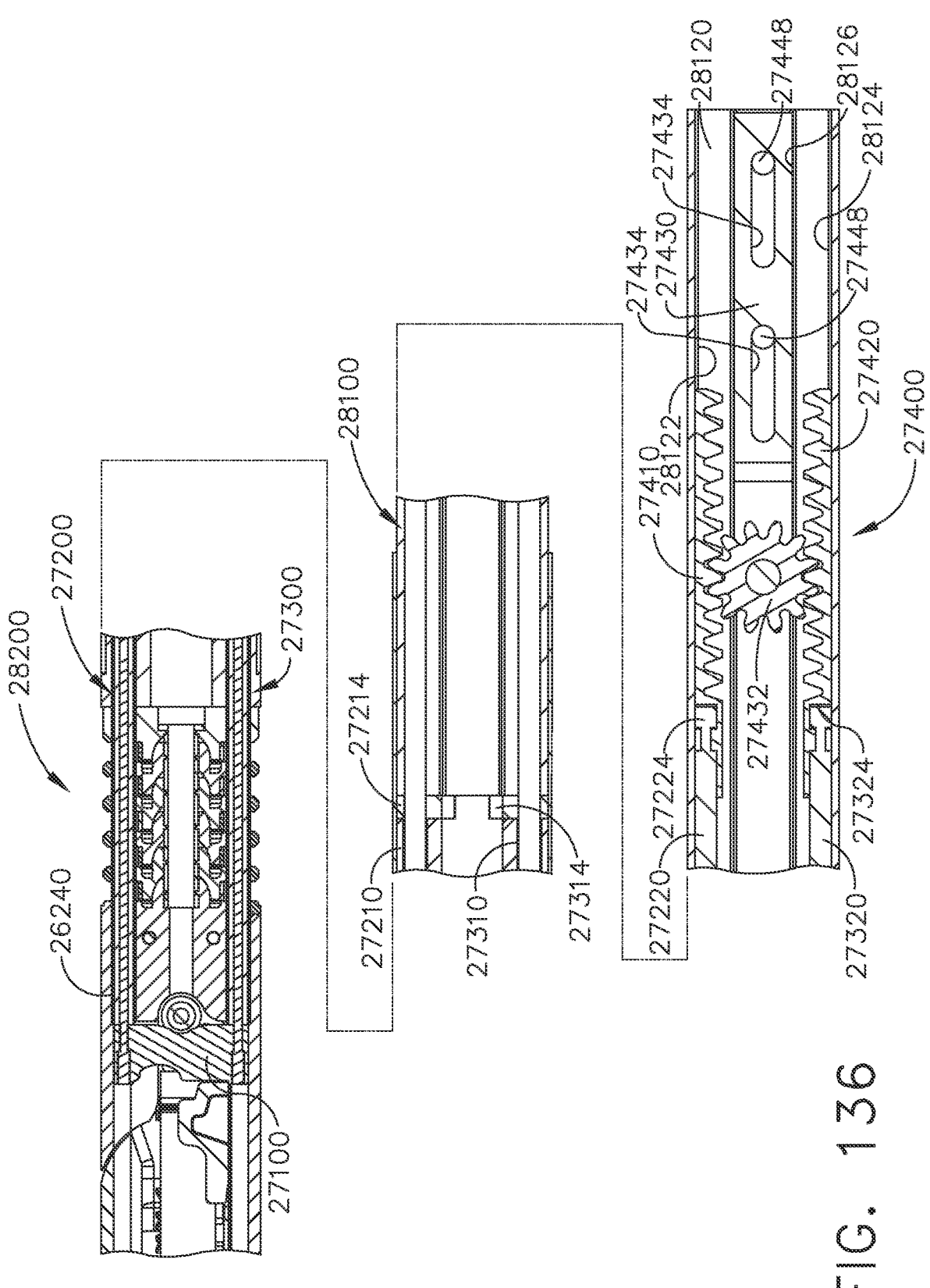
Figure 137:
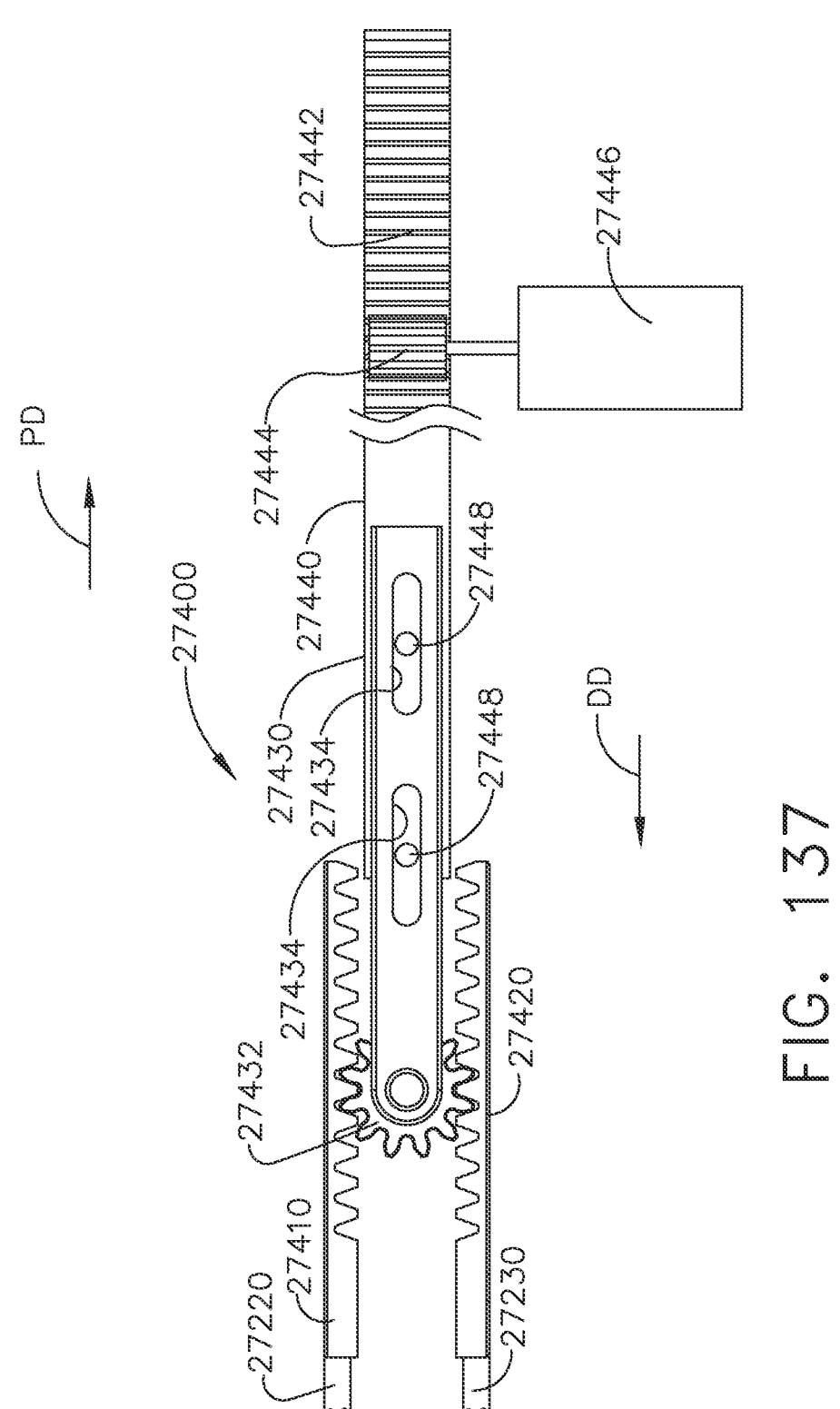
Figures 138, 139:
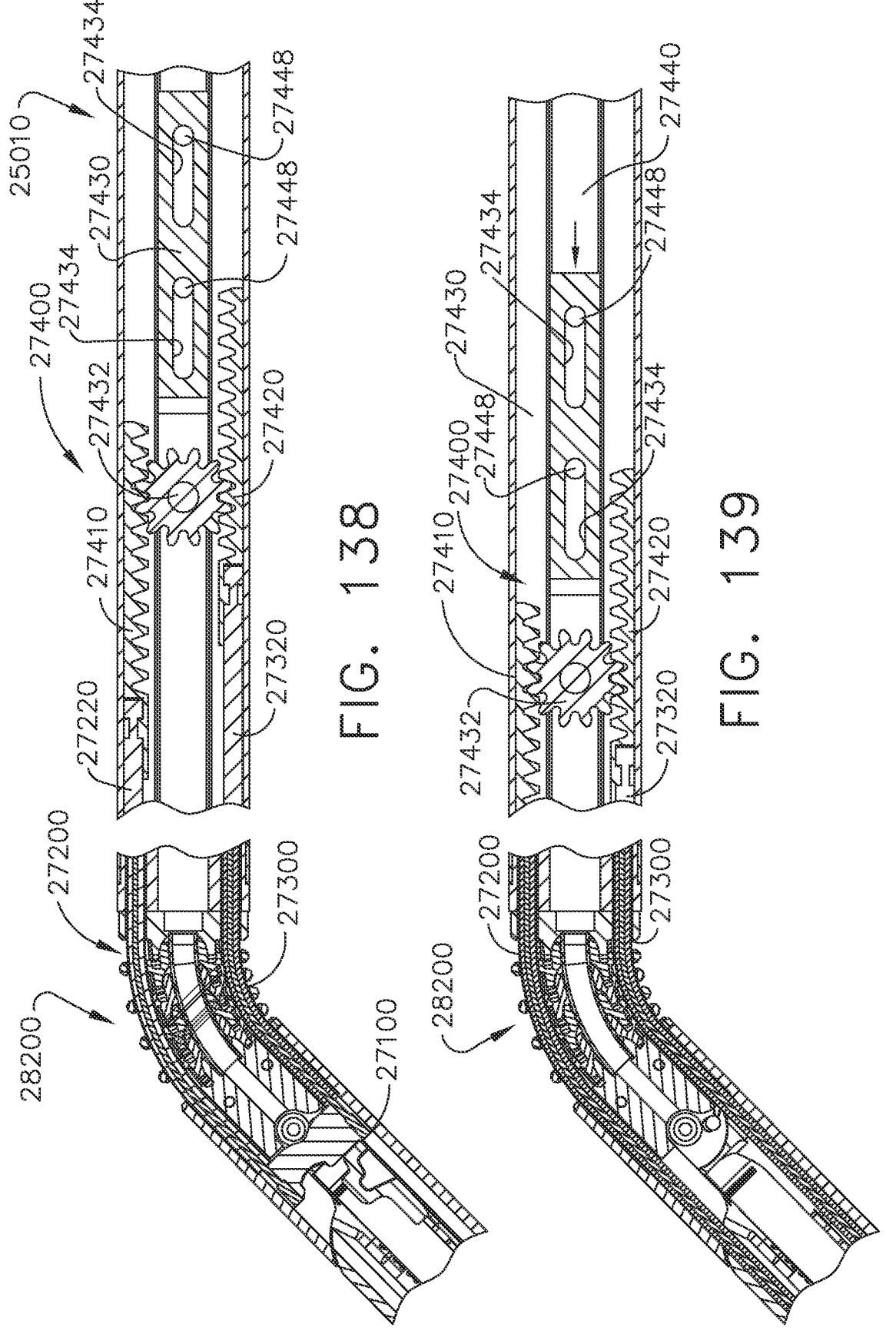
Figure 140:
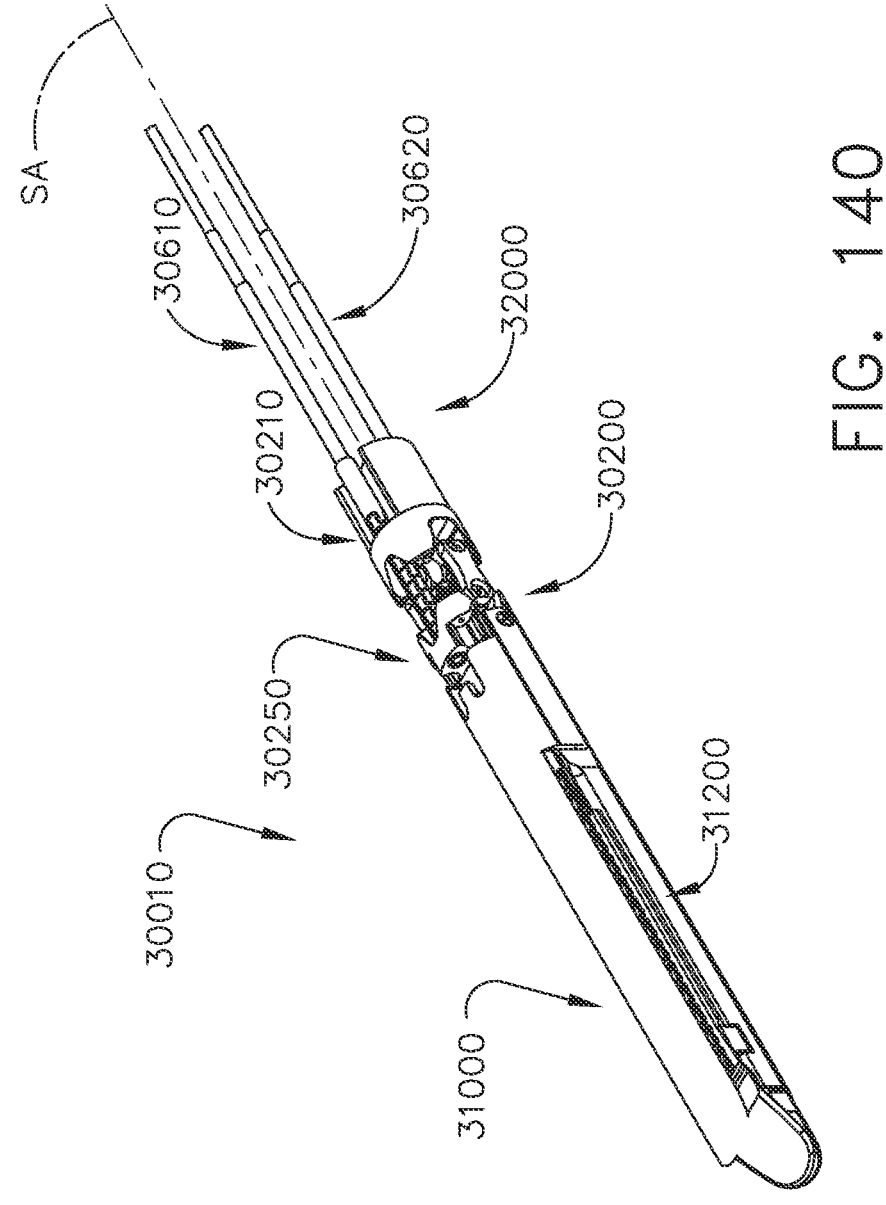
Figure 141:
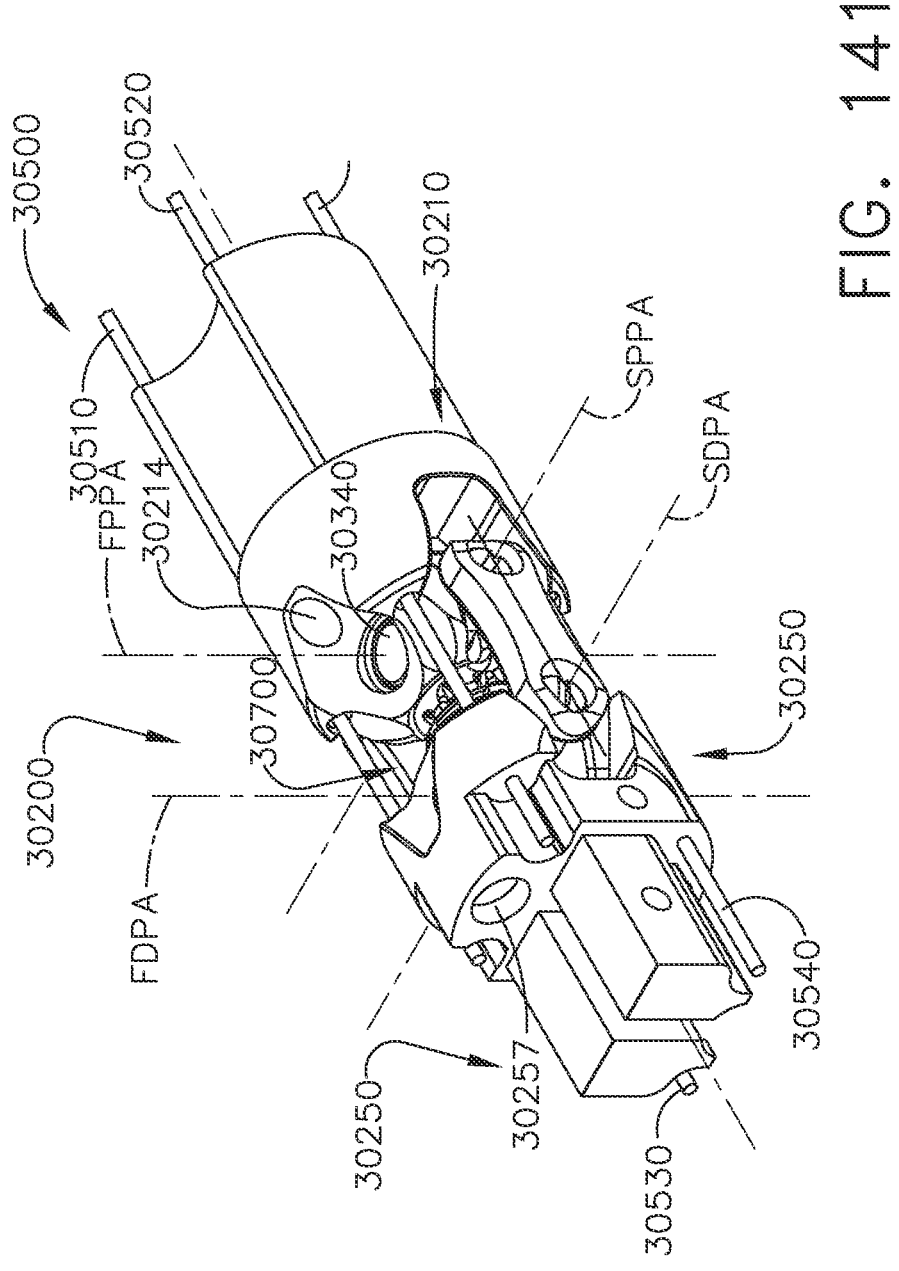
Figure 142:
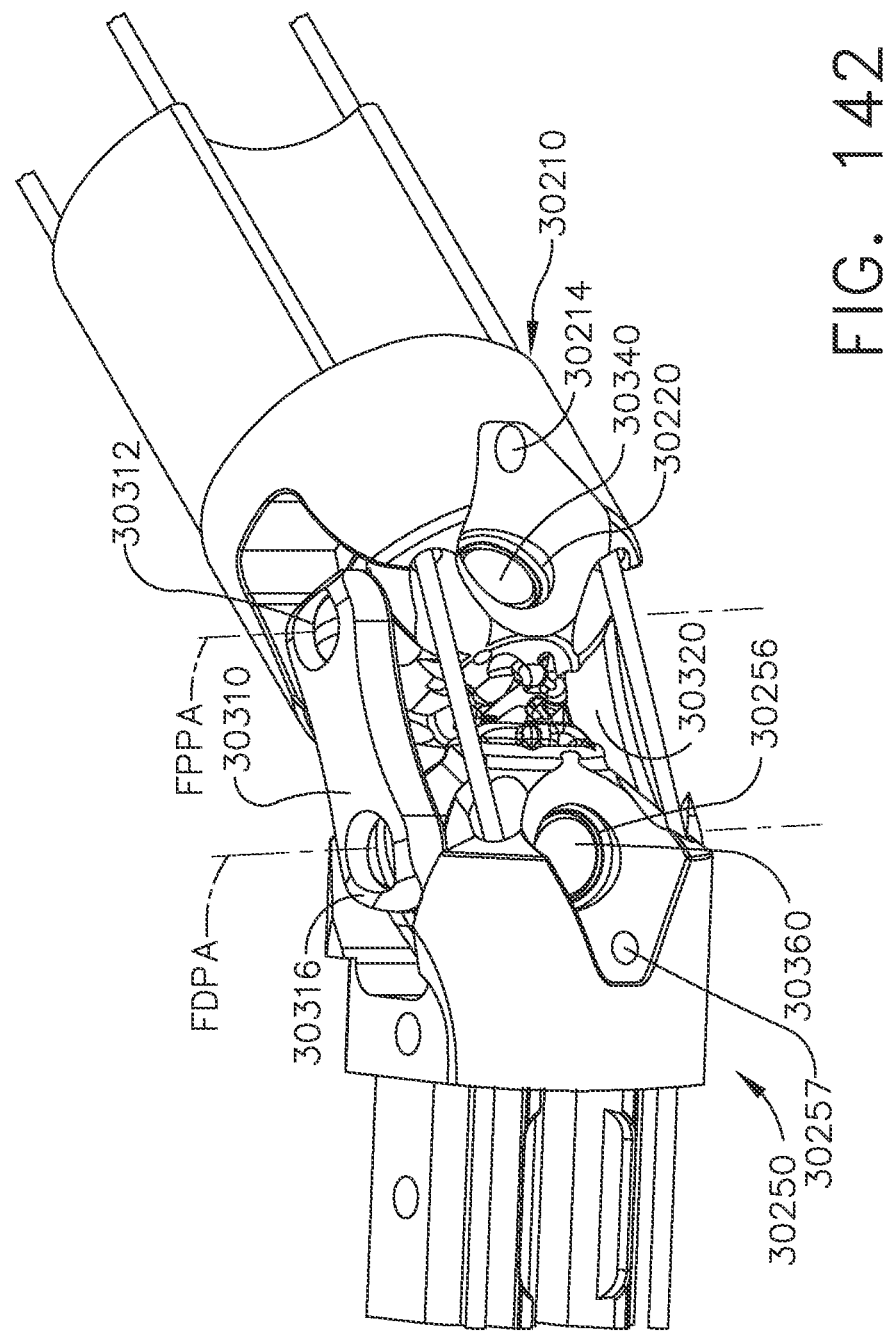
Figure 143:
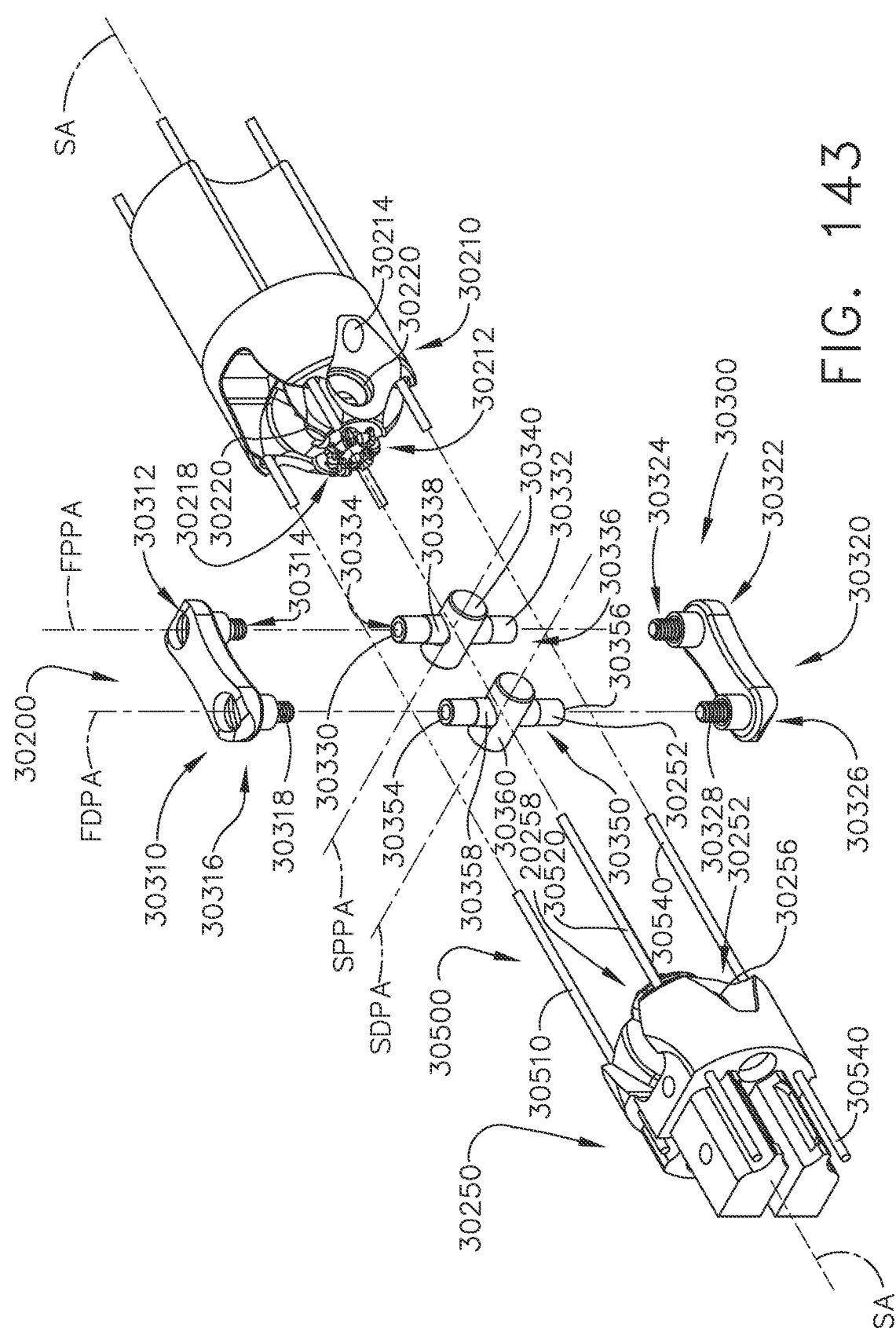
Figure 144:
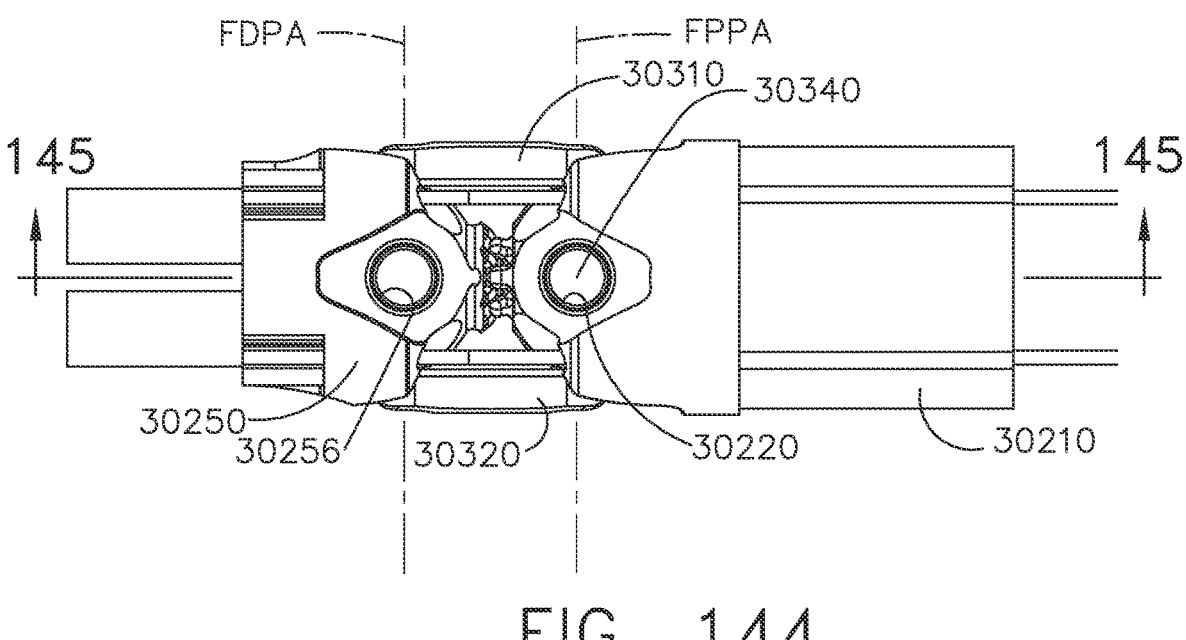
Figure 145:
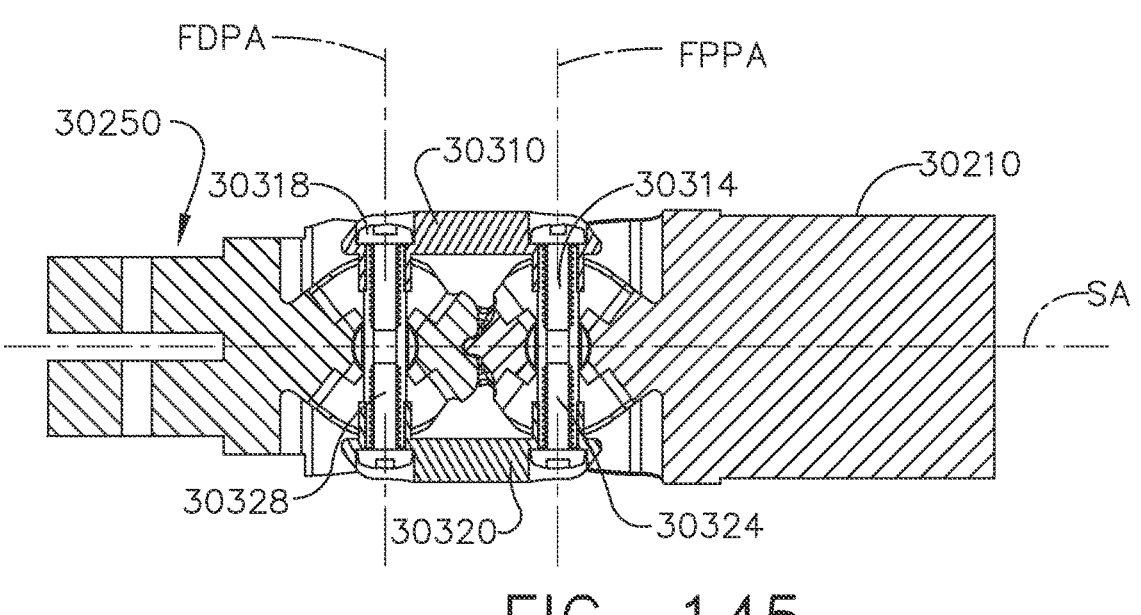
Figure 146:
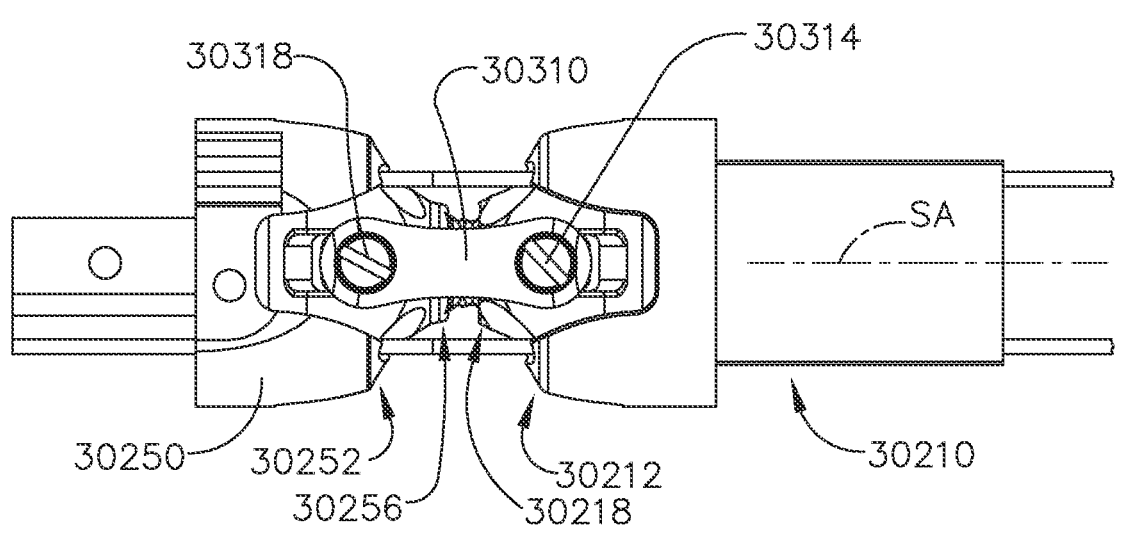
Figure 147:
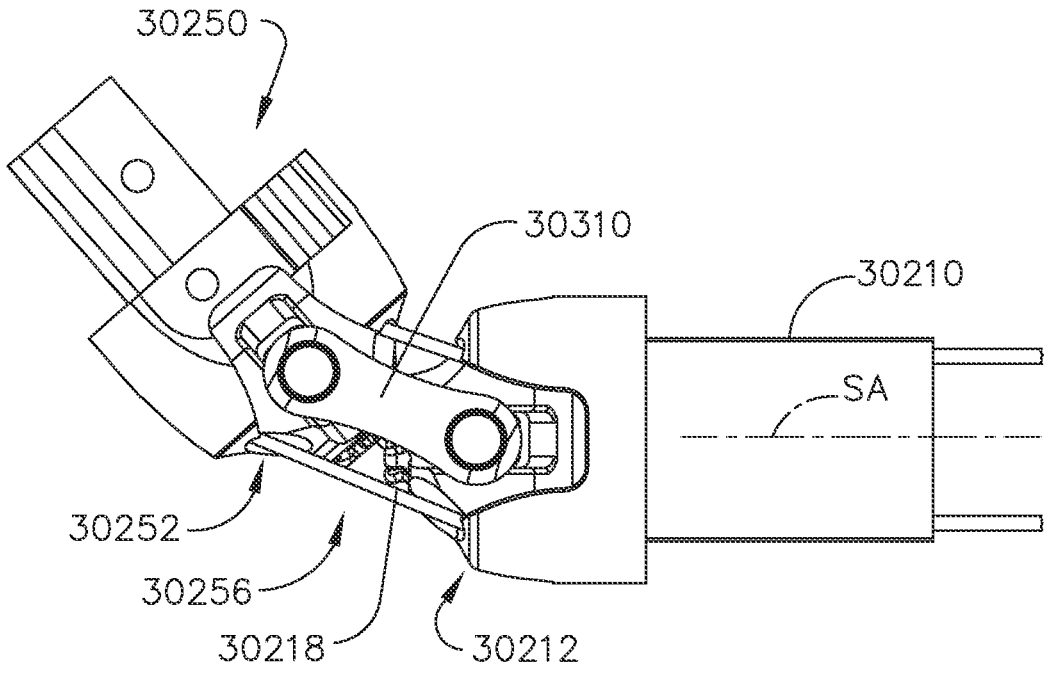
Figure 148:
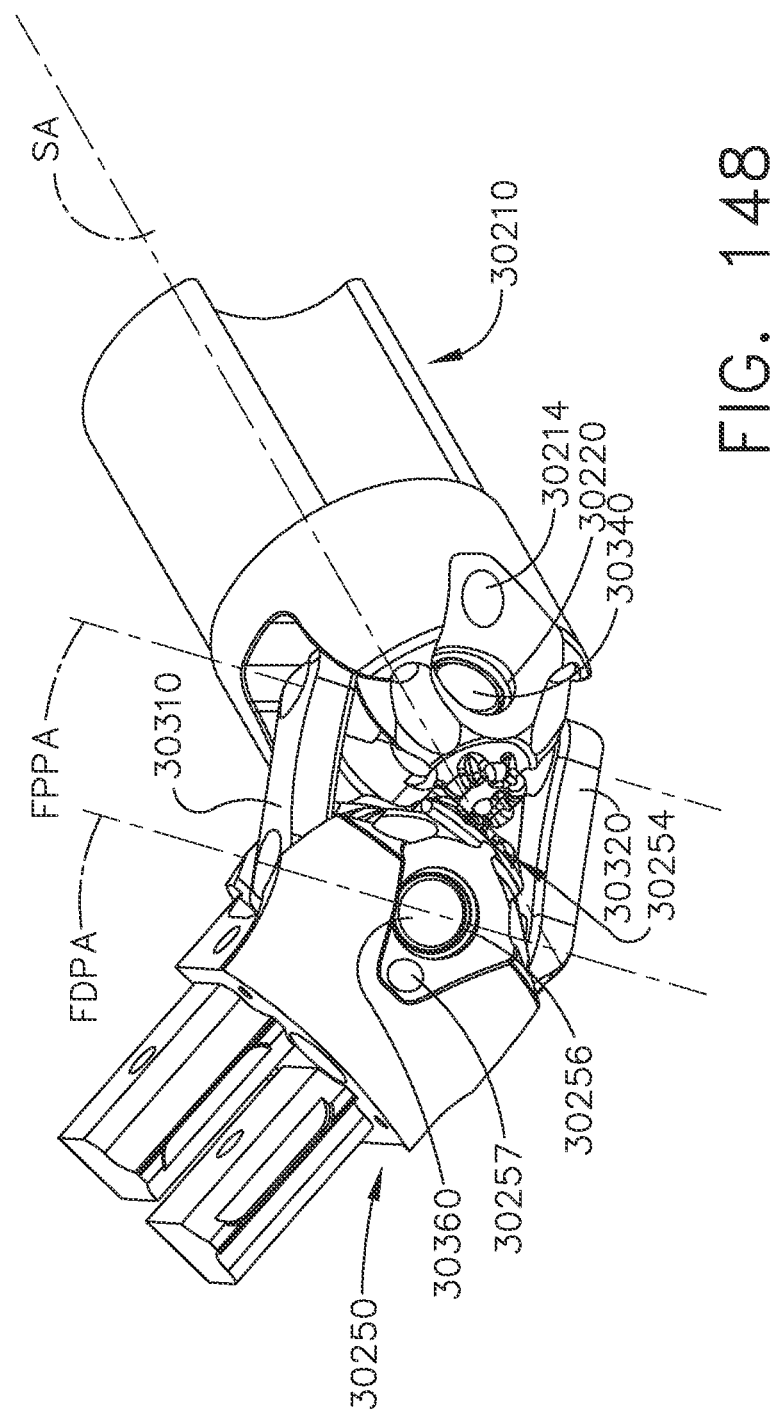
Figure 149:
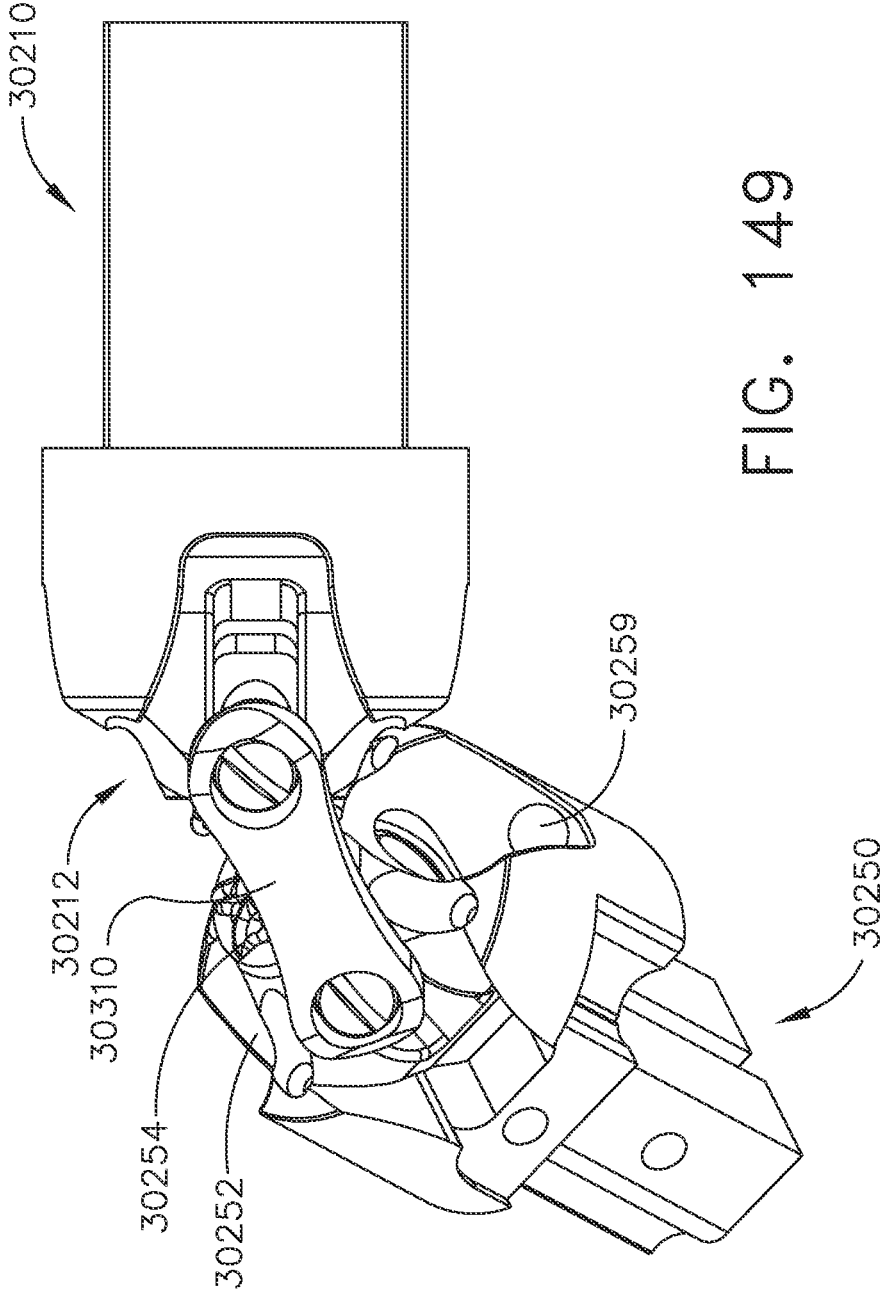
Figures 150, 151:
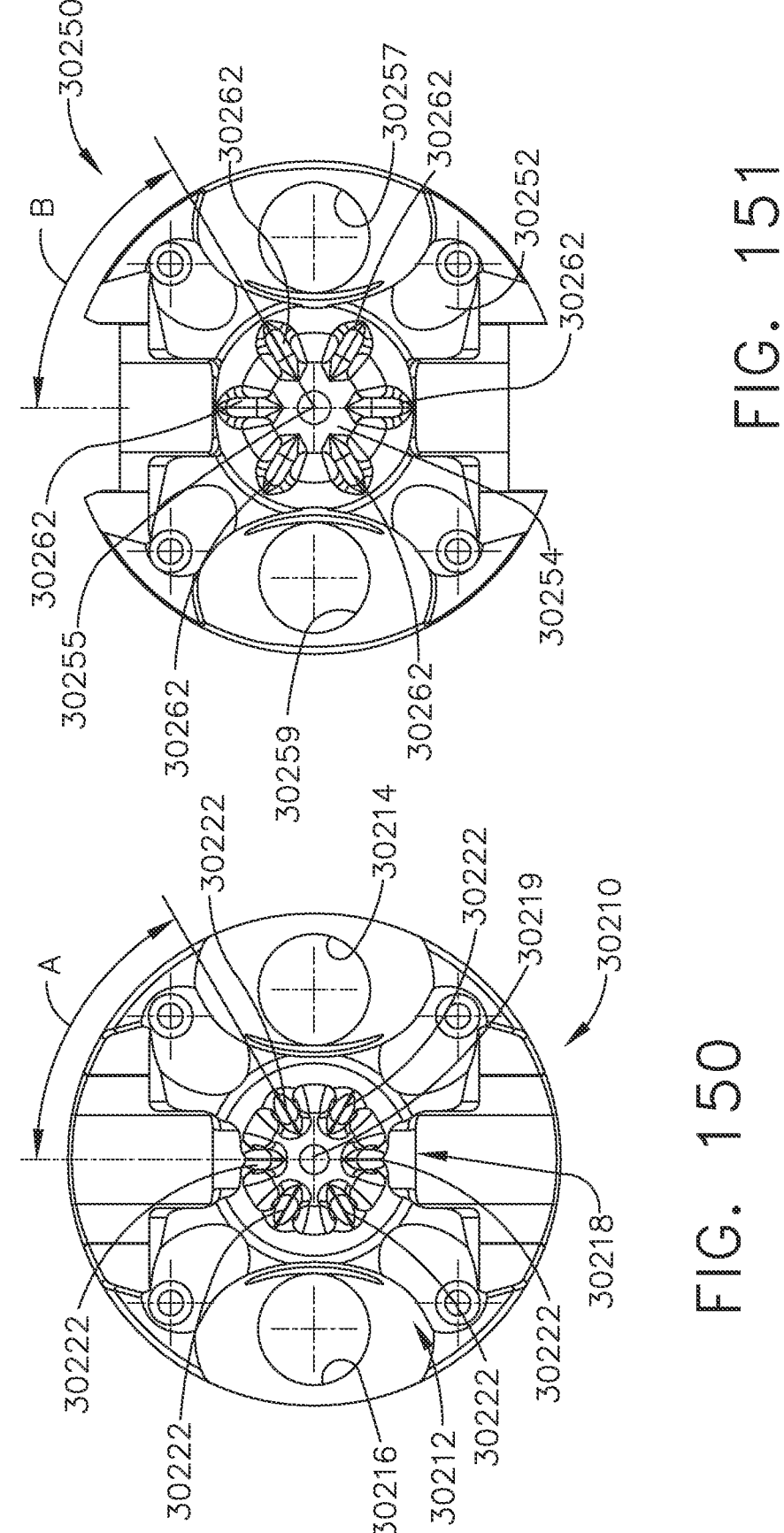
Figure 152:
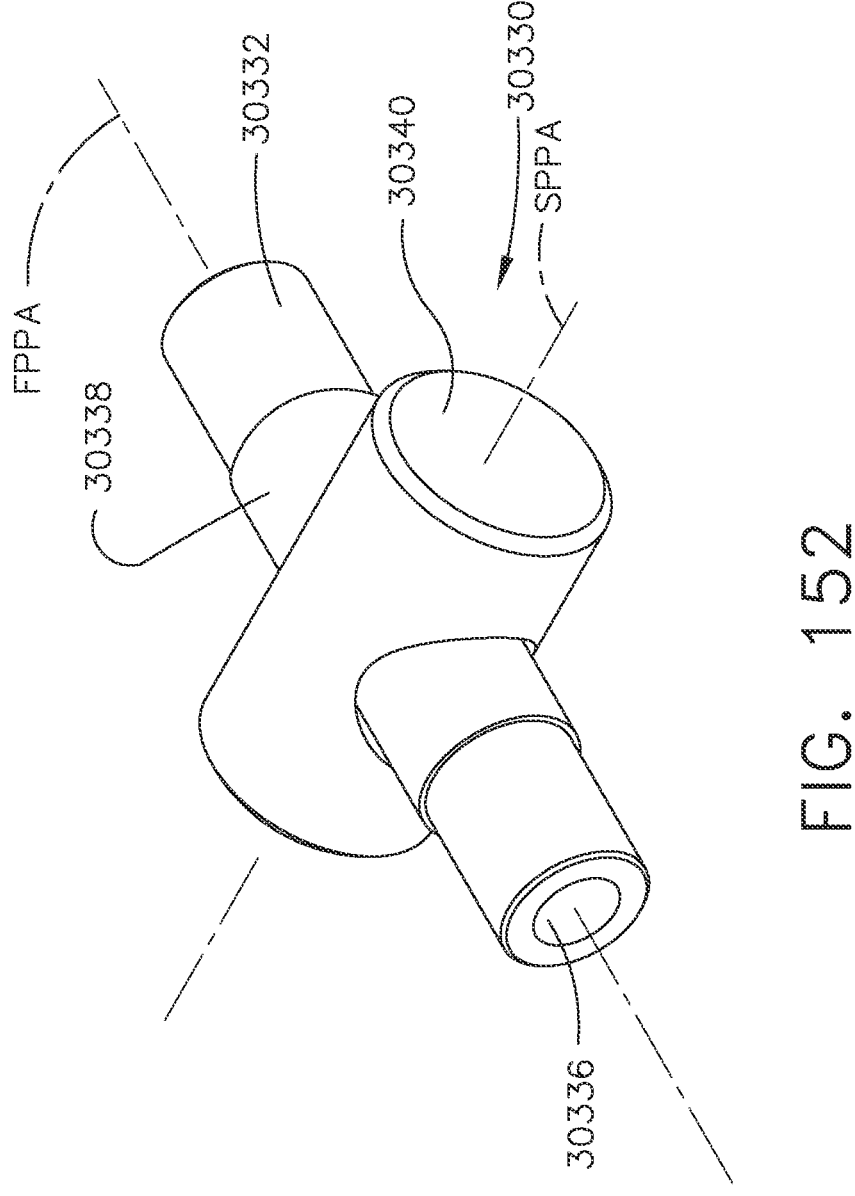
Figure 153:
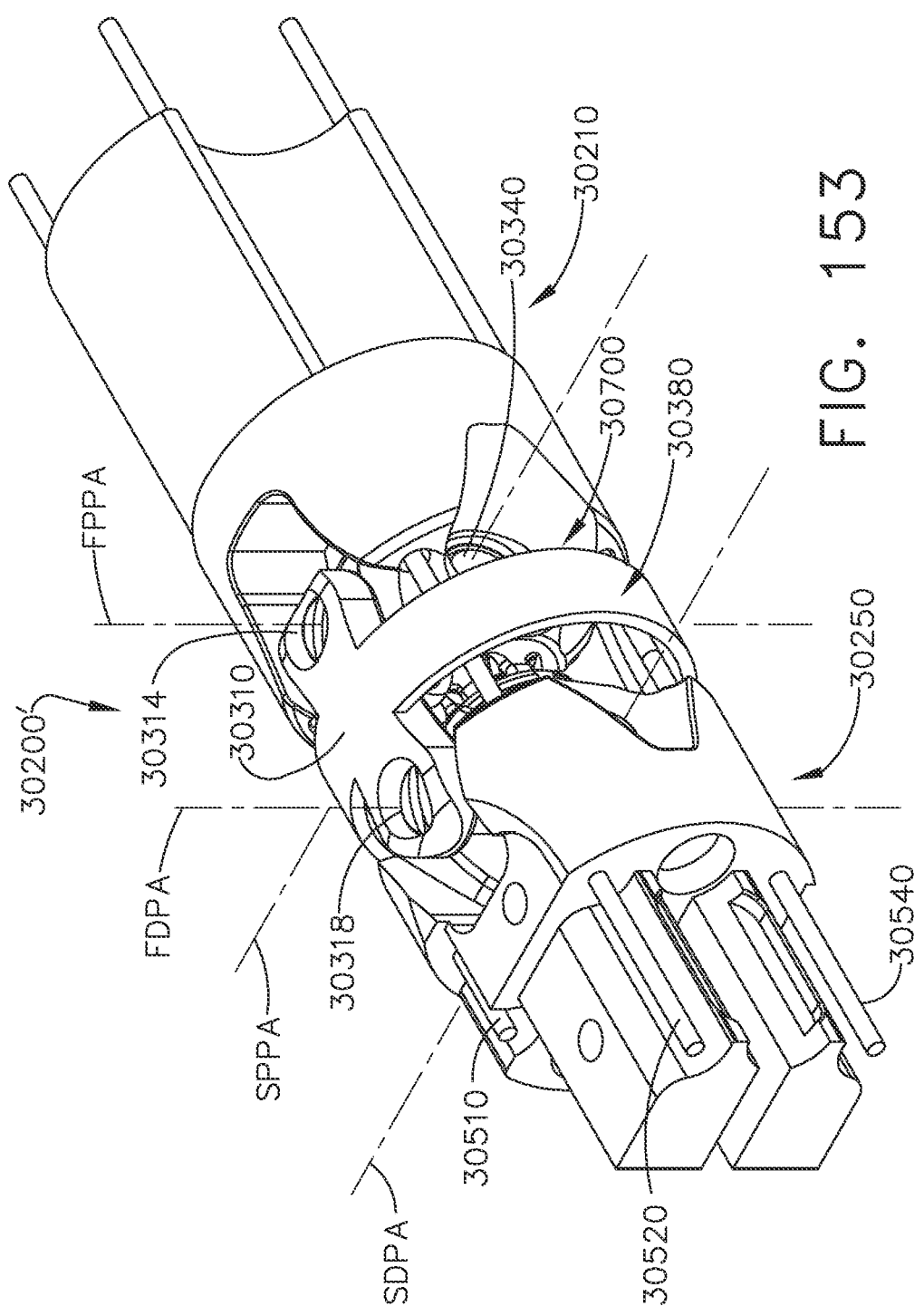
Figure 154:
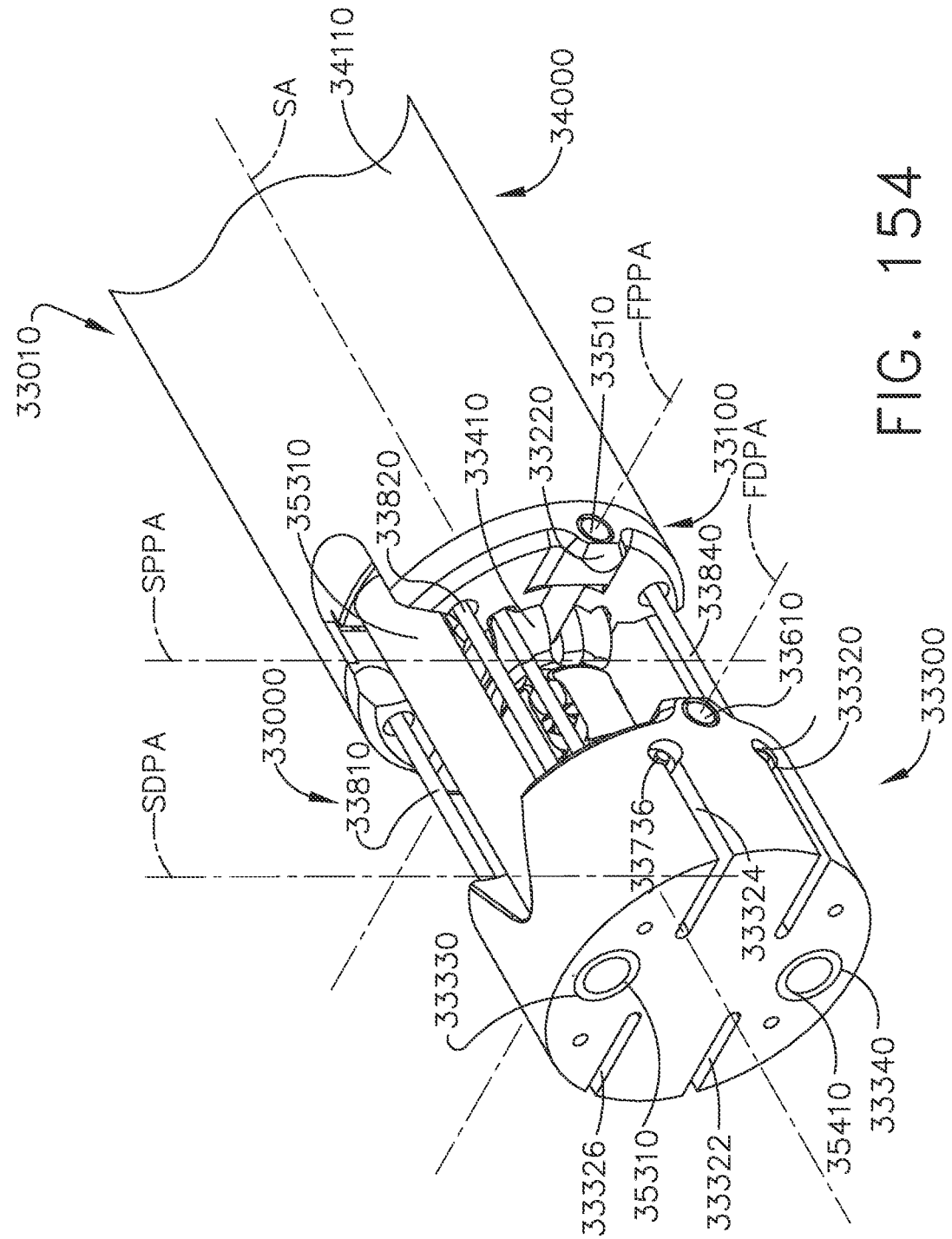
Figure 155:
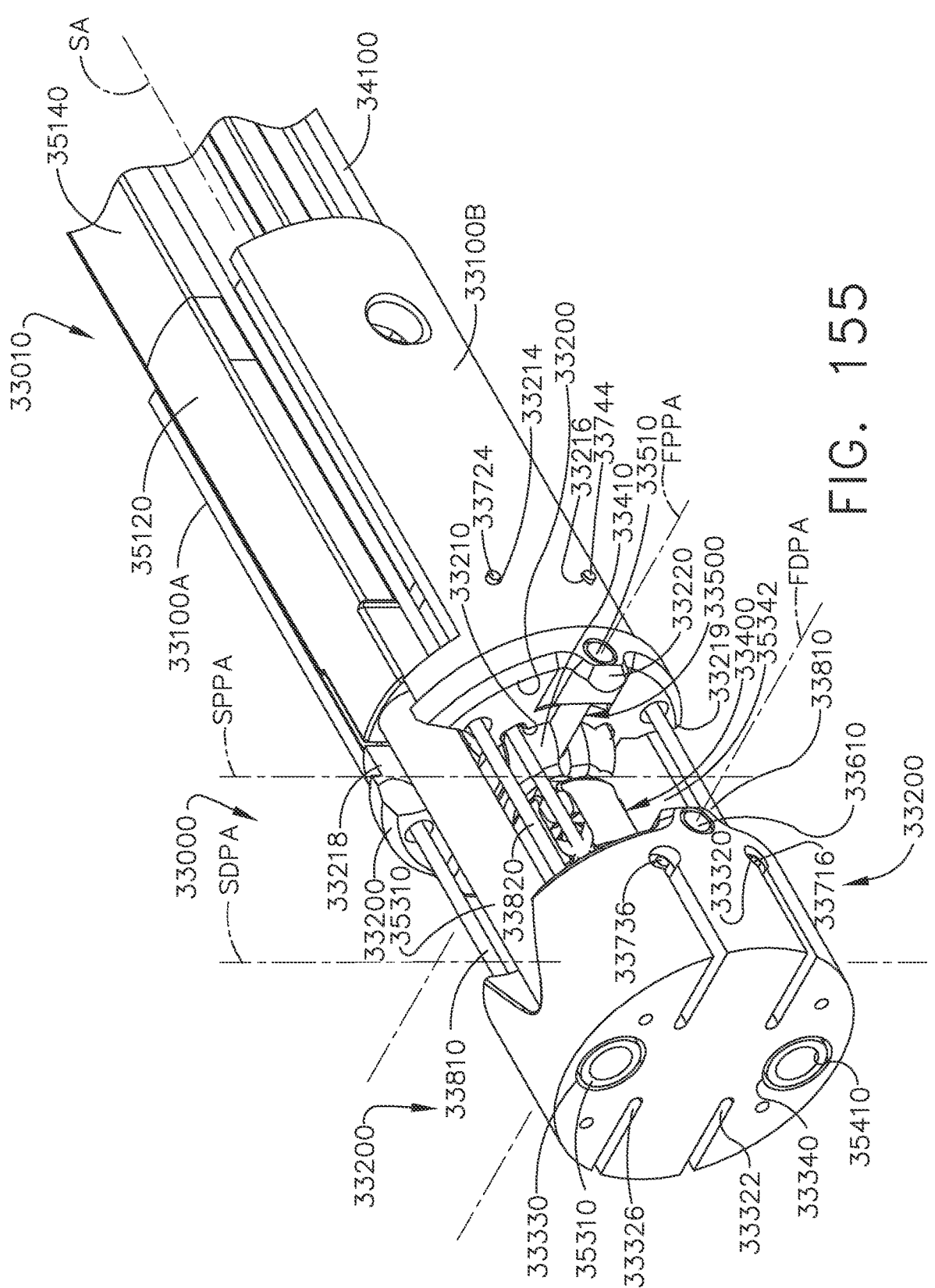
Figure 156:
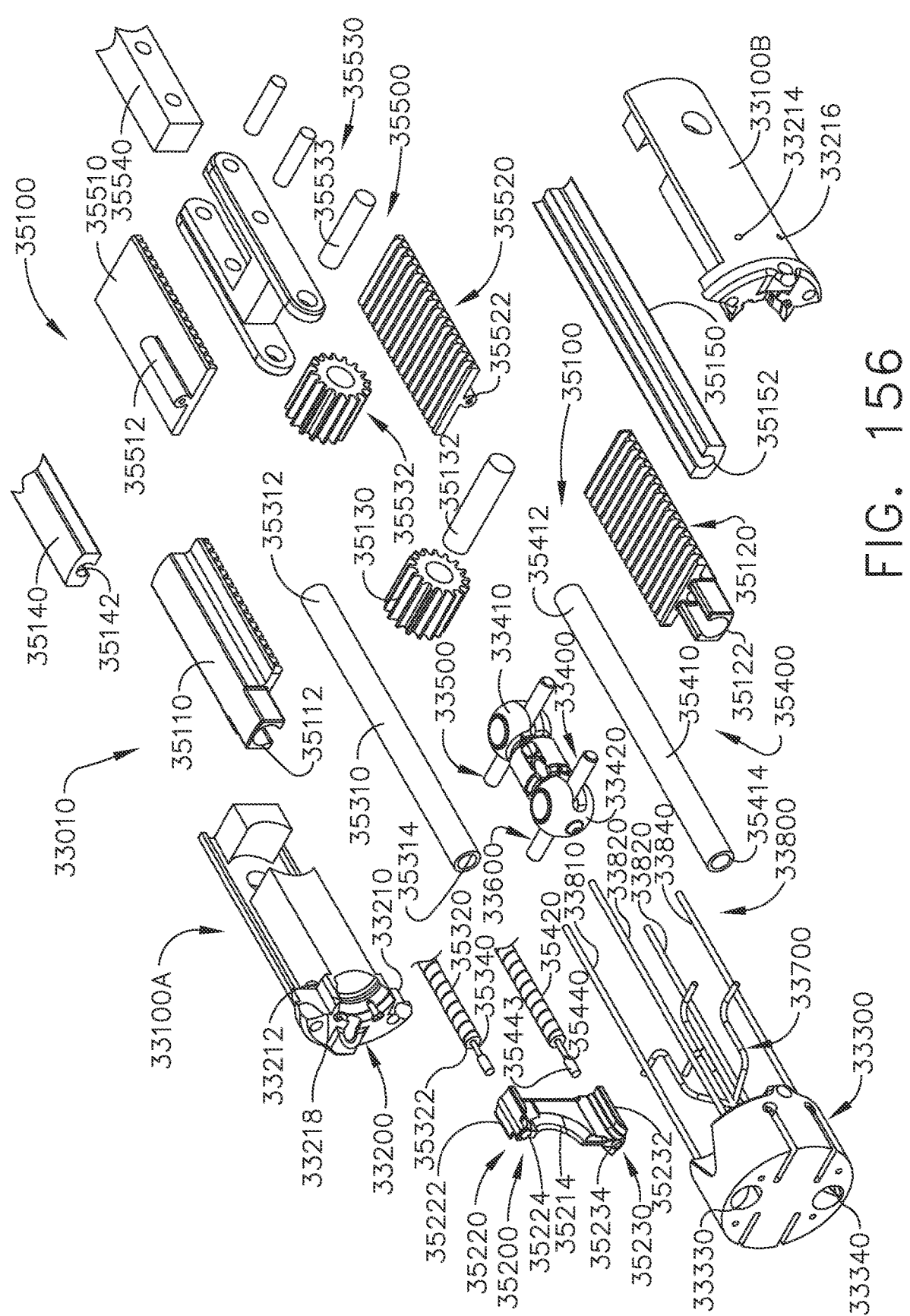
Figures 157, 158:
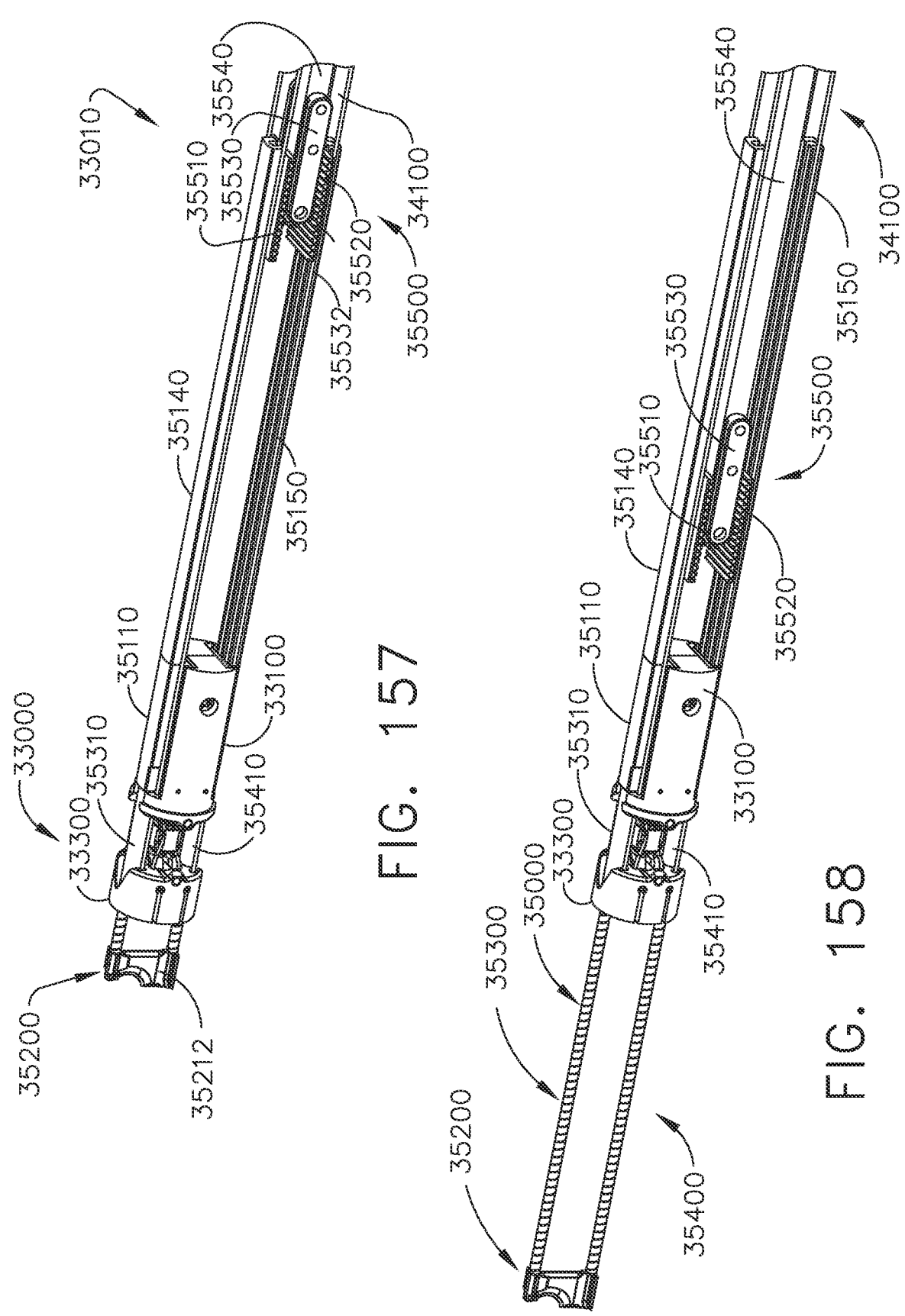
Figure 159:
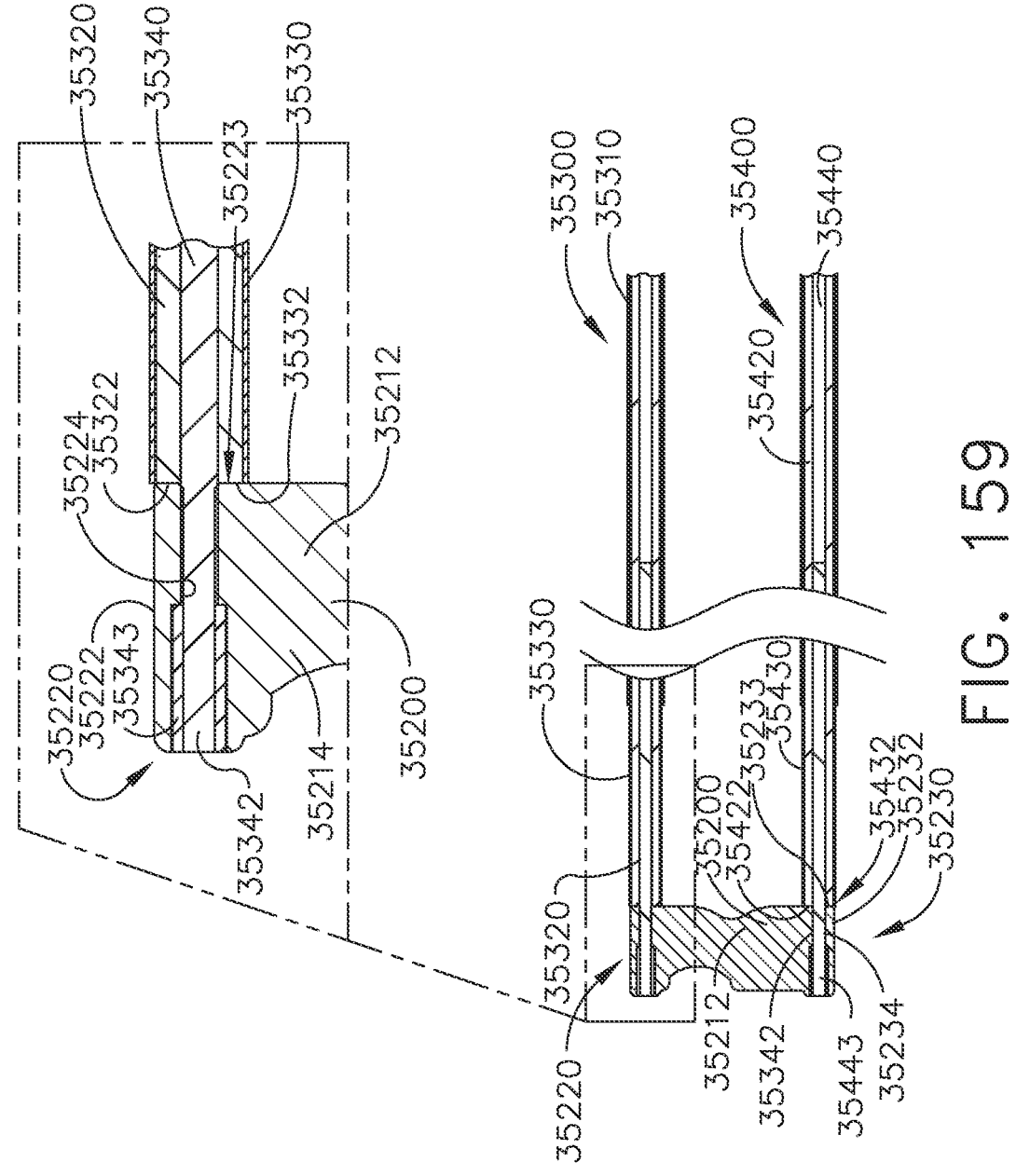
Figure 160:
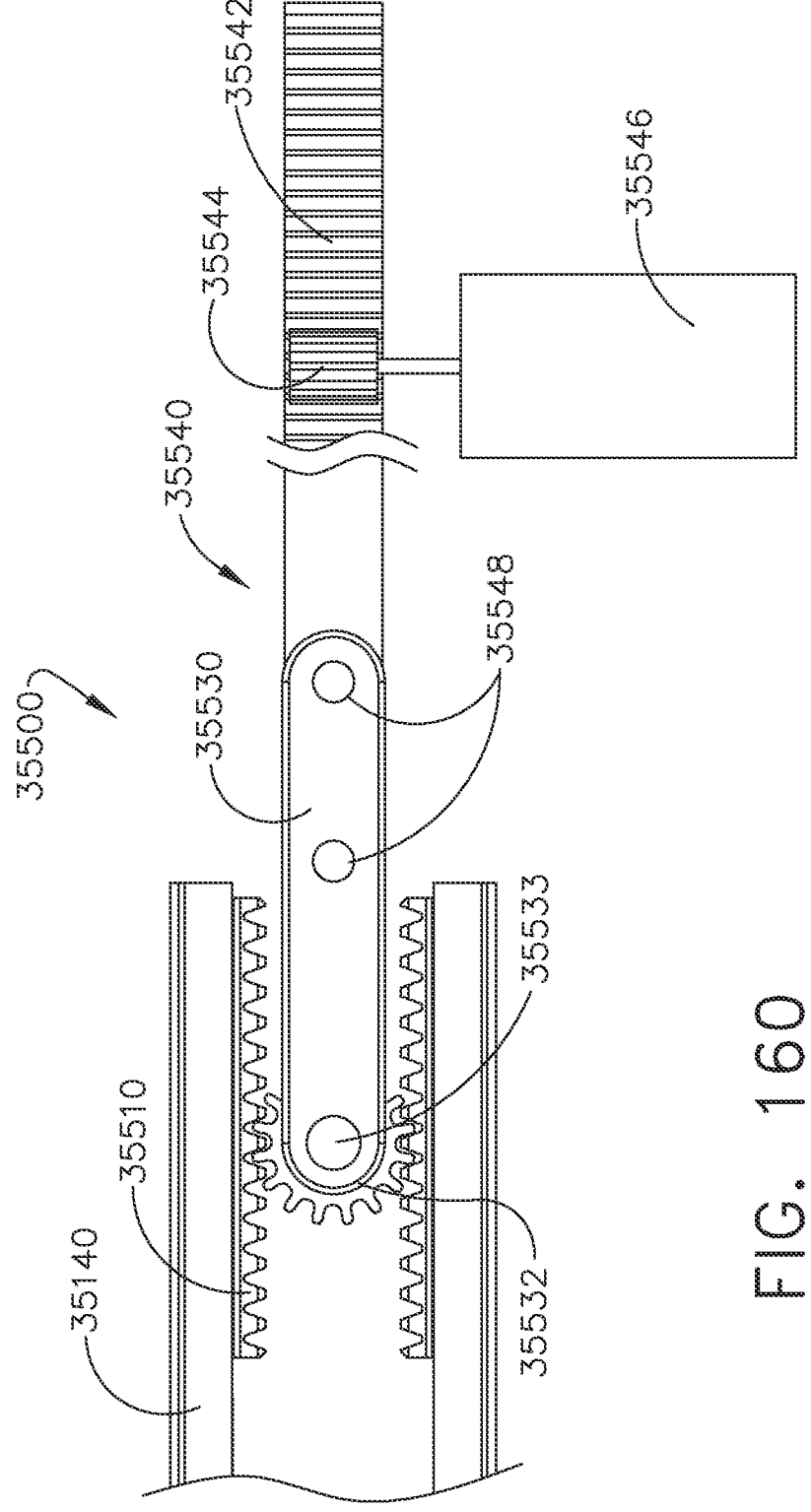
Figure 161:
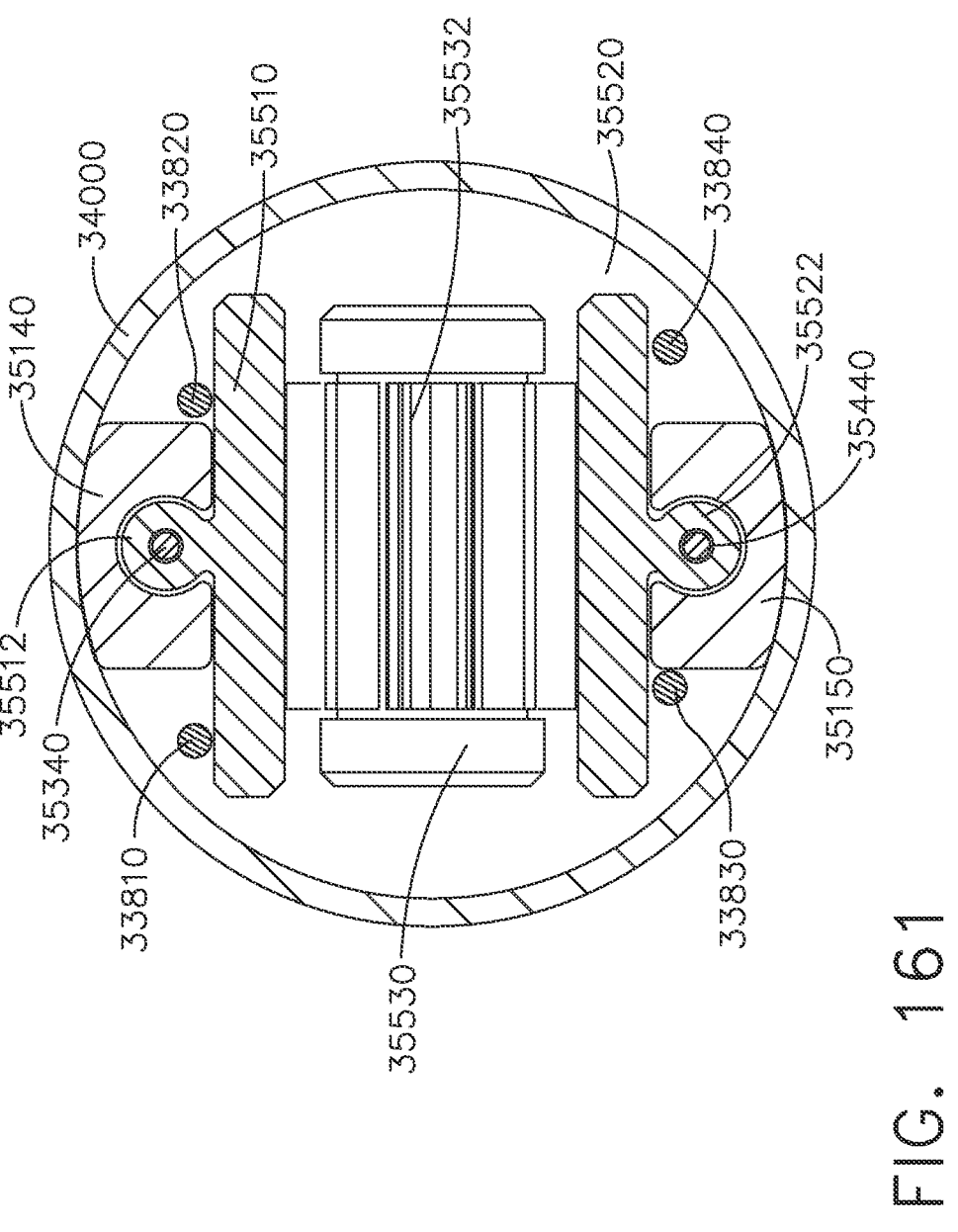
Figure 162:
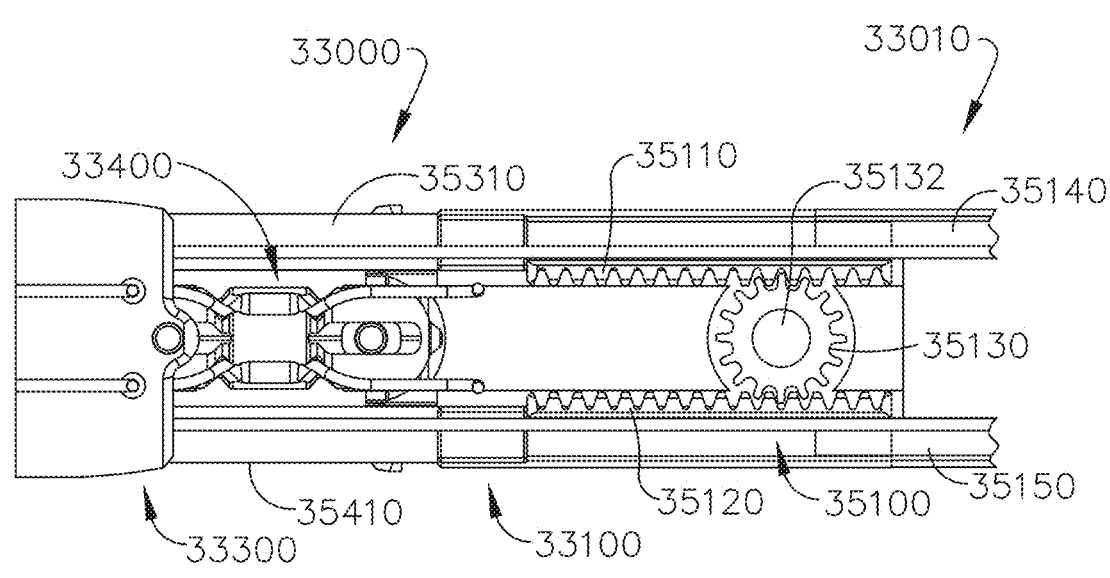
Figure 163:
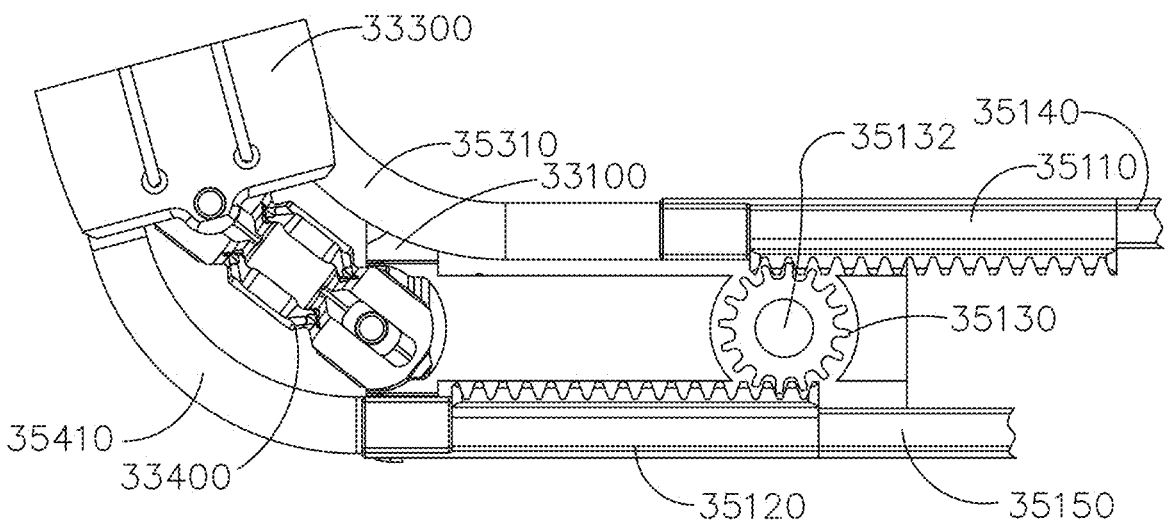
Figure 165:
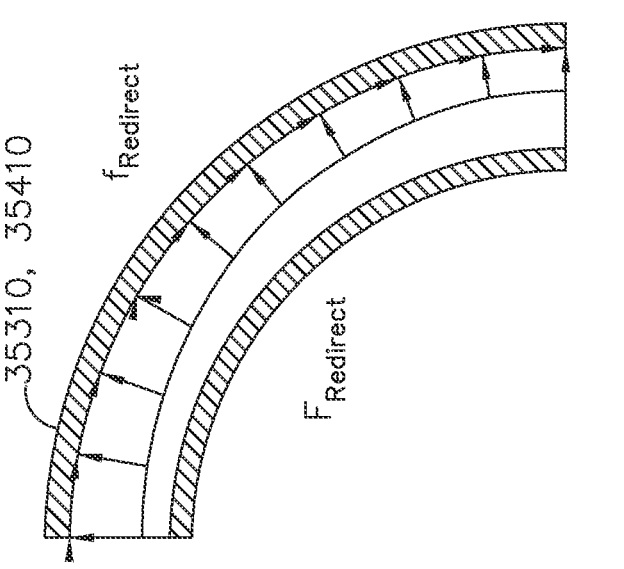
Figure 164:
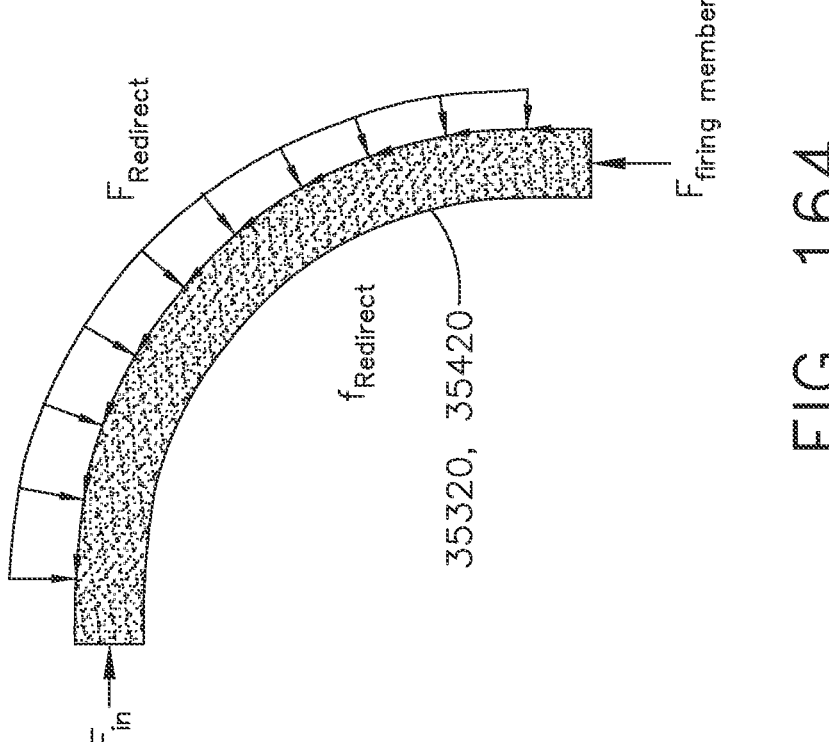
Figure 166:
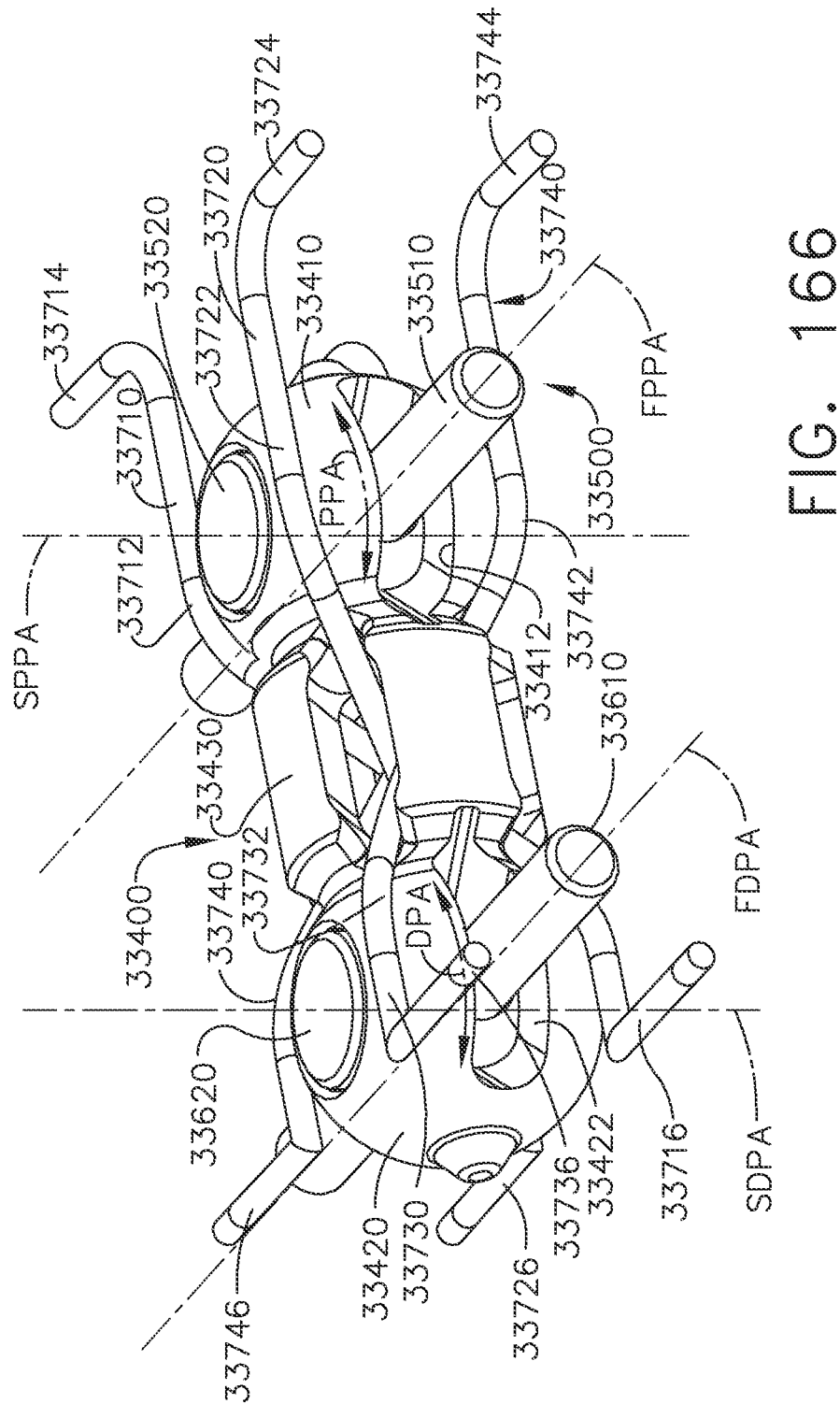
Figure 167:
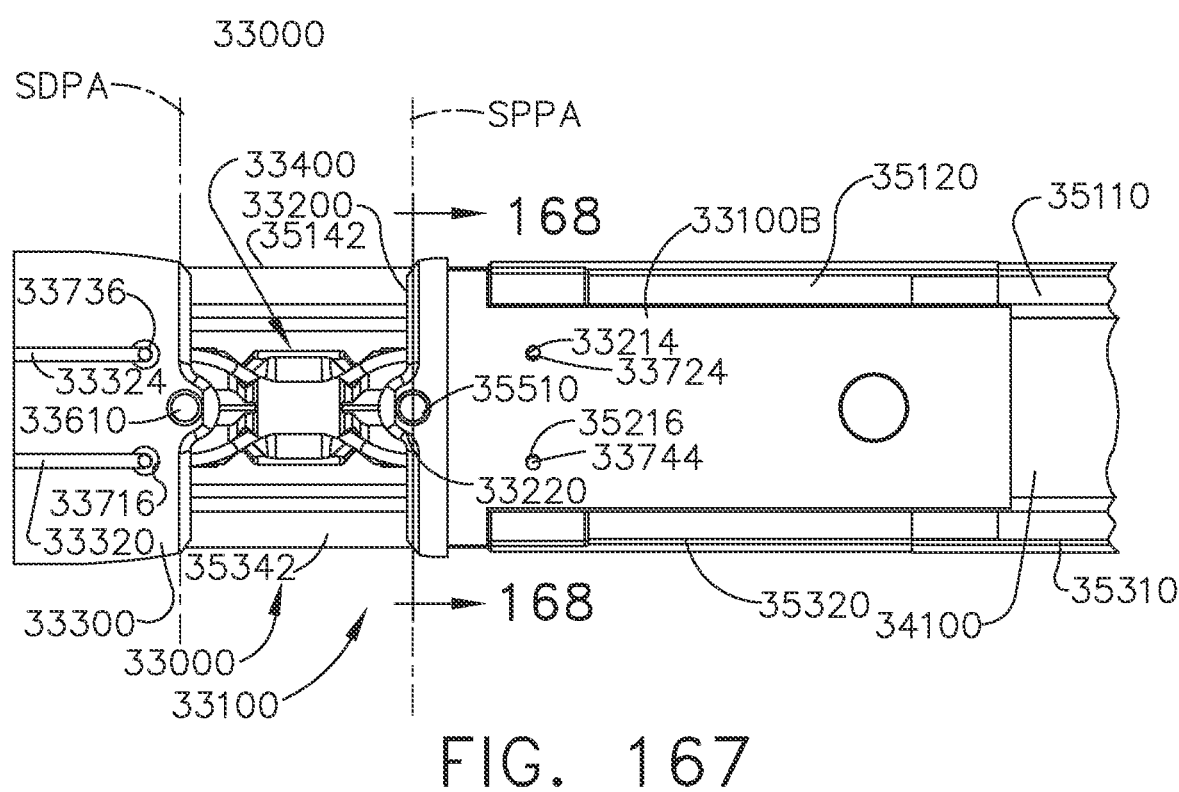
Figure 168:
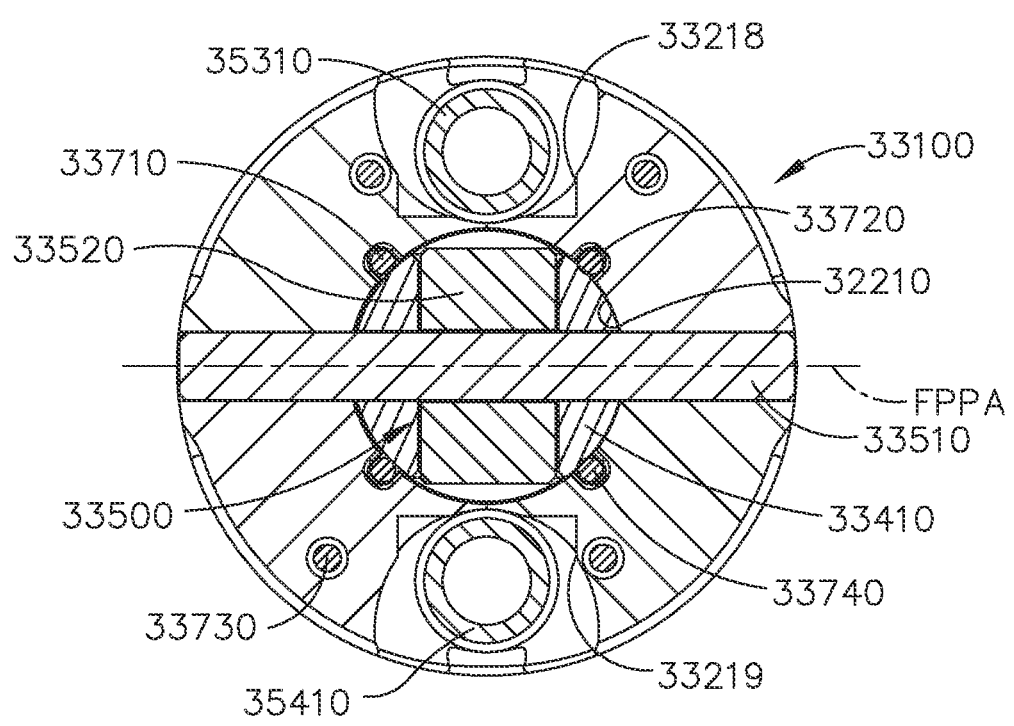
Figure 169:
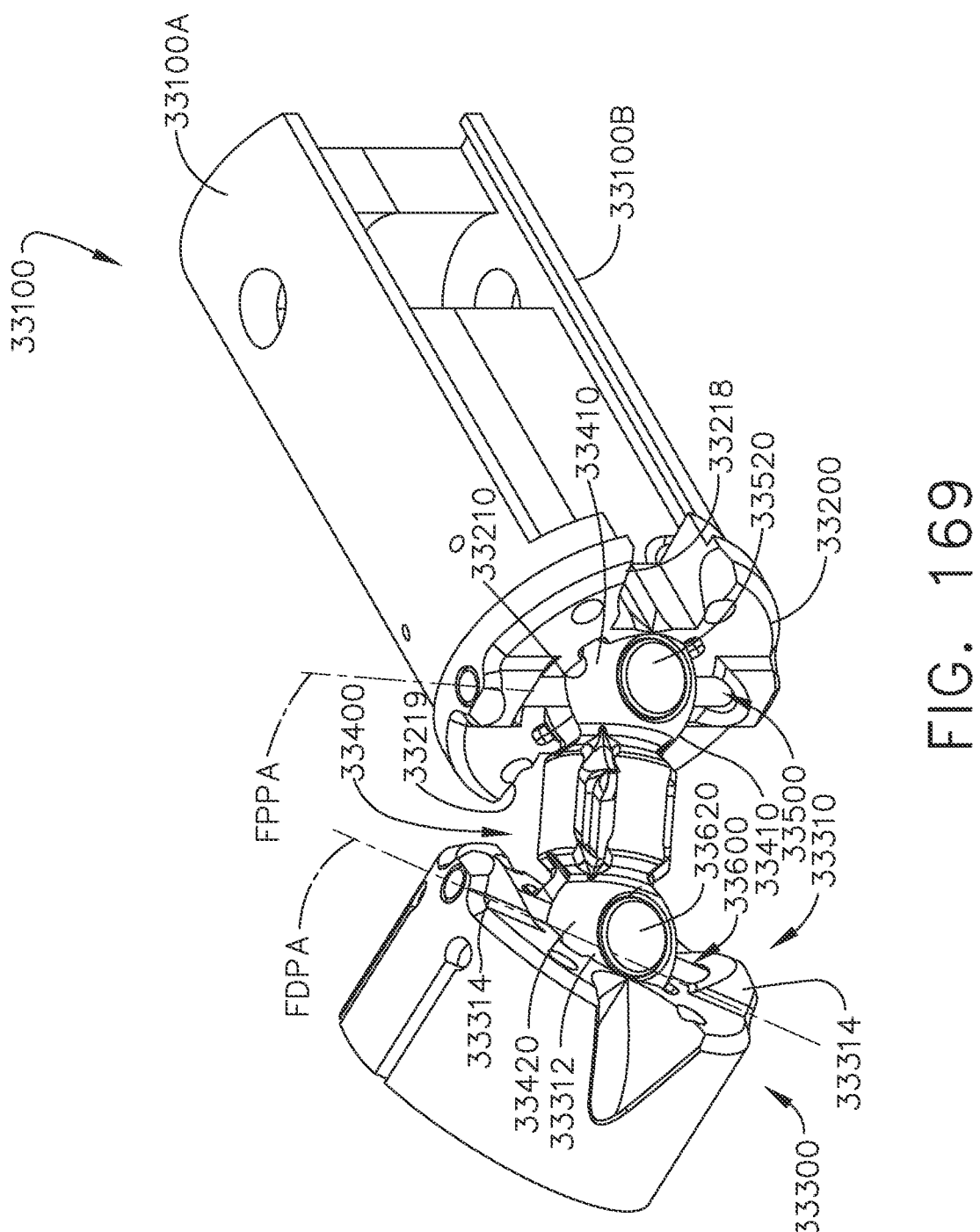
Figure 170:
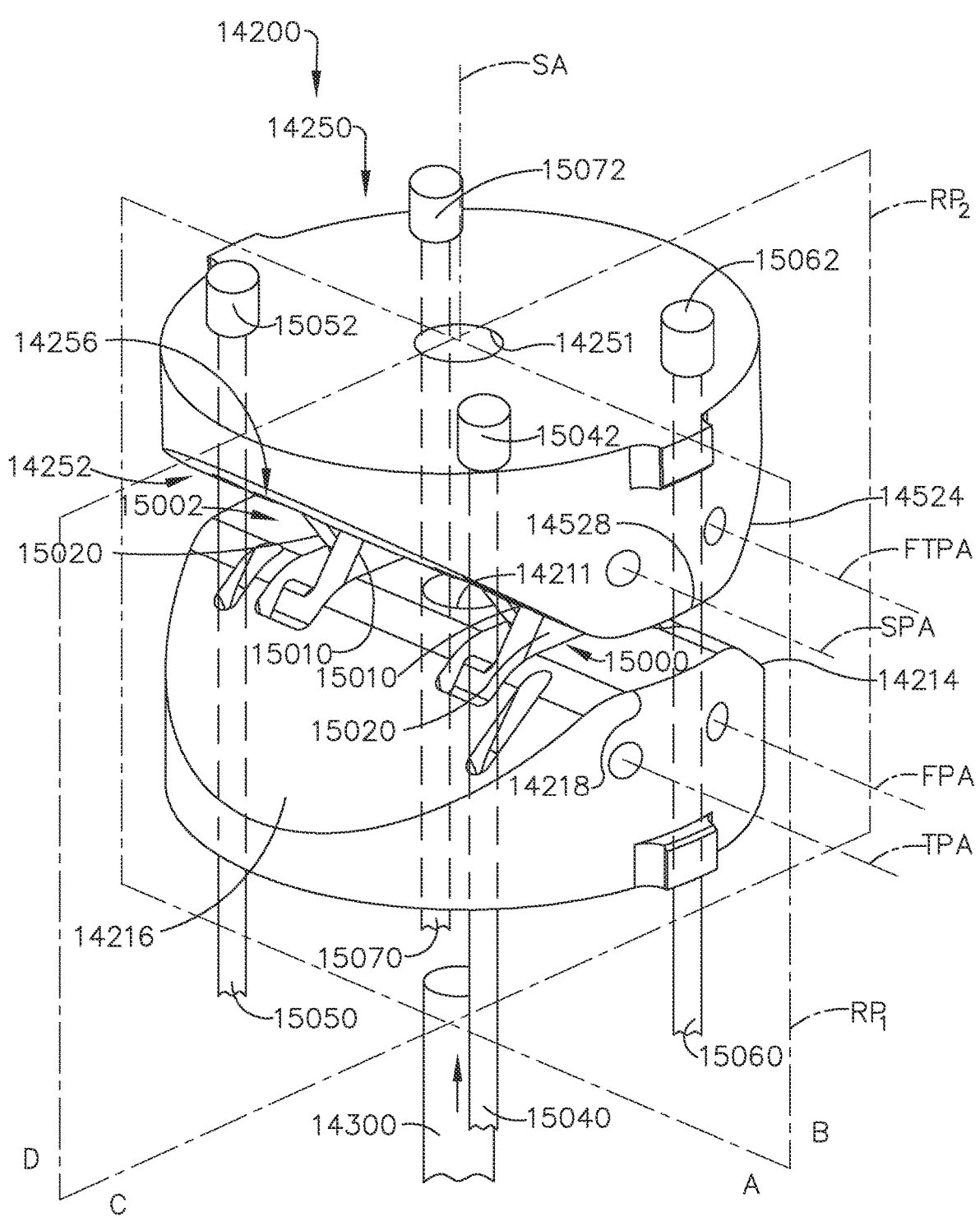
Figures 171, 172, 173:
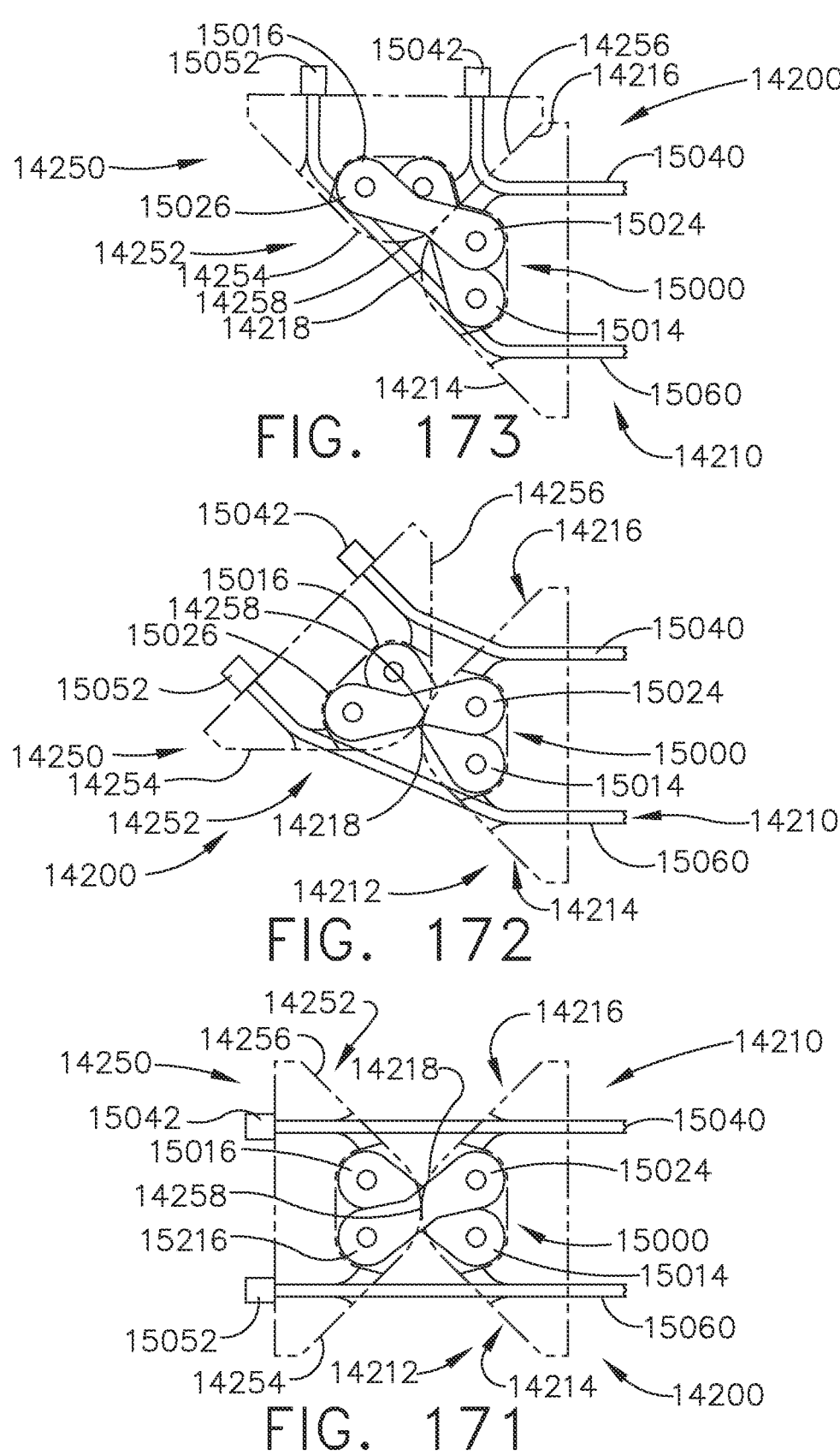
Figures 174, 175:
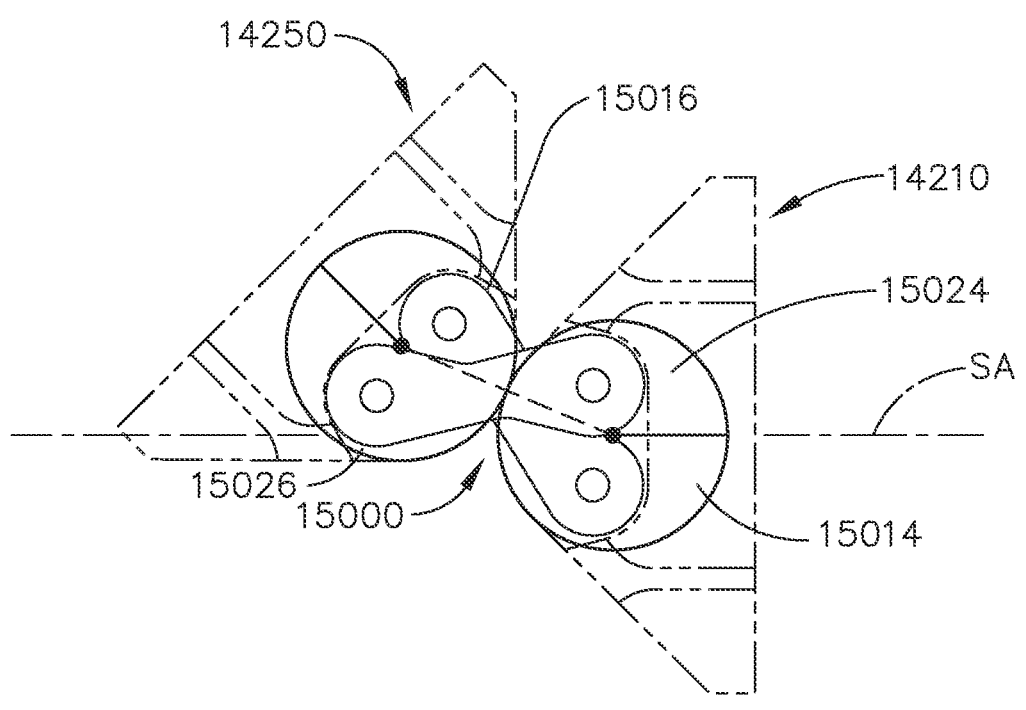
Figure 177:
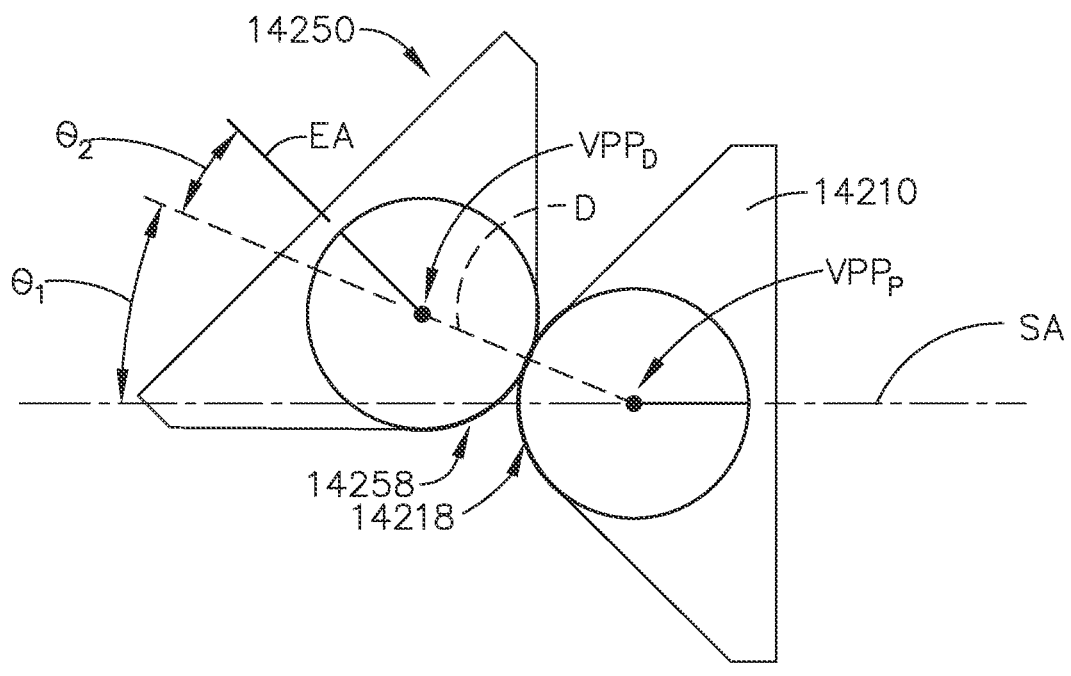
Figure 176:
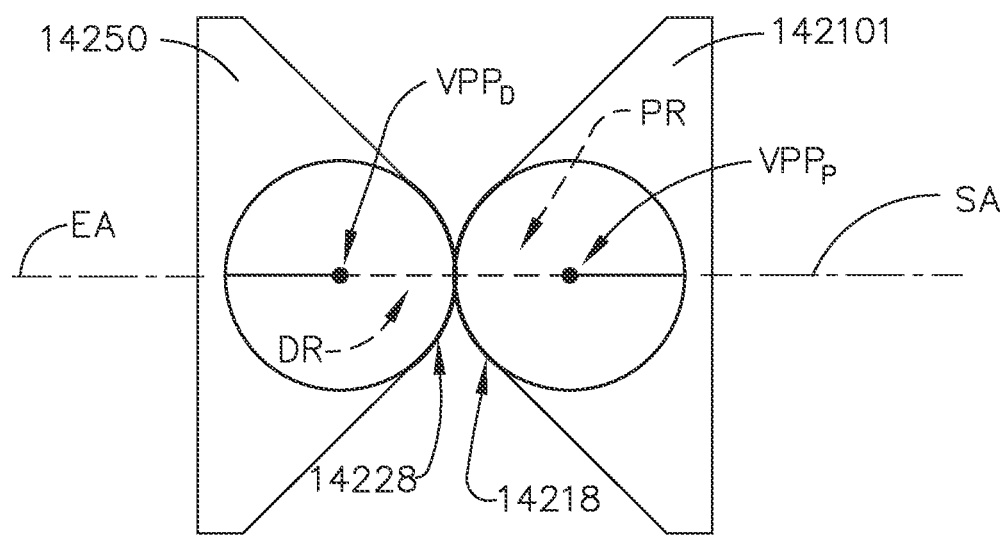
Figure 178:
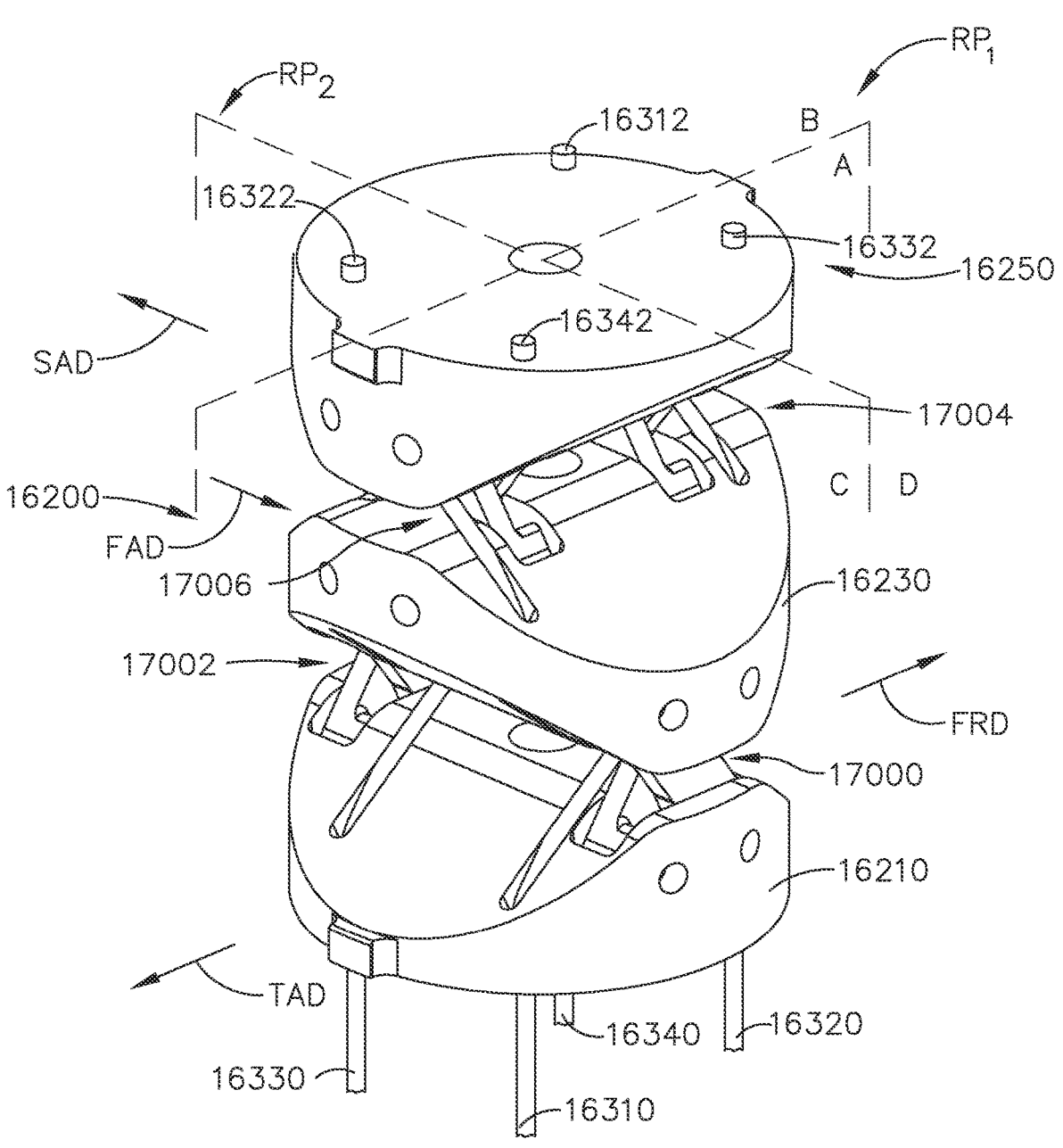
Figure 179:
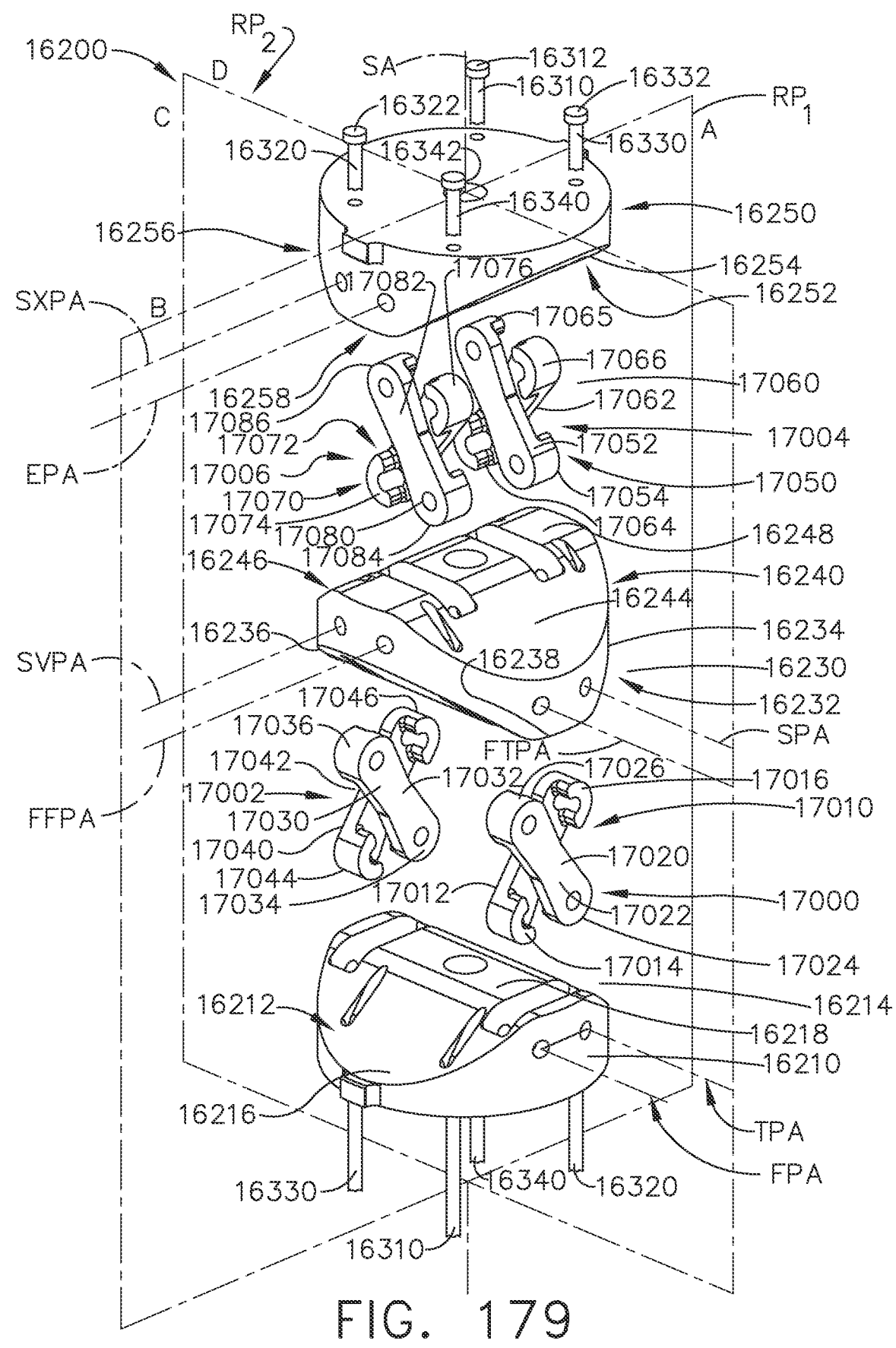
Figure 180:
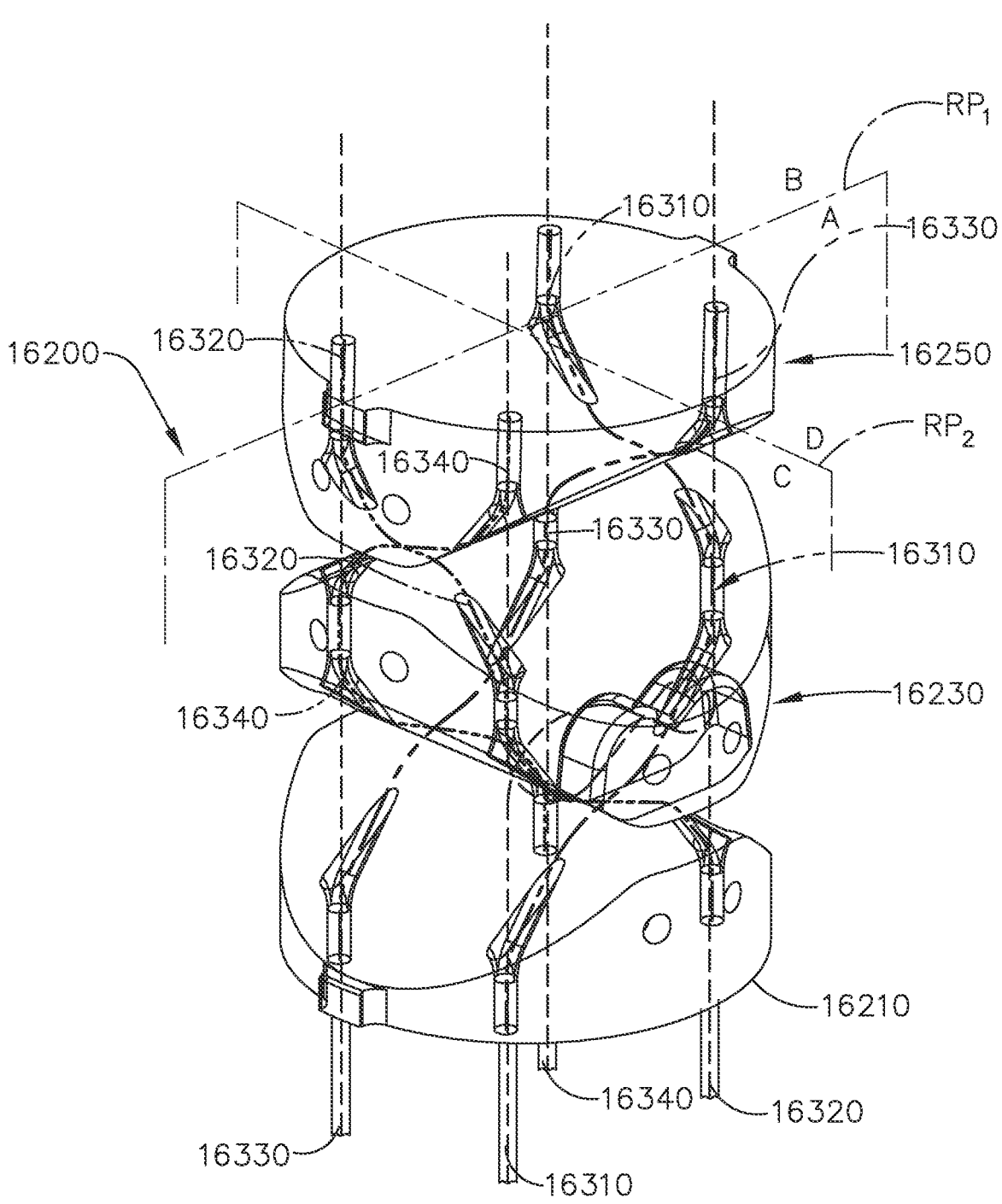
Figure 181:
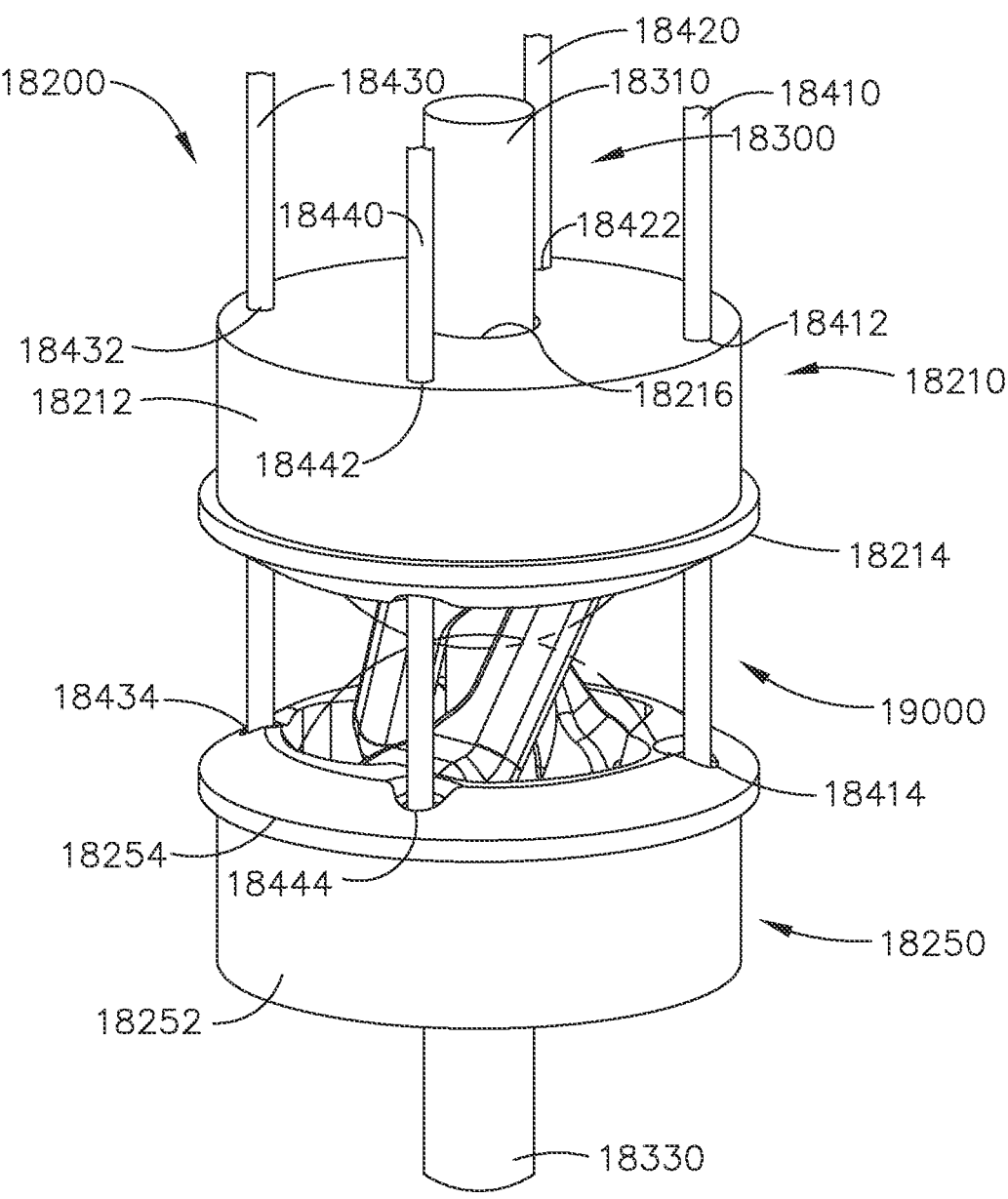
Figure 182:
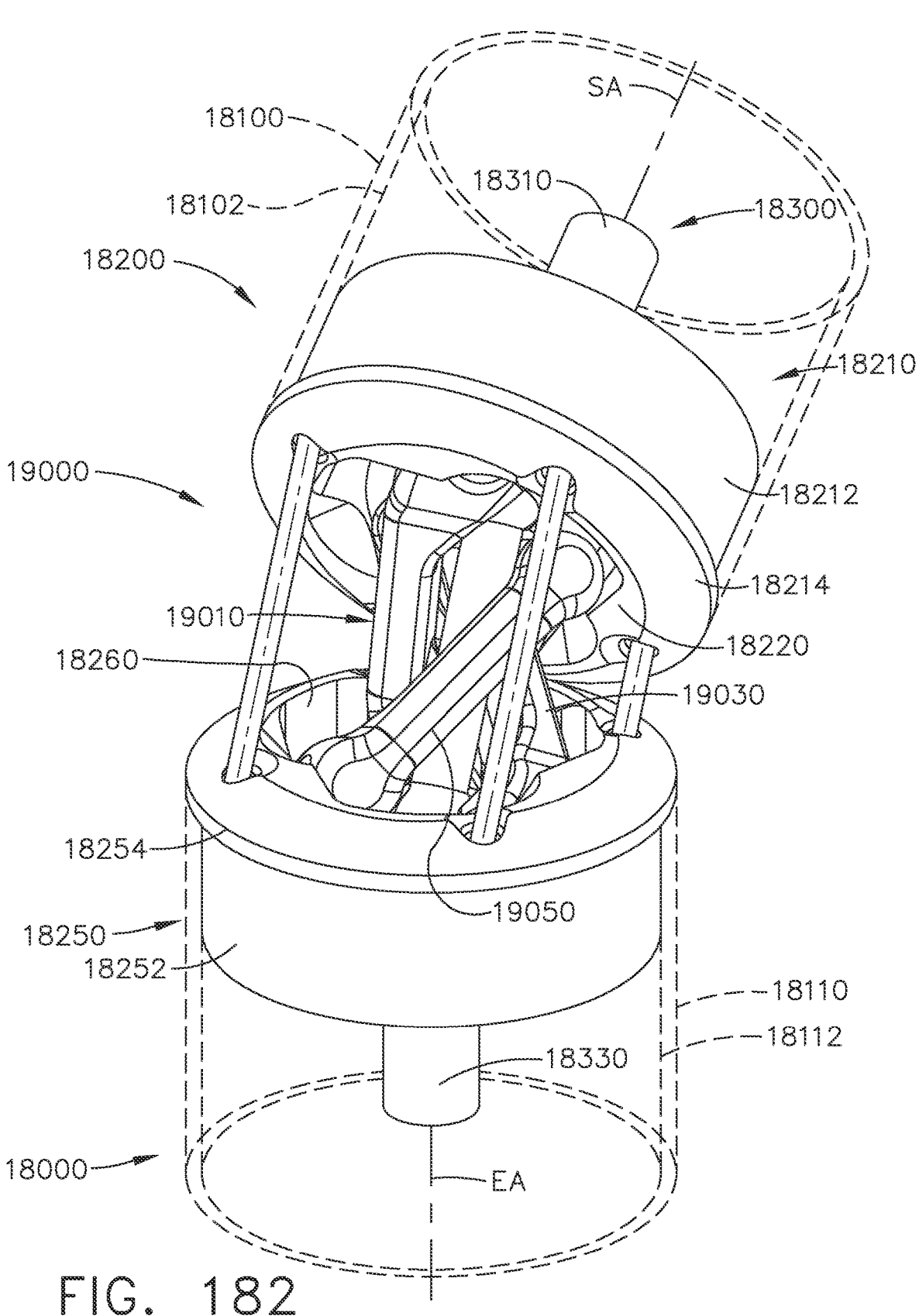
Figure 183:
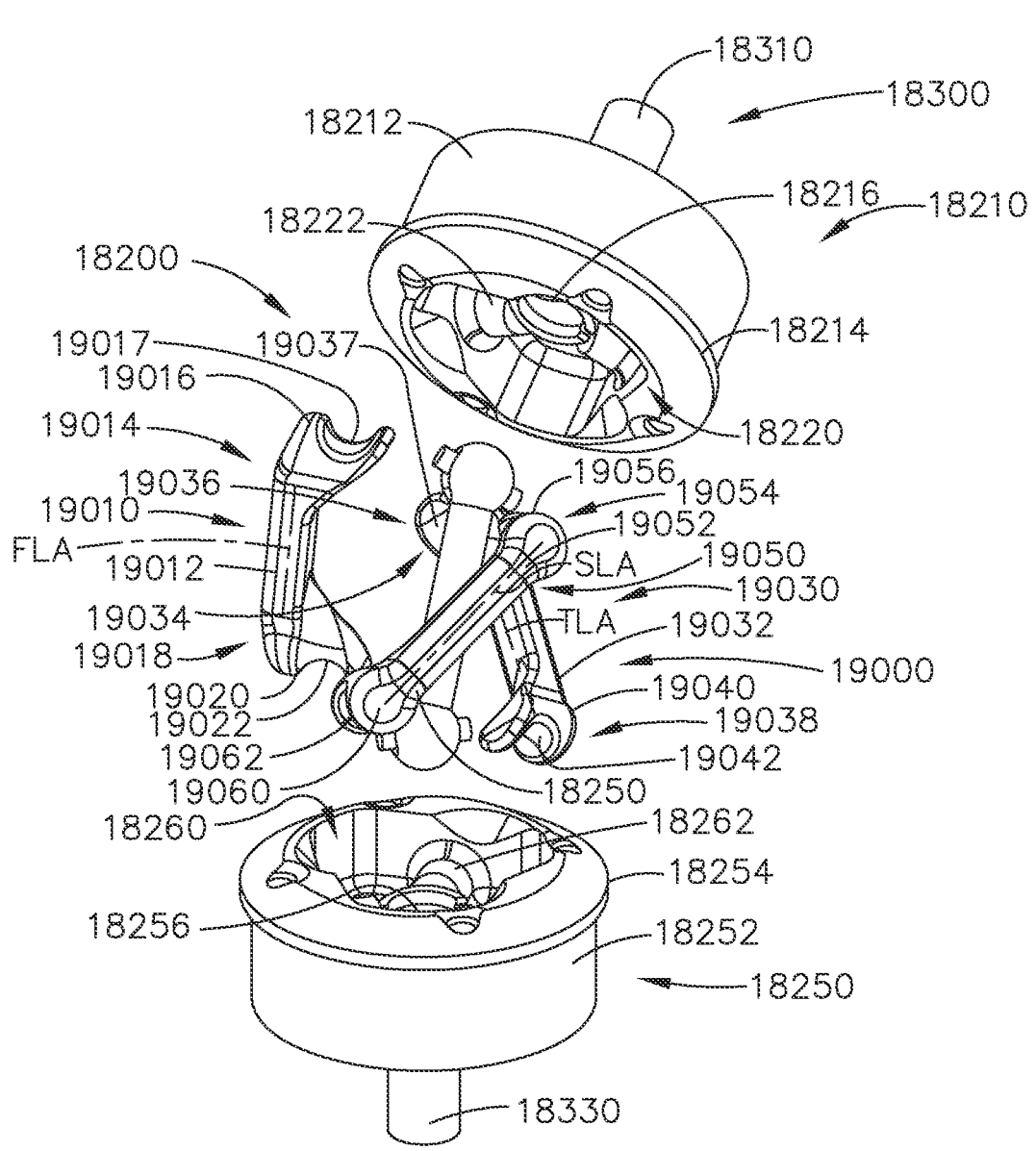
Figures 184, 185:
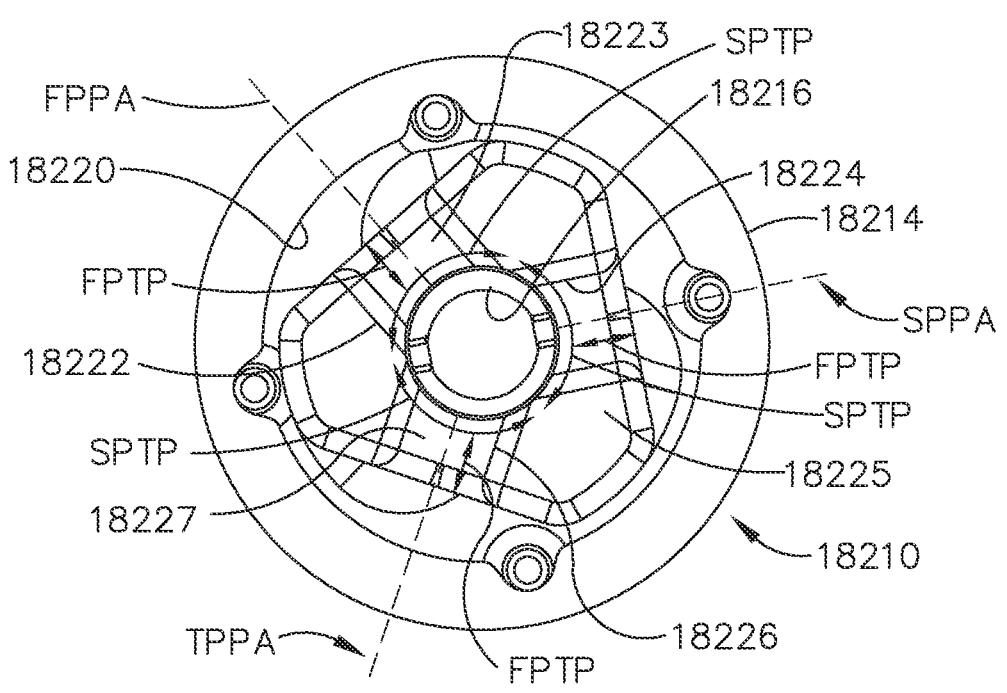
Figures 186, 187:
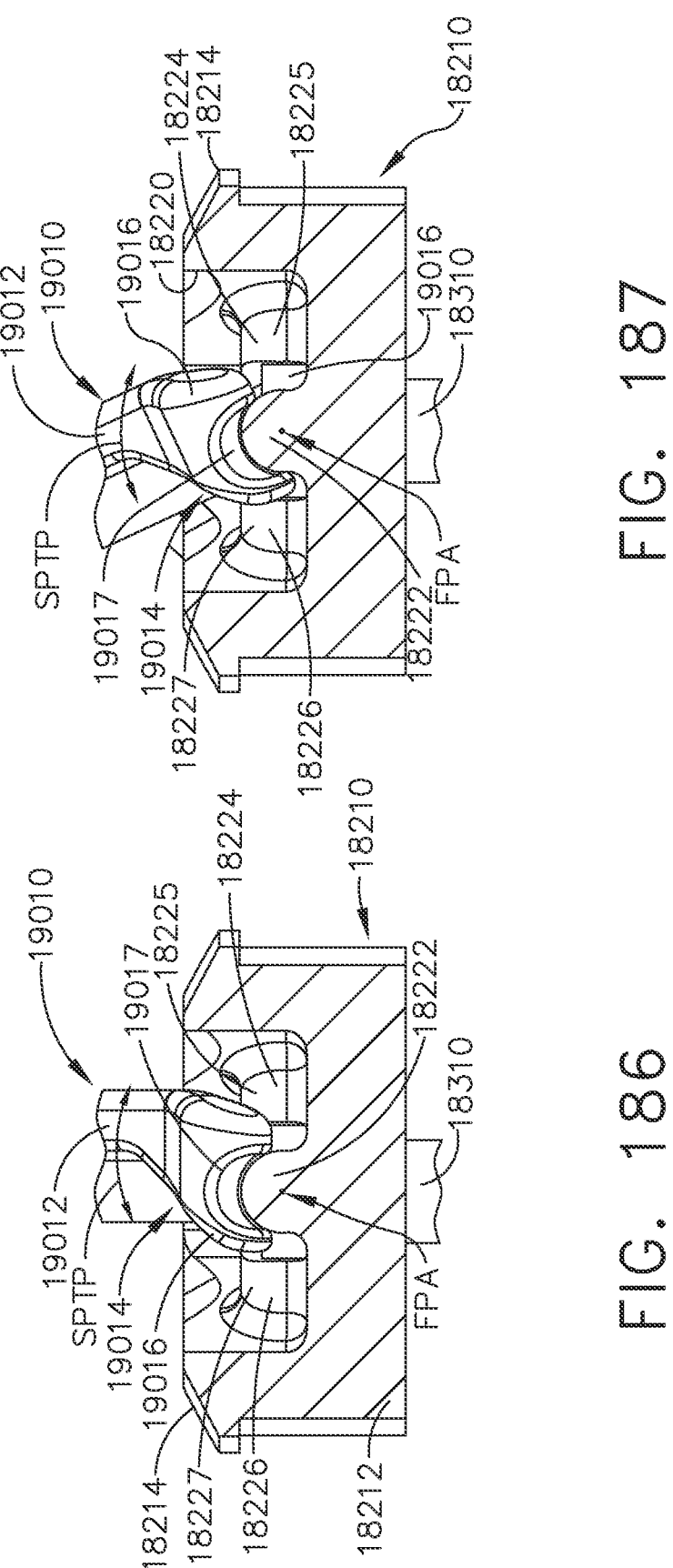
Figures 188, 189:
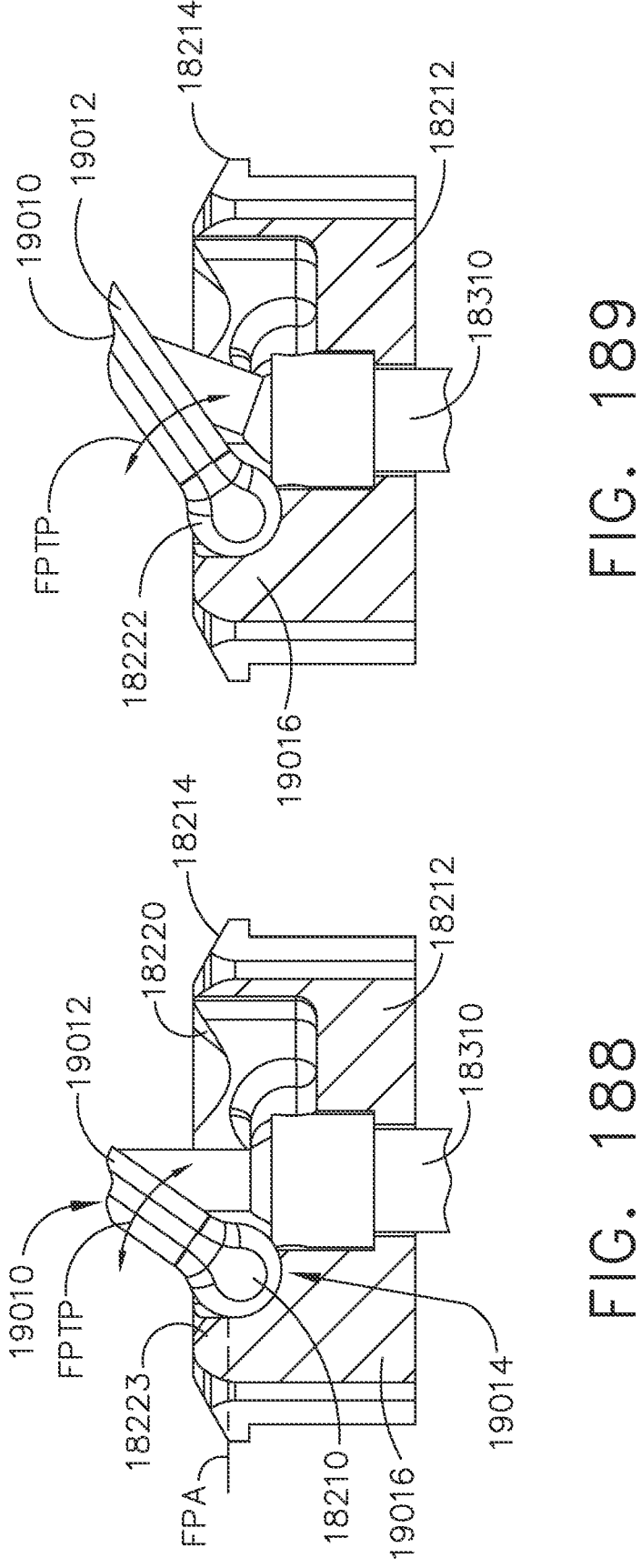
Figures 190, 191:
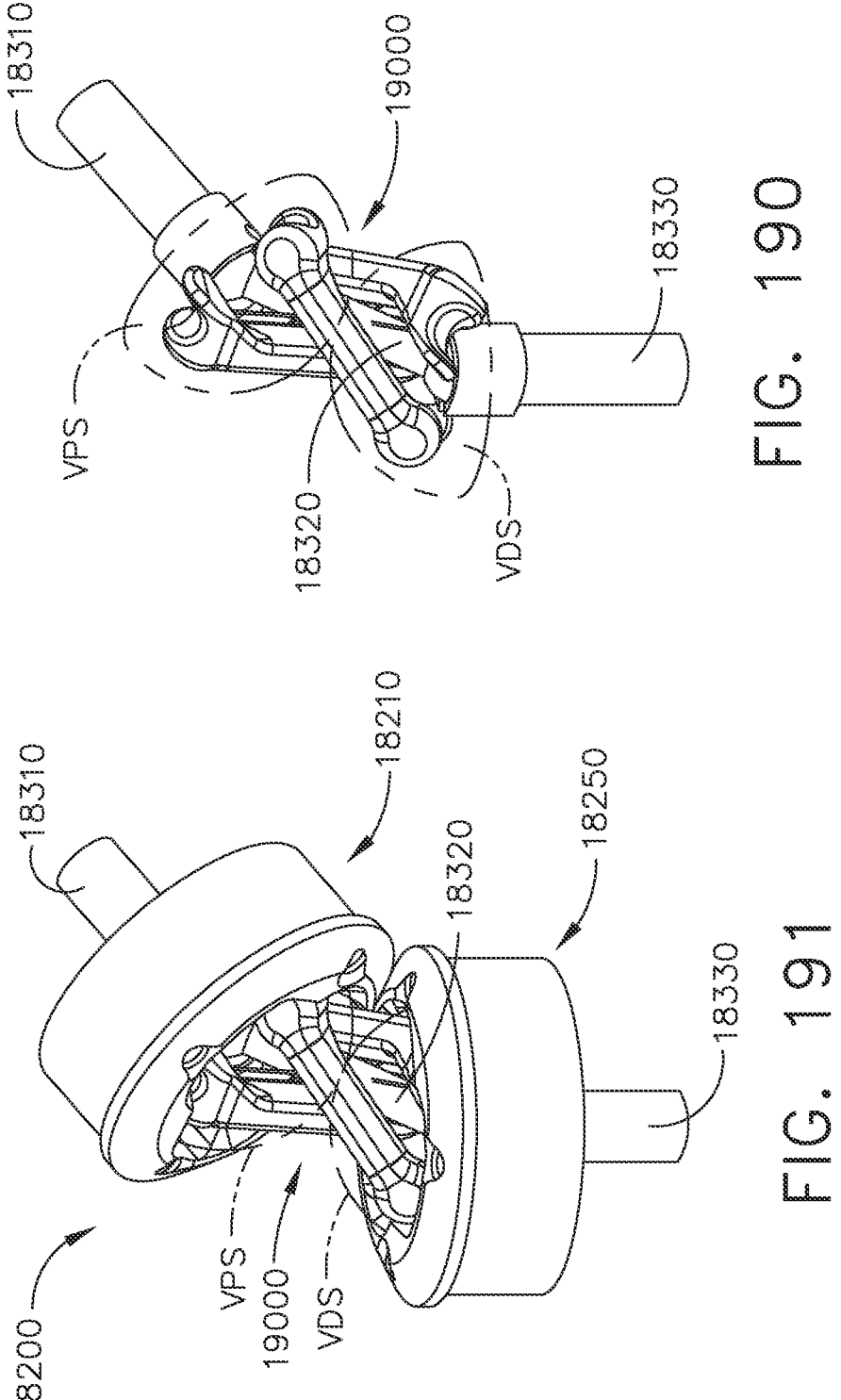
Figure 192:
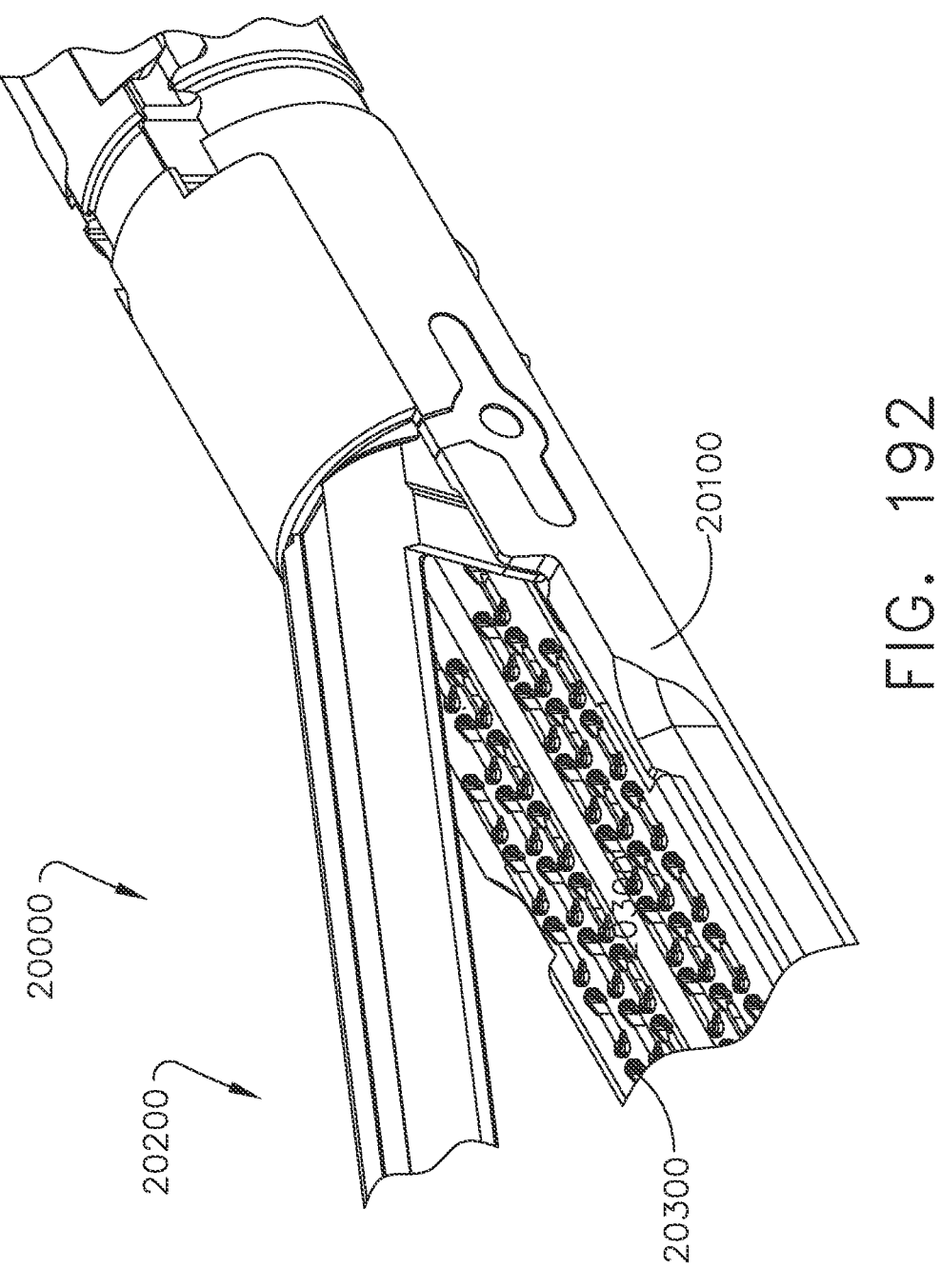
Figure 193:
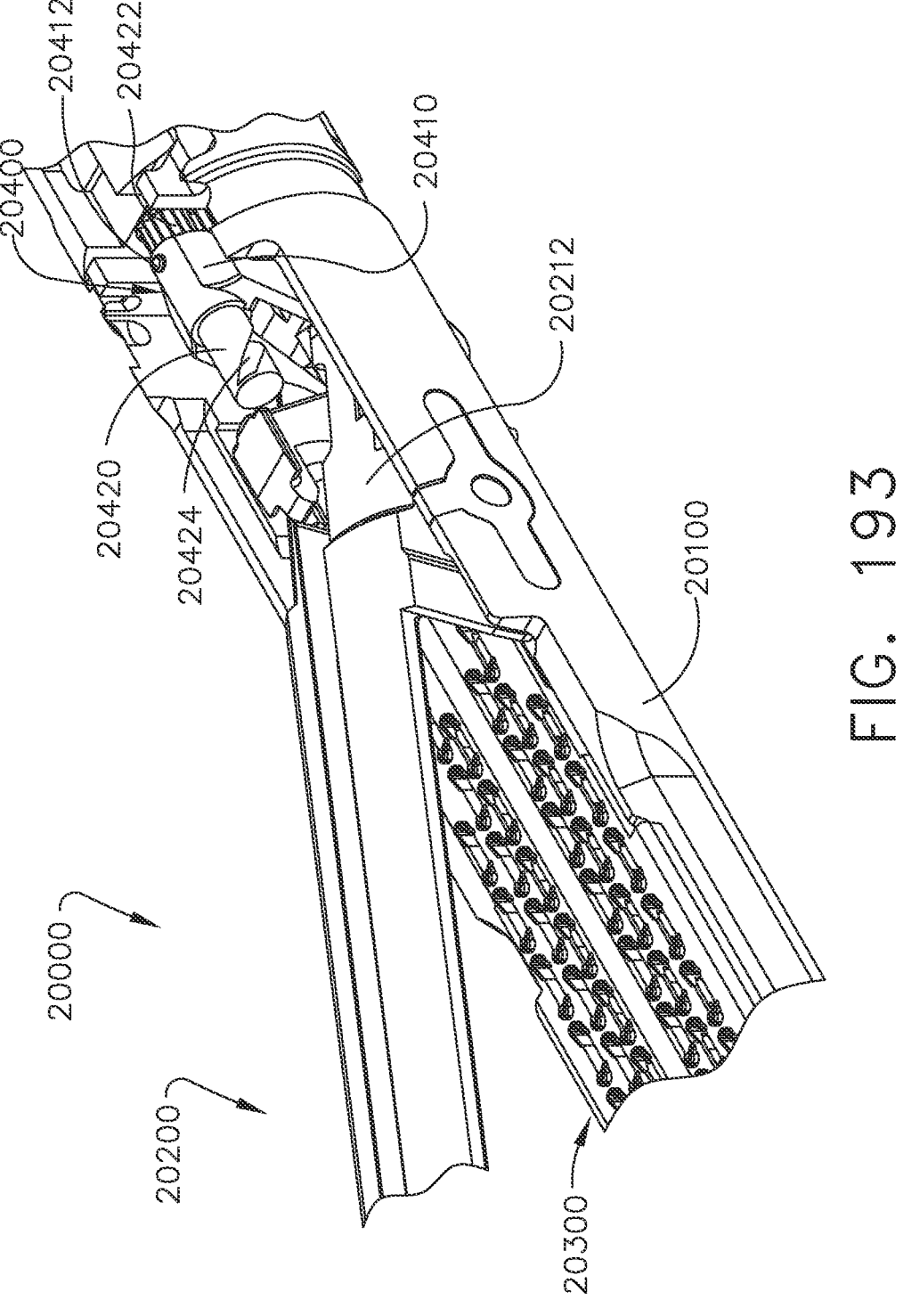
Figure 195:
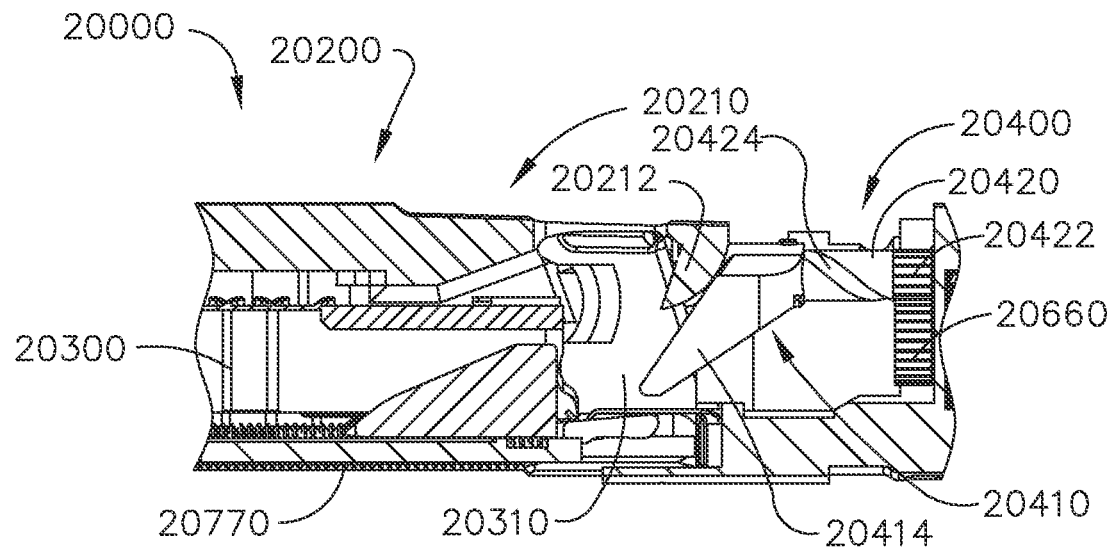
Figure 194:
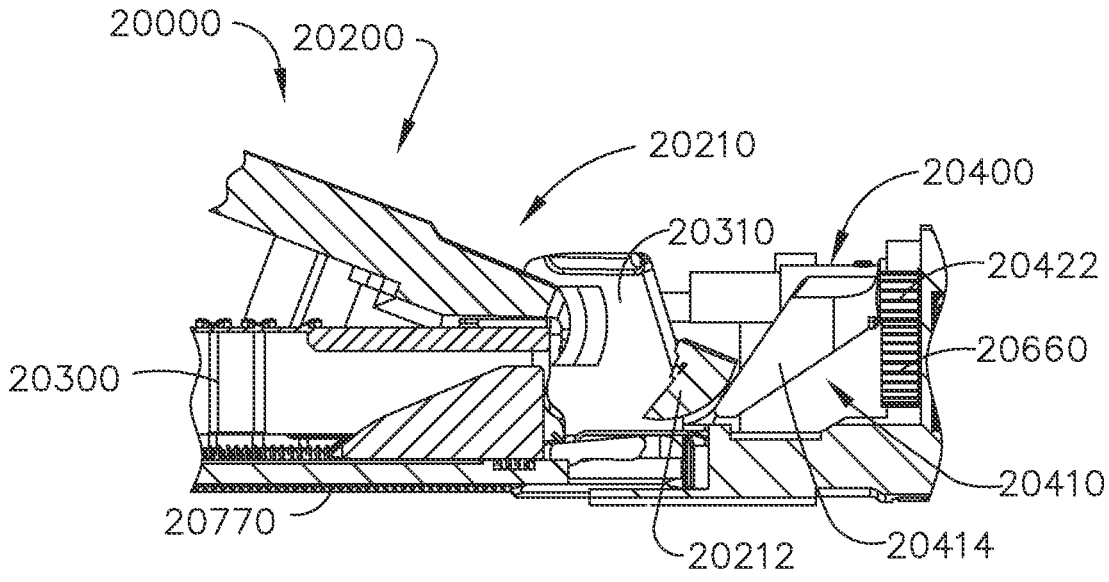
Figures 196, 197:
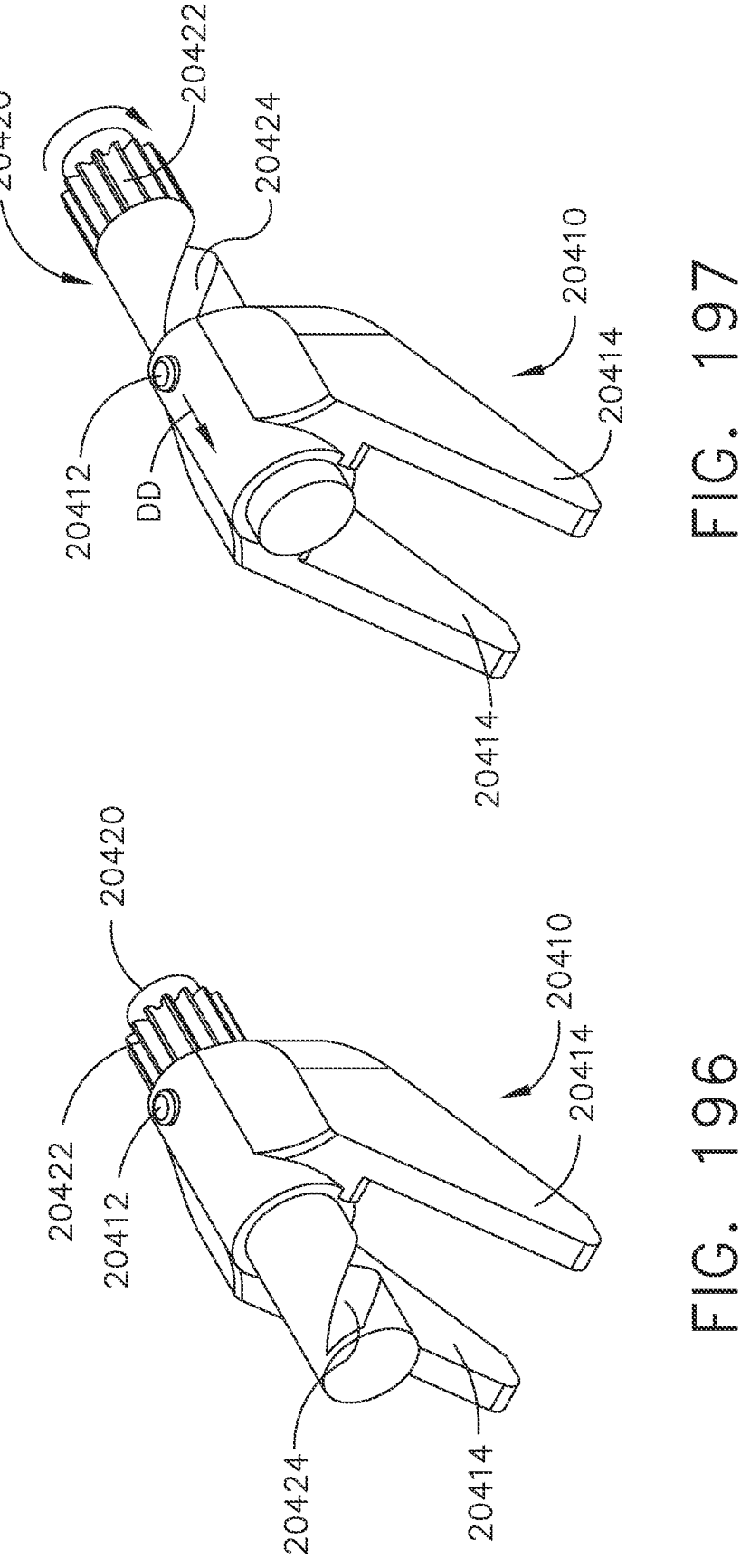
Figure 198:
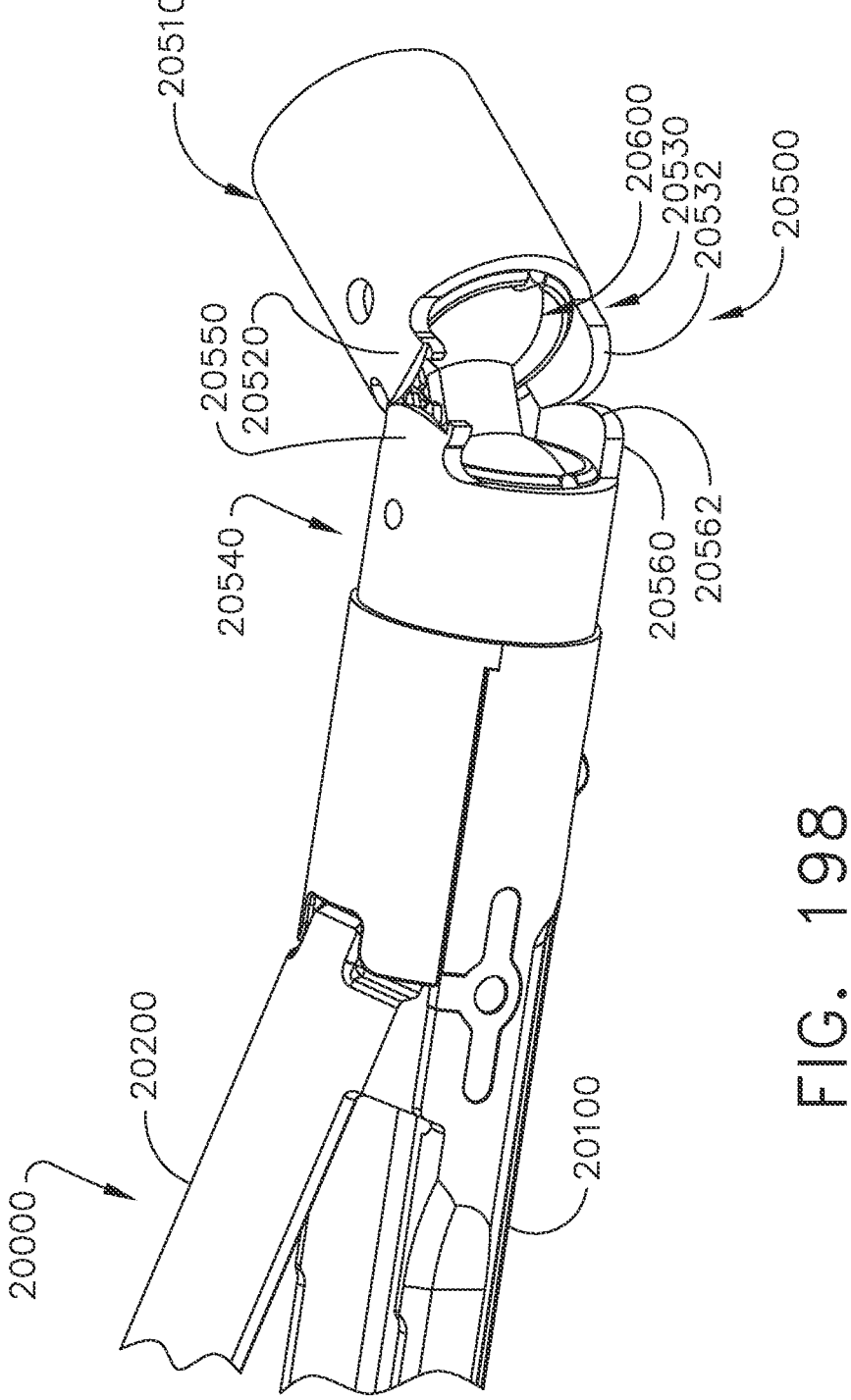
Figure 199:
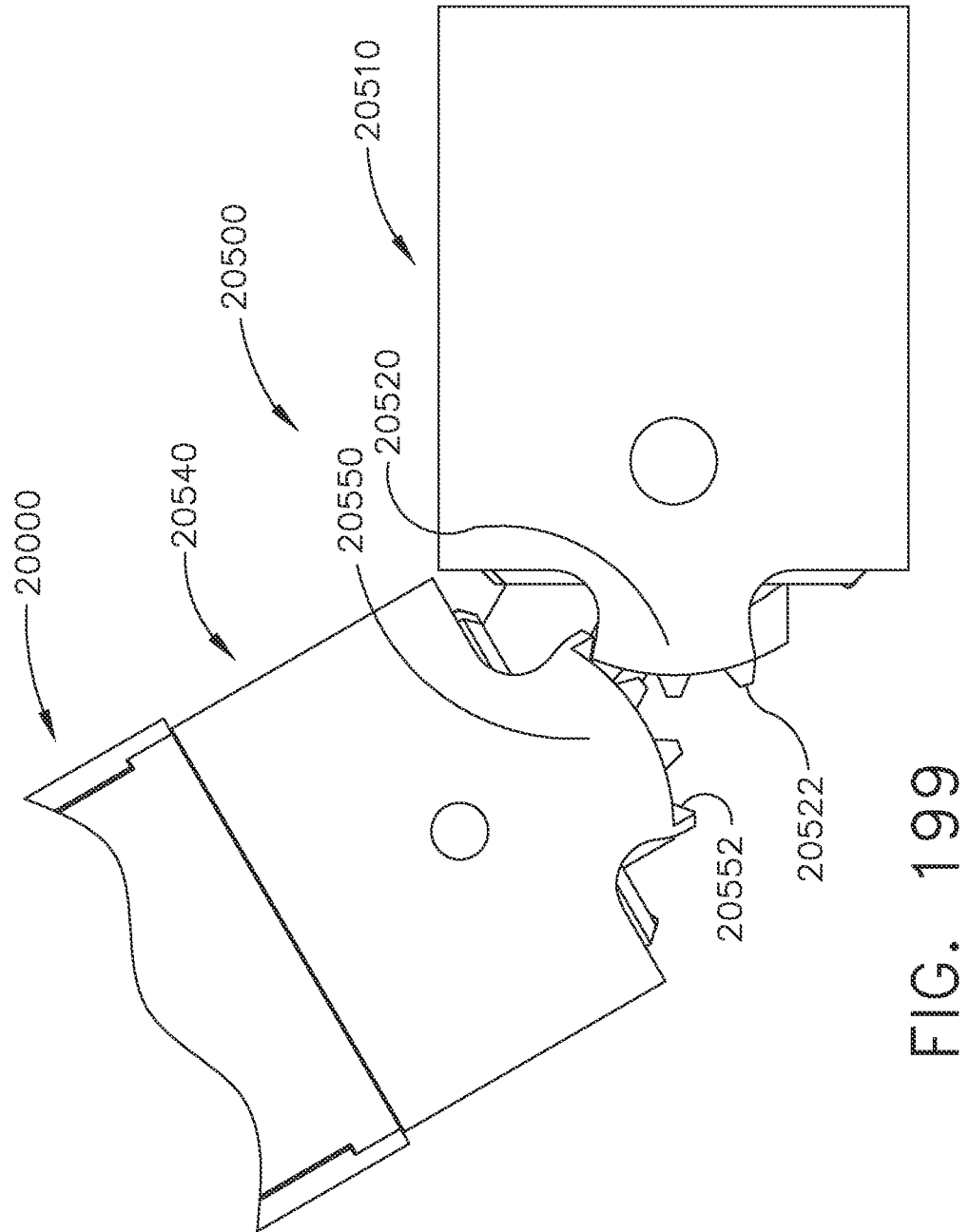
Figure 200:
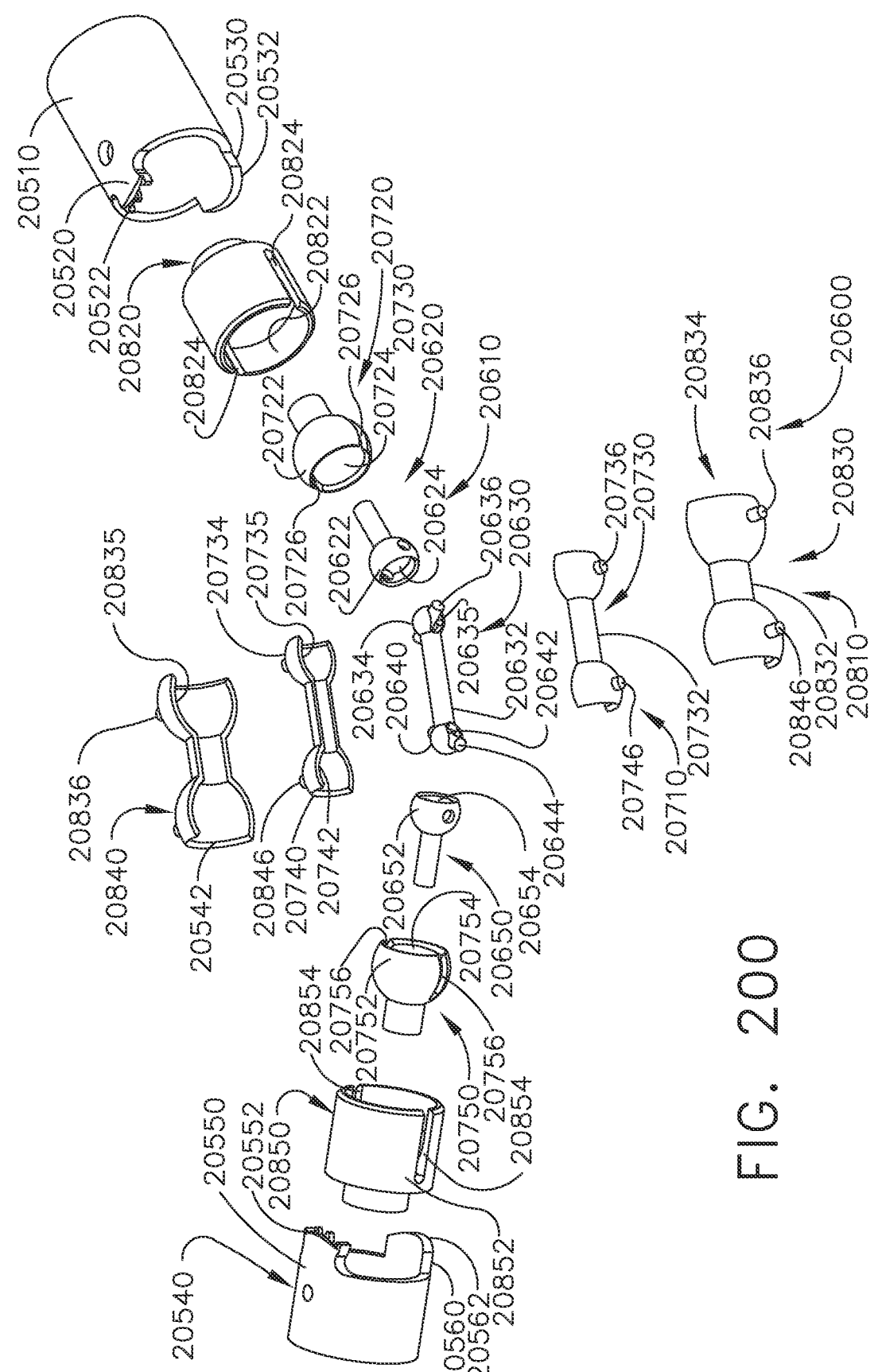
Figure 201:
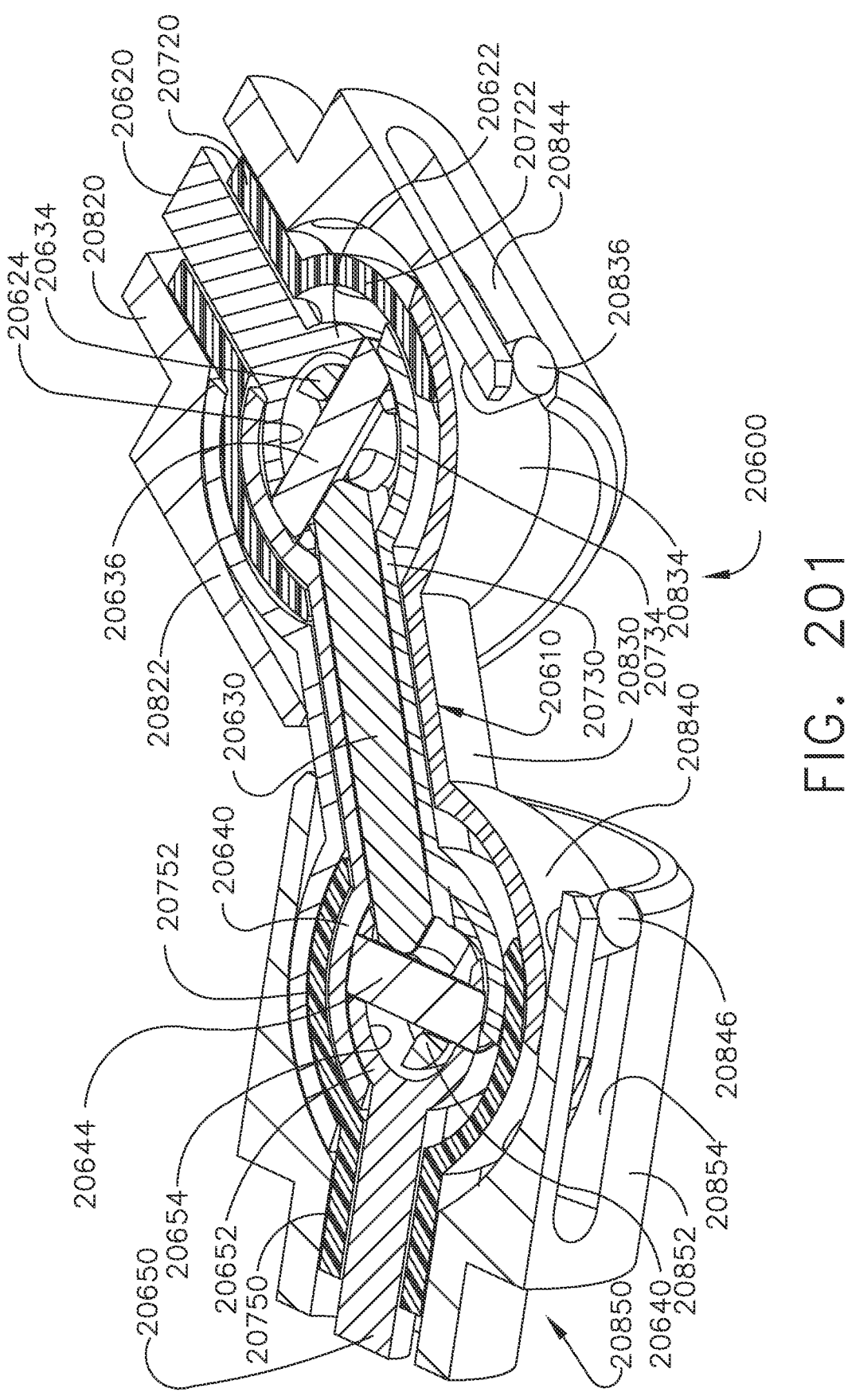
Figure 202:
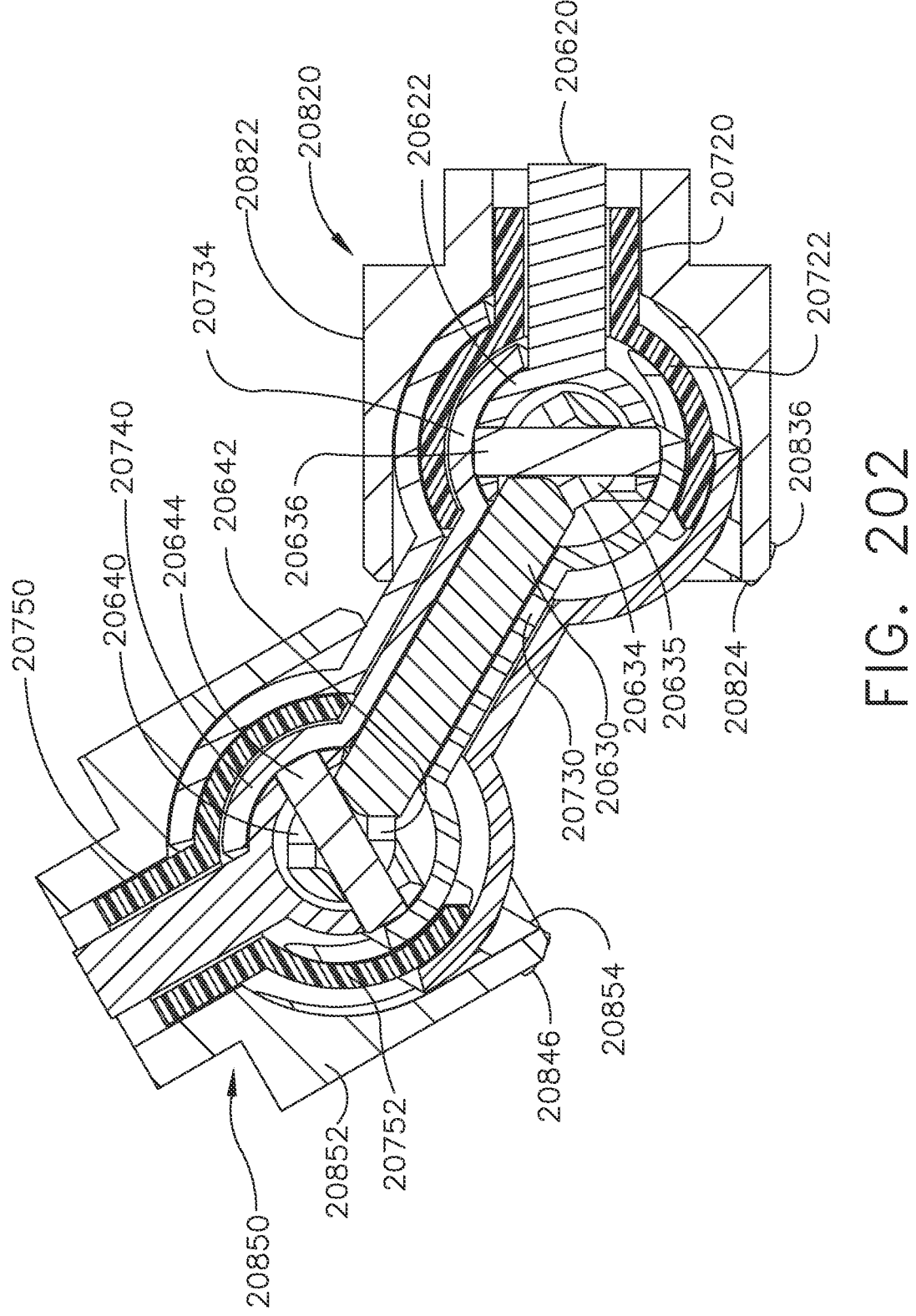
Figure 203:
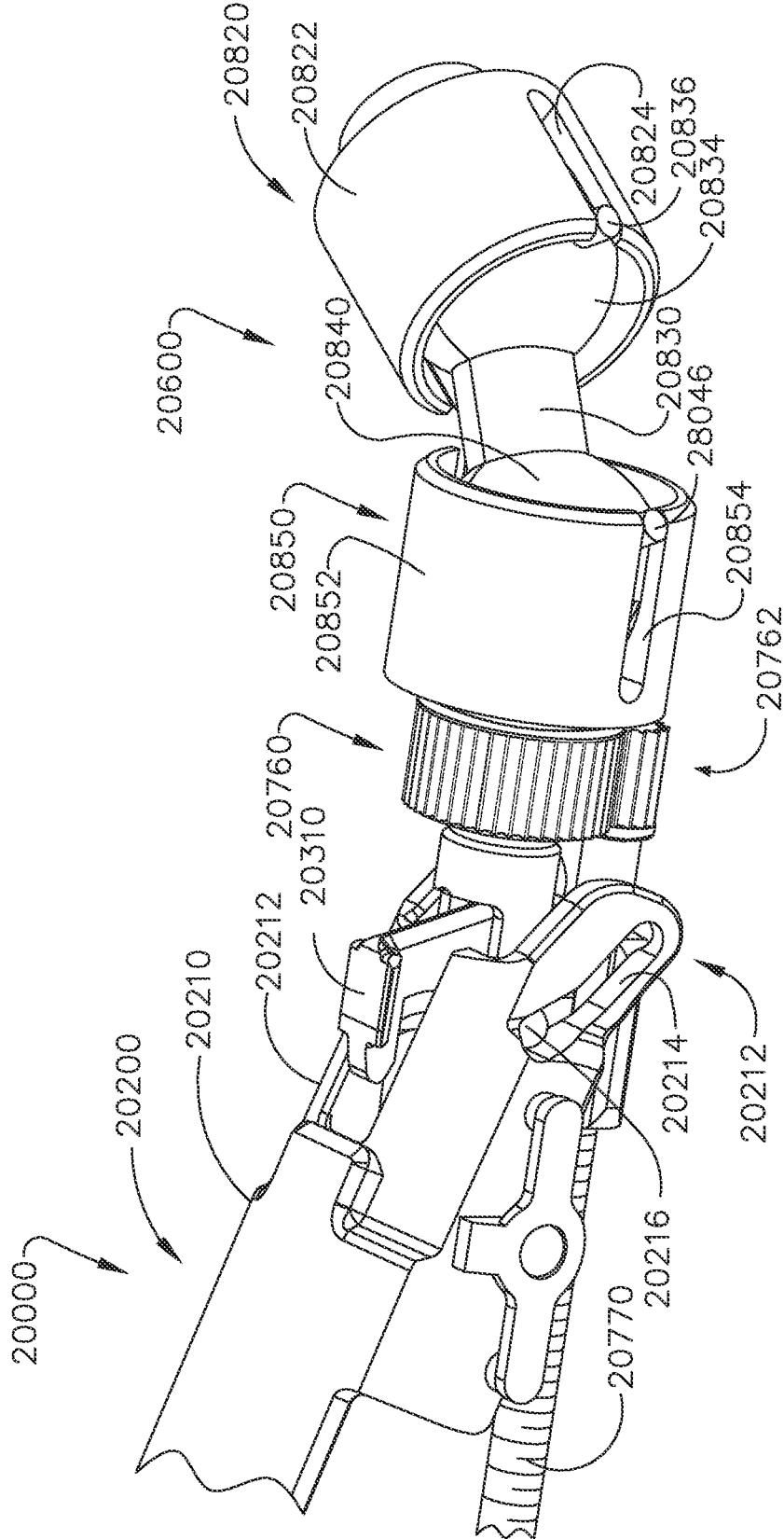
Figure 204:
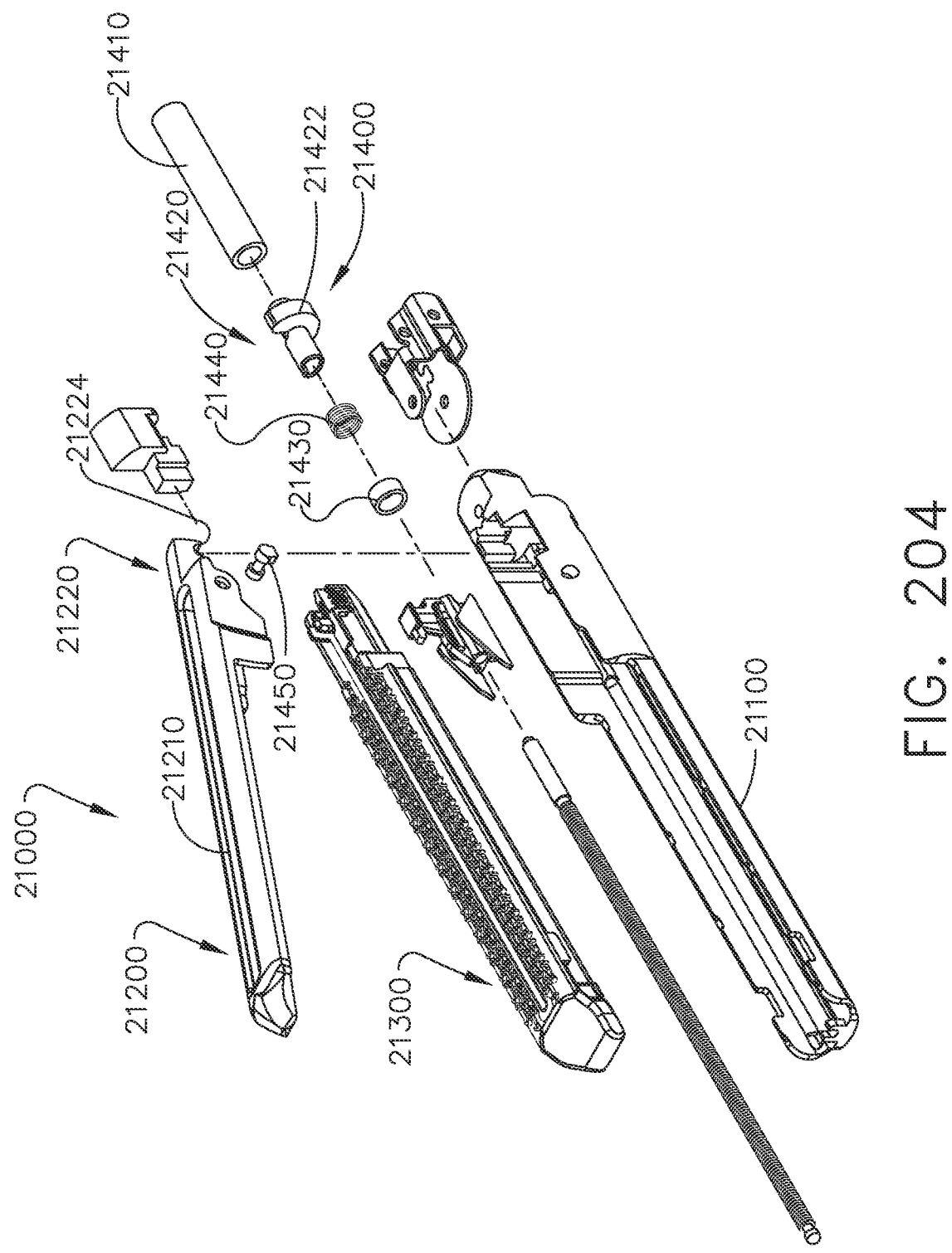
Figure 205:
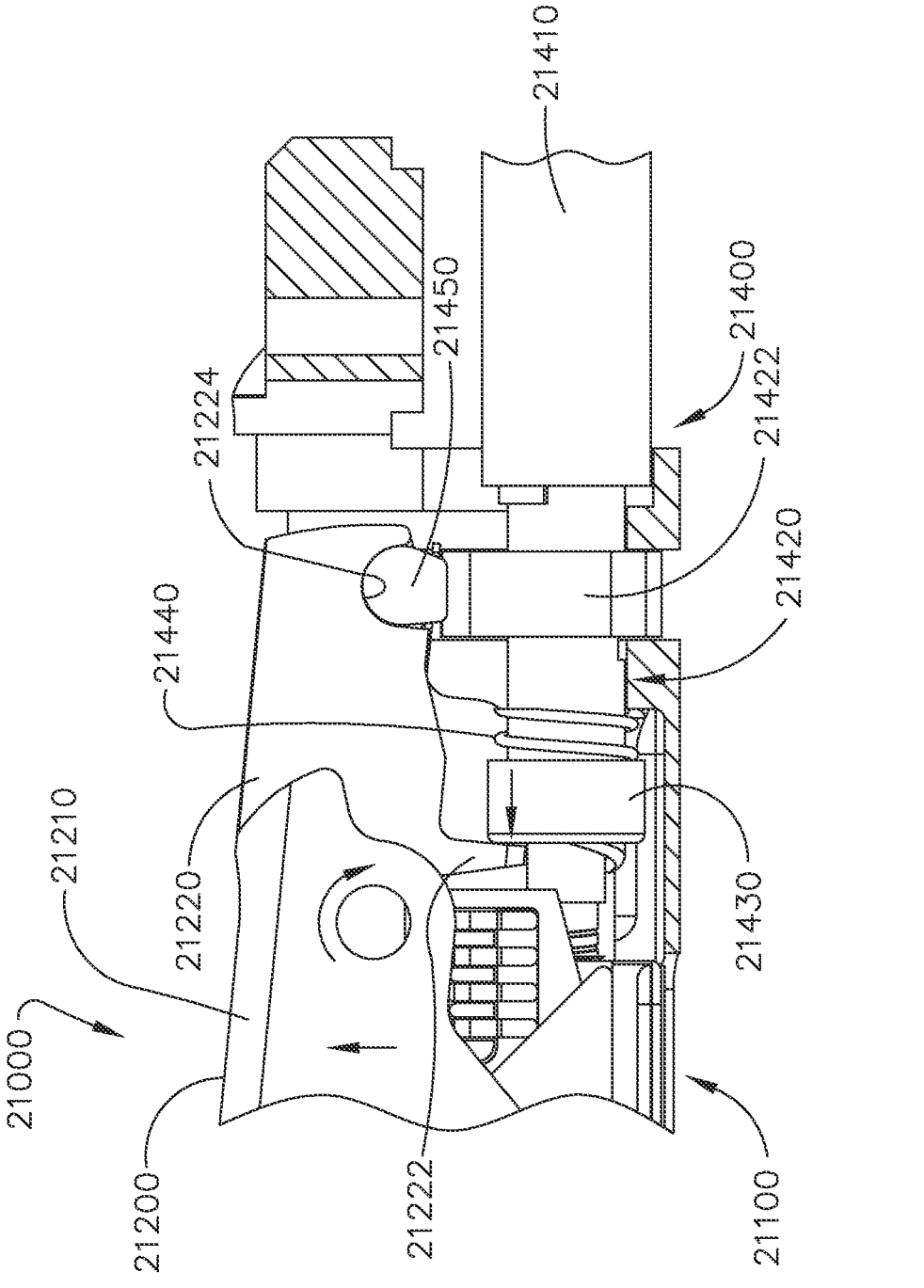
Figure 206:
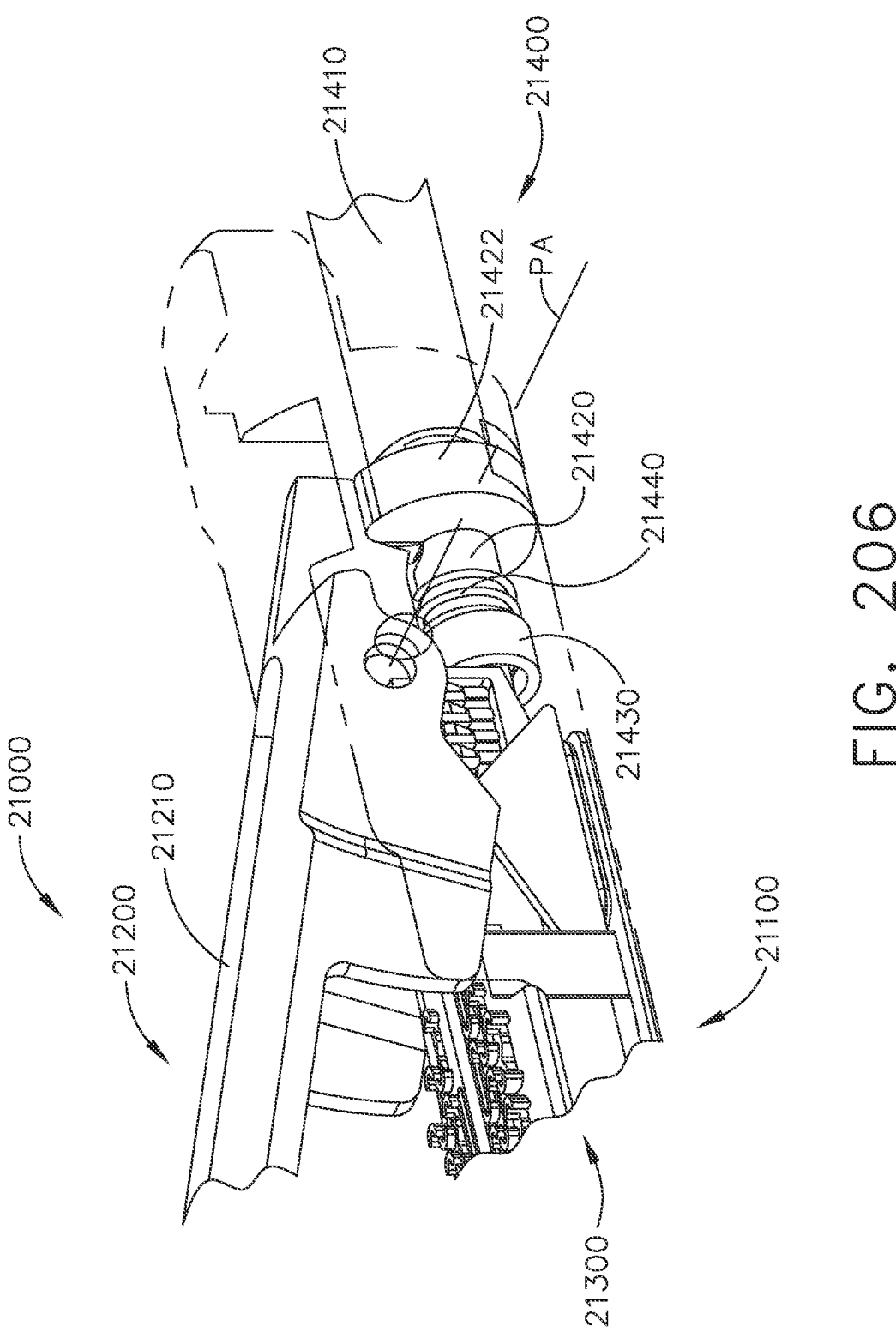
Figures 207, 208, 209:
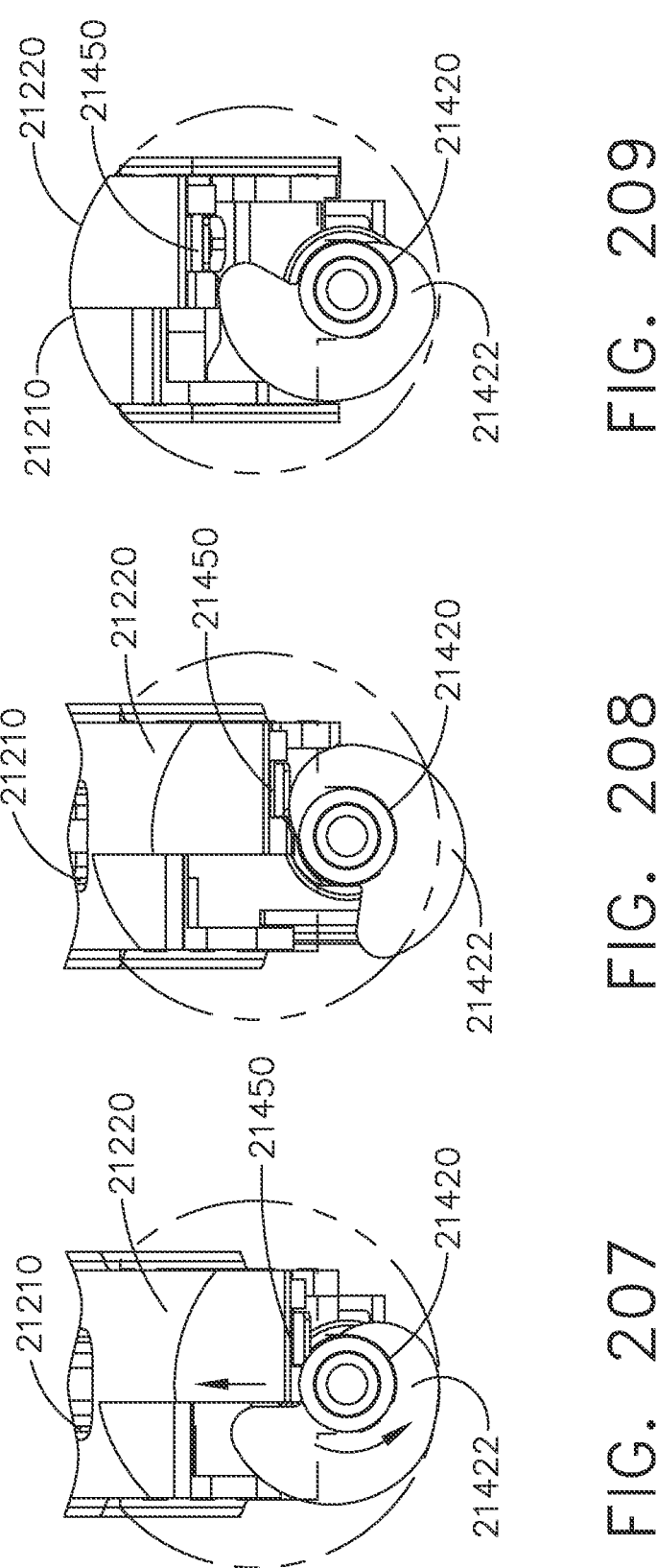
Figure 210:
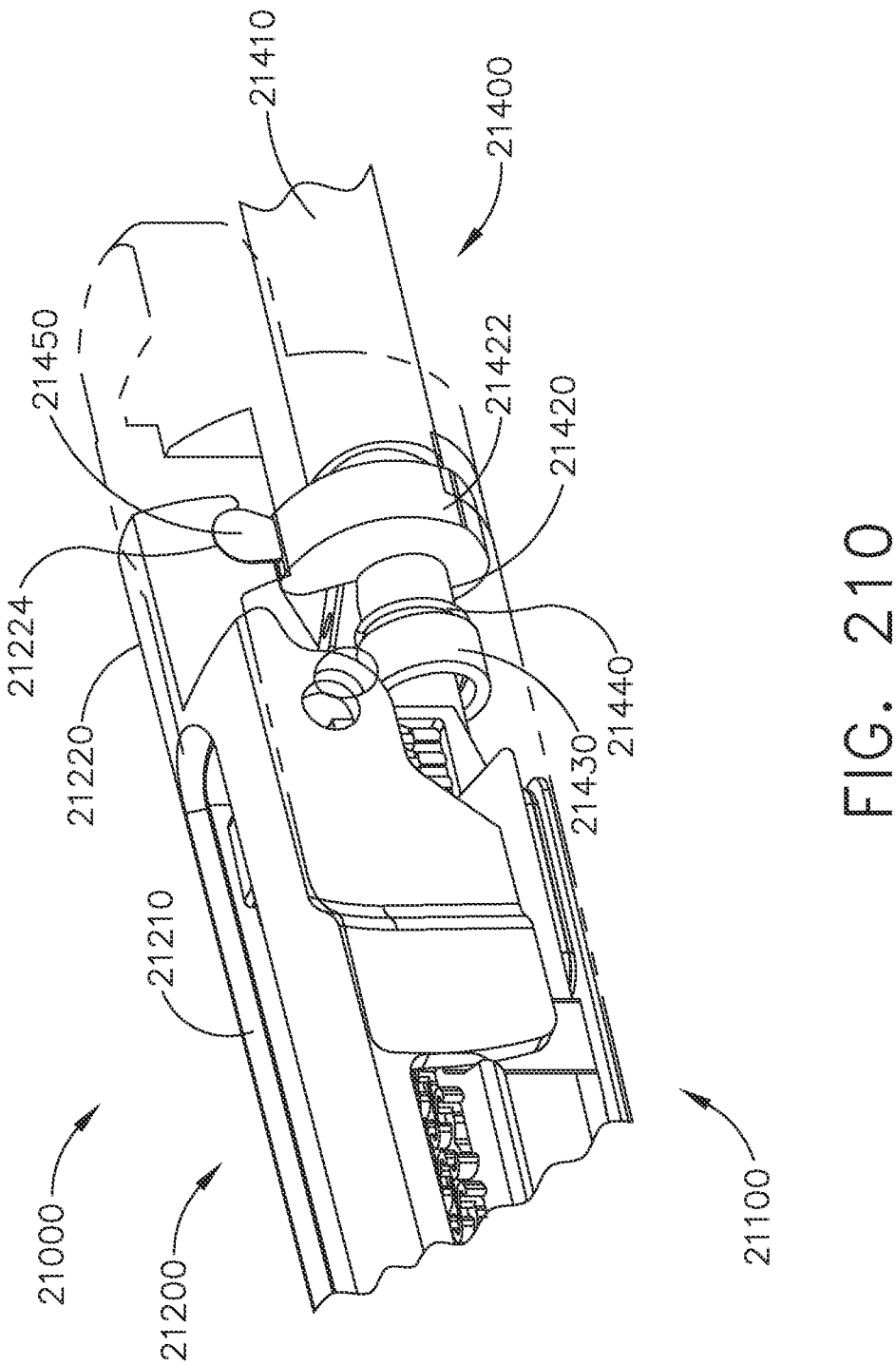
Figure 211:
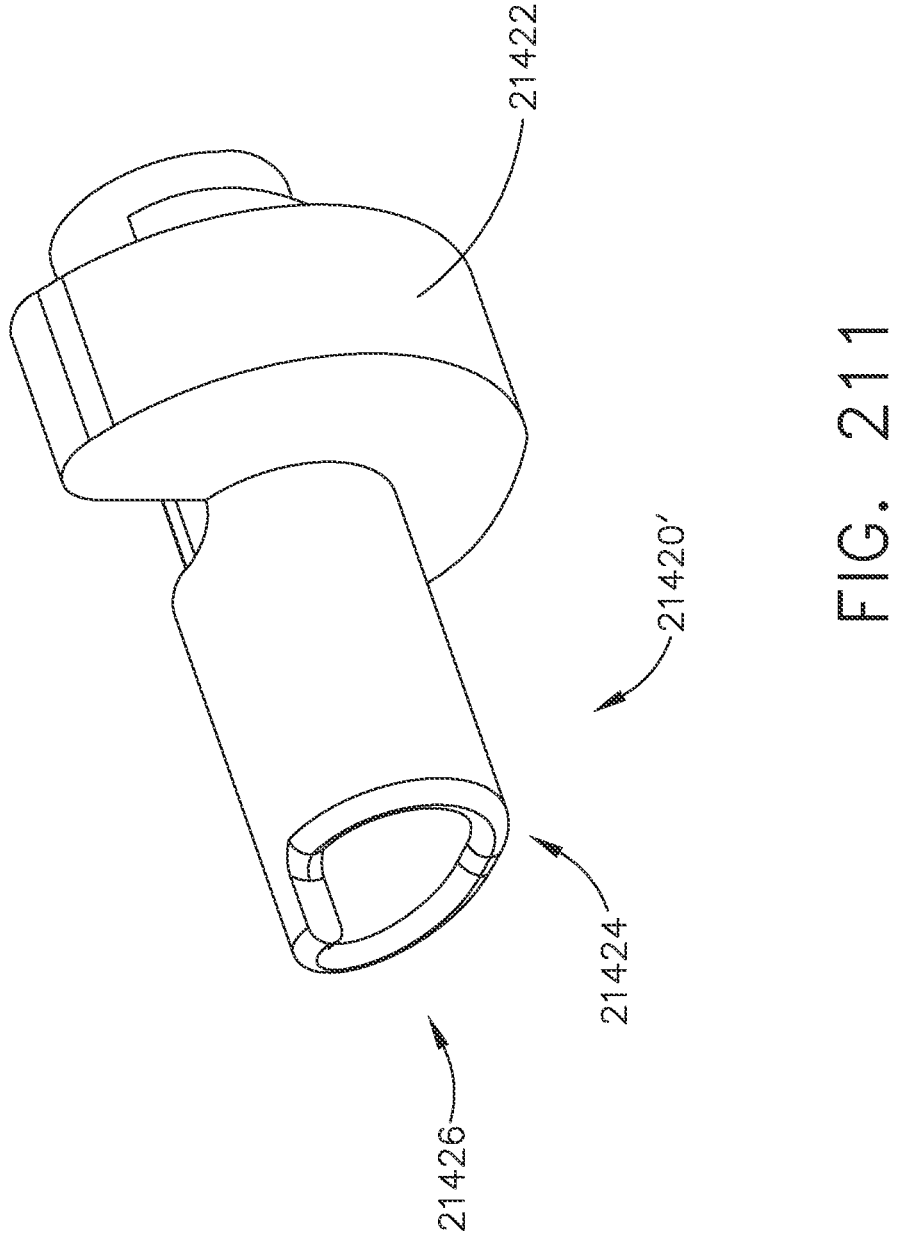

FIG. 131 is another perspective view of the pulley unit of FIG. 126 and a series of elastomeric annular spacer members of the articulation joint of the surgical instrument of FIG. 115;

FIG. 132 is another perspective view of the pulley unit, portions of a firing system and the articulation joint of the surgical instrument of FIG. 115;

FIG. 133 is a perspective view of a portion of a firing system of the surgical instrument of FIG. 115;

FIG. 134 is a partial cross-sectional view of the firing system of FIG. 133;

FIG. 135 is a perspective view of the firing system, articulation joint, and a closure system of the surgical instrument of FIG. 115;

FIG. 136 is a partial cross sectional view of the surgical instrument of FIG. 115 with the surgical end effector thereof in an unarticulated position;

FIG. 137 is a partial view of a differential drive assembly embodiment of the firing system of the surgical instrument of FIG. 115;

FIG. 138 is another partial cross sectional view of the surgical instrument of FIG. 115 with the surgical end effector thereof in an articulated position;

FIG. 139 is another partial cross sectional view of the surgical instrument of FIG. 115 with the surgical end effector thereof in an articulated position;

FIG. 140 is a perspective of a portion of another surgical instrument embodiment;

FIG. 141 is a perspective view of an articulation joint of the surgical instrument of FIG. 140 in an unarticulated orientation;

FIG. 142 is another perspective view of the articulation joint of FIG. 141 in another articulated orientation;

FIG. 143 is an exploded perspective view of the articulation joint of FIG. 141;

FIG. 144 is a top view of the articulation joint of FIG. 141;

FIG. 145 is a cross-sectional view of the articulation joint of FIG. 144 taken along line 145-145 in FIG. 144;

FIG. 146 is a side elevational view of the articulation joint of FIG. 144;

FIG. 147 is another side elevation al view of the articulation joint of FIG. 146 in an articulated orientation;

FIG. 148 is a perspective view of the articulation join of FIG. 141 in another articulated orientation;

FIG. 149 is another perspective view of the articulation join of FIG. 141 in another articulated orientation;

FIG. 150 is an end view of the proximal joint member of the articulation joint of FIG. 141;

FIG. 151 is an end view of the distal joint member of the articulation joint of FIG. 141;

FIG. 152 is a perspective view of a proximal cross pin assembly of the articulation joint of FIG. 141;

FIG. 153 is a perspective view of another articulation joint embodiment;

FIG. 154 is a perspective view of an articulation joint portion of another surgical instrument embodiment;

FIG. 155 is another perspective view of the articulation joint arrangement of FIG. 154 with an outer shaft tube omitted for clarity;

FIG. 156 is an exploded perspective assembly view of the articulation joint arrangement and firing drive system of the surgical instrument of FIG. 154;

FIG. 157 is a perspective view of the articulation joint and firing system arrangement of FIG. 156 with an outer shaft tube omitted for clarity and wherein a firing member is in a starting position;

FIG. 158 is another perspective view of the articulation joint and firing system of FIG. 157 after the firing member has been advanced to a distal position;

FIG. 159 is a partial cross-sectional view of a portion of the firing system of the surgical instrument of FIG. 154;

FIG. 160 is a partial view of a proximal differential drive assembly of the surgical instrument embodiment of FIG. 154;

FIG. 161 is a cross sectional end view through the proximal differential drive assembly of FIG. 160;

FIG. 162 is a side elevational view of the articulation joint and distal differential drive assembly of the surgical instrument of FIG. 154;

FIG. 163 is another side elevational view of the articulation joint and distal differential drive assembly of FIG. 162 in an articulated orientation;

FIG. 164 is a partial graphical depiction of reactive forces acting on push coils of the surgical instrument of FIG. 154 when the articulation joint thereof is in an articulated orientation and the firing member is being distally advanced;

FIG. 165 is another partial graphical depiction of reactive forces acting on flexible outer tubes of the surgical instrument of FIG. 154 when the articulation joint thereof is in an articulated orientation;

FIG. 166 is a perspective view of a central link member and flexible joint support assembly of the surgical instrument of FIG. 154;

FIG. 167 is a side elevational view of the articulation joint of the surgical instrument of FIG. 154 in an unarticulated orientation;

FIG. 168 is a cross-sectional view of the articulation joint of FIG. 167 taken along line 168-168 in FIG. 167;

FIG. 169 is a partial perspective view of the articulation joint of the surgical instrument of FIG. 154 in an articulated orientation with the flexible joint support assembly omitted for clarity;

FIG. 170 is a perspective view of another articulation joint embodiment for a surgical instrument;

FIG. 171 is a side view of the articulation joint of FIG. 170 in an unarticulated orientation;

FIG. 172 is another side view of the articulation joint of FIG. 170 partially articulated in a first articulation direction;

FIG. 173 is another side view of the articulation joint of FIG. 170 fully articulated in the first articulation direction;

FIG. 174 is another side view of the articulation joint of FIG. 170 illustrating virtual pivot points and a position of a first pair of links when the articulation joint is in an unarticulated orientation;

FIG. 175 is another side view of the articulation joint and links of FIG. 170 partially articulated in the first articulation direction;

FIG. 176 is another side view of the articulation joint of FIG. 174 illustrating the virtual pivot points and with the links omitted for clarity;

FIG. 177 is another side view of the articulation joint of FIG. 174 partially articulated in a first articulation direction;

FIG. 178 is a perspective view of another articulation joint embodiment for a surgical instrument;

FIG. 179 is an exploded assembly view of the articulation joint of FIG. 178;

FIG. 180 is a perspective view of the articulation joint of FIG. 178 illustrating cable control paths;

FIG. 181 is a perspective view of another articulation joint embodiment for a surgical instrument with the joint in an unarticulated orientation;

FIG. 182 is another perspective view of the articulation joint of FIG. 181 in an articulated orientation;

FIG. 183 is an exploded assembly view of the articulation joint of FIG. 181;

FIG. 184 is an end view of a proximal joint member of the articulation joint of FIG. 181;

FIG. 185 is an end view of a distal joint member of the articulation joint of FIG. 181;

FIG. 186 is a cross-sectional view of the proximal joint member of FIG. 184 and a portion of a first link of the articulation joint in a first position;

FIG. 187 is another cross-sectional view of the proximal joint member of FIG. 184 with the first link in another position;

FIG. 188 is another cross-sectional view of the proximal joint member and the first link of FIG. 186;

FIG. 189 is another cross-sectional view of the proximal joint member and first link of FIG. 187;

FIG. 190 is another perspective view of the articulation joint of FIG. 181 depicting virtual spheres for illustrating the articulation travel between a proximal portion of the articulation joint relative to a distal portion of the articulation joint;

FIG. 191 is another perspective view of the articulation joint of FIG. 190 depicting the virtual spheres in relation to the proximal joint member and distal joint member of the articulation joint of FIG. 181;

FIG. 192 is a perspective view of a portion of a surgical end effector of a surgical instrument with an anvil thereof in an open position;

FIG. 193 is another perspective view of the surgical end effector of FIG. 192 with a portion of the surgical end effector omitted to illustrate positions of various closure system components of the surgical instrument;

FIG. 194 is a cross-sectional view of the surgical end effector and closure system components of FIG. 193 with the anvil in an open position;

FIG. 195 is another cross-sectional view of the surgical end effector and closure system components of FIG. 193 with the anvil in a closed position;

FIG. 196 is a perspective view of a closure cam member in a starting position on a rotatable cam shaft corresponding to an open position of the anvil of the surgical end effector of FIG. 194;

FIG. 197 is another perspective view of the closure cam member in an ending position on the rotatable cam shaft that corresponds to the closed position of the anvil as shown in FIG. 195;

FIG. 198 is another perspective view of the surgical end effector of FIG. 192 oriented in an articulated orientation about an articulation joint that is attached thereto;

FIG. 199 is a top view of a distal joint portion of the articulation joint of FIG. 198 articulated relative to a proximal articulation joint portion of the articulation joint of FIG. 198;

FIG. 200 is an exploded assembly view of the articulation joint of FIG. 192 and a rotary drive assembly;

FIG. 201 is a cross-sectional view of the rotary drive assembly of FIG. 200;

FIG. 202 is another cross-sectional view of the rotary drive assembly of FIG. 201;

FIG. 203 is another perspective view of the surgical end effector and articulation joint of FIG. 198 with portions thereof omitted for clarity;

FIG. 204 is an exploded assembly view of another surgical end effector and rotary driven closure system;

FIG. 205 is a partial side view of a portion of the surgical end effector and rotary drive closure system of FIG. 204 with the anvil in a closed orientation;

FIG. 206 is a partial perspective view of a portion of the surgical end effector and rotary drive system of FIG. 204 with the anvil in an open orientation;

FIG. 207 is a partial end view of a portion of a rotary cam shaft and cam follower of the rotary drive system of FIG. 204 in a position when the anvil is in the open position;

FIG. 208 is another partial end view of the rotary cam shaft and cam follower of FIG. 207 after the closure process has started;

FIG. 209 is another partial end view of the rotary cam shaft and cam follower of FIG. 207 after a cam lobe on the rotary cam shaft has cammed the cam follower into a position wherein the anvil is pivoted to an open position;

FIG. 210 is another perspective view of a portion of the surgical end effector and rotary drive system of FIG. 204 with the anvil in a closed position;

FIG. 211 is a perspective view of another rotary cam shaft; and

Figure 212:
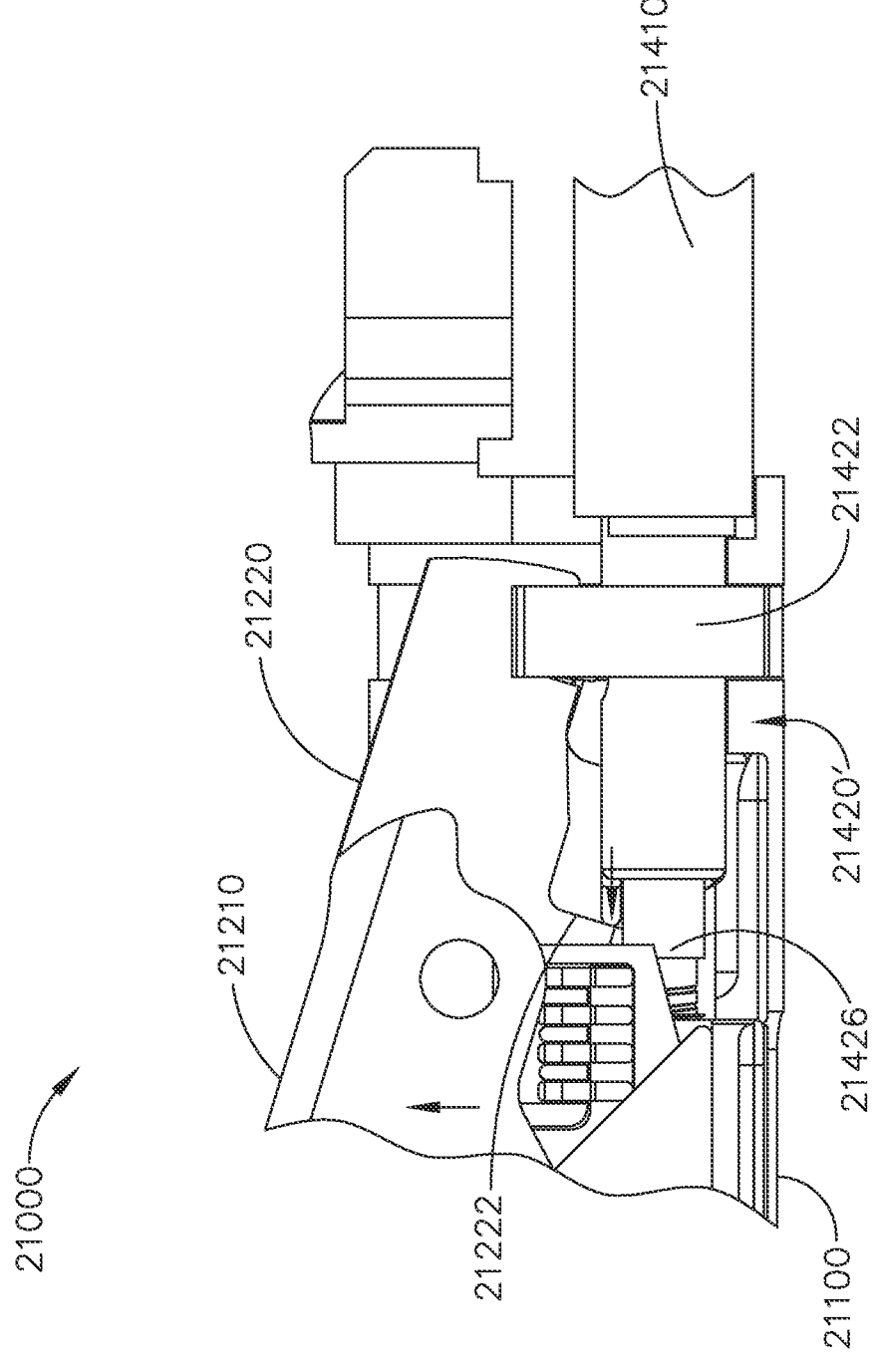

FIG. 212 is a partial side elevational view of a portion of the surgical end effector and rotary drive system of FIG. 204 employing the rotary cam shaft of FIG. 211 and with the anvil in an open position.

DETAILED DESCRIPTION

Applicant of the present application owns the following U.S. patent applications that were filed on Jun. 28, 2021 even date herewith and which are each herein incorporated by reference in their respective entireties:

U.S. patent application Ser. No. 17/360,133, entitled SURGICAL INSTRUMENTS WITH TORSION SPINE DRIVE ARRANGEMENTS, now U.S. Patent Application Publication No. 2022-0031313;

U.S. patent application Ser. No. 17/360,139, entitled SURGICAL INSTRUMENTS WITH FIRING MEMBER CLOSURE FEATURES, now U.S. Patent Application Publication No. 2022-0031322;

U.S. patent application Ser. No. 17/360,149, entitled SURGICAL INSTRUMENTS WITH SEGMENTED FLEXIBLE DRIVE ARRANGEMENTS, now U.S. Patent Application Publication No. 2022-0031314;

U.S. patent application Ser. No. 17/360,162, entitled SURGICAL INSTRUMENTS WITH FLEXIBLE BALL CHAIN DRIVE ARRANGEMENTS, now U.S. Patent Application Publication No. 2022-0031319;

U.S. patent application Ser. No. 17/360,176, entitled SURGICAL INSTRUMENTS WITH DOUBLE SPHERICAL ARTICULATION JOINTS WITH PIVOTABLE LINKS, now U.S. Patent Application Publication No. 2022-0031345;

U.S. patent application Ser. No. 17/360,192 entitled SURGICAL INSTRUMENTS WITH DOUBLE PIVOT ARTICULATION JOINT ARRANGEMENTS, now U.S. Patent Application Publication No. 2022-0031350;

U.S. patent application Ser. No. 17/360,197, entitled SURGICAL INSTRUMENTS WITH COMBINATION FUNCTION ARTICULATION JOINT ARRANGEMENTS, now U.S. Patent Application Publication No. 2022-0031323;

U.S. patent application Ser. No. 17/360,211, entitled SURGICAL INSTRUMENTS WITH DUAL SPHERICAL ARTICULATION JOINT ARRANGEMENTS, now U.S. Patent Application Publication No. 2022-0031324;

U.S. patent application Ser. No. 17/360,220, entitled SURGICAL INSTRUMENTS WITH FLEXIBLE FIRING MEMBER ACTUATOR CONSTRAINT ARRANGEMENTS, now U.S. Patent Application Publication No. 2022-0031320;

U.S. patent application Ser. No. 17/360,244, entitled ARTICULATABLE SURGICAL INSTRUMENTS WITH ARTICULATION JOINTS COMPRISING FLEXIBLE EXOSKELETON ARRANGEMENTS, now U.S. Patent Application Publication No. 2022-0031346; and U.S. patent application Ser. No. 17/360,249, entitled SURGICAL INSTRUMENTS WITH DIFFERENTIAL ARTICULATION JOINT ARRANGEMENTS FOR ACCOMMODATING FLEXIBLE ACTUATORS, now U.S. Patent Application Publication No. 2022-0031351.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

A variety of surgical end effectors exist that are configured to cut and staple tissue. Such surgical end effectors commonly include a first jaw feature that supports a surgical staple cartridge and a second jaw that comprises an anvil. The jaws are supported relative to each other such that they can move between an open position and a closed position to position and clamp target tissue therebetween. Many of these surgical end effectors employ an axially moving firing member. In some end effector designs, the firing member is configured to engage the first and second jaws such that as the firing member is initially advanced distally, the firing member moves the jaws to the closed position. Other end effector designs employ a separate closure system that is independent and distinct from the system that operates the firing member.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, in these surgical end effectors, the sled is moved distally by the firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Many surgical end effectors employ an axially movable firing beam that is attached to the firing member and is used to apply axial firing and retraction motions to the firing member. Many of such firing beams comprise a laminated construction that affords the firing beam with some degree of flexure about the articulation joint. As the firing beam traverses the articulation joint, the firing beam can apply de-articulation forces to the joint and can cause the beam to buckle. To prevent the firing beam from buckling under pressure, the articulation joint is commonly provided with lateral supports or "blow-out" plate features to support the portion of the beam that traverses the articulation joint. To advance the firing beam through an angle of greater than sixty degrees, for example, a lot of axial force is required. This axial force must be applied to the firing member in a balanced manner to avoid the firing member from binding with the jaws as the firing member moves distally. Any binding of the firing member with the jaws can lead to component damage and wear as well as require an increased amount of axial drive force to drive the firing member through the clamped tissue.

Other end effector designs employ a firing member that is rotary powered. In many of such designs, a rotary drive shaft extends through the articulation joint and interfaces with a rotatable firing member drive shaft that is rotatably supported within one of the jaws. The firing member threadably engages the rotatable firing member drive shaft and, as the rotatable firing member drive shaft is rotated, the firing member is driven through the end effector. Such arrangements require the supporting jaw to be larger to accommodate the firing member drive shaft. In such devices, a lower end of the firing member commonly operably interfaces with the drive shaft which can also result in an application of forces that tend to unbalance the firing member as it is driven distally.

FIGS. 1-4 illustrate one form of a surgical instrument 10 that may address many of the challenges facing surgical instruments with articulatable end effectors that are configured to cut and fasten tissue. In various embodiments, the surgical instrument 10 may comprise a handheld device. In other embodiments, the surgical instrument 10 may comprises an automated system sometimes referred to as a robotically-controlled system, for example. In various forms, the surgical instrument 10 comprises a surgical end effector 1000 that is operably coupled to an elongate shaft assembly 2000. The elongate shaft assembly 2000 may be operably attached to a housing 2002. In one embodiment, the housing 2002 may comprise a handle that is configured to be grasped, manipulated, and actuated by the clinician. In other embodiments, the housing 2002 may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGE-MENTS, which is incorporated by reference herein in its entirety.

In one form, the surgical end effector 1000 comprises a first jaw 1100 and a second jaw 1200. In the illustrated arrangement, the first jaw 1100 comprises an elongate channel 1110 that comprises a proximal end 1112 and a distal end 1114 and is configured to operably support a surgical staple cartridge 1300 therein. The surgical staple cartridge 1300 comprises a cartridge body 1302 that has an elongate slot 1304 therein. A plurality of surgical staples or fasteners (not shown) are stored therein on drivers (not shown) that are arranged in rows on each side of the elongate slot 1304. The drivers are each associated with corresponding staple cavities 1308 that open through a cartridge deck surface 1306. The surgical staple cartridge 1300 may be replaced after the staples/fasteners have been discharged therefrom. Other embodiments are contemplated wherein the elongate channel 1110 and/or the entire surgical end effector 1000 may is discarded after the surgical staple cartridge 1300 has been used. Such end effector arrangements may be referred to as "disposable loading units", for example.

In the illustrated arrangement, the second jaw 1200 comprises an anvil 1210 that comprises an elongate anvil body 1212 that comprises a proximal end 1214 and a distal end 1216. In one arrangement, a pair of stiffening rods or members 1213 may be supported in the anvil body 1212 to provide the anvil body 1212 with added stiffness and rigidity. The anvil body 1212 comprises a staple-forming undersurface 1218 that faces the first jaw 1100 and may include a series of staple-forming pockets (not shown) that corresponds to each of the staples or fasteners in the surgical staple cartridge 1300. The anvil body 1212 may further include a pair of downwardly extending tissue stop features 1220 that are formed adjacent the proximal end 1214 of the anvil body 1212. One tissue stop feature 1220 extends from each side of the anvil body 1212 such that a distal end 1222 on each tissue stop corresponds to the proximal-most staples/fasteners in the surgical staple cartridge 1300. When the anvil 1210 is moved to a closed position onto tissue positioned between the staple-forming undersurface 1218 of the anvil 1210 and the cartridge deck surface 1306 of the surgical staple cartridge 1300, the tissue contacts the distal ends 1222 of the tissue stop features 1220 to prevent the tissue from migrating proximally past the proximal-most staples/fasteners to thereby ensure that the tissue that is cut is also stapled. When the surgical staple cartridge is "fired" as will be discussed in further detail below, the staples/fasteners supported within each staple cavity are driven out of the staple cavity 1308 through the clamped tissue and into forming contact with the staple-forming undersurface 1218 of the anvil 1210.

Figure 1:
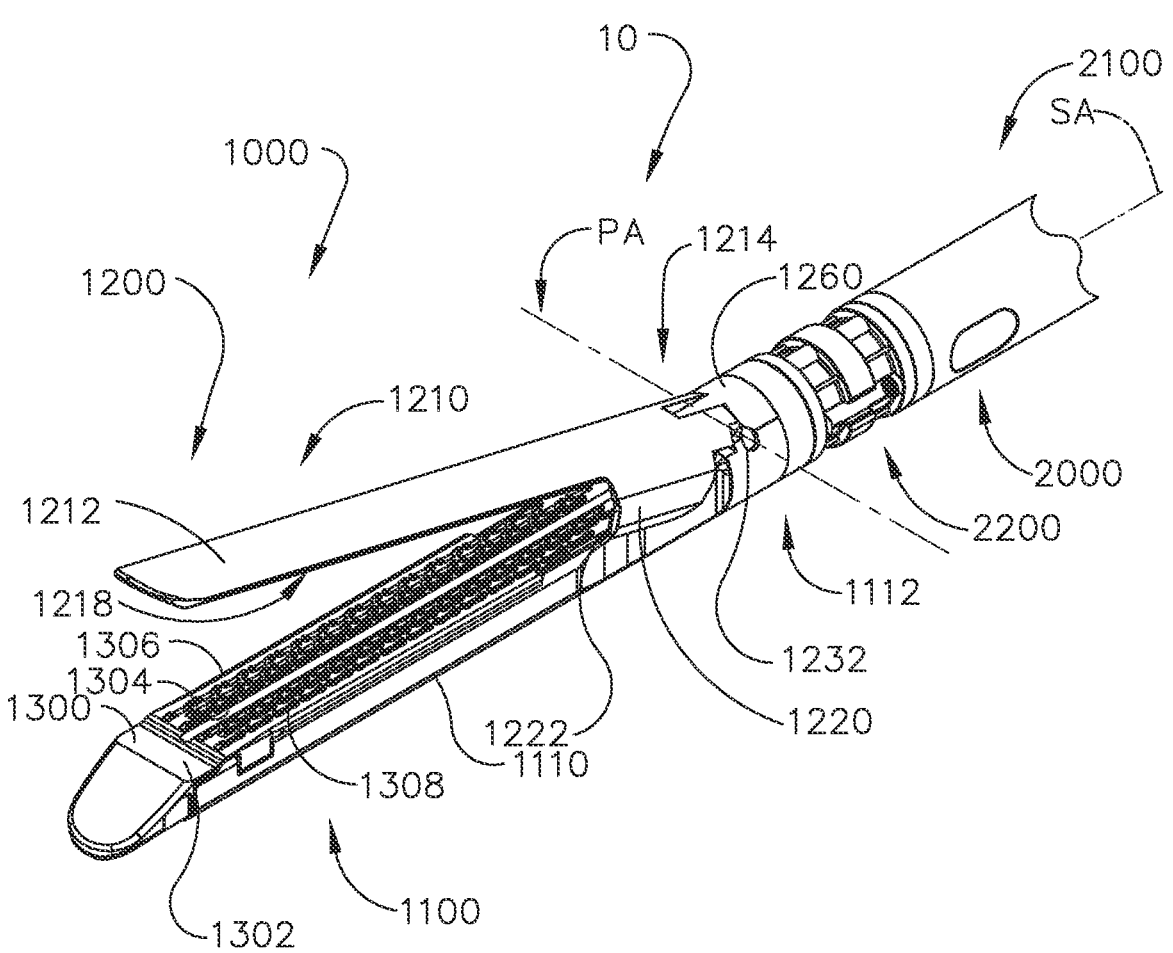
FIG. 1 is a perspective view of a surgical end effector portion of a surgical instrument in accordance with at least one aspect of the present disclosure.
Figure 2:
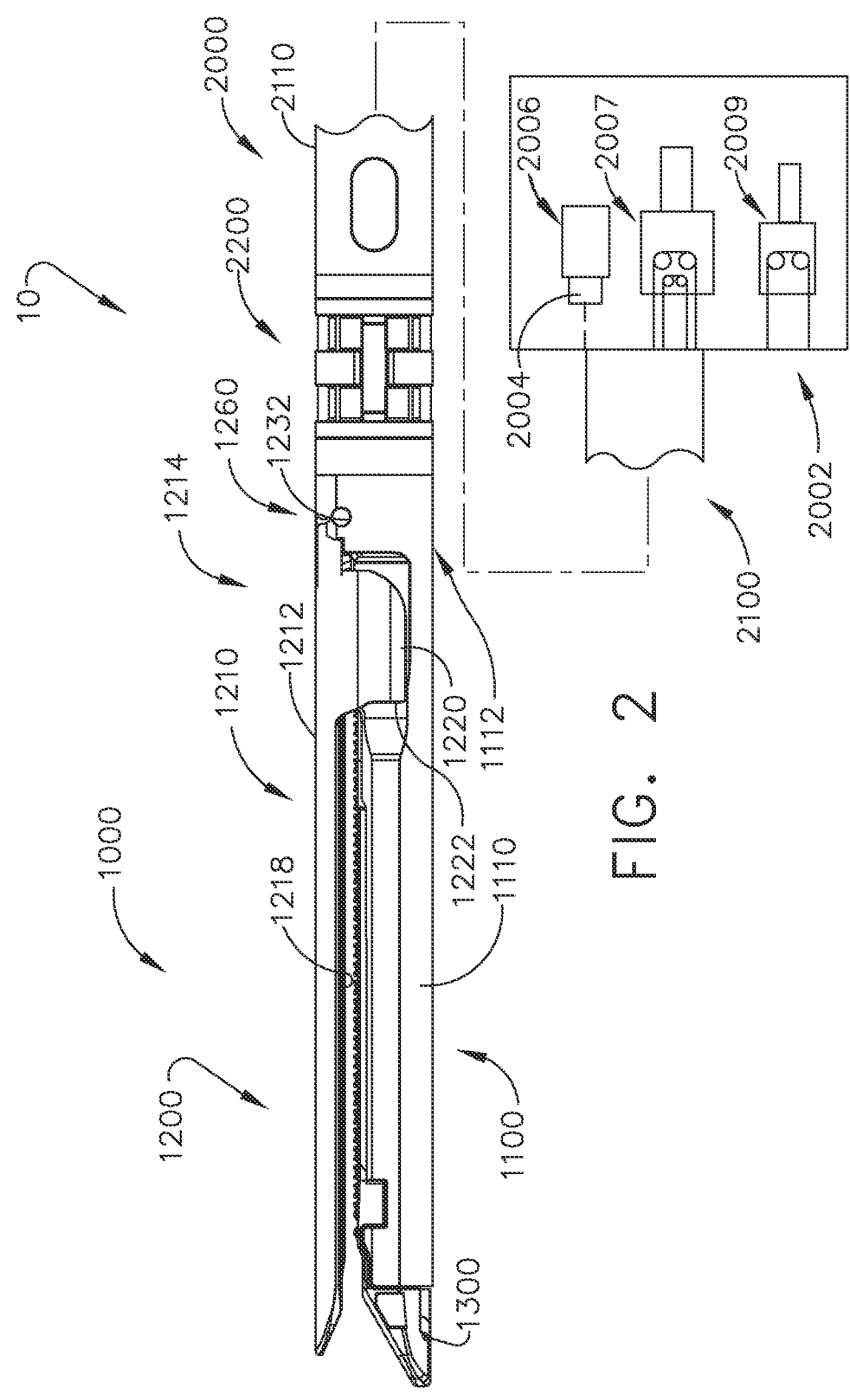
FIG. 2 is a side view of the surgical end effector portion instrument of FIG. 1 in a closed orientation.
Figure 3:
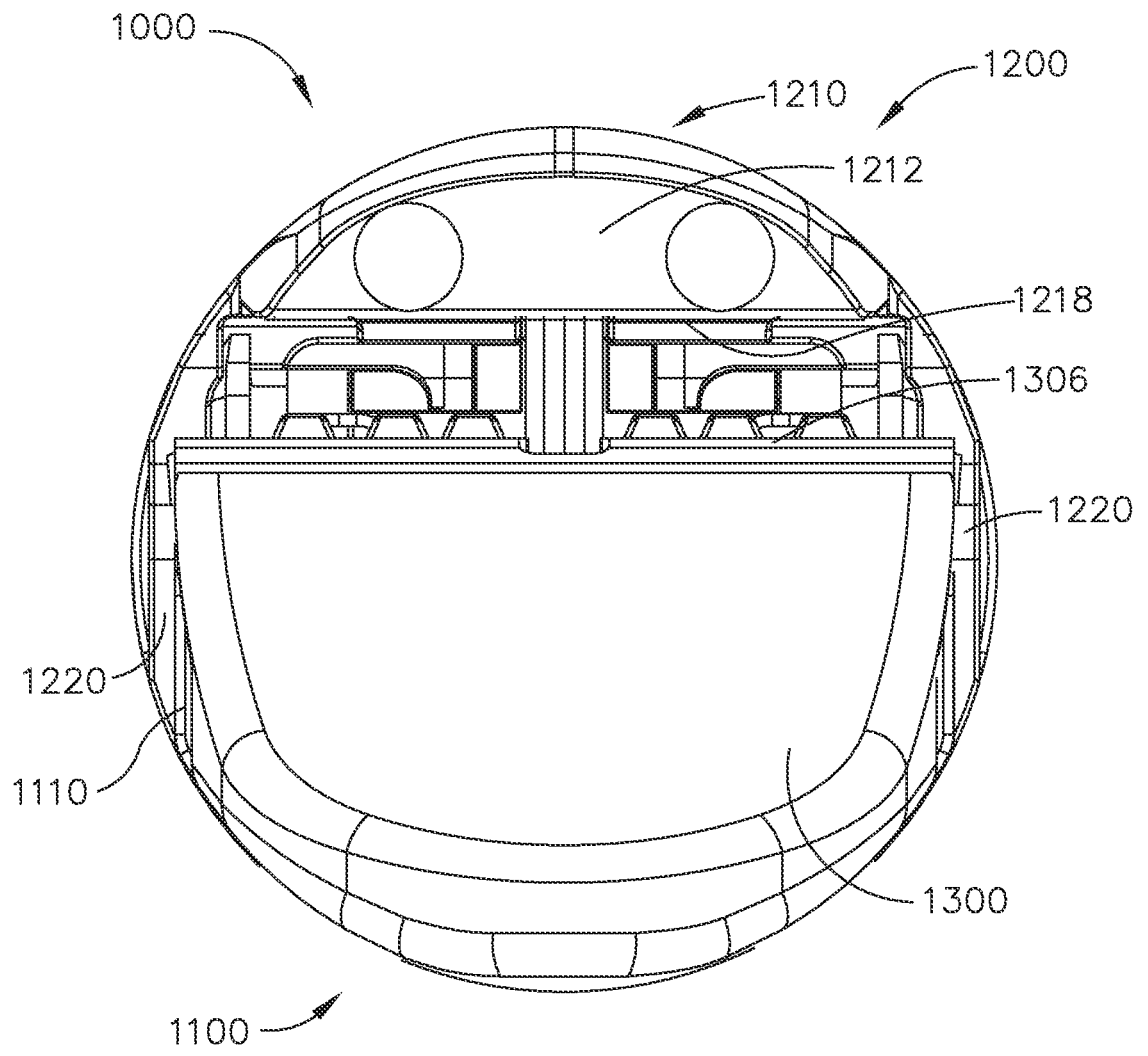
FIG. 3 is an end view of the surgical end effector of FIG. 2.
Figure 4:
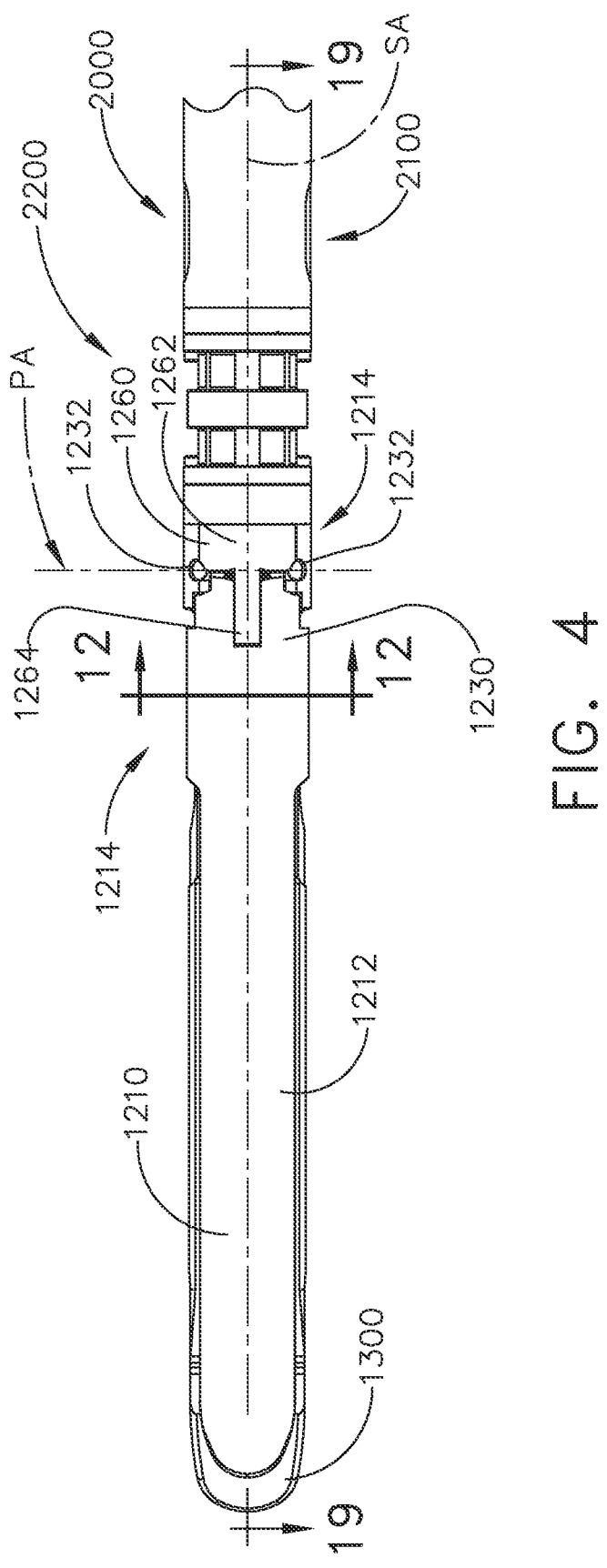
FIG. 4 is a top view of the surgical end effector of FIG. 2.
Figure 5:
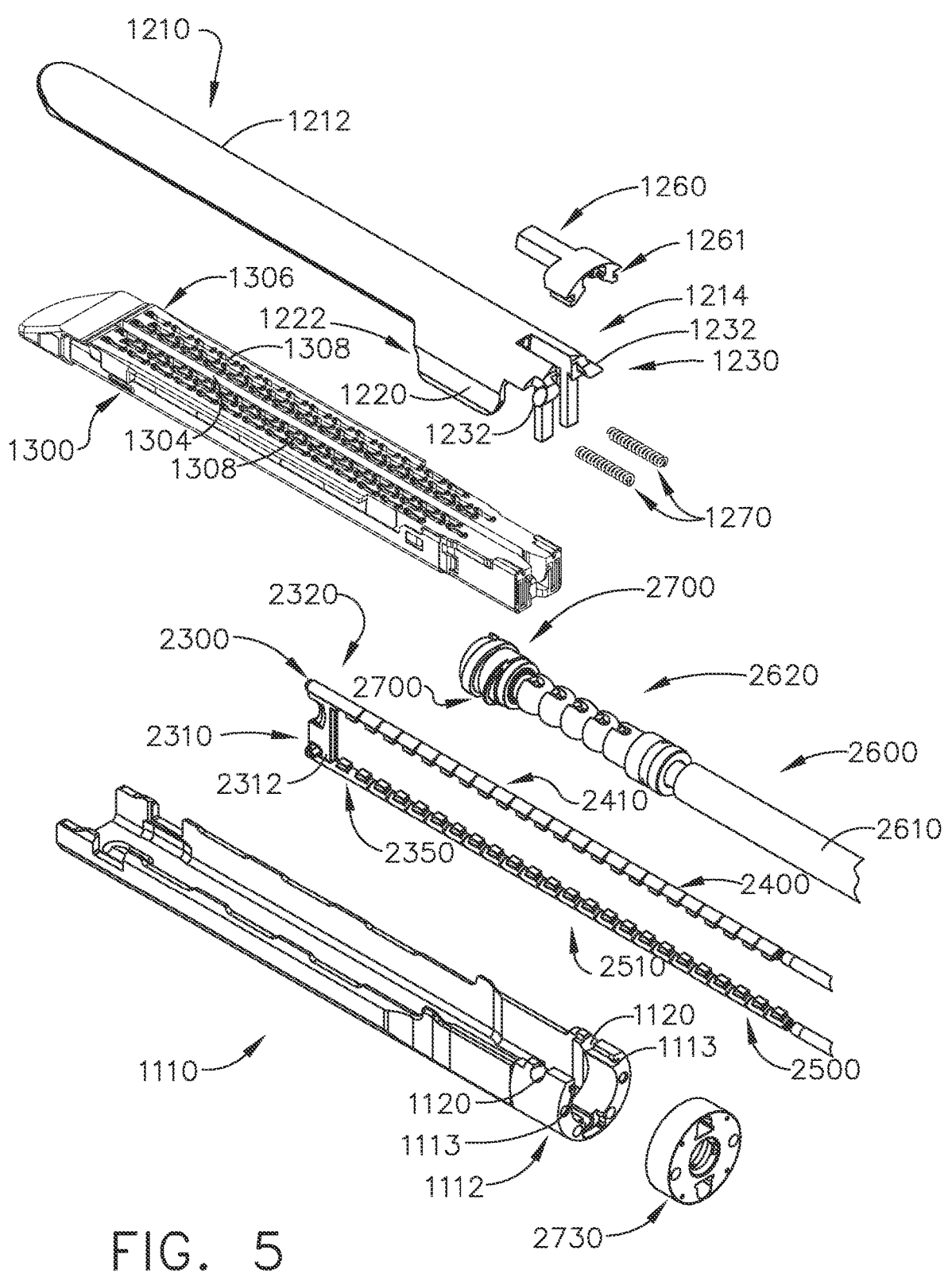
FIG. 5 is an exploded assembly view of a portion of the surgical instrument of FIG. 1.
Figure 6:
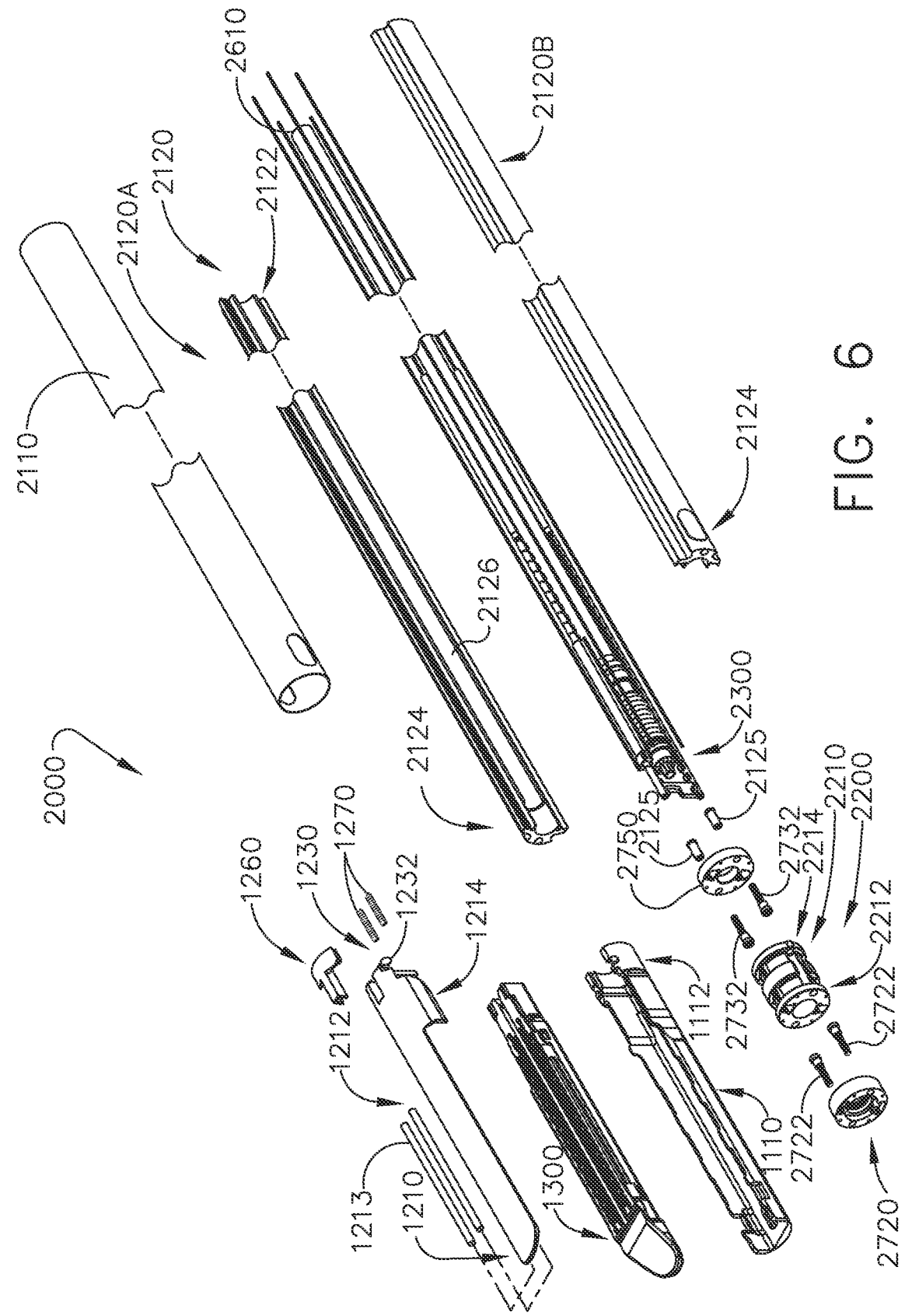
FIG. 6 is an exploded assembly view of an elongate shaft assembly of the surgical instrument of FIG. 1.

As can be seen in FIGS. 5 and 6, the proximal end 1214 of the anvil body 1212 comprises an anvil mounting portion 1230 that includes a pair of laterally extending mounting pins 1232 that are configured to be received in corresponding mounting cradles or pivot cradles 1120 formed in the proximal end 1112 of the elongate channel 1110. The mounting pins 1232 are pivotally retained within the mounting cradles 1120 by an anvil cap 1260 that may be attached to the proximal end 1112 of the elongate channel 1110 by mechanical snap features 1261 that are configured to engage retention formations 1113 on the elongate channel 1110. See FIG. 5. In other arrangements, the anvil cap 1260 may be attached to the elongate channel 1110 by welding, adhesive, etc. Such arrangement facilitates pivotal travel of the anvil 1210 relative to the surgical staple cartridge 1300 mounted in the elongate channel 1110 about a pivot axis PA between an open position (FIG. 1) and a closed position (FIGS. 2-5). Such pivot axis PA may be referred to herein as being "fixed" in that the pivot axis does not translate or otherwise move as the anvil 1200 is pivoted from an open position to a closed position.

In the illustrated arrangement, the elongate shaft assembly 2000 defines a shaft axis SA and comprises a proximal shaft portion 2100 that may operably interface with a housing of the control portion (e.g., handheld unit, robotic tool driver, etc.) of the surgical instrument 10. The elongate shaft assembly 2000 further comprises an articulation joint 2200 that is attached to the proximal shaft portion 2100 and the surgical end effector 1000. In various instances, the proximal shaft portion 2100 comprises a hollow outer tube 2110 that may be operably coupled to a housing 2002. See FIG. 2. As can be seen in FIG. 6, the proximal shaft portion 2100 may further comprise a rigid proximal support shaft 2120 that is supported within the hollow outer tube 2110 and extends from the housing to the articulation joint 2200. The proximal support shaft 2120 may comprise a first half 2120A and a second half 2120B that may be coupled together by, for example, welding, adhesive, etc. The proximal support member 2120 comprises a proximal end 2122 and a distal end 2124 and includes an axial passage 2126 that extends therethrough from the proximal end 2122 to the distal end 2124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 10 employs a firing system 2300 that may address many if not all of these issues as well as others.

As can be seen in FIGS. 5-11, in at least one embodiment, the firing system 2300 comprises a firing member 2310 that includes a vertically-extending firing member body 2312 that comprises a top firing member feature 2320 and a bottom firing member feature 2350. A tissue cutting blade 2314 is attached to or formed in the vertically-extending firing member body 2312. See FIGS. 9 and 11. In at least one arrangement, it is desirable for the firing member 2310 to pass through the anvil body 1212 with low friction, high strength and high stiffness. In the illustrated arrangement, the top firing member feature 2320 comprises a top tubular body 2322 that has a top axial passage 2324 extending therethrough. See FIG. 10. The bottom firing member feature 2350 comprises a bottom tubular body 2352 that has a bottom axial passage 2354 extending therethrough. In at least one arrangement, the top firing member feature 2320 and the bottom firing member feature 2350 are integrally formed with the vertically-extending firing member body 2312. As can be seen in FIG. 12, the anvil body 1212 comprises an axially extending anvil slot 1240 that has a cross-sectional shape that resembles a "keyhole". Similarly, the elongate channel 1110 comprises an axially extending channel slot 1140 that also has a keyhole cross-sectional shape.

Traditional firing member arrangements employ long flexible cantilever wings that extend from a top portion and a bottom portion of the firing member. These cantilever wings slidably pass through slots in the anvil and channel that are commonly cut with a rectangular t-cutter which tended to produce higher friction surfaces. Such long cantilever wings have minimum surface area contact with the anvil and channel and can result in galling of those components. The keyhole-shaped channel slot 1140 and keyhole-shaped anvil slot 1240 may be cut with a round t-cutter and may be finished with a reamer/borer which will result in the creation of a lower friction surface. In addition, the top tubular body 2322 and the bottom tubular body 2352 tend to be stiffer than the prior cantilever wing arrangements and have increased surface area contact with the anvil and channel, respectively which can reduce galling and lead to a stronger sliding connection. Stated another way, because the anvil slot 1240 and the channel slot 1140 are keyhole-shaped and have less material removed than a traditional rectangular slot, the geometry and increased material may result in a stiffer anvil and channel when compared to prior arrangements.

Figures 9, 10:
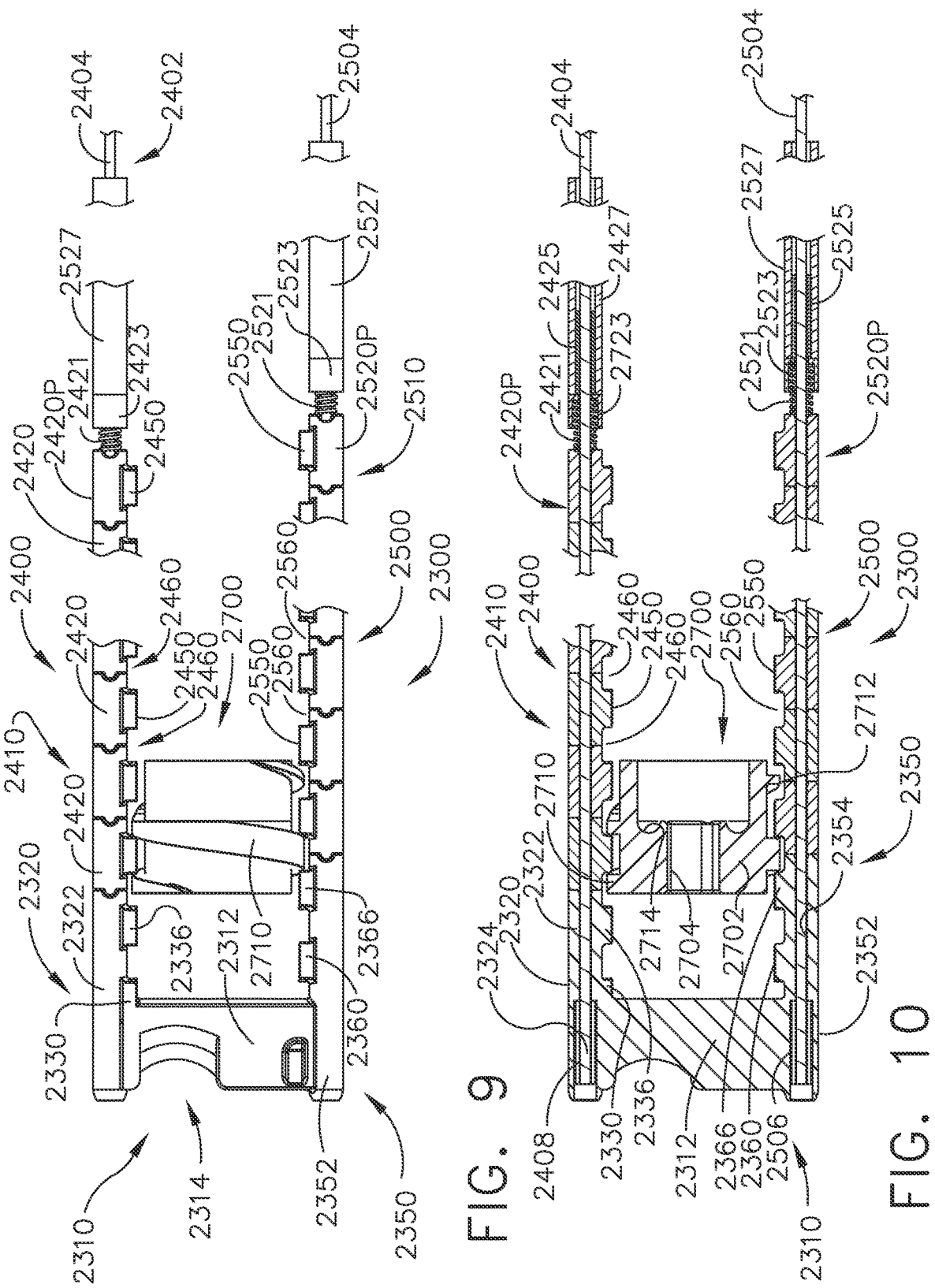
FIG. 9 is a side view of a firing member and upper and lower flexible spine assemblies of the firing system in engagement with a rotary drive screw of the rotary drive system of FIG. 8.
FIG. 10 is a cross-sectional view of the firing member and upper and lower flexible spine assemblies of FIG. 9.
Figure 11:
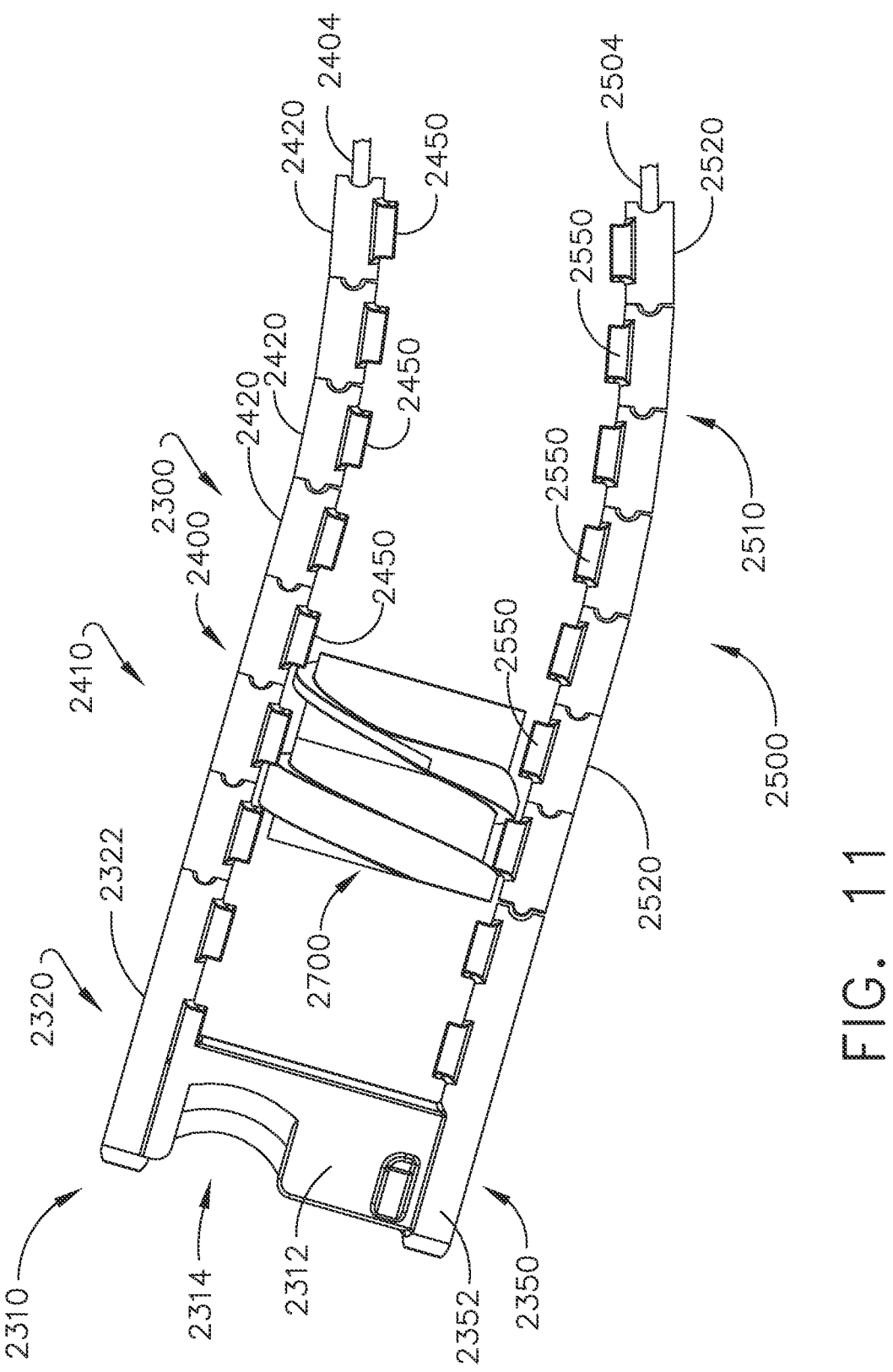
FIG. 11 is a side elevational view of the firing member and upper and lower flexible spine assemblies in engagement with the rotary drive screw of FIG. 9.
Figure 12:
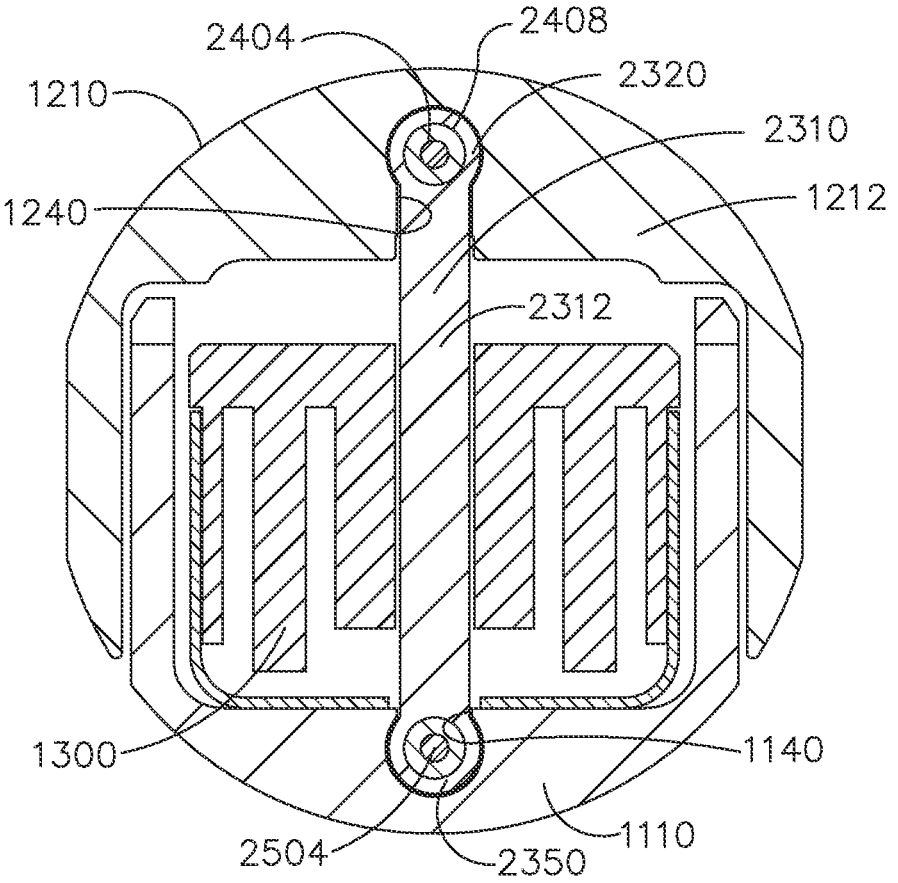
FIG. 12 is a cross-sectional end view of the surgical end effector of FIG. 4 taken along line 12-12 in FIG. 4.

Turning to FIGS. 9-11, in one arrangement, the firing system 2300 further comprises an upper flexible spine assembly 2400 that is operably coupled to the top firing member feature 2320 and a lower flexible spine assembly 2500 that is operably coupled to the bottom firing member feature 2350. In at least one embodiment, the upper flexible spine assembly 2400 comprises an upper series 2410 of upper vertebra members 2420 that are loosely coupled together by an upper flexible coupler member 2402 that is attached to the top firing member feature 2320. The upper flexible coupler member 2402 may comprises a top cable 2404 that extends through the top axial passage 2324 in the top firing member feature 2320 and a distal end 2406 of the top cable 2404 is attached to a retainer ferrule 2408 that is secured with the top axial passage 2324.

Figures 13, 14:
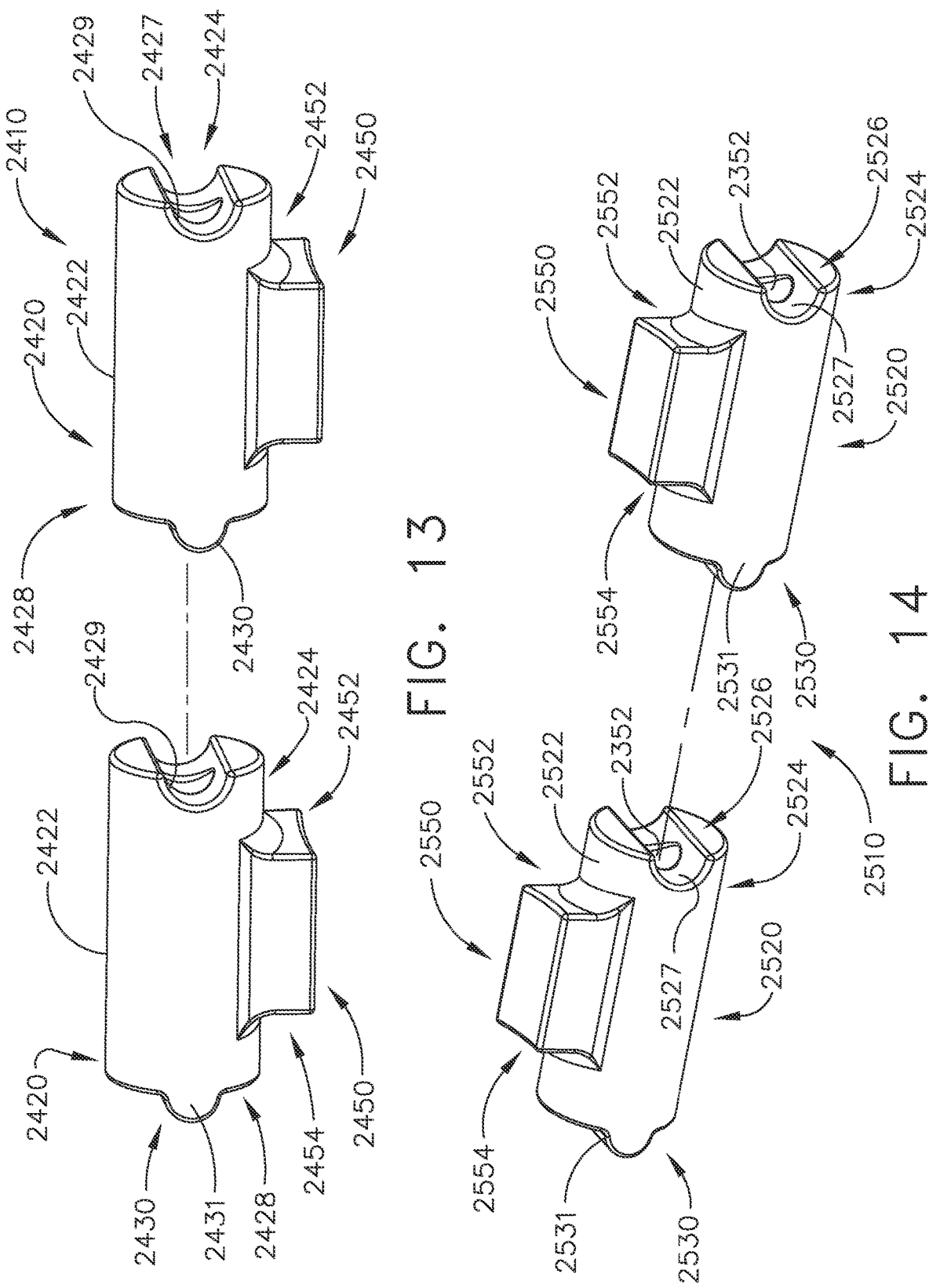
FIG. 13 is an exploded perspective view of two adjacent upper vertebra members of the upper flexible spine assembly of FIG. 10.
FIG. 14 is an exploded perspective view of two adjacent lower vertebra members of the lower flexible spine assembly of FIG. 10.

As can be seen in FIG. 13, each upper vertebra member 2420 comprises an upper vertebra body portion 2422 that has a proximal end 2424 and a distal end 2428. An upper hollow passage 2429 extends through the upper vertebra body portion 2422 to accommodate passage of the upper flexible coupler member 2402 therethrough. Each upper vertebra member 2420 further comprises a downwardly extending upper drive feature or upper vertebra member tooth 2450 that protrudes from the upper vertebra body portion 2422. Each upper vertebra member tooth 2450 has a helix-shaped proximal upper face portion 2452 and a helix-shaped distal upper face portion 2454. Each proximal end 2424 of the upper vertebra body portions 2422 has an upper proximal mating feature 2426 therein and each distal end 2428 has an upper distal mating feature 2430 formed therein. In at least one embodiment, the upper proximal mating feature 2426 comprises a concave recess 2427 and each upper distal mating feature 2430 comprises a convex mound 2431. When arranged in the upper series 2410, the convex mound 2431 on one upper vertebra member 2420 contacts and mates with the concave recess 2427 on an adjacent upper vertebra member 2420 in the upper series 2410 to maintain the upper vertebra members 2420 roughly in alignment so that the helix-shaped proximal upper face portion 2452 and a helix-shaped distal upper face portion 2454 on each respective upper tooth 2450 can be drivingly engaged by a rotary drive screw 2700 as will be discussed in further detail below.

Similarly, in at least one embodiment, the lower flexible spine assembly 2500 comprises a lower series 2510 of lower vertebra members 2520 that are loosely coupled together by a lower flexible coupler member 2502 that is attached to the bottom firing member feature 2350. The lower flexible coupler member 2502 may comprises a lower cable 2504 that extends through the bottom axial passage 2354 in the bottom firing member feature 2350 and a distal end 2506 of the bottom cable 2504 is attached to a retainer ferrule 2508 that is secured with the bottom axial passage 2354.

As can be seen in FIG. 14, each lower vertebra member 2520 comprises a lower vertebra body portion 2522 that has a proximal end 2524 and a distal end 2528. A lower hollow passage 2529 extends through the lower vertebra body portion 2522 to accommodate passage of the lower flexible coupler member 2502 therethrough. Each lower vertebra member 2520 further comprises an upwardly extending lower drive feature or lower vertebra member tooth 2550 that protrudes upward from the lower vertebra body portion 2522. Each lower vertebra member tooth 2550 has a helix-shaped proximal lower face portion 2552 and a helix-shaped distal lower face portion 2554. Each proximal end 2524 of the lower vertebra body portions 2522 has a lower proximal mating feature 2526 therein and each distal end 2528 has a lower distal mating feature 2530 formed therein. In at least one embodiment, the lower proximal mating feature 2526 comprises a concave recess 2527 and each lower distal mating feature 2530 comprises a convex mound 2531. When arranged in the lower series 2510, the convex mound 2531 on one lower vertebra member 2520 contacts and mates with the concave recess 2527 on an adjacent lower vertebra member 2520 in the lower series 2510 to maintain the lower vertebra members 2520 roughly in alignment so that the helix-shaped proximal lower face portion 2552 and a helix-shaped distal lower face portion 2554 on each respective lower vertebra member tooth 2550 can be drivingly engaged by a rotary drive screw 2700 as will be discussed in further detail below.

Figure 7:
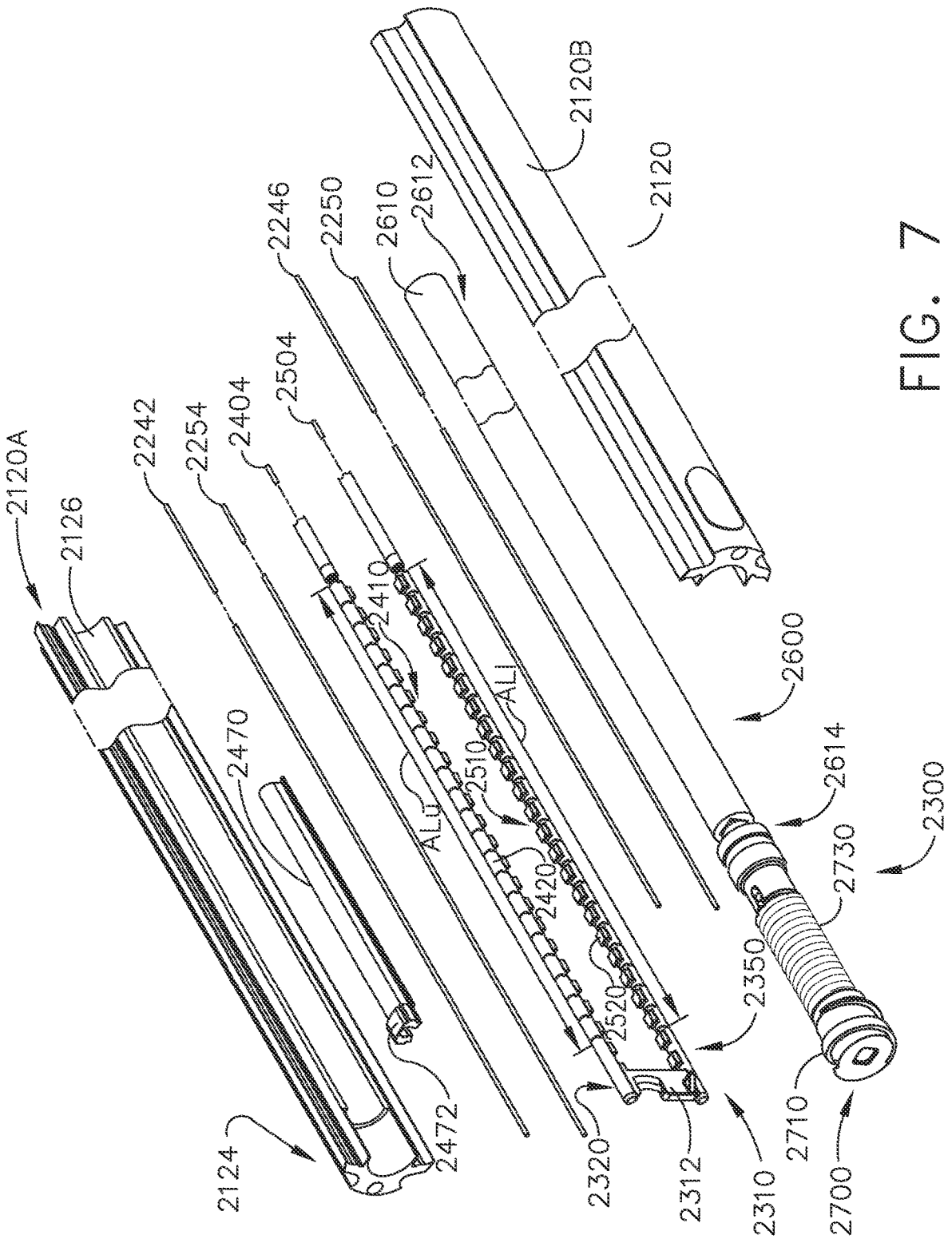
FIG. 7 is another exploded assembly view of the elongate shaft assembly of FIG. 6.
Figure 8:
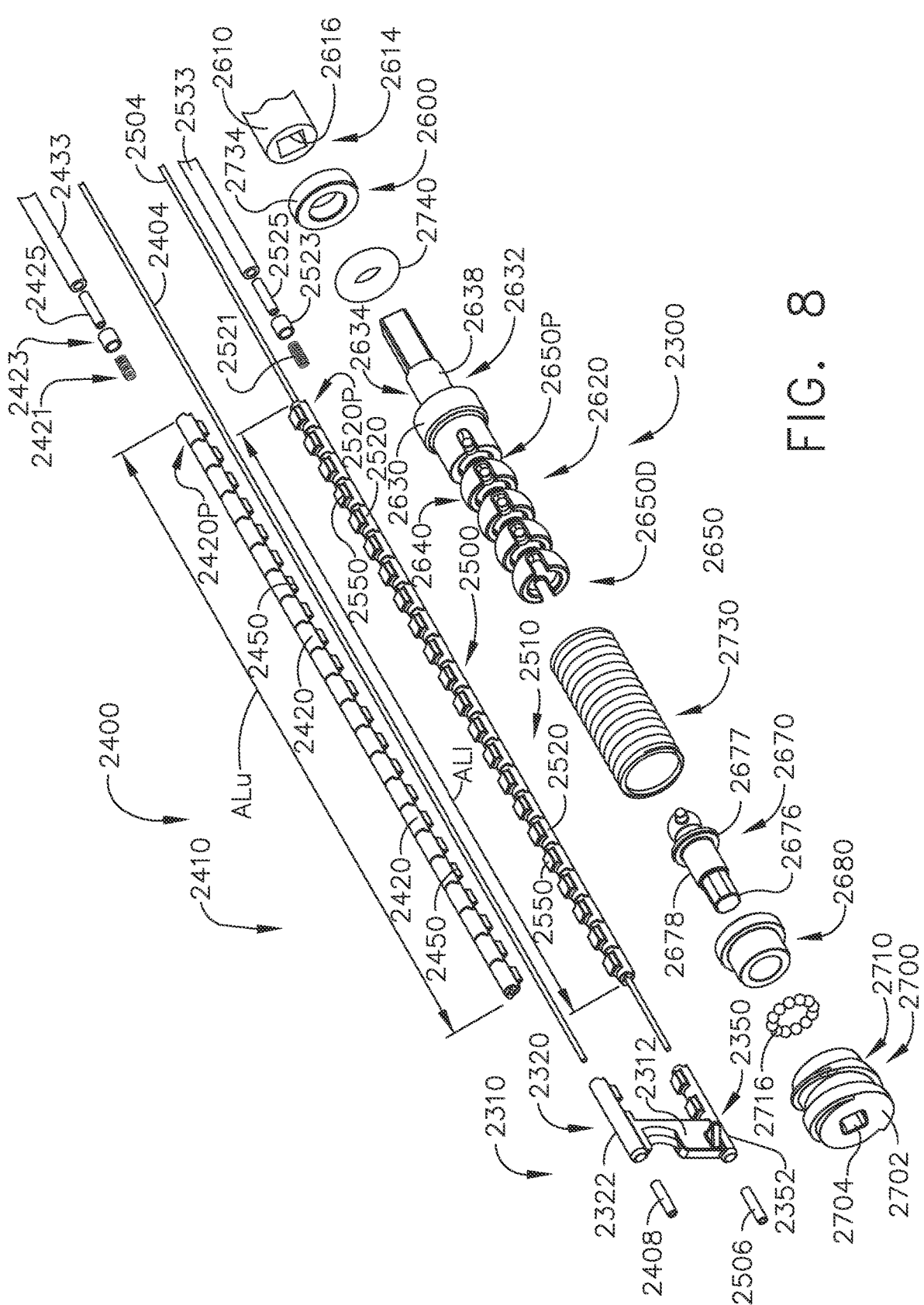
FIG. 8 is an exploded assembly view of a firing system and a rotary drive system according to at least one aspect of the present disclosure.

Now turning to FIGS. 5, 7, and 8, in at least one arrangement, the firing drive system 2300 further comprises a rotary drive screw 2700 that is configured to drivingly interface with the upper series 2410 of upper vertebra members 2420 and the lower series 2510 of lower vertebra members 2520. In the illustrated arrangement, the rotary drive screw 2700 is driven by a rotary drive system 2600 that comprises a proximal rotary drive shaft 2610 that is rotatably supported within the axial passage 2126 within the proximal support shaft 2120. See FIG. 7. The proximal rotary drive shaft 2610 comprises a proximal end 2612 and a distal end 2614. The proximal end 2612 may interface with a gear box 2004 or other arrangement that is driven by a motor 2006 or other source of rotary motion housed in the housing of the surgical instrument. See FIG. 2. Such source of rotary motion causes the proximal rotary drive shaft to rotate about the shaft axis SA within the axial passage 2126 in the proximal support shaft 2120.

Figure 16:
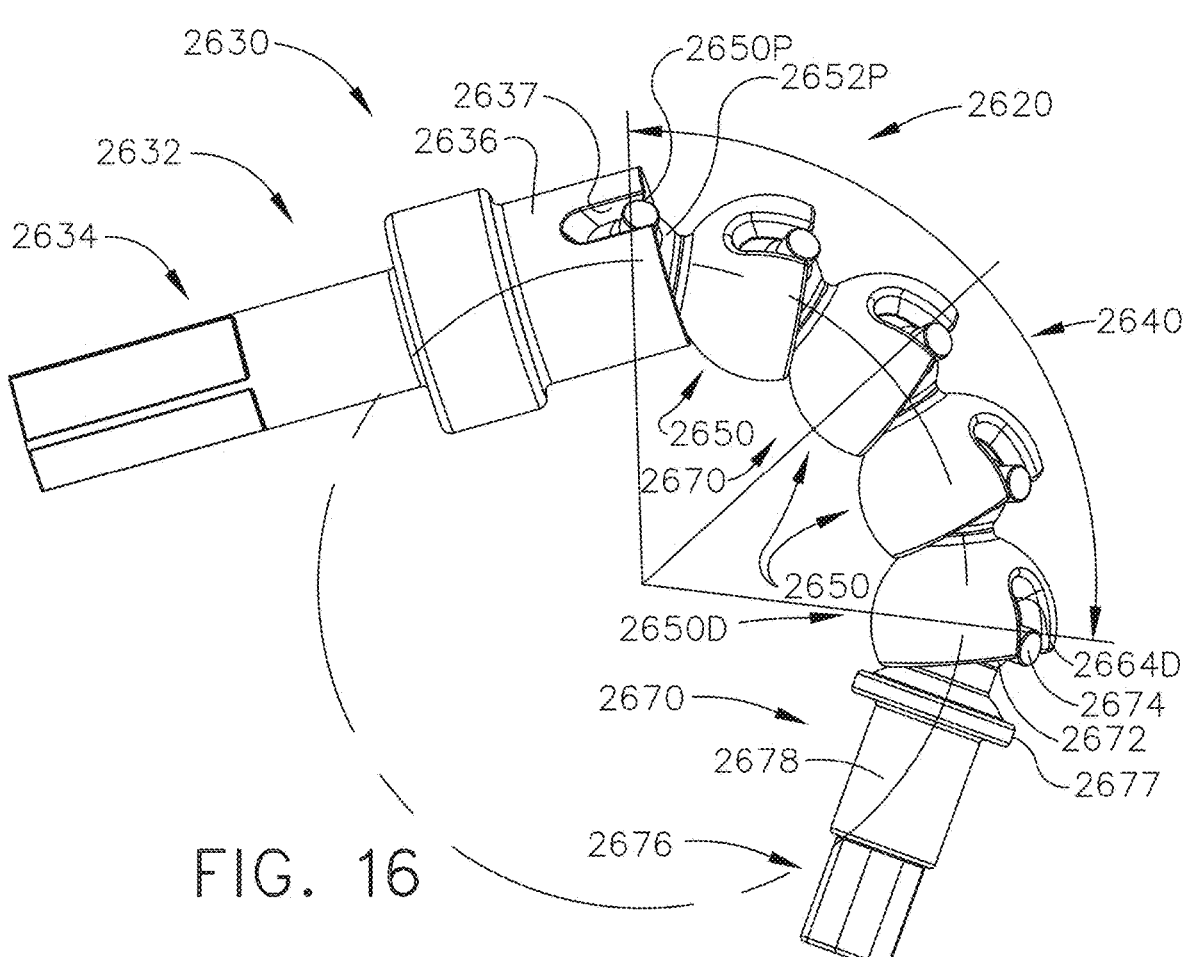
FIG. 16 is a perspective view of a CV drive shaft assembly of the rotary drive system of FIG. 8 in an articulated orientation.
Figure 17:
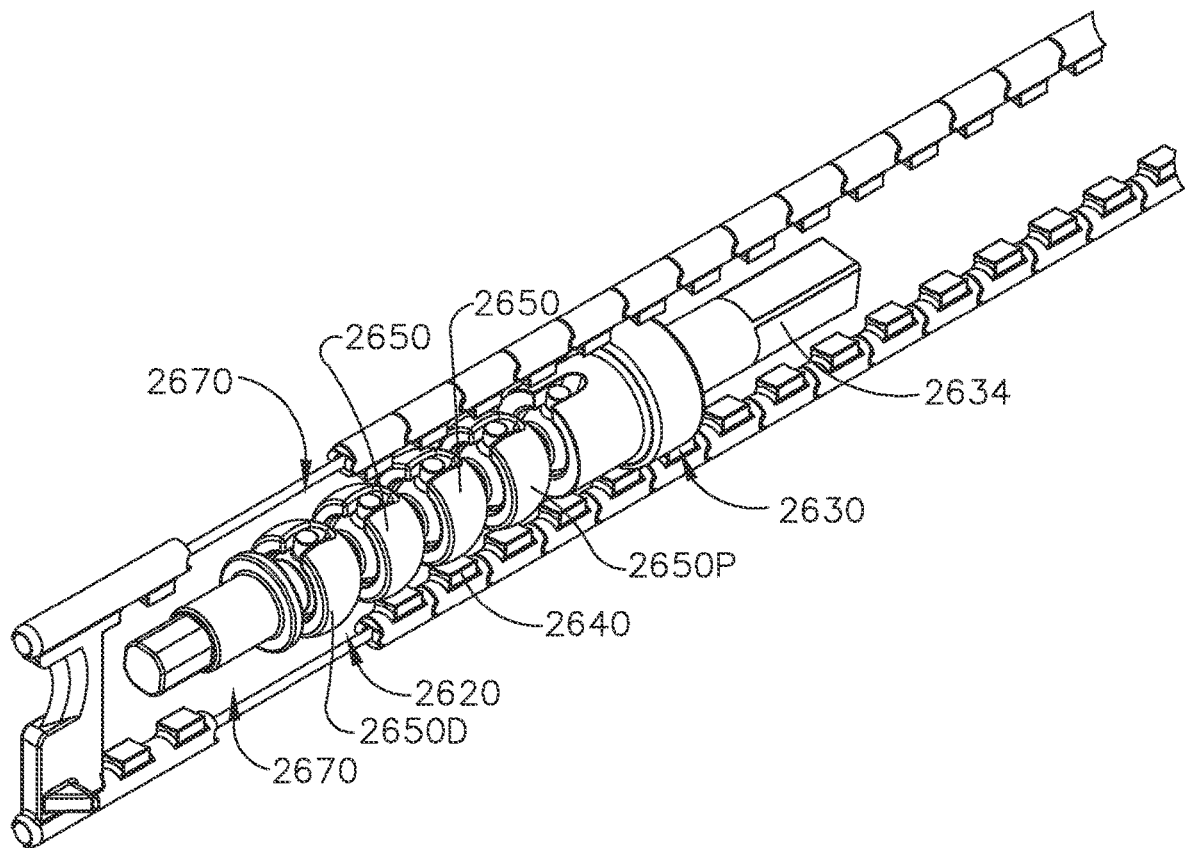
FIG. 17 is a perspective view of the firing system of FIG. 8 in driving engagement with the CV drive shaft assembly of FIG. 16 in accordance with at least one aspect of the present disclosure.

The proximal rotary drive shaft 2610 is operably supported within the elongate shaft assembly 2000 in a location that is proximal to the articulation joint 2200 and operably interfaces with a constant velocity (CV) drive shaft assembly 2620 that "spans" or extends axially through the articulation joint 2200. As can be seen in FIGS. 8, 16, and 17, in at least one arrangement, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft segment 2632 operably interfaces with a series 2640 of movably coupled drive joints 2650.

Figure 18:
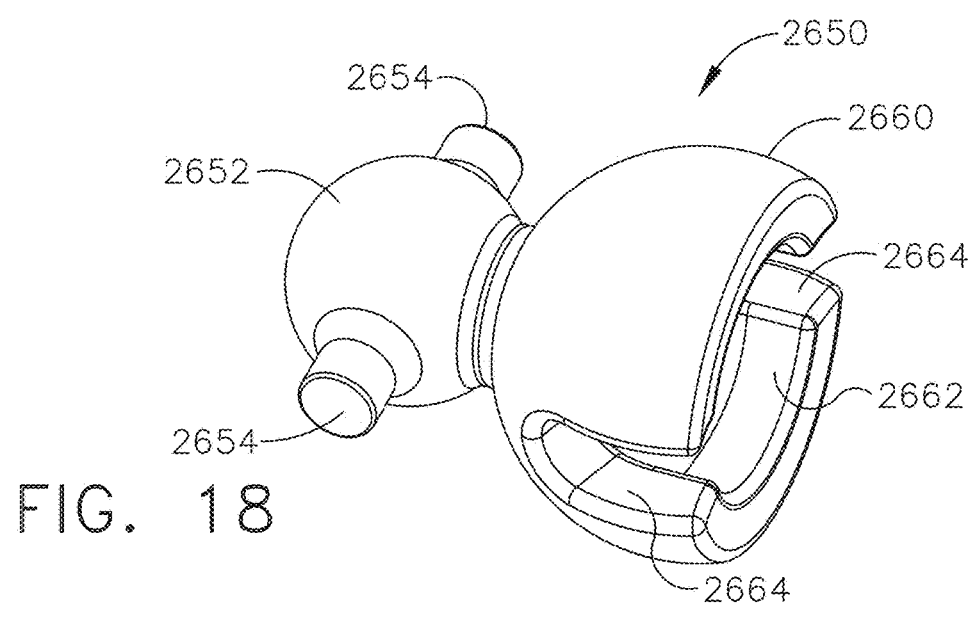
FIG. 18 is a perspective view of a drive joint of the CV drive shaft assembly of FIG. 16.

As can be seen in FIG. 18, in at least one arrangement, each drive joint 2650 comprises a first or distal sphere portion 2660 and a second or proximal sphere portion 2652. The distal sphere portion 2660 is larger than the proximal sphere portion 2652. The distal sphere portion 2660 comprises a socket cavity 2662 that is configured to rotatably receive a proximal sphere portion 2652 of an adjacent drive joint 2650 therein. Each proximal sphere portion 2652 comprises a pair of diametrically opposed joint pins 2654 that are configured to be movably received in corresponding pin slots 2664 in the distal sphere portion 2660 of an adjacent drive joint 2650 as can be seen in FIG. 16. A proximal sphere portion 2652P of a proximal-most drive joint 2650P is rotatably received in a distal socket portion 2636 of the proximal shaft segment 2632 as shown in FIG. 16. The joint pins 2654P are received within corresponding pin slots 2637 in the distal socket portion 2636. As can be further seen in FIG. 16, a distal-most drive joint 2650D in the series 2640 of movably coupled drive joints 2650 is movably coupled to a distal CV drive shaft 2670.

In at least one arrangement, the distal CV drive shaft 2670 comprises a proximal sphere portion 2672 that is sized to be movably received in the socket cavity 2662D in the distal-most drive joint 2650D. The proximal sphere portion 2672 includes joint pins 2674 that are movably received in the pin slots 2664D in the distal-most drive joint 2650D. The distal CV drive shaft 2670 further comprises a distally extending shaft stem 2676 that is configured to be non-rotatably coupled to the rotary drive screw 2700 that is positioned distal to the articulation joint 2200. The distal CV drive shaft 2670 includes a flange 2677 and a mounting barrel portion 2678 for receiving a thrust bearing housing 2680 thereon.

In the illustrated arrangement, when the series 2640 of movably coupled drive joints 2650 articulates, the joint pins 2674 remain in the corresponding pin slots 2664 of an adjacent drive joint 2650. In the example illustrated in FIG. 18, each drive joint may be capable of approximately eighteen degrees of articulation in the pitch and yaw directions. FIG. 16 illustrates an angle of the series 2640 of drive joints 2650 when each drive joint 2650 in the series are fully articulated ninety degrees in pitch and yaw which yields an angle α of approximately 100.9 degrees. In such arrangement, the outer surface of each distal sphere portion 2660 clears the outer surface of the adjacent or adjoining proximal sphere portion 2652 allowing for unrestricted motion until the eighteen degree limit is reached. The rigid design and limited small angles allow the series 2640 of movably coupled drive joints 2650 to carry high loads torsionally at an overall large angle.

In the illustrated arrangement, the articulation joint 2200 comprises an articulation joint spring 2230 that is supported within an outer elastomeric joint assembly 2210. The outer elastomeric joint assembly 2210 comprises a distal end 2212 that is attached to the proximal end 1112 of the elongate channel 1110. For example, as can be seen in FIG. 6, the distal end 2212 of the outer elastomeric joint assembly 2210 is attached to the proximal end 1112 of the elongate channel 1110 by a pair of cap screws 2722 that extend through a distal mounting bushing 2720 to be threadably received in the proximal end 1112 of the elongate channel 1110. A proximal end 2214 of the elastomeric joint assembly 2210 is attached to the distal end 2124 of the proximal support shaft 2120. The proximal end 2214 of the elastomeric joint assembly 2210 is attached to the distal end 2124 of the proximal support member 2120 by a pair of cap screws 2732 that extend through a proximal mounting bushing 2750 to be threadably received in threaded inserts 2125 mounted within the distal end 2124 of the proximal support shaft 2120.

To prevent the drive joints 2650 from buckling during articulation, the series 2640 of movably coupled drive joints 2650 extend through at least one low friction articulation joint spring 2730 that is supported within the outer elastomeric joint assembly 2210. See FIG. 19. The articulation joint spring 2730 is sized relative to the drive joints 2650 such that a slight radial clearance is provided between the articulation joint spring 2730 and the drive joints 2650. The articulation joint spring 2730 is designed to carry articulation loads axially which may be significantly lower than the torsional firing loads. The joint spring(s) is longer than the series 2640 of drive joints 2650 such that the drive joints are axially loose. If the "hard stack" of the series 2640 of drive joints 2650 is longer than the articulation joint spring(s) 2730 hard stack, then the drive joints 2650 may serve as an articulation compression limiter causing firing loads and articulation loads to resolve axially through the series 2640 of the drive joints 2650. When the firing loads resolve axially through the series 2640 of the drive joints 2650, the loads may try to straighten the articulation joint 2200 or in other words cause de-articulation. If the hard stack of the articulation joint spring(s) 2730 is longer than the hard stack of the series 2640 of the drive joints 2650, the firing loads will then be contained within the end effector and no firing loads will resolve through the drive joints 2650 or through the springs(s) 2730.

Figure 19:
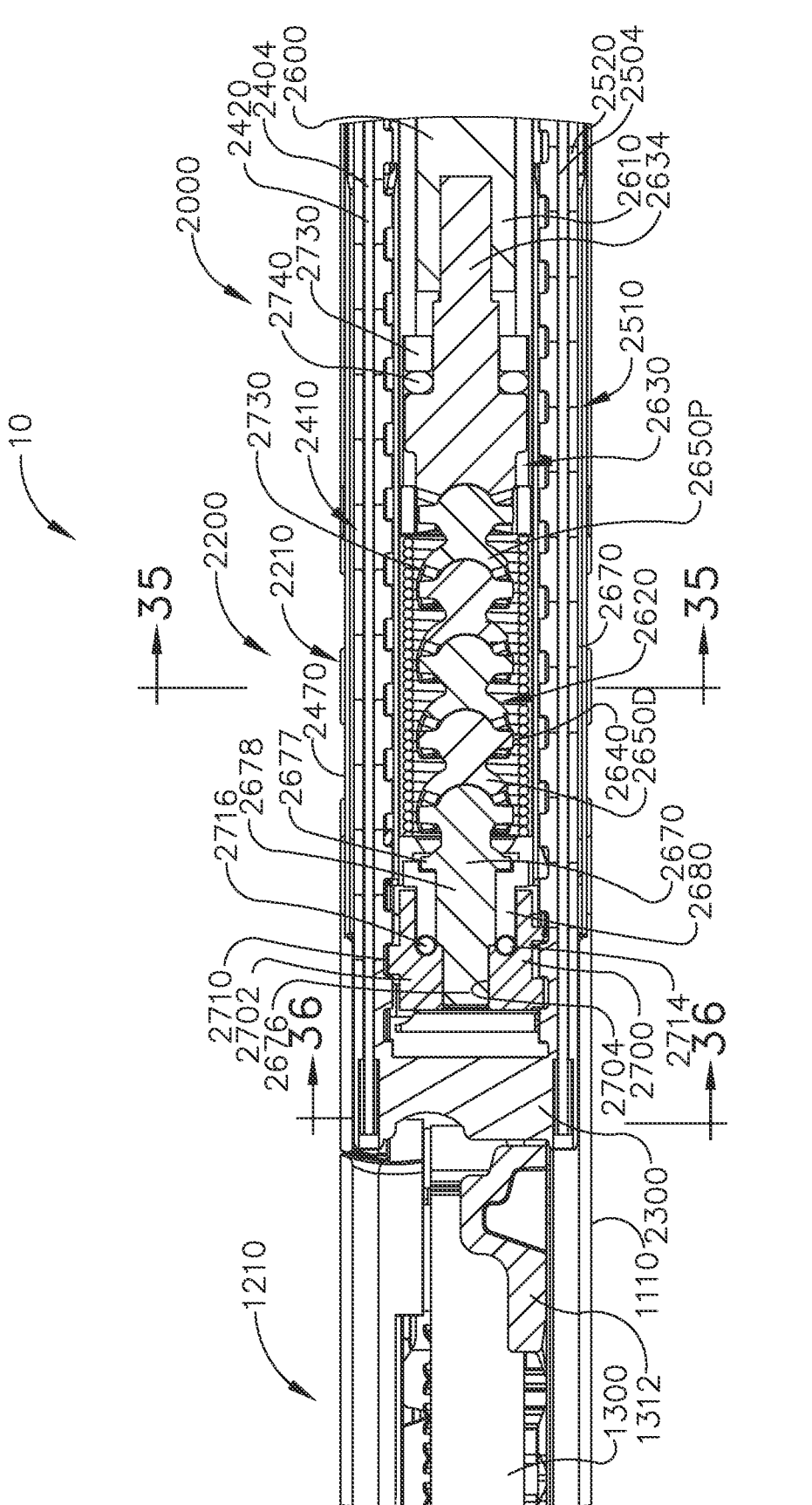
FIG. 19 is a cross-sectional view of a portion of the surgical instrument of FIG. 4 taken along line 19-19 in FIG. 4.
Figure 20:
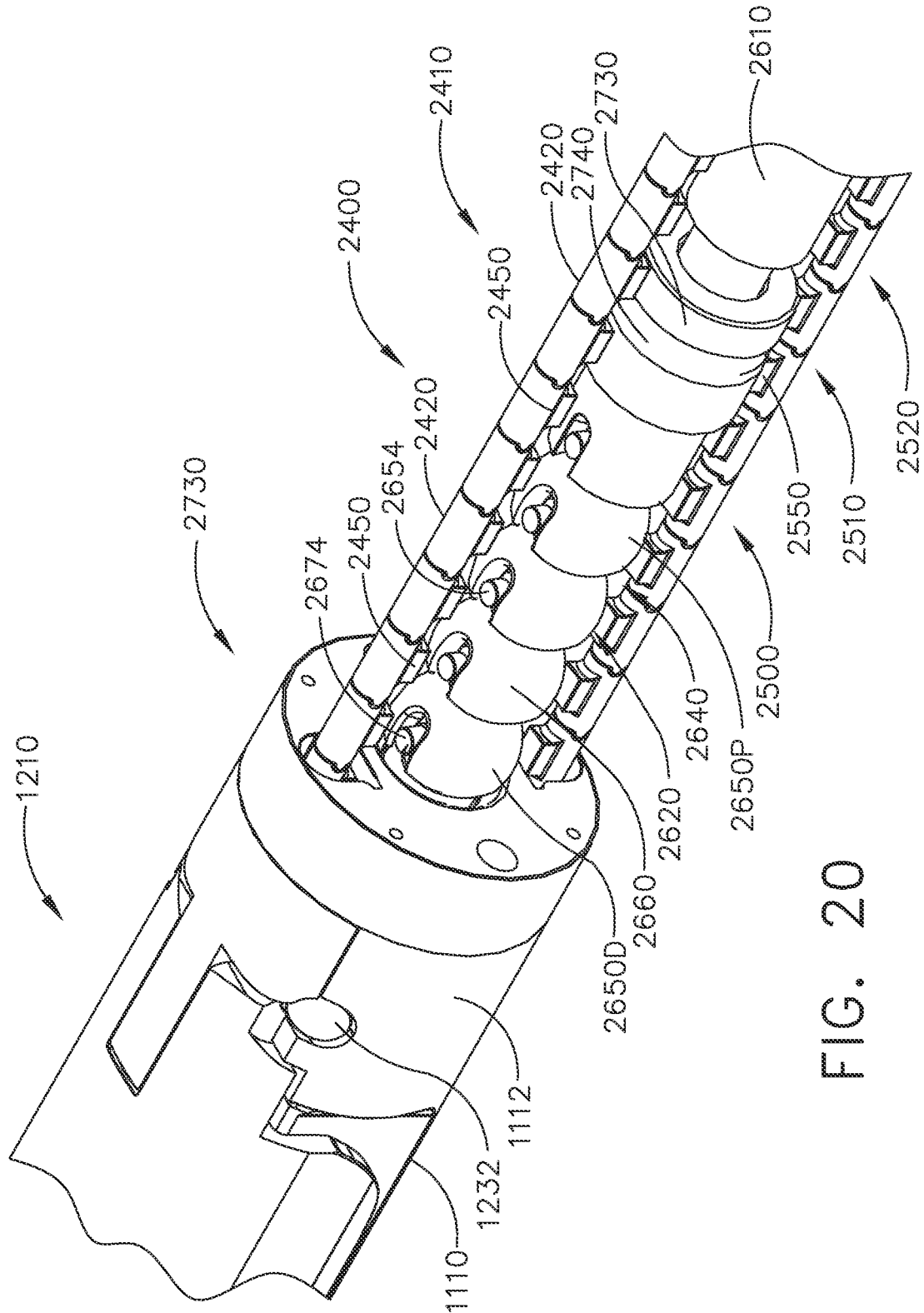
FIG. 20 is a partial perspective view of a proximal end portion of the surgical end effector and portions of the firing system and the rotary drive system of the surgical instrument of FIG. 1.
Figure 21:
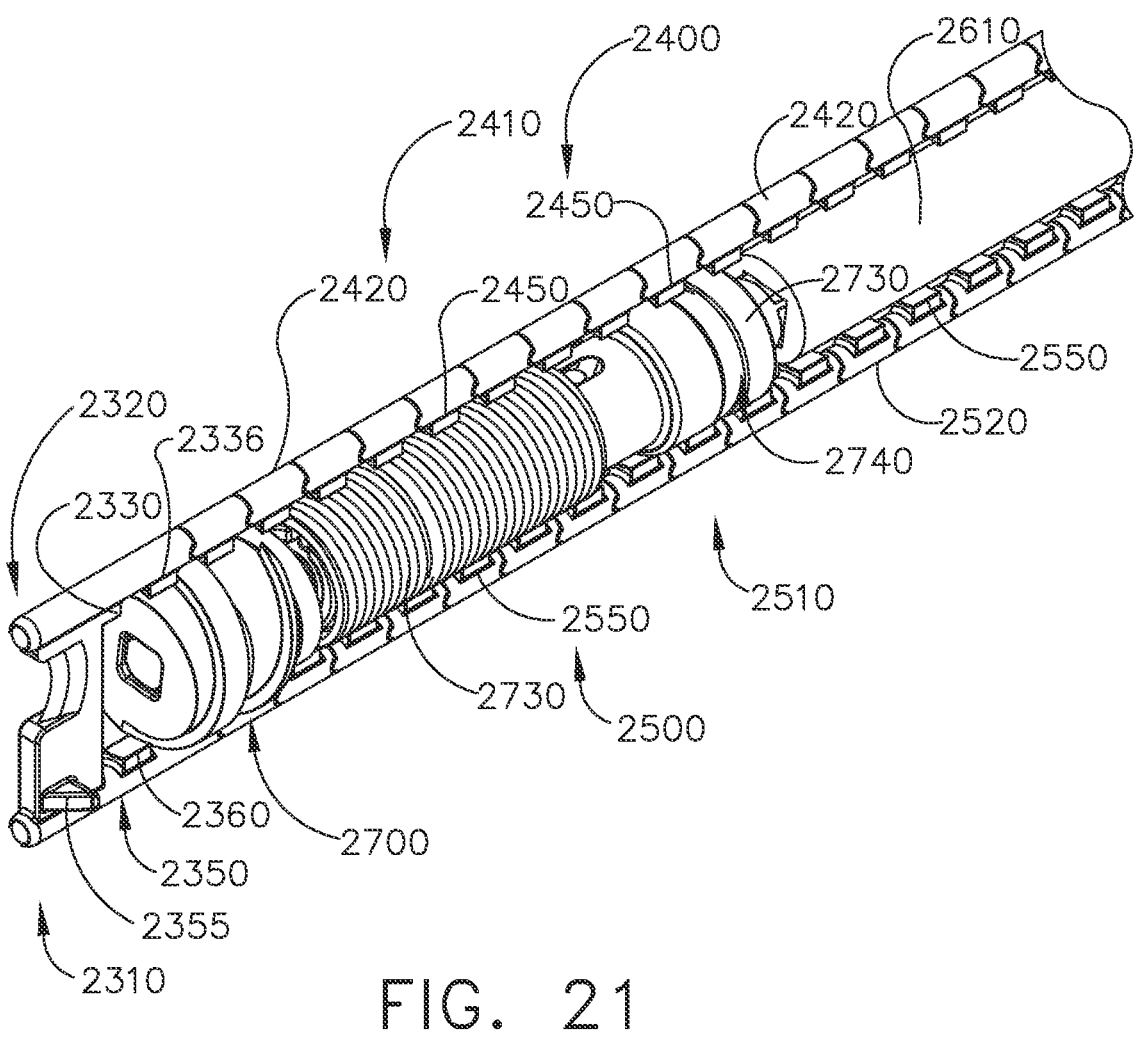
FIG. 21 is a perspective view of the rotary drive system of the surgical instrument of FIG. 1 in driving engagement with the firing system thereof in accordance with at least one aspect of the present disclosure.

To further ensure that the drive joints 2650 are always engaged with each other, a proximal drive spring 2740 is employed to apply an axial biasing force to the series 2640 of drive joints 2650. For example, as can be seen in FIGS. 8, 19, and 20, the proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring/bushing received on the proximal barrel portion 2638 of the proximal shaft segment 2632. The proximal drive spring 2740 lightly biases the drive joints 2650 together to decrease any gaps that may occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

As can be seen in FIGS. 9 and 10, the top firing member feature 2320 on the firing member 2310 comprises a distal upper firing member tooth segment 2330 that is equivalent to one half of an upper tooth 2450 on each upper vertebra member 2420. In addition, a proximal upper firing member tooth 2336 that is identical to an upper tooth 2450 on each upper vertebra member 2420 is spaced from the distal upper firing member tooth segment 2330. The distal upper firing member tooth segment 2330 and the proximal upper firing member tooth 2336 may be integrally formed with the top firing member feature 2320 of the firing member 2310. Likewise, the bottom firing member feature 2350 of the firing member 2310 comprises a distal lower firing member tooth 2360 and a proximal lower firing member tooth 2366 that are integrally formed on the bottom firing member feature 2350. For example, in at least one arrangement, the firing member 2310 with the rigidly attached teeth 2330, 2336, 2360, and 2366 may be fabricated at one time as one unitary component using conventional metal injection molding techniques.

As indicated above, each of the upper vertebra members 2520 is movably received on an upper flexible coupler member 2402 in the form of a top cable 2404. As was described above, the distal end 2406 of the top cable 2404 is secured to the top firing member feature 2320 of the firing member 2310. Similarly, each of the lower vertebra members 2520 is movably received on a lower flexible coupler member 2502 in the form of a lower cable 2504. A distal end 2506 of the lower cable 2504 is secured to the bottom firing member feature 2350 of the firing member 2310. In at least one arrangement, the top cable 2404 and the bottom cable 2504 extend through the proximal shaft portion 2100 and, as will be discussed in further detail below, may interface with a bailout arrangement supported in the housing for retracting the firing member 2310 back to its home or starting position should the firing member drive system fail.

Turning again to FIG. 8, the axial length $AL_u$ of the upper series 2410 of upper vertebra members 2420 and the axial length $AL_l$ of the lower series 2510 of lower vertebra members 2520 are equal and must be sufficiently long enough to facilitate the complete distal advancement of the firing member 2310 from the home or starting position to a distal-most ending position within the staple cartridge while the proximal-most upper vertebra members 2420 in the upper series 2410 of upper vertebra members 2420 and the proximal-most lower vertebra members 2520 in the lower series 2510 of lower vertebra members 2520 remain in driving engagement with the rotary drive screw 2700. As can be seen in FIG. 8, an upper compression limiting spring 2421 is configured to interface with a proximal-most upper vertebra member 2420P in the upper series 2410 of upper vertebra members 2420. The upper compression limiting spring 2421 is journaled on the top cable 2404 and is retained in biasing engagement with the proximal-most upper vertebra member 2420P by an upper spring holder 2423 that is retained in position by an upper ferrule 2425 that is crimped onto the top cable 2404. The top cable 2404 extends through an upper hypotube 2433 that is supported in the proximal support shaft. Likewise, a lower compression limiting spring 2521 is configured to interface with a proximal-most, lower vertebra member 2520P in the lower series 2510 of lower vertebra members 2520. The lower compression spring 2521 is journaled on the lower cable 2504 and is retained in biasing engagement with the proximal-most, lower vertebra member 2520P by a lower spring holder 2523 that is retained in position by a lower ferrule 2525 that is crimped onto the lower cable 2504. The lower cable 2504 extends through a lower hypotube 2533 that is supported in the proximal support shaft.

When the upper vertebra members 2420 and the lower vertebra members 2520 angle through the articulation joint (after the end effector has been positioned in an articulated position), the gaps between the respective vertebra members 2420, 2520 increase in each series 2410, 2510 which causes the springs 2421, 2521 to become tighter. The compression limiting springs 2421, 2521 provide enough slack in the cables 2404, 2504, respectively to enable the vertebra members 2420, 2520 angle through the most extreme articulation angles. If the cables 2404, 2504 are pulled too tight, the spring holders 2423, 2523 will contact their respective proximal-most vertebra members 2420P, 2520P. Such compression limiting arrangements ensure that the vertebra members 2420, 2520 in their respective series 2410, 2510 always remain close enough together so that the rotary drive screw 2700 will always drivingly engage them in the manner discussed in further detail below. When the vertebra members 2420, 2520 are aligned straight again, the compression limiting springs 2421, 2521 may partially relax while still maintaining some compression between the vertebra members.

As indicated above, when the upper vertebra members 2420 are arranged in the upper series 2410 and lower vertebra members 2520 are arranged in the lower series 2510, the convex mounds and concave recesses in each vertebra member as well as the compression limiter springs serve to maintain the upper and lower vertebra members in relatively linear alignment for driving engagement by the rotary drive screw 2700. As can be seen in FIGS. 9 and 10, when the upper vertebra members 2420 are in linear alignment, the upper teeth 2450 are spaced from each other by an opening space generally designated as 2460 that facilitates driving engagement with the helical drive thread 2170 on the rotary drive screw. Similarly, when the lower vertebra members 2520 are in linear alignment, the lower vertebra member teeth 2550 are spaced from each other by an opening space generally designated as 2560 that facilitates driving engagement with the helical drive thread 2170 of the rotary drive screw 2700.

Figure 22:
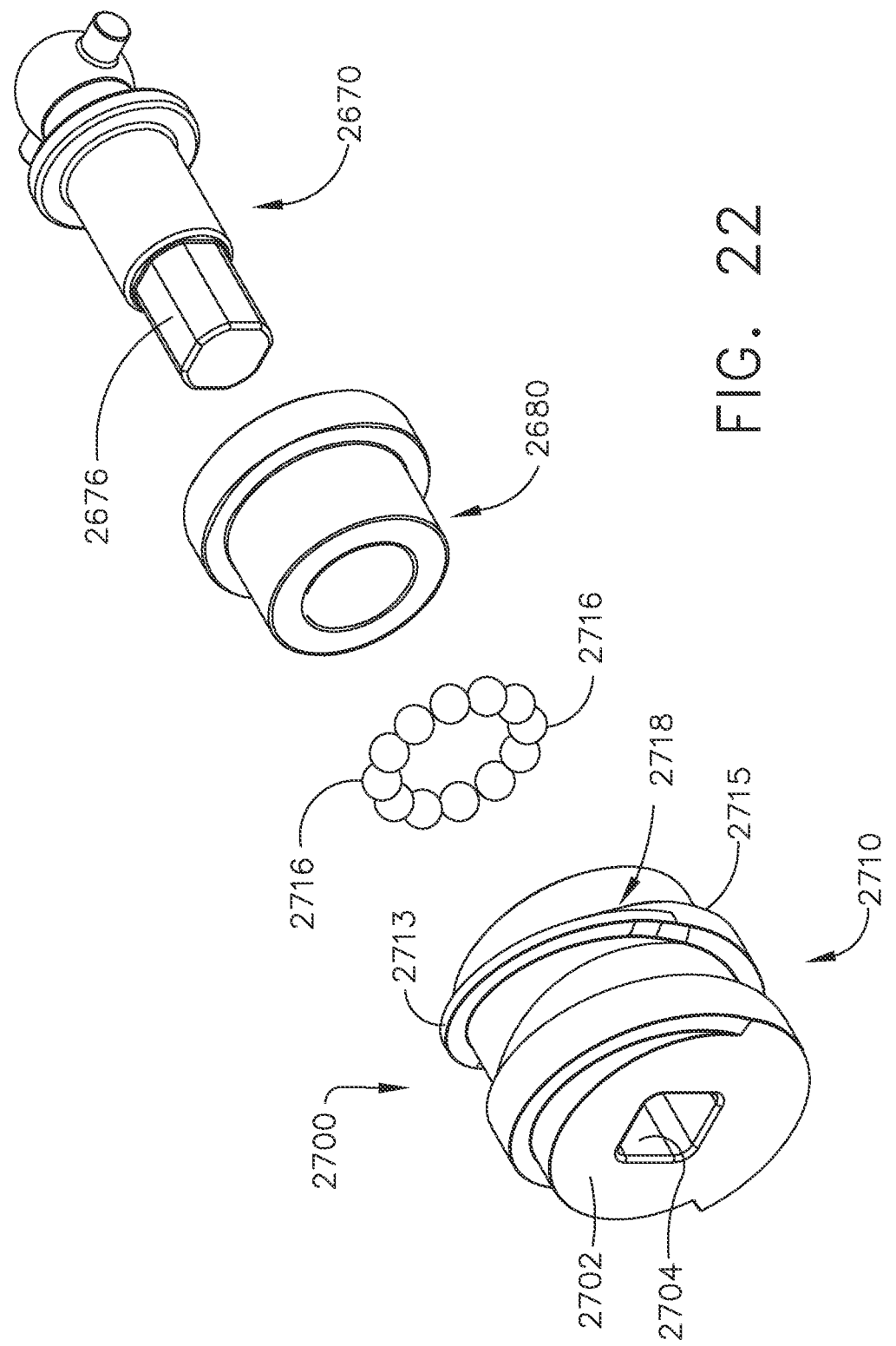
FIG. 22 is an exploded perspective view of the rotary drive screw and thrust bearing arrangement of the firing system of FIG. 21.

Turning to FIGS. 8 and 22, the rotary drive screw 2700 comprises a screw body 2702 that has a socket 2704 therein for receiving the distally extending shaft stem 2676 of the distal CV drive shaft 2670. An internal radial groove 2714 (FIG. 10) is formed in the screw body 2702 for supporting a plurality of ball bearings 2716 therein. In one arrangement, for example, 12 ball bearings 2716 are employed. The radial groove 2714 supports the ball bearings 2716 between the screw body 2702 and a distal end of the thrust bearing housing 2680. The ball bearings 2716 serve to distribute the axial load of the rotary drive screw 2700 and significantly reduce friction through the balls' rolling motion.

Figures 23, 24:
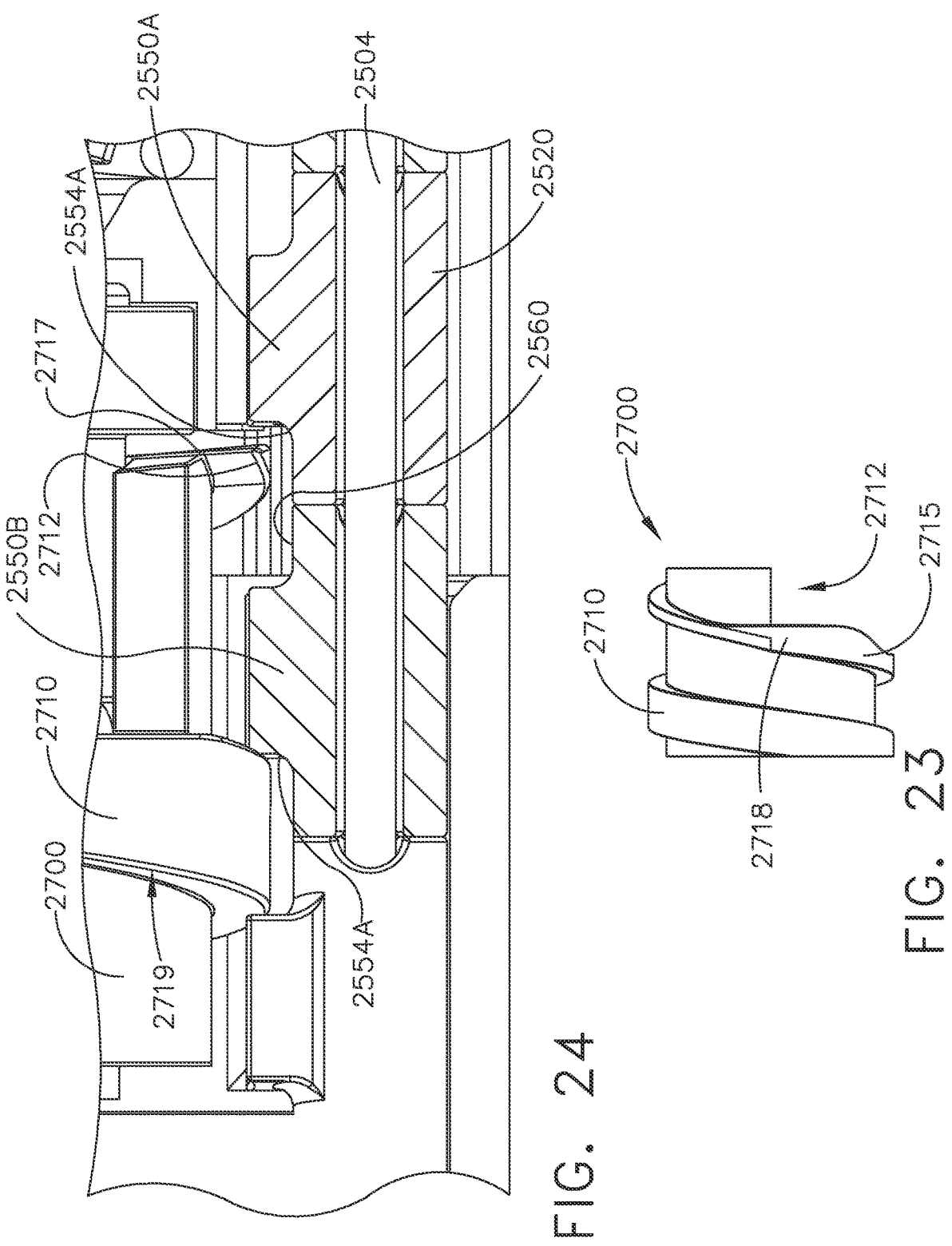
FIG. 23 is a side view of the rotary drive screw of FIG. 22.
FIG. 24 is a partial cross-sectional side view of a portion of the lower flexible spine assembly and a portion of the firing member of FIG. 21 in driving engagement with a portion of the rotary drive screw.

As can be seen in FIG. 23, a helical drive thread 2710 is provided around the screw body 2702 and serves to form a proximal thread scoop feature 2712. The proximal thread scoop feature 2712 is formed with a first pitch 2713 and the remaining portion of the helical drive thread 2710 is formed with a second pitch 2715 that differs from the first pitch 2713. In FIGS. 22 and 23, area 2718 illustrates where the first pitch 2713 and the second pitch 2715 converge. In at least one embodiment, the first pitch 2713 is larger than the second pitch 2715 to ensure that the rotary drive screw 2700 captures and "scoops up" or drivingly engages every upper vertebra member 2420 and every lower vertebra member 2520. As can be seen in FIG. 24, a proximal end 2717 of the helical drive thread 2710 that has the first pitch 2713 has scooped into the into the opening space 2560 between two adjacent lower vertebra member teeth 2550A and 2550B while the center portion 2719 of the helical drive thread 2710 that has the second pitch 2715 is in driving engagement with the helix-shaped distal lower face portion 2554 on the lower vertebra member tooth 2550B and the helix-shaped proximal lower face portion 2552 on the proximal lower firing member tooth 2366. As can also be appreciated, the scoop feature 2712 may not contact the helix-shaped distal lower face portion 2554A of the lower vertebra member tooth 2550A as it scoops up the lower vertebra member tooth 2550B when driving the firing member 2310 distally. The helical drive thread 2710 interacts with the teeth 2450 of the upper vertebra members 2420 in a similar manner.

A power screw is a threaded rod with a full three hundred sixty degree nut around it. Rotation of the power screw causes the nut to advance or move longitudinally. In the present arrangements, however, due to space constraints, a full three hundred sixty degree nut cannot fit inside the end effector. In a general sense, the upper flexible spine assembly 2400 and the lower flexible spine assembly 2500 comprise a radially/longitudinally segmented "power screw nut" that is rotatably driven by the rotary drive screw 2700. When the rotary drive screw is rotated in a first rotary direction, the rotary drive screw 2700 drives one or more vertebra members in each of the upper series and lower series of vertebra members longitudinally while the vertebra members 2420, 2520 stay in the same locations radially. The upper series 2410 and lower series 2510 are constrained from rotating around the rotary drive screw 2700 and can only move longitudinally. In one arrangement, the upper vertebra members 2420 in the upper series 2410 and the lower vertebra members 2520 in the lower series 2510 only surround the rotary drive screw 2700 with less than ten degrees each.

Figure 25:
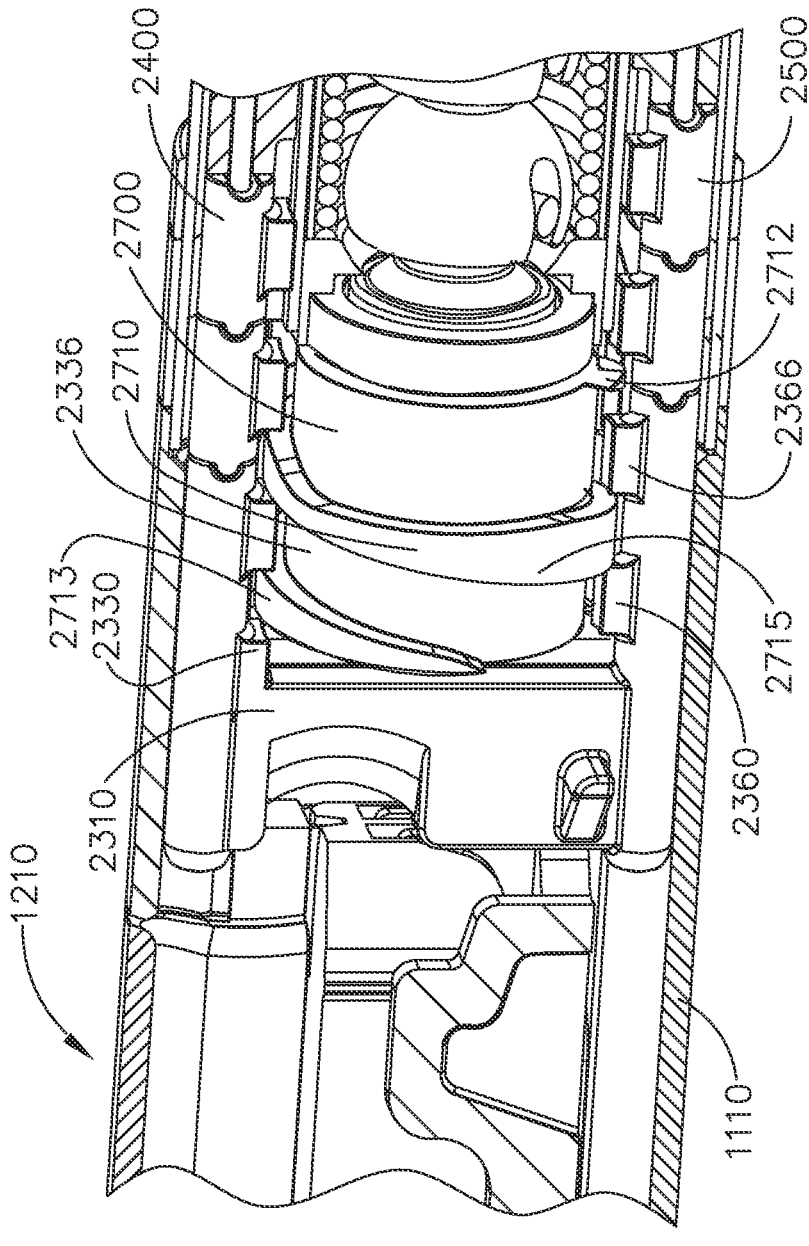
FIG. 25 is a perspective view of the firing member in a home or starting position within the surgical end effector of the surgical instrument of FIG. 1.
Figure 26:
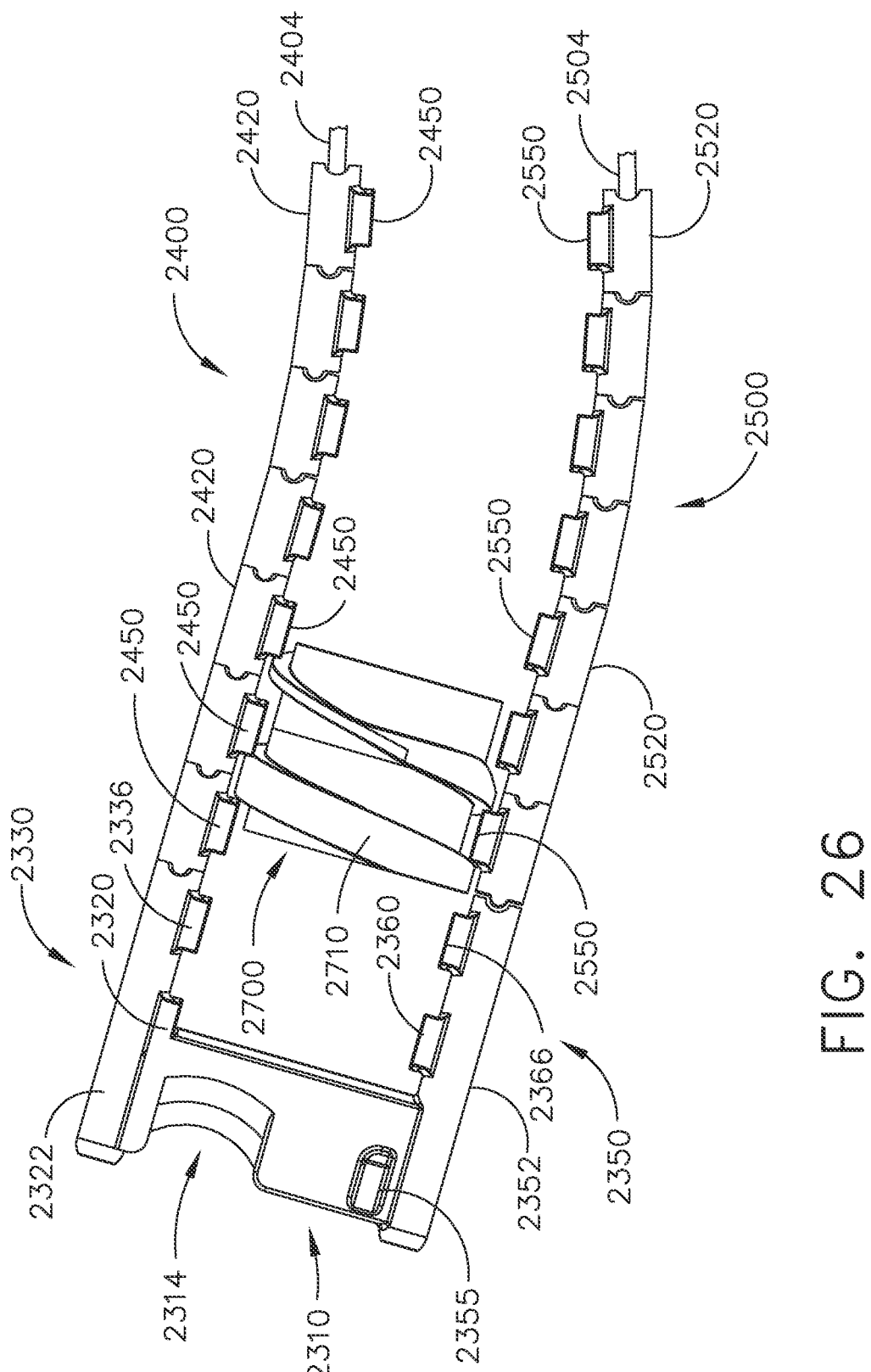
FIG. 26 is a side view illustrating the upper flexible spine assembly and the lower flexible spine assembly of FIG. 21 in driving engagement with the rotary drive screw after the firing member has been driven distally from a home or starting position.

FIG. 25 illustrates the firing member 2310 in the home or starting position. As can be seen in FIG. 25, a portion of the helical drive thread 2710 on the rotary drive screw 2700 is engaged between the distal upper firing member tooth segment 2330 and the proximal upper firing member tooth 2336 and another portion of the helical drive thread 2710 is engaged between the distal lower firing member tooth 2360 and a proximal lower firing member tooth 2366 on the firing member 2310. Such arrangement enables the rotary drive screw 2700 to precisely control the distal and proximal movement of the firing member 2310 which, as will be discussed in further detail below, can result in the precise movement of the anvil 1210. Once the firing member 2310 has been sufficiently distally advanced during a firing stroke, the helical drive thread 2710 operably engages the teeth on the upper and lower vertebras. See FIG. 26.

Figure 27:
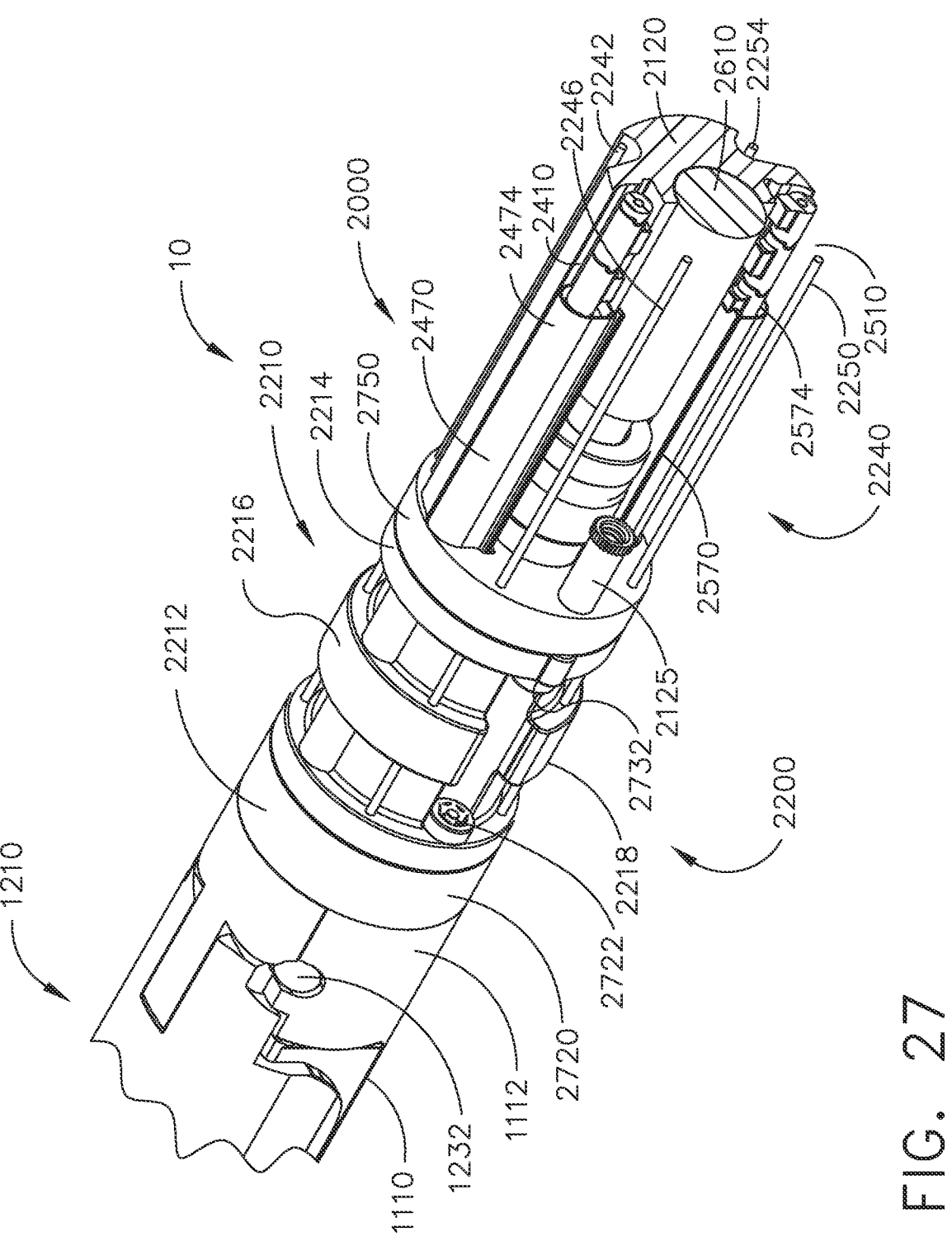
FIG. 27 is a partial cross-sectional perspective view of a portion of the surgical end effector, firing system and rotary drive system of the surgical instrument of FIG. 1 according to at least one aspect of the present disclosure with an outer elastomeric joint assembly of an articulation joint omitted for clarity.
Figure 29:
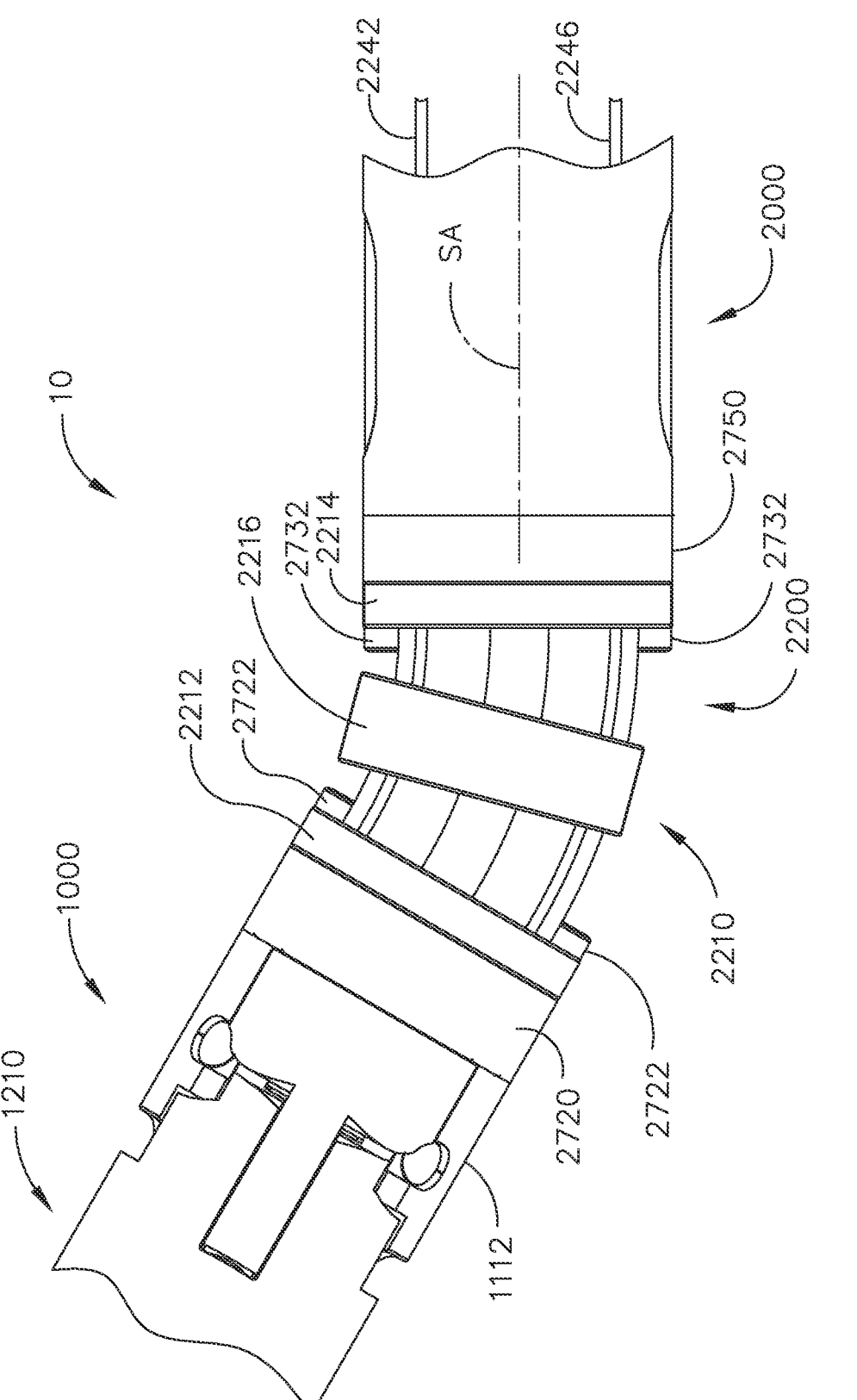
FIG. 29 is a top view of the surgical end effector of FIG. 27 articulated in a first direction relative to a portion of the elongate shaft assembly in accordance with at least one aspect of the present disclosure.
Figure 30:
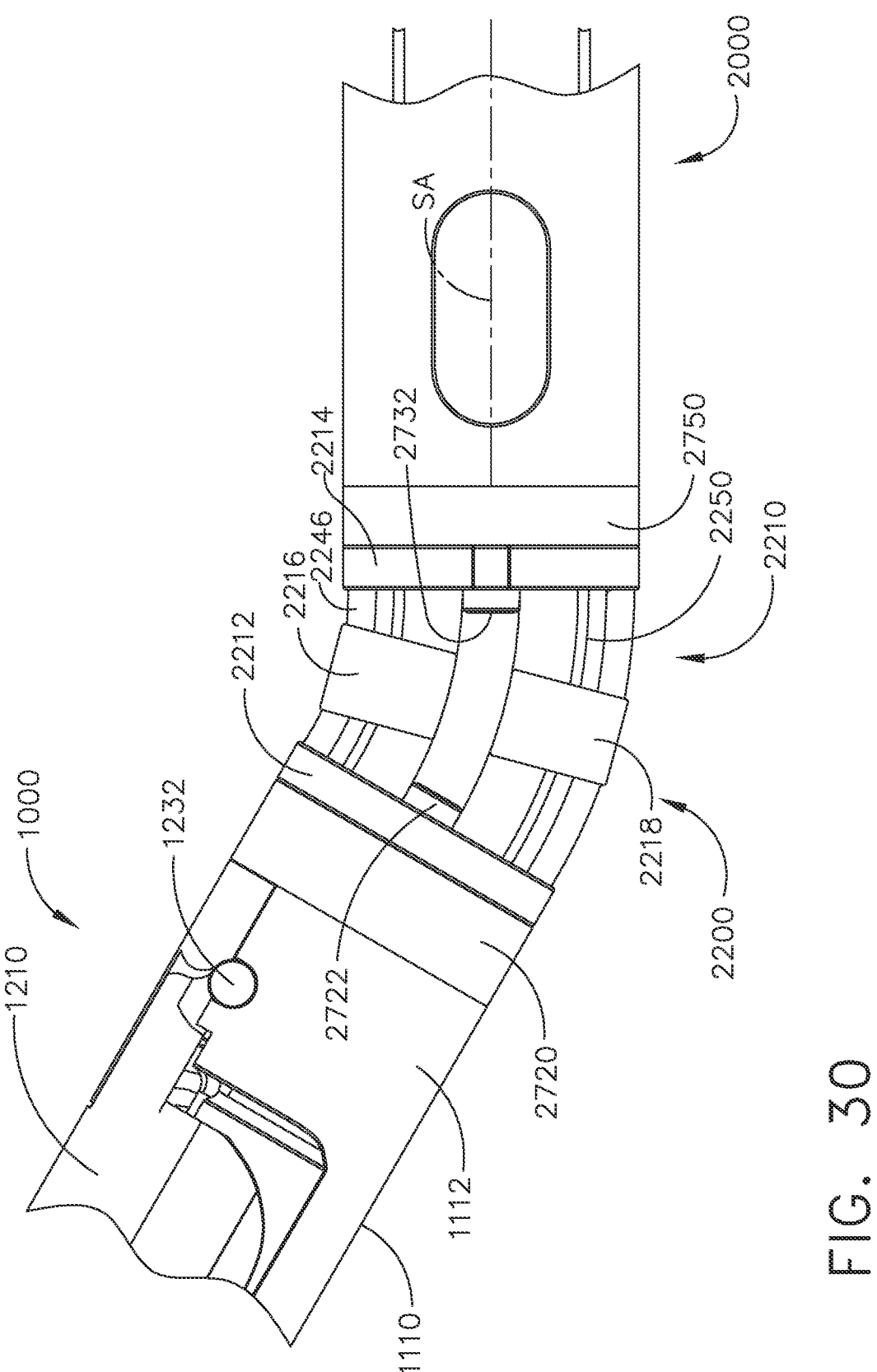
FIG. 30 is a side view of the surgical end effector of FIG. 29 articulated in another direction relative to a portion of the elongate shaft assembly in accordance with at least one aspect of the present disclosure.
Figure 31:
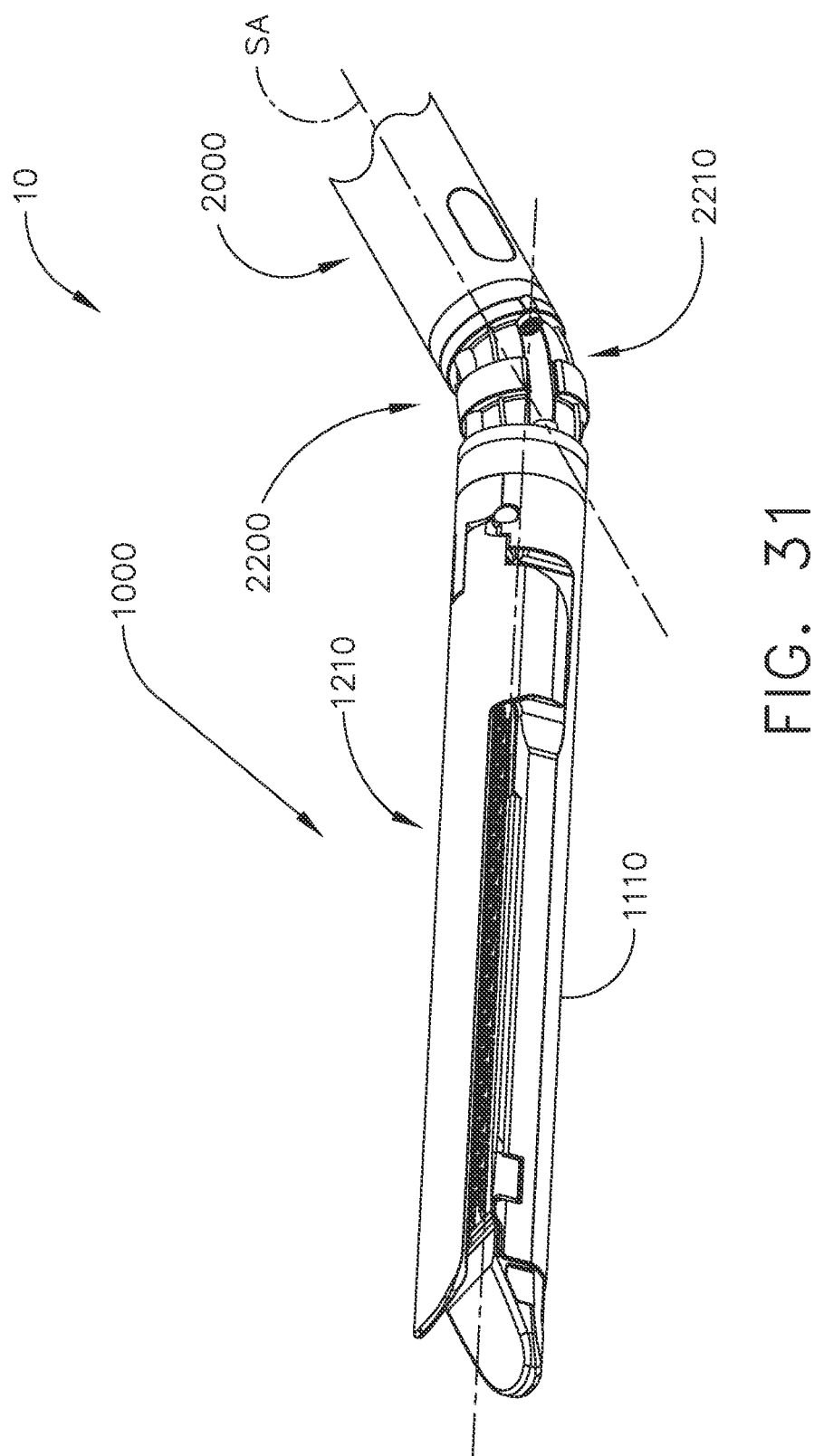
FIG. 31 is a perspective view of the surgical end effector of FIG. 29 articulated in multiple planes with respect to a portion of the elongate shaft assembly in accordance with at least one aspect of the present disclosure.

The surgical instrument 10 also comprises an articulation system 2240 that is configured to apply articulation motions to the surgical end effector 1000 to articulate the surgical end effector relative to the elongate shaft assembly 2000. In at least one arrangement, for example, the articulation system comprises four articulation cables 2242, 2246, 2250, and 2254 that extend through the elongate shaft assembly 2000. See FIG. 27. In the illustrated arrangement, the articulation cables 2242, 2246 pass through the proximal mounting bushing 2750, the proximal end 2214 of the elastomeric joint assembly 2210, as well as a central rib segment 2216 to be secured to the distal end 2212 of the elastomeric joint assembly 2210 or other portion of the surgical instrument. Likewise, the articulation cables 2250 and 2254 extend through the proximal mounting bushing 2750, the proximal end 2214 of the elastomeric joint assembly 2210, as well as a central rib segment 2218 to be secured to the distal end 2212 of the elastomeric joint assembly 2210 or other portion of the surgical end effector. The cables 2242, 2246, 2250, and 2254 operably interface with an articulation control system that is supported in the housing of the surgical instrument 10. For example, a proximal portion of each cable 2242, 2246, 2250, and 2254 may be spooled on a corresponding rotary spool or cable-management system 2007 (FIG. 2) in the housing portion of the surgical instrument 10 that is configured to payout and retract each cable 2242, 2246, 2250, and 2254 in desired manners. The spools/cable management system may be motor powered or manually powered (ratchet arrangement, etc.). FIG. 29 illustrates articulation of the surgical end effector 1000 through a first articulation plane relative to the elongate shaft assembly 2000. FIG. 30 illustrates articulation of the surgical end effector 1000 through a second articulation plane relative to the elongate shaft assembly 2000. FIG. 31 illustrates articulation of the surgical end effector 1000 through multiple articulation planes relative to the elongate shaft assembly 2000.

Figure 32:
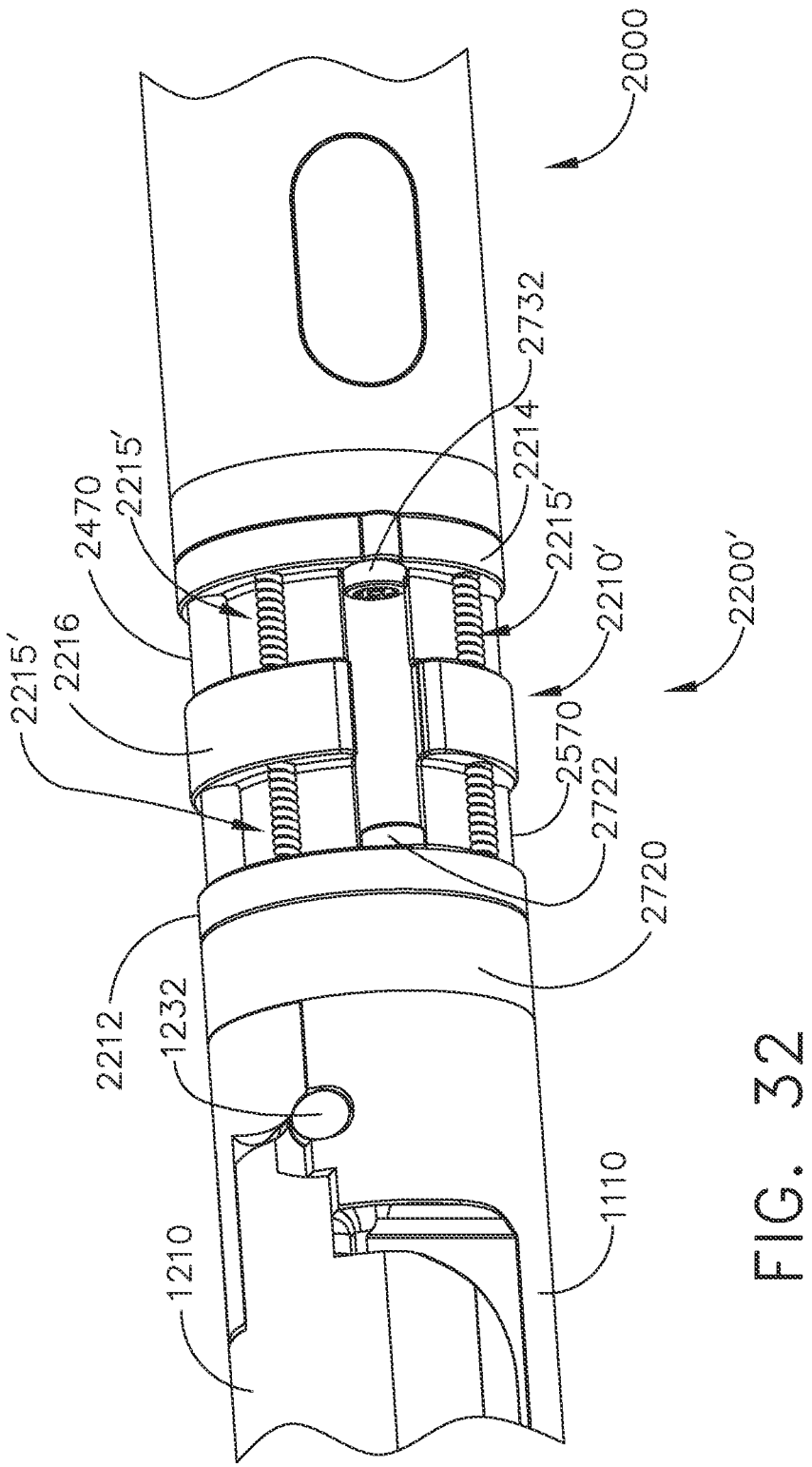
FIG. 32 is a side elevational view of a portion of another surgical instrument that employs another outer elastomeric joint assembly in accordance with at least one aspect of the present disclosure.
Figure 33:
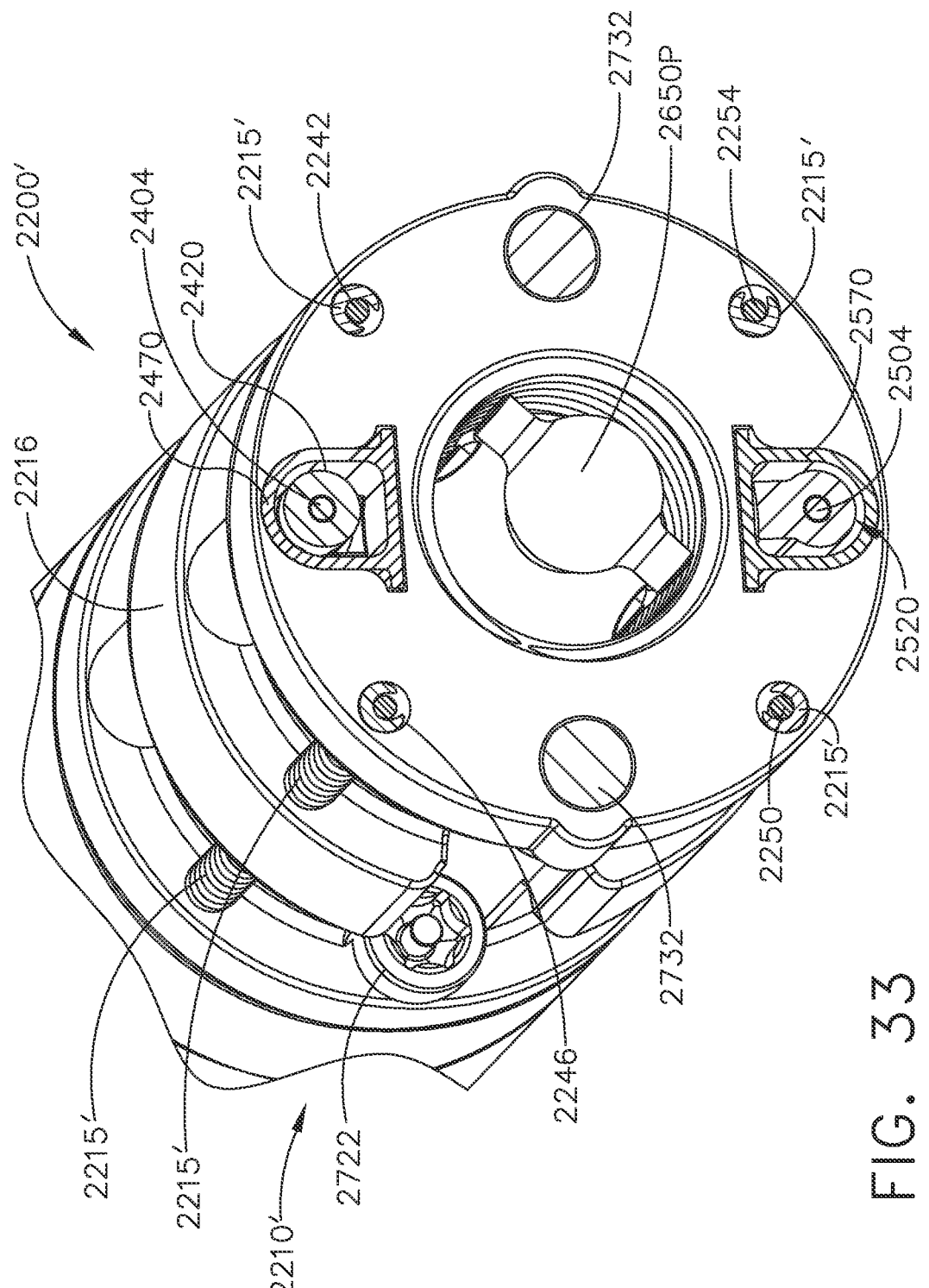
FIG. 33 is a partial cross-sectional perspective view of the surgical instrument of FIG. 32.
Figure 34:
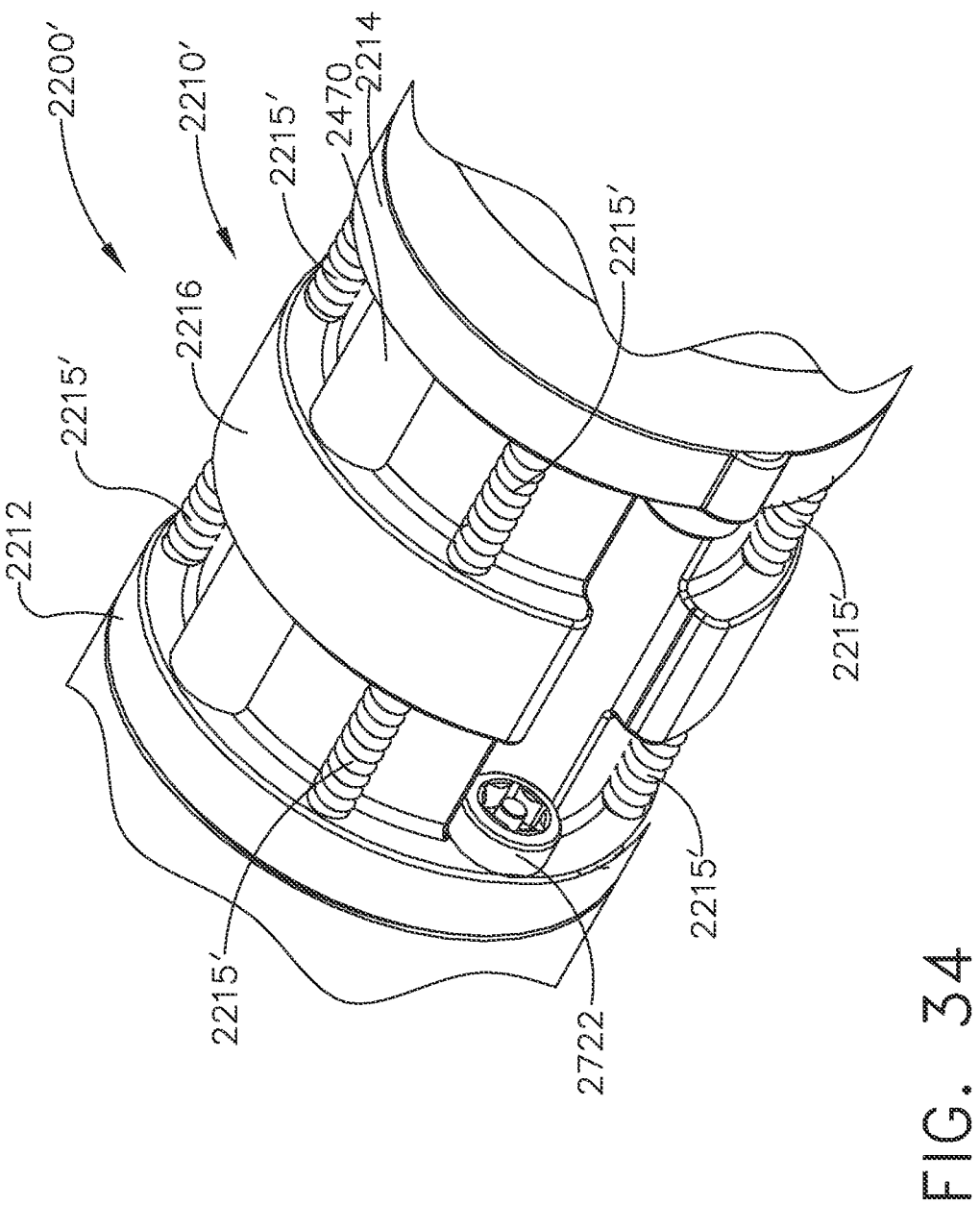
FIG. 34 is a perspective view of a portion of the outer elastomeric joint assembly of FIG. 32.

FIGS. 32-34 illustrate an alternative articulation joint 2200' in the form of an elastomeric joint assembly 2210'. As can be seen in FIG. 33, each articulation cable passes through a corresponding spring 2215' that is mounted in the ribs 2216' of the elastomeric joint assembly 2210'. For example, cable 2242 extends through spring 2244. Cable 2246 extends through spring 2248. Cable 2250 extends through spring 2252 and cable 2254 extends through spring 2256. As indicated above, the end effector is articulated by pulling on and relaxing the appropriate cables 2242, 2246, 2250 and 2254. To achieve higher articulation angles with greater joint stability, each of the springs 2244, 2248, 2252, and 2256 can slide through the ribs of the elastomeric joint to push the end effector and pull on the cables extending therethrough. The springs 2244, 2248, 2252, and 2256 will also retract into the ribs when the cables 2242, 2246, 2250, and 2254 are pulled tight. Each of the springs 2244, 2248, 2252, and 2256 loosely seat over the particular cable that passes therethrough. Each cable and corresponding spring may terminate or otherwise be coupled to a corresponding solid rod that is supported in the elongate shaft assembly 2000 and may be pushed and pulled from its proximal end. When the cable is pulled, the corresponding spring would carry little to no load. When the spring is pushed, the cable would carry little load, but will help limit the end effector movement. This interaction between the cable and spring may facilitate higher articulation angles that may approach ninety degrees, for example.

Figure 28:
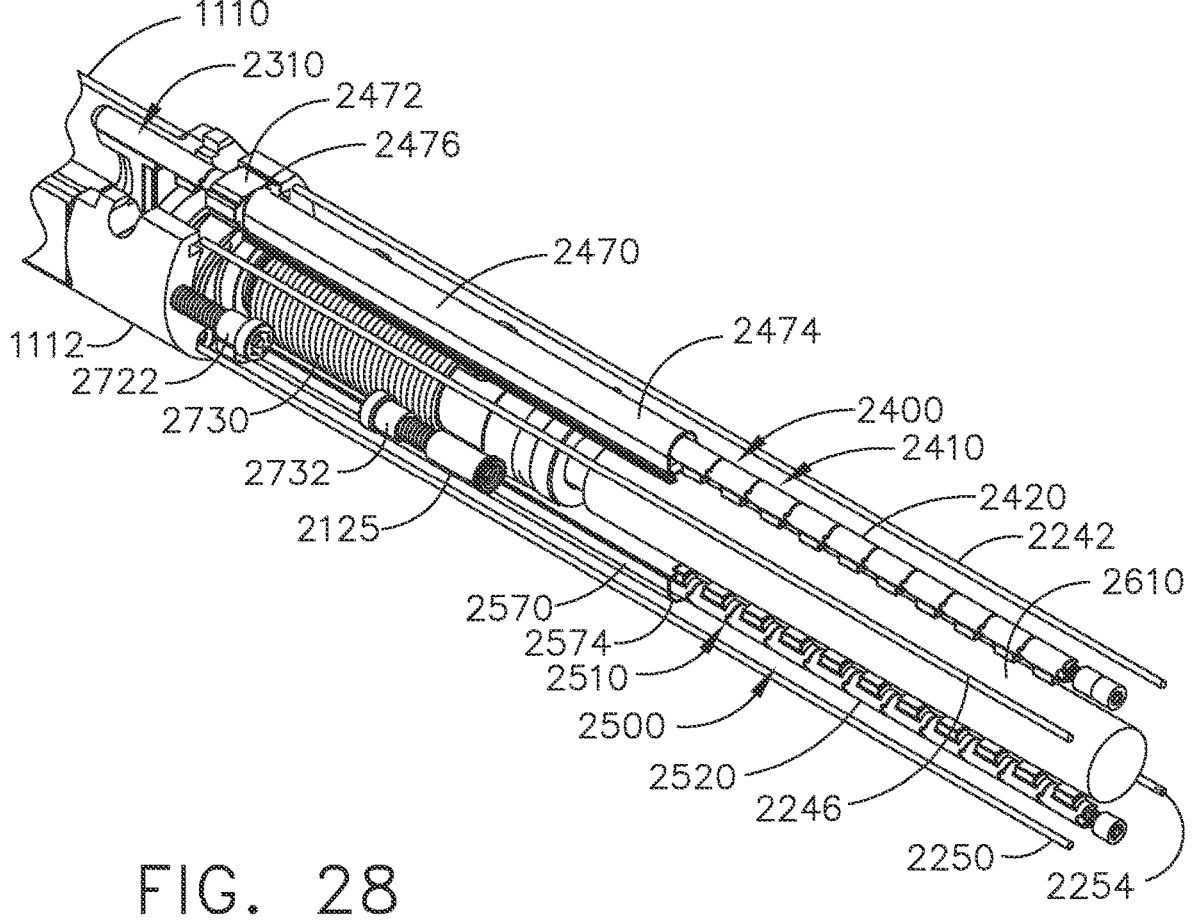
FIG. 28 is another partial perspective view of a portion of the surgical end effector, firing system and rotary drive system of FIG. 27 with an outer elastomeric joint assembly of an articulation joint and portions of the elongate shaft assembly omitted for clarity.
Figure 35:
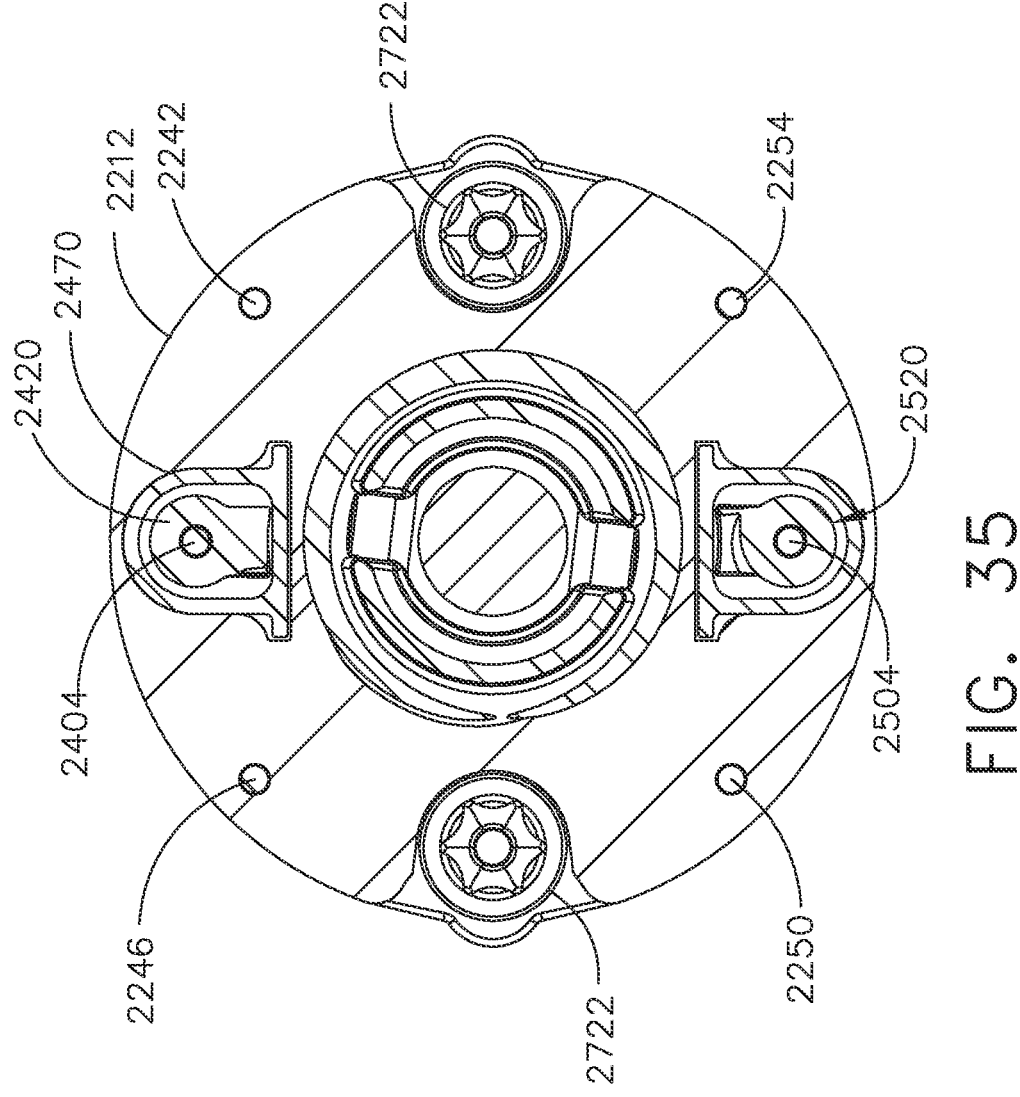
FIG. 35 is a cross-sectional end view of a portion of the surgical instrument of FIG. 19 taken along lines 35-35 in FIG. 19.

Because the radially/longitudinally segmented power screw nut arrangement disclosed herein does not have the same constraints as a three hundred sixty degree nut, the upper vertebra members 2420 in the upper series 2410 and the lower vertebra members 2520 in the lower series 2510 are constrained to ensure that their loads are transferred to the firing member in a longitudinal direction. To maintain each of the upper vertebra members 2420 in the desired orientation and to prevent the upper vertebra members 2420 from becoming snagged or disoriented when traversing through the articulation joint 2200, the upper vertebra members 2420 are aligned to pass through an upper sleeve 2470 that extends through an upper portion of the outer elastomeric joint assembly 2210 of the articulation joint 2200. See FIGS. 27, 28, and 35. A distal end 2472 of the upper sleeve 2470 is supported in the proximal end 1112 of the elongate channel 1110 and a proximal end 2474 of the upper sleeve 2470 is supported in the distal end of the proximal support shaft 2120. The upper sleeve 2470 is fabricated from a polymer or plastic material that has a low coefficient of friction and is flexible to enable the upper sleeve 2470 to flex with the outer elastomeric joint assembly 2210. The upper sleeve 2470 protects the upper vertebra members 2420 from contacting the outer elastomeric joint assembly 2210 that is fabricated from an elastomeric material that may have a higher coefficient of friction than the coefficient of friction of the material of the upper sleeve 2470. Stated another way, the upper sleeve 2470 forms a low friction, flexible, continuous, uninterrupted, and fully encapsulating path for the upper vertebra members 2420 as they traverse the articulation joint 2200.

Similarly, a lower sleeve 2570 is employed to support the lower vertebra members 2520 as they pass through the articulation joint 2200. A distal end 2572 of the lower sleeve 2570 is supported in the proximal end of the elongate channel and a proximal end of the lower sleeve 2570 is supported in the distal end of the proximal support shaft 2120. Like the upper sleeve 2470, the lower sleeve 2570 is fabricated from a polymer or plastic material that has a low coefficient of friction and is flexible to enable the lower sleeve 2570 to flex with the outer elastomeric joint assembly 2210. The lower sleeve 2570 protects the lower vertebra members 2520 from contacting the outer elastomeric joint assembly 2210 as they pass through the articulation joint 2200. Stated another way, the lower sleeve 2570 forms a low friction, flexible, continuous, uninterrupted, and fully encapsulating path for the lower vertebra members 2520 as they traverse the articulation joint 2200. In various embodiments, the upper sleeve 2470 and the lower sleeve 2570 are configured to bend freely without creating a kink. To prevent the formation of kinks in the sleeves, in at least one arrangement, the sleeves 2470, 2570 are supported within the outer elastomeric joint assembly 2210 such that the sleeves may move axially. For example, when the articulation joint angles up, the lower sleeve 2570 may slide distally and have a large bend radius; the upper sleeve 2470 in the same example, may slide proximally and have a tighter bend radius. By moving axially, the amount of material exposed outside of the joint assembly 2210 which might otherwise be susceptible to kinking under a tight bend radius is reduced. In at least one arrangement, the distal end 2472 of the upper sleeve 2470 is formed with an upper scoop 2476 that is configured to funnel the upper vertebra members 2420 into the anvil cap 1260. Similarly, the distal end of the lower sleeve 2570 may be formed with a lower scoop that is configured to funnel the lower vertebra members 2520 into the channel slot 1140 in the elongate channel 1110.

Figure 36:
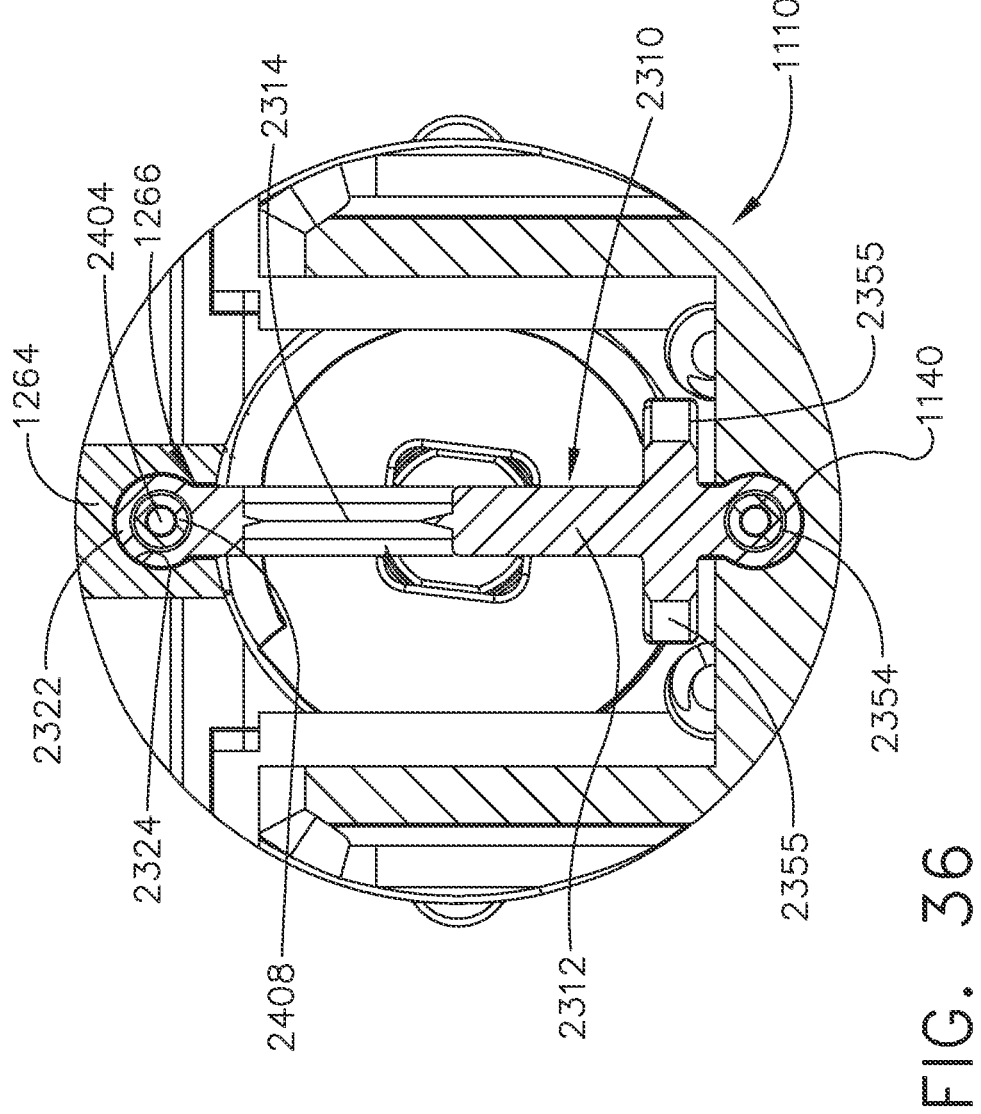
FIG. 36 is a cross-sectional end view of a portion of the surgical instrument of FIG. 19 taken along lines 36-36 in FIG. 19.
Figure 37:
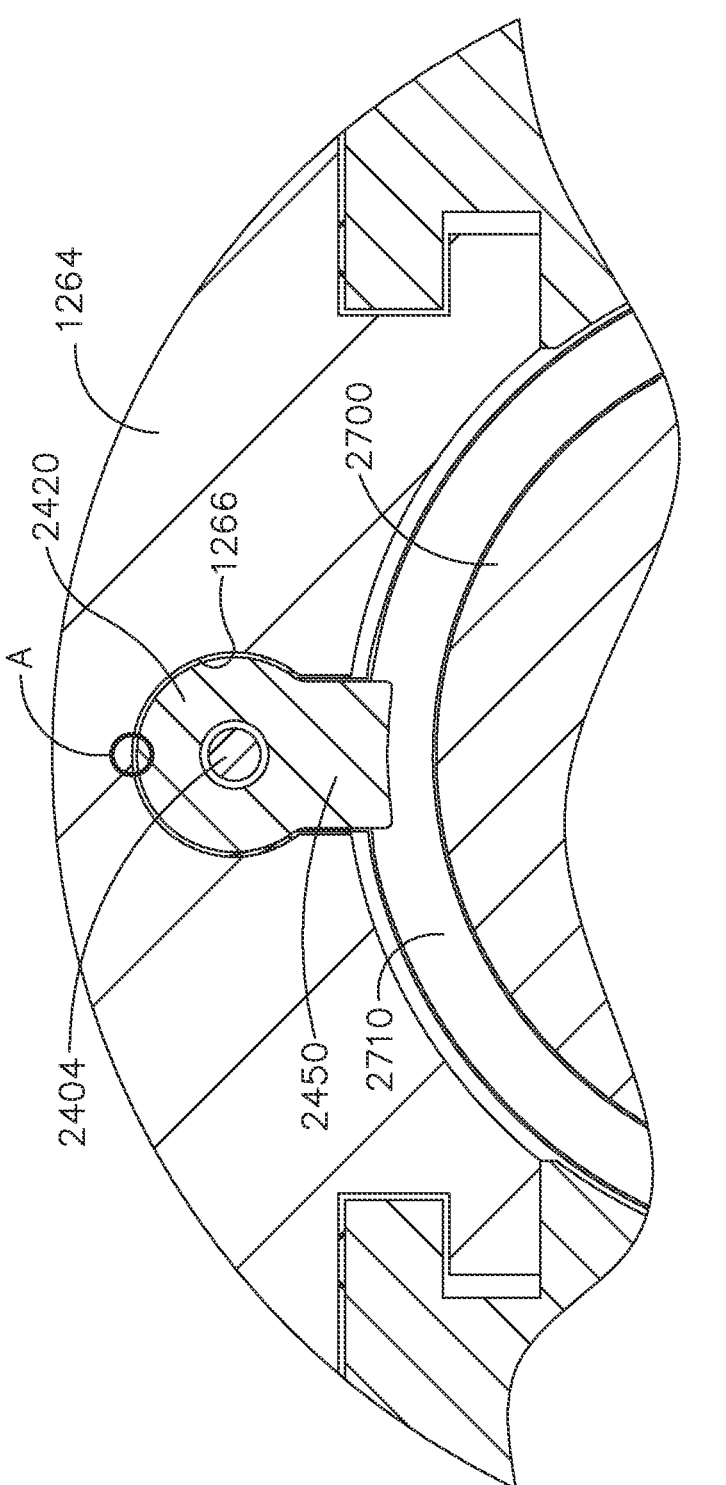
FIG. 37 is a partial cross-sectional view of a portion of an anvil cap and an upper vertebra member of the surgical instrument of FIG. 19 in accordance with at least one aspect of the present disclosure.

As indicated above, the anvil mounting portion 1230 comprises a pair of laterally extending mounting pins 1232 that are configured to be received in corresponding mounting cradles or pivot cradles 1120 that are formed in the proximal end 1112 of the elongate channel 1110. The mounting pins 1232 are pivotally retained within the mounting cradles 1120 by an anvil cap 1260 that is attached to the proximal end 1112 of the elongate channel 1110 in the above-described manners. The anvil cap 1260 comprises a proximal end 1262 and a distal end 1264 and has a keyhole-shaped vertebra passage 1266 extending therethrough to accommodate passage of the top firing member feature 2320 and upper vertebra members 2420 therethrough. FIG. 36 illustrates the vertebra passage 1266 in the anvil cap 1260. When the rotary drive screw 2700 applies load to the upper vertebra members 2420, the vertebra members 2420 will tend to tilt about the area A in FIG. 37, so the upper vertebra member tooth 2450 is no longer square with the rotary drive screw 2700 and may instead experience a higher-pressure line contact. Areas B in FIG. 37 show where the upper vertebra member 2420 stops tilting. To ensure that most of the loads stay in the longitudinal direction to perform useful work, the upper vertebra member tooth 2450 must be angled the same amount as the upper vertebra member 2420 tilts. Thus, when the upper vertebra member 2420 tilts, the upper vertebra member tooth 2450 will still maintain surface contact with the helical drive member 2710 on the rotary drive screw 2700 and all loads will be directed longitudinally and not vertically. The slightly angled upper vertebra member tooth 2450 may behave like a square thread when the vertebra member 2420 is tilted and better distributes loads to lower the pressure contact. By directing most of the loads in the longitudinal direction, vertical loads are avoided which could result in the establishment of friction that would counter the longitudinal loads. The upper vertebra members 2420 react similarly as they pass down the keyhole-shaped anvil slot 1240. Likewise, the lower vertebra members 2520 react similarly as they pass through the keyhole-shaped axially extending channel slot 1140 in the elongate channel 1110.

Figure 38:
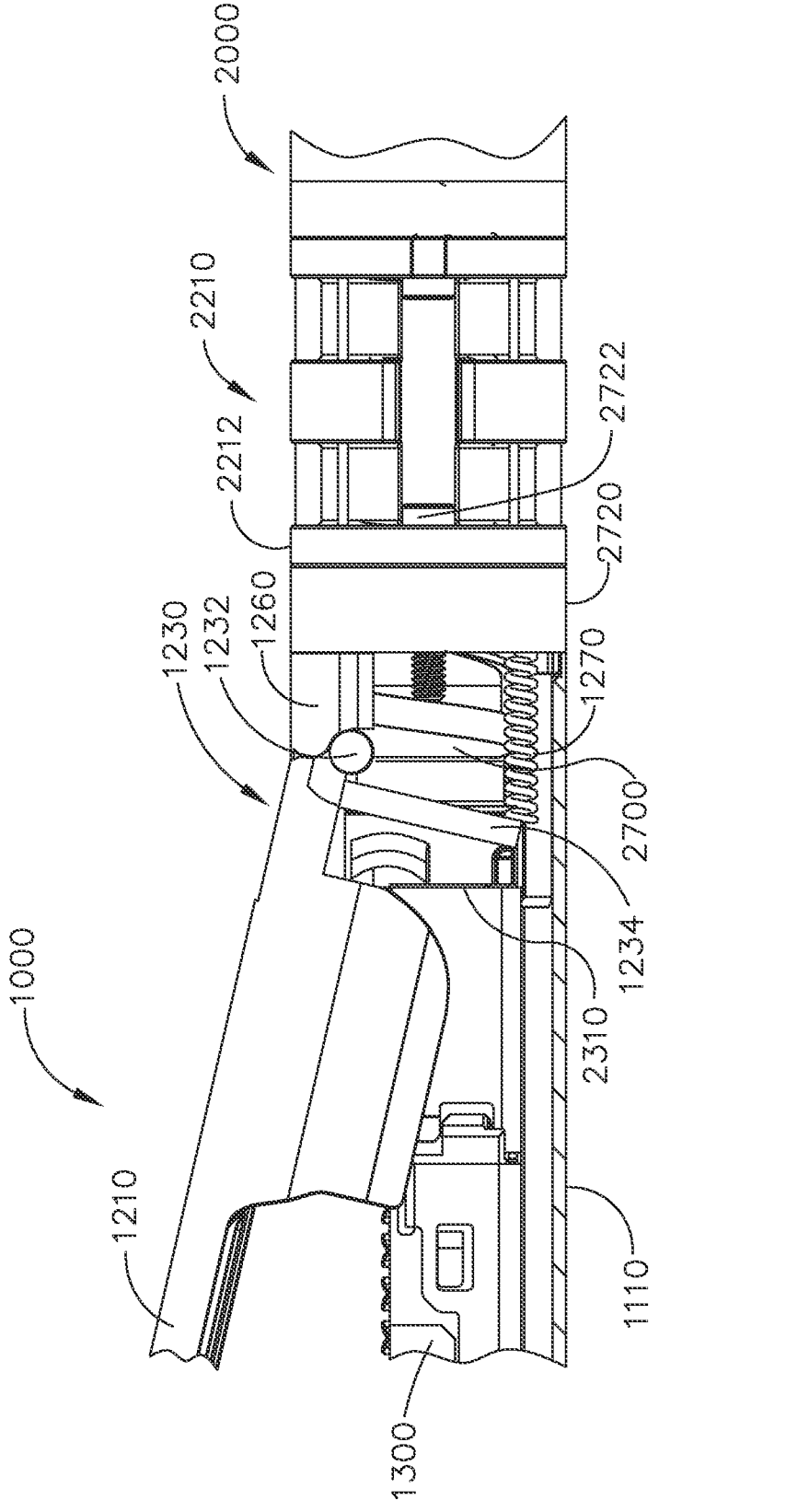
FIG. 38 is a side view of a portion of the surgical end effector of the surgical instrument of FIG. 19 with an anvil thereof in an open position in accordance with at least one aspect of the present disclosure and with portions of the surgical end effector omitted for clarity.
Figure 43:
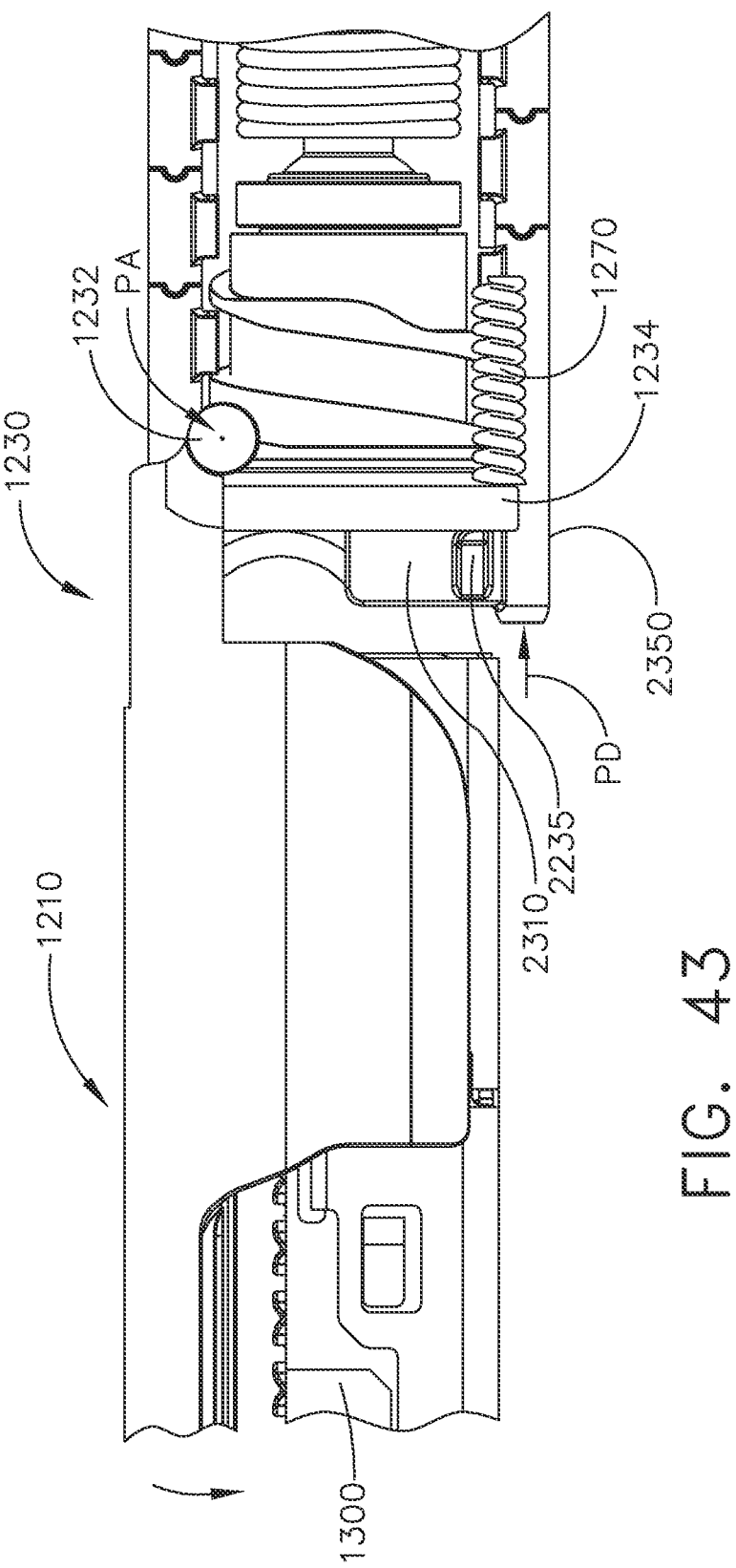
FIG. 43 is another partial side view of the surgical end effector of FIG. 42, after the firing member has moved proximally a short distance to apply a quick closure motion to the anvil for grasping purposes.

In the illustrated arrangement, the anvil 1210 is moved to the open position by a pair of anvil springs 1270 that are supported within the proximal end of the elongate channel. See FIGS. 38, 42, and 43. The springs 1270 are positioned to apply a pivotal biasing force to corresponding anvil control arms 1234 that may be integrally formed with anvil mounting portion 1230 and extend downwardly therefrom. See FIG. 38.

Figures 39, 40, 41:
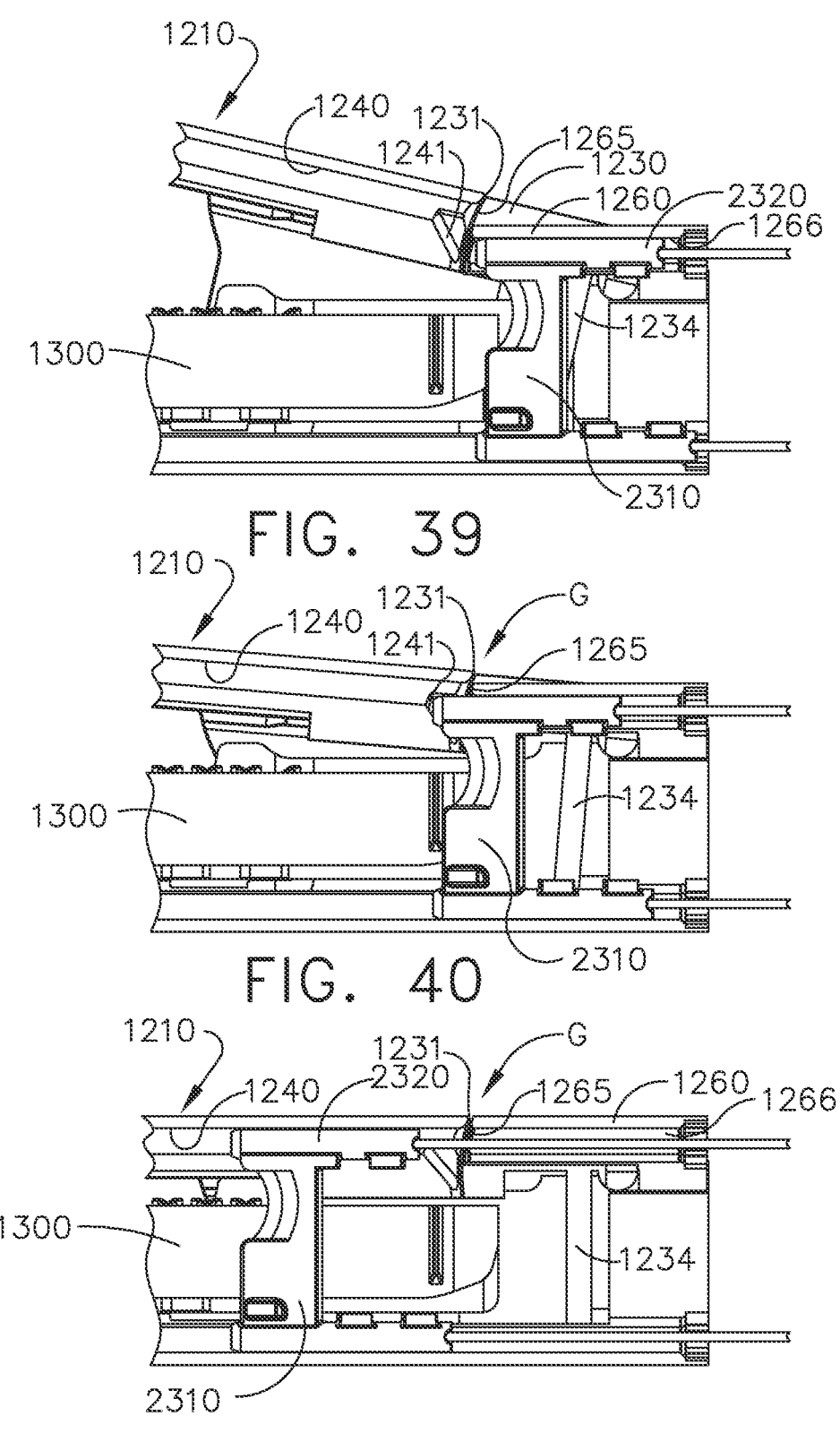
FIG. 39 is a partial cross-sectional side view of the surgical end effector of FIG. 38 with the anvil in an open position and the firing member in the home or starting position in accordance with at least one aspect of the present disclosure.
FIG. 40 is another partial cross-sectional side view of the surgical end effector of FIG. 39 with the anvil in a partially closed position.
FIG. 41 is another partial cross-sectional side view of the surgical end effector of FIG. 39 with the anvil in a fully closed position and the firing member distally advancing through the surgical end effector.

FIGS. 39-41 illustrate portions of the anvil 1210, the firing member 2310, and the anvil cap 1260 when the anvil 1210 is open (FIG. 39), when the anvil 1210 is partially closed (FIG. 40) and after the firing member has been advanced distally from the home or starting position (FIG. 41). As can be seen in FIG. 39, when the firing member 2310 is in the home or starting position, the top firing member feature 2320 is completely received within the vertebra passage 1266 in the anvil cap 1260. During a firing stroke, the top firing member feature 2320 and the upper vertebra members 2420 in the upper series 2410 must transition from the vertebra passage 1266 in the anvil cap 1260 to the keyhole-shaped anvil slot 1240. Thus, it is desirable to minimize any gap "G" between the anvil mounting portion 1230 and a distal end 1264 of the anvil cap 1260. To minimize this gap G while facilitate unimpeded pivotal travel of the anvil 1210, the distal end 1264 of the anvil cap 1260 is formed with a curved cap surface 1265 that matches a curved mating surface 1231 on the anvil mounting portion 1230. Both surfaces 1265, 1231 are curved and concentric about the pivot axis PA or some other reference point. Such arrangement allows the anvil 1210 to move radially and not interfere with the anvil cap 1260 while maintaining a minimal gap G therebetween. The gap G between the anvil mounting portion 1230 and the distal end 1264 of the anvil cap 1260 is significantly shorter than a length of an upper vertebra member 2420 which facilitates easy transition of each upper vertebra member 2420 from the vertebra passage 1266 in the anvil cap 1260 to the keyhole-shaped anvil slot 1240. In addition, to further assist with the transition of the top firing member feature 2320 into the keyhole-shaped anvil slot 1240, a ramped surface 1241 is formed adjacent the curved mating surface 1231 on the anvil mounting portion 1230. As the firing member 2310 is initially advanced distally from the home or starting position, a distal end of the top firing member feature 2320 contacts the ramped surface 1241 and begins to apply a closing motion to the anvil 1210 as can be seen in FIG. 40. Further distal advancement of the firing member 2310 during the firing stroke or firing sequence causes the top firing member feature to enter the keyhole shaped anvil slot 1240 to completely close the anvil 1210 and retain the anvil 1210 in the closed position during the firing sequence. See FIG. 41.

Figure 15:
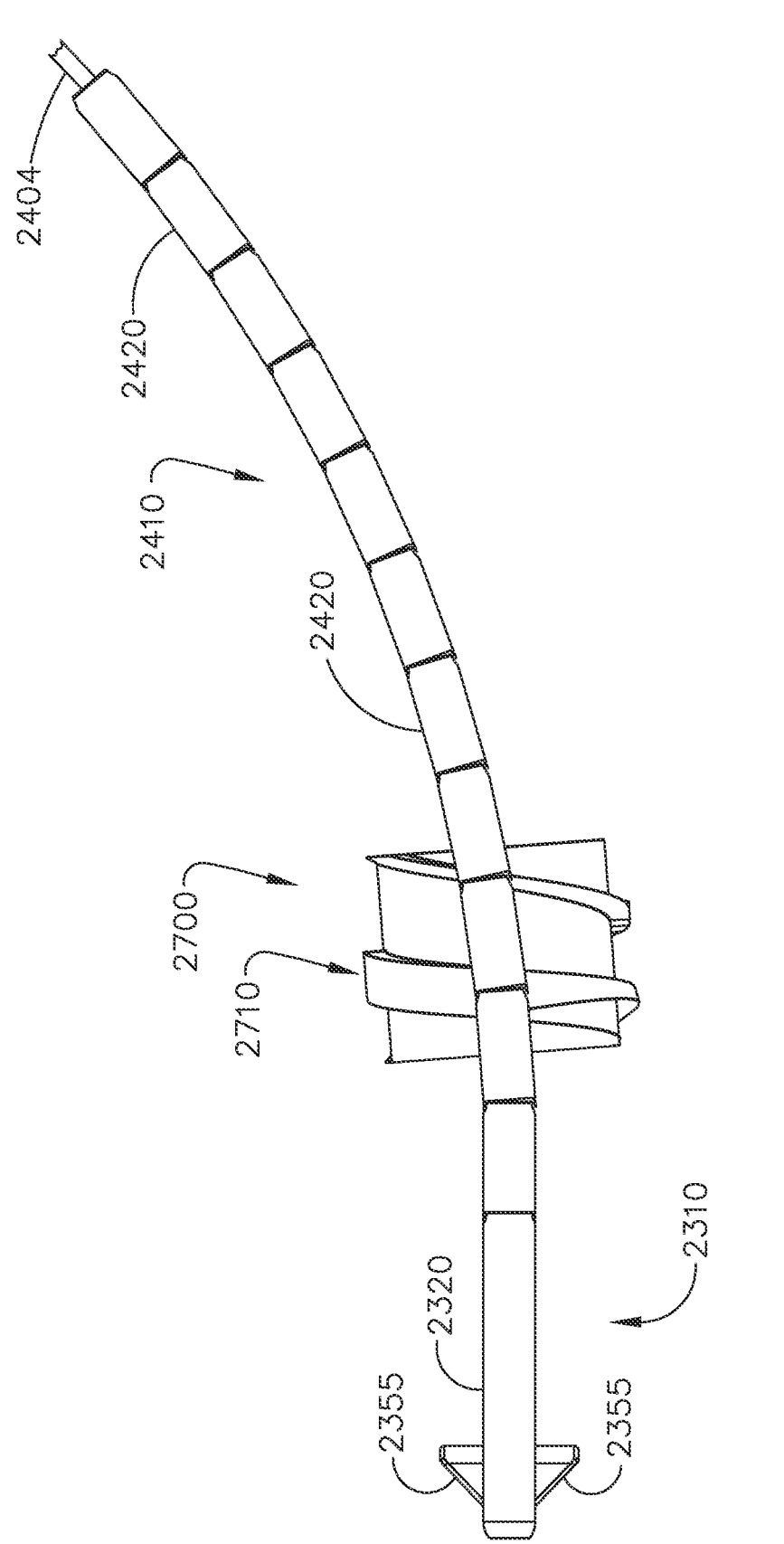
FIG. 15 is a top view of a firing member and upper and lower flexible spine assemblies in engagement with the rotary drive screw of FIG. 9.

In general, the highest firing forces established in an endocutter are associated with cutting and stapling tissue. If those same forces can be used to close the anvil, then the forces generated during pre-clamping and grasping of tissue can be high as well. In at least one arrangement, the firing member body 2312 further comprises a firing member wing or tab 2355 that extends laterally from each lateral side of the firing member body 2312. See FIGS. 15 and 36. The firing member wings 2355 are positioned to contact the corresponding anvil control arms 1234 when the firing member 2310 is driven in the proximal direction PD from the home or starting position to quickly close the anvil 1210 for grasping purposes. In at least one arrangement, when the firing member 2310 is in the home or starting position, the firing member wings 2355 are located distal to the anvil control arms 1234 as shown in FIG. 42. When the firing member 3210 is moved proximally, the firing member wings 2355 push the anvil control arms 1234 (pivotal direction C) against the bias of the anvil springs 1270. See FIG. 42. In one arrangement, the firing member 2310 only has to move a short distance D to pivot the anvil 1210 to a closed position. In one embodiment, distance D may be approximately 0.070 inches long, for example. This short movement allows for a quick response. Because the anvil pivot point or pivot axis PA is relatively far from the firing member wings 2355 which creates a substantial moment arm, the proximal movement of the firing member 2310 (and firing member wings 2355) results in an application of high pre-compression torque to the anvil 1210 to move the anvil 1210 to a closed position. Thus, the firing member wings 2355 may be referred to herein as "pre-compression features". See FIG.

43. Thus, the clinician may use the surgical end effector 1000 to grasp and manipulate tissue between the anvil 1210 and the surgical staple cartridge 1300 without cutting the tissue and forming the staples, by advancing the firing member 2310 proximally the short distance D to cause the anvil 1210 to quickly pivot to a closed position.

The firing member 2310 may be moved in the proximal direction PD by rotating the rotary drive screw 2700 in a second rotary direction. Thus, when the firing member 2310 is in the "home" or starting position, the anvil 1210 may be biased into the fully open position by the anvil springs 1270. Activation of the rotary drive system 2600 to apply a rotary motion to the rotary drive screw 2700 in a first rotary direction will cause the firing member 2310 to be advanced distally from the home or starting position to apply an anvil closure motion to the anvil 1210 to move the anvil closed to clamp the target tissue between the anvil 1210 and the surgical staple cartridge 1300. Continued rotation of the rotary drive screw in the first rotary direction will cause the firing member 2310 to continue to distally advance through the surgical end effector 1000. As the firing member 2310 moves distally, the firing member 2310 contacts a sled 1312 (FIG. 19) that is supported in the surgical staple cartridge 1300 and drives the sled 1312 distally through the staple cartridge body 1302. When the firing member 2310 is in the home or starting position, the surgeon may wish to use the surgical end effector to grasp and manipulate tissue. To do so, the rotary drive system is actuated to apply a second rotary drive motion to the rotary drive screw 2700 in a second rotary direction that is opposite to the first rotary direction. Such rotary movement of the rotary drive screw 2700 in the second rotary direction will drive the firing member 2310 proximally from the starting position and cause the anvil 1210 to quickly pivot to the closed position. Thus, in accordance with at least one embodiment, the "home or starting position" of the firing member 2310 is not its proximal-most position.

If during the firing process, the rotary drive system 2600 quits rotating, the firing member 2310 may become stuck within the surgical end effector. In such instance, the top firing member feature 2320 may remain engaged with the anvil 1210 and the bottom firing member feature 2350 may remain engaged with the elongate channel 1110 and thereby prevent the surgeon from moving the anvil 1210 to an open position to release the tissue clamped between anvil 1210 and surgical staple cartridge 1300. This could occur, for example, if the motor or other control arrangement supplying the rotary drive motions to the rotary drive shaft 2610 fails or otherwise becomes inoperative. In such instances, the firing member 2310 may be retracted back to the home or starting position within the surgical end effector 1000 by pulling the top cable 2404 and the lower cable 2504 in a proximal direction. For example, a proximal portion of the top cable 2404 and a proximal portion of the lower cable 2505 may be spooled on a rotary spool or cable-management system 2009 (FIG. 2) in the housing portion of the surgical instrument 10 that is configured to payout the top cable 2404 and lower cable 2504 during the firing stroke and also retract the cables 2404, 2504 in a proximal direction should the firing member 2310 need to be retracted. The cable management system 2009 may be motor powered or manually powered (ratchet arrangement, etc.) to apply retraction motions to the cables 2404, 2504. When the cables 2404, 2504 are retracted, the upper vertebra members 2420 and lower vertebra members 2520 will cause the rotary drive screw 2700 to spin in reverse.

US 12,611,211 B2

29 / 30

The following equation may be used to determine whether the rotary drive screw 2700 will spin in reverse depending upon the lead (L), pitch diameter ($d_p$), tooth angle ($\alpha$) and friction ($\mu$): $\mu \geq L\_\cos \alpha$ $$\pi d_p$$

The rotary drive screw 2700 may self-lock if the above equation is true. For the most part, in many instances, the pitch diameter is mostly fixed for an endocutter, but the lead and tooth angle are variable. Because the upper vertebra member teeth 2450 and lower vertebra member teeth 2550 are mostly square, the rotary drive screw 2700 is more likely to be back drivable (cos (90)=1). The leads of the upper vertebra member teeth 2450 and lower vertebra member teeth 2550 may also be advantageous in that the rolling friction between the vertebra members 2420, 2520 and the rotary drive screw 2700 is more likely to enable the rotary drive screw 2700 to be back driven. Thus, in the event of an emergency, the surgeon can pull on the upper and lower cables 2404, 2504 in the proximal direction to cause the firing member 2310 to fully retract for a quick "bailout".

As indicated above, the relative control motions for the rotary drive system 2600, as well as the various cable-management systems employed in connection with the firing system 2300 and the articulation control system 2240, may be supported within a housing 2002 which may be handheld or comprise a portion of a larger automated surgical system. The firing system 2300, articulation control system 2240, and the rotary drive system 2600 may, for example, be motor-controlled and operated by one or more control circuits.

Figure 44:
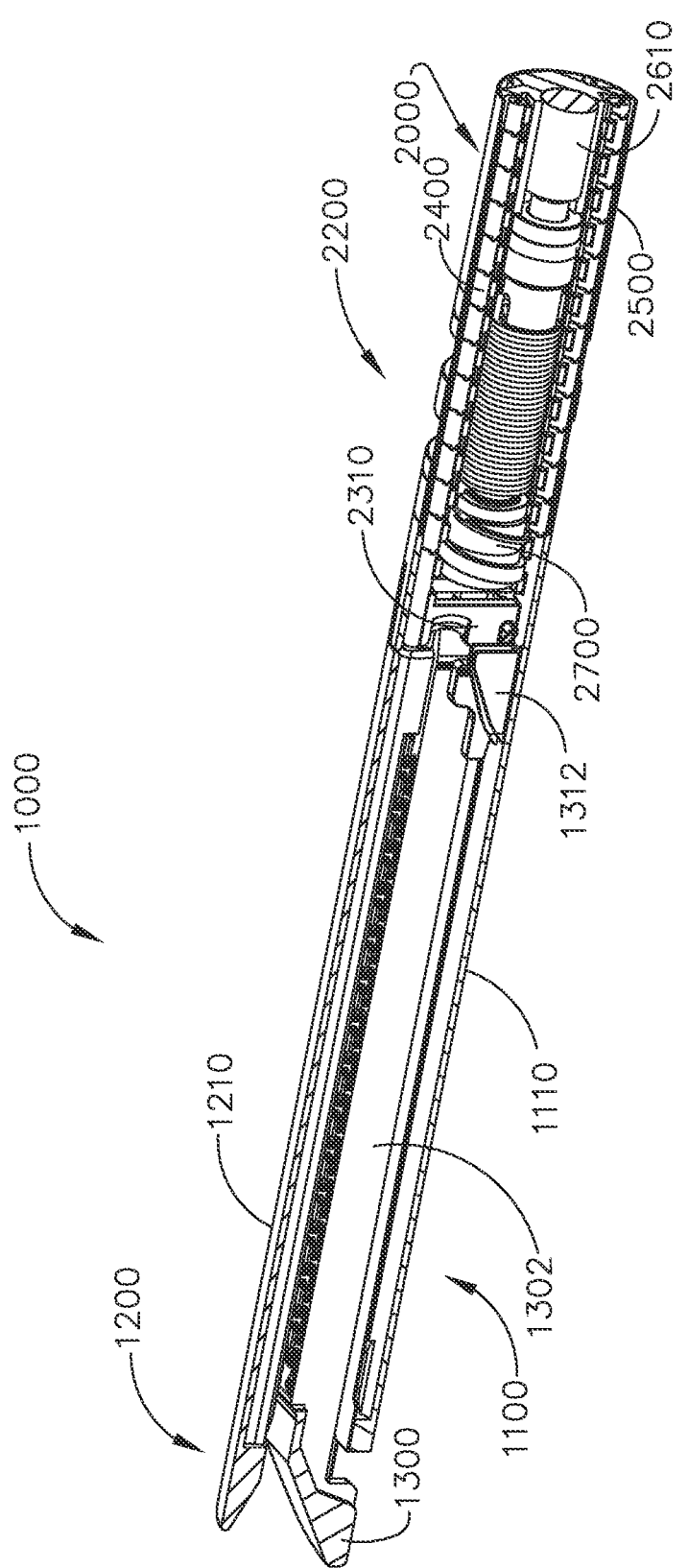
FIG. 44 is a cross-sectional view of the surgical end effector of FIG. 19 with the jaws thereof in a closed position and the firing member thereof in a proximal-most position.

One method of using the surgical instrument 10 may involve the use of the surgical instrument 10 to cut and staple target tissue within a patient using laparoscopic techniques. For example, one or more trocars may have been placed through the abdominal wall of a patient to provide access to a target tissue within the patient. The surgical end effector 1000 may be inserted through one trocar and one or more cameras or other surgical instruments may be inserted through the other trocar(s). To enable the surgical end effector 1000 to pass through the trocar cannula, the surgical end effector 1000 is positioned in an unarticulated orientation and the jaws 1100 and 1200 must be closed. To retain the jaws 1100 and 1200 in the closed position for insertion purposes, for example, the rotary drive system 2600 may be actuated to apply the second rotary motion to the rotary drive screw 2700 to cause the firing member 2310 to move proximally from the starting position to move the anvil 1210 (jaw 1200) to the closed position. See FIG. 44. The rotary drive system 2600 is deactivated to retain the firing member 2310 in that position. Once the surgical end effector has passed into the abdomen through the trocar, the rotary drive system 2600 may be activated to cause the rotary drive screw 2700 to drive the firing member 2310 distally back to the starting position wherein the anvil springs 1270 will pivot the anvil 1210 to the open position. See FIG. 38.

Once inside the abdomen and before engaging the target tissue, the surgeon may need to articulate the surgical end effector 1000 into an advantageous position. The articulation control system 2240 is then actuated to articulate the surgical end effector in one or more planes relative to a portion of the elongate shaft assembly 2000 that is received within the cannula of the trocar. Once the surgeon has oriented the surgical end effector 1000 in a desirable position, the articulation control system 2240 is deactivated to retain the surgical end effector 1000 in the articulated orientation. The surgeon may then use the surgical end effector to grasp the target tissue or adjacent tissue by activating the rotary drive system to rotate the rotary drive screw in the second rotary direction to move the firing member proximally to cause the anvil 1210 to rapidly close to grasp the tissue between the anvil 1210 and the surgical staple cartridge 1300. The anvil 1210 may be opened by reversing the rotation of the rotary drive screw 2700. This process may be repeated as necessary until the target tissue has be properly positioned between the anvil 1210 and the surgical staple cartridge 1300.

Once the target tissue has been positioned between the anvil 1210 and the surgical staple cartridge, the surgeon may commence the closing and firing process by activating the rotary drive system 2600 to drive the firing member 2310 distally from the starting position. As the firing member 2310 moves distally from the starting position, the firing member 2310 applies a closure motion to the anvil 1210 and moves the anvil 1210 from the open position to the closed position in the manners discussed above. As the firing member 2310 moves distally, the firing member 2310 retains the anvil 1210 in the closed position thereby clamping the target tissue between the anvil 1210 and the surgical staple cartridge 1300. As the firing member 2310 moves distally, the firing member 2310 contacts a sled 1312 supported in the surgical staple cartridge 1300 and also drives the sled 1312 distally through the staple cartridge body 1302. The sled 1312 serially drives rows of drivers supported in the staple cartridge toward the clamped target tissue. Each driver has supported thereon one or more surgical staples or fasteners which are then driven through the target tissue and into forming contact with the underside of the anvil 1210. As the firing member 2310 moves distally, the tissue cutting edge 2314 thereon cuts through the stapled tissue.

Figure 45:
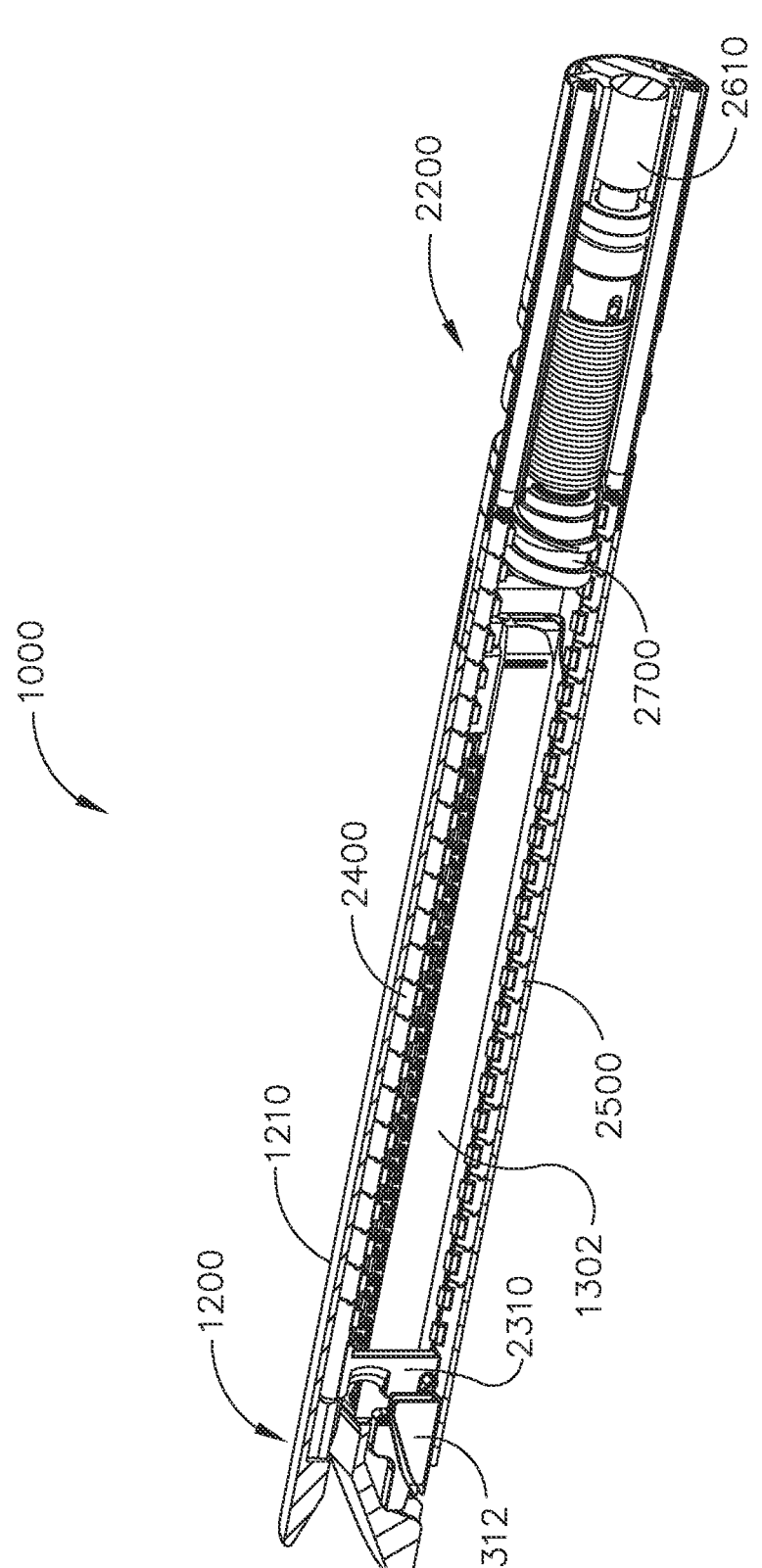
FIG. 45 is another cross-sectional view of the surgical end effector of FIG. 44, after the firing member has been distally advanced to the ending position within the surgical end effector.
Figure 46:
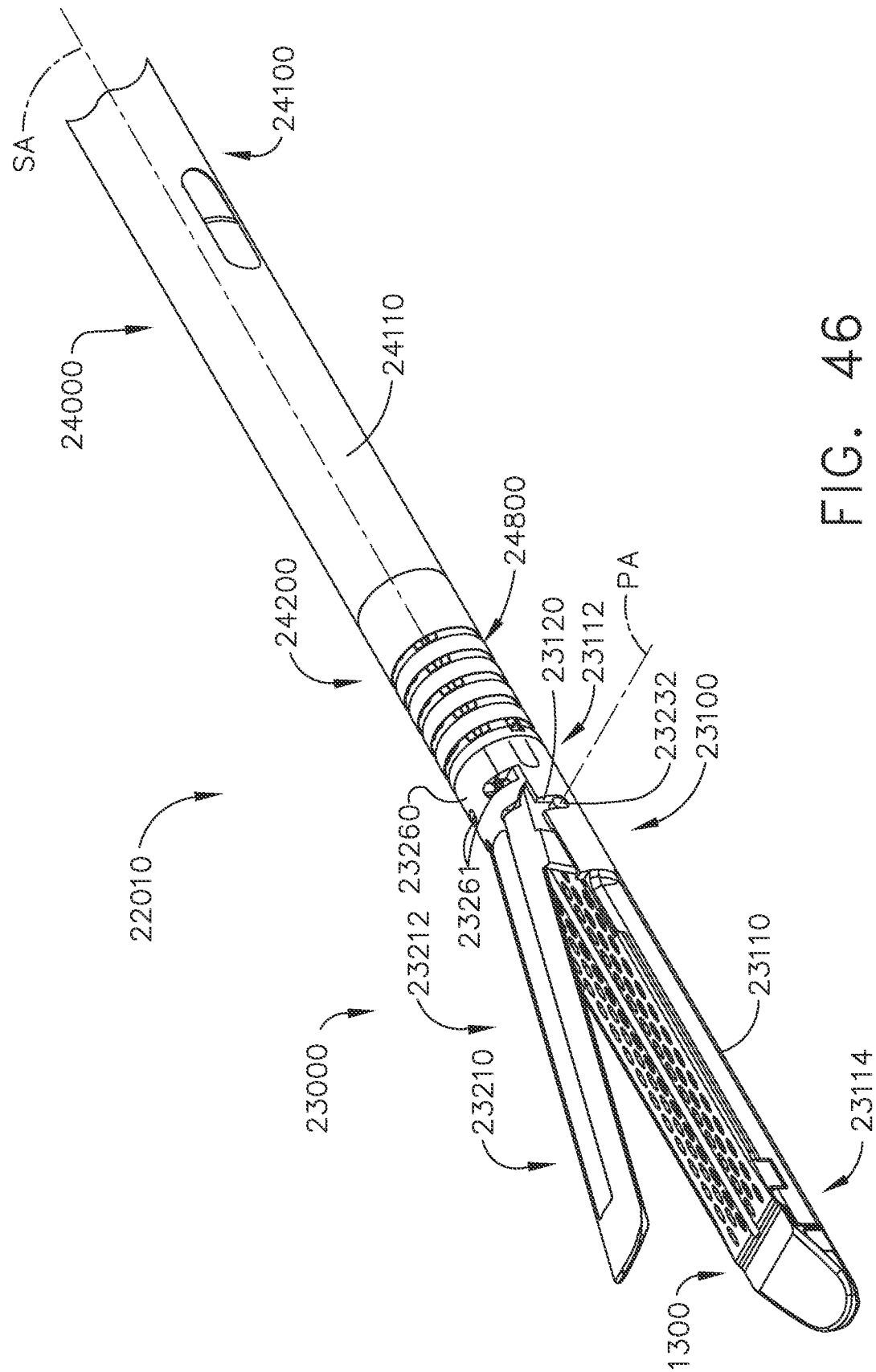
FIG. 46 is a perspective view of a portion of another surgical instrument.
Figure 47:
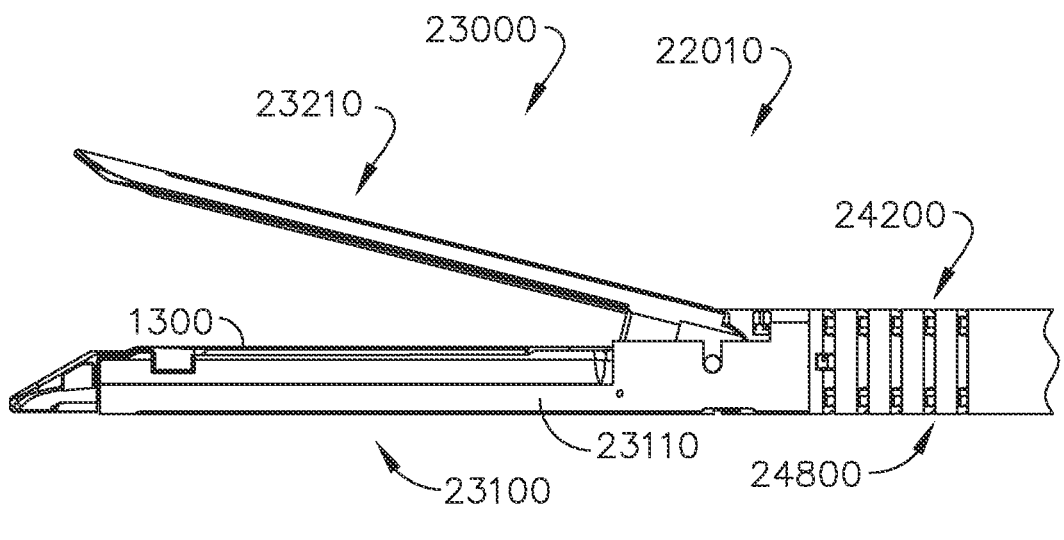
FIG. 47 is a side elevational view of a surgical end effector of the surgical instrument of FIG. 46, with the jaws thereof in an open position.

After the firing member 2310 has been driven distally to the ending position within the surgical end effector 1000 (FIG. 45), the rotary drive system 2600 is reversed which causes the firing member 2310 to retract proximally back to the home or starting position. Once the firing member 2310 has returned to the starting position, the anvil springs 1270 will pivot the anvil 1210 to the open position to enable the surgeon to release the stapled tissue from the surgical end effector 1000. Once the stapled tissue has been released, the surgical end effector may be withdrawn out of the patient through the trocar cannula. To do so, the surgeon must first actuate the articulation control system 2240 to return the surgical end effector 1000 to an unarticulated position and actuate the rotary drive system to drive the firing member 2310 proximally from the home or starting position to close the jaws. Thereafter, the surgical end effector 1000 may be withdrawn through the trocar cannula. If during the firing process or during the retraction process, the firing system becomes inoperative, the surgeon may retract the firing member 2310 back to the starting position by applying a pulling motion to the cables 2404, 2505 in the proximal direction in the various manners described herein.

FIGS. 46-68 illustrate another surgical instrument 22010 that in many aspects is identical or very similar to the surgical instrument 10 described above, except for the various differences discussed below. Like surgical instrument 10, surgical instrument 22010 may address many of the challenges facing surgical instruments with articulatable end effectors that are configured to cut and fasten tissue. In various embodiments, the surgical instrument 22010 may comprise a handheld device. In other embodiments, the surgical instrument 22010 may comprises an automated system sometimes referred to as a robotically-controlled system, for example. In various forms, the surgical instrument 22010 comprises a surgical end effector 23000 that is operably coupled to an elongate shaft assembly 24000. The elongate shaft assembly 24000 may be operably attached to a housing that is handheld or otherwise comprises a portion of a robotic system as was discussed above.

Figure 48:
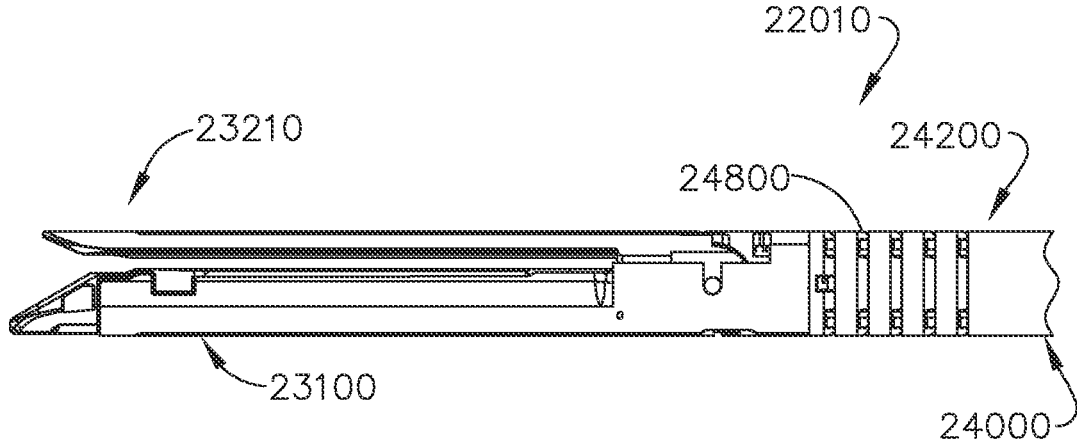
FIG. 48 is another side view of the surgical end effector of FIG. 48 with the jaws thereof in a closed position.
Figure 49:
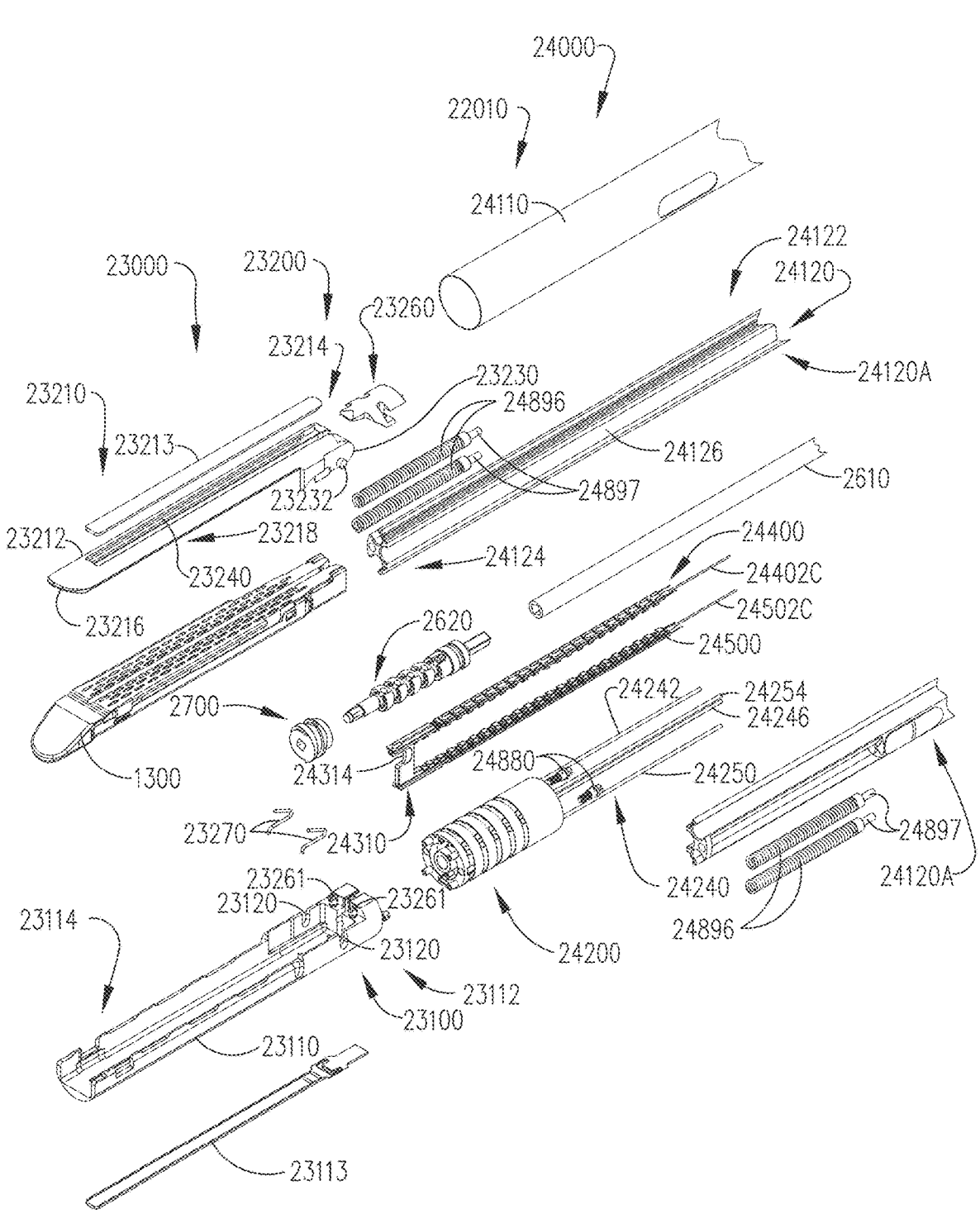
FIG. 49 is an exploded assembly view of a portion of the surgical instrument of FIG. 46.
Figure 50:
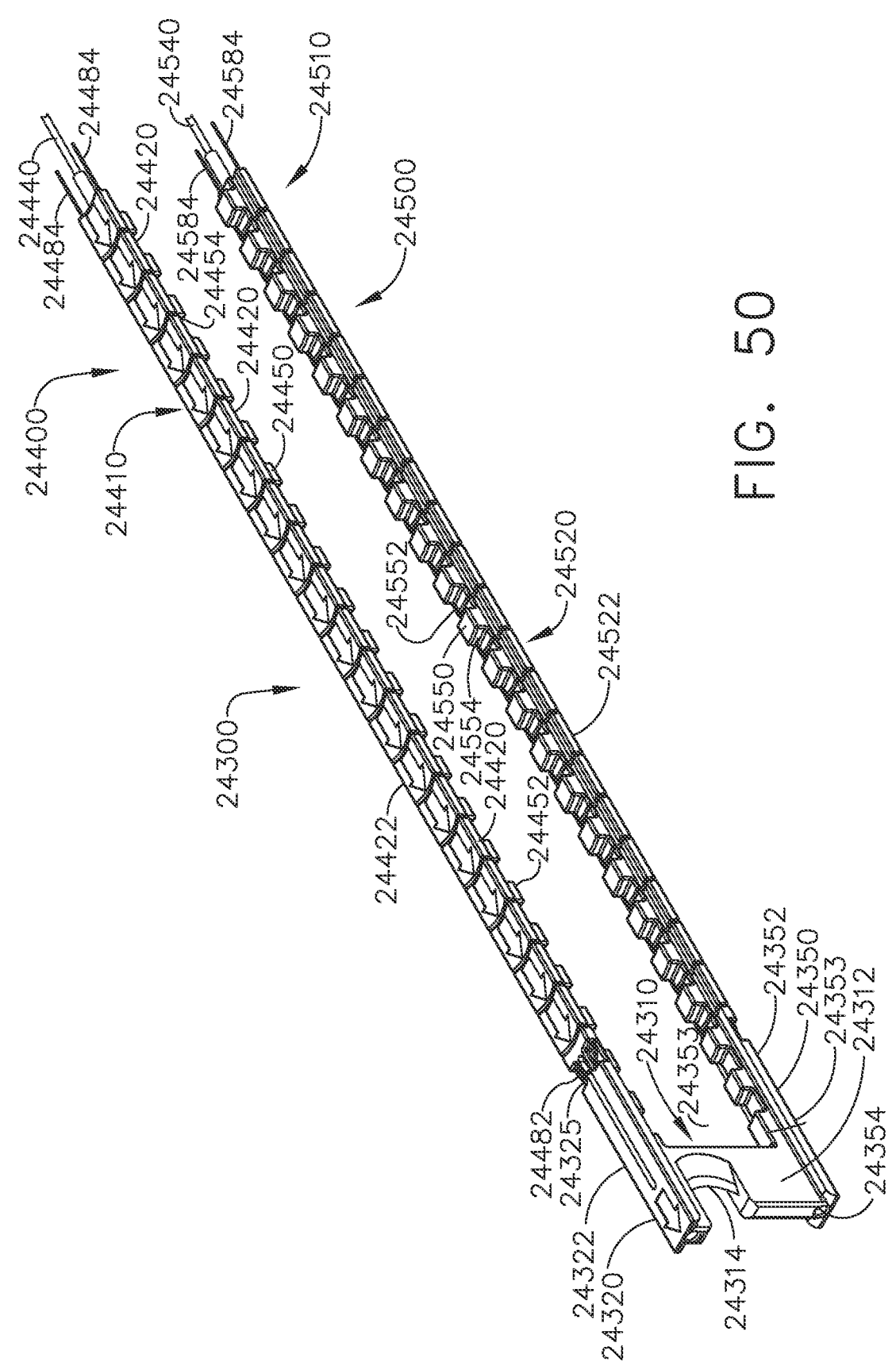
FIG. 50 is a perspective view of a firing member and portions of an upper flexible spine assembly and a lower flexible spine assembly of a firing system of the surgical instrument of FIG. 46.

As can be seen in FIG. 49, in one form, the surgical end effector 23000 comprises a first jaw 23100 and a second jaw 23200. In the illustrated arrangement, the first jaw 23100 comprises an elongate channel 23110 that comprises a proximal end 23112 and a distal end 23114 and is configured to operably support a surgical staple cartridge 1300 therein. The elongate channel 23110 has an open bottom to facilitate ease of assembly and has a channel cover 23113 that is configured to be attached thereto (welded, etc.) to cover the opening and add rigidity to the elongate channel 23110. In the illustrated arrangement, the second jaw 23200 comprises an anvil 23210 that comprises an elongate anvil body 23212 that comprises a proximal end 23214 and a distal end 23216. In one arrangement, an anvil cover 23213 is provided to facilitate assembly of the device and add rigidity to the anvil 23210 when it is attached (welded, etc.) to the anvil body 23212. The anvil body 23212 comprises a staple-forming undersurface 23218 that faces the first jaw 23100 and may include a series of staple-forming pockets (not shown) that corresponds to each of the staples or fasteners in the surgical staple cartridge 1300. The proximal end 23214 of the anvil body 23212 comprises an anvil mounting portion 23230 that includes a pair of laterally extending mounting pins 23232 that are configured to be received in corresponding mounting cradles or pivot cradles 23120 formed in the proximal end 23112 of the elongate channel 23110. The mounting pins 23232 are pivotally retained within the mounting cradles 23120 by an anvil cap 23260 that may be attached to the proximal end 23112 of the elongate channel 23110 by screws 23261. In other arrangements, the anvil cap 23260 may be attached to the elongate channel 23110 by welding, adhesive, etc. Such arrangement facilitates pivotal travel of the anvil 23210 relative to the surgical staple cartridge 1300 mounted in the elongate channel 23110 about a pivot axis PA between an open position (FIG. 47) and a closed position (FIG. 48). Such pivot axis PA may be referred to herein as being "fixed" in that the pivot axis does not translate or otherwise move as the anvil 23210 is pivoted from an open position to a closed position.

In the illustrated arrangement, the anvil 23210 is moved to the open position by a pair of anvil springs 23270 that are supported within the proximal end 23112 of the elongate channel 23110. See FIGS. 49 and 62. The springs 23270 are positioned to apply a pivotal biasing force to corresponding portions of the anvil 23210 to apply opening forces thereto. See FIG. 47.

In the illustrated arrangement, the elongate shaft assembly 24000 defines a shaft axis SA and comprises a proximal shaft portion 24100 that may operably interface with a housing of the control portion (e.g., handheld unit, robotic tool driver, etc.) of the surgical instrument 22010. The elongate shaft assembly 24000 further comprises an articulation joint 24200 that is attached to the proximal shaft portion 24100 and the surgical end effector 23000. In various instances, the proximal shaft portion 24100 comprises a hollow outer tube 24110 that may be operably coupled to a housing in the various manners discussed above. As can be seen in FIG. 49, the proximal shaft portion 24100 may further comprise a rigid proximal support shaft 24120 that is supported within the hollow outer tube 24110 and extends from the housing to the articulation joint 24200. The rigid proximal support shaft 24120 may comprise a first half 24120A and a second half 24120B that may be coupled together by, for example, welding, adhesive, etc. The rigid proximal support shaft 24120 comprises a proximal end 24122 and a distal end 24124 and includes an axial passage 24126 that extends therethrough from the proximal end 24122 to the distal end 24124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 22010 employs a firing system 24300 that is identical to or very similar in many aspects as firing system 2300 described above. As such, only those aspects of the firing system 24300 needed to understand the operation of the surgical instrument 22010 will be discussed below.

Figure 54:
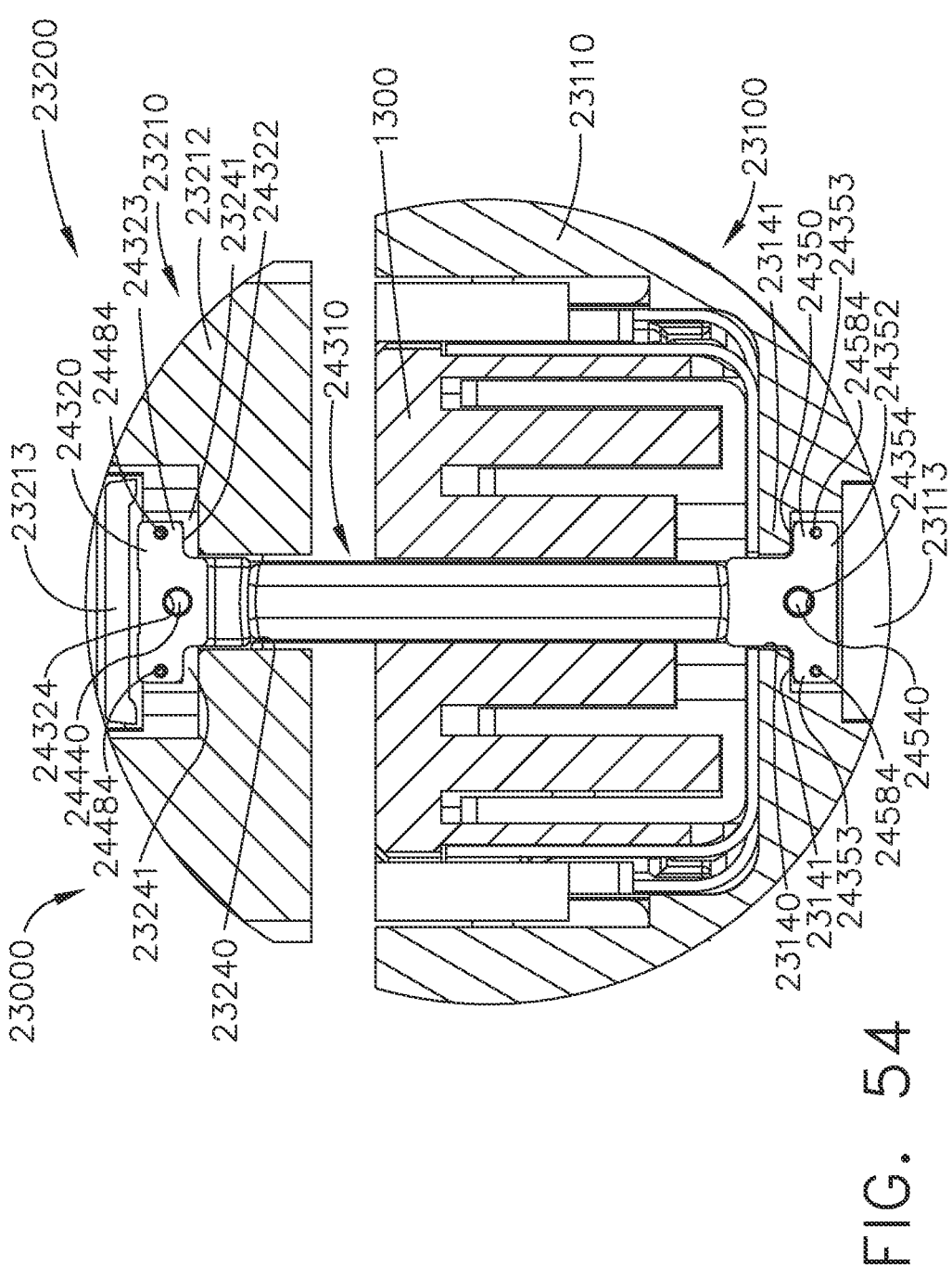
FIG. 54 is a cross-sectional end view of the surgical end effector of the surgical instrument of FIG. 46, with the jaws thereof in a closed position.

As can be seen in FIGS. 50-54, in at least one embodiment, the firing system 24300 comprises a firing member 24310 that includes a vertically-extending firing member body 24312 that comprises a top firing member feature 24320 and a bottom firing member feature 24350. A tissue cutting blade 24314 is attached to or formed in the vertically-extending firing member body 24312. See FIGS. 50 and 51. In at least one arrangement, it is desirable for the firing member 24310 to pass through the anvil body 23212 with low friction, high strength and high stiffness. In the illustrated arrangement, the top firing member feature 24320 comprises a T-shaped body 24322 that has two laterally extending tabs 24323 protruding therefrom and a top axial passage 24324 extending therethrough. See FIG. 53. The bottom firing member feature 24350 comprises a T-shaped body 24352 that has two laterally extending tabs 24353 protruding therefrom and a bottom axial passage 24354 extending therethrough. See FIG. 50. In at least one arrangement, the top firing member feature 24320 and the bottom firing member feature 24350 are integrally formed with the vertically-extending firing member body 24312. As can be seen in FIG. 54, the anvil body 23212 comprises an axially extending anvil slot 23240 that defines two opposed ledges 23241 for slidably receiving the laterally extending tabs 24323 thereon. Similarly, the elongate channel 23110 comprises an axially extending channel slot 23140 that defines axially extending channel ledges 23141 that are configured to slidably receive the laterally extending tabs 24353 thereon.

In the illustrated arrangement, the firing system 24300 comprises an upper flexible spine assembly 24400 that is operably coupled to the top firing member feature 24320 of the firing member 24310. In at least one embodiment, the upper flexible spine assembly 24400 comprises an upper series 24410 of upper vertebra members 24420 that are loosely coupled together by an upper flexible coupler member 24440 that extends through each of the upper vertebra members 24420 and is attached to the top firing member feature 24320.

Figure 52:
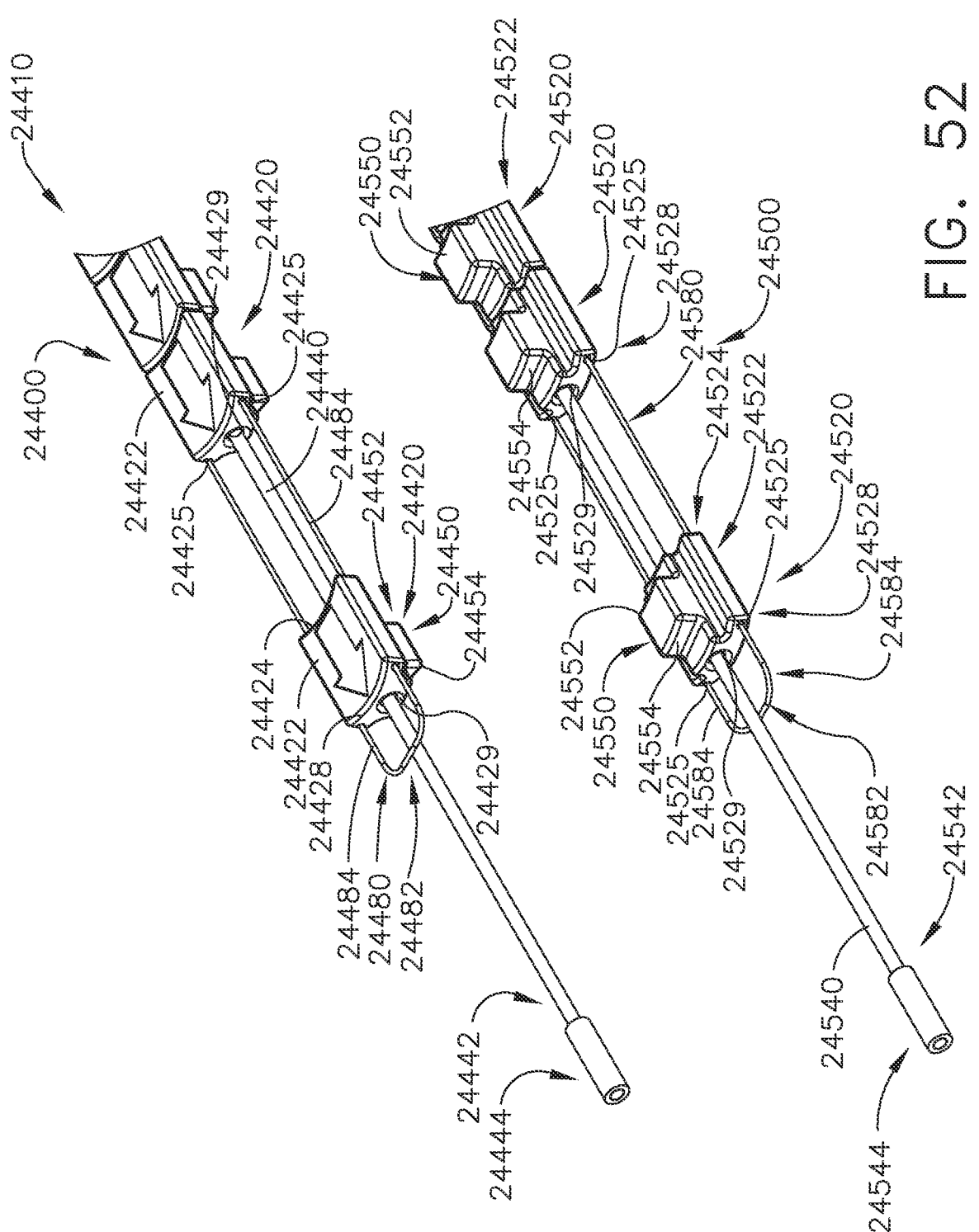
FIG. 52 is a partial exploded assembly view of the upper flexible spine assembly and lower flexible spine assembly depicted in FIG. 51.
Figure 53:
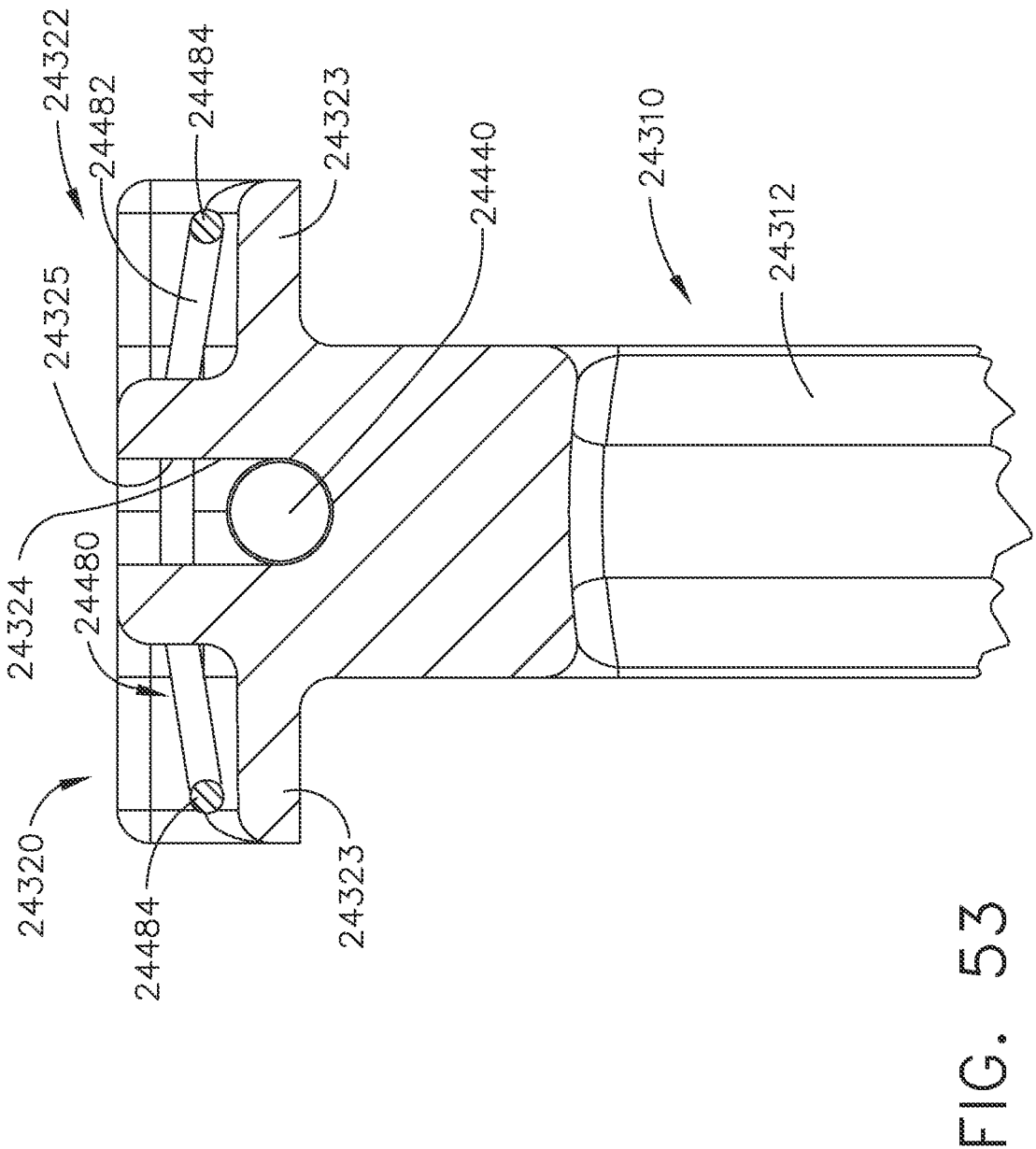
FIG. 53 is a partial cross-sectional end view of an upper portion of the firing member depicted in FIG. 50.

As can be seen in FIG. 52, each upper vertebra member 24420 is substantially T-shaped when viewed from an end thereof. In one aspect, each upper vertebra member 24420 comprises an upper vertebra body portion 24422 that has a proximal end 24424 and a distal end 24428. Each upper vertebra member 24420 further comprises a downwardly extending upper drive feature or upper vertebra member tooth 24450 that protrudes from the upper vertebra body portion 24422. Each upper vertebra member tooth 24450 has a helix-shaped proximal upper face portion 24452 and a helix-shaped distal upper face portion 24454. Each proximal end 24424 of the upper vertebra body portions 24422 has an arcuate or slightly concave curved shape and each distal end 24428 has an arcuate or slightly convex curved shape. When arranged in the upper series 24410, the convex distal end 24428 on one upper vertebra member 24420 contacts and mates with the concave proximal end 24424 on an adjacent upper vertebra member 24420 in the upper series 24410 to maintain the upper vertebra members 24420 roughly in alignment so that the helix-shaped proximal upper face portion 24452 and a helix-shaped distal upper face portion 24454 on each respective upper vertebra member tooth 24450 can be drivingly engaged by a rotary drive screw 2700 in the various manners disclosed herein. These curved mating surfaces on the upper vertebra members 24420 allow the upper vertebras members 24420 to better transfer loads between themselves even when they tilt.

In at least one embodiment, an upper alignment member 24480 is employed to assist with the alignment of the upper vertebra members 24420 in the upper series 24410. In one arrangement, the alignment member 24480 comprises a spring member or metal cable which may be fabricated from Nitinol wire, spring steel, etc., and be formed with a distal upper looped end 24482 and two upper leg portions 24484 that extend through corresponding upper passages 24425 in each upper vertebra body portion 24422. The upper flexible coupler member 24440 extends through an upper passage 24429 in each of the upper vertebra members 24420 to be attached to the firing member 24310. In particular, a distal end portion 24442 extends through the top axial passage 24324 in the top firing member feature 24320 and is secured therein by an upper retention lug 24444. A proximal portion of the upper flexible coupler member 24440 may interface with a corresponding rotary spool or cable-management system of the various types and designs disclosed herein that serve to payout and take up the upper flexible coupler member 24440 to maintain a desired amount of tension therein during operation and articulation of the surgical end effector 23000. The cable management system may be motor powered or manually powered (ratchet arrangement, etc.) to maintain a desired amount of tension in the upper flexible coupler member 24440. The amount of tension in each flexible coupler member may vary depending upon the relative positioning of the surgical end effector 23000 to the elongate shaft assembly 24000.

The firing system 24300 further comprises a lower flexible spine assembly 24500 that is operably coupled to the bottom firing member feature 24350. The lower flexible spine assembly 24500 comprises a lower series 24510 of lower vertebra members 24520 that are loosely coupled together by a lower flexible coupler member 24540 that extends through each of the lower vertebra members 24520 and is attached to the bottom firing member feature 24350. As can be seen in FIG. 52, each lower vertebra member 24520 is substantially T-shaped when viewed from an end thereof. In one aspect, each lower vertebra member 24520 comprises a lower vertebra body portion 24522 that has a proximal end 24524 and a distal end 24528. Each lower vertebra member 24520 further comprises an upwardly extending lower drive feature or lower vertebra member tooth 24550 that protrudes from the lower vertebra body portion 24522. Each lower vertebra member tooth 24550 has a helix-shaped proximal lower face portion 24552 and a helix-shaped distal lower face portion 24554. The proximal end 24524 of each lower vertebra body portions 24522 has an arcuate or slightly concave curved shape and each distal end 24528 has an arcuate or slightly convex curved shape. When arranged in the lower series 24510, the convex distal end 24528 on one lower vertebra member 24520 contacts and mates with the concave proximal end 24524 on an adjacent lower vertebra member 24520 in the lower series 24510 to maintain the lower vertebra members 24520 roughly in alignment so that the helix-shaped proximal lower face portion 24552 and a helix-shaped distal lower face portion 24554 on each respective lower vertebra member tooth 24550 can be drivingly engaged by the rotary drive screw 2700 in the various manners disclosed herein. These curved mating surfaces on the lower vertebra members 24520 allow the lower vertebra members 24520 to better transfer loads between themselves even when they tilt.

In at least one embodiment, a lower alignment member 24580 is employed to assist with the alignment of the lower vertebra members 24520 in the lower series 24510. In one arrangement, the lower alignment member 24580 comprises a spring member or metal cable which may be fabricated from Nitinol wire, spring steel, etc., and be formed with a distal lower looped end 24582 and two lower leg portions 24584 that extend through corresponding lower passages 24525 in each lower vertebra body portion 24522. The lower flexible coupler member 24540 extends through the bottom axial passage 24529 in each of the lower vertebra members 24520 to be attached to the firing member 24310. In particular, a distal end portion 24542 of the lower flexible coupler member 24540 extends through the bottom axial passage 24354 in the bottom firing member feature 24350 and is secured therein by a lower retention lug 24544. A proximal portion of the lower flexible coupler member 24540 may interface with a corresponding rotary spool or cable-management system of the various types and designs disclosed herein that serve to payout and take up the lower flexible coupler member 24540 to maintain a desired amount of tension therein during operation and articulation of the surgical end effector 23000. The cable management system may be motor powered or manually powered (ratchet arrangement, etc.) to maintain a desired amount of tension in the lower flexible coupler member 24540. The amount of tension in each flexible coupler member may vary depending upon the relative positioning of the surgical end effector 23000 to the elongate shaft assembly 24000.

In accordance with at least one aspect, a large surface area is advantageous for distributing the force between the vertebra members when they push so that the vertebra members cannot twist relative to each other. The available area in the anvil and channel is limited and the anvil and channel must remain stiff. The T-shaped upper vertebra members 24420 and the T-shaped lower vertebra members 24520 are designed to fit in the limited spaces available in the anvil 23210 and the elongate channel 23110 while ensuring that there is a large amount of area to distribute the firing loads. The curved surfaces on each upper vertebra member 24420 and each lower vertebra member 24520 allow each of those vertebras to better transfer loads between themselves even when they tilt. The upper alignment member 24480 and the lower alignment member 24580 may also serve to prevent the upper vertebra members 24420 and the lower vertebra members 24520 from twisting relative to each other. The large surface area may also help to prevent galling of the vertebra members and/or the anvil and channel. The upper flexible spine assembly 24400 and the lower flexible spine assembly 24500 otherwise operably interface with the rotary drive screw 2700 arrangements as disclosed herein. The upper flexible coupler member 24440 and the lower flexible coupler member 24540 may also be used in the manners discussed above to retract the firing member 24310 back to its starting position if, during a firing stroke, the firing drive system 24300 fails.

Figure 51:
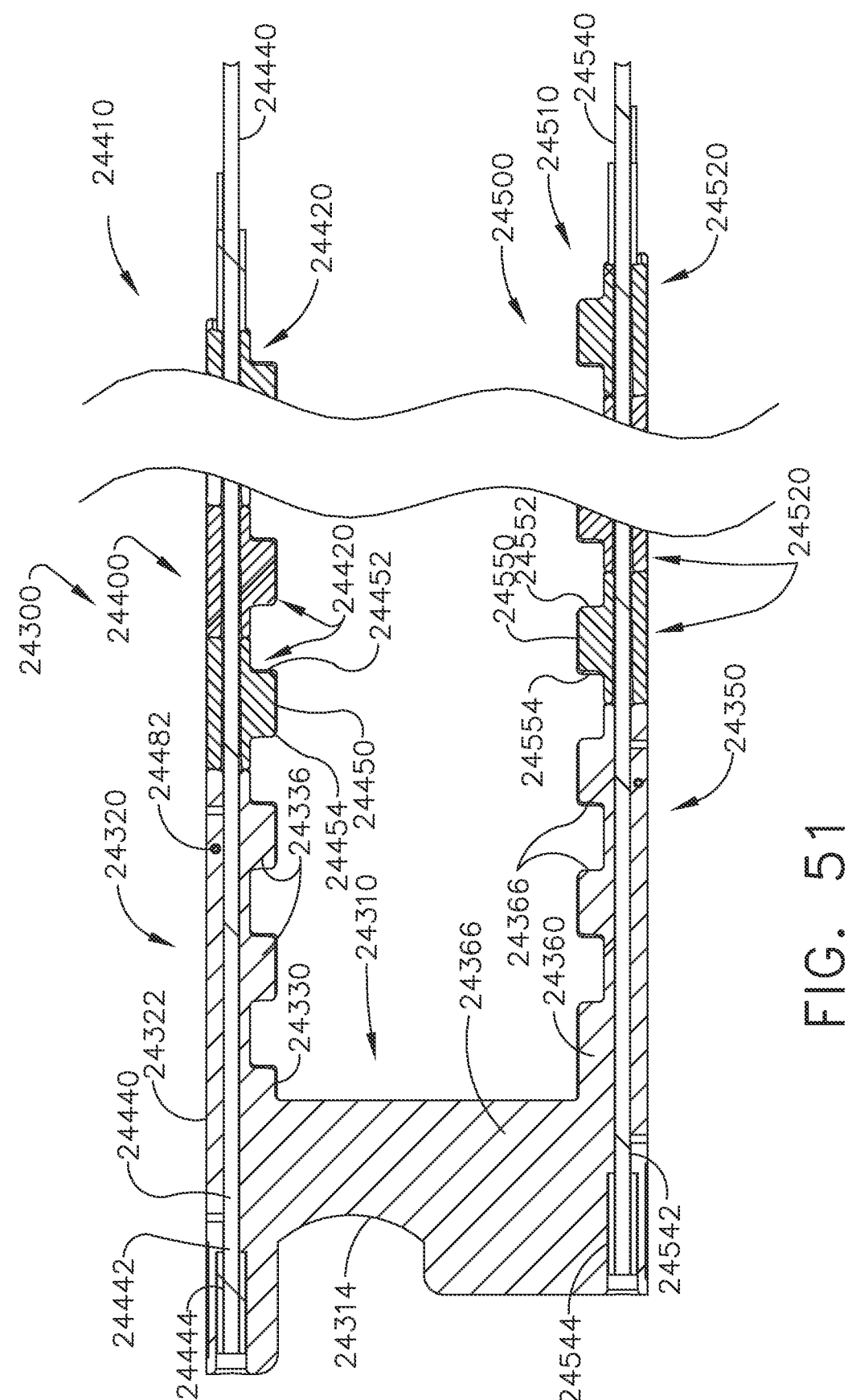
FIG. 51 is a cross-sectional side view of portions of the firing system depicted in FIG. 50.

As can be seen in FIG. 51, the top firing member feature 24320 on the firing member 24310 comprises a distal upper firing member tooth segment 24330 that is equivalent to one half of an upper vertebra member tooth 24450 on each upper vertebra member 24420. In addition, two proximal upper firing member teeth 24336 that are identical to an upper vertebra member tooth 24450 on each upper vertebra member 24420 are spaced from the distal upper firing member tooth segment 24330. The distal upper firing member tooth segment 24330 and the proximal upper firing member teeth 24336 may each be integrally formed with the top firing member feature 24320 of the firing member 24310. Likewise, the bottom firing member feature 24350 of the firing member 24310 comprises a distal lower firing member tooth 24360 and two proximal lower firing member teeth 24366 that are integrally formed on the bottom firing member feature 24350. For example, in at least one arrangement, the firing member 24310 with the rigidly attached teeth 24330, 24336, 24360, and 24366 may be fabricated at one time as one unitary component using conventional metal injection molding techniques. The person of ordinary skill in the art will recognize that the firing member 24310 operates in essentially the same manner as the firing member 2310 as was described in detail herein.

Figures 55, 56:
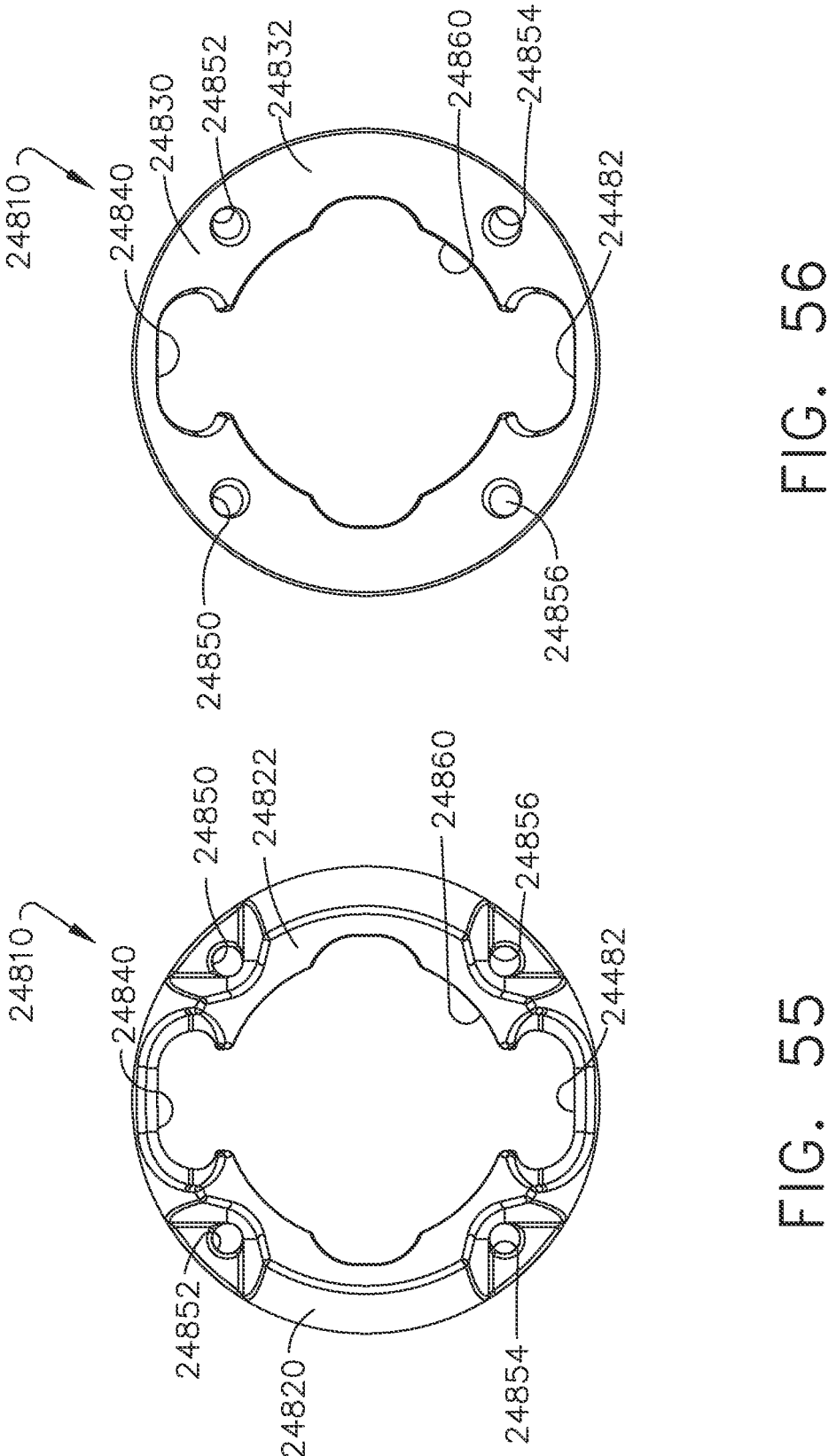
FIG. 55 is a view of a proximal face of an annular rib member of a movable exoskeleton assembly of the surgical instrument of FIG. 46.
FIG. 56 is a view of a distal face of the annular rib member of FIG. 55.
Figure 57:
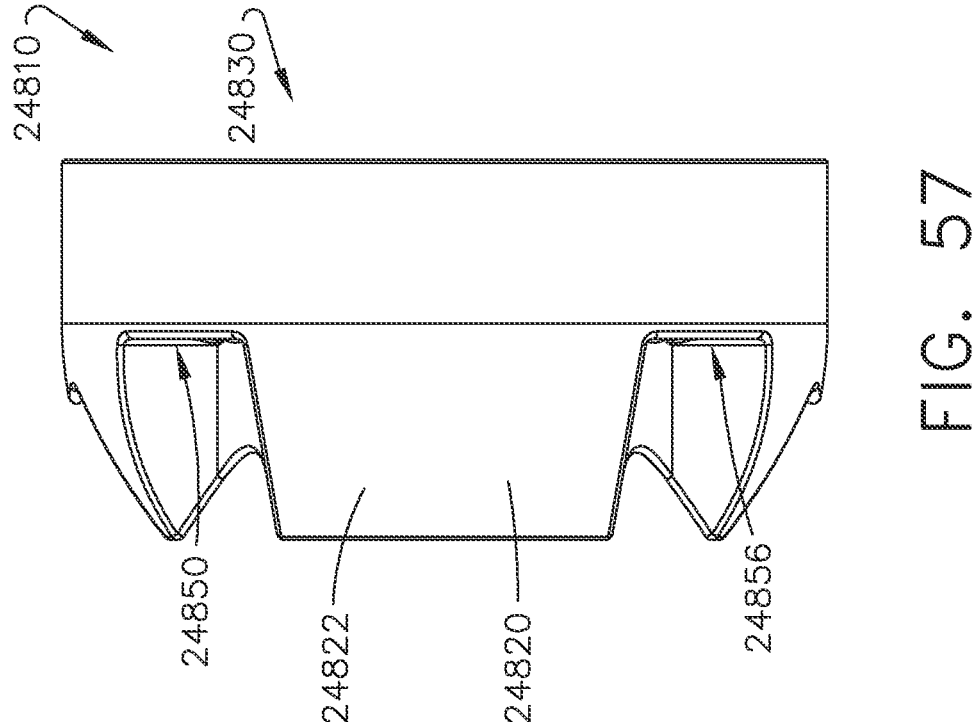
FIG. 57 is a side view of the annular rib member of FIGS. 55 and 56.

Turning now to FIGS. 55-58, in accordance with at least one aspect, the articulation joint 24200 comprises a movable exoskeleton assembly 24800. In one form, the movable exoskeleton assembly 24800 comprises a series 24802 of movably interfacing annular rib members 24810. As can be seen in FIGS. 55-57, each annular rib member 24810 comprises a first or proximal face 24820 that comprises a convex or domed portion 24822. Each annular rib member 24810 further comprises a second or distal face 24830 that is concave or dished. Each annular rib member 24810 further comprises an upper spine passage 24840 that is configured to accommodate passage of the upper flexible spine assembly 24400 therethrough and a lower spine passage 24842 that is configured to accommodate passage of the lower flexible spine assembly 24500 therethrough. In addition, each annular rib member 24810 further comprises four articulation passages 24850, 24852, 24854, and 24856 to accommodate passage of articulation actuators in the form of articulation cables 24242, 22446, 24250, and 24254 therethrough. See FIG. 49. Each annular rib member 24810 further comprises a central drive passage 24860 that is configured to accommodate passage of the constant velocity (CV) drive shaft assembly 2620 therethrough.

Figure 58:
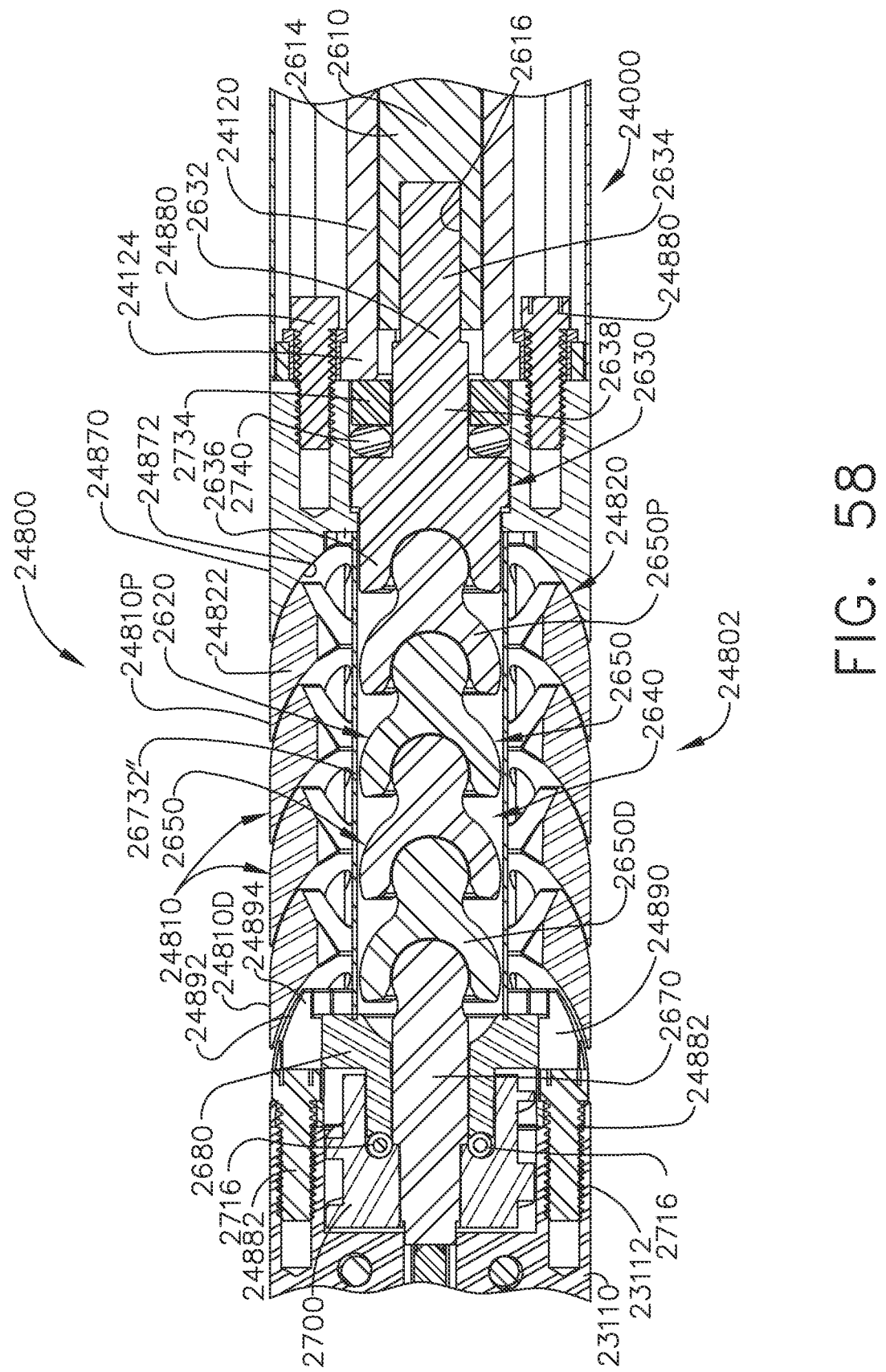
FIG. 58 is a partial cross-sectional view of a portion of the surgical instrument of FIG. 46.

As can be seen in FIG. 58, the movable exoskeleton assembly 24800 comprises a proximal attachment rib 24870 that is configured to attach the movable exoskeleton assembly 24800 to the distal end 24124 of the proximal support shaft 24120 by cap screws 24880 or other suitable fastener arrangements. The proximal attachment rib 24870 comprises a first or distal face 24872 that is concave or dished to receive or movably interface with the convex or domed portion 24822 of the proximal face 24820 of a proximal-most annular rib member 24810P. Similarly, the movable exoskeleton assembly 24800 comprises a distal attachment rib 24890 that is configured to attach the movable exoskeleton assembly 24800 to the proximal end 23112 of the elongate channel 23110 by cap screws 24882 or other suitable fasteners. The distal attachment rib 24890 comprises a first or proximal face 24892 that comprises a convex or domed portion 24894 that configured to be received in or movably interface with the concave or dished distal face 24832 of a distal-most annular rib member 24810D. In various embodiments, the annular rib members 24810, 24810P, and 24810D may be fabricated from any suitable metal (e.g., stainless steel, titanium, etc.) or other suitable material. The annular rib members 24810, 24810P, and 24810D may be formed by suitable drawing or forming operations, by machining or casting. The proximal faces 24820 and the distal faces 24830 may be polished or otherwise finished to a desirable smooth finish to reduce friction and facilitate movement between the annular rib members 24810, 24810P, and 24810D. In accordance with one aspect, all edges on each annular rib member 24810, 24810P, 24810D are rounded to facilitate relative movement between the annular rib members. The proximal attachment rib 24870 and the distal attachment rib 24890 may be formed with similar attributes.

The surgical instrument 22010 also comprises an articulation system 24240 that is configured to apply articulation motions to the surgical end effector 23000 to articulate the surgical end effector 23000 relative to the elongate shaft assembly 24000. In at least one arrangement, for example, as mentioned above, the articulation system 24240 comprises four articulation cables 24242, 24246, 24250, and 24254 that extend through the elongate shaft assembly 2400. See FIG. 49. In the illustrated arrangement, the articulation cables 24242, 24246 pass through the proximal attachment rib 24870 and through each of the annular rib members 24810P, 24810, and 24810D to be secured to the distal attachment rib 24890. In one arrangement for example, each of the articulation cables 24242, 24246 are secured to the distal attachment rib 24890 by corresponding attachment lugs 24243. See FIGS. 61 and 63. Likewise, the articulation cables 24250 and 24254 extend through the proximal attachment rib 24870 and through each of the annular rib members 24810P, 24810, and 24810D to be secured to the distal attachment rib 24890 by corresponding attachment lugs 24243.

Figure 59:
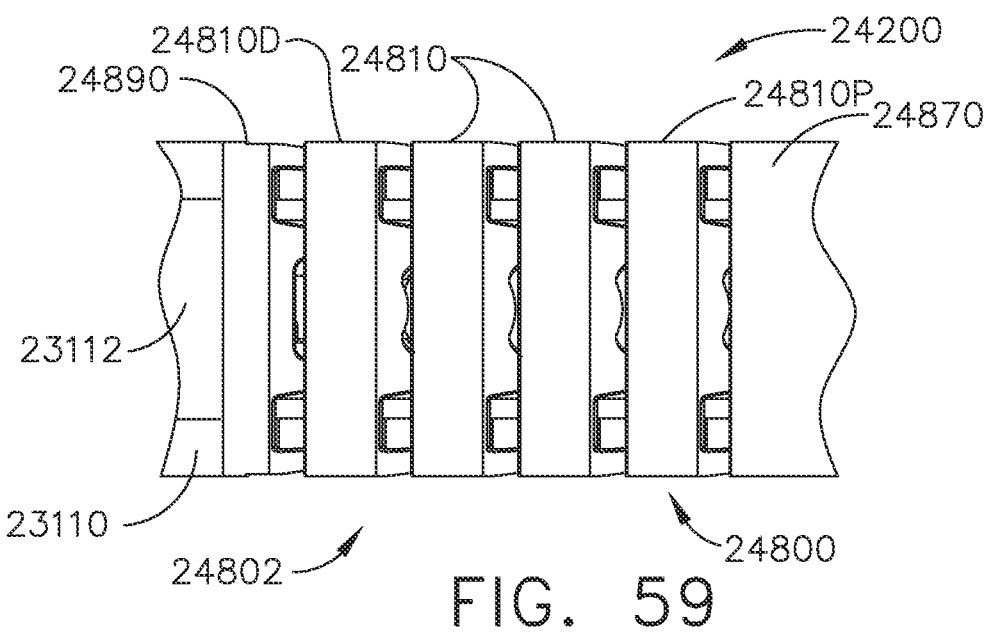
FIG. 59 is a side view of an articulation joint of the surgical instrument of FIG. 46 when the surgical end effector thereof is in an unarticulated position.
Figure 60:
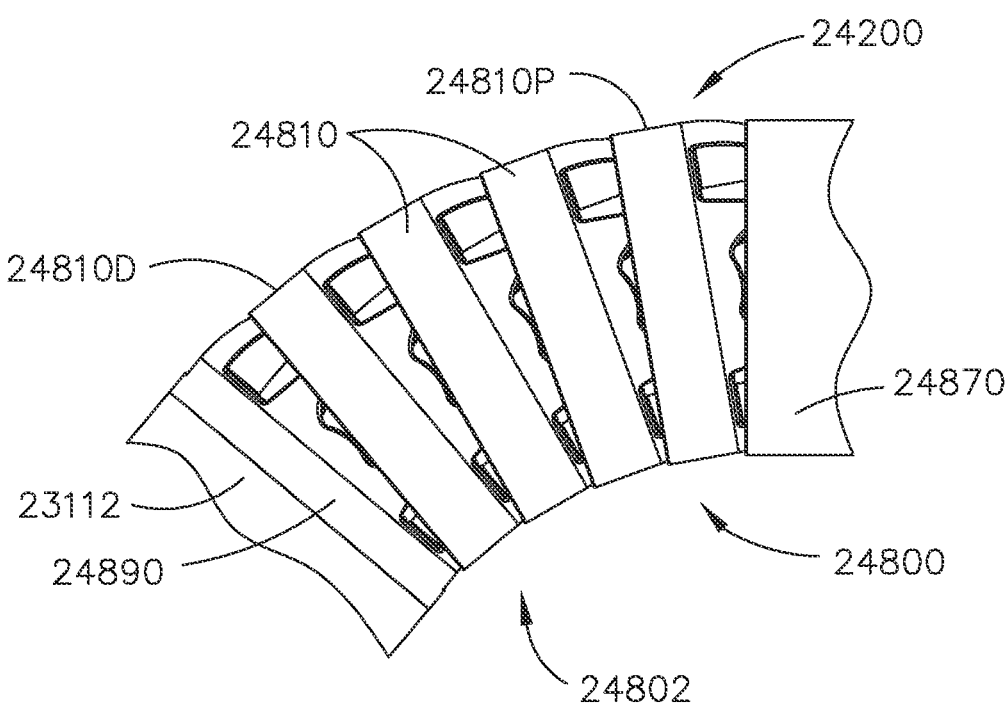
FIG. 60 is another side view of the articulation joint of FIG. 59 when the surgical end effector is in an articulated position.
Figure 61:
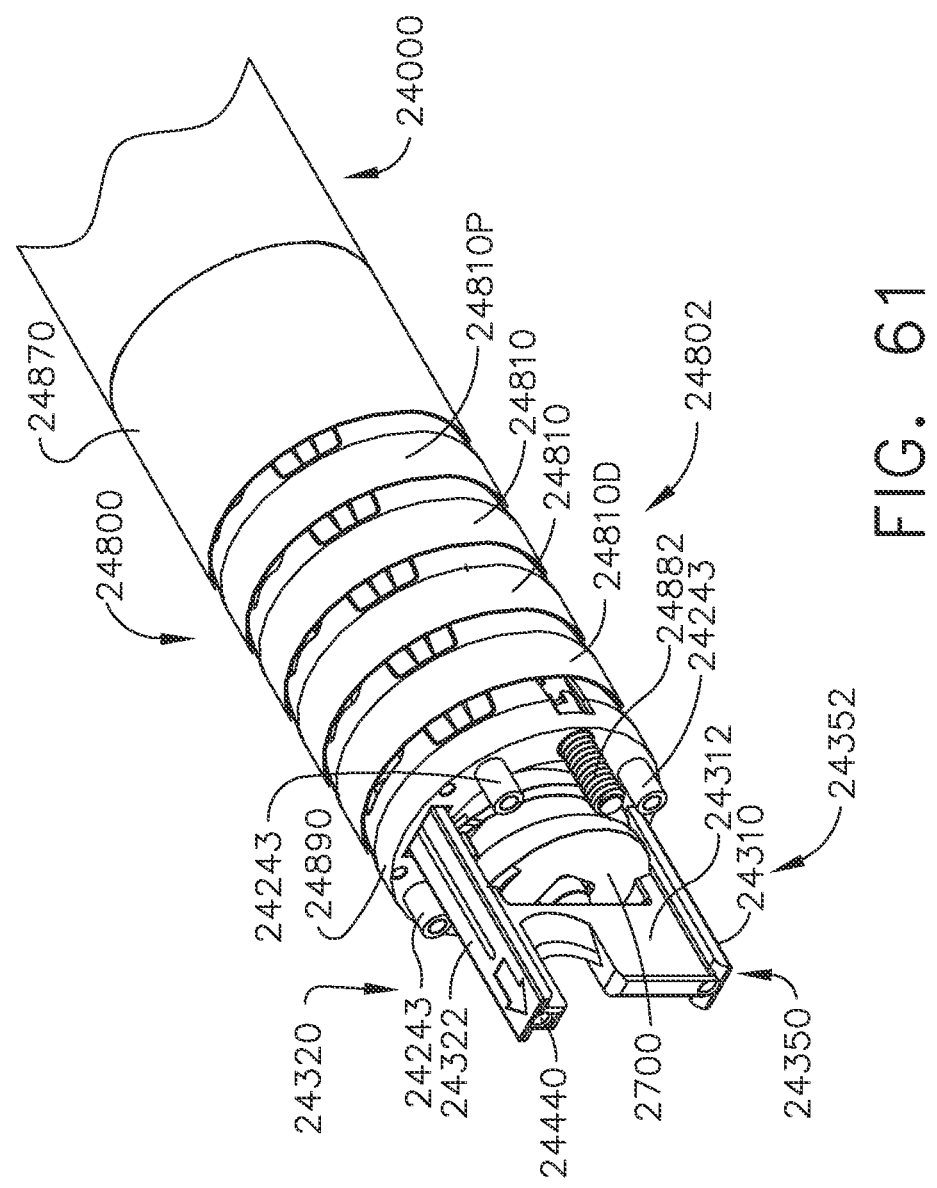
FIG. 61 is partial perspective view of a portion of the surgical instrument of FIG. 46 with the surgical end effector omitted for clarity.
Figure 62:
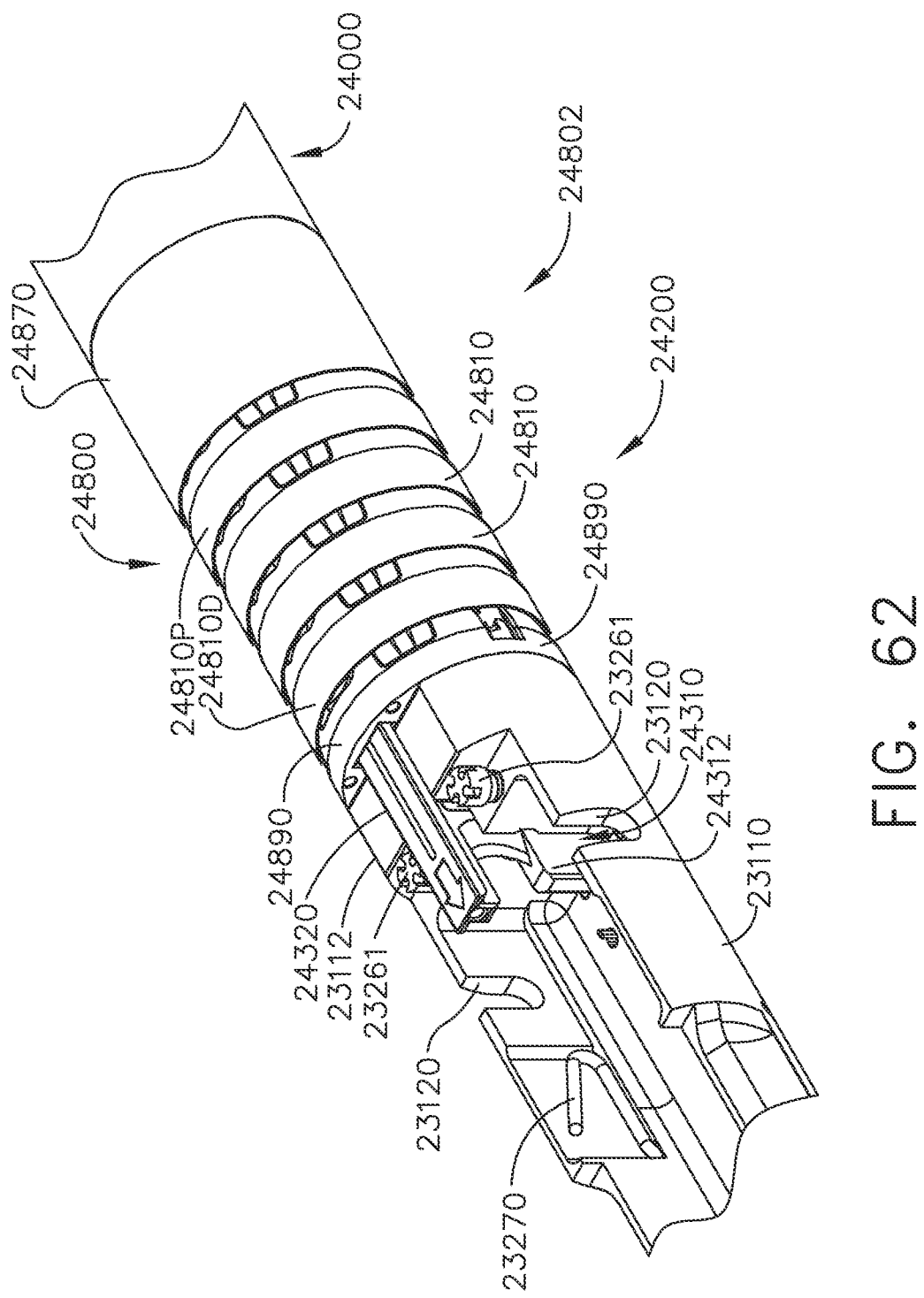
FIG. 62 is another partial perspective view of a portion of the surgical instrument of FIG. 46.
Figure 63:
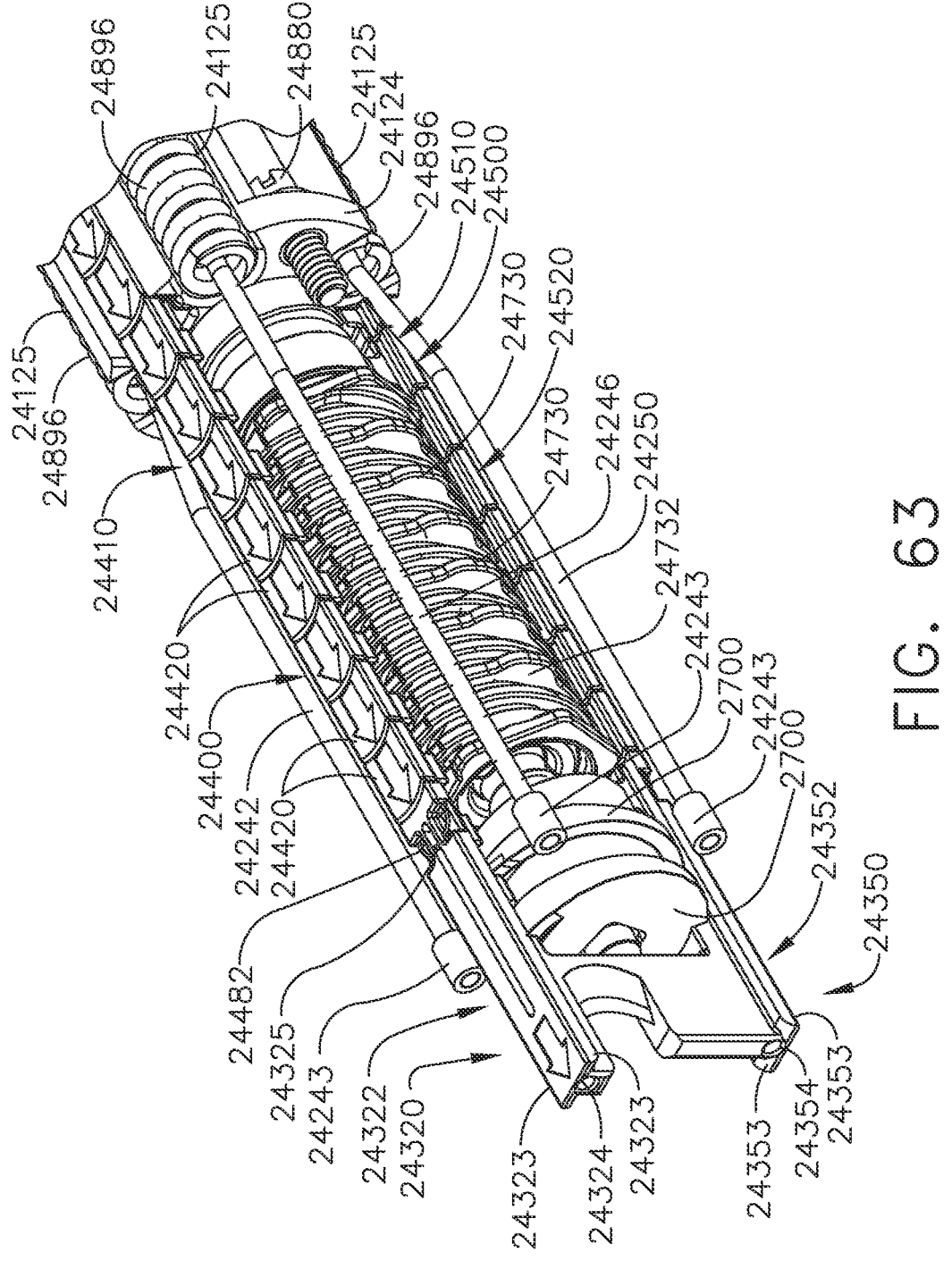
FIG. 63 is another partial perspective view of a portion of the surgical instrument of FIG. 46.

In one arrangement, each of the articulation cables 24242, 24246, 24250, and 24254 extend through corresponding coil springs 24896 that are supported in cavities 24125 in the distal end 24124 of the rigid proximal support shaft 24120. In addition, each coil spring 24896 is associated with a tensioning lug 24897 that is also journaled onto each respective articulation cable 24242, 24246, 24250, and 24524 and is secured thereon to attain a desired amount of compression in each spring 24896 which serves to retain the annular rib members 24810P, 24810, and 24810D in movable engagement with each other and with the proximal attachment rib 24870 and the distal attachment rib 24890. The cables 24242, 24246, 24250, and 24254 operably interface with an articulation control system that is supported in the housing of the surgical instrument 22010. For example, as was discussed above, a proximal portion of each cable 24242, 24246, 24250, and 24254 may be spooled on a corresponding rotary spool or cable-management system 2007 (FIG. 2) in the housing portion of the surgical instrument 22010 that is configured to payout and retract each cable 24242, 24246, 24250, and 24254 in desired manners. The spools/cable management system may be motor powered or manually powered (ratchet arrangement, etc.). FIG. 59 illustrates the articulation joint 24200 in an unarticulated position and FIG. 60 illustrates the articulation joint in one articulated con-figuration. Such arrangement permits the surgical end effec-tor 23000 to be articulated through multiple articulation planes relative to the elongate shaft assembly 24000.

Figure 64:
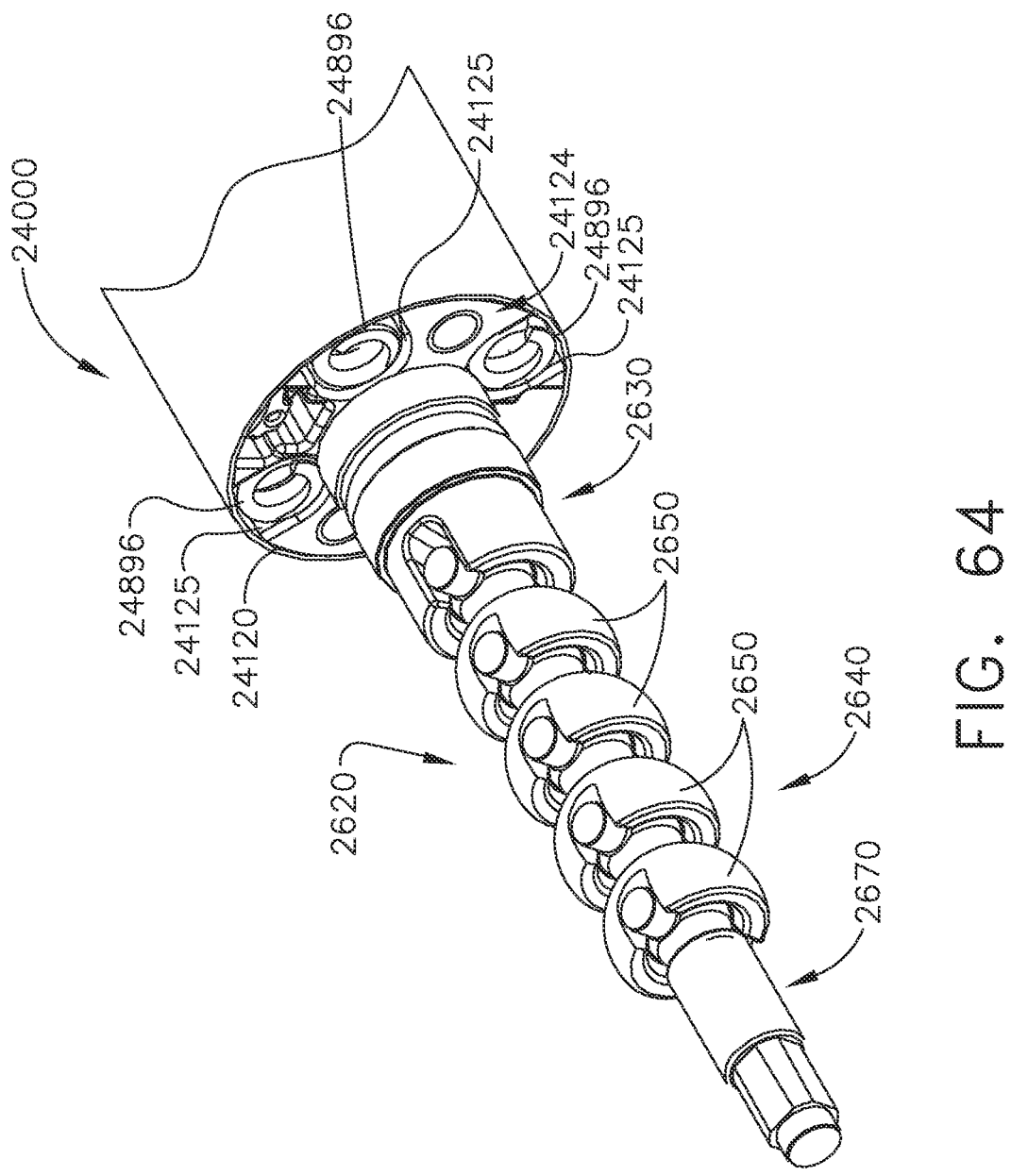
FIG. 64 is a perspective view of a CV drive shaft assembly and a portion of the elongate shaft assembly of the surgical instrument of FIG. 46.
Figure 65:
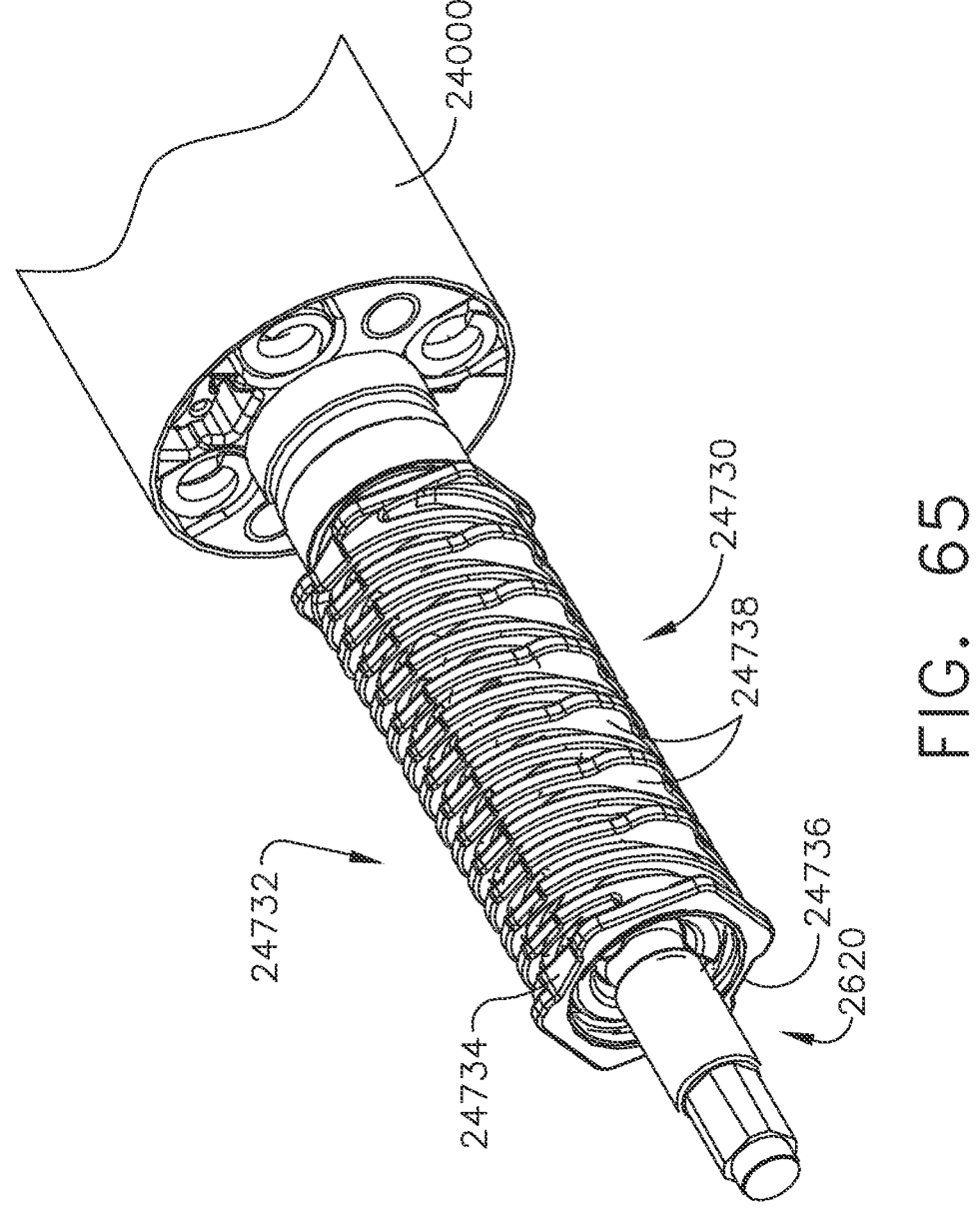
FIG. 65 is another perspective view of the CV drive shaft assembly and elongated shaft assembly of FIG. 64 with a drive cover embodiment installed around the CV drive shaft assembly.

As can be seen in FIGS. 49, 58, and 64, the surgical instrument 22010 employs a constant velocity (CV) drive shaft assembly 2620 that spans or extends axially through the articulation joint 24200. The operation and construction of the CV drive shaft assembly 2620 was described in detail above and will not be repeated here beyond what is neces-sary to understand the operation of the surgical instrument 22010. Briefly as described above, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft seg-ment 2632 operably interfaces with a series 2640 of mov-ably coupled drive joints 2650. As can be seen in FIG. 58 as was also described previously, to ensure that the drive joints 2650 are engaged with each other, a proximal drive spring 2740 is employed to apply an axial biasing force to the series 2640 of drive joints 2650. For example, as can be seen in FIG. 58, proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring received on the proxi-mal barrel portion 2638 of the proximal shaft segment 2632. The proximal drive spring 2740 lightly biases the drive joints 2650 together to decrease any gaps that occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

Figure 66:
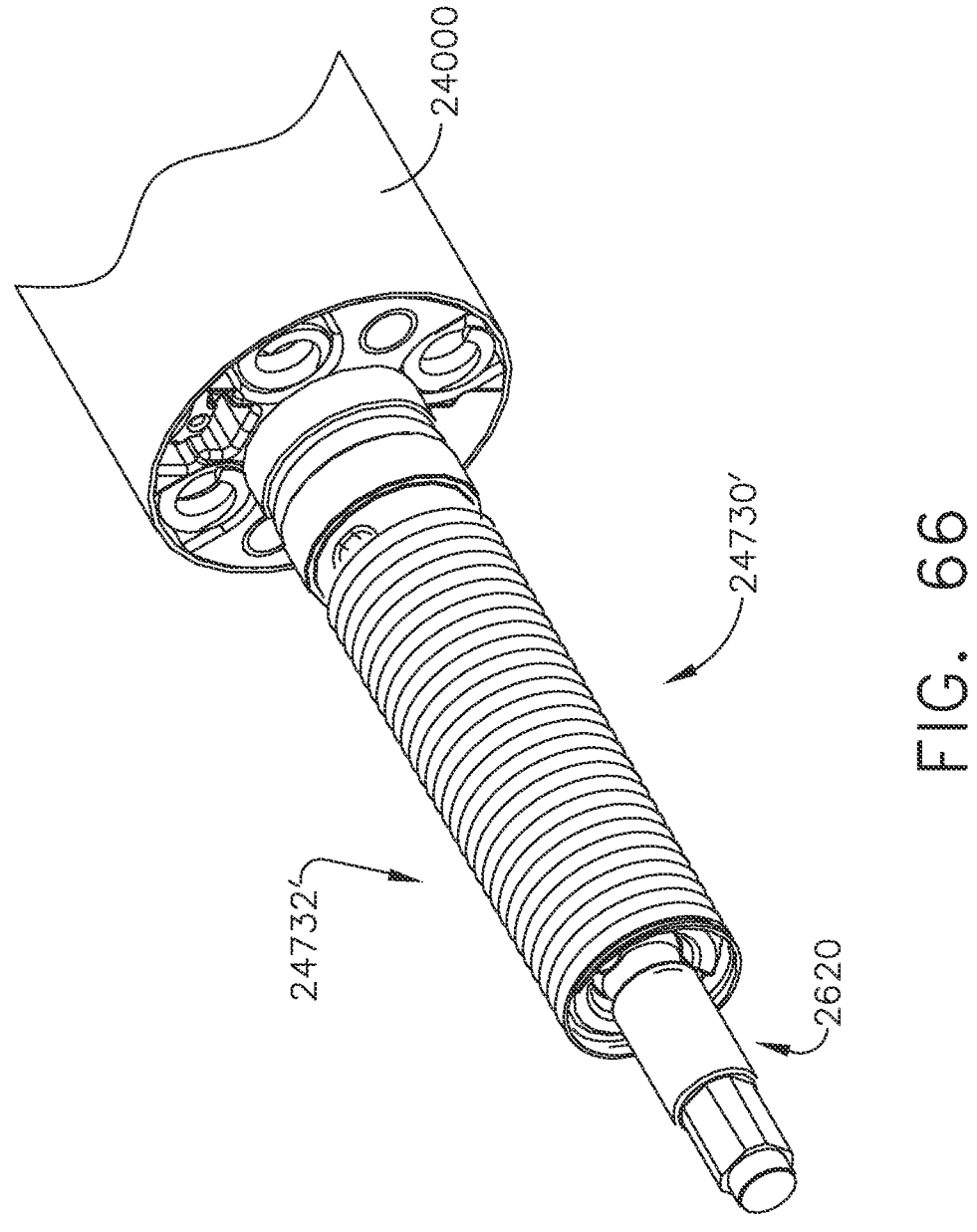
FIG. 66 is another perspective view of the CV drive shaft assembly and elongated shaft assembly of FIG. 64 with another drive cover embodiment installed around the CV drive shaft assembly.
Figure 67:
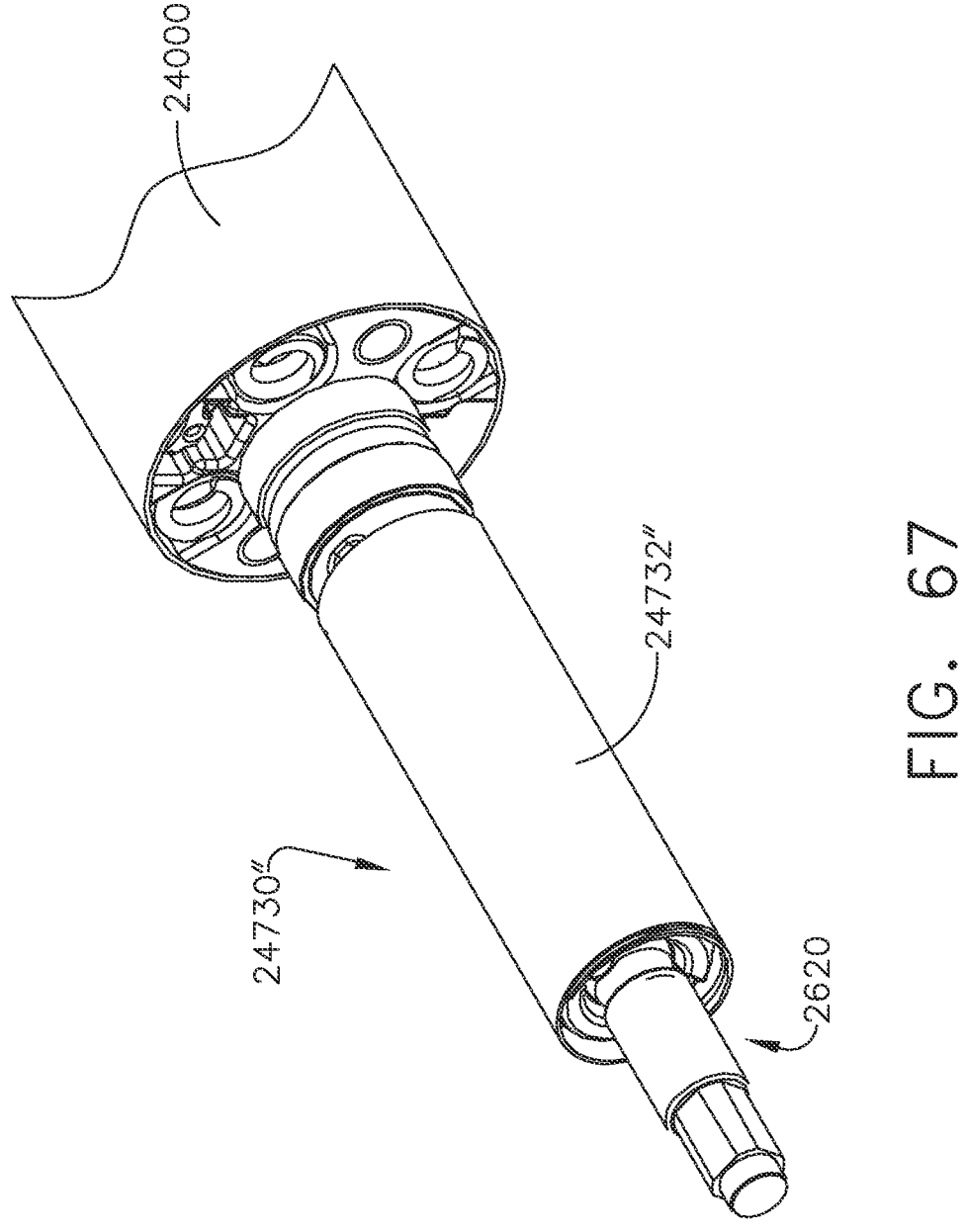
FIG. 67 is another perspective view of the CV drive shaft assembly and elongated shaft assembly of FIG. 64 with another drive cover embodiment installed around the CV drive shaft assembly.
Figure 68:
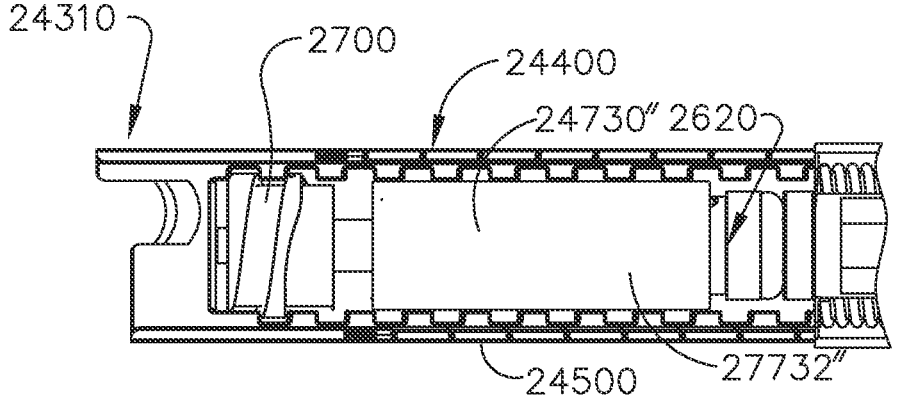
FIG. 68 is a side view of a portion of the firing system of the surgical instrument of FIG. 46 with the drive cover of FIG. 67 installed around the CV drive shaft assembly.
Figure 69:
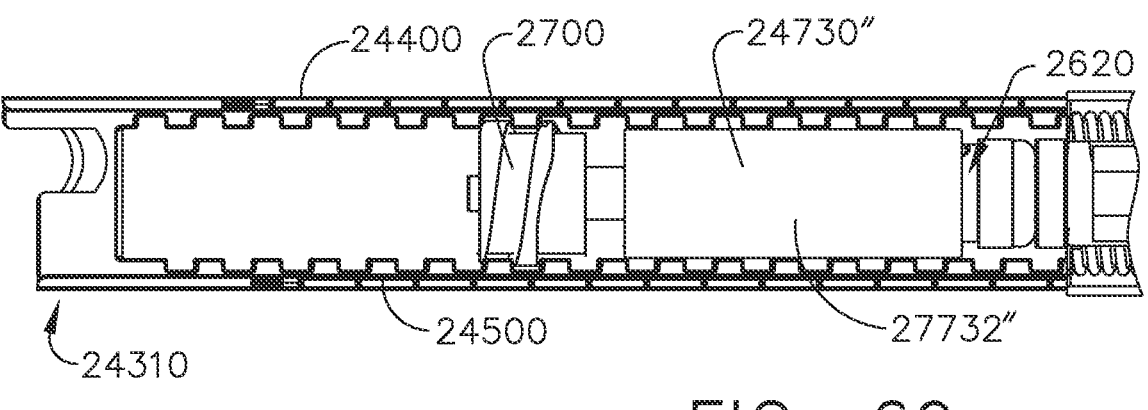
FIG. 69 is another side view of the portion of the firing system and drive cover of FIG. 68.
Figure 70:
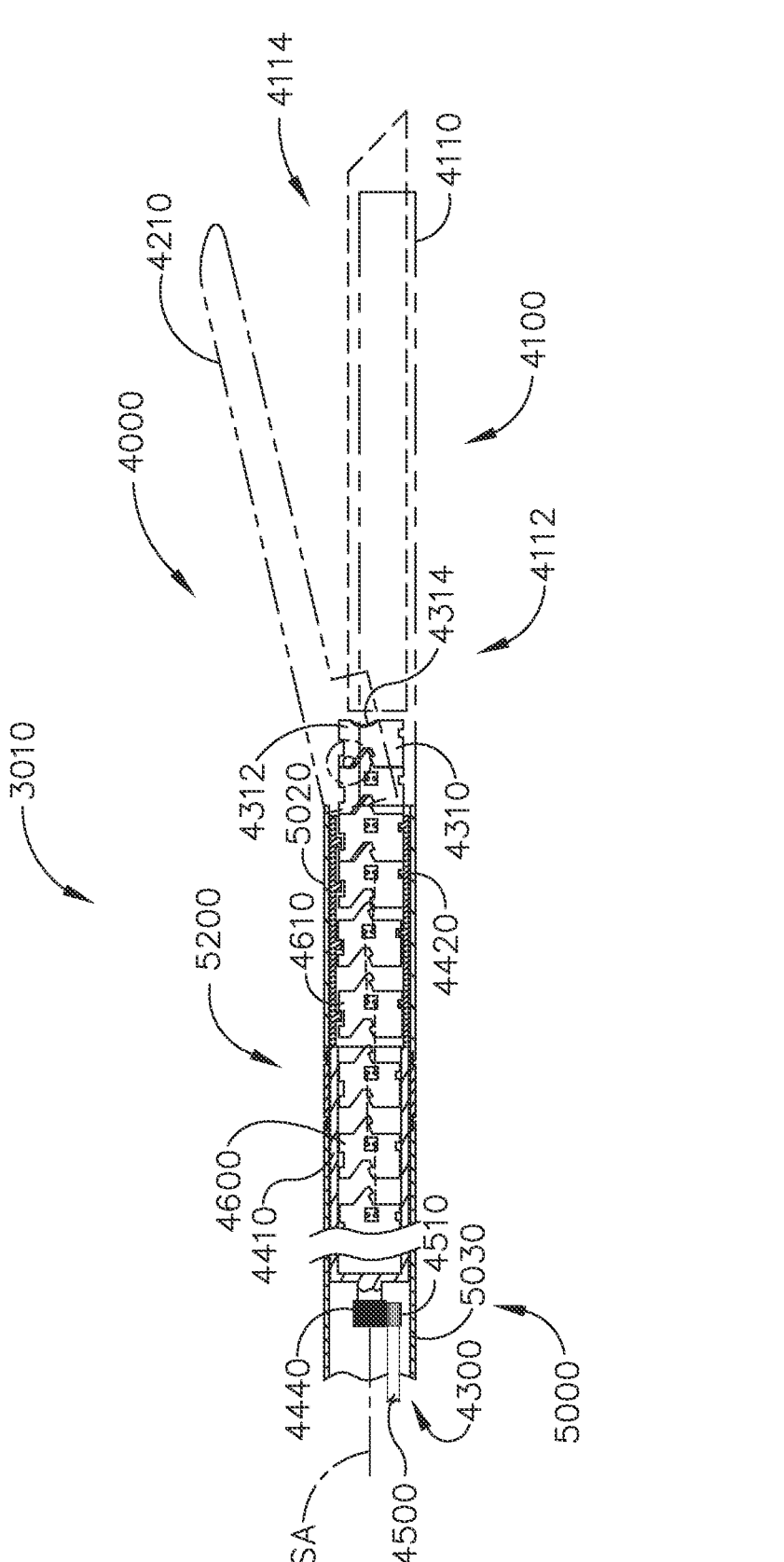
FIG. 70 is a cross-sectional view of a portion of another surgical instrument.
Figure 71:
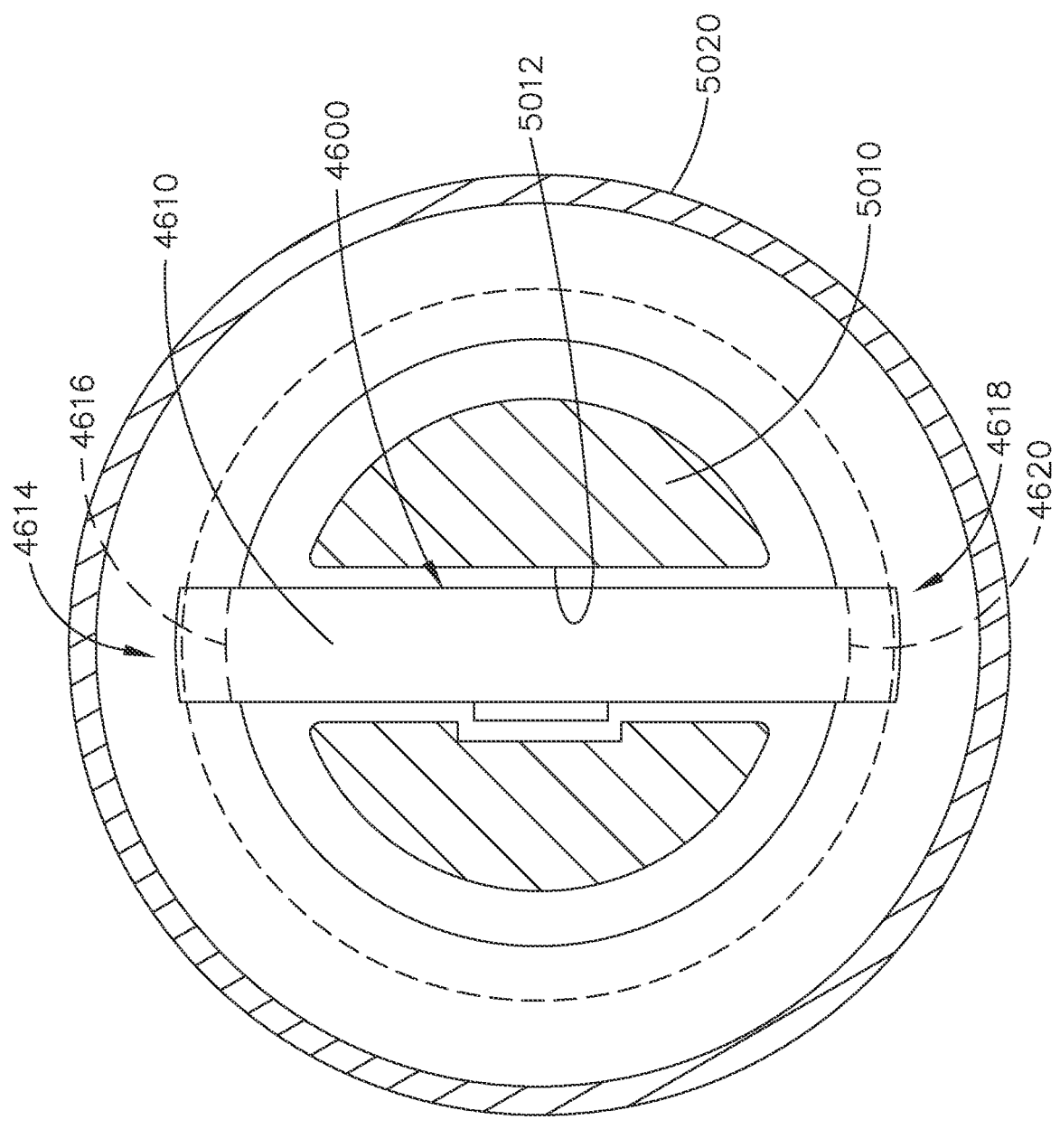
FIG. 71 is a cross-sectional end view of a surgical end effector of the surgical instrument of FIG. 70.

To further prevent the drive joints 2650 from buckling during articulation, the series 2640 of movably coupled drive joints 2650 extend through at least one low friction drive cover 24730 that extends through the central drive passage 24860 in each of the annular rib members 24810. In the arrangement depicted in FIGS. 63 and 65, the drive cover 24730 comprises an outer and inner cut hypotube 24732. Such hypotube 24732 may be fashioned from metal (e.g., stainless steel, etc.) and have multiple series of cuts or slits therein that may be made using laser cutter arrangements. In the illustrated arrangement, the hypotube 24732 may be fabricated with an upper relief passage 24734 that provides clearance for the upper flexible spine assembly 24400 to pass thereover during operation while the surgical end effector 23000 is in an articulated position and articulated positions. In addition, the hypotube 24732 may have a lower relief passage 24736 to provide similar clearance for the lower flexible spine assembly 24500. As can also be seen in FIG. 65, the hypotube 24732 may be shaped with diametri-cally opposed lateral tab portions 24738 to provide lateral stability during articulation. FIG. 66 illustrates an alternative drive cover 24730' that comprises an inner cut hypotube 24732'. FIGS. 58, 67, 68, and 69 illustrate an alternative drive cover 24730" that comprises flexible heat shrink tubing 24732" that is applied over the constant velocity (CV) drive shaft assembly 2620. In still other arrangements, the drive cover may comprise a coiled spring or coiled member as well.

Various embodiments of the present disclosure provide advantages over previous surgical endocutter configurations that are capable of articulation. For example, pushing a firing member forward in an articulating end effector gen-erally requires a lot of force and that force must be balanced. For example, when firing the firing member at an angle of greater than sixty degrees, it becomes very difficult to push a beam through the articulation joint. The joint also expe-riences significant loads which may cause the articulation joint to de-articulate. By employing an upper flexible drive arrangement and a lower flexible drive arrangement that are each flexible through the articulation joint, but then become rigid when they are distal to the articulation joint can allow for a large degree of articulation (e.g., articulation angles over seventy degrees) while applying balanced loads to the firing member that are constrained to the firing member and not to the articulation joint. Stated another way, torsional loads are applied proximal to the articulation joint instead of longitudinal loads which could lead to de-articulation of the end effector. The torsional loads are converted to longitudi-nal loads at a position that is distal to the articulation joint. Thus, the rotary drive screw serves to actually convert torsional motion or loads to longitudinal loads that are applied to the firing member at a location that is distal to the articulation joint.

Further, by longitudinally breaking up the threaded drive arrangements, the threaded drive arrangements pass through the articulation joint while also effectively decreasing the length of the surgical end effector. For example, each single vertebra tooth is significantly shorter than multiple pitches rigidly connected. The vertebra can angle as they pass through the articulation joint. This flexible interconnection enables the rotary drive screw to be closely positioned to the articulation joint as compared to being significantly spaced therefrom if all of the pitches were rigidly connected.

FIGS. 70-73 illustrate another surgical end effector 4000 that may be employed with a surgical instrument 3010 that may be similar to the surgical instrument 10 in many aspects. The surgical end effector 4000 may be similar to the surgical end effector 1000 except for the differences discussed below. The surgical end effector 4000 is operably coupled to an elongate shaft assembly 5000. The elongate shaft assembly 5000 may be operably attached to a housing portion of the surgical instrument 3010. The housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents.

In at least one form, the surgical end effector 4000 comprises a first jaw 4100 and a second jaw 4200. In the illustrated arrangement, the first jaw 4100 comprises an elongate channel 4110 that comprises a proximal end 4112 and a distal end 4114 and is configured to operably support a surgical staple cartridge 1300 therein. In the illustrated arrangement, the second jaw 4200 comprises an anvil 4210 that may be similar to anvil 1210 described above. In the illustrated arrangement, the elongate shaft assembly 5000 defines a shaft axis SA and comprises a proximal shaft segment that operably interfaces with a housing of the control portion (e.g., handheld unit, robotic tool driver, etc.)

of the surgical instrument 3010. The elongate shaft assembly 5000 further comprises an articulation joint 5200 that is attached to a proximal shaft portion and the surgical end effector 4000.

The elongate shaft assembly 5000 may comprise a distal spine assembly 5010 that is attached to the proximal end 4112 of the elongate channel 4110 and the articulation joint 5200. See FIG. 70. The distal spine assembly 5010 is non-movably supported in a distal outer tube segment 5020 that operably interfaces with the surgical end effector 4000. The elongate shaft assembly 5000 further includes a proximal spine member (not shown) that operably interfaces with a proximal end of the articulation joint 5200 and may be attached to or otherwise operably interface with the housing of the surgical instrument 3010. A proximal outer tube segment 5030 extends from the articulation joint 5200 back to the housing to operably interface therewith.

The surgical instrument 3010 employs a firing drive system 4300 that comprises a firing member 4310 that includes a vertically-extending firing member body 4312 that comprises a top firing member feature and a bottom firing member feature. A tissue cutting blade 4314 is attached to or formed in the vertically-extending firing member body 4312. The firing drive system 4300 comprises a rotary drive nut 4400 that is configured to rotatably drive a series 4600 of drive components 4610 that operably interface with the firing member 4310. The rotary drive nut 4400 comprises a flexible proximal segment 4410 that spans the articulation joint 5200 and a threaded distal segment 4420 that is distal to the articulation joint 5200. The threaded distal segment 4420 comprises a series of variable pitched threads 4430, with coarse spacing 4432 at the proximal end, and tighter spacing 4434 at the distal or exit end. See FIG. 72. The threaded rotary drive nut 4400 comprises a proximal drive gear 4440 that meshingly interfaces with a distal drive gear 4510 that is attached to a rotary drive shaft 4500. See FIG. 70. The rotary drive shaft 4500 may interface with a gearbox/motor arrangement supported in the housing of the surgical instrument 3010. Rotation of the rotary drive shaft 4500 causes the drive nut 4400 to rotate about the shaft axis SA.

The rotary drive nut 4400 comprises a proximal segment 4410 and a threaded distal segment 4420. The threaded distal segment 4420 is located distal to the articulation joint 5200 and is configured to threadably engage a series 4600 of drive components 4610 that are loosely linked together by flexible tethers 4640. In at least one arrangement, for example, each drive component 4610 comprises a vertically extending plate member 4612 that each includes a top end 4614 and a bottom end 4618. The top end 4614 includes a top thread segment 4616 and the bottom end 4418 includes a bottom thread segment 4620. The top thread segment 4616 and the bottom thread segment 4620 are configured to threadably engage the threads 4430 of the rotary drive nut 4400. The series 4600 of drive components 4610 is configured to flexibly pass through the articulation joint 5200 and into a vertical passage 5012 in the distal spine assembly 5010. Rotation of the rotary drive nut 4400 in a first rotary direction causes the series 4600 of drive components 4610 to move axially in the distal direction and rotation of the rotary drive nut 4400 in a second rotary direction will cause the series 4600 of drive components 4610 to move axially in the proximal direction.

Figure 72:
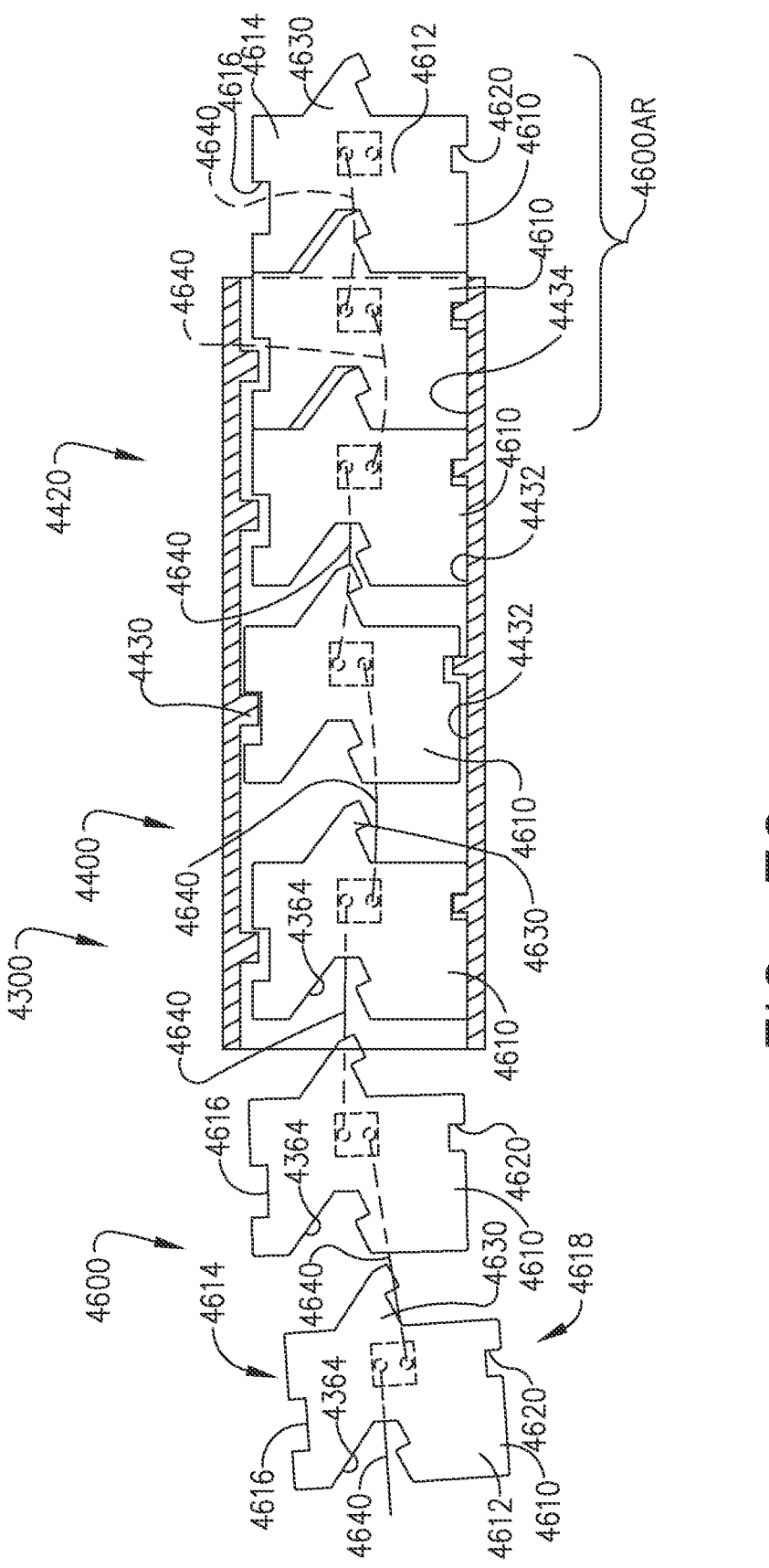
FIG. 72 is a cross-sectional side view of a rotary drive nut in engagement with drive components of the surgical instrument of FIG. 70.

Turning to FIG. 72, in at least one arrangement, each drive component 4610 further comprises a distally protruding latch feature 4630. Each latch feature 4360 is configured to be releasably received in latching engagement within a latch cavity 4364 that is formed in the adjacent drive component 4610 that is immediately distal thereto. When the drive components 4610 are latched together, they form an axially rigid series 4600AR of drive components for applying an axial drive motion to the firing member 5310 to drive the firing member 5310 through the surgical end effector 4000 from a starting to an ending position and then from the ending position back to the starting position. As can be seen in FIG. 72, as the drive components 4610 enter the threaded distal segment 4420 of the rotary drive nut 4400, they are loosely linked together. As the drive components 4610 threadably engage the finely pitched threads 4430 in the threaded distal segment 4420 of the rotary drive nut 4400, the latch features 4630 are latchingly received within the corresponding latch cavity 4364 in the distally adjacent drive component 4610 to form the axially rigid series 4600AR of drive components 4610. In one arrangement, a distal-most drive component 4610 may be configured to latchingly engage the firing member 4310 in a similar manner or in alternative arrangements, the distal-most drive component may be non-removably attached to the firing member 4310.

In the illustrated example, the drive components 4610 in the series 4600 of drive components are flexibly linked together such that they can move relative to each other to accommodate the articulation joint and without the need for reinforcing and support plates that are commonly required when pushing a firing beam through an articulated joint. As the series of drive components 4610 enters and is drivingly engaged by the threaded distal segment 4420 which is distal to the articulation joint, the drive components 4610 form the axially rigid series of drive components for driving the firing member 4310 through the surgical end effector 4000. The anvil 4210 may be pivoted into an open position by a spring or other arrangement in the various manners disclosed herein and then closed by the firing member 4310 as the firing member 4310 is driven distally from a starting position to an ending position in the various manners discussed herein. Other jaw control arrangements may also be employed to control the opening and closing of the jaws.

FIGS. 73-76 illustrate another surgical end effector 6000 that employs a drive system 6300 that comprises a series 6600 of flexibly linked drive components 6610 that can be used to traverse an articulation joint 6200 and rigidly advance a firing member 6130 through the surgical end effector 6000. The surgical end effector 6000 may comprise a channel 6010 that is configured to operably support a surgical staple cartridge (not shown) therein. An anvil 6020 may be pivotally coupled to the channel 6010 and is movable between an open position and a closed position by the firing member 6130 or other closure system arrangement. The anvil 6020 may be moved to an open position by a spring or other arrangement in the various manners disclosed herein.

Figures 74, 75:
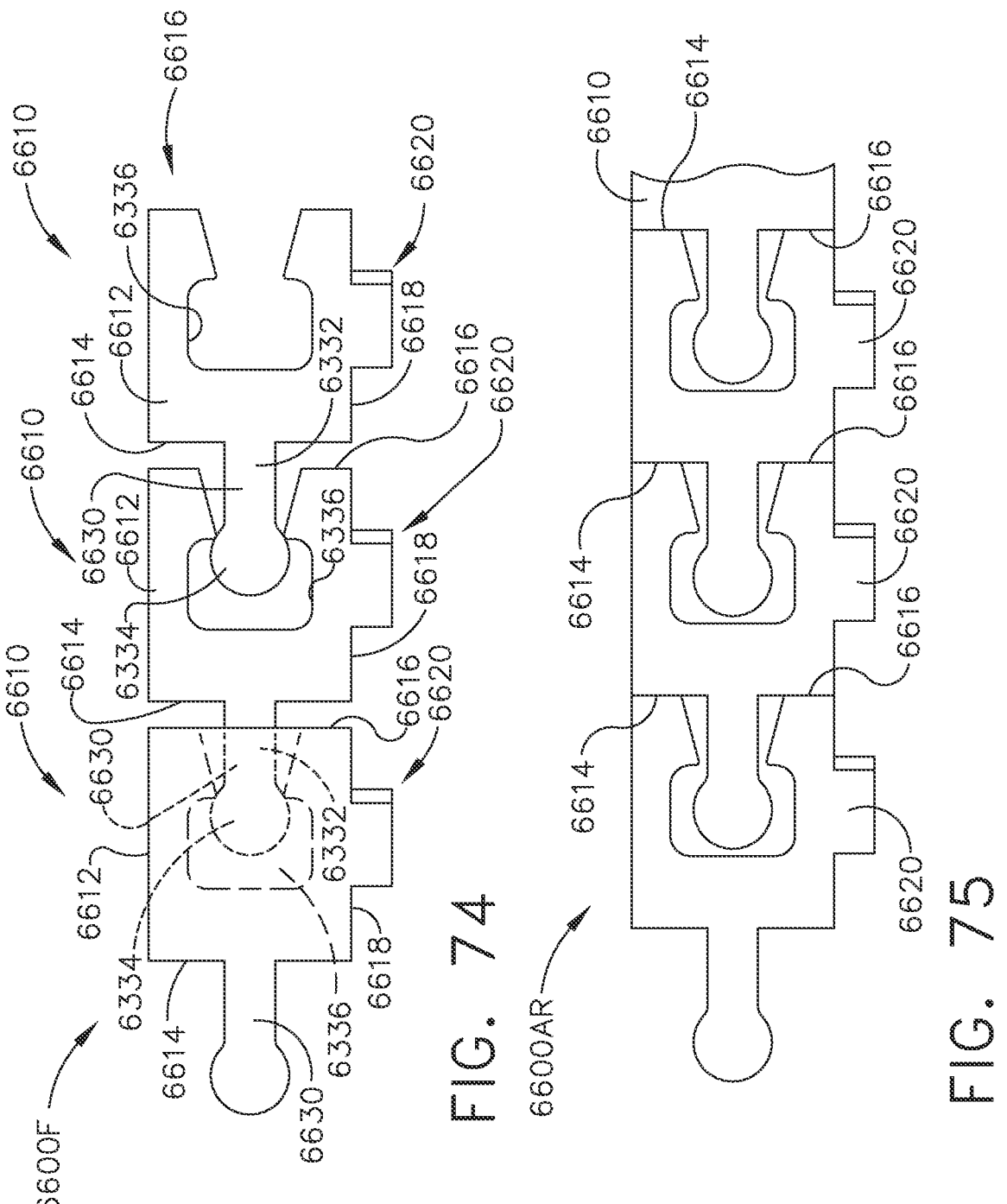
FIG. 74 is a side view of a portion of the series of flexibly linked drive components of the surgical instrument of FIG. 73 prior to engagement with a rotary drive gear in the surgical end effector.
FIG. 75 is another side view of the portion of drive components of FIG. 74 after being engaged with the rotary drive gear to form a rigid series of drive components.
Figure 76:
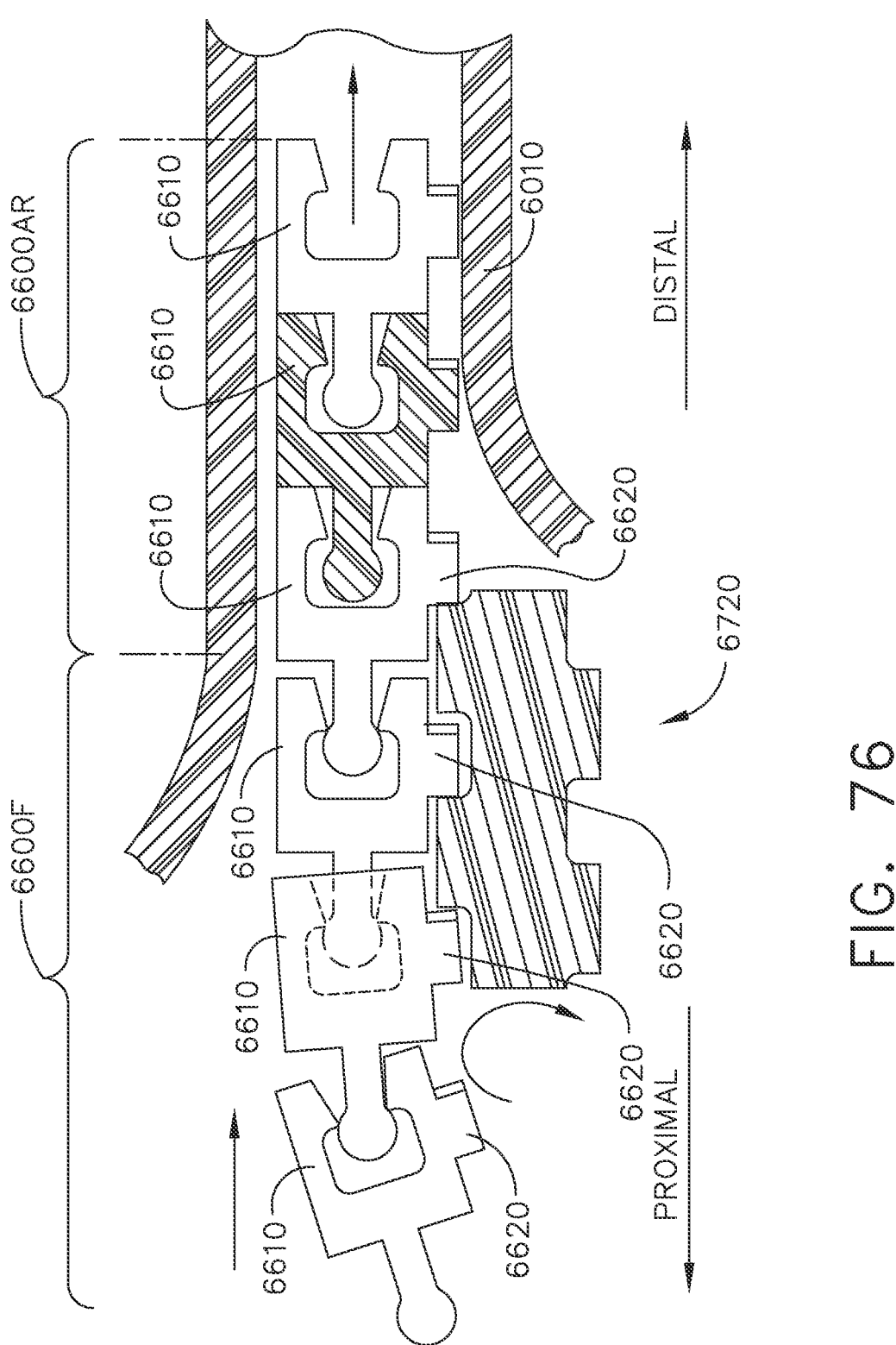
FIG. 76 is a partial cross-sectional view of the rotary drive system of the surgical instrument of FIG. 74 with components in the series of flexible drive components in driving engagement with the rotary drive gear thereof.

Turning to FIG. 74, in at least one arrangement, each drive component 6610 comprises a drive component body 6612 that has a proximal face 6614, a distal face 6616, and thread segment 6620 that is formed on a bottom surface 6618. Each drive component 6610 further comprises a proximally protruding latch feature 6630. Each latch feature 6630 comprises a neck feature 6632 that has a spherical latch head 6634 formed on an end thereof. The latch feature 6630 is configured to be movably received within a latch cavity 6336 that is formed in the adjacent drive component 6610 that is immediately distal thereto. To facilitate movable attachment of the drive components 6610 in movable serial arrangement, the spherical latch head 6634 is inserted through a tapered passage 6338 in the drive component body 6612 and into the latch cavity 6636. The spherical latch head 6634 is sized and shaped relative to the latch cavity 6636 to permit relative movement between the drive components 6610 when arranged as shown in FIG. 74. However, when the drive components are axially aligned such that the distal face 6616 of one drive component 6610 is in abutting engagement with the proximal face 6614 of the drive component that is immediately distal thereto, the drive components 6610 form an axially rigid series 6600AR of drive components that can drive the firing member 6130 through the surgical end effector 6000.

Figure 73:
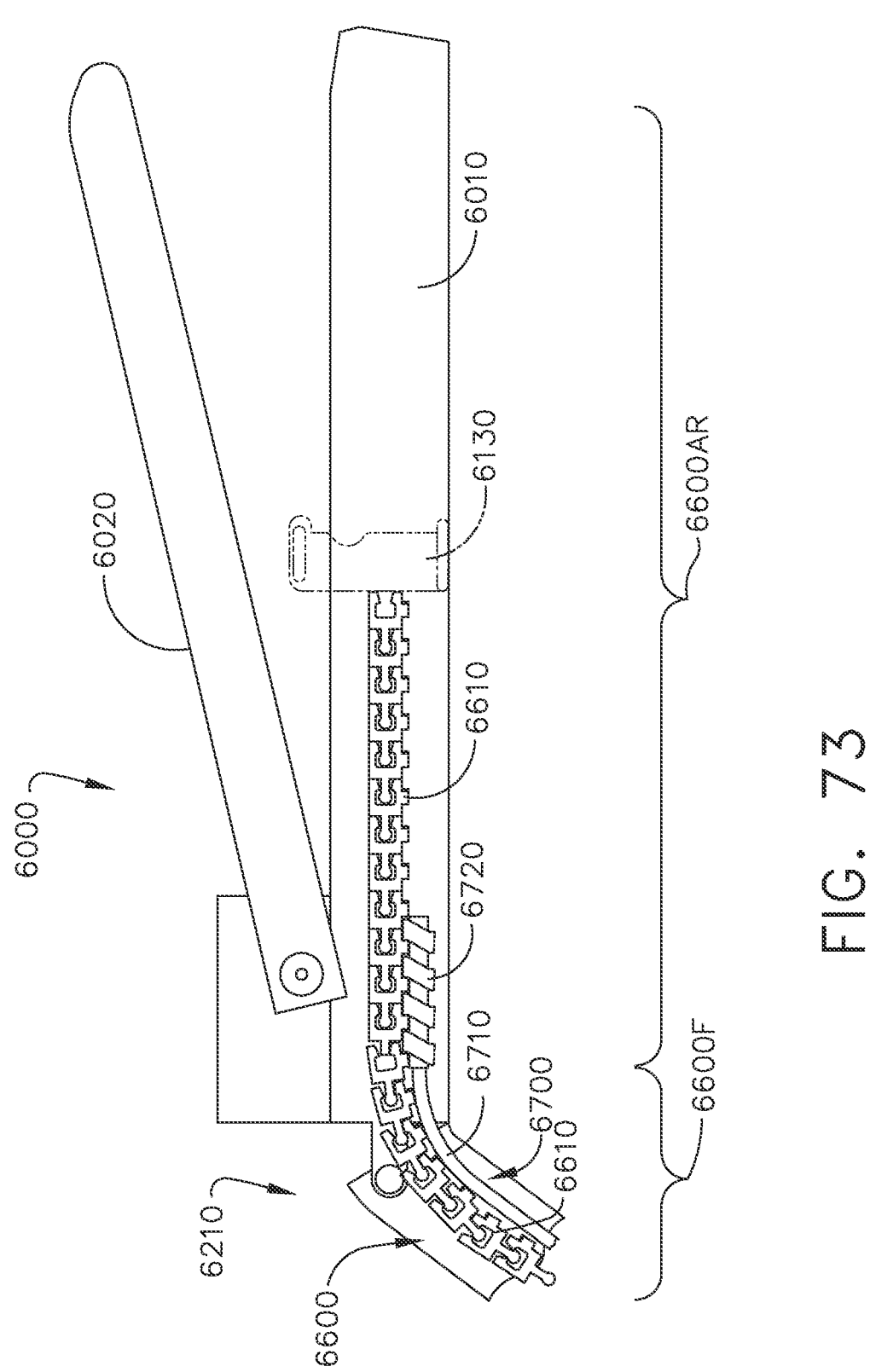
FIG. 73 is a partial side view of a surgical end effector of another surgical instrument that employs a series of flexibly linked drive components to drive a firing member through the surgical end effector.

As can be seen in FIG. 73, a flexible rotary drive system 6700 is employed to drive the series of 6600 drive components 6610. In one arrangement, the flexible rotary drive system 6700 comprises a flexible rotary drive shaft 6710 that can pass through the articulation joint 6210 and includes a rotary drive gear 6720 that is configured to threadably engage the thread segments 6620 on each drive component 6610. The flexible rotary drive shaft 6710 may be rotated by a motor/gear arrangement supported in a housing of a surgical instrument. The portion 6600F of the series 6600 of drive components 6610 that is proximal to the rotary drive gear 6720, remains flexibly linked or "floppy". As the drive components 6610 are threadably engaged by the rotary drive gear 6720 they are driven through a passage in the channel 6010 that causes the drive components to form the axially rigid series 6600AR for driving the firing member 6130 through the surgical end effector 6000.

Figure 77:
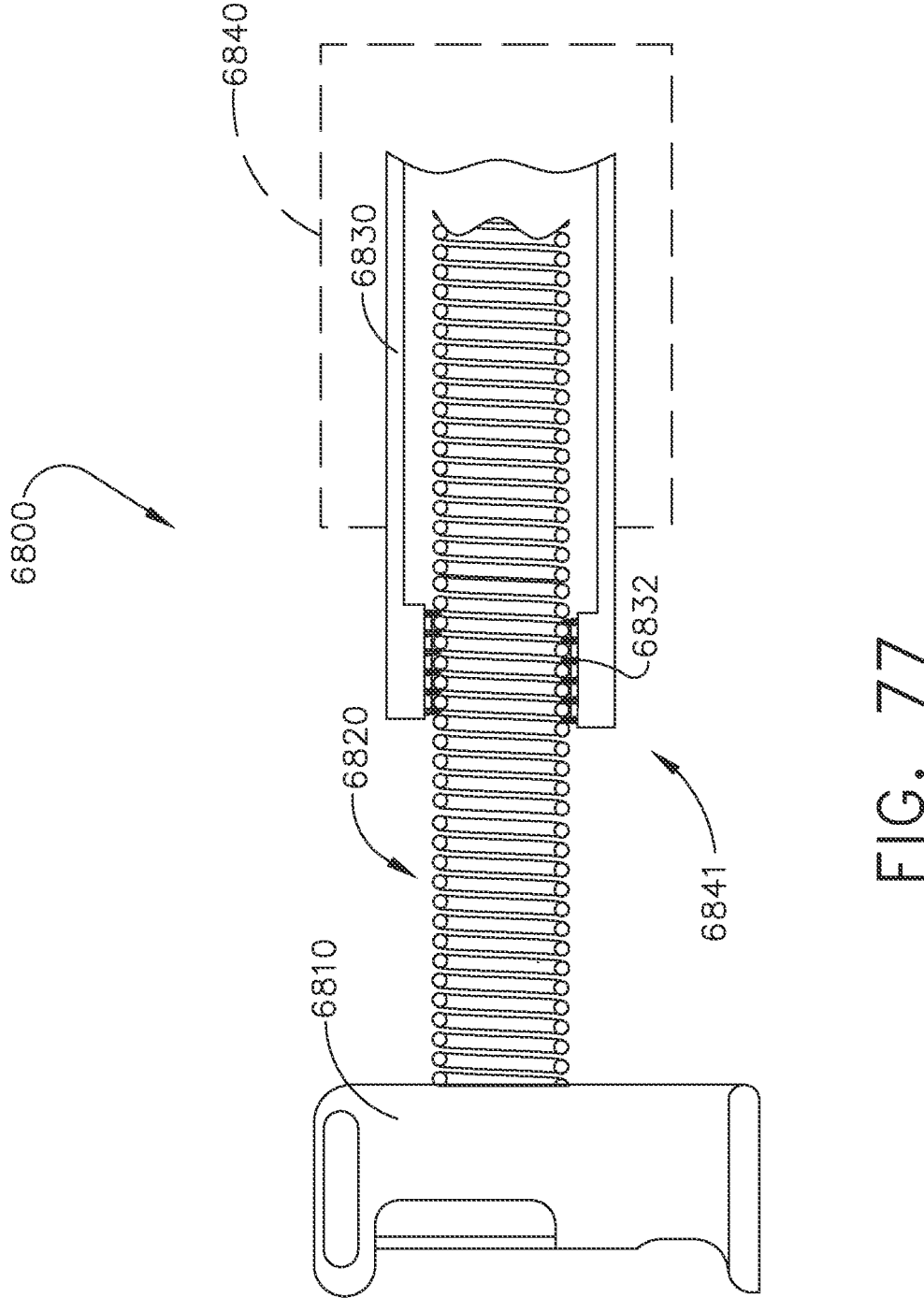
FIG. 77 is a side view of a portion of rotary firing system and firing member of another surgical instrument.

Torsional loads that are applied to firing system components as they traverse the articulation joint are less likely to de-articulate the articulation joint than axial loads. Various embodiments disclosed herein transfer torsional loads to longitudinal loads in a location that is distal of the articulation joint. Because the longitudinal loads are contained in the end effector, de-articulation is prevented. FIG. 77 illustrates one firing system 6800 example that can provide such advantages. The firing system 6800 comprises a firing member 6810 that is configured to be operably supported in a surgical end effector in the various manners described herein. A flexible spring-like driven member 6820 is attached to the firing member 6810. Such flexible, spring-like driven member 6820 can span an articulation joint area 6840 that can attain relatively large ranges of articulation. The flexible, spring-like driven member 6820 is configured to be driven axially by a flexible, spring-like torsion drive member 6830 that is rotatably supported to span the articulation joint area 6840. The flexible, spring-like torsion drive member 6830 includes a threaded insert 6832 that is configured to threadably engage the spring-like driven member 6820 at a location 6841 that is distal to the articulation joint area 6840. The flexible, spring-like torsion drive member 6830 may be rotated by a motor/gear arrangement supported in a housing of a surgical instrument. As the flexible, spring-like torsion drive member 6830 rotates in a first direction, the flexible, spring-like driven member 6820 translates longitudinally to drive the firing member 6810. Rotation of the flexible torsion drive member 6830 in a second direction will cause the flexible, spring-like driven member to move proximally.

Figure 78:
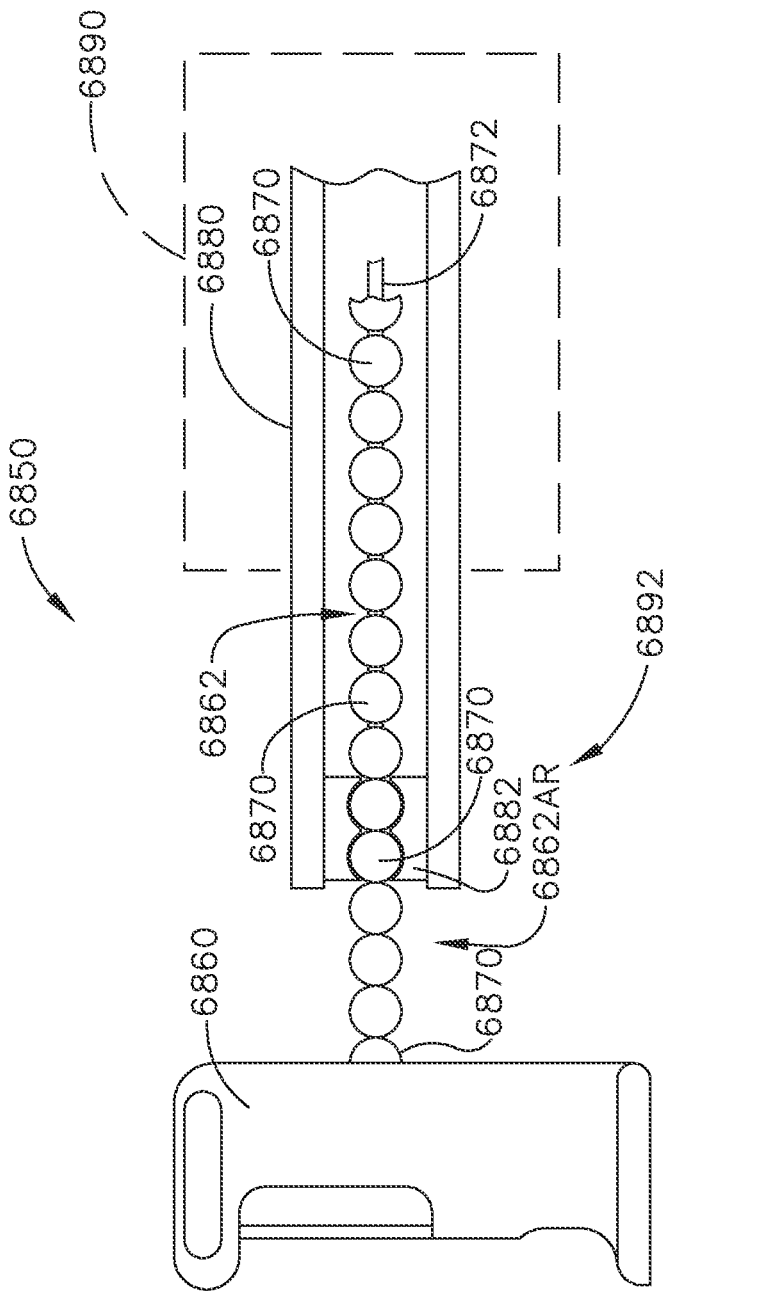
FIG. 78 is a side view of a portion of a rotary firing system and firing member of another surgical instrument.

FIG. 78 illustrates another firing system 6850 that comprises a firing member 6860 that is configured to be operably supported in a surgical end effector in the various manners described herein. The firing member 6860 is driven by firing member drive assembly 6861 which comprises a series 6862 of spherical ball members 6870 that are coupled together by a flexible cable 6872. Such series 6862 of flexible spherical ball members 6870 can span an articulation joint area 6840 that can attain relatively large ranges of articulation. The series 6862 of flexible spherical ball members 6870 is configured to be driven axially by a flexible torsion drive member 6880 that is rotatably supported to span an articulation joint area 6890. The flexible torsion drive member 6880 includes an insert 6882 that is configured to drivingly engage the spherical ball members 6870 at a location 6892 that is distal to the articulation joint area 6890. The flexible torsion drive member 6880 may be rotated by a motor/gear arrangement supported in a housing of a surgical instrument. As the flexible torsion drive member 6880 rotates in a first direction, the spherical ball members 6870 are driven distally into contact with each other to form an axially rigid series 6862AR that translates longitudinally to drive the firing member 6860 distally. Rotation of the flexible torsion drive member 6880 in a second direction will cause the series of spherical ball members 6870 to move proximally.

Figure 79:
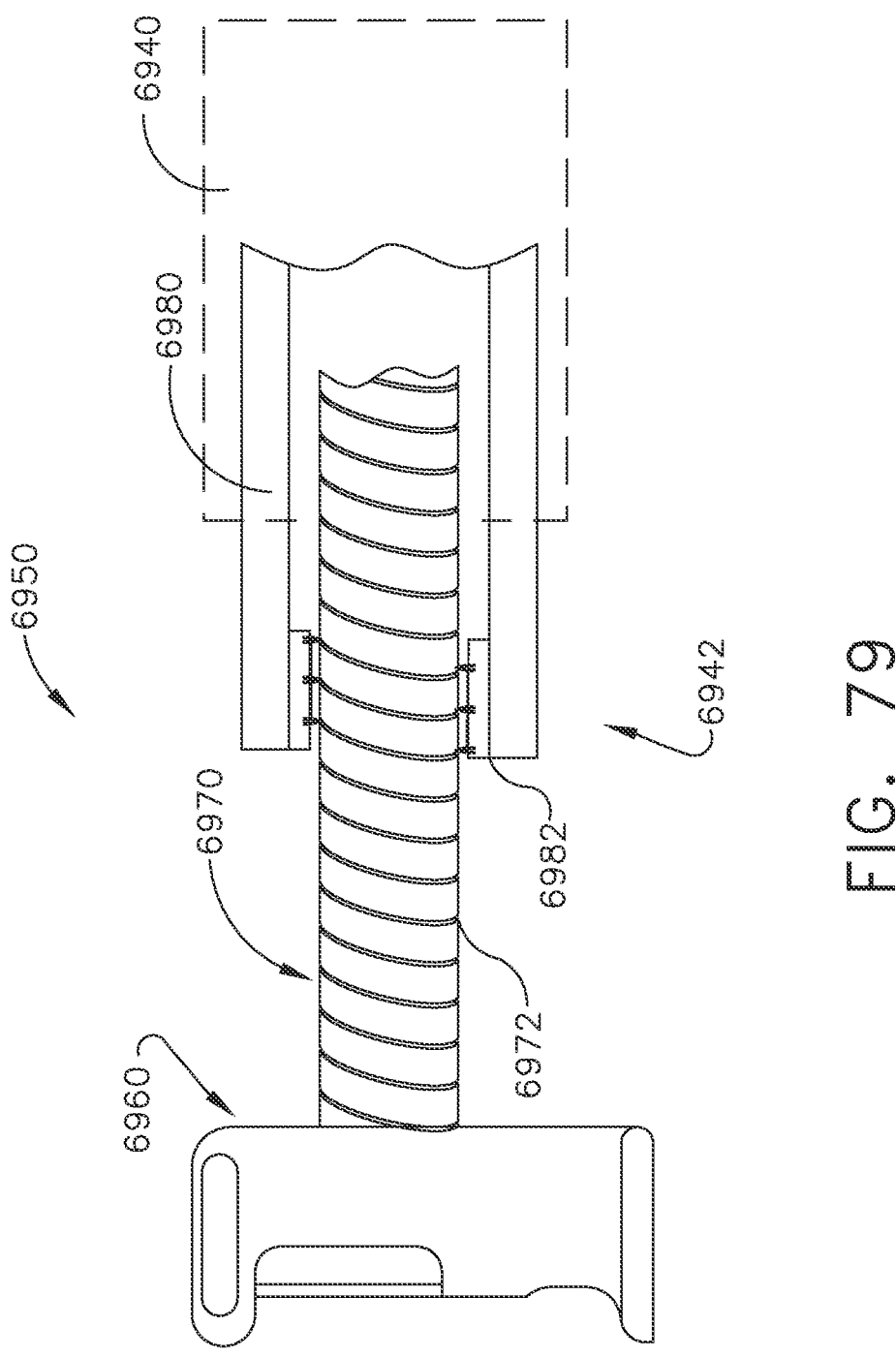
FIG. 79 is a side view of a portion of a rotary firing system and firing member of another surgical instrument.

FIG. 79 illustrates another firing system 6950 that comprises a firing member 6960 that is configured to be operably supported in a surgical end effector in the various manners described herein. A laser cut, hypotube driven member 6970 is attached to the firing member 6960. Such flexible driven member 6970 can span an articulation joint area 6940 that can attain relatively large ranges of articulation. The flexible driven member 6970 is configured to be driven axially by a flexible torsion drive member 6980 that is rotatably supported to span the articulation joint area 6940. The flexible torsion drive member 6980 includes a threaded insert 6982 that is configured to threadably engage the laser cuts 6972 on the flexible driven member 6970 at a location 6942 that is distal to the articulation joint area 6940. The flexible torsion drive member 6980 may be rotated by a motor/gear arrangement supported in a housing of a surgical instrument. As the flexible torsion drive member 6980 rotates in a first direction, the flexible driven member 6970 translates longitudinally to drive the firing member 6960. Rotation of the flexible torsion drive member 6980 in a second direction will cause the flexible driven member 6970 to move proximally.

Figures 80, 81:
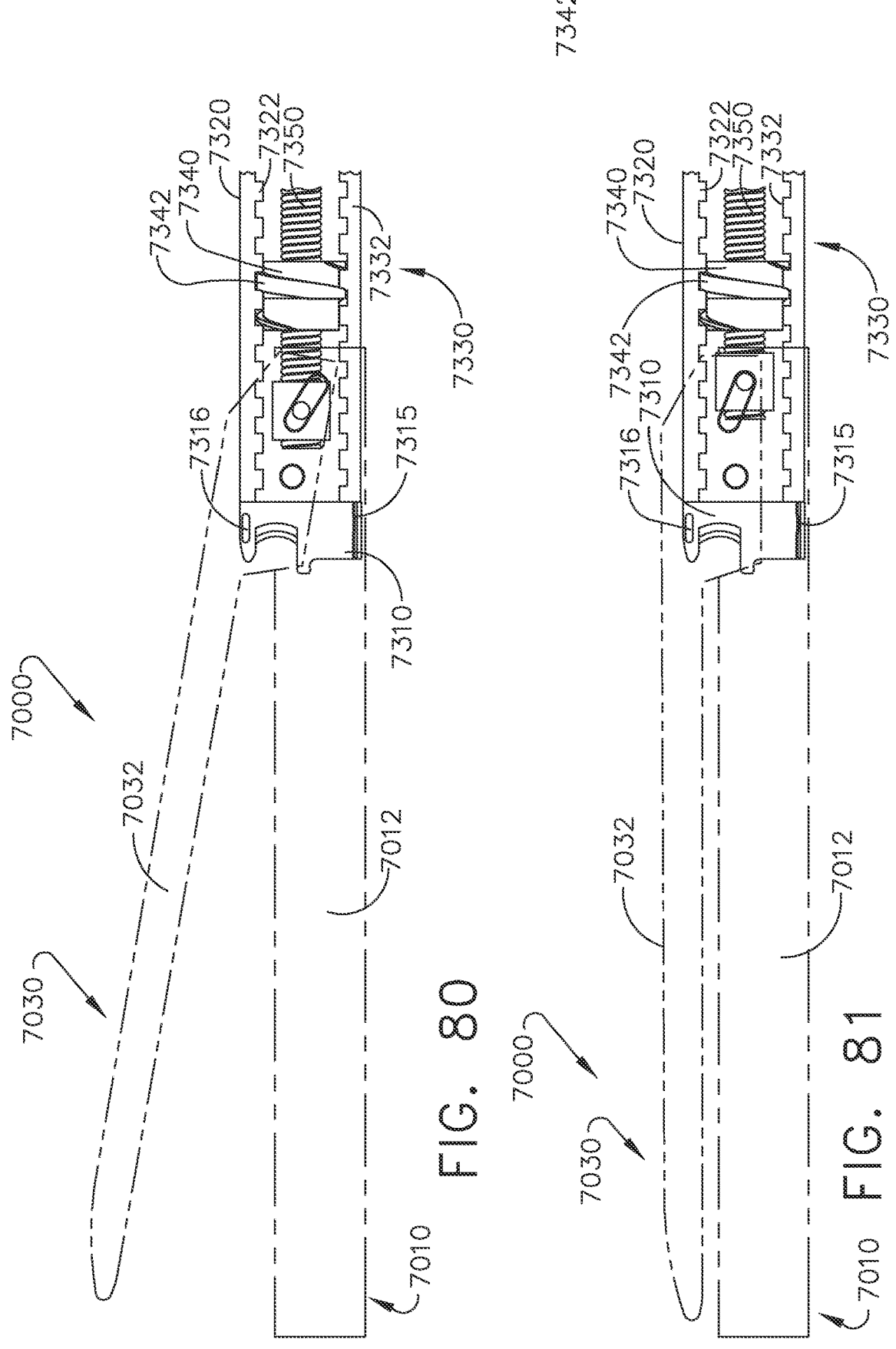
FIG. 80 is a partial view of another surgical instrument that employs a rotary driven firing system to drive a firing member through a surgical end effector with an anvil of the surgical end effector in an open position.
FIG. 81 is another partial side view of the surgical instrument and end effector of FIG. 80 with the anvil thereof in a closed position.
Figure 82:
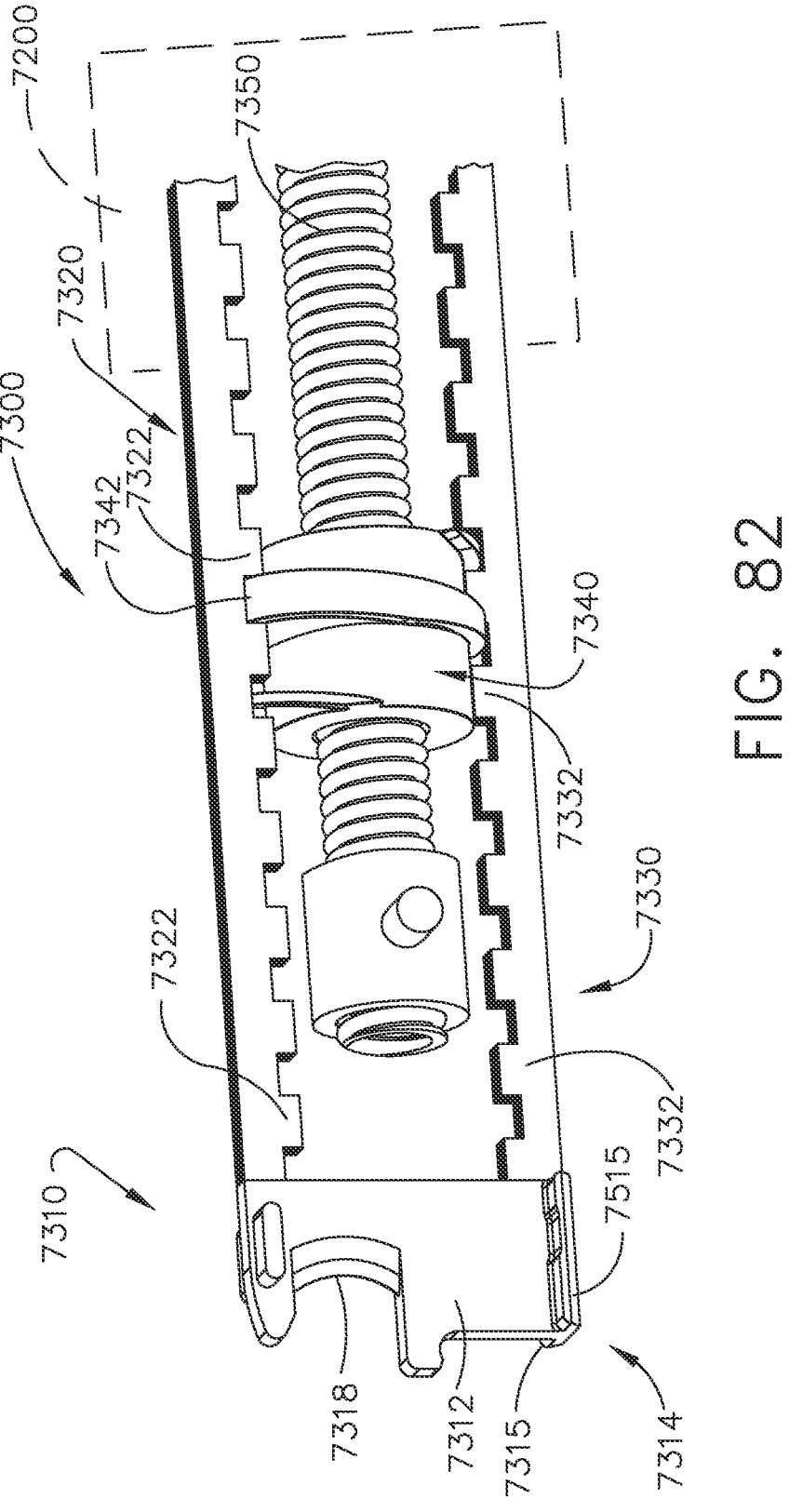
FIG. 82 is a perspective view of portions of the rotary driven firing system of the surgical instrument of FIG. 80.
Figure 83:
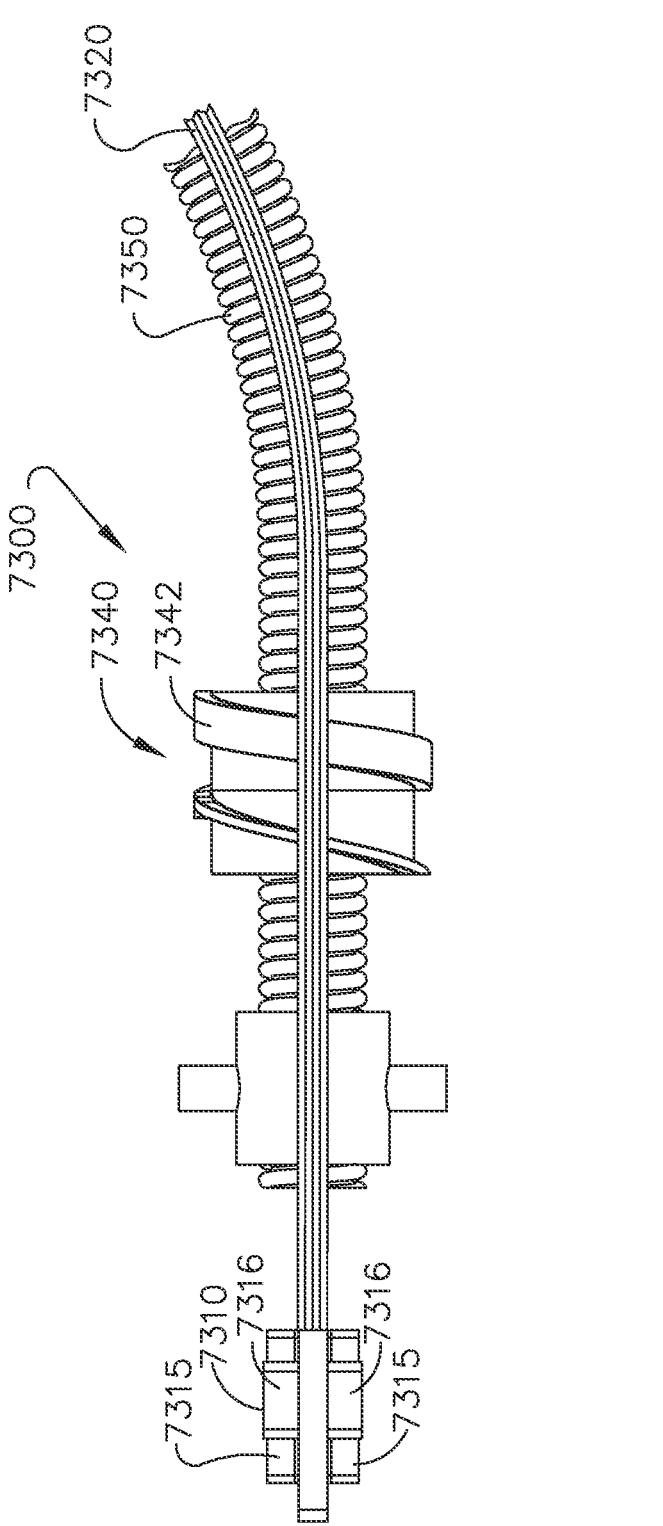
FIG. 83 is a top view of a portion of the rotary driven firing system depicted in FIG. 82.
Figure 84:
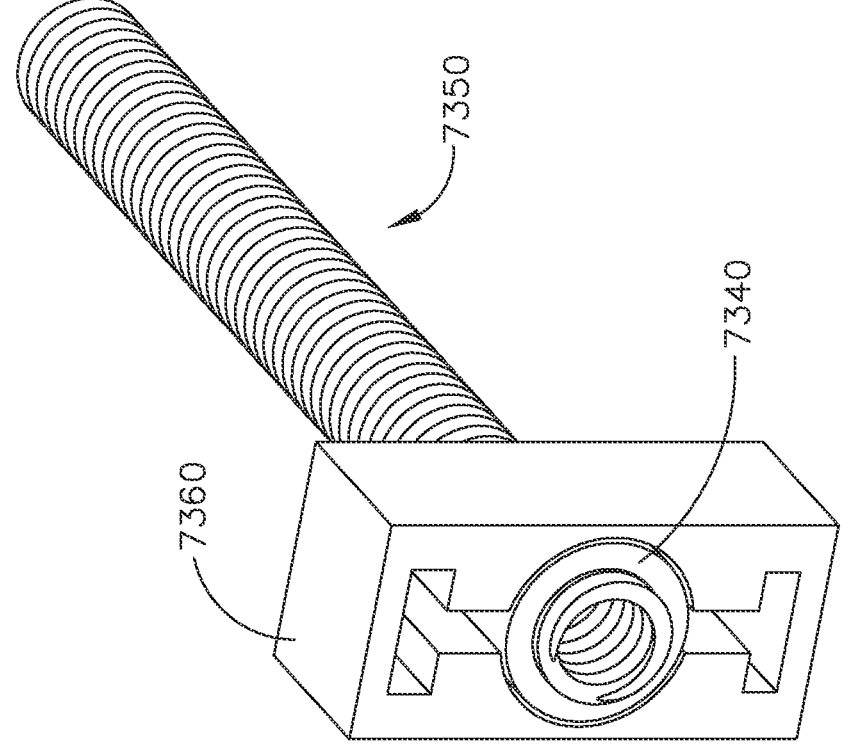
FIG. 84 is a perspective view of a guide member and rotary drive shaft of the rotary driven firing system of FIG. 83.

Pushing a firing beam forward in an articulating end effector generally requires a lot of force and such force needs to be balanced. For example, it is generally difficult to push a firing beam through an articulation joint that has been articulated to angles of greater than sixty degrees. As the firing beam traverses through the articulation joint, the firing beam can apply significant loads onto the articulation joint components which can cause the articulation joint to de-articulate. FIGS. 80-84 illustrate a firing drive system 7300 that comprises a flexible upper drive band 7320 and a flexible lower drive band 7330 that are attached to a firing member 7310 that is configured to move within a surgical end effector 7000 between a starting and ending position. As can be seen in FIGS. 80-82, the flexible upper drive band 7320 comprises a plurality of spaced upper drive teeth 7322 that are configured to threadably engage a helical thread 7342 on a rotary drive nut 7340. Similarly, the flexible lower drive band 7330 comprises a plurality of spaced lower drive teeth 7332 that are configured to threadably engage the helical thread 7342 on the rotary drive nut 7340. In at least one arrangement, the flexible upper drive band 7320 and the flexible lower drive band 7330 are formed from a metal material and are welded to or otherwise attached to the firing member 7310. Such arrangement serves to balance the firing loads that are applied to the firing member 7310.

The rotary drive nut 7340 is received on a flexible rotary drive shaft 7350 that is centrally disposed between the flexible upper drive band 7320 and the flexible lower drive band 7330 and traverses through the articulation joint area generally designated as 7200. The flexible rotary drive shaft 7350 may be rotated by a motor/gear arrangement supported in a housing of a surgical instrument. As the flexible rotary drive shaft 7350 rotates in a first direction, the flexible upper drive band 7320 and the flexible lower drive band 7330 will drive the firing member 7310 distally. Rotation of the flexible rotary drive shaft 7350 in a second direction will cause the flexible upper drive band 7320 and the flexible lower drive band 7330 to pull the firing member 7310 proximally. In at least one arrangement, flexible upper drive band 7320 and the flexible lower drive band 7330 pass through a guide member 7360 that surrounds the rotary drive nut 7340 to prevent the flexible upper drive band 7320 and the flexible lower drive band 7330 from bypassing the rotary drive nut 7340 during actuation of the flexible rotary drive shaft 7350. See FIG. 84.

In the illustrated arrangement, the firing member 7310 is configured to move through the surgical end effector 7000 that comprises a first jaw 7010 and a second jaw 7030 that is configured to move relative to the first jaw 7010. In one embodiment, the first jaw 7010 comprises an elongate channel 7012 that is configured to operably support a surgical staple cartridge therein. See FIGS. 80 and 81. The second jaw 7030 comprises an anvil 7032 that is pivotally supported on the elongate channel 7012 and is movable between an open position and a closed position relative to the elongate channel 7012. As can be seen in FIG. 82, in at least one form, the firing member 7310 comprises a shape that is commonly referred to as an "E-beam". The firing member 7310 comprises a vertically extending firing member body 7312 that has a lower foot feature 7314 that comprises two laterally extending tabs 7315 that are configured to be slidably engage the elongate channel 7012 as the firing member is driven axially therein. In addition, a pair of upper tabs 7316 protrude from the upper portion of the firing member body 7312 to engage the anvil 7032 as the firing member 7310 is driven distally through the closed anvil 7032. During the firing stroke, the tabs 7315 and 7316 may serve to space the anvil 7032 relative to the surgical staple cartridge supported in the elongate channel 7012. The firing member body 7312 also comprises a tissue cutting feature 7318. The tabs 7316 may also serve to apply a closing motion to the anvil 7032 as the firing member 7310 is moved distally from the starting position.

In the illustrated example, the firing drive system 7300 may also be employed to apply opening and closing motions to the anvil 7032. As can be seen in FIGS. 80-83, a closure nut 7370 is threadably received on the flexible rotary drive shaft 7350. The closure nut 7370 comprises a cam pin 7372 that extends laterally from each side of the closure nut 7370 to be received in corresponding cam slots 7036 in an anvil mounting portion 7034 of the anvil 7032. See FIGS. 80 and 81. Such cam pins 7372 prevent the closure nut 7370 from rotating with the flexible rotary drive shaft 7350 such that rotation of the flexible rotary drive shaft 7350 causes the closure nut 7370 to move axially. Thus, rotation of the flexible rotary drive shaft 7350 in a first direction causes the closure nut 7370 to move distally and cam the anvil 7032 from the open position to the closed position. Rotation of the flexible rotary drive shaft 7350 in the second rotary direction will cause the closure nut 7370 to move proximally and cam the anvil 7032 back to the open position. Thus, alternating the rotation of the flexible rotary drive shaft 7350 may allow the surgeon to quickly open and close the anvil 7032 for grasping purposes, for example.

Figure 85:
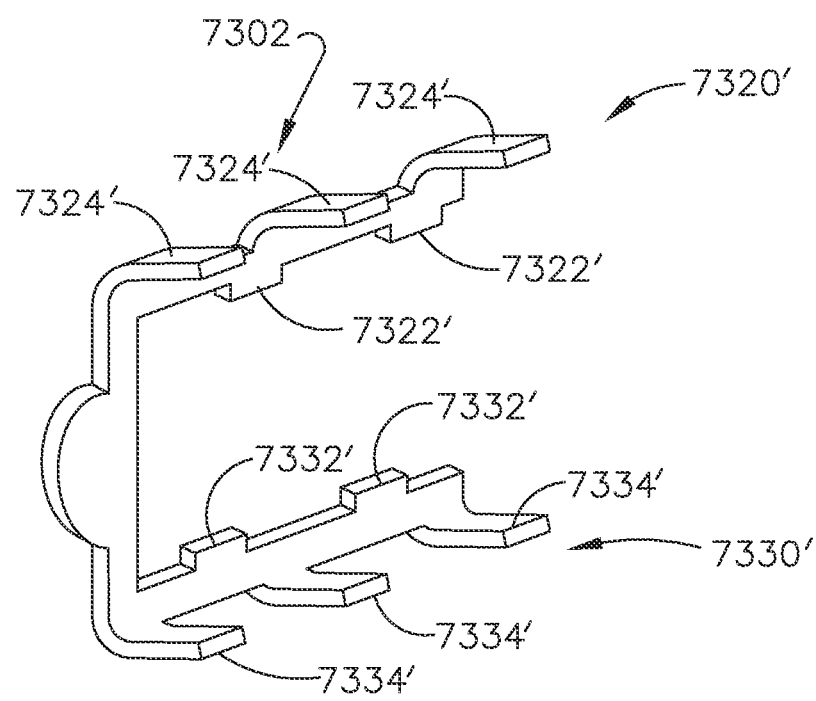
FIG. 85 is a perspective view of a portion of another flexible firing drive assembly that may be employed with the firing drive system of FIG. 83.
Figure 86:
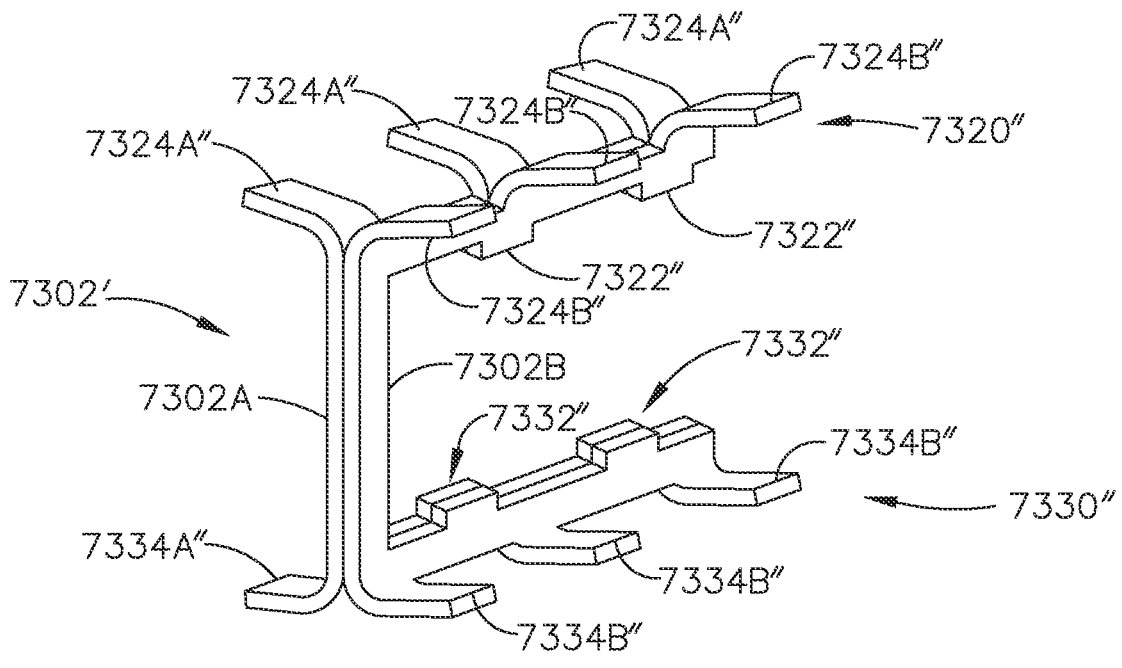
FIG. 86 is another perspective view of a portion of another flexible firing drive assembly embodiment that may be employed with the firing drive system of FIG. 83.

FIG. 85 illustrates an alternative firing drive assembly 7302 that comprises the flexible upper drive band 7320' that has upper drive teeth 7322' and a flexible lower drive band 7330' that has lower drive teeth 7332' that is formed out of one piece of material such as metal. The flexible upper drive band 7320' also includes upper strength tabs 7324' that are provided to pass through the anvil 7032 similar to the upper tabs 7316 on the firing member 7310 as well as lower strength tabs 7334 that are provided to pass through the channel 7012 similar to the tabs 7315 on the firing member 7310. FIG. 86 illustrates an alternative firing drive assembly 7302' that is fabricated from two band assemblies 7302A and 7302B that are laminated together to form the flexible upper drive band 7320" that has the upper drive teeth 7322" and a flexible lower drive band 7330" that has the lower drive teeth 7332". Each band assembly 7302A, 7302B also comprise upper strength tabs 7324A", 7324B" and lower strength tabs 7334A", 7334B" that are provided to pass through the anvil 7032 and the elongate channel 7012, respectively.

The firing drive system 7300 serves to apply a uniform drive motion to the firing member 7310 and can accommodate articulation angles that may be greater than seventy degrees, for example. In addition, because the rotary drive nut 7340 engages the flexible upper drive band 7320 and flexible lower drive band 7330 at a location that is distal to the articulation joint area 7200, the linear firing loads are confined to the end effector and do not go through the articulation joint.

Figure 87:
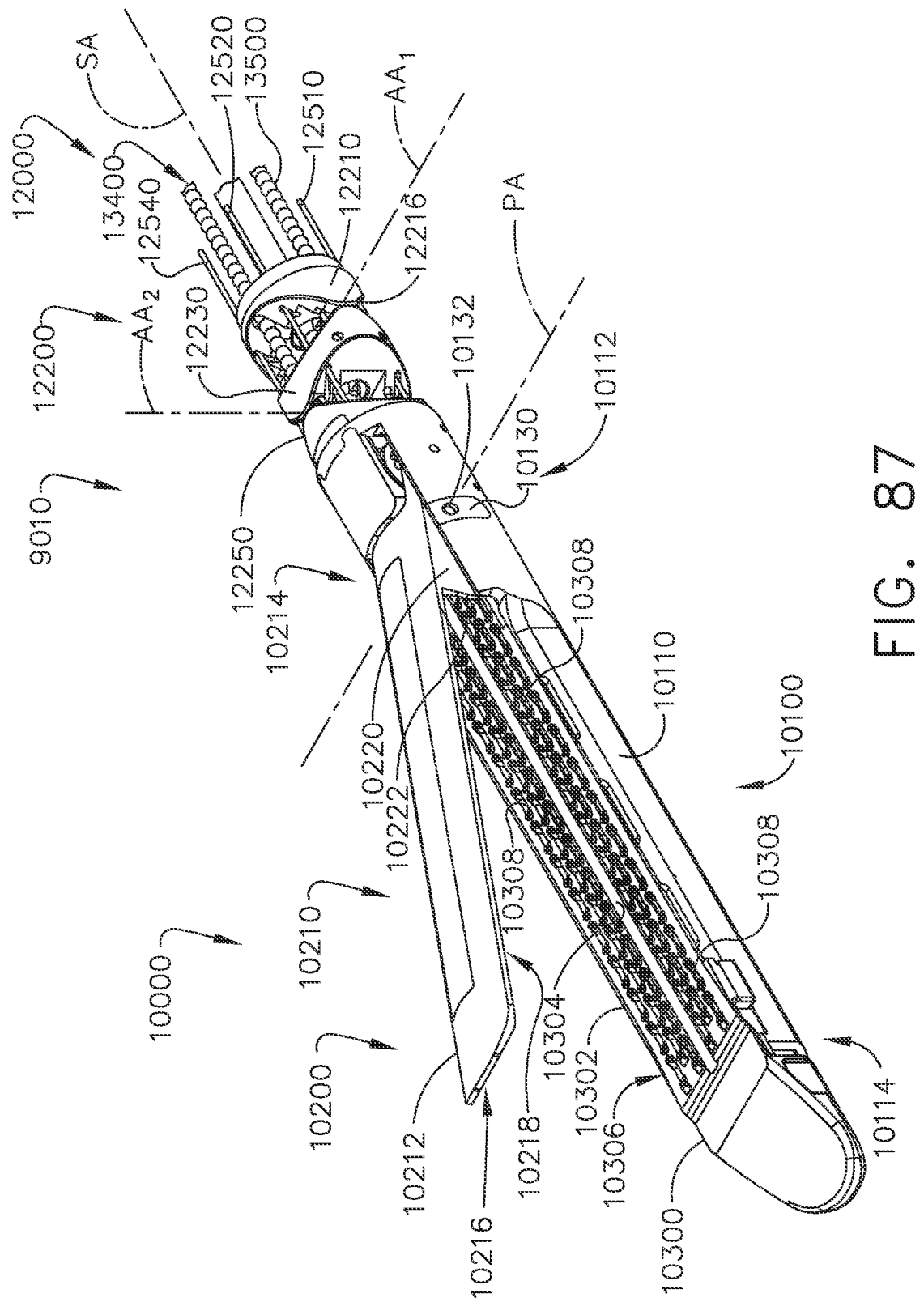
FIG. 87 is a perspective view of a surgical end effector of another surgical instrument with an anvil thereof in an open position and the surgical end effector in an unarticulated orientation.
Figure 88:
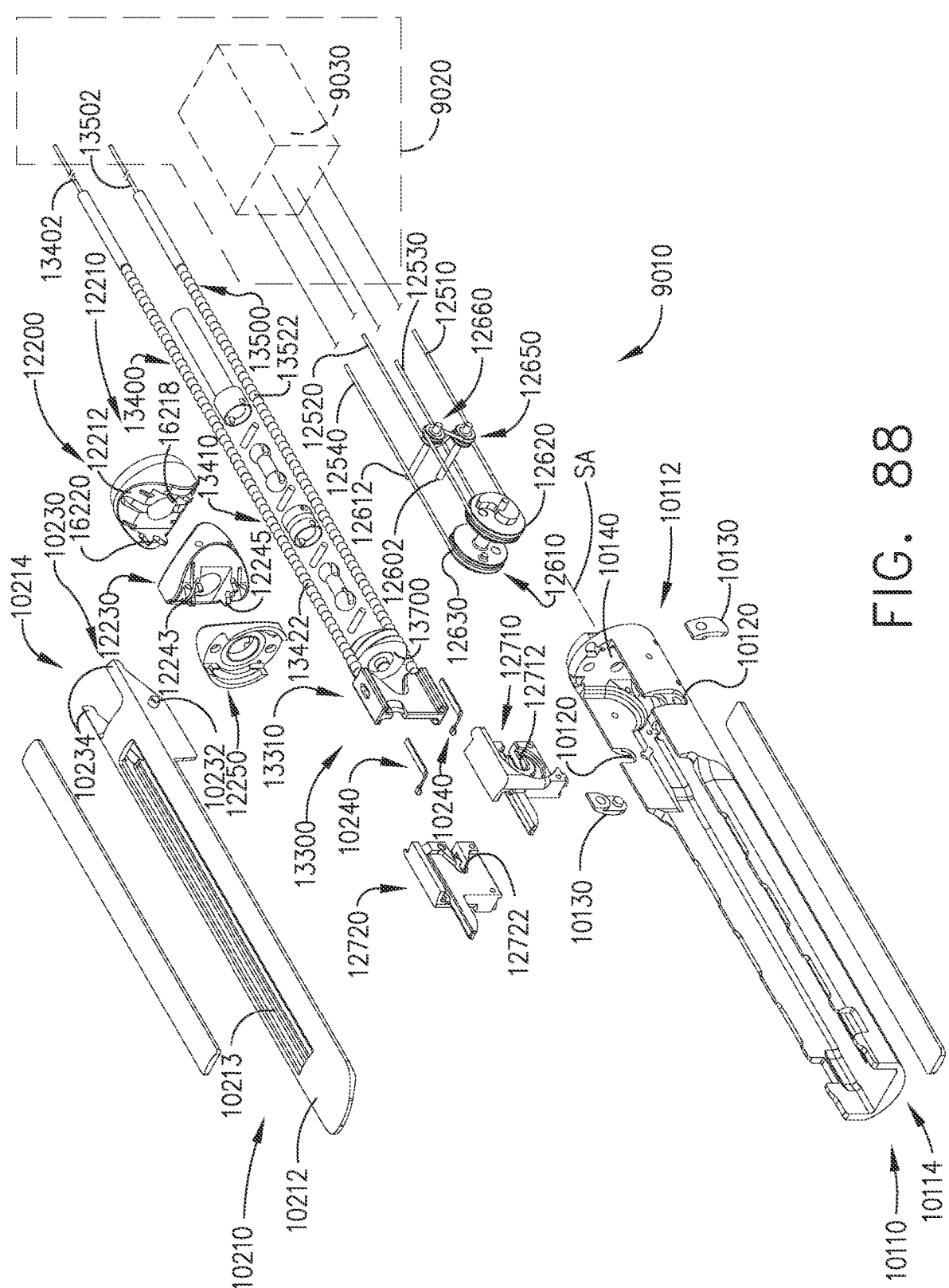
FIG. 88 is an exploded assembly view of the surgical end effector and surgical instrument of FIG. 87.
Figures 89, 90:
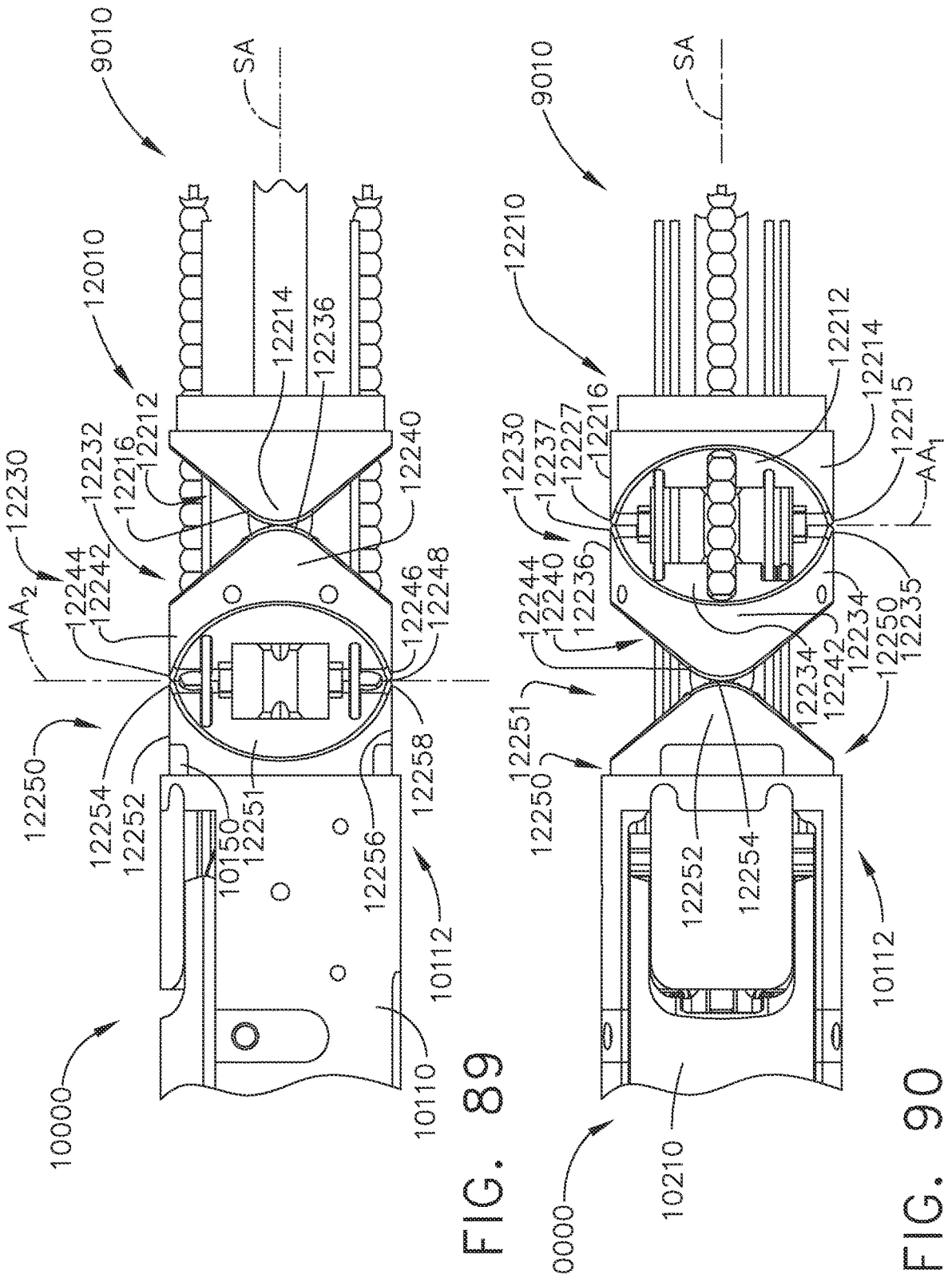
FIG. 89 is a side elevational view of an articulation joint of the surgical instrument of FIG. 87.
FIG. 90 is a top view of the articulation joint of FIG. 89.

FIGS. 87-89 illustrate another form of surgical instrument 9010 that may address many of the challenges facing surgical instruments with end effectors that are articulatable to large articulation angles and that are configured to cut and fasten tissue. In various embodiments, the surgical instrument 9010 may comprise a handheld device. In other embodiments, the surgical instrument 9010 may comprise an automated system sometimes referred to as a robotically-controlled system, for example. In various forms, the surgical instrument 9010 comprises a surgical end effector 10000 that is operably coupled to an elongate shaft assembly 12000. The elongate shaft assembly 12000 may be operably attached to a housing. In one embodiment, the housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 10000 comprises a first jaw 10100 and a second jaw 10200. In the illustrated arrangement, the first jaw 10100 comprises an elongate channel 10110 that comprises a proximal end 10112 and a distal end 10114 and is configured to operably support a surgical staple cartridge 10300 therein. The surgical staple cartridge 10300 comprises a cartridge body 10302 that has an elongate slot 10304 therein. A plurality of surgical staples or fasteners (not shown) are stored therein on drivers (not shown) that are arranged in rows on each side of the elongate slot 10304. The drivers are each associated with corresponding staple cavities 10308 that open through a cartridge deck surface 10306. The surgical staple cartridge 10300 may be replaced after the staples/fasteners have been discharged therefrom. Other embodiments are contemplated wherein the elongate channel 10110 and/or the entire surgical end effector 10000 is discarded after the surgical staple cartridge 10300 has been used.

In the illustrated arrangement, the second jaw 10200 comprises an anvil 10210 that comprises an elongate anvil body 10212 that has a proximal end 10214 and a distal end 10216. The anvil body 10212 comprises a staple-forming undersurface 10218 that faces the first jaw 10100 and may include a series of staple-forming pockets (not shown) that correspond to each of the staples or fasteners in the surgical staple cartridge 10300. The anvil body 10212 may further include a pair of downwardly extending tissue stop features 10220 that are formed adjacent the proximal end 10214 of the anvil body 10212. One tissue stop feature 10220 extends from each side of the anvil body 10212 such that a distal end 10222 on each tissue stop 10220 corresponds to the proximal-most staples/fasteners in the surgical staple cartridge 10300. When the anvil 10200 is moved to a closed position onto tissue positioned between the staple-forming undersurface 10218 of the anvil 10200 and the cartridge deck surface 10306 of the surgical staple cartridge 10300, the tissue contacts the distal ends 10222 of the tissue stops 10220 to prevent the tissue from migrating proximally past the proximal-most staples/fasteners to thereby ensure that the tissue that is cut is also stapled. When the surgical staple cartridge is "fired" as will be discussed in further detail below, the staples/fasteners supported within each staple cavity are driven out of the staple cavity 10308 through the clamped tissue and into forming contact with the staple forming undersurface 10218 of the anvil 10200.

As can be seen in FIG. 88, the proximal end 10214 of the anvil body 10212 comprises an anvil mounting portion 10230 that comprises a pair of laterally extending mounting pins 10232 that are configured to be received in corresponding mounting inserts 10130 that are configured to be retainingly received within mounting cradles 10120 formed in the proximal end 10112 of the elongate channel 10110. The mounting pins 10232 are pivotally received within pivot holes 10132 in the mounting inserts 10130 and then the mounting inserts 10130 are inserted into their corresponding cradle 10120 and affixed to the elongate channel 10110 by welding, adhesive, snap fit, etc. Such arrangement facilitates pivotal travel of the anvil 10210 relative to the elongate channel 10110 about a fixed (i.e., non-translating, non-moving) pivot axis PA. See FIG. 87.

In the illustrated arrangement, the elongate shaft assembly 12000 defines a shaft axis SA and comprises a hollow outer tube (omitted for clarity) that operably interfaces with a housing of the control portion (e.g., handheld unit, robotic tool driver, etc.) of the surgical instrument 9010. The elongate shaft assembly 12000 further comprises an articulation joint 12200 that may be attached to the hollow outer tube as well as the surgical end effector 10000 to facilitate selective articulation of the surgical end effector 10000 relative to the elongate shaft assembly 12000 about multiple articulation axes in multiple articulation planes. In at least one arrangement, for example, the articulation joint 12200 comprises a proximal joint member 12210, a central joint member 12230, and a distal joint member 12250. In one example, the central joint member 12230 operably interfaces with the proximal joint member 12210 such that the central joint member 12230 is selectively articulatable through a first or proximal articulation plane that is defined by a first or proximal articulation axis AA 1 that is transverse to the shaft axis SA. Also in one example, the distal joint member 12250 operably interfaces with the central joint member 12230 such that the distal joint member 12250 is selectively articulatable through a second or distal articulation plane that is defined by a second or distal articulation axis $AA_2$ that is transverse to the shaft axis SA and transverse to the first or proximal articulation axis $AA_1$.

As can be seen in FIGS. 89 and 90, the proximal joint member 12210 comprises a proximal joint distal face 12212 that defines two spaced, lateral apex portions 12214, 12216. The apex portion 12214 defines a radial surface 12215 and the apex portion 12216 defines a radial surface 12217 (FIG. 90). The central joint member 12230 comprises proximal face 12232 that defines two spaced lateral proximal apex portions 12234, 12236. The proximal apex portion 12234 defines a radial surface 12235 and the apex portion 12236 defines a radial surface 12237. As can be seen in FIG. 89, the proximal face 12232 of the central joint member 12230 confronts the proximal joint distal face 12212 of the proximal joint member 12210 such that the central joint member 12230 is articulatable through a first articulation plane defined by the first or proximal articulation axis AA 1 that extends between a point where the lateral apex portion 12214 on the proximal joint member contacts the proximal apex portion 12234 on the central joint member 12230 and the point where the lateral apex portion 12216 on the proximal joint member 12210 contacts the proximal apex portion 12236 on the central joint member 12230. In one arrangement, the radial surfaces 12215, 12217 on the lateral apex portions 12214, 12216, respectively, and the radial surfaces 12235 and 12237 on the proximal apex portions 12234, 12236, respectively, may act as rocker points/surfaces about which the central joint member 12230 may articulate relative to the proximal joint member 12210. Additionally, the central joint member 12230 comprises proximal first gear tooth segments that are configured to rotatably mesh with distal gear segments 12218, 12220 on the proximal joint member 12210. See FIG. 88. In various arrangements, the radial surface 12235 on the central joint member 12230 may be spaced from the radial surface 12215 on the proximal joint member 12210 and the radial surface 12237 on the central joint member 12230 may be spaced from the radial surface 12217 on the proximal joint member 12210.

Figure 92:
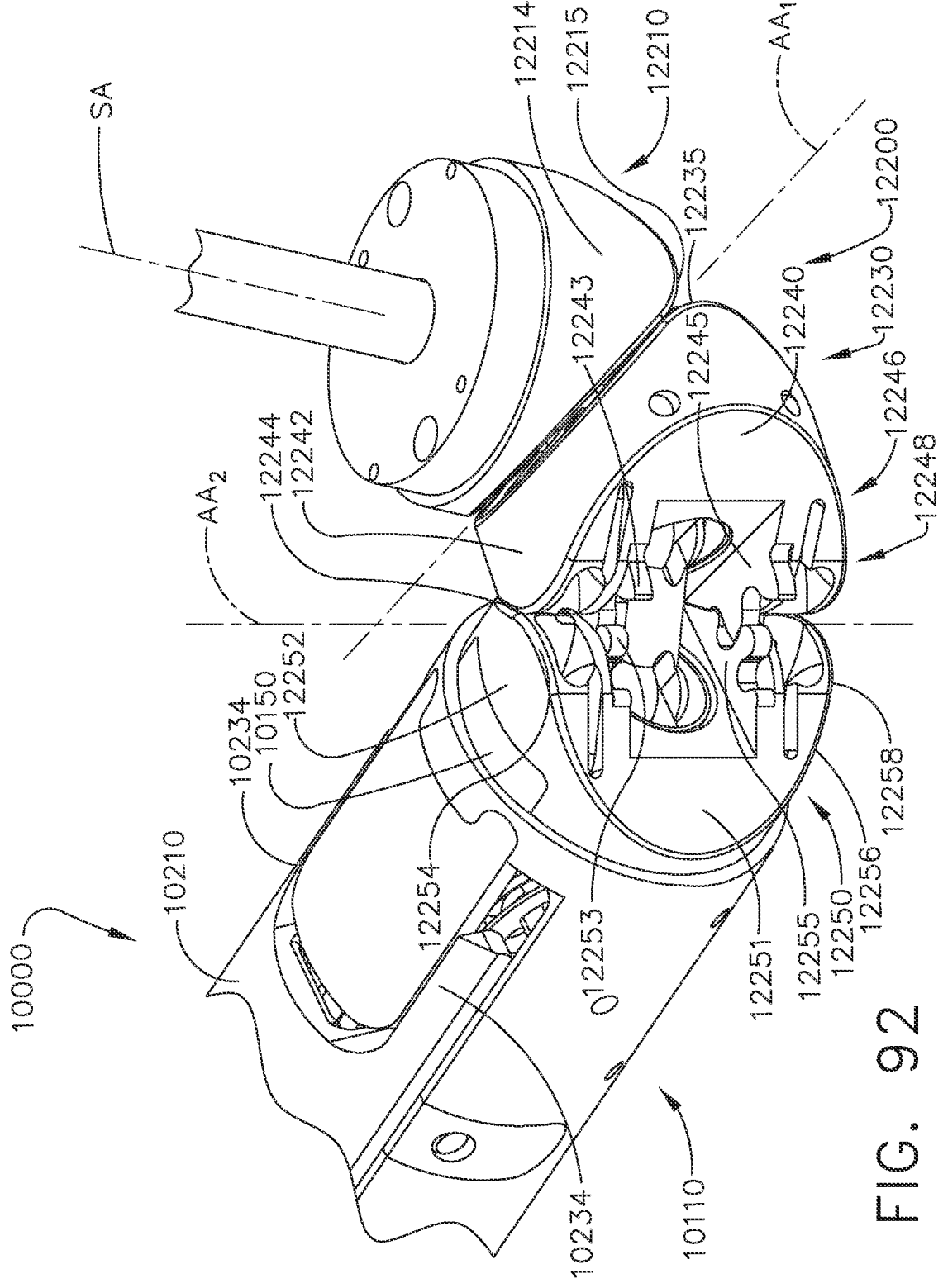
FIG. 92 is a perspective view of a portion of the surgical end effector of FIG. 89 articulated by the articulation joint of FIG. 89.
Figure 95:
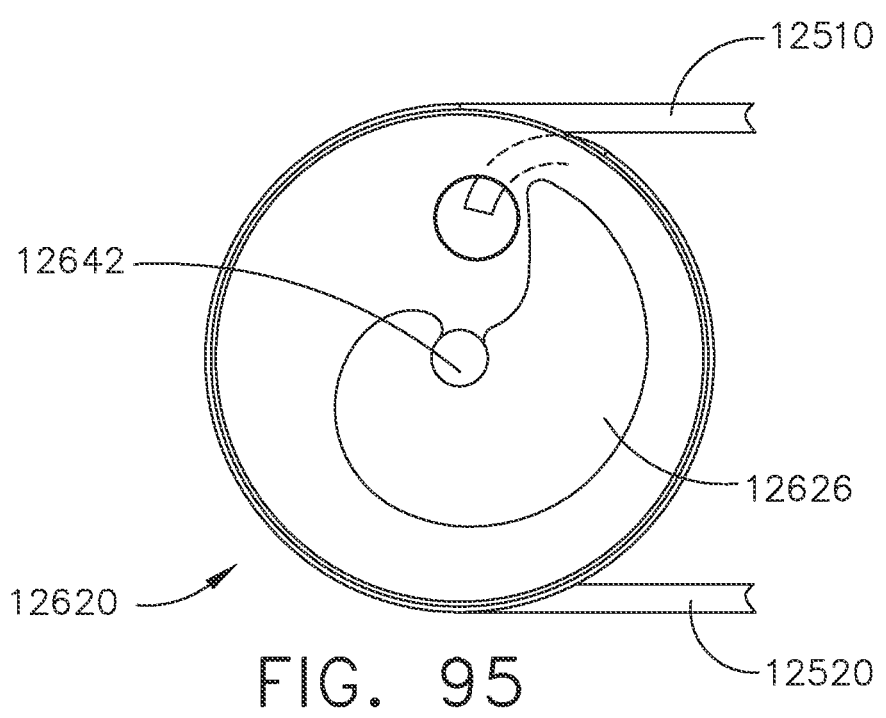
FIG. 95 is a side elevational view of a first lateral alpha wrap pulley of the pulley unit of FIG. 94.

The central joint member 12230 further comprises a central joint distal face 12240 that defines a centrally disposed upper apex portion 12242 that forms an upper radial surface 12244 and a lower apex portion 12246 that forms a lower radial surface 12248. See FIG. 89. The distal joint member 12250 is attached to the proximal end 10112 of the elongate channel 10110 by a mounting bushing 10150 and comprises a proximal face 12251 that faces or confronts the central joint distal face 12240 on the central joint member 12230. See FIGS. 89 and 92. As can be seen in FIGS. 89 and 92, the proximal face 12251 defines a centrally disposed upper apex portion 12252 that forms an upper radial surface 12254 that is configured to confront or abut the upper radial surface 12244 on the central joint member 12230. The proximal face 12251 further defines a centrally disposed lower apex portion 12256 that forms a lower radial surface 12258 that is configured to confront or abut the lower radial surface 12248 on the central joint member 12230. See FIG.

89. The distal joint member 12250 further comprises an upper gear tooth segment 12253 that is configured to rotatably mesh with an upper gear tooth segment 12243 on the central joint member 12230. In addition, the distal joint member 12250 comprises a lower gear tooth segment 12255 that is configured to rotatably mesh with a lower gear tooth segment 12245 on the central joint member 12230. See FIG. 92.

The distal joint member 12250 is configured to articulate through a second or distal articulation plane defined by the second or distal articulation axis $AA_2$ that extends between a point where the upper apex portion 12252 on the distal joint member 12250 contacts or confronts the upper apex portion 12242 on the central joint member 12230 and the point where the lower apex portion 12256 on the distal joint member 12250 contacts or confronts the lower apex portion 12246 on the central joint member 12230. See FIGS. 89 and 92. In one arrangement, the radial surfaces 12254, 12258 on the upper and lower apex portions 12252, 12256, respectively of the distal joint member 12250 and the radial surfaces 12244 and 12248 on the upper and lower apex portions 12242, 12246, respectively on the central joint member 12230 may act as rocker points/surfaces about which the distal joint member 12250 may articulate relative to the central joint member 12230. In alternative arrangements, however, the radial surface 12254 on the distal joint member 12250 is spaced from the radial surface 12244 on the central joint member 12230 and the radial surface 12258 on the distal joint member 12250 is spaced from the radial surface 12248 on the central joint member 12230.

Returning to FIG. 88, in the illustrated example, the articulation joint 12200 is operably controlled by a cable control system 9030 that comprises four cables 12510, 12520, 12530, and 12540 that extend through the elongate shaft assembly 12000. The cable control system 9030 may be supported within a housing 9020 of the surgical instrument 9010. The cable control system 9030 may comprise a plurality of cable support members/capstans, pulleys, etc. that are controlled by one or more corresponding motors that are controlled by a control circuit portion of the surgical instrument 9010. In various embodiments, the cable control system 9030 is configured to manage the tensioning (pulling) and paying out of cables at precise times during the articulation process. In addition, in at least one arrangement, the cable control system 9030 is employed to control the opening and closing of the anvil 10210 as will be discussed in further detail below.

As can be seen in FIG. 88, the cables 12510, 12520, 12530, and 12540 are configured to operably interface with a closure system 12600 that is rotatably mounted in the proximal end 10112 of the elongate channel 10110. In at least one arrangement, the closure system 12600 comprises a pulley unit 12610 that comprises a first lateral alpha wrap pulley 12620 and a second lateral alpha wrap pulley 12630 that are interconnected by a central shaft 12640. See FIGS. 93 and 94. The pulley unit 12610 is rotatably supported within the proximal end 10112 of the elongate channel 10110 by mounting brackets 12710 and 12720. See FIG. 88. More particularly, the proximal end 10112 of the elongate channel 10110 defines a firing member parking area 10140 that is proximal to the mounting cradles 10120 and is configured to operably support a firing member 12310 when in a starting position. Each mounting bracket 12710, 12720 is mounted within the firing member parking area 10140 on each side of the shaft axis SA to enable the firing member 12310 to be received in the parking area 10140 when the firing member 12310 is in a starting position. The mounting brackets 12710, 12720 may be attached to the proximal end 10112 of the elongate channel 10110 by welding, adhesive, snap features, etc. The mounting bracket 12710 comprises a first shaft cradle 12712 that is configured to rotatably support a first pivot shaft 12621 protruding from the first lateral alpha wrap pulley 12620 and the second mounting bracket 12720 comprises a second shaft cradle 12722 that is configured to rotatably support a second pivot shaft 12644 protruding from the second lateral alpha wrap pulley 12630. In addition, each mounting bracket 12710, 12720 further includes a relief area 12732 that is shaped to receive the corresponding first and second alpha wrap pulleys 12620, 12630 therein.

Figure 94:
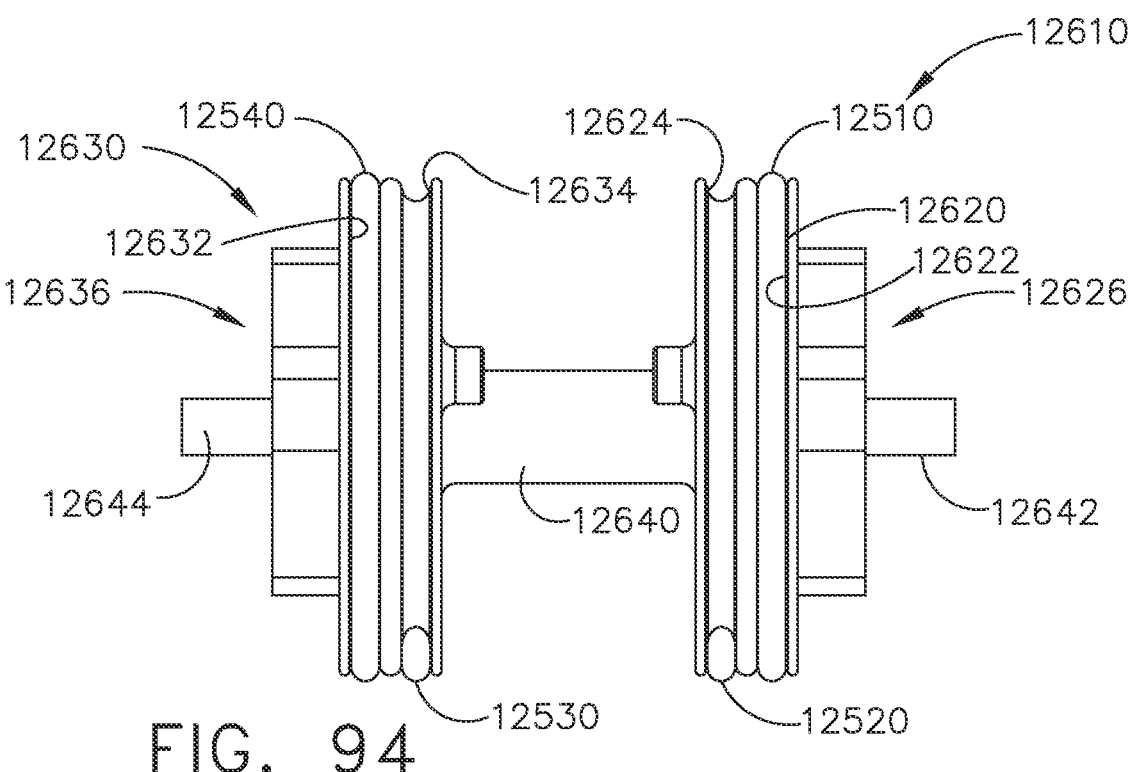
FIG. 94 is an end view of a pulley unit of the cable-controlled pulley system of FIG. 93.

As can be seen in FIG. 94, the first alpha wrap pulley 12620 comprises a first circumferential groove 12622 and a second circumferential groove 12624. In the illustrated example, the first cable 12510 is received in the first circumferential groove 12622 and is attached thereto and the second cable 12520 is received in the second circumferential groove 12624 and is attached thereto. Pulling on the first cable 12510 will result in the rotation of the first lateral alpha wrap pulley 12620 in a first direction and pulling the second cable 12520 will result in the rotation of the first lateral alpha wrap pulley 12620 in a second opposite direction. Similarly, the second lateral alpha wrap pulley 12630 comprises a first circumferential groove 12632 and a second circumferential groove 12634. In the illustrated arrangement, cable 12540 is received in the first circumferential groove 12632 and is attached thereto and the second cable 12520 is received in the second circumferential groove 12634 and is attached thereto. Pulling on the fourth cable 12540 will result in the rotation of the first second alpha wrap pulley 12630 in the first direction and pulling the third cable 12530 will result in the rotation of the second lateral alpha wrap pulley 12630 in the second opposite direction. The lateral alpha wrap pulleys 12620, 12630 can rotate approximately three hundred thirty degrees. This range of rotational travel is in contrast to a normal pulley that may have a range of rotational travel that is less than one hundred eighty degrees of rotation.

Figure 96:
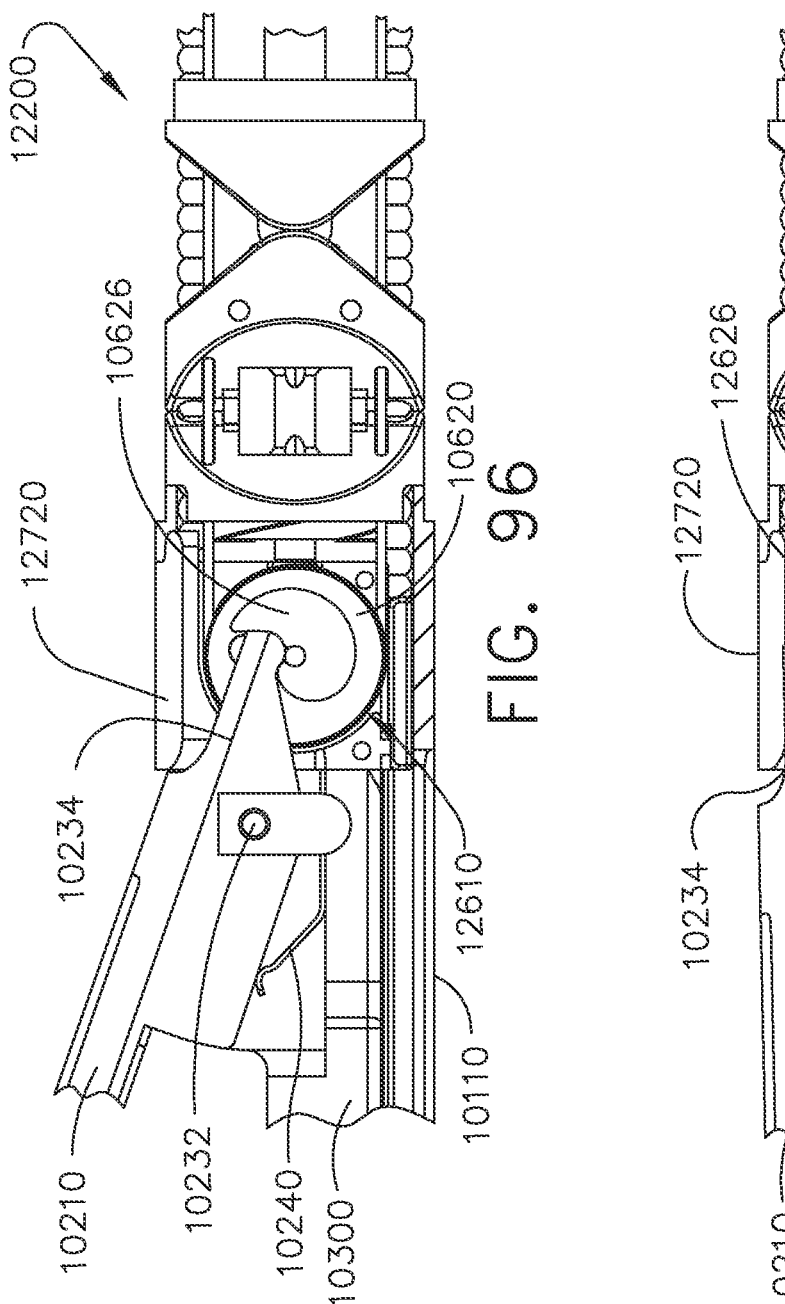
FIG. 96 is a side cross-sectional view of a portion of the surgical end effector of FIG. 89 with the anvil of the surgical end effector in an open position.
Figure 97:
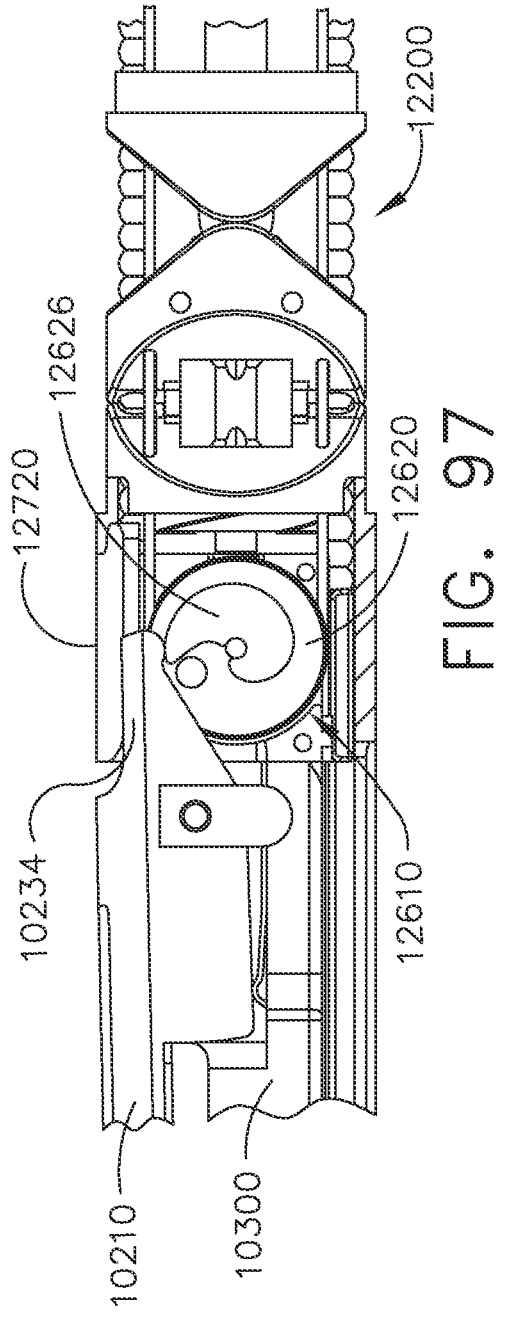
FIG. 97 is another side elevational view of the surgical end effector of FIG. 96 with the anvil in a closed position.

Each of the first and second lateral alpha wrap pulleys 12620, 12630 also comprises a corresponding spiral closure cam that is configured to apply closure motions to the anvil 10210. As can be seen in FIG. 94, the first lateral alpha wrap pulley 12620 includes a first spiral closure cam 12626 and the second lateral alpha wrap pulley 12630 has a second spiral closure cam 12636 thereon. The spiral closure cams 12626, 12636 are configured to cammingly interact with corresponding anvil closure arms 10234 on the anvil mounting portion 10230 of the anvil 10210 to apply closure motions thereto. FIG. 96 illustrates the position of a spiral closure cam 12626 on the first lateral alpha wrap pulley 12620 when the anvil 10210 is biased into the open position by an anvil spring 10240. Rotation of the pulley unit 12610 in a first rotary direction will cause the spiral closure cams 12626 to cam the anvil 1210 to the closed position shown in FIG. 97. To open the anvil 10210, the pulley unit 12610 is rotated in opposite direction back to the position shown in FIG. 96.

Figures 91, 93:
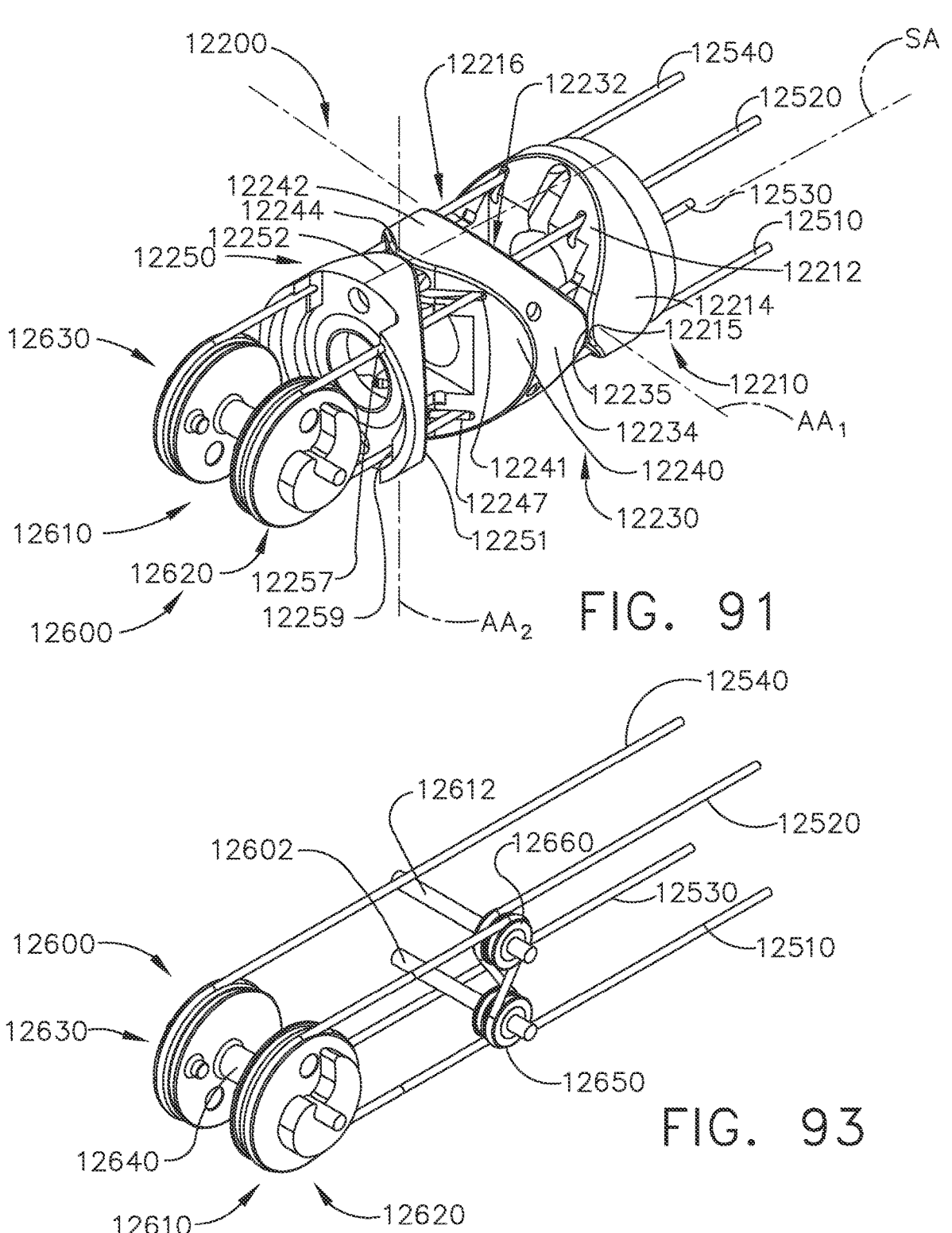
FIG. 91 is a perspective view of the articulation joint of FIG. 89 and a cable-controlled closure pulley system for applying closing motions to the anvil of the surgical end effector of FIG. 89.
FIG. 93 is another perspective view of the cable-controlled closure pulley system of FIG. 91.

Referring now to FIGS. 91 and 93, the first cable 12510 extends from the cable control system through the elongate shaft assembly and through a passage in the proximal joint member 12210 and is looped around two redirect pulleys 12650, 12660 that are supported on shafts 12602, 12612 that are mounted in the central joint member 12230. The first cable 12510 exits the central joint member 12230 through passage 12231 and extends through passage 12257 in the distal joint member 12250 to be received within the first circumferential groove 12622 in the first lateral alpha wrap pulley 12620 where it is attached thereto. A second cable 12520 extends from the cable control system through the elongate shaft assembly and through passage 12213 in the proximal joint member 12210 to be looped around the redirect pulleys 12650, 12660 in the central joint member 12230. The second cable 12520 exits the central joint member 12230 through a corresponding passage 12241 and extends through passage 12259 in the distal joint member 12250 to be received within the second circumferential groove 12624 in the first lateral alpha wrap pulley 12620 where it is attached thereto.

In the illustrated example, the third cable 12530 extends from the cable control system 9030 through the elongate shaft assembly 12000 and through a corresponding passages in the proximal joint member 12210, the central joint member 12230, and the distal joint member 12250 to be received within a corresponding circumferential groove in the second lateral alpha wrap pulley 12630 where it is attached thereto. In addition, a fourth cable 12540 extends from the cable control system 9030 through the elongate shaft assembly 12000 and through corresponding passages in the proximal joint member 12210, the central joint member 12230, and the distal joint member 12250 to be received within a corresponding circumferential groove in the second lateral alpha wrap pulley 12630 where it is attached thereto.

Figure 98:
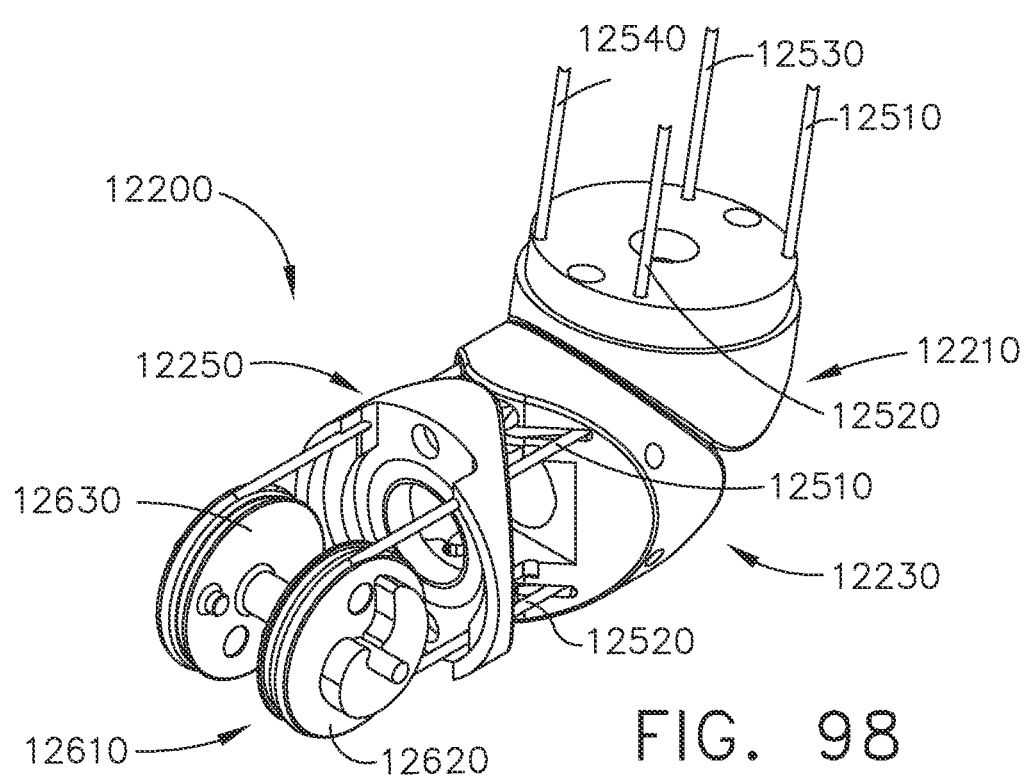
FIG. 98 is a perspective view of the articulation joint and cable-controlled closure system of the surgical instrument of FIG. 87 with a central joint member and a distal joint member articulated relative to a proximal joint member of the articulation joint.
Figure 99:
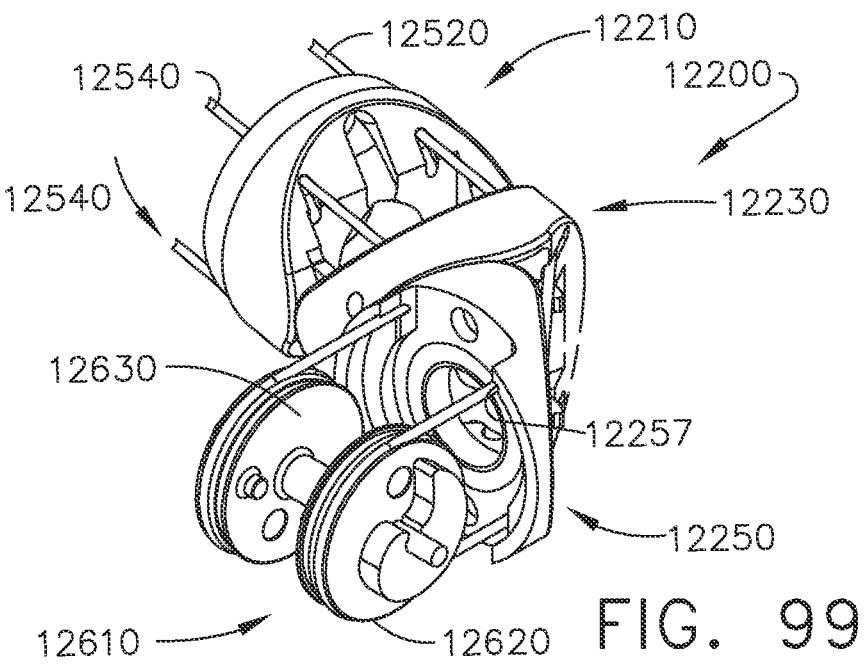
FIG. 99 is another perspective view of the articulation joint and cable-controlled closure system of the surgical instrument of FIG. 87 with the distal joint member articulated through a second articulation plane relative to a central joint member of the articulation joint.

In at least one example, to articulate the surgical end effector 10000 relative to the elongate shaft assembly 12000 through a first articulation plane that is defined by the first articulation axis $AA_1$, the cable control system 9030 is actuated to pull on the second cable 12520 and the fourth cable 12540 simultaneously with a same amount of tension being applied to each cable 12520 and 12540. Because the cables 12520, 12540 apply equal amounts of tension on both sides of the pulley unit 12610, the pulley unit 12610 does not rotate. However, the pulling action of the cables 12520 and 12540 is translated through the articulation joint 12200 to the surgical end effector 10000 which results in the articulation of the central joint member 12230 relative to the proximal joint member 12210 about the first articulation axis $AA_1$. See FIGS. 92 and 98. To articulate the surgical end effector 10000 through a second plane of articulation that is defined by the second articulation axis $AA_2$ and is transverse to the first plane of articulation, the cable control system 9030 is actuated to pull the third cable 12530 and the fourth cable 12540 simultaneously with a same amount of tension being applied to each cable 12530 and 12540. Because the cables 12530, 12540 apply equal amounts of tension on both sides of the second lateral alpha wrap pulley 12630 of the pulley unit 12610, the pulley unit 12610 does not rotate. However, the pulling action of the cables 12530 and 12540 is translated through the articulation joint 12200 to the surgical end effector 10000 which results in the articulation of the distal joint member 12250 relative to the central joint member 12230 about the second articulation axis $AA_2$. See FIGS. 92 and 99.

The cable control system 9030 may also be used to control the opening and closing of the anvil 10210 in the following manner. As indicated above, when the spiral cams 10626 on the first lateral alpha wrap pulley 10620 and the second lateral alpha wrap pulley 10630 are in the position shown in FIG. 96, the anvil 10210 is biased into the open position by the anvil spring 10240. To close the anvil 10210 from that position, the cable control system 9030 is actuated to pull the first cable 12510 and the fourth cable 12540 simultaneously with a same amount of tension being applied to each cable

12510 and 12540. These cables 12510 and 12540 will cause the pulley unit 12610 to rotate into the closure position shown in FIG. 97 which causes the closure cams 10626 to cammingly contact the anvil closure arms 10234 to pivot the anvil 10210 into the closed position. It will be appreciated that by applying equal amounts of tension into the cables 12510 and 12540, no moment is applied to the central joint member 12230 and/or distal joint member 12250 because there are equal amounts of tension being applied on each side of the articulation joint 12200. See FIG. 91. Such arrangement allows the jaw closure to be profiled as desired. This cable-controlled system 9030 allows for a faster closure when the anvil is fully open. The cable-controlled system 9030 can also function as a lower speed/higher force generating closure mechanism for clamping onto tissue. The present cable controlled system 9030 may also not produce the backlash that commonly occurs with other cable-controlled systems and thus can also be used to control the articulation position of the end effector. As will be further discussed below, this cable actuated closure and articulation system does not cross across the center axis or shaft axis of the articulation joint which provides critical space for a firing drive system 13000.

The above-described articulation joint 12200 and cable controlled system 9030 can facilitate two plane articulation while also supplying an additional actuation motion to the surgical end effector 10000 while keeping the central area of the articulation joint 12200 free for other control systems as will be discussed in further detail below. The articulation joint 12200 uses the last degree of freedom to actuate the jaw closure of the surgical end effector. In one aspect, the articulation joint 12200 comprises an N+1 joint, meaning that for N degrees of freedom, the joint requires N+1 cables to actuate it. Thus, in the above-described example, the articulation joint 12200 employs four actuation cables.

As can be seen in FIGS. 100-103, the firing drive system 13000 comprises a firing member 13310 that includes a vertically-extending firing member body 13312 that has two laterally extending tabs 13314 protruding from a bottom portion 13313 of the firing member body 13312. The tabs 13314 are configured to be slidably engage ledges 10113 in the elongate channel 10110 as the firing member 13310 is driven axially therein. In addition, a pair of upper tabs 13316 protrudes from a top portion 13315 of the firing member body 13312. The upper tabs 13316 are configured to engage ledges 10213 (FIG. 103) in the anvil body 10212 as the firing member 13310 is driven distally through the closed anvil 10210. During the firing stroke, the tabs 13314 and 13316 may serve to space the anvil 10210 relative to a surgical staple cartridge that is supported in the elongate channel 10110. The firing member body 13312 also comprises a tissue cutting feature 13318 and a proximally-facing notch 13319 that is configured to accommodate the central shaft 12640 of the pulley unit 12610 when the firing member 13310 is in its proximal-most starting position within the firing member parking area 10140 in the proximal end 10112 of the elongate channel 10110.

Figure 100:
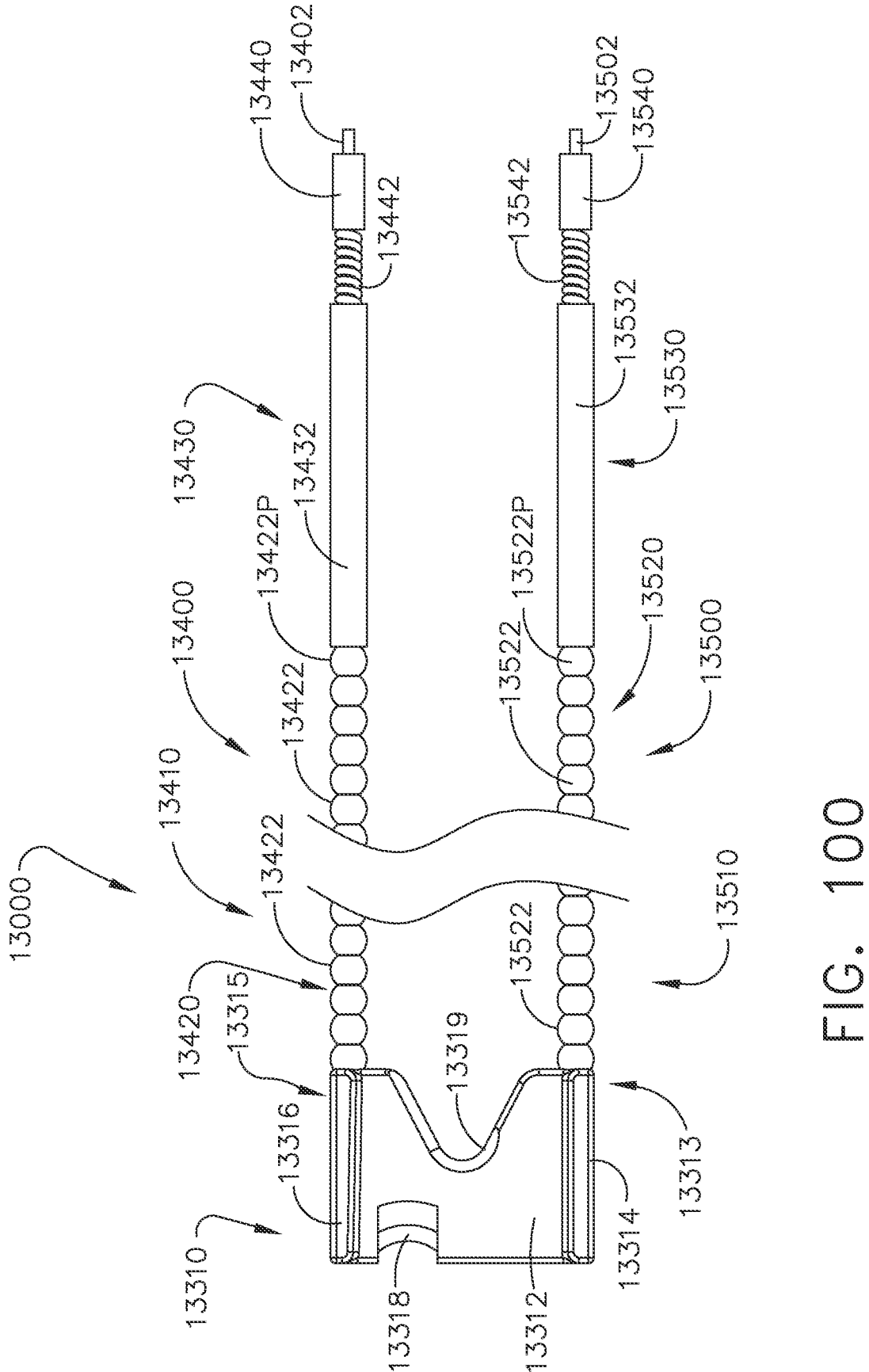
FIG. 100 is a side elevational view of portions of a firing drive system of the surgical instrument of FIG. 87.
Figure 101:
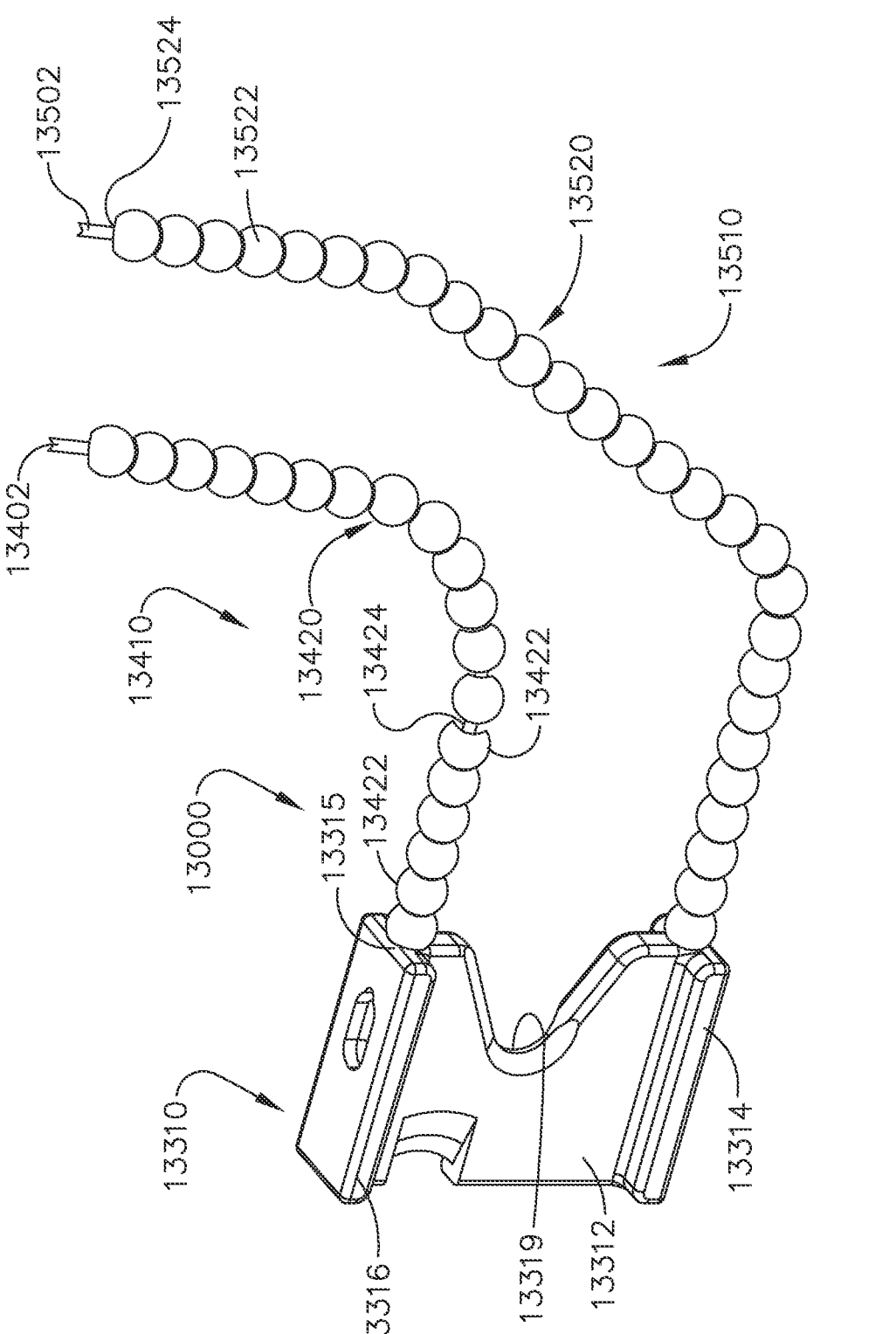
FIG. 101 is another perspective view of the firing drive system of FIG. 100 with upper chain link features and lower chain link features in articulated positions.
Figure 102:
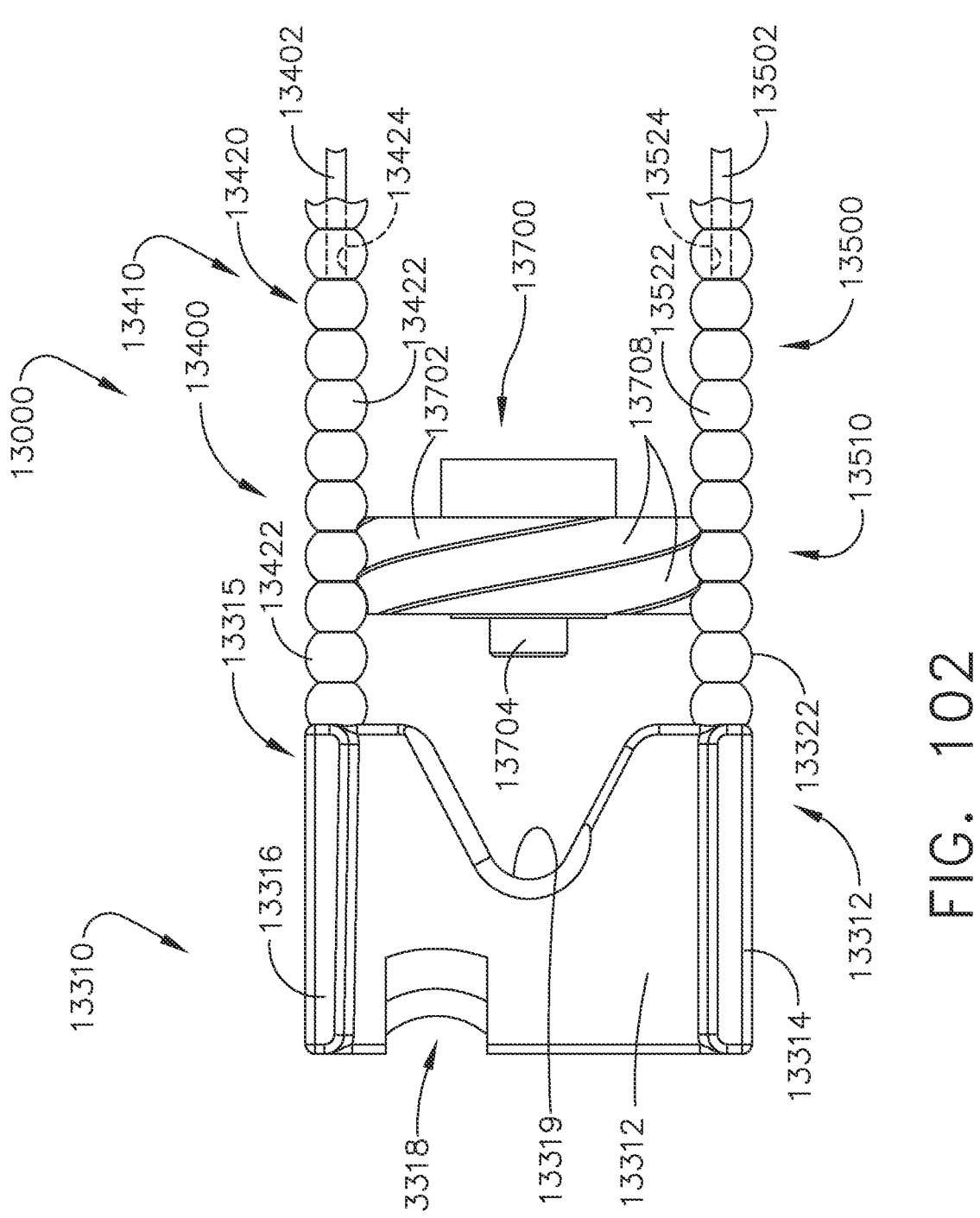
FIG. 102 is another side view of the firing drive system of FIG. 100 with the upper chain link features and lower chain link features in driving engagement with a rotary drive screw of the firing drive system.
Figure 103:
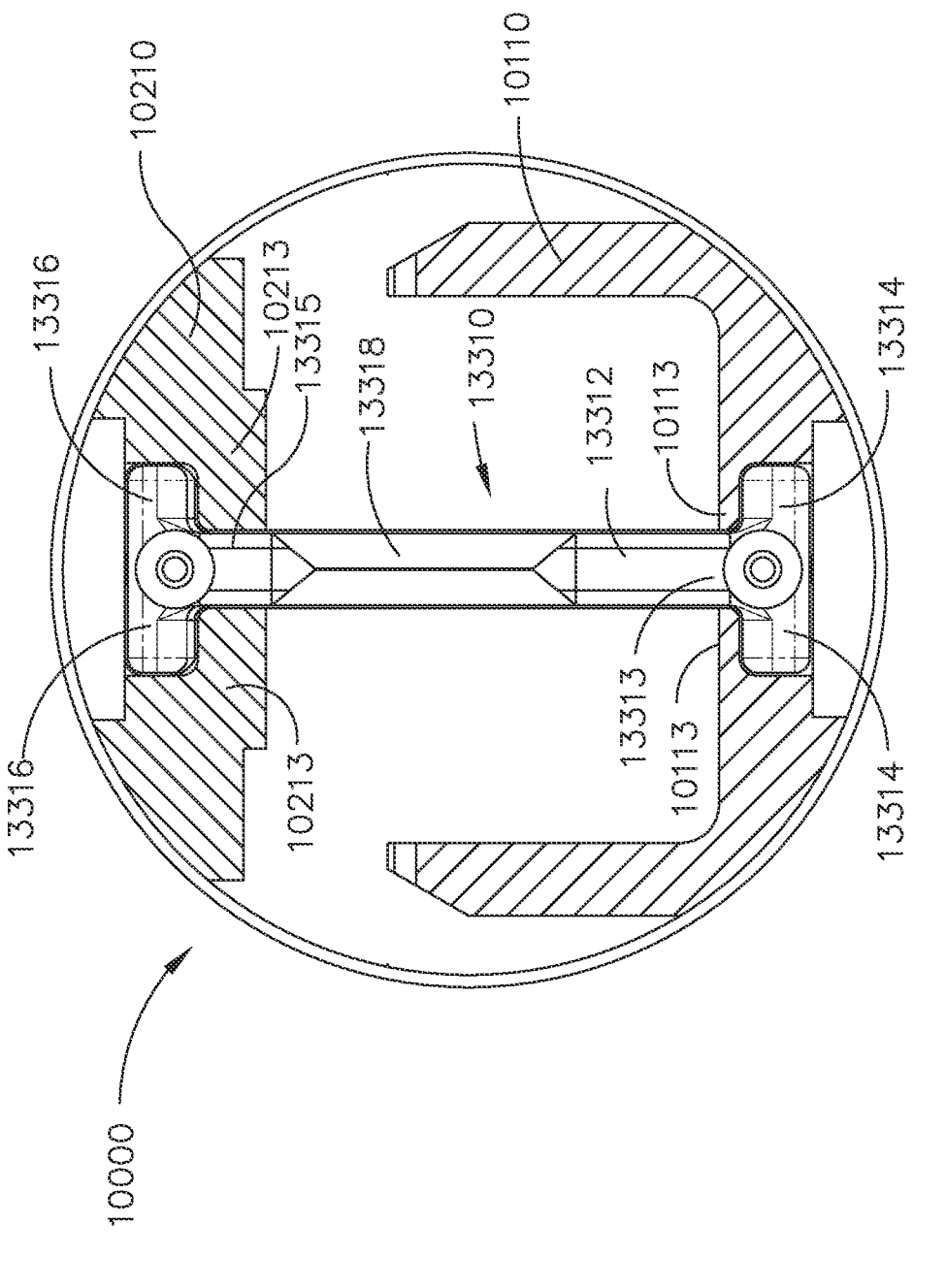
FIG. 103 is a cross-sectional end view of the surgical end effector of FIG. 87 with the anvil thereof in a closed position.

As shown in FIGS. 100-102, the firing drive system 13000 further comprises an upper flexible chain drive assembly 13400 that is operably coupled to the top portion 13315 of the firing member 13310 and a lower flexible chain drive assembly 13500 that is operably coupled to the bottom portion 13313 of the firing member 13310. In at least one embodiment, the upper flexible chain drive assembly 13400 comprises an upper series 13410 of upper chain link features 13420 that are loosely coupled together by an upper flexible coupler member 13402 that is attached to the top portion 13315 of the firing member 13310. In at least one example, each upper chain link feature 13420 comprises an upper ball or sphere 13422 that has an upper hollow passage 13424 therein that is configured to permit the upper flexible coupler member 13402 to pass therethrough. As can be seen in FIG. 100, the upper flexible chain drive assembly 13400 further comprises an upper compression assembly 13430 for compressing the upper balls 13422 in the upper series 13410 together. In one arrangement, the upper compression assembly 13430 comprises a hollow flexible compression tube 13432 that is received on the upper flexible coupler member 13402. An upper ferrule 13440 is crimped onto the upper flexible coupler member 13402 and an upper compression spring 13442 is journaled between the upper ferrule 13440 and the upper flexible compression tube 13432 to distally bias the upper flexible compression tube 13432 into contact with the proximal-most upper ball 13422P in the upper series 13410 of upper chain link features 13420.

Similarly, in at least one embodiment, the lower flexible chain drive assembly 13500 comprises a lower series 13510 of lower chain link features 13520 that are loosely coupled together by a lower flexible coupler member 13502 that is attached to the bottom portion 13313 of the firing member 13310. In at least one example, each lower chain link feature 13520 comprises a lower ball or sphere 13522 that has a lower hollow passage 13524 therein that is configured to permit the lower flexible coupler member 13502 to pass therethrough. The lower flexible chain drive assembly 13500 further comprises an upper compression assembly 13530 for compressing the lower balls 13522 in the lower series 13510 together. In one arrangement, the lower compression assembly 13530 comprises a hollow flexible compression tube 13532 that is received on the lower flexible coupler member 13502. A lower ferrule 13540 is crimped onto the lower flexible coupler member 13502 and a lower compression spring 13542 is journaled between the lower ferrule 13540 and the lower flexible compression tube 13532 to distally bias the lower flexible compression tube 13532 into contact with the proximal-most lower ball 13522P in the lower series 13510 of lower chain link features 13520.

Figure 104:
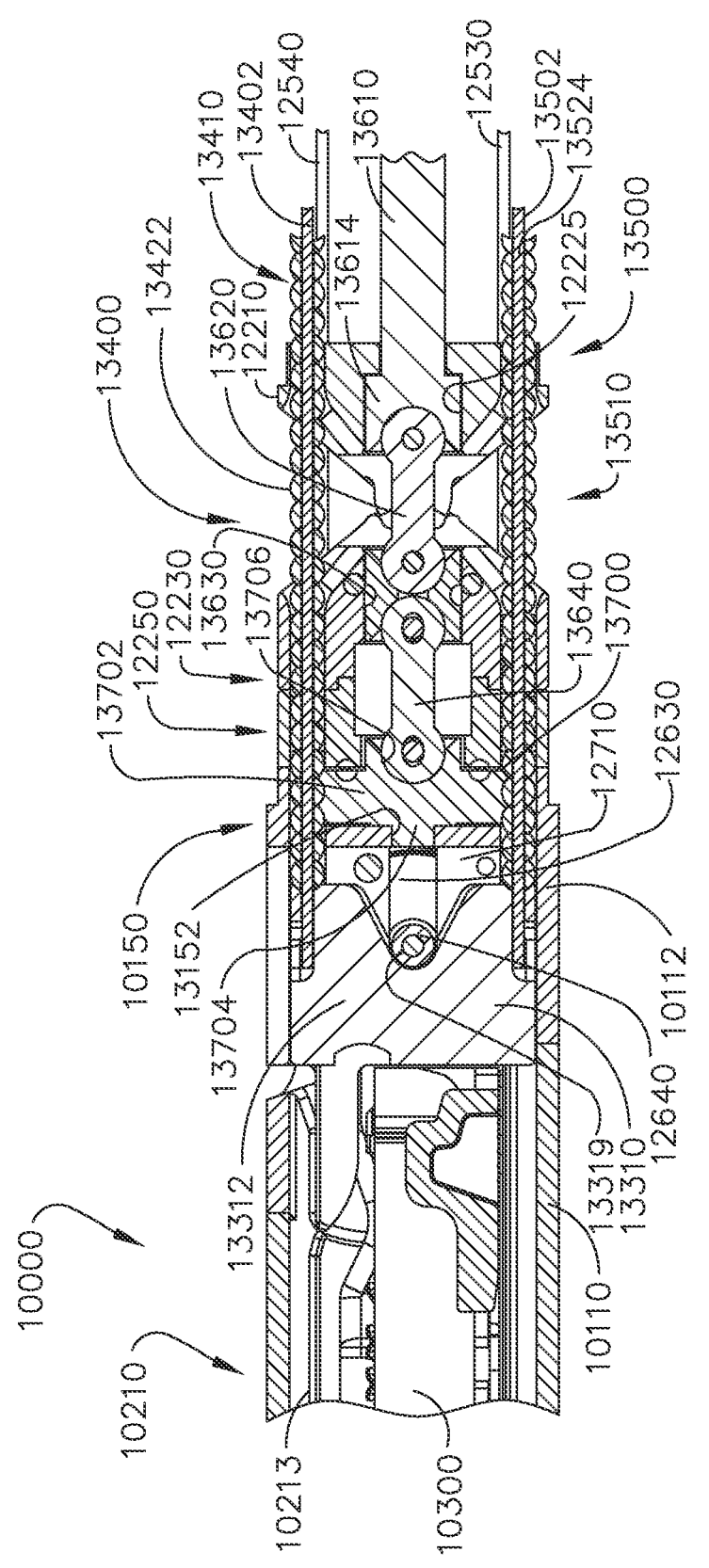
FIG. 104 is a cross-sectional side view of a portion of the surgical instrument of FIG. 87 with the firing member in a starting position and the anvil in a closed position.

Now turning to FIG. 104, in at least one arrangement, the firing drive system 13000 further comprises rotary drive screw 13700 that is configured to drivingly interface with the upper series 13410 of upper chain link features 13420 and the lower series 13510 of lower chain link features 13520. As can be seen in FIG. 104, in the illustrated arrangement, the rotary drive screw 13700 is rotatably supported in the mounting bushing 10150 that is attached to the proximal end 10112 of the elongate channel 10110. For example, the rotary drive screw 13700 comprises a body portion 13702 that has a central axle 13704 protruding therefrom that is rotatably mounted in a mounting hole 10152 in the mounting bushing 10150. Such arrangement permits the rotary drive screw 13700 to rotate about the shaft axis SA.

Figure 105:
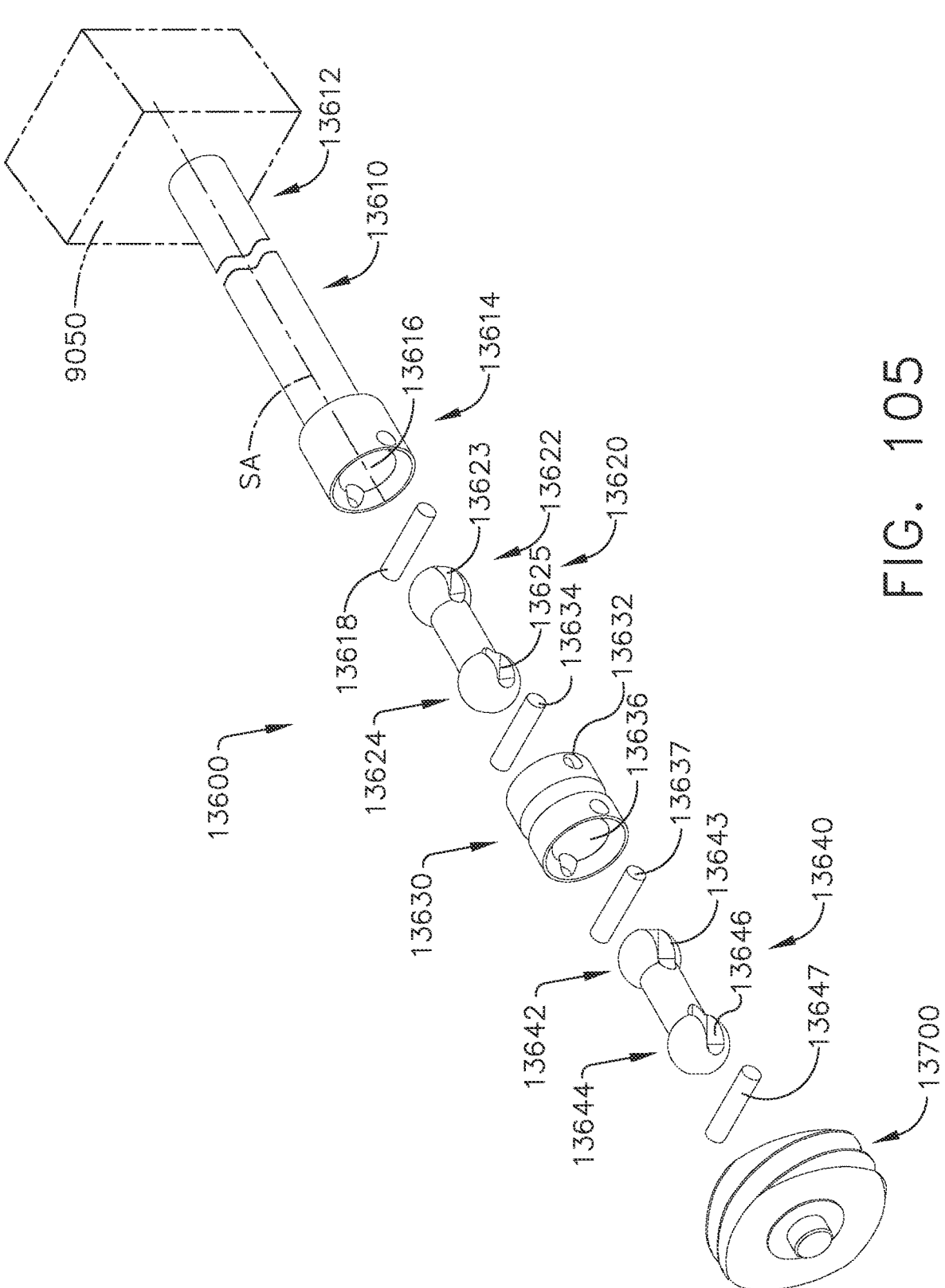
FIG. 105 is an exploded assembly view of a rotary drive system of the surgical instrument of FIG. 87.
Figure 106:
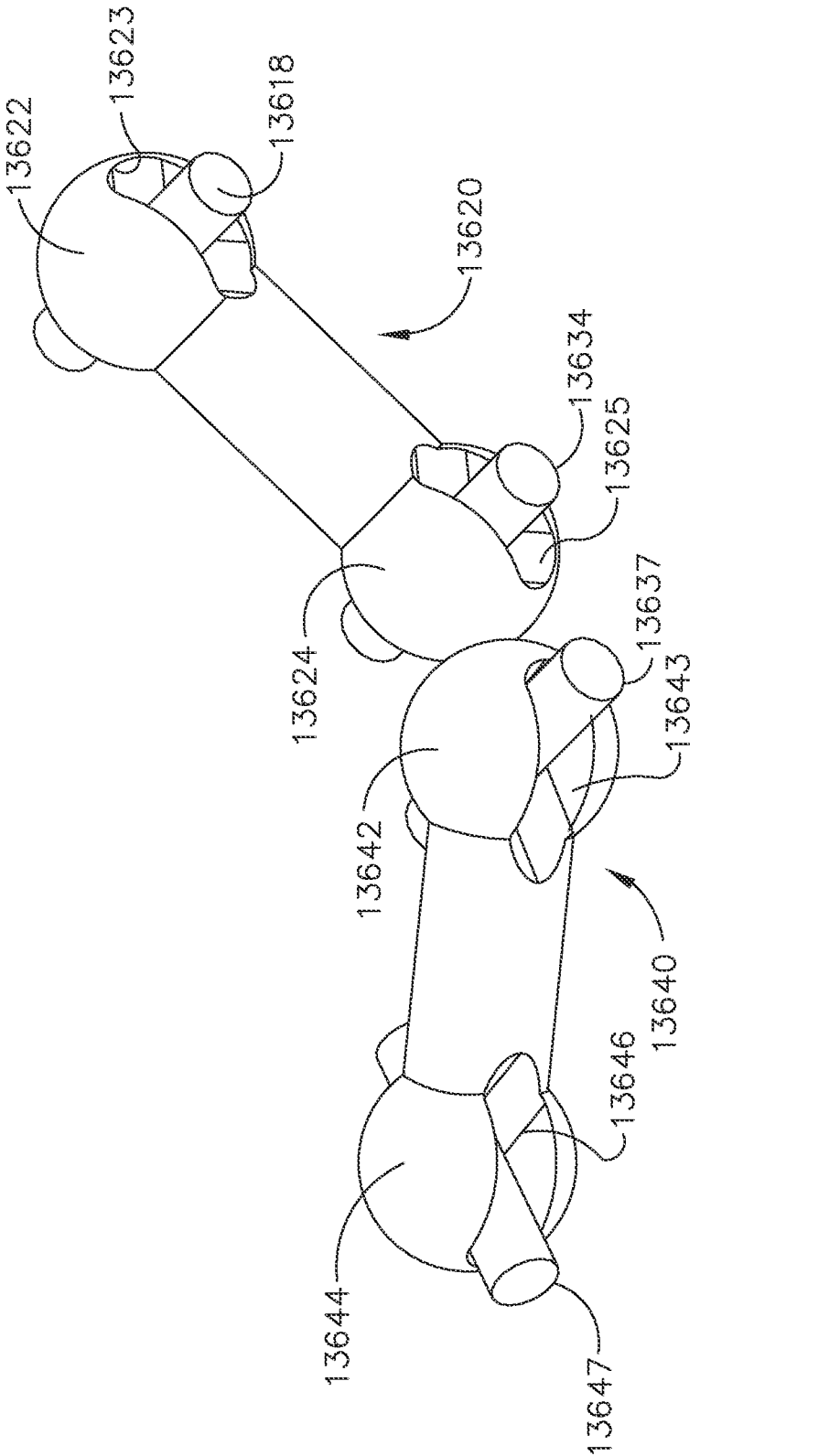
FIG. 106 is a perspective view of a first drive shaft segment and a second drive shaft segment of the rotary drive system of FIG. 105.
Figure 107:
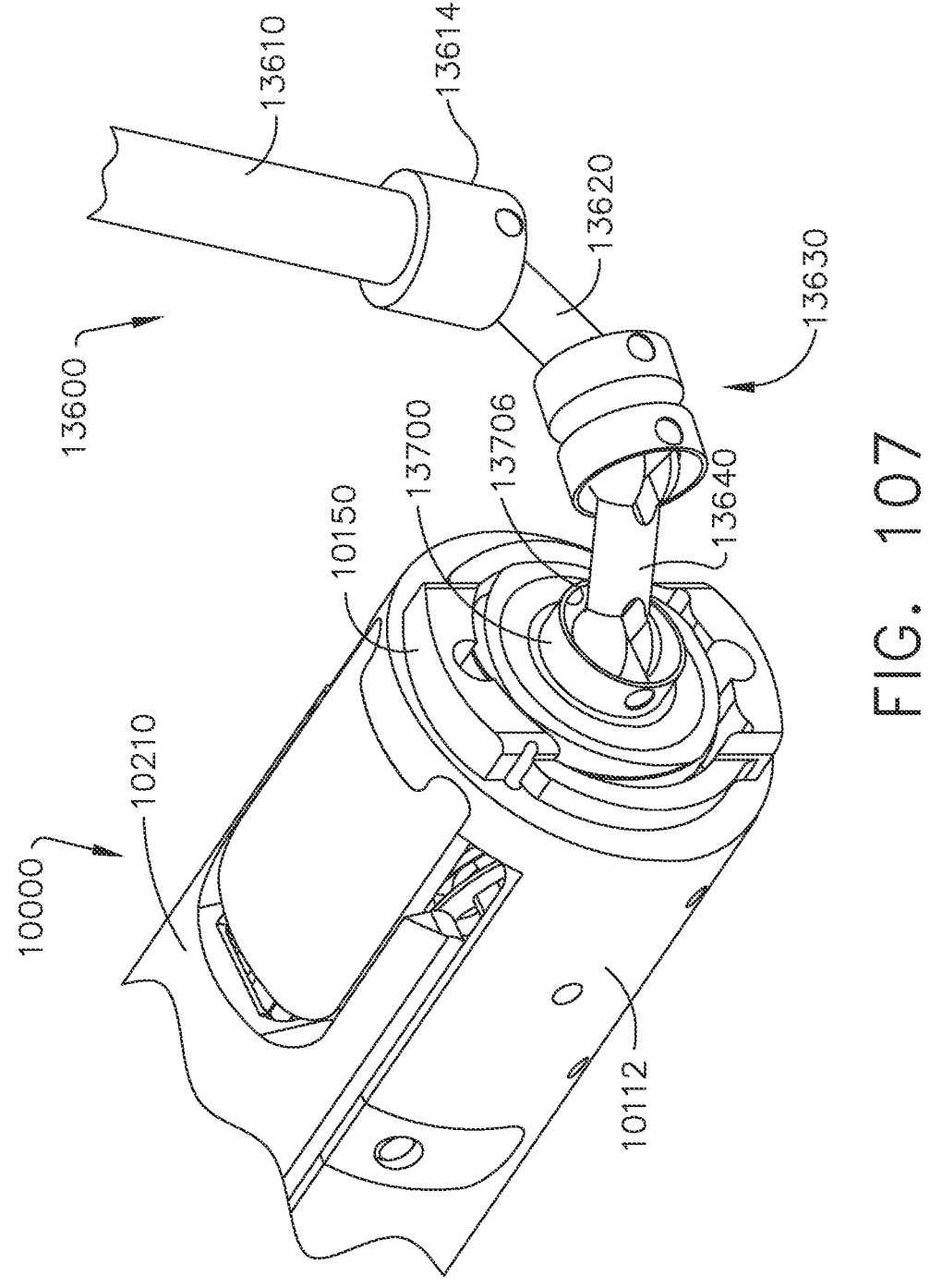
FIG. 107 is a perspective view of the surgical end effector of FIG. 87 with the rotary drive system in an articulated orientation.
Figure 108:
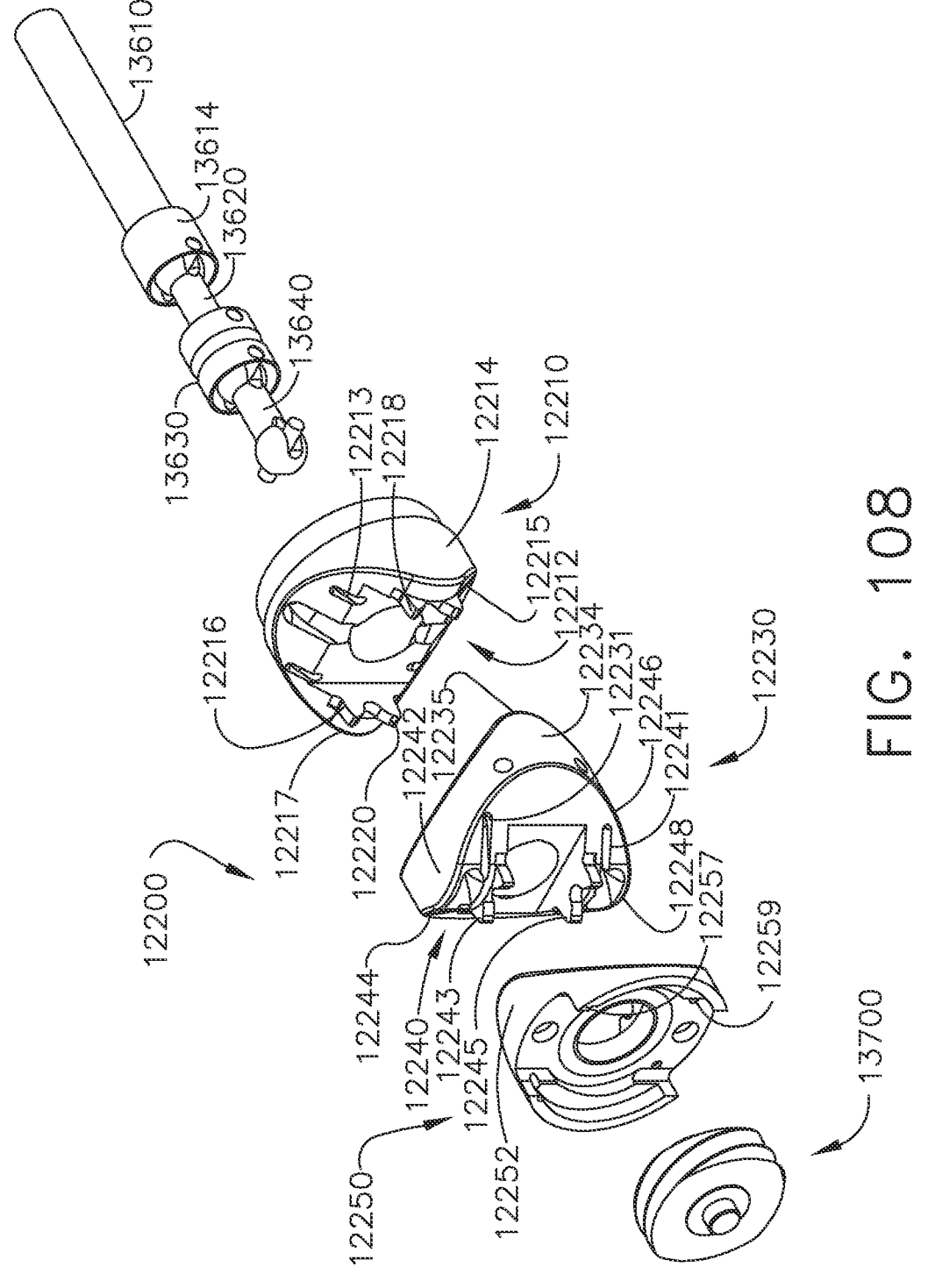
FIG. 108 is an exploded assembly view of an articulation joint and a portion of the rotary drive system of the surgical instrument of FIG. 87.
Figure 109:
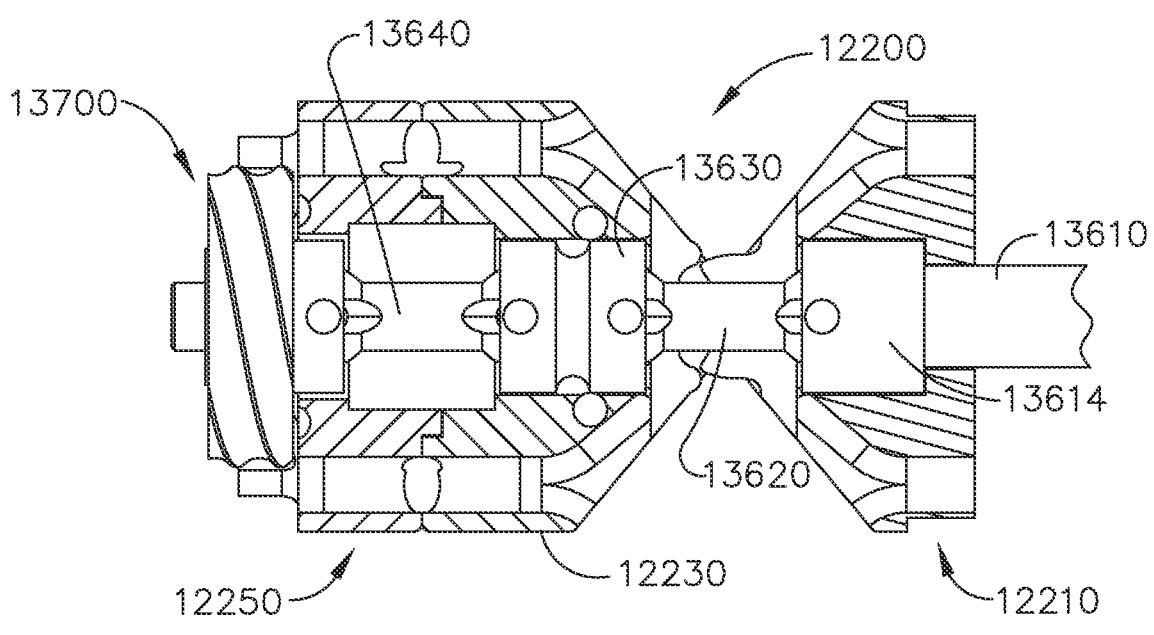
FIG. 109 is a cross-sectional view of the articulation joint and rotary drive system of FIG. 108 in an unarticulated orientation.
Figure 110:
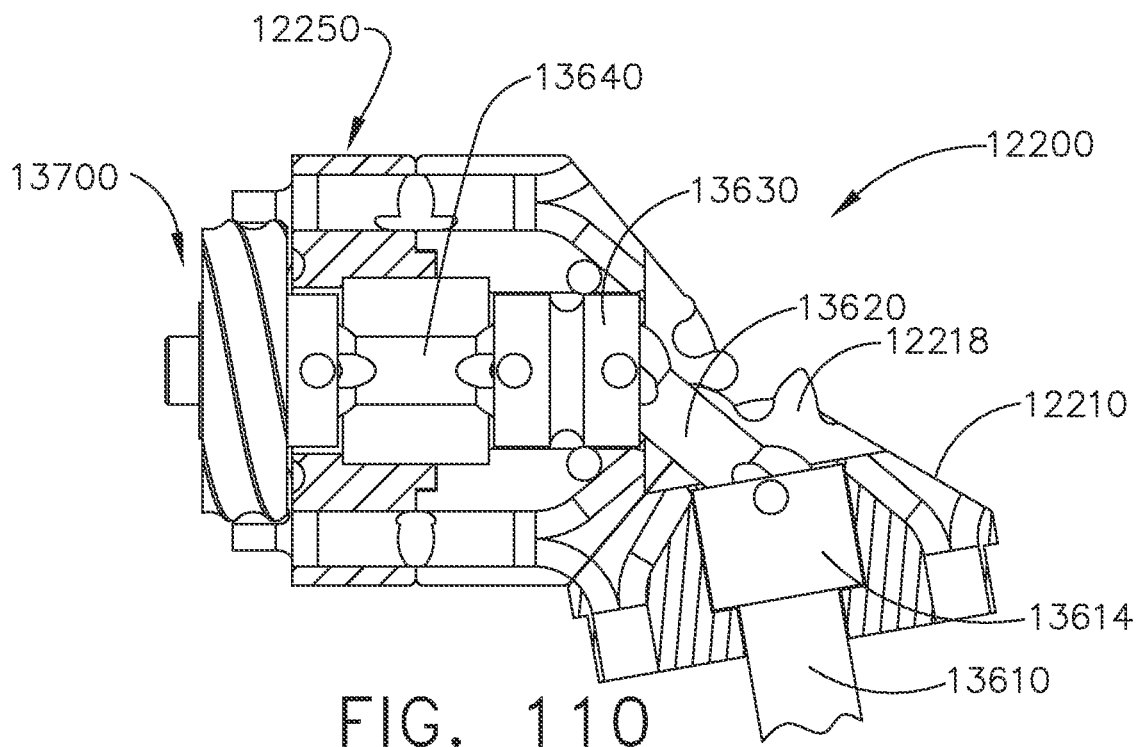
FIG. 110 is another cross-sectional view of the articulation joint and rotary drive system of FIG. 109 with a proximal joint member of the articulation joint articulated relative to a central joint member of the articulation joint.

In the illustrated example, the rotary drive screw 13700 is driven by a rotary drive system 13600 that comprises a proximal rotary drive shaft 13610 that is rotatably supported within an axial passage 12225 within the proximal joint member 12210. As can be seen in FIG. 105, the proximal rotary drive shaft 13610 comprises a proximal end 13612 and a distal end 13614. The proximal end 13612 may interface with a gear box/motor arrangement 9050 or other source of rotary motion housed in the housing 9020 of the surgical instrument 9010. Such source of rotary motion causes the proximal rotary drive shaft 13610 to rotate about the shaft axis SA within the axial passage 12225 in the proximal joint member 12210. See FIG. 104. As can be seen in FIG. 105, the distal end 13614 of the proximal rotary drive shaft 13610 is movably coupled to a first drive shaft segment 13620. In the illustrated example, the first drive shaft segment 13620 resembles a "dog bone" with a first spherical proximal end 13622 and a first spherical distal end 13624. See FIG. 106. The first spherical proximal end 13622 is movably pinned within a first distal socket 13616 formed in the distal end 13614 of the proximal rotary drive shaft 13610 by a first proximal pin 13618. The first proximal pin 13618 extends through an arcuate transverse slot 13623 in the first spherical proximal end 13622. Such arrangement permits the first spherical proximal end 13622 to move in multiple directions within the first distal socket 13616 while remaining attached thereto. The first spherical distal end 13624 is received within a first proximal socket 13632 in a central bearing housing 13630 that is mounted within the central joint member 12230. The first spherical distal end 13624 is movably pinned within the first proximal socket 13632 by a first distal pin 13634. The first distal pin 13634 extends through an arcuate transverse slot 13625 in the first spherical distal end 13624. Such arrangement permits the first spherical distal end 13624 to move in multiple directions within the first proximal socket 13632 while remaining attached to the central bearing housing 13630.

As can be seen in FIG. 105, the rotary drive system 13600 further comprises a second drive shaft segment 13640 that resembles the first drive shaft segment 13620 and includes a second spherical proximal end 13642 and a second spherical distal end 13644. The second spherical proximal end 13642 is movably pinned within a second distal socket 13636 that is formed in the central bearing housing 13630 by a second proximal pin 13637. The second proximal pin 13637 extends through an arcuate transverse slot 13643 in the second spherical proximal end 13642. Such arrangement permits the second spherical proximal end 13642 to move in multiple directions within the second distal socket 13636 while remaining attached thereto. The second spherical distal end 13644 is received within a second proximal socket 13706 in the rotary drive screw 13700 and is movably pinned within the second proximal socket 13706 by a second distal pin 13647. The second distal pin 13647 extends through a transverse slot 13646 in the second spherical distal end 13644. Such arrangement permits the second spherical distal end 13644 to move in multiple directions relative to the rotary drive screw 13700.

The double joint rotary drive maintains a linear velocity output by using the angle constraint of the joint members of the articulation joint. This universal rotary joint arrangement on its own may have a sinusoidal output based on the angle of the joint. If the angles are equal and the phases are aligned correctly, the sine output of the first universal joint will be canceled out by the second universal joint, producing a linear rotational velocity. This is an advantage to putting a constraint in the rotary drive because it decreases the complexity of the components and prevents the need to remove material from the components to attain the requisite clearance. Thus, the components of this embodiment are more robust and stronger than prior arrangements. Further, the constant velocity of the rotary drive system will allow for smoother firing and reduced wear that may be otherwise caused by vibration.

Returning to FIG. 102, the rotary drive screw 13700 comprises helical grooves or drive features 13708 formed on a circumference thereof that are configured to engage and drive the upper balls or spheres 13422 in the upper series 13410 of upper chain link features 13420 and the lower balls or spheres 13522 in the lower series 13510 of lower chain link features 13520. Thus, to drive the firing member 13310 from a starting position in the surgical end effector 10000 to an ending position within the end effector, the rotary drive system 13600 is actuated to apply a rotary drive motion to the rotary drive screw 13700. As the rotary drive screw 13700 rotates in the first rotary direction, the helical drive features 13708 engage the upper balls or spheres 13422 in the upper series 13410 of upper chain link features 13420 and the lower balls or spheres 13522 in the lower series 13510 of lower chain link features 13520 and drive the upper flexible chain drive assembly 13400 and the lower flexible chain drive assembly 13500 distally. As each upper ball 13422 and lower ball 13522 engage the rotary drive screw 13700, the upper balls 13422 in the upper series 13410 that are distal to the rotary drive screw 13700 (and the articulation joint 12200) and the lower balls 13522 in the lower series 13510 that are distal to the rotary drive screw 13700 (and the articulation joint 12200) are placed under compression to apply balanced axial drive forces to the firing member 13310. When the upper flexible chain drive assembly 13400 and the flexible lower chain drive assembly 13500 are in compression, they are constrained by the slots in the anvil 10210 and the elongate channel 10110, respectively. Such arrangement ensures that, when the upper flexible chain drive assembly 13400 and lower flexible chain drive assembly 13500 are compressed, they do not buckle.

This arrangement enables two degrees of articulation freedom for a few reasons. For example, the upper flexible chain drive assembly 13400 and lower flexible chain drive assembly 13500 can bend freely both in the pitch and yaw axes. Thus, the upper flexible chain drive assembly 13400 and lower flexible chain drive assembly 13500 can assume a variety of configurations that can accommodate various articulated positions that are attainable with the articulation joint 12200. Once the firing member 13310 has traveled through the surgical end effector 10000 distally to an ending position therein, the rotary drive system 13600 is actuated to apply a second rotary drive motion to the rotary drive screw 13700 to cause the rotary drive screw 13700 to rotate about the shaft axis in a second rotary direction. As the rotary drive screw 13700 rotates in the second rotary direction, the upper flexible chain drive assembly 13400 and the lower flexible chain drive assembly 13500 serve to retract the firing member 13310 in the proximal direction back to the starting position. As the upper flexible chain drive assembly 13400 and the lower flexible chain drive assembly 13500 retract the firing member 13310 proximally, a portion of the upper flexible chain drive assembly 13400 and the lower flexible chain drive assembly 13500 traverse back through the articulation joint 12200 and into the elongate shaft. Such arrangement allows the firing member 13310 to translate a long distance, without increasing the length of the end effector joint. Additionally, because the rotary drive screw 13700 drivingly engages the upper flexible chain drive assembly 13400 and the lower flexible chain drive assembly 13500 at a location that is distal to the articulation joint 12200, the high compressive loads are contained within the surgical end effector 10000 and do not create a moment on the articulation joint 12200. This arrangement may greatly reduce the strength requirements of the articulation joint. See FIG. 104.

Figures 111, 112:
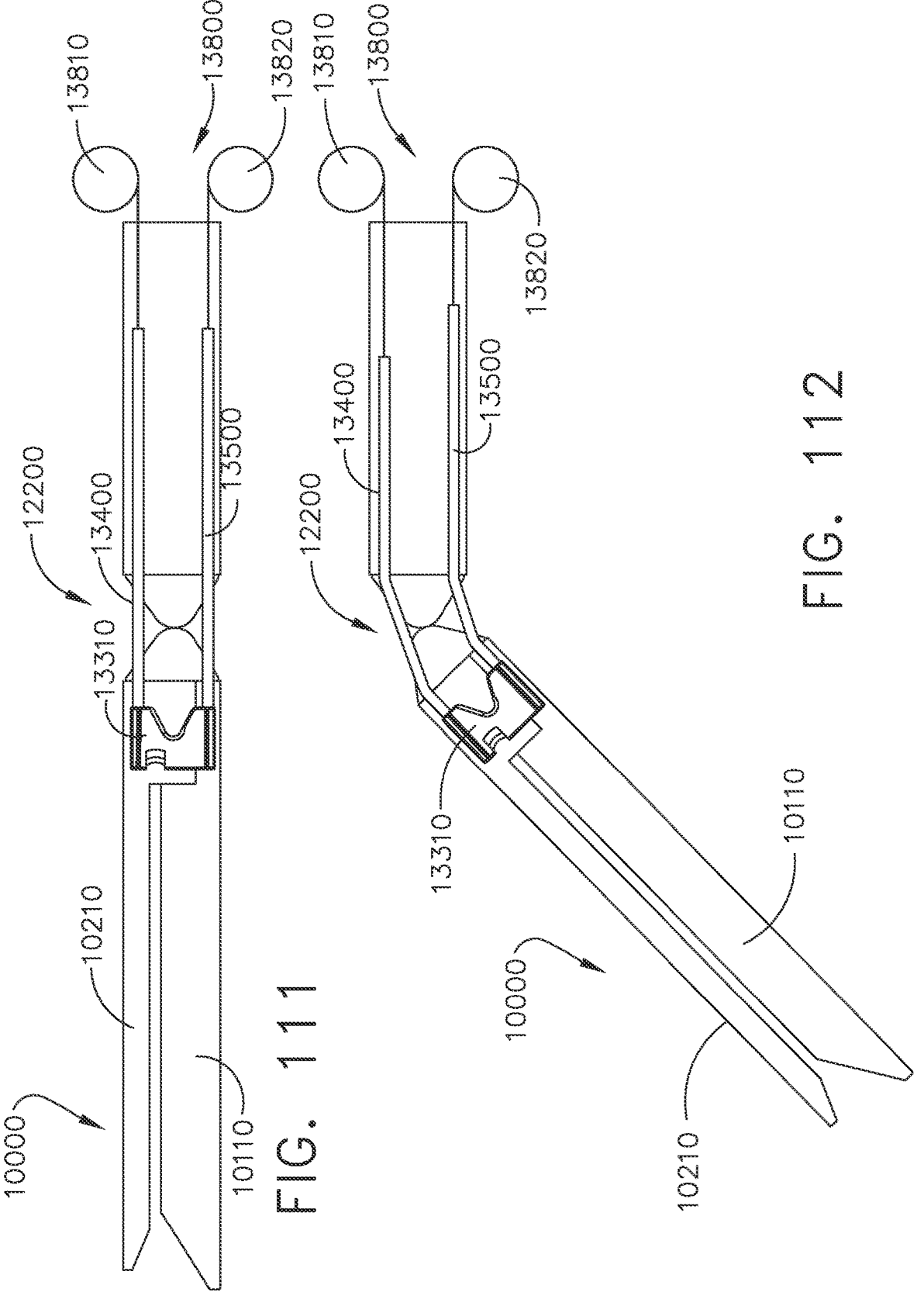
FIG. 111 is a partial side elevational view of the surgical instrument of FIG. 87 illustrating one form of a cable tensioning system with the surgical end effector in an unarticulated orientation.
FIG. 112 is another partial side view of the surgical instrument and cable tensioning system of FIG. 111 with the surgical end effector in an articulated orientation.

In at least one arrangement, the surgical instrument 9010 may further comprise a cable tensioning system 13800 that is configured to maintain a desired amount of tension on the upper flexible chain drive assembly 13400 and the lower flexible chain drive assembly 13500 as they bend through the articulation joint 12200. Keeping the upper flexible chain drive assembly 13400 and the lower flexible chain drive assembly 13500 under a desired amount of tension as they traverse through the articulation joint 12200 may prevent slack from forming in those flexible chain drive assemblies 13400, 13500 which might otherwise cause them to undesirably bunch up in the articulation joint 12200. FIGS. 111 and 112 illustrate one form of cable tensioning system 13800 which comprises constant force spring arrangements 13810 and 13820. Such solution has the benefit of not requiring length conservation of the flexible chain drive assemblies 13400, 13500.

Figures 113, 114:
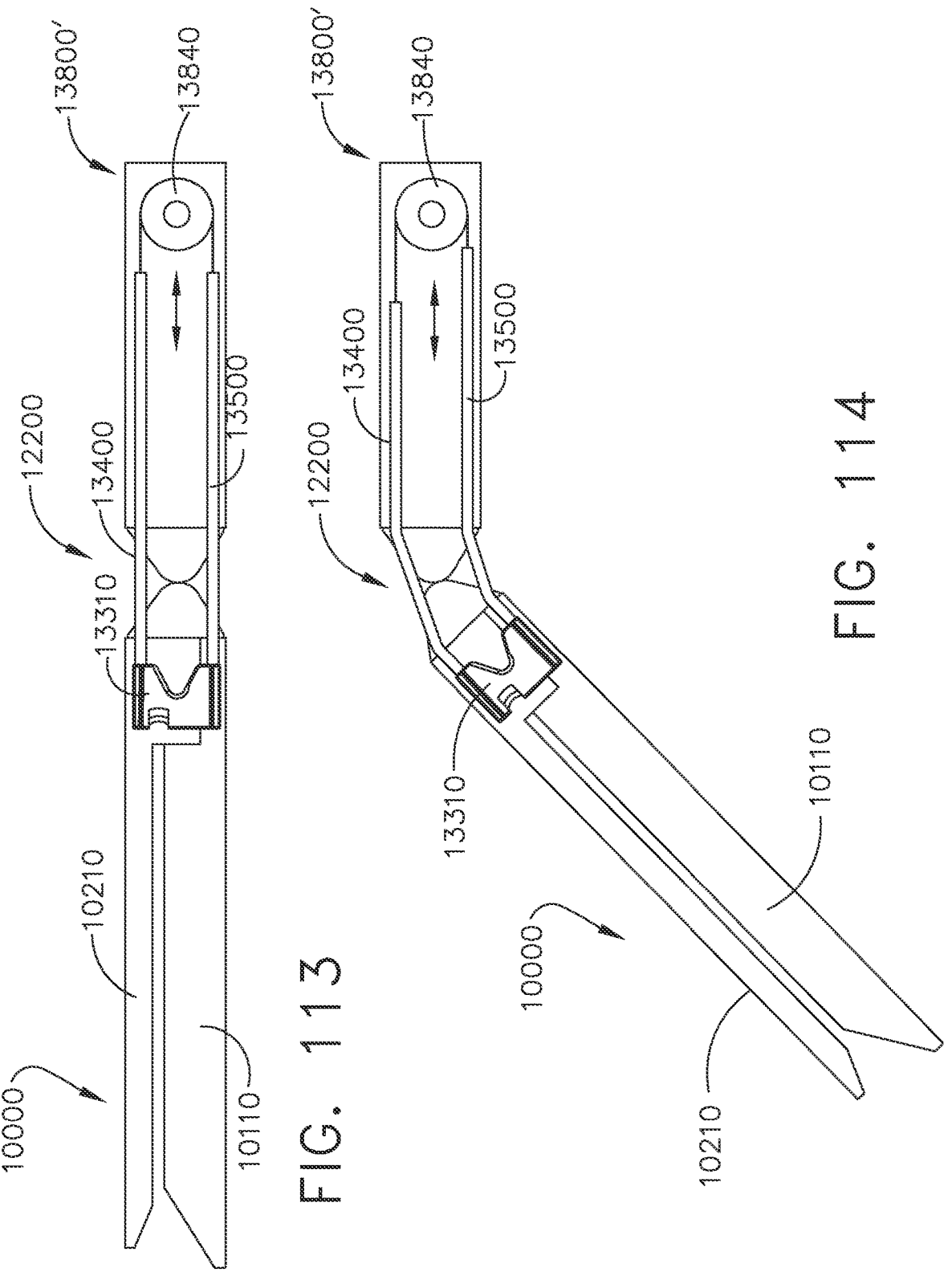
FIG. 113 is a partial side elevational view of the surgical instrument of FIG. 87 illustrating another form of a cable tensioning system with the surgical end effector in an unarticulated orientation.
FIG. 114 is another partial side view of the surgical instrument and cable tensioning system of FIG. 113 with the surgical end effector in an articulated orientation.

Another cable management system 13800' is illustrated in FIGS. 113 and 114. In this arrangement, the proximal ends of the flexible chain drive assemblies 13400, 13500 are coupled together and journaled around a cable management pulley 13840 that is configured to translate with the firing member 13310. When the firing member 13310 is distally advanced during the firing stroke, the cable management pulley 13840 also translates distally maintaining tension in the flexible chain drive assemblies 13400, 13500. During articulation, a length of one of the flexible chain drive assemblies 13400, 13500 would increase, while the other would decrease. Such arrangement serves to minimize the lengths of the flexible chain drive assemblies 13400, 13500 required to fully actuate and articulate the surgical end effector 10000.

One method of using the surgical instrument 9010 may involve the use of the surgical instrument to cut and staple target tissue within a patient using laparoscopic techniques. For example, one or more trocars may have been placed through the abdominal wall of a patient to provide access to a target tissue within the patient. The surgical end effector 10000 may be inserted through one trocar and one or more cameras or other surgical instruments may be inserted through the other trocar(s). To enable the surgical end effector 10000 to pass through the trocar cannula, the surgical end effector 10000 is positioned in an unarticulated orientation (FIG. 63) and the jaws 10100 and 10200 must be closed. To retain the jaws 10100 in the closed position for insertion purposes, for example, the cable control system 9030 is actuated to pull the first cable 12510 and the fourth cable 12540 simultaneously which causes the pulley unit 12610 to rotate and cause the closure cams 10626, 10636 to contact the anvil closure arms 10234 to pivot the anvil 10210 into the closed position. See FIG. 97. The cable control system 9030 is deactivated to retain the anvil 10210 in the closed position. Once the surgical end effector 10000 has passed into the abdomen through the trocar, the cable control system 9030 is activated to rotate the pulley unit 12610 in an opposite direction to the position shown in FIG. 96 to permit the anvil 10210 to be biased open by the anvil springs 10240.

Once inside the abdomen and before engaging the target tissue, the surgeon may need to articulate the surgical end effector 10000 into an advantageous position. The cable control system 9030 may then be actuated to articulate the surgical end effector 10000 in one or more planes relative to a portion of the elongate shaft assembly 12000 that is received within the cannula of the trocar. Once the surgeon has oriented the surgical end effector 10000 in a desirable position, the cable control system 9030 is deactivated to retain the surgical end effector 10000 in the articulated orientation. Thereafter, the surgeon may activate the cable control system 9030 in the above-described manner to cause the anvil 10210 to rapidly close to grasp the tissue between the anvil 10210 and the surgical staple cartridge 10300. This process may be repeated as necessary until the target tissue has be properly positioned between the anvil 10210 and the surgical staple cartridge 10300.

Once the target tissue has been positioned between the anvil 10210 and the surgical staple cartridge 10300, the surgeon may activate the cable control system 9030 to close the anvil 10210 to clamp the target tissue in position. Thereafter, the firing process may be commenced by activating the rotary drive system 13600 to drive the firing member 13310 distally from the starting position. As the firing member 13310 moves distally, the firing member 13310 contacts a sled that is supported in the surgical staple cartridge 10300 and also drives the sled distally through the staple cartridge body. The sled serially drives rows of drivers supported in the staple cartridge toward the clamped target tissue. Each driver has supported thereon one or more surgical staples or fasteners which are then driven through the target tissue and into forming contact with the underside of the anvil 10210. As the firing member 13310 moves distally, the tissue cutting edge 13318 thereon cuts through the stapled tissue.

After the firing member 13310 has been driven distally to the ending position within the surgical end effector 10000, the rotary drive system 13600 is reversed which causes the firing member 13310 to retract proximally back to the starting position. Once the firing member 13310 has returned to the starting position, the cable control system 9030 may be activated to rotate the pulley unit 12610 back to an open position wherein the anvil springs 10240 can pivot the anvil 10210 to the open position to enable the surgeon to release the stapled tissue from the surgical end effector 10000. Once the stapled tissue has been released, the surgical end effector 10000 may be withdrawn out of the patient through the trocar cannula. To do so, the surgeon must first actuate the cable control system 9030 to return the surgical end effector 10000 to an unarticulated position and actuate the cable control system 9030 to pivot the anvil 10210 to the closed position. Thereafter, the surgical end effector 10000 may be withdrawn through the trocar cannula.

In previous endocutter arrangements, the firing member is pushed by a flexible beam. In such arrangements, the articulation joint must redirect the linear motion of the flexible beam as it enters the articulation joint back to that linear motion as it exits the articulation joint and enters the end effector. Because of the high loads required to push the flexible beam and the firing member, the flexible beam commonly experiences high amounts of friction as it exits the articulation joint and is linearly redirected into the end effector. This added amount of friction increases the amount of driving forces that are required to drive the firing member from the starting to ending position within the end effector while the end effector is articulated. Further, as the flexible beam traverses the articulation joint, it may apply de-articulation motions to the articulation joint components. Thus, the articulation joint components must be sufficiently robust so as to resist such de-articulation motions.

Other forms of surgical endocutters employ rotary forces to drive the firing member through the end effector. Such arrangements commonly employ a rotary drive screw that is housed within the channel that supports the staple cartridge. During use, the sled and tissue place large moments on the firing member which decrease the efficiency of the system and ultimately require higher rotary forces to actuate the firing member. It is difficult to move the rotary drive screw closer to the center of such forces because of the cartridge and the location of the tissue. It is also difficult to package a screw on top and bottom of the firing member without increasing the overall diameter of the surgical end effector. The various embodiments discussed above may address many if not all of these issues and challenges.

FIGS. 115-139 illustrate another form of surgical instrument 25010 that may address many of the challenges facing surgical instruments that comprise end effectors that are articulatable to large articulation angles and that are configured to cut and fasten tissue. In various embodiments, the surgical instrument 25010 may comprise a handheld device. In other embodiments, the surgical instrument 25010 may comprises an automated system sometimes referred to as a robotically-controlled system, for example. In various forms, the surgical instrument 25010 comprises a surgical end effector 26000 that is operably coupled to an elongate shaft assembly 28000. The elongate shaft assembly 28000 may be operable attached to a housing. In one embodiment, the housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

Figure 119:
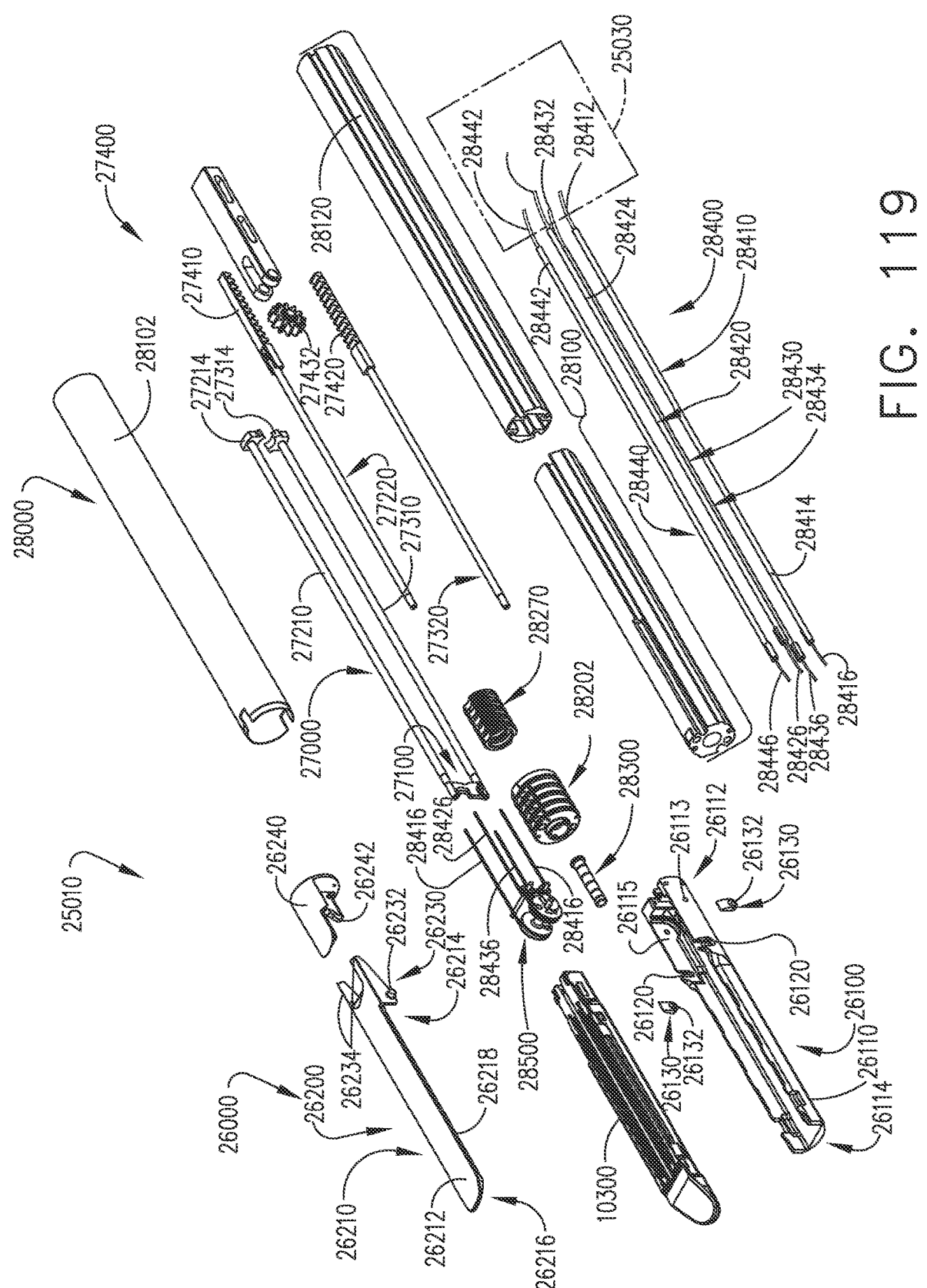

In one form, the surgical end effector 26000 comprises a first jaw 26100 and a second jaw 26200. In the illustrated arrangement, the first jaw 26100 comprises an elongate channel 26110 that comprises a proximal end 26112 and a distal end 26114 and is configured to operably support a surgical staple cartridge 10300 therein. An example of a surgical staple cartridge 10300 was described in detail above. The second jaw 26200 comprises an anvil 26210 that comprises an elongate anvil body 26212 that has a proximal end 26214 and a distal end 26216. The anvil body 26212 comprises a staple-forming undersurface 26218 that faces the first jaw 26100 and may include a series of staple-forming pockets (not shown) that corresponds to each of the staples or fasteners in the surgical staple cartridge 10300. As can be seen in FIG. 119, the proximal end 26214 of the anvil body 26212 comprises an anvil mounting portion 26230 that comprises a pair of laterally extending mounting pins 26232 that are configured to be received in corresponding mounting inserts 26130 that are configured to be retainingly received within mounting cradles 26120 formed in a proximal end 26112 of the elongate channel 26110. The mounting pins 26232 are pivotally received within pivot holes 26132 in the mounting inserts 26130 and then the mounting inserts 26130 are inserted into their corresponding cradle 26120 and affixed to the elongate channel 26110 by welding, adhesive, snap fit, etc. Such arrangement facilitates pivotal travel of the anvil 26210 relative to the elongate channel 26110 about a fixed pivot axis PA. See FIG. 115. As stated above, as used in this context, the term "fixed" means that the pivot axis PA is non-translating or non-moving relative to the elongate channel 26110.

In the illustrated arrangement, the elongate shaft assembly 28000 defines a shaft axis SA and comprises a shaft spine assembly 28100 that is received in a hollow outer shaft tube 28102. See FIG. 119. The shaft spine assembly 28100 may operably interface with a housing of the control portion (e.g., handheld unit, robotic tool driver, etc.) of the surgical instrument 25010 and in one example, comprises a proximal spine segment 28120 and a distal spine segment 28140.

Figure 120:
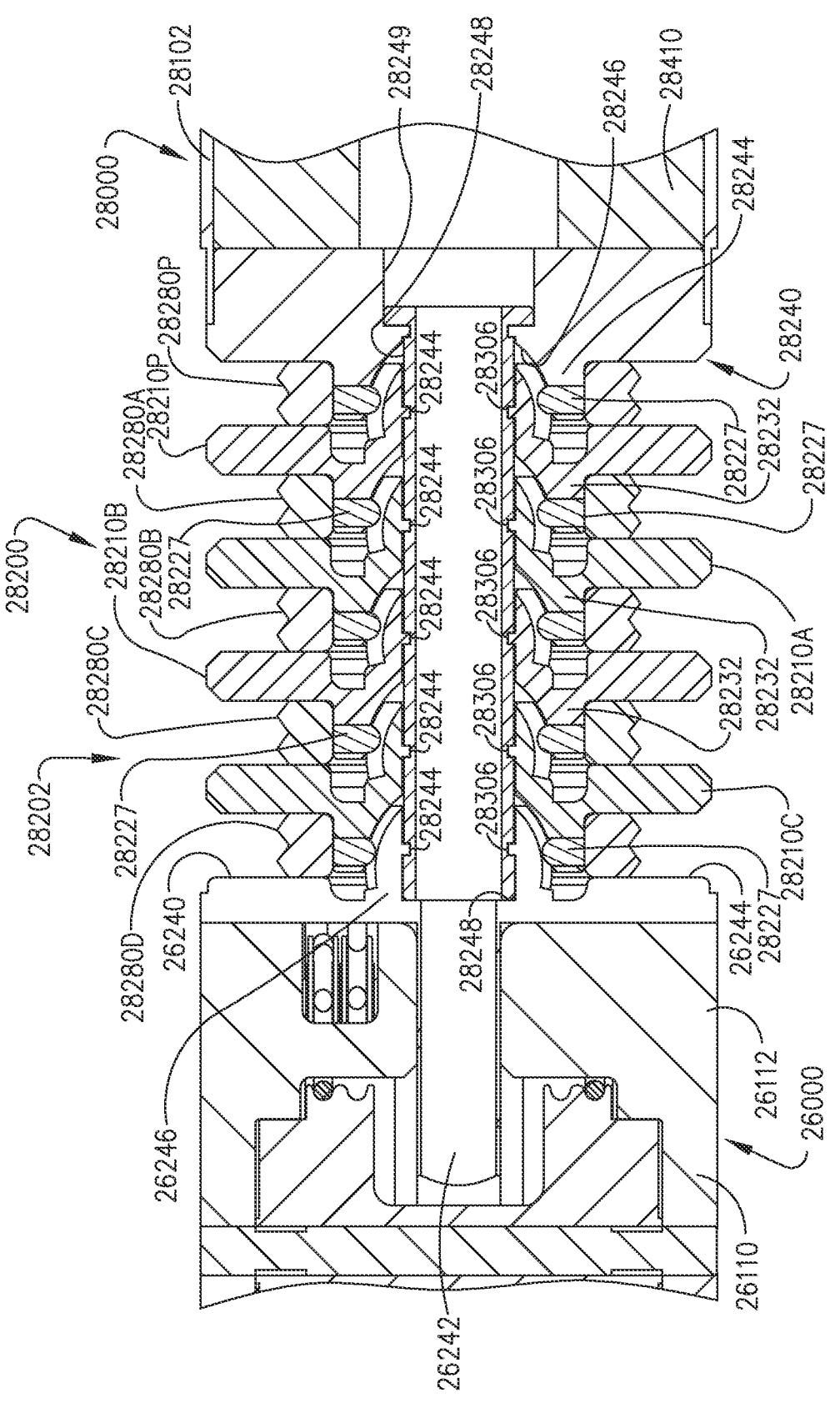
Figure 121:
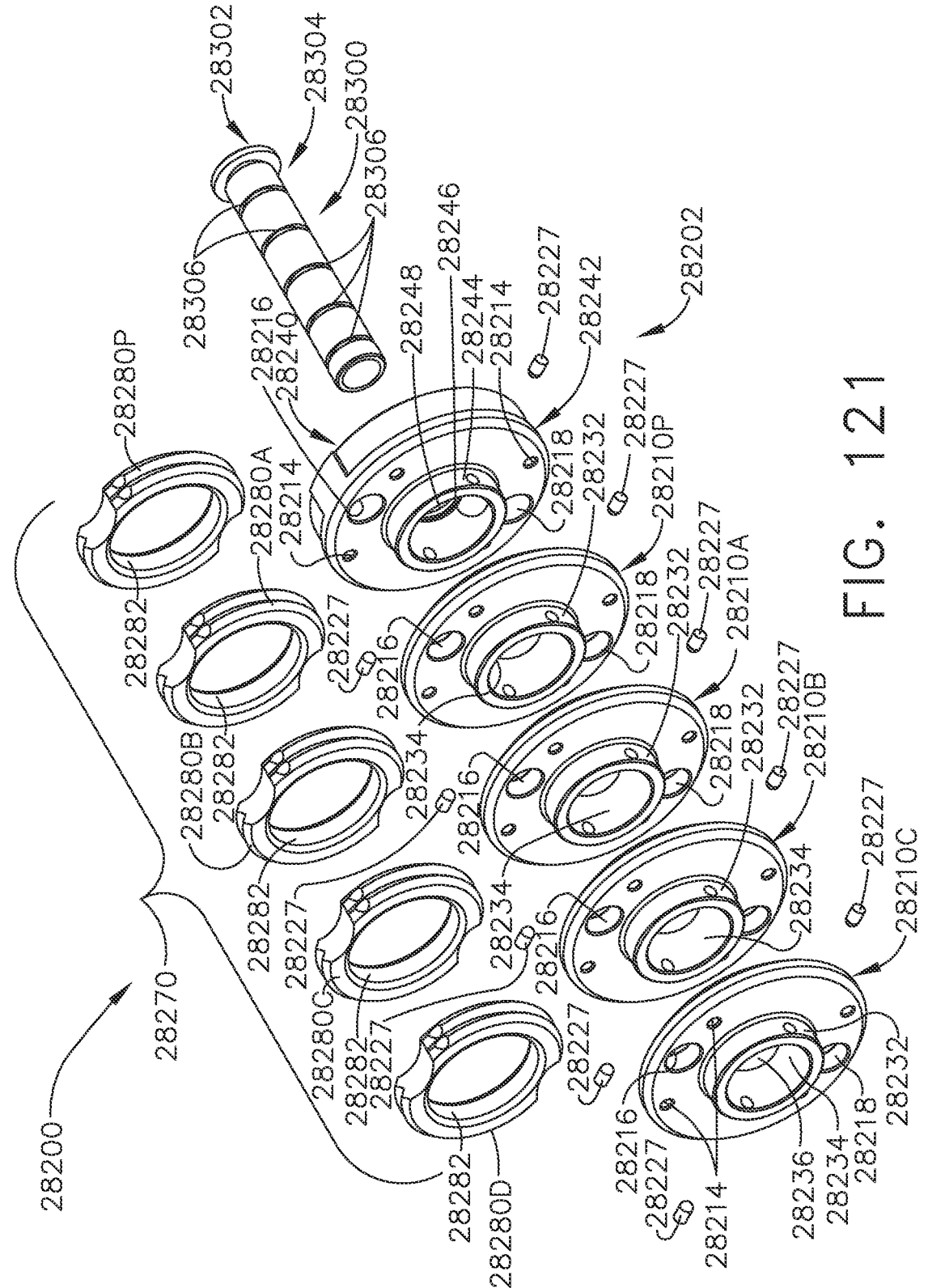
Figures 122, 123:
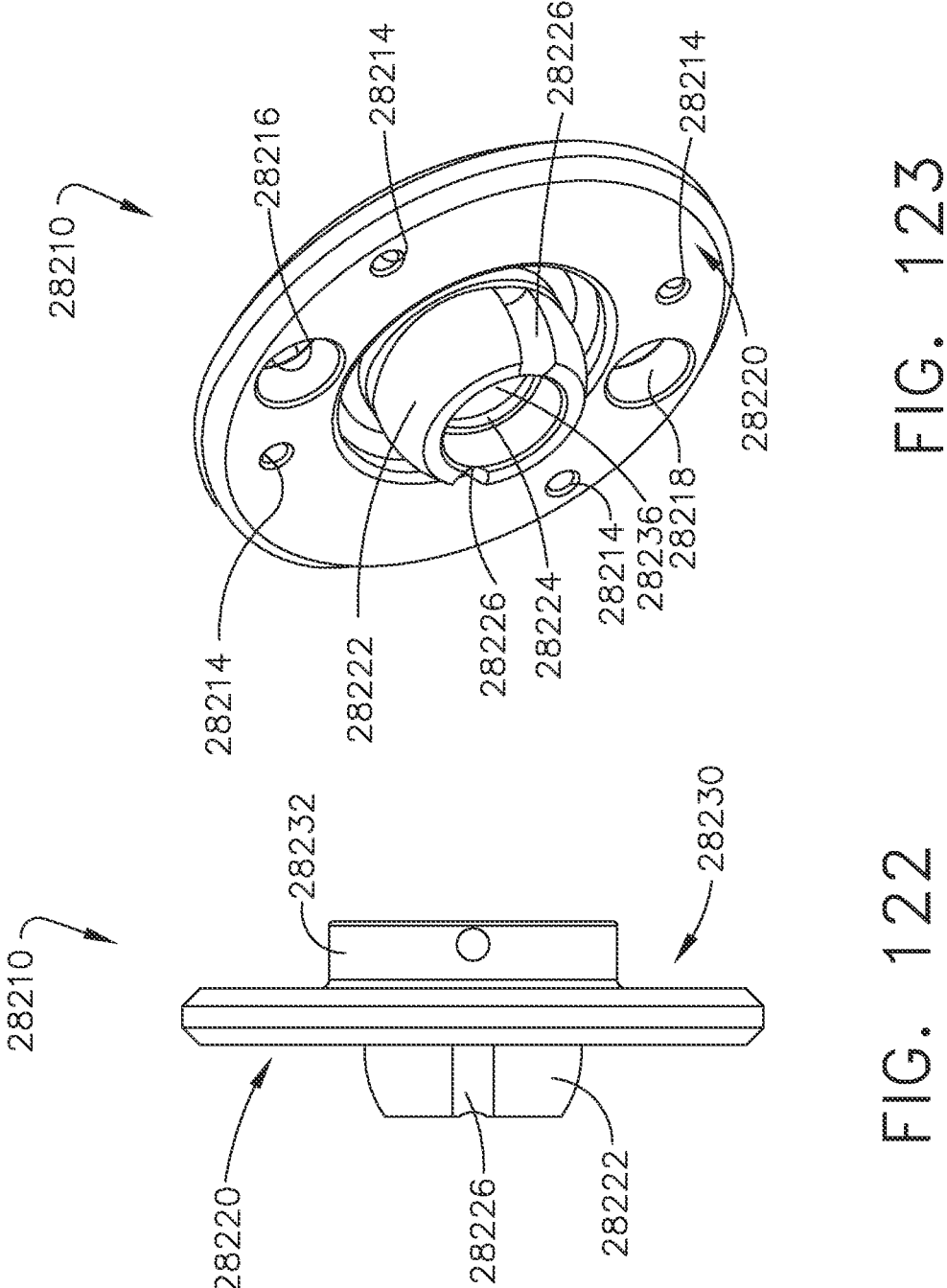
Figures 124, 125:
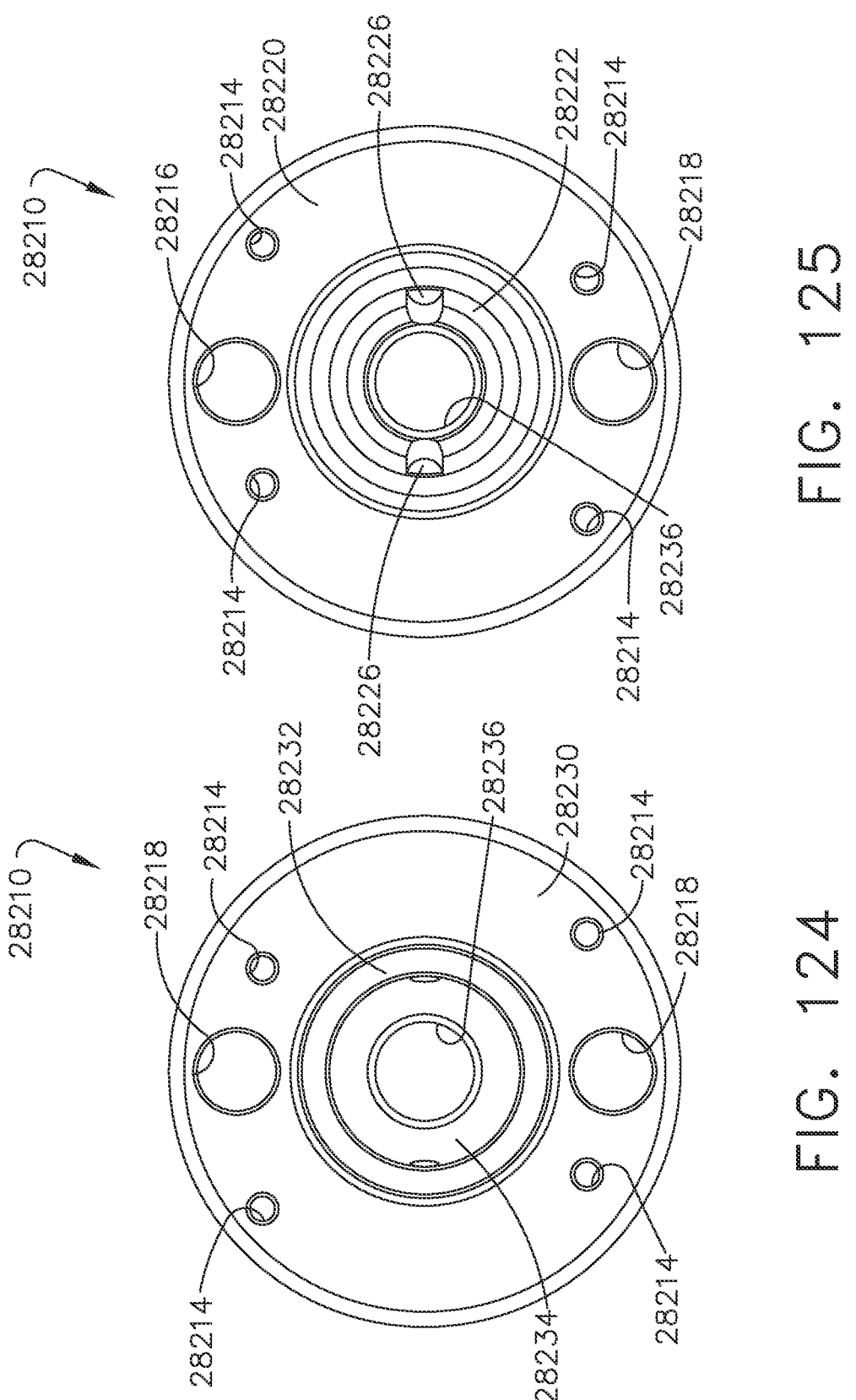

The elongate shaft assembly 28000 further comprises an articulation joint 28200 that may be attached to the distal spine segment 28140 as well as the surgical end effector 26000 to facilitate selective articulation of the surgical end effector 26000 relative to the elongate shaft assembly 28000 in multiple articulation planes. Turning now to FIGS. 120-125, the articulation joint 28200 comprises a series 28202 of movably interfacing annular disc members 28210. As can be seen in FIGS. 122, 123, and 125, each annular disc member 28210 comprises a "first" or proximal face 28220 that comprises a centrally-disposed spherical feature or protrusion 28222. Each annular disc member 28210 further comprises a second or distal face 28230 that comprises an annular hub portion 28232 that defines a concave socket 28234 therein. See FIGS. 122 and 124. Each annular disc member 28210 further has a central shaft passage 28236 therethrough. As can be seen in FIGS. 120 and 121, the articulation joint 28200 further comprises a proximal attachment disc assembly 28240 that is configured to be attached to a distal end of the distal spine segment 28140 by welding, adhesive, or other suitable fastener arrangement. The proximal attachment disc assembly 28240 comprises a distal face 28242 that includes an annular hub portion 28244 that defines a concave socket 28246 therein. The proximal attachment disc 28240 further has a central shaft passage 28248 therethrough. Also in the illustrated arrangement, the anvil mounting bracket 26240 is configured to operably interface with the articulation joint 28200. The anvil mounting bracket 26240 is attached to the proximal end 26112 of the elongate channel 26110 of the surgical end effector 26000 by welding, adhesive or other suitable fastener arrangements and comprises a proximal face 26244 that has a centrally-disposed spherical feature or protrusion 26246 protruding therefrom. See FIG. 120. The anvil mounting bracket 26240 further has a central shaft passage 26248 therethrough.

In at least one embodiment, the articulation joint further comprises a series 28270 of elastomeric annular spacer members 28280 that serve to space and provide elastic support between each annular disc member 28210. The elastomeric annular spacer members 28280 define a spacer opening 28282 such that each elastomeric spacer member 28280 may be journaled on an annular hub portion 28232 of a corresponding annular disc member 28210. Each annular disc member 28210 is journaled on a central elastomeric support or continuum shaft 28300 that is mounted to the proximal attachment disc assembly 28240 and the anvil mounting bracket 26240. In one arrangement, the central continuum shaft 28300 is fabricated from an elastomeric material (e.g., rubber, polymer, etc.) and comprises a flanged proximal end 28302 and a cylindrical body portion 28304. The cylindrical body portion 28304 comprises a series of annular grooves 28306 therein. Each annular groove 28306 corresponds to one of the annular disc members 28210. The annular disc members 28210 and annular spacer members 28280 are journaled on the central continuum shaft 28300 as shown in FIG. 120. The flanged proximal end 28302 of the central continuum shaft 28300 is supported in a proximal passage 28249 in the proximal attachment disc 28240. The cylindrical body portion 28304 of the central continuum shaft 28300 extends through the central passage 28236 in each of the annular disc members 28210 in the series 28202 of movably interfacing annular disc members 28210. Each centrally-disposed spherical feature or protrusion 28222 comprises an annular key member 28224 that is configured to be received in a corresponding annular groove 28306 in the central continuum shaft 28300. Such arrangement may serve to orient each annular disc member 28210 in a desired spacing orientation on the central continuum shaft 28300, for example.

Still referring to FIG. 120, a proximal-most elastomeric spacer member 28280P is journaled on the annular hub portion 28244 of the proximal attachment disc assembly 28240 such that it is positioned between a proximal-most annular disc member 28210P and the proximal attachment disc 28240. The annular key member 28224 of the proximal-most annular disc member 28210P is received within a corresponding annular groove 28306 in the central continuum shaft 28300 to position the centrally-disposed spherical feature or protrusion 28222 of the proximal-most annular disc member 28210P within the concave socket 28246 in the annular hub portion 28244 of the proximal attachment disc 28240. As can further be seen in FIG. 120, another elastomeric spacer member 28280A is journaled on the annular hub portion 28232 of the proximal-most annular disc member 28210P such that is positioned between the next annular disc member 28210A in the series 28202 of movably interfacing annular disc members 28202 and the proximal-most annular disc member 28210P. The annular key member 28224 of the annular disc member 28210A is received within a corresponding annular groove 28306 in the central continuum shaft 28300 to position the centrally-disposed spherical feature or protrusion 28222 of the annular disc member 28210A within the concave socket 28246 in the annular hub portion 28244 of the proximal attachment disc 28210P. Still referring to FIG. 120, another elastomeric spacer member 28280B is journaled on the annular hub portion 28232 of the annular disc member 28210A such that is positioned between the next annular disc member 28210B in the series 28202 of movably interfacing annular disc members 28210. The annular key member 28224 of the annular disc member 28210B is received within a corresponding annular groove 28306 in the central continuum shaft 28300 to position the centrally-disposed spherical feature or protrusion 28222 of the annular disc member 28210B within the concave socket 28246 in the annular hub portion 28244 of the annular disc member 28210A. Also in this arrangement, another elastomeric spacer member 28280C is journaled on the annular hub portion 28232 of the annular disc member 28210B such that is positioned between the distal-most annular disc member 28210C in the series of movably interfacing annular disc members 28202. The annular key member 28224 of the distal-most annular disc member 28210C is received within a corresponding annular groove 28306 in the central continuum shaft 28300 to position the centrally-disposed spherical feature or protrusion 28222 of the distal-most annular disc member 28210C within the concave socket 28246 in the annular hub portion 28244 of the annular disc member 28210B. Finally, another elastomeric spacer member 28280D is journaled on the annular hub portion 28232 of the distal-most annular disc member 28210C such that is positioned between the anvil mounting bracket 26240 and the distal-most annular disc member 28210C. The annular key member 28224 of the centrally-disposed spherical feature or protrusion 26246 of the anvil mounting bracket 26240 is received within a corresponding annular groove 28306 in the central continuum shaft 28300 to position the centrally-disposed spherical feature or protrusion 226246 of the anvil mounting bracket 26240 within the concave socket 28246 in the annular hub portion 28244 of the distal-most annular disc member 28210C.

In at least one arrangement, to limit pivotal travel of the annular disc members to a range of relative pivotal travel and prevent complete relative rotation of the annular disc members 28210 relative to each other, the centrally-disposed spherical feature or protrusion 28222 of each of the annular disc member 28210P, 28210A, 28210B, 28210C, as well as the distal spherical feature or protrusion 26246 of the anvil mounting bracket 26240, includes a pair of arcuate pin grooves 28226 therein. As can be seen in FIG. 120, a corresponding travel-limiting pin member 28227 is pressed into or otherwise attached to each annular hub portion 28232 and is received within the corresponding pin groove 28226 in the centrally-disposed spherical feature or protrusions 28222, 26246.

Returning to FIG. 119, in the illustrated example, the articulation joint 28200 may be operably controlled by an articulation system 28400 that comprises four cable assemblies 28410, 28420, 28430, and 28440 that extend through the elongate shaft assembly 28000. In one arrangement, the cable assembly 28410 comprises a proximal cable portion 28412 that is attached to an articulation rod 28414 that is supported in a corresponding axial groove in the shaft spine assembly 28100 for axial travel therein. A distal cable portion 28416 is attached to the articulation rod 28414. The cable assembly 28420 comprises a proximal cable portion 28422 that is attached to an articulation rod 28424 that is supported in a corresponding axial groove in the shaft spine assembly 28100 for axial travel therein. A distal cable portion 28426 is attached to the articulation rod 28414. The cable assembly 28430 comprises a proximal cable portion 28432 that is attached to an articulation rod 28434 that is supported in a corresponding axial groove in the shaft spine assembly 28100 for axial travel therein. A distal cable portion 28436 is attached to the articulation rod 28434. The cable assembly 28440 comprises a proximal cable portion 28442 that is attached to an articulation rod 28444 that is supported in a corresponding axial groove in the shaft spine assembly 28100 for axial travel therein. A distal cable portion 28446 is attached to the articulation rod 28444.

The proximal cable portions 28412, 28422, 28432, 28442 may operably interface with a portion of a cable control system 25030 that is supported within or is otherwise associated with a housing of the surgical instrument 25010. The cable control system 25030 may comprise a plurality of cable support members/capstans, pulleys, etc. that are controlled by one or more corresponding motors that are controlled by a control circuit portion of the surgical instrument 25010. In various embodiments, the cable control system 25030 is configured to manage the tensioning (pulling) and paying out of cables at precise times during the articulation process. In addition, in at least one arrangement, the cable control system 25030 may be employed to control the opening and closing of the anvil 26210 as will be discussed in further detail below.

Turning now to FIG. 126, the distal cable portions 28416, 28426, 28436, 28446 are configured to operably interface with a closure system 28500 that is rotatably mounted in the proximal end 26112 of the elongate channel 26110. As can be seen in FIG. 126, the closure system 28500 comprises a pulley unit 28510 that comprises a first lateral alpha wrap pulley 28520 and a second lateral alpha wrap pulley 28530 that are interconnected by a central shaft 28540. The pulley unit 28510 is rotatably supported within the proximal end

26112 of the elongate channel 26110 and retained therein by an anvil mounting bracket 26240 that is attached to the proximal end 26112 of the elongate channel 26112. See FIG. 119. The anvil mounting bracket 26240 may be attached to the proximal end 26112 of the elongate channel 26110 by welding, adhesive, snap features, etc. The anvil mounting bracket 26240 comprises a shaft cradle 26242 that is configured to rotatably support the central shaft 28540 within the elongate channel 26110. In the illustrated arrangement, a first pivot shaft 28521 protrudes from the first lateral alpha wrap pulley 28520 and is pivotally supported in a pivot hole 26113 in the proximal end of the elongate channel. Similarly, a second pivot shaft 28531 protrudes from the second lateral alpha wrap pulley 28530 and is pivotally supported in a pivot hole 26115 in the proximal end 26112 of the elongate channel 26110.

As can be seen in FIG. 126, the first alpha wrap pulley 28520 comprises a first circumferential groove 28522 and a second circumferential groove 28524. In the illustrated example, the first distal cable portion 28416 is received in the first circumferential groove 28522 and is attached thereto and the second distal cable portion 28426 is received in the second circumferential groove 28524 and is attached thereto. Pulling on the first distal cable portion 28416 will result in the rotation of the first lateral alpha wrap pulley 28520 in a first direction and pulling the second distal cable portion 28426 will result in the rotation of the first lateral alpha wrap pulley 28520 in a second opposite direction. Similarly, the second lateral alpha wrap pulley 28530 comprises a first circumferential groove 28532 and a second circumferential groove 28534. In the illustrated arrangement, the distal cable portion 28446 is received in the first circumferential groove 28532 and is attached thereto and the third distal cable portion 28436 is received in the second circumferential groove 28534 and is attached thereto. Pulling on the fourth distal cable portion 28446 will result in the rotation of the second alpha wrap pulley 28530 in the first direction and pulling the third distal cable portion 28436 will result in the rotation of the second lateral alpha wrap pulley 28530 in the second opposite direction. In accordance with one aspect, the lateral alpha wrap pulleys 28520, 28530 can rotate approximately three hundred thirty degrees. This range of rotational travel is in contrast to a normal pulley that may have a range of rotational travel that is less than one hundred eighty degrees of rotation.

Each of the first and second lateral alpha wrap pulleys 28520, 28530 also comprise a corresponding spiral closure cam that is configured to apply closure motions to the anvil 26210. As can be seen in FIG. 126, the first lateral alpha wrap pulley 28520 includes a first spiral closure cam 28526 and the second lateral alpha wrap pulley 28530 has a second spiral closure cam 28536 thereon. The spiral closure cams 28526, 28536 are configured to cammingly interact with corresponding anvil closure arms 26234 on the anvil mounting portion 26230 of the anvil 26210 to apply closure motions thereto. See FIG. 119. Rotation of the pulley unit 28510 in a first rotary direction will cause the spiral closure cams 28526, 28536 to cam the anvil 26210 to the closed position. To open the anvil 26210, the pulley unit 28510 is rotated in opposite direction to position the spiral closure cams 28526, 28536 in positions wherein the anvil 26210 can be pivoted open by an anvil spring (not shown).

Figure 127:
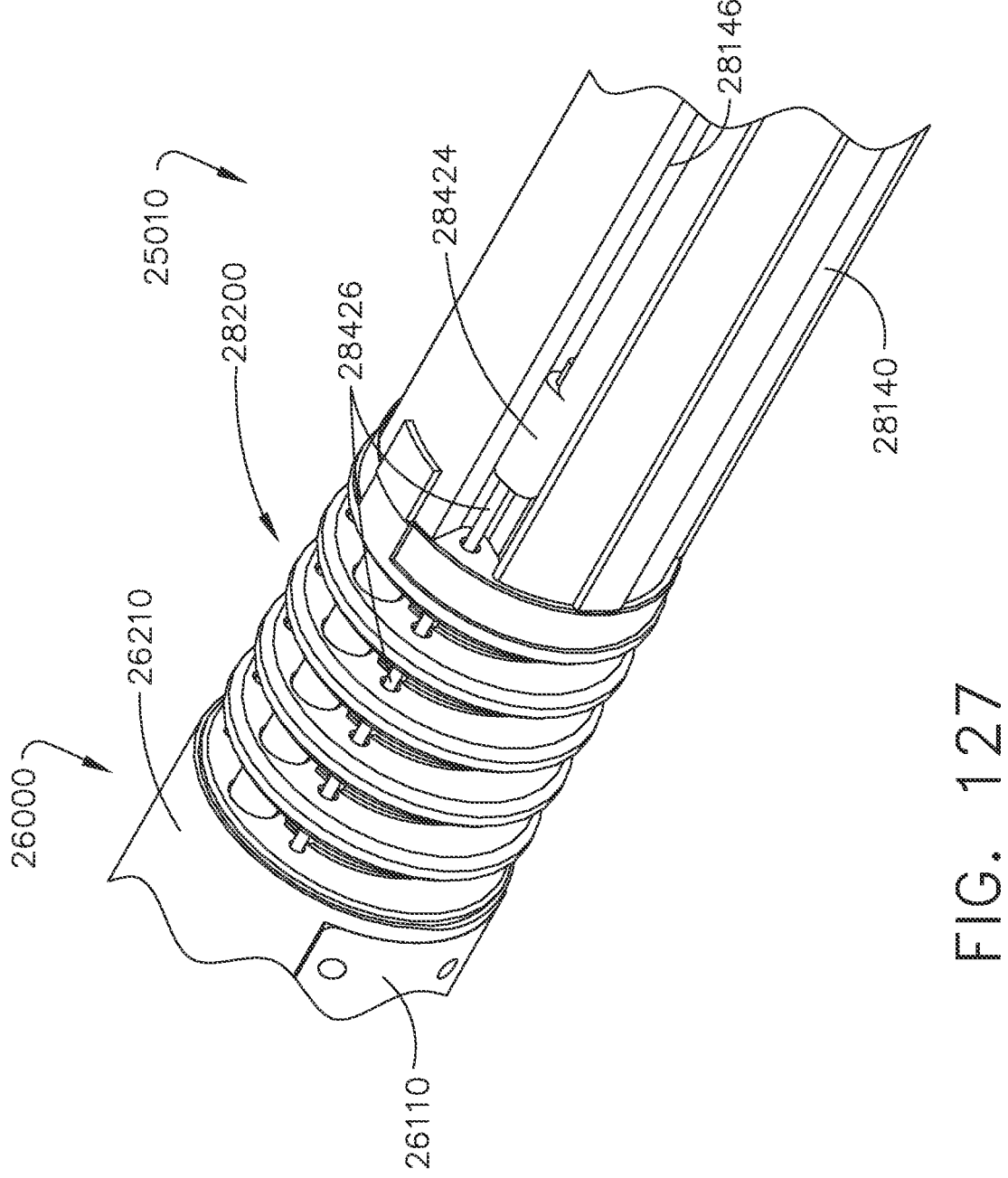
Figures 128, 129:
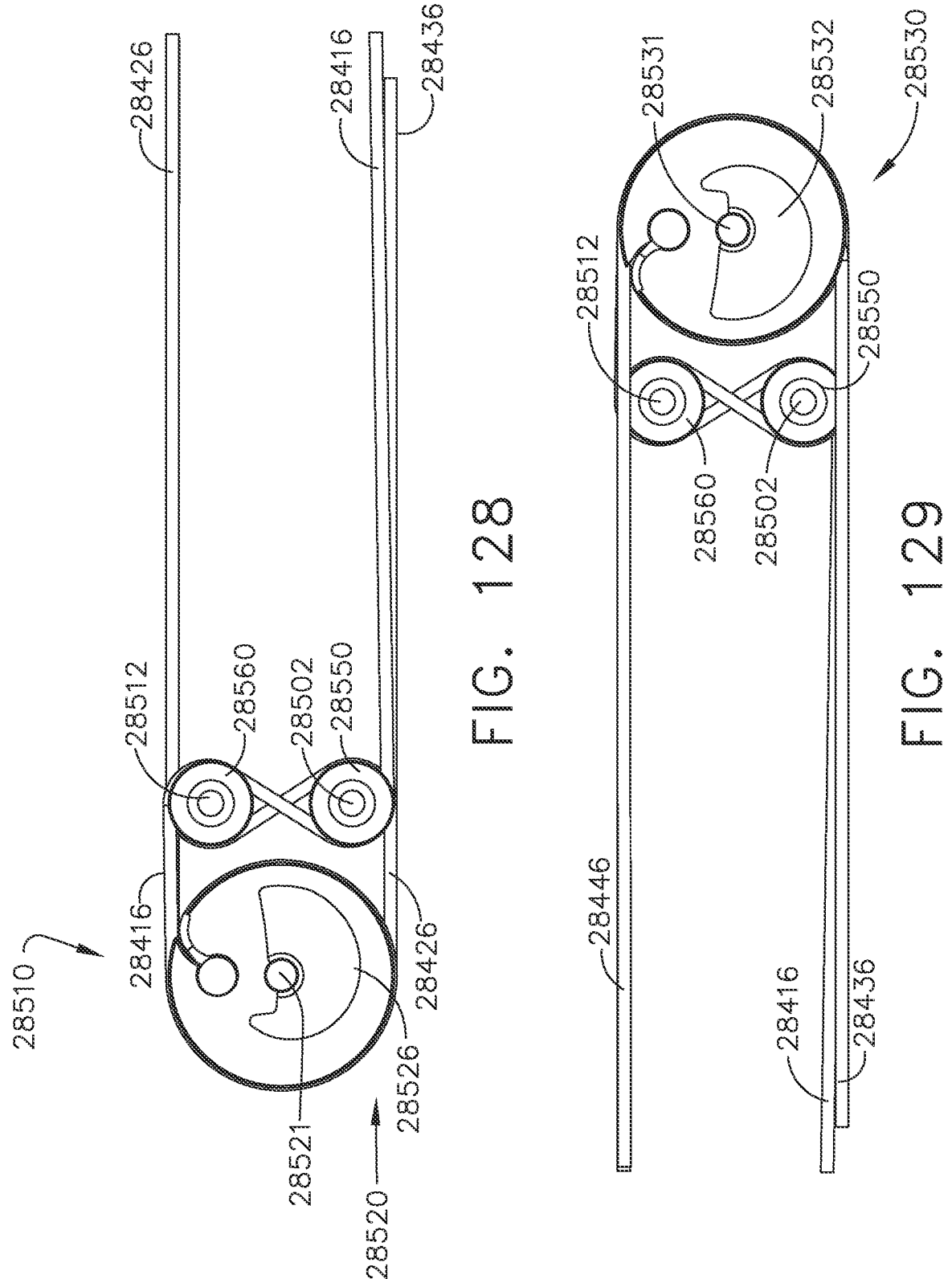
Figure 130:
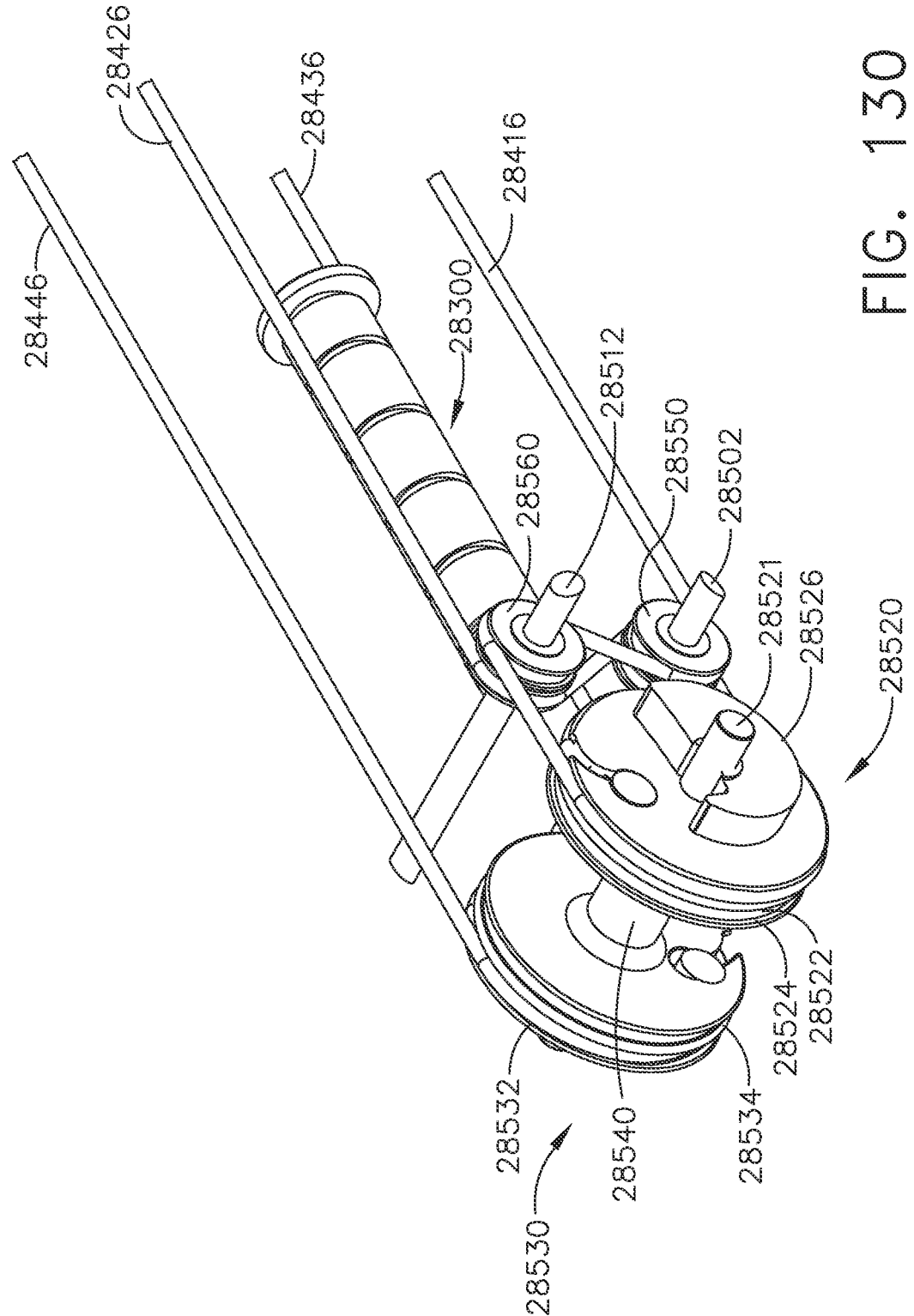

In the illustrated arrangement, the proximal attachment disc 28240, the proximal-most annular disc member 28210P, annular proximal disc members 28210A, 28210B, 28210C and anvil mounting bracket 26240 all include fourth articulation cable passages 28214 that are configured to permit each of the distal cable portions 28416, 28426, 28436, and 28446 to pass therethrough. FIG. 127 illustrates the articulation rod 28424 slidably supported in a corresponding axial groove 28146 in the distal spine segment 28140 for axial travel therein. Each of the other articulation rods 28414, 28434, 28444 is similarly supported in axial grooves in the distal spine segment 28140 as well as corresponding grooves in the proximal spine segment 28120.

Referring now to FIGS. 119 and 128-130, the distal cable portion 28416 extends from the articulation rod 28414 through the articulation joint 28200 and is looped around two redirect pulleys 28550, 28560 that are supported on shafts 28502, 28512 that are rotatably mounted in the proximal end 26112 of the elongate channel 26110. The distal cable portion 28416 exits the articulation joint 28200 to be received within the first circumferential groove 28522 in the first lateral alpha wrap pulley 28520 where it is secure therein. The distal cable portion 28426 extends from the articulation rod 28424 through the articulation joint 28200 to be looped around the redirect pulleys 28560, 28550 to be received within the second circumferential groove 28524 in the first lateral alpha wrap pulley 28520 where it is secure therein.

In the illustrated example, distal cable portion 28436 extends from the articulation rod 28434 through the articulation joint 28200 to be received within a corresponding circumferential groove 28534 in the second lateral alpha wrap pulley 28530 where it is secured therein. In addition, the distal cable portion 28446 extends from the articulation rod 28444 through the articulation joint 28200 to be received within a corresponding circumferential groove 28532 in the second lateral alpha wrap pulley 28530 where it is secure therein.

In at least one example, to articulate the surgical end effector 26000 relative to the elongate shaft assembly 28000 through a first articulation plane, the cable control system 25030 is actuated to pull on the distal cable portion 28426 and the distal cable portion 28446 simultaneously with a same amount of tension being applied to each distal cable portion 28426, 28446. Because the distal cable portions 28426, 28446 apply equal amounts of tension on both sides of the pulley unit 28510, the pulley unit 28510 does not rotate. However, the pulling action of the distal cable portions 28426, 28446 is translated through the articulation joint 28200 to the surgical end effector 26000 which results in the articulation of the articulation joint 28200 through a first articulation plane. To articulate the surgical end effector 26000 through a second plane of articulation that is transverse to the first plane of articulation, the cable control system 25030 is actuated to pull the distal cable portion 28436 and the distal cable portion 28446 simultaneously with a same amount of tension being applied to each distal cable portion 28436, 28446. Because the distal cable portions 28436, 28446 apply equal amounts of tension on both sides of the second lateral alpha wrap pulley 25830 of the pulley unit 28510, the pulley unit 28510 does not rotate. However, the pulling action of the distal cable portions 28436, 28446 is translated through the articulation joint 28200 to the surgical end effector 26000 which results in the articulation of the articulation joint 28200 in a second articulation plane.

The cable control system 25030 may also be used to control the opening and closing of the anvil 26210 in the following manner. As indicated above, when the spiral closure cams 28526 on the first lateral alpha wrap pulley 28520 and the second lateral alpha wrap pulley 28530 are in a first position, the anvil 26210 may be pivoted to an open position by an anvil spring or springs (not shown) that are positioned in the proximal end 26112 of the elongate channel 26110 and are position to contact the anvil mounting portion 26230 or anvil closure arms 26234 to pivot the anvil 26210 to the open position. To close the anvil 26210 from that position, the cable control system 25030 is actuated to pull the distal cable portion 28416 and the distal cable portion 28446 simultaneously with a same amount of tension being applied to each distal cable portion 28416 and 28446. These distal cable portions 28416, 28446 will cause the pulley unit 28510 to rotate causing the spiral closure cams 28526, 28536 to contact the anvil closure arms 26234 and cam the anvil 26210 to a closed position. It will be appreciated that by applying equal amounts of tension into the distal cable portions 28416, 28446, no moment is applied to the articulation joint 28200 because there are equal amounts of tension being applied on each side of the shaft axis SA. Such arrangement allows the jaw closure to be profiled as desired. This cable-control system 25030 may allow for a faster closure when the anvil 26210 is fully open. The cable-control system 25030 can also function as a lower speed/higher force generating closure mechanism for clamping onto tissue. The present cable controlled system 25030 may not produce the backlash that commonly occurs with other cable-controlled systems and thus can also be used to control the articulation position of the end effector. The above-described articulation joint 28200 and cable controlled system 25030 can facilitate multiple plane articulation while also supplying an additional actuation motion to the surgical end effector 26000.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 25010 employs a firing system 27000 that may address many if not all of such issues.

Referring now to FIGS. 133 and 134, in at least one embodiment, the firing system 27000 comprises a firing member 27100 that includes a vertically-extending firing member body 27112 that comprises a top firing member feature 27120 and a bottom firing member feature 27130. A tissue cutting blade 27114 is attached to or formed in the vertically-extending firing member body 27112. In at least one arrangement, the top firing member feature 27120 comprises a top tubular body 27122 that has a top axial passage 27124 extending therethrough. See FIG. 134. The bottom firing member feature 27130 comprises a bottom tubular body 27132 that has a bottom axial passage 27134 extending therethrough. In at least one arrangement, the top firing member feature 27120 and the bottom firing member feature 27130 are integrally formed with the vertically-extending firing member body 27112. In at least one example, the anvil body 26212 comprises an axially extending anvil slot that has a cross-sectional shape that resembles a "keyhole" to accommodate passage of the top firing member feature 27120 in the various manners discussed herein. Similarly, the elongate channel 26110 comprises an axially extending channel slot that also has a keyhole cross-sectional shape for accommodating passage of the bottom firing member feature 27130 as described above.

In the illustrated arrangement, the firing system 27000 comprises an upper firing assembly 27200 that operably interfaces with the top firing member feature 27120. The upper firing assembly 27200 includes an upper flexible outer tube or conduit 27210 that has a proximal end 27212 that is fixed to an upper insert 27214 that is non-movably attached to the shaft spine assembly 28100. For example, the upper insert 27214 may be welded to the shaft spine assembly 28100 or otherwise be attached thereto by adhesive or other appropriate fastening means. The flexible outer tube or conduit 27210 extends through upper passages 28216 provided through the proximal attachment disc assembly 28240, the proximal-most annular disc member 28210P, the annular disc members 28210A, 28210B, 28210C and the anvil mounting bracket 26240. A distal end 27216 of the flexible outer tube or conduit 27210 may be affixed to the anvil mounting bracket 26240.

In the illustrated embodiment, the upper firing assembly 27200 further includes an upper push rod 27220 that is slidably supported in a corresponding axial passage in the shaft spine assembly 28100. The upper firing assembly 27200 further comprises an upper push coil 27230 that is supported in an inner flexible upper sleeve 27240 which extends through the upper flexible outer tube or conduit 27210. A proximal end 27232 of the upper push coil 27230 and a proximal end 27242 of the inner flexible upper sleeve 27240 abut a distal end 27222 of the upper push rod 27220. The upper push coil 27230 is hollow and may comprise a coil spring that is fabricated from Nitinol, titanium, stainless steel, etc. In other arrangements, the upper push coil 27230 comprises a laser cut "hypotube" that essentially comprises a hollow tubular member with offset laser cuts therein which enable the hypotube to flex and bend while being capable of transmitting axial forces or motions. The inner flexible upper sleeve 27240 may be fabricated from a polymer or similar material and prevent tissue, fluid, and/or debris from infiltrating into the upper push coil 27230 which may hamper its ability to flex and bend during articulation of the surgical end effector relative to the elongate shaft assembly.

As can be seen in FIG. 134, a distal end 27234 of the upper push coil 27230 as well as a distal end 27244 of the inner flexible upper sleeve 27240 abut a proximal end 27123 of the top tubular body 27122 or the top firing member feature 27120. Also in the illustrated arrangement, the upper firing assembly further comprises an upper push coil cable 27250 that extends through the hollow upper push coil 27230. The upper push coil cable 27250 comprises an upper cable proximal end 27252 that is secured to the distal end 27222 of the upper push rod 27220 and an upper cable distal end 27254 that is secured within the top axial passage 27124 in the top tubular body 27122 of the top firing member feature 27120 by an upper attachment lug 27256. The upper push coil cable 27250 is held in tension between the top firing member feature 27120 an the upper push rod 27220 which serves to retain the distal end 27234 of the upper push coil 27230 as well as a distal end 27244 of the inner flexible upper sleeve 27240 in abutting contact with the proximal end 27123 of the top tubular body 27122 of the top firing member feature 27120 and the proximal end 27232 of the upper push coil 27230 and a proximal end 27242 of the inner flexible upper sleeve 27240 in abutting contact with the distal end 27222 of the upper push rod 27220.

In the illustrated example, the firing system 27000 further comprises a lower firing assembly 27300 that operably interfaces with the bottom firing member feature 27130. The lower firing assembly 27300 includes a lower flexible outer tube or conduit 27310 that has a proximal end 27312 that is fixed to a lower insert 27314 that is non-movably attached to the shaft spine assembly 28100. For example, the lower insert 27314 may be welded to the shaft spine assembly 28100 or otherwise be attached thereto by adhesive or other appropriate fastening means. The lower flexible outer tube or conduit 27310 extends through lower passages 28218 provided in each of the proximal attachment disc assembly 28240, the proximal-most annular disc member 28210P, annular disc members 28210A, 28210B, 28210C and anvil mounting bracket 26240. A distal end 27316 of the flexible outer tube or conduit 27310 is affixed to the anvil mounting bracket 26240.

In the illustrated embodiment, the lower firing assembly 27300 further includes a lower push rod 27320 that is slidably supported in a corresponding axial passage in the shaft spine assembly 28100. The lower firing assembly 27300 further comprises a lower push coil 27330 that is supported in an inner flexible lower sleeve 27340 which extends through the lower flexible outer tube or conduit 27310. A proximal end 27332 of the lower push coil 27330 and a proximal end 27342 of the inner flexible lower sleeve 27340 abut a distal end 27322 of the lower push rod 27320. The lower push coil 27330 is hollow and may comprise a coil spring that is fabricated from Nitinol, titanium, stainless steel, etc. In other arrangements, the lower push coil 27330 comprises a laser cut hypotube that essentially comprises a hollow tubular member with offset laser cuts therein which enable the hypotube to flex and bend. The inner flexible lower sleeve 27340 may be fabricated from a polymer or similar material and prevent tissue, fluid, and/or debris from infiltrating into the lower push coil 27330 which may hamper its ability to flex during articulation.

As can be seen in FIG. 134, a distal end 27334 of the lower push coil 27330 as well as a distal end 27344 of the inner flexible lower sleeve 27340 abut a proximal end 27133 of the bottom tubular body 27132 of the bottom firing member feature 27130. Also in the illustrated arrangement, the lower firing assembly 27300 further comprises a lower push coil cable 27350 that extends through the hollow lower push coil 27330. The lower push coil cable 27350 comprises a lower cable proximal end 27352 that is secured to the distal end 27322 of the lower push rod 27320 and a lower cable distal end 27354 that is secured within the bottom axial passage 27134 in the bottom tubular body 27132 of the bottom firing member feature 27130 by a lower attachment lug 27356. The lower push coil cable 27350 is held in tension between the bottom firing member feature 27130 an the lower push rod 27320 which serves to retain the distal end 27334 of the lower push coil 27330 as well as a distal end 27344 of the inner flexible lower sleeve 27340 in abutting contact with the proximal end 27133 of the bottom tubular body 27132 of the bottom firing member feature 27130 and the proximal end 27332 of the lower push coil 27330 and a proximal end 27342 of the inner flexible lower sleeve 27340 in abutting contact with the distal end 27322 of the lower push rod 27320.

In the illustrated arrangement, the firing system 27000 further comprises a differential drive assembly 27400 that is configured to axially drive the upper firing assembly 27200 and the lower firing assembly 27300. Turning to FIGS.

136-139, in at least one arrangement, a proximal end 27224 of the upper push rod 27220 is coupled to a first or upper gear rack 27410 of the differential drive assembly 27400. As can be seen in FIG. 136, the first or upper gear rack 27410 is slidably supported in an upper proximal axial cavity 28122 in the proximal spine segment 28120. Similarly, a proximal end 27324 of the lower push rod 27320 is coupled to a second or lower gear rack 27420 that is supported for axial travel within a lower proximal axial cavity 28124 in the proximal spine segment 28120. The differential drive assembly 27400 further comprises an axially movable carrier member 27430 that is centrally disposed between the first or upper gear rack 27410 and the second or lower gear rack 27420 and is supported for axial travel within a proximal axial cavity 28126 in the proximal spine segment 28120. See FIG. 136. Still referring to FIGS. 136-139, a pinion gear 27432 is pivotally pinned to the axially movable carrier member 27430 such that the pinion gear 27432 is meshing engagement with the first or upper gear rack 27410 and the second or lower gear rack 27420. The axially movable carrier member 27430 is driven axially within the proximal axial cavity 28126 in the proximal spine segment 28120 by a firing drive actuator 27440. See FIG. 137. In one arrangement, the firing drive actuator 27440 comprises a firing drive gear rack 27442 that drivingly interfaces with a drive gear 27444 that is driven by a firing motor 27446 that may be operably supported in or otherwise associated with the housing of the surgical instrument 25010. In other arrangements, the firing drive actuator 27440 may be axially driven distally and proximally by a cylinder arrangement or other suitable actuator interfacing therewith. As can be seen in FIGS. 137-139, the firing drive actuator 27440 may be attached to the axially movable carrier member 27430 by a pair of spaced coupler pins 27448 that are attached to the firing drive actuator 27440 and are received within corresponding axial slots 27434 in the axially movable carrier member 27430. Such arrangement permits some relative axial movement between the firing drive actuator 27440 and the axially movable carrier member 27430. For example, when the firing drive actuator 27440 is driven distally in the distal direction DD, the axially movable carrier member 27430 will not move distally until the coupler pins 27448 reach the distal ends of their corresponding axial slots 27434 at which point the axially movable carrier member 27430 will move distally. Likewise, the when the firing drive actuator 27440 is driven in the proximal direction PD, the axially movable carrier member 27430 will not move proximally until the coupler pins 27448 reach the proximal ends of their corresponding axial slots 27434 at which point the axially movable carrier member 27430 will move proximally.

Surgical stapling devices need to apply a high force on the firing member over a long displacement to form the staples and cut tissue. Transmitting that force through an articulated joint is especially challenging because it is difficult to redirect the forces in the desired direction and withstand the loads applied to it. The differential drive assembly 27400 described herein addresses and solves many, if not all of such challenges by employing two flexible outer tubes or conduits 27210, 27310 to constrain the paths of the flexible push coils 27230, 27330, respectively. As described herein, the upper flexible outer tube or conduit 27210 surrounds a portion of the upper push coil 27230 and the upper flexible outer tube or conduit 27310 surrounds a portion of the lower push coil 27330. Each of the outer tubes or conduits 27210, 27310 can bend but they also can resolve an axial tensile load. The ability to bend allows for the firing member force to be redirected through the articulated joint, and the ability to resolve tension allows for it to change the direction in which the push coil goes. When the push coil 27230, 27330 is put in compression, the flexible outer tube or conduit 27210, 27310 is put in tension. The outer tubes or conduits 27210, 27310 prevent the push coils 27230, 27330 from buckling. The outer tubes 27210, 27310 are terminated in a manner to resolve the tensile loads. As described above, the distal end 27216 of the flexible outer tube or conduit 27210 and the distal end 27316 of the flexible outer tube or conduit 27310 are both affixed to the anvil mounting bracket 26240. The proximal end 27212 of the flexible outer tube or conduit 27210 and the proximal end 27312 of the flexible outer tube or conduit 27310 are both affixed to the shaft spine assembly 28100. The pinion gear 27432 is in meshing engagement with the first or upper gear rack 27410 and the second or lower gear rack 27420 such that when one of the racks 27410, 27420 moves in one axial direction, the other rack 27410, 27420 axially moves in an opposite direction. As can be seen in FIGS. 138 and 139, during articulation, the pinion gear 27432 rotates so the flexible outer tubes or conduits 27210, 27310 can move to account for the change in path length. However, when the firing drive actuator 27440 is driven in the distal direction DD, the axially movable carrier member 27430 is actuated to push the push coils 27230, 27330 distally through the outer tubes or conduits 27210, 27310 to fire (i.e., drive the firing member 27100 distally) the tensile loads in the two flexible outer tubes or conduits 27210, 27310 react against one another without any motion of the pinion gear 27432.

In accordance with one general aspect, the upper passages 28216 form an upper pathway 28221 (FIG. 117) through the articulation joint 28200. Similarly, the lower passages 28218 form a lower pathway 28223 through the articulation joint 28200. When the surgical end effector 26000 is in an unarticulated position (i.e., the surgical end effector is axially aligned with the elongate shaft assembly 28000 on the shaft axis SA—FIGS. 115, 117, 118), the upper pathway 28221 and the lower pathway 28223 are parallel to each other. See FIG. 117. When the surgical end effector 26000 is in an articulated position relative to the elongate shaft assembly 28000, the upper pathway 28221 and the lower pathway 28223 are concentric to each other. See FIG. 116.

When the surgical end effector 26000 is in the unarticulated position, the firing system 27000 may be actuated to drive the firing member 27100 from a starting position within the proximal end 26112 of the elongate channel 26100 to an ending position within the distal end 26114 of the elongate channel 26110. When the surgical end effector 26000 is in the unarticulated position, and the firing system 27000 is actuated, the differential drive assembly 27400 drives the upper firing assembly 27200 and the lower firing assembly 27300 equal axial distances in a same axial direction (i.e., the distal direction DD) to apply an upper axial drive motion and a lower axial drive motion to the firing member 27100. The upper axial drive motion and the lower axial drive motion are substantially equal in magnitude which serves to distally advance the firing member 27100 through the surgical end effector 26000 without binding which might otherwise occur should the upper axial drive motion and the lower axial drive motions be different in magnitude. Similarly, when the surgical end effector 26000 is in an articulated position relative to the elongate shaft assembly 28000, the firing system 27000 may be actuated to drive the firing member 27100 from the starting position to the ending position. In such instances, the differential drive assembly 27400 is configured to permit the upper firing assembly 27200 and the lower firing assembly 27300 to move in substantially equal distances in opposite axial directions to accommodate the articulated position. The differential drive assembly 27400 may then apply an upper axial drive motion and a lower axial drive motion that are equal to each other to the firing member 27100. For example, depending upon the articulated position of the surgical end effector 26000 relative to the elongate shaft assembly 28000, the upper firing assembly 27200, upon articulation of the surgical end effector 26000, may be moved proximally a first distance and the lower firing assembly 27300 may be positioned relative thereto distally a second distance that is substantially equal to the first distance by the pinion gear 27432. Thereafter, distal actuation of the firing drive actuator 27440 will cause the upper firing assembly 27200 and the lower firing assembly 27300 to apply an upper axial drive motion and a lower axial drive motion that are equal to each other to the firing member 27100. As used herein, when the carrier is moved distally, the carrier may apply "axial control motions" to the upper firing assembly 27200 and the lower firing assembly 27300. Thus, when the surgical end effector 26000 is in an unarticulated configuration, the carrier may apply equal amounts of axial control motions to the upper firing member 27200 and the lower firing member 27300 in the same axial direction (distal direction DD) and when the surgical end effector 26000 is in an articulated configuration, the carrier may apply "other equal amounts" of axial control motions to the upper firing member 27200 and the lower firing member 27300 in the same axial direction (distal direction DD) to move the firing member 27100 from the starting position to the ending position.

FIGS. 140-152 illustrate another surgical instrument 30010 that employs another form of articulation joint 30200 for coupling a surgical end effector 31000 to an elongate shaft assembly 32000. The elongate shaft assembly 32000 may be identical or very similar to various other elongate shaft assemblies described herein. As can be seen in FIGS. 140-143, the articulation joint 30200 comprises a proximal joint member 30210 and a distal joint member 30250. The proximal joint member 30210 is configured to be attached to a distal end of the elongate shaft assembly 32000 that is coupled to a housing or other portion of a surgical instrument. The distal joint member 30250 is configured to be attached to the surgical end effector 31000. For example, the distal joint member 30250 may be attached to the elongate channel 31200 of the surgical end effector 31000. The end effector 31000 may be identical or very similar to various surgical end effectors disclosed herein.

As can be seen in FIGS. 143 and 150, the proximal joint member 30210 comprises a proximal face 30212 that defines a proximal apex 30218. Similarly, the distal joint member 30250 comprises a distal face 30252 that defines a distal apex 30254. See FIG. 151. The proximal joint member 30210 and the distal joint member 30250 are pivotally retained together with their respective apex portions 30218, 30254 in "rolling inter-engagement" by a linkage assembly 30300. As can be seen in FIGS. 141-143, the linkage assembly 30300 comprises a first link 30310 and a second link 30320. In the illustrated example, the first link 30310 and the second link 30320 are coupled to the proximal joint member 30210 by a proximal cross pin assembly 30330. In accordance with one aspect, the proximal cross pin assembly 30330 comprises a first proximal cross pin 30332 that defines a first proximal pivot axis FPPA. See FIG. 152. A proximal end 30312 of the first link 30310 is configured to receive a first proximal threaded fastener 30314 therethrough that is configured to be threadably received in a first threaded hole 30334 in the first proximal cross pin 30332. See FIG. 143. Likewise, a proximal end 30322 of the second link 30320 is configured to receive a second proximal threaded fastener 30324 therethrough that is configured to be threadably received in a second threaded hole 30336 in the first proximal cross pin 30332.

In at least one embodiment, the first proximal cross pin assembly 30330 further comprises a second proximal cross pin 30340 that is rotatably journaled on the first proximal cross pin 30332. In one arrangement, the first proximal cross pin 30332 may comprise a first proximal bushing or low friction sleeve 30338 that is configured to facilitate free rotation between the first proximal cross pin 30332 and the second proximal cross pin 30340. The second proximal cross pin 30340 defines a second proximal pivot axis SPPA that is transverse to the first proximal pivot axis FPPA and a shaft axis SA that is defined by the elongate shaft assembly 32000. As can be seen in FIG. 143, the second proximal cross pin 30340 is received within laterally aligned proximal pin openings 30220 in the proximal joint member 30210 to attach the linkage assembly 30300 to the proximal joint member 30210 such that the linkage assembly 30300 may pivot relative to the proximal joint member 30210 about the first proximal pivot axis FPPA and the second proximal pivot axis SPPA.

In the illustrated example, the first link 30310 and the second link 30320 are coupled to the distal joint member 30250 by a distal cross pin assembly 30350. In accordance with one aspect, the distal cross pin assembly 30350 comprises a first distal cross pin 30352 that defines a first distal pivot axis FDPA. A distal end 30316 of the first link 30310 is configured to receive a first distal threaded fastener 30318 therethrough that is configured to be threadably received in a third threaded hole 30354 in the first distal cross pin 30352. Likewise, a distal end 30326 of the second link 30320 is configured to receive a second distal threaded fastener 30328 therethrough that is configured to be threadably received in a fourth threaded hole 30356 in the first distal cross pin 30352.

In at least one embodiment, the first distal cross pin assembly 30350 further comprises a second distal cross pin 30360 that is rotatably journaled on the first distal cross pin 30352. In one arrangement, the first distal cross pin 30352 may comprise a first proximal bushing or low friction sleeve 30358 that is configured to facilitate free rotation between the first distal cross pin 30352 and the second distal cross pin 30360. The second distal cross pin 30360 defines a second distal pivot axis SDPA that is transverse to the first distal pivot axis FDPA and the shaft axis SA. As can be seen in FIG. 142, the second distal cross pin 30360 is received within laterally aligned distal pin openings 30256 in the distal joint member 30250 to attach the linkage assembly 30300 to the distal joint member 30250 such that the linkage assembly 30300 may pivot relative to the distal joint member 30250 about the first distal pivot axis FDPA and the second distal pivot axis SDPA.

Turning now to FIG. 150, the proximal face 30212 of the proximal joint member 30210 defines a proximal apex 30218 that comprises a plurality of radially-spaced recessed regions 30222 formed thereon. In the illustrated arrangement, six total recessed regions 30222 are equally spaced about a center 30219 of the proximal apex 30218. As can be seen in FIG. 151, the distal face 30252 of the distal joint member 30250 comprises a total of six distal fins or protuberances 30262 that are equally spaced about a center 30255 of the distal apex 30254 such that each fin 30262 is corresponds to one of the recessed regions 30222 when the surgical end effector is in an unarticulated position. For example, angle B may be approximately sixty degrees. See FIG. 151. Each of the fins 30262 and each of the recessed regions 30222 comprise rounded edges configured to facilitate rolling inter-engagement between the proximal apex 30218 and the distal apex 30254 during articulation of the surgical end effector 31000 relative to the elongate shaft assembly 32000. Such rolling inter-engagement may be somewhat similar to the rolling inter-engagement between the teeth of intermeshing bevel gears, for example such that the proximal apex 30218 and the distal apex 30254 remain in engagement with each other during articulation of the surgical end effector 31000.

Returning to FIG. 141, the surgical instrument 30010 also comprises an articulation system 30500 that is configured to apply articulation motions to the surgical end effector 31000 to articulate the surgical end effector 31000 relative to the elongate shaft assembly 32000. In at least one arrangement, the articulation system 30500 comprises four articulation cables 30510, 30520, 30530, and 30540 that extend through the elongate shaft assembly 32000. In the illustrated arrangement, the articulation cables 30510, 30520, 30530, and 30540 pass through the proximal joint member 30210 and the distal joint member 30250 and are secured to the surgical end effector 31000 in the various manners disclosed herein. The articulation cables 30510, 30520, 30530, and 30540 operably interface with an articulation control system that is supported in or otherwise associated with the housing of the surgical instrument 300010. For example, as was discussed above, a proximal portion of each cable 30510, 30520, 30530, and 30540 may be spooled on a corresponding rotary spool or cable-management system 2007 (FIG. 2) in the housing portion of the surgical instrument 30010 that is configured to payout and retract each cable 30510, 30520, 30530, and 30540 in desired manners. The spools/cable management system may be motor powered or manually powered (ratchet arrangement, etc.). FIGS. 140, 141, and 144-146 illustrate the position of the articulation joint 30200 when the surgical end effector is in an unarticulated position and FIGS. 142 and 147-149 illustrate various positions of the articulation joint 30200 when the surgical end effector has been articulated in various positions relative to the elongate shaft assembly 32000. The surgical instrument 30010 may also employ a firing system 30600 of the various types and constructions disclosed in detail herein to drive a firing member (not shown) within the surgical end effector 31000. For example, the proximal joint member 30210 may be provided with an upper proximal firing member passage 30214 that is configured to accommodate passage of an upper flexible firing assembly 30610 therethrough. The upper flexible firing assembly 30610 may span across an area generally designated as 30700 between the proximal face 30212 of the proximal joint member 30210 and the distal face 30252 of the distal joint member 30250 to and slidably pass through an upper distal firing member passage 30257 in the distal joint member 30250. Similarly, the proximal joint member 30210 is provided with a lower proximal firing member passage 30216 that is configured to accommodate passage of a lower flexible firing assembly 30620 member therethrough. The lower flexible firing assembly 30620 spans area 30700 and is received in a lower distal firing member passage 30259 in the distal joint member 30250. The upper flexible firing assembly 30610 and the lower flexible firing assembly 30620 operably interface with a firing member in the surgical end effector 31000. The upper flexible firing assembly 30610 and the lower flexible firing assembly 30620 may be identical or very similar in construction to the various flexible firing member drive arrangements disclosed herein.

FIG. 153 illustrates another form of articulation joint 30200' that is identical in construction and operation to articulation joint 30200 described above, except that the first link 30310 and the second link 30320 are connected together by an annular ring 30380 that is located in the area 30700 between the proximal face 30212 of the proximal joint member 30210 and the distal face 30252 of the distal joint member 30250. In at least one arrangement, the annular ring 30380 comprises an outer diameter which is equal to or less than an outer diameter of the proximal joint member 30210 and an outer diameter of the distal joint member 30250. In one arrangement, for example, the outer diameter of the distal joint member 30250 is equal to the outer diameter of the proximal joint member 30210 which is equal to or less than the maximum outer diameter of the elongate shaft assembly 32000. Thus, such arrangement permits the surgical instrument 30010 to be inserted into a patient through a trocar cannula that can accommodate the maximum outer diameter of the elongate shaft assembly 32000. The annular ring 30380 may be particularly advantageous as it may prevent tissue or a flexible exterior joint cover (not shown) from potentially getting caught between the joint components.

The articulation joints 30200, 30200' utilize an outer linkage assembly 30300 arrangement that connects the proximal cross pin assembly 30330 and the distal cross pin assembly 30350 together and resolve torsional and axial loads that are applied to the joint which may be particular important for resolving loads in the instrument during firing of the firing member. Such joint arrangement further leaves space between the proximal joint member and distal joint member to accommodate additional components/features. As can be seen in the various Figures, the proximal joint member and the distal joint member each are provided with clearance pockets/features/contours to accommodate the linkage assembly when the joint articulates.

FIGS. 154-156 illustrate another form of articulation joint 33000 that may be used to couple a surgical end effector of the various types disclosed herein to an elongate shaft assembly 34000 of a surgical instrument 33010. The elongate shaft assembly 34000 comprises a central spine member 34100 (FIG. 155) that may be coupled to or otherwise operably interfaces with a housing (not shown) of the surgical instrument 33010. The elongate shaft assembly 34000 further comprises an outer tube member 34110 that is extends over the central spine member 34100. In at least one form, the articulation joint 33000 comprises a proximal joint member 33100 that is attached to the central spine member 34100 and a distal joint member 33300 that is attached to a surgical end effector (not shown). For example, the distal joint member 33300 may be attached to an elongate channel of an endo-cutter arrangement in the various manners disclosed herein.

In the illustrated arrangement, the proximal joint member 33100 comprises a first or right half segment 33100A and a second or left half segment 33100B that are attached to a distal end of the central spine member 34100. The first half segment 33100A and the second half segment 33100B may be attached to the central spine member 34100 or other similar component of the elongate shaft assembly 34000 by welding, adhesive, mechanical fasteners, pins, etc. In accordance with one aspect, the surgical instrument 33010 comprises a firing system 35000 that comprises a distal differential drive assembly 35100 and a proximal differential drive assembly 35500.

As can be seen in FIG. 156, the proximal joint member 33100 operably supports the distal differential drive assembly 35100. In one arrangement, the distal differential drive assembly 35100 comprises an upper distal rack assembly 35110 that is supported for axial travel within the proximal joint member 33100. As can be seen in FIGS. 156, 157, and 158, the upper distal rack assembly 35110 is supported in meshing engagement with a distal differential gear 35130 that is rotatably supported on a pivot axle 35132 that is supported in the proximal joint member 33100. The upper distal rack assembly 35110 is supported for axial travel within the proximal joint member 33100. The distal differential drive assembly 35100 also comprises a lower distal rack assembly 35120 that is supported in meshing engagement with the distal differential gear 35130 and is configured to travel axially within the proximal joint member 33100.

In accordance with one aspect, the firing system 35000 further comprises an upper flexible firing assembly 35300 and a lower flexible firing assembly 35400 that are configured to operably interface with a firing member 35200. As can be seen in FIGS. 156 and 159, the firing member 35200 includes a vertically-extending firing member body 35212 that comprises a top firing member feature 35220 and a bottom firing member feature 35230. A tissue cutting blade 35214 is attached to or formed in the vertically-extending firing member body 35212. In at least one arrangement, the top firing member feature 35220 comprises a top finned portion 35222 that has a top axial passage 35224 extending therethrough. The bottom firing member feature 35230 comprises a bottom finned portion 35232 that has a bottom axial passage 35234 extending therethrough. In at least one arrangement, the top firing member feature 35220 and the bottom firing member feature 35230 are integrally formed with the vertically-extending firing member body 35212. In at least one example, the anvil body comprises an axially extending anvil slot that is configured to accommodate passage of the top firing member feature 35220 in the various manners discussed herein. Similarly, the elongate channel comprises an axially extending channel slot that is configured to accommodate passage of the bottom firing member feature 35230 as described herein.

In one example, the upper flexible firing assembly 35300 comprises an upper flexible tube or conduit 35310 that has a proximal end 35312 that is supported in a distal socket 3512 in the upper distal rack assembly 35110 and is secured thereto by welding, adhesive, etc. The upper flexible tube or conduit 35310 extends through an upper opening 33218 in the proximal joint member 33100 and spans across the articulation joint 33000. The upper flexible tube or conduit 35310 comprises a distal end 35314 that is received in an opening 33330 in the distal joint member 33300 and is terminated or secured therein by welding, adhesive, etc. The upper flexible firing assembly 35300 further comprises an upper push coil 35320. The upper push coil 35320 is hollow and may comprise a coil spring that is fabricated from Nitinol, titanium, stainless steel, etc. In other arrangements, the upper push coil 35320 comprises a laser cut hypo-tube that essentially comprises a hollow tubular member with offset laser cuts or spiral cuts therein which enable the hypotube to flex and bend. The upper push coil 35320 may additionally be received within an inner flexible upper sleeve 35330 that may be fabricated from a polymer or similar material and prevent tissue, fluid, and/or debris from infiltrating into the upper push coil 35320 which may hamper its ability to flex and bend during articulation.

The upper push coil 35320 extends through the upper flexible tube 35310 and through an axial passage in the upper distal rack 35110. An upper support beam 35140 is supported by the central spine member 34100 and has an upper passage 35142 to constrain and permit passage of the upper push coil 35320 therethrough. As can be seen in FIG. 159, a distal end 35322 of the upper push coil 35320 as well as a distal end 35332 of the inner flexible upper sleeve 35330 abut a proximal end 35223 of the top finned portion 35222 of the top firing member feature 35220. Also in the illustrated arrangement, the upper firing assembly 35300 further comprises an upper cable 35340 that extends through the hollow upper push coil 35320. The upper cable 35340 comprises an upper cable distal end 35342 that is secured within the top axial passage 35224 in the top finned portion 35222 of the top firing member feature 35220 by an upper attachment lug 35343.

Turning to FIGS. 156-161, the proximal differential drive assembly 35500 comprises an upper gear rack 35510 that is slidably supported within the central spine member 34100. The proximal differential drive assembly 35500 further comprises a lower proximal gear rack 35520 that is supported for axial travel within the central spine member 34100. The proximal differential drive assembly 35500 also comprises an axially movable carrier member 35530 that is centrally disposed between the upper proximal gear rack 35510 and the lower proximal gear rack 35520 and is supported for axial travel within the central spine member 34100. A proximal pinion gear 35532 is pivotally supported on a pin 35533 that is mounted to the axially movable carrier member 35530 such that the proximal pinion gear 35532 is meshing engagement with the upper proximal gear rack 35510 and the lower proximal gear rack 35520. The axially movable carrier member 35530 is driven axially within an axial cavity in the central spine member 34100 by a firing drive actuator 35540. As can be seen in FIG. 160, the firing drive actuator 35540 comprises a firing drive gear rack 35542 that drivingly interfaces with a drive gear 35544 that is driven by a firing motor 35546 that may be operably supported in the housing of the surgical instrument 33010. In other arrangements, the firing drive actuator 35540 may be axially driven distally and proximally by a cylinder arrangement or other suitable actuator interfacing therewith. As can be seen in FIGS. 156 and 160, the firing drive actuator 35540 may be attached to the axially movable carrier member 35530 by a pair of spaced coupler pins 35548.

In the illustrated arrangement, the upper proximal gear rack 35510 further comprises an upper cable attachment feature 35512 that protrudes therefrom and is configured to slide within the upper passage 35142 in the upper support beam 35140. In accordance with one aspect, the upper cable 35340 extends through the hollow upper push coil 35320 and a proximal end of the upper cable 35340 is secured to the upper cable attachment feature 35512. The upper cable 35340 is held in tension between the top firing member feature 35220 and the upper cable attachment feature 35512 which serves to retain the distal end 35322 of the upper push coil 35320 as well as a distal end 35332 of the inner flexible upper sleeve 35330 in abutting contact with the proximal end 35323 of the top finned portion 35222 of the top firing member feature 35220 and the proximal end of the upper push coil 35320 and a proximal end of the inner flexible upper sleeve 35330 in abutting contact with the distal end of the upper cable attachment feature 35512.

In one example, the lower flexible firing assembly 35400 comprises a lower flexible tube or conduit 35410 that has a proximal end 35412 that is supported in a distal socket 35122 in the lower distal rack 35120 and is secured thereto by welding, adhesive, etc. The lower flexible tube or conduit 35410 extends through a lower opening 33219 in the proximal joint member 33100 and spans across the articulation joint 33000. The lower flexible tube or conduit 35410 comprises a distal end 35414 that is received in an opening 33340 in the distal joint member 33300 and is terminated or secured therein by welding, adhesive, etc. The lower flexible firing assembly 35400 further comprises a lower push coil 35420. The lower push coil 35420 is hollow and may comprise a coil spring that is fabricated from Nitinol, titanium, stainless steel, etc. In other arrangements, the lower push coil 35420 comprises a laser cut hypotube that essentially comprises a hollow tubular member with offset laser cuts or spiral cuts therein which enable the hypotube to flex and bend. The lower push coil 35420 may additionally be received within an inner flexible lower sleeve 35430 may be fabricated from a polymer or similar material and prevent tissue, fluid, and/or debris from infiltrating into the lower push coil 35420 which may hamper its ability to flex and bend during articulation.

The lower push coil 35420 extends through the lower flexible tube 35410 and through an axial passage in the lower distal rack 35120. A lower support beam 35150 is supported by the central spine member 34100 and has a lower passage 35152 to constrain and permit passage of the lower push coil 35420 therethrough. As can be seen in FIG. 159, a distal end 35422 of the lower push coil 35420 as well as a distal end 35432 of the inner flexible lower sleeve 35430 abut a proximal end 35233 of the bottom finned portion 35232 of the bottom firing member feature 35230. Also in the illustrated arrangement, the lower flexible firing assembly 35400 further comprises a lower cable 35440 that extends through the hollow lower push coil 35420. The lower cable 35440 comprises a lower cable distal end 35442 that is secured within the bottom axial passage 35234 in the bottom finned portion 35232 of the bottom firing member feature 35230 by a lower attachment lug 35443. In accordance with one aspect, the lower cable 35440 extends through the hollow lower push coil 35420 and a distal end of the lower cable 35440 is secured to a lower cable attachment feature 35522 on the lower proximal gear rack 35520. The lower cable 35440 is held in tension between the bottom firing member feature 35230 and the lower cable attachment feature 35522 which serves to retain the distal end 35422 of the lower push coil 35420 as well as a distal end 35332 of the inner flexible upper sleeve 35330 in abutting contact with the proximal end 35233 of the bottom finned portion 35232 of the bottom firing member feature 35230 and the proximal end of the lower push coil 35420 and a proximal end of the inner flexible lower sleeve 35430 in abutting contact with the distal end of the lower cable attachment feature 35522.

Surgical stapling devices need to apply a high force on the firing member over a long displacement to form the staples and cut tissue. Transmitting that force through an articulated joint is especially challenging because it is difficult to redirect the forces in the desired direction and withstand the loads applied to it. The firing system 35000 described herein addresses and solves many, if not all of such challenges by employing two flexible tubes 35310, 35410 to constrain the paths of the push coils 35320, 35420, respectively. As described herein, the upper flexible tube 35310 surrounds the upper push coil 35320 and the lower flexible tube 35410 surrounds the lower push coil 35420. Each of the tubes 35310, 35410 can bend but they also can resolve an axial tensile load. See FIGS. 164 and 165. The ability to bend allows for the firing member force to be redirected through the articulated joint, and the ability to resolve tension allows for it to change the direction in which the push coil goes. When the push coil 35320, 35420 is put in compression, the flexible tube 35310, 35410 is put in tension. The tube 35310, 35410 prevents the push coil 35320, 35420 from buckling. To resolve the tensile loads the tubes 35310, 35410 need to be terminated in a manner to resolve the loads. In the illustrated example, the respective distal ends 35314, 35414 of the flexible tubes 35310, 35410, respectively are secured to the distal joint member 33300. The proximal ends 35312, 35412 of the flexible tubes 35310, 35410 are secured to the upper distal rack assembly 35110 and the lower distal rack 35120, respectively. The distal differential gear 35130 is in meshing engagement with each of the upper distal rack assembly 35110 and the lower distal rack 35120 such that when one of the rack assemblies 35110, 35120 moves in one axial direction, the other rack assembly 35110, 35120 would axially move in an opposite axial direction. As can be seen in FIGS. 163-165, during articulation, the distal differential gear 35130 rotates so the flexible tubes 35310, 35410 can move to account for the change in path length. However, when the firing drive system is actuated to push the push coils 35320, 35420 distally through the tubes 35310, 35410 to fire (i.e., drive the firing member distally) the tensile loads in the two flexible tubes 35310, 35410 react against one another without any motion of the distal differential gear 35130.

In accordance with one aspect, the upper flexible tube or conduit 35310 forms an upper pathway that spans the articulation joint 33000 and the lower flexible tube or conduit 35410 forms a lower pathway that spans the articulation joint 33000. The upper pathway supports the upper push coil 35320 for axial travel therethrough and the lower push coil 35420 for axial travel therethrough. When the surgical end effector to which the articulation joint 33000 is attached is in an unarticulated position (i.e., the surgical end effector is axially aligned articulated with the elongate shaft assembly along the shaft axis) the upper pathway and the lower pathway are parallel. Stated another way, when the surgical end effector is in an unarticulated position, an end effector axis is axially aligned with the shaft axis and the upper pathway and the lower pathway are parallel. When the surgical end effector is in an unarticulated position (i.e., the end effector axis is not axially aligned with the shaft axis), the upper pathway and the lower pathway are concentric to each other. When the surgical end effector is in the unarticulated position, the proximal differential drive assembly is configured to drive the upper push coil 35320 and the lower push coil 35420 equal distances in the same axial direction (distal direction DD) to apply an upper axial drive motion and a lower axial drive motion to the firing member. The upper axial drive motion and the lower axial drive motion are substantially equal in magnitude which serves to distally advance the firing member through the surgical end effector without binding which might otherwise occur should the upper axial drive motion and the lower axial drive motions be different in magnitude. Similarly, the when the surgical end effector is in an articulated position relative to the elongate shaft assembly, the proximal differential drive assembly is configured to permit the upper push coil 35320 and the lower push coil 35420 to move in substantially equal distances in opposite axial directions and thereafter apply an upper axial drive motion and a lower axial drive motion that are equal to each other to the firing member.

As can be seen in FIG. 156, the proximal joint member 33100 defines a proximal face 33200 that is configured to receive a spherical proximal end of 33410 of a central link member 33400. In the illustrated arrangement, the spherical proximal end 33410 is configured to be pivotally received in a proximal socket 33210 in the proximal face 33200 of the proximal joint member 33100. The spherical proximal end 33410 of the central link member 33400 is retained within the proximal socket 33210 by a proximal cross pin assembly 33500. In accordance with one aspect, the proximal cross pin assembly 33500 comprises a first proximal cross pin 33510 that defines a first proximal pivot axis FPPA. The first proximal cross pin 33510 is pivotally supported in a pair of attachment lugs 33220 formed on the proximal face 33200 of the proximal joint member 33100 and extends through two opposing arcuate slots 33412 to permit pivotal as well as rotational travel of the first proximal cross pin 33510 within the spherical proximal end 33410 of the central link member 33400. Stated another way, the spherical proximal end 33410 of the central link member 33400 is rotatable about the first proximal cross pin 33510 as well as pivotable through a proximal pivot angle PPA defined by the arcuate slots 33412.

The proximal cross pin assembly 33500 further comprises a second proximal cross pin 33520 that is rotatably journaled on the first proximal cross pin 33510 to permit relative pivotal rotation between the first proximal cross pin 33510 and the second proximal cross pin 33520. The second proximal cross pin 33520 is pivotally supported within the spherical proximal end 33410 of the central link member 33400 and defines a second proximal pivot axis SPPA. The first proximal pivot axis FPPA is transverse to the shaft axis SA. The second proximal pivot axis SPPA is transverse to the shaft axis SA as well as the first proximal pivot axis FPPA. The proximal cross pin assembly 33500 facilitates pivotal travel of the spherical proximal end 33410 of the central link member 33400 relative to the proximal joint member 33100 about the first proximal pivot axis FPPA as well as the second proximal pivot axis SPPA.

In the illustrated arrangement, the distal joint member 33100 defines a distal face 33310 that is configured to receive a spherical distal end 33420 of a central link member 33400. In the illustrated arrangement, the spherical distal end 33420 is configured to be pivotally received in a distal socket 33312 in the distal face 33310 of the distal joint member 33300. The spherical distal end 33420 of the central link member 33400 is retained within the distal socket 33312 by a distal cross pin assembly 33600. In accordance with one aspect, the distal cross pin assembly 33600 comprises a first distal cross pin 33610 that defines a first distal pivot axis FDPA. The first distal cross pin 33610 is pivotally supported in a pair of attachment lugs 33314 formed on the distal face 33312 of the distal joint member 33300 and extends through two opposing arcuate slots 33422 to permit pivotal as well as rotational travel of the first distal cross pin 33610 within the spherical distal end 33420 of the central link member 33400. Stated another way, the spherical distal end 33420 of the central link member 33400 is rotatable about the first distal cross pin 33610 as well as pivotable through a distal pivot angle DPA defined by the arcuate slots 33412.

The distal cross pin assembly 33600 further comprises a second distal cross pin 33620 that is rotatably journaled on the first distal cross pin 33610 to permit relative pivotal rotation between the first distal cross pin 33610 and the second distal cross pin 33620. The second distal cross pin 33620 is pivotally supported within the spherical distal end 33420 of the central link member 33400 and defines a second distal pivot axis SDPA. The first distal pivot axis FDPA is transverse to the shaft axis SA. The second distal pivot axis SDPA is transverse to the shaft axis SA as well as the first distal pivot axis FDPA. The distal cross pin assembly 33600 facilitates pivotal travel of the spherical distal end 33420 of the central link member 33400 relative to the distal joint member 33300 about the first distal pivot axis FDPA as well as the second distal pivot axis SDPA.

In accordance with at least one aspect, the articulation joint 33000 further comprises a flexible joint support assembly generally designated as 33700 which provides flexible support between the proximal joint member 33100 and the distal joint member 33200 during articulation as well as to assist the articulation joint 33000 in returning to an unarticulated position (FIGS. 155-158). In at least one arrangement, the flexible joint support assembly 33700 comprises a series of flexible members 33710, 33720, 33730, and 33740 that cross through a hollow central link portion 33430 that is attached to the spherical proximal end 33410 and the spherical distal end 33420 and extends therebetween. The flexible members 33710, 33720, 33730, and 33740 may comprise cables or spring members that are fabricated from, for example, spring steel, stainless steel, Nitinol, titanium, etc. More particularly and with reference to FIG. 166, a first flexible member 33710 comprises a central portion 33712 and a proximal end portion 33714 that is configured to be received in a corresponding attachment hole 33212 (FIG. 156) in the first or right half segment 33100A of the proximal joint member 33100 and attached or secured therein. The first flexible member 33710 further comprises a distal end portion 33716 that is configured to be received in a corresponding slotted hole 33320 in the distal joint member 33300 and be attached therein. In such arrangement, the central portion 33712 of the first flexible member 33710 extends diagonally through the hollow central link portion 33430. The second flexible member 33720 comprises a central portion 33722 and a proximal end portion 33724 that is configured to be received in a corresponding attachment hole 33214 (FIG. 156) in the second or left segment 33100B of the proximal joint member 33100 and be secured therein. The second flexible member 33720 further comprises a distal end portion 33726 that is configured to be received in a corresponding slotted hole 33322 in the distal joint member 33300 and be secured therein. In such arrangement, the central portion 33722 of the second flexible member 33720 extends diagonally through the hollow central link portion 33430. The third flexible member 33730 comprises a central portion 33732 and a proximal end portion (not shown) that is configured to be inserted into a corresponding attachment hole (not shown) in the first or right segment 33100A of the proximal joint member 33100 and be secured therein. The third flexible member 33730 further comprises a distal end portion 33736 that is configured to be received in a corresponding slotted hole 33324 in the distal joint member 33300 and be secured therein. In such arrangement, the central portion 33732 of the third flexible member 33730 extends diagonally through the hollow central link portion 33430. The fourth flexible member 33740 comprises a central portion 33742 and a proximal end portion 33744 that is configured to be inserted into a corresponding attachment hole 33216 in the second or left segment 33100B of the proximal joint member 33100 and be secured therein. The fourth flexible member 33740 further comprises a distal end portion 33746 that is configured to be received in a corresponding slotted hole 33326 in the distal joint member 33300 and be secured therein. In such arrangement, the central portion 33742 of the fourth flexible member 33740 extends diagonally through the hollow central link portion 33430.

The surgical instrument 33010 also comprises an articulation system 33800 that is configured to apply articulation motions to the surgical end effector to articulate the surgical end effector relative to the elongate shaft assembly 34000. In at least one arrangement, the articulation system 33800 comprises four articulation cables 33810, 33820, 33830, and 33840 that extend through the elongate shaft assembly 34000. In the illustrated arrangement, the articulation cables 33810, 33820, 33830, and 33840 pass through the proximal articulation joint member 33100 and the distal articulation joint member 33300 and are secured to the surgical end effector in the various manners disclosed herein. The articulation cables 33810, 33820, 33830, and 33840 operably interface with an articulation control system that is supported in or is otherwise associated with the housing of the surgical instrument 33010. For example, as was discussed above, a proximal portion of each cable 33810, 33820, 33830, and 33840 may be spooled on a corresponding rotary spool or cable-management system 2007 (FIG. 2) in the housing portion of the surgical instrument 330010 that is configured to payout and retract each cable 33810, 33820, 33830, and 33840 in desired manners. The spools/cable management system may be motor powered or manually powered (ratchet arrangement, etc.). FIGS. 154, 155, 157, 158, 162, and 167 illustrate the position of the articulation joint 33000 when the surgical end effector is in an unarticulated position and FIGS. 163 and 169 illustrate various positions of the articulation joint 33000 when the surgical end effector has been articulated in various positions relative to the elongate shaft assembly.

The articulation joint 33000 comprises a spherical pitch and yaw joint that is controlled by cables and is used for articulation of the surgical end effector. The articulation joint comprises a double spherical joint, meaning that it has a pair of joints that each can perform pitch and yaw. This arrangement creates redundancy in the joint as now there are two joints that can perform pitch and yaw. The flexible joint support assembly 33700 serves to constrain how each joint moves during articulation so that the four degrees of freedom act as two. The flexible joint support assembly 33700 ties the two spherical joints together such that if one rotates, the other one rotates the same amount. When a joint rotates it applies tension in the cable that forces the other joint to rotate as well. Such joint arrangement has a very compact form factor and very little backlash in the wrist design.

FIGS. 170-177 illustrate another form of articulation joint 14200 that comprises a proximal joint member 14210 and a distal joint member 14250. The proximal joint member 14210 is configured to be attached to a distal end of an elongate shaft assembly that is coupled to a housing or other portion of a surgical instrument. The distal joint member 14250 is configured to be attached to a surgical end effector. For example, the distal joint member 14250 may be attached to an elongate channel of an endo-cutter arrangement in the various manners disclosed herein. As can be seen in FIGS. 170-173, the proximal joint member 14210 comprises a proximal face 14212 that defines two face segments 14214, 14216 that angle away from an arcuate proximal apex 14218. Similarly, the distal joint member 14250 comprises a distal face 14252 that defines two face segments 14254, 14256 that angle away from an arcuate distal apex 14258. The proximal joint member 14210 and the distal joint member 14250 are pivotally retained together with their respective arcuate apex portions 14218, 14258 in a confronting arrangement by at least one and preferably two linkage assemblies 15000, 15002.

As can be seen in FIGS. 171-175, the first linkage assembly 15000 comprises a first link 15101 and a second link 15020 that are located on one lateral side of the shaft axis SA. The second linkage assembly 15002 comprises a first link 15010 and a second link 15020 that are located on an opposite lateral side of the shaft axis SA from the first linkage assembly 15000. As can be seen in FIGS. 171-175, the first link 15010 of each linkage assembly 15000, 15002 comprises a rigid body 15012 that defines a proximal end 15014 and a distal end 15016. The proximal end 15014 is pivotally coupled to or pinned to the proximal joint 14210 on one side (side A—FIG. 174) of a first reference plane $RP_1$ that is defined by the shaft axis SA. The proximal end 15014 pivots about a first pivot axis FPA that is transverse to the shaft axis SA. See FIG. 170. The distal end 15016 is pivotally coupled to or pinned to the distal joint member 14250 on an opposite side (Side B—FIG. 174) of the first reference plane $RP_1$ such that the first link 15010 crosses through the first reference plane $RP_1$. The distal end 15016 pivots about a second pivot axis SPA that is also transverse to the shaft axis SA.

The second link 15020 of each linkage assembly 15000, 15002 comprises a rigid body 15022 that defines a proximal end 15024 and a distal end 15026. The proximal end 15024 is pivotally coupled to or pinned to the proximal joint member 14210 on side B of the first reference plane $RP_1$ and the distal end 15016 is pivotally coupled to or pinned to the distal joint member 14250 on side A of the first reference plane $RP_1$ such that the second link 15020 crosses the first link 15010 and passes through the first reference plane $RP_1$. The proximal end 15024 pivots about a third pivot axis TPA that is transverse to the shaft axis SA and the distal end 15026 pivots about a fourth pivot axis FTPA that is transverse to the shaft axis. In at least one example, all of the pivot axes FPA, SPA, TPA, FTPA are parallel to each other and transverse to the shaft axis SA.

Turning now to FIGS. 176 and 177, the linkage assemblies 15000, 15002 of links 15010, 15020 serve to position the proximal joint member 14210 and the distal joint member 14250 relative to each other for pivotal travel about two virtual pivot points $VPP_P$ and $VPP_D$. In at least one arrangement, the proximal joint member 14210 defines the proximal virtual pivot point $VPP_P$ which is located a proximal radius PR from the arcuate proximal apex 14218 on the shaft axis SA. The distal joint member 14250 defines the distal virtual pivot point $VPP_D$ which is located a distal radius DR from the arcuate distal apex 14228 on an end effector axis EA. The virtual pivot points $VPP_P$ and $VPP_D$ lie on a common joint axis JA that has a length of PR+DR which is held constant by the link assemblies 15000, 15002. FIG. 176 illustrates the articulation joint 14200 in an unarticulated orientation wherein the end effector axis EA, the joint axis JA and the shaft axis SA are axially aligned. FIG. 177 illustrates the articulation joint 14200 in an articulated orientation. During articulation, the linkage assemblies 15000, 15002 facilitate rotation of the distal joint member 14250 relative to the proximal joint member 14210 such that the angle $\Theta_1$ between the shaft axis SA and the joint axis JA is equal to the angle $\Theta_2$ between the end effector axis EA and the joint axis JA. See FIG. 177.

Returning to FIG. 170, in the illustrated example, the articulation joint 14200 is operably controlled by a cable control system that comprises four cables 15040, 15050, 15060, and 15070 that extend through the elongate shaft assembly to operably interface with a cable control system 9030 that may be supported within the housing of the surgical instrument. The cable control system 9030 may comprise a plurality of cable support members/capstans, pulleys, etc. that are controlled by one or more corresponding motors that are controlled by a control circuit portion of the surgical instrument. The cable control system 9030 is configured to manage the tensioning (pulling) and paying out of cables at precise times during the articulation process. As can be seen in FIG. 170, the cables 15040, 15050 extend through passages in the proximal joint member 14210 on side A of the first reference plane $RP_1$ and into corresponding passages in the distal joint member 14250. Cable 15040 has a retainer lug 15042 thereon to prevent it from pulling through the distal joint member 14250. Cable 15050 also has a retainer lug 15052 to prevent cable 15050 from pulling through the distal joint member 14250. Cables 15060, 15070 extend through passages in the proximal joint member 14210 on side B of the first reference plane $RP_1$ and into corresponding passages in the distal joint member 14250. Cable 15060 has a retainer lug 15062 thereon to prevent it from pulling through the distal joint member 14250. Cable 15070 also has a retainer lug 15072 to prevent cable 15050 from pulling through the distal joint member 14250.

FIG. 171 illustrates the articulation joint 14200 in an unarticulated orientation. FIG. 172 illustrates articulation of the distal joint member 14250 in a first articulation direction on one side of the shaft axis SA which is accomplished by applying tension to the cables 15040, 15050 and allowing cables 15060 and 15070 to slacken. FIG. 173 illustrates the distal joint member 14250 articulated in a maximum articulated orientation that has an articulation angle relative to the shaft axis SA of approximately ninety degrees. The distal joint member 14250 may be articulated in an opposite direction by applying tension to cables 15060 and 15070 and allowing cables 15040, 15050 to slacken. In this arrangement, the links 15010, 15020 retain the proximal joint member 14210 and the distal joint member 14250 together without relying on maintaining tension in the cables 15040, 15050, 15060, and 15070. The virtual pivot point arrangement also allows the pairs 15000, 15002 of links 15010, 15020 to be attached to the proximal joint member 14210 and distal joint member 14250 away from those virtual pivot points. Such arrangement provides maximum clearance in the center area of the articulation joint 14200 to accommodate a variety of actuation members/shafts. As can be seen in FIG. 170, the proximal joint member 41210 comprises a central proximal opening 14211 and the distal joint member 14250 comprises a central distal opening 14251. In various embodiments, various control members/drive members 14300 may extend through the openings 14211, 14251 to provide drive/control motions to the end effector. Such drive members 14300 must be flexible to accommodate articulation of the articulation joint components. In one arrangement, the apex areas 14218, 14528 may contact each other and in other embodiments, the apex areas 14218, 14258 are spaced from each other. Such arrangement also enables pivotal travel of the distal joint member 14250 relative to the proximal joint member 14210 without the use of intermeshing gear segments that are employed in other embodiments.

FIGS. 178-180 illustrate another form of articulation joint 16200 that can facilitate articulation of a surgical end effector in multiple planes of articulation. In one arrangement, the articulation joint 16200 comprises a proximal joint member 16210, a central joint member 16230 and a distal joint member 16250. The proximal joint member 16210 is configured to be attached to a distal end of an elongate shaft assembly that is coupled to a housing or other portion of a surgical instrument. The distal joint member 16250 is configured to be attached to a surgical end effector. For example, the distal joint member 16250 may be attached to an elongate channel of an endo-cutter arrangement in the various manners disclosed herein. The proximal joint member 16210 comprises a proximal joint distal face 16212 that defines two face segments 16214, 16216 that angle away from an arcuate proximal apex 16218.

The central joint member 16230 comprises proximal face 16232 that defines two face segments 16234, 16236 that angle away from a first arcuate center apex 16238. The central joint member 16230 further comprises a central joint distal face 16240 that defines two face segments 16244, 16246 that angle away from a second arcuate center apex 16248. The distal joint member 16250 comprises a distal joint proximal face 16252 that defines two face segments 16254, 16256 that angle away from an arcuate distal apex 16258. In the illustrated example, the proximal joint member 16210 and the central joint member 14230 are pivotally retained together with their respective apex portions 16218, 16238 in a confronting arrangement by a first proximal linkage assembly 17000 that comprises proximal links 17010, 17020 that are located on one side (side A) of a first reference plane $RP_1$ that extends through the shaft axis SA and a second proximal linkage assembly 17002 that comprises proximal links 17030, 17040 that are located on side B of the first reference plane $RP_1$. The first proximal link 17010 comprises a rigid body 17012 that defines a proximal end 17014 and a distal end 17016. The proximal end 17014 is pivotally coupled to or pinned to the proximal joint member 16210 on side C of a second reference plane $RP_2$ that is defined by the shaft axis SA and is orthogonal to the first reference plane $RF_1$. The proximal end 17014 pivots about a first pivot axis FPA that is transverse to the shaft axis SA. See FIG. 179. The distal end 17016 is pivotally coupled to or pinned to the central joint member 16230 on an opposite side (Side D) of the second reference plane $RP_2$ such that the first proximal link 17010 crosses through the second reference plane $RP_2$. The distal end 17016 pivots about a second pivot axis SPA that is also transverse to the shaft axis SA.

The second proximal link 17020 of the proximal linkage assembly 17000 comprises a rigid body 17022 that defines a proximal end 17024 and a distal end 17026. The proximal end 17024 is pivotally coupled to or pinned to the proximal joint member 16210 on side D of the second reference plane $RP_2$ and the distal end 17026 is pivotally coupled to or pinned to the central joint member 16230 on side C of the second reference plane $RP_2$ such that the second proximal link 17020 crosses the first proximal link 17010 and passes through the second reference plane $RP_2$. The proximal end 17024 pivots about a third pivot axis TPA that is transverse to the shaft axis SA and the distal end 17026 pivots about a fourth pivot axis FTPA that is transverse to the shaft axis SA. In at least one example, all of the pivot axes FPA, SPA, TPA, FTPA are parallel to each other and transverse to the shaft axis SA.

A "third" proximal link 17030 in the second proximal linkage assembly 17002 comprises a rigid body 17032 that defines a proximal end 17034 and a distal end 17036. The proximal end 17034 is pivotally coupled to or pinned to the proximal joint member 16210 on side D of the second reference plane $RP_2$. The proximal end 17014 pivots about the third pivot axis TPA. The distal end 17036 is pivotally coupled to or pinned to the central joint member 16230 on side C) of the second reference plane RP$_2$ such that the third proximal link 17030 crosses through the second reference plane RP$_2$. The distal end 17016 pivots about the fourth pivot axis FTPA.

The "fourth" proximal link 17040 of the proximal linkage assembly 17002 comprises a rigid body 17042 that defines a proximal end 17044 and a distal end 17046. The proximal end 17044 is pivotally coupled to or pinned to the proximal joint member 16210 on side C of the second reference plane RP$_2$ and the distal end 17046 is pivotally coupled to or pinned to the central joint member 16230 on side D of the second reference plane RP$_2$ such that the fourth proximal link 17040 crosses the third proximal link 17030 and passes through the second reference plane RP$_2$. The proximal end 17044 pivots about the first pivot axis TPA and the distal end 17046 pivots about the second pivot axis STPA.

In the illustrated example, the distal joint member 16250 and the central joint member 16230 are pivotally retained together with their respective arcuate apexes 16258, 16248 in a confronting arrangement by a third distal linkage assembly 17004 that comprises distal links 17050, 17060 that are located on side D of the second reference plane RP$_2$ and a fourth distal linkage assembly 17006 that comprises distal links 17070, 17080 that are located on side C of the second reference plane RP$_2$. A first distal link 17050 comprises a rigid body 17052 that defines a proximal end 17054 and a distal end 17056. The proximal end 17054 is pivotally coupled to or pinned to the central joint member 16230 on side A of the first reference plane RP$_1$. The proximal end 17054 pivots about a fifth pivot axis FFPA that is transverse to the shaft axis SA. The distal end 17016 is pivotally coupled to or pinned to the distal joint member 16250 on side B of the first reference plane RP$_1$ such that the first distal link 17050 crosses through the first reference plane RP$_1$. The distal end 17056 pivots about a sixth pivot axis SXPA that is also transverse to the shaft axis SA.

A second distal link 17060 comprises a rigid body 17062 that defines a proximal end 17064 and a distal end 17066. The proximal end 17064 is pivotally coupled to or pinned to the central joint member 16230 on side B of the first reference plane RP$_1$ and the distal end 17066 is pivotally coupled to or pinned to the distal joint member 16250 on side A of the first reference plane RP$_1$ such that the second distal link 17060 crosses the first distal link 17050 and passes through the first reference plane RP$_1$. The proximal end 17064 pivots about a seventh pivot axis SVPA that is transverse to the shaft axis SA and the distal end 17066 pivots about an eighth pivot axis EPA that is transverse to the shaft axis SA. In at least one example, all of the pivot axes FFPA, SXPA, SVPA and EPA are parallel to each other and transverse to the shaft axis SA.

A "third" distal link 17070 comprises a rigid body 17072 that defines a proximal end 17074 and a distal end 17076. The proximal end 17074 is pivotally coupled to or pinned to the central joint 16230 on side B of the first reference plane RP$_1$. The proximal end 17074 pivots about the seventh pivot axis SVPA. The distal end 17036 is pivotally coupled to or pinned to the distal joint member 16250 on side A of the first reference plane RP$_1$ such that the third distal link 17070 crosses through the first reference plane RP$_1$. The distal end 17076 pivots about the eighth pivot axis EPA.

The "fourth" distal link 17080 comprises a rigid body 17082 that defines a proximal end 17084 and a distal end 17086. The proximal end 17084 is pivotally coupled to or pinned to the central joint member 16230 on side A of the first reference plane RP$_1$ and the distal end 17086 is pivotally coupled to or pinned to the distal joint member 16250 on side B of the first reference plane RP$_1$ such that the fourth distal link 17080 crosses the third distal link 17070 and passes through the first reference plane RP$_1$. The proximal end 17084 pivots about the fifth pivot axis FFPA and the distal end 17086 pivots about the sixth pivot axis SXPA.

In the illustrated example, the articulation joint 16200 is operably controlled by a cable control system that comprises four cables 16310, 16320, 16330, and 16340 that extend through the elongate shaft assembly to operably interface with a cable control system that is supported within the housing of the surgical instrument. The cable control system may comprise a plurality of cable support members/capstans, pulleys, etc. that are controlled by one or more corresponding motors that are controlled by a control circuit portion of the surgical instrument. The cable control system is configured to manage the tensioning (pulling) and paying out of cables at precise times during the articulation process. As can be seen in FIGS. 178 and 180, the cable 16310 extends through corresponding passage in the proximal joint member 16210 on side A of the first reference plane RP$_1$ and side C of the second reference plane RP$_2$ into a corresponding passage in the central joint member 14530 located on side D of the second reference plane RP$_2$. The cable 16310 exits the central joint member 16230 and enters a corresponding passage in the distal joint member 16250 that crosses through the first reference plane RP$_1$ to exit the distal joint member 16250 at a location that is on side B of the first reference plane RP$_1$ and side D of the second reference plane RP$_2$. Cable 16310 has a retainer lug 163122 thereon to prevent it from pulling through the distal joint member 16250.

Still referring to FIGS. 178 and 180, the cable 16320 extends through a corresponding passage in the proximal joint member 16210 on side A of the first reference plane RP$_1$ and side D of the second reference plane RP$_2$ into a corresponding passage in the central joint member 14530 located on side C of the second reference plane RP$_2$. The cable 16320 exits the central joint member 16230 and enters a corresponding passage in the distal joint member 16250 that crosses through the first reference plane RP$_1$ to exit the distal joint member 16250 at a location that is on side B of the first reference plane RP$_1$ and side C of the second reference plane RP$_2$. Cable 16320 has a retainer lug 16322 thereon to prevent it from pulling through the distal joint member 16250.

As can also be seen in FIGS. 178 and 180, the cable 16330 extends through a corresponding passage in the proximal joint member 16210 on side B of the first reference plane RP$_1$ and side C of the second reference plane RP$_2$ into a corresponding passage in the central joint member 14530 located on side D of the second reference plane RP$_2$. The cable 16330 exits the central joint member 16230 and enters a corresponding passage in the distal joint member 16250 that crosses through the first reference plane RP$_1$ to exit the distal joint member 16250 at a location that is on side A of the first reference plane RP$_1$ and side D of the second reference plane RP$_2$. Cable 16330 has a retainer lug 16332 thereon to prevent it from pulling through the distal joint member 16250.

As can be further seen in FIGS. 178 and 180, the cable 16340 extends through a corresponding passage in the proximal joint member 16210 on side B of the first reference plane RP$_1$ and side D of the second reference plane RP$_2$ into a corresponding passage in the central joint member 14530 located on side C of the second reference plane RP$_2$. The cable 16330 exits the central joint member 16230 and enters a corresponding passage in the distal joint member 16250 that crosses through the first reference plane RP$_1$ to exit the distal joint member 16250 at a location that is on side A of the first reference plane RP$_1$ and side C of the second reference plane RP$_2$. Cable 16340 has a retainer lug 16342 thereon to prevent it from pulling through the distal joint member 16250.

To articulate the distal joint member 16250 in a first articulation direction FAD relative to the central joint member 16230, the cable control system is actuated to apply tension to cables 16330 and 16340 while allowing cables 16310 and 16320 to sufficiently slacken. To articulate the distal joint member 16250 in a second articulation direction SAD, the cable control system is actuated to apply tension to cables 16310 and 16320 while allowing cables 16330 and 16340 to sufficiently slacken. To articulate the central joint member 16230 relative to the proximal joint member 16210 in a third articulation direction TAD, the cable control system is actuated to apply tension to cables 16320 and 16340 while allowing cables 16310 and 16330 to sufficiently slacken. To articulate the central joint member 16230 relative to the proximal joint member 16210 in a fourth articulation direction FRD, the cable control system is actuated to apply tension to cables 16310 and 16330 while allowing cables 16320 and 16340 to sufficiently slacken.

FIGS. 181-183 illustrate another form of articulation joint 18200 that comprises a proximal joint member 18210 and a distal joint member 18250. The proximal joint member 18210 is configured to be attached to a distal end of an elongate shaft assembly 18100 (FIG. 182) that is coupled to a housing or other portion of a surgical instrument in the various manners disclosed herein. The distal joint member 18250 may be attached to a closure tube arrangement 18110 (FIG. 182) that is configured to apply closing and/or opening motions to a movable jaw of an end effector 18000. In alternative arrangements, the distal joint member 18250 may be attached to one of the end effector jaws or other mounting portion of the end effector 18000. For example, the distal joint member 18250 may be attached to an elongate channel of an endo-cutter arrangement in the various manners disclosed herein. In at least one arrangement, for example, the shaft assembly 18100 defines a shaft axis SA and the end effector 18000 defines and end effector axis EA. The articulation joint facilitates selective articulation of the end effector 18000 relative to the shaft assembly 18100 in an articulation plane between an unarticulated position wherein the end effector axis EA is axially aligned with the shaft axis SA and articulated positions wherein the end effector axis EA is not aligned with the shaft axis SA.

As can be seen in FIGS. 181-183, the proximal joint member 18210 comprises a proximal mounting hub 18212. The proximal mounting hub, for example, may be configured to be inserted into a hollow outer shaft or tube portion 18102 of an elongate shaft assembly 18100 and be attached thereto by welding, adhesive, etc. The illustrated example further comprises a distally-facing collar portion 18214 that defines a distally-facing mounting area, generally designated as 18220. See FIG. 183. To accommodate passage of various control shafts/drive members through the articulation joint 18200, the proximal joint member 18210 further comprises a proximal central passage 18216 that extends through the proximal mounting hub 18212 into the distally-facing mounting area 18220. In the illustrated example, the proximal central passage 18216 is configured to accommodate a proximal drive shaft 18310 that is a portion of a rotary drive system 18300. In other arrangements, a flexible drive shaft (not shown) may extend through the proximal central passage 18216.

The distal joint member 18250 comprises a distal mounting hub 18252 that is configured to be inserted into a hollow outer shaft 18114 or closure tube or mounting hub of a surgical end effector 18000 and be attached thereto by welding, adhesive, etc. The surgical end effector 18000 may comprise any of the surgical end effector examples disclosed herein. The illustrated example further comprises a proximally-facing collar portion 18254 that defines a proximally-facing mounting area, generally designated as 18260. In addition, the distal joint member 18250 further comprises a distal central passage 18256 that extends from the distally-facing mounting area 18220 through the distal mounting hub 18252. In the illustrated example, the distal central passage 18256 is configured to accommodate a distal drive shaft 18330 that is a portion of the rotary drive system 18300 or in other embodiments, the distal central passage 18256 may support another portion of a flexible drive shaft arrangement.

The illustrated example further comprises an articulation linkage assembly 19000 that extends between the proximal joint member 18210 and the distal joint member 18250 and is configured to operably interface therewith to facilitate articulation of the distal joint member 18250 (and the surgical end effector coupled thereto) relative to proximal joint member 18210 (and the elongate shaft assembly 18100 coupled thereto). As can be seen in FIG. 183, the articulation linkage assembly 19000 comprises a first link 19010, a second link 19030, and a third link 19050. Each of the links 19010, 19030 and 19050 is movably captured between the proximal joint member 18210 and the distal joint member 18250, but, as will be discussed in further detail below, none of the links 19010, 19030, 19050 are directly attached to either of the proximal joint member 18210 and the distal joint member 18250.

In one example, the first link 19010 comprises a rigid first link body 19012 that defines a first proximal end 19014 and a first distal end 19018. The first proximal end 19104 has a first proximal saddle 19016 formed therein that is configured to be pivotally received on a corresponding first proximal mounting lug 18222 formed in the distally-facing mounting area 18220. The first proximal mounting lug 18222 has an arcuate proximal pivot surface 18223 thereon and defines a first proximal pivot axis FPPA. See FIG. 184. The first proximal saddle 19016 comprises a U-shaped proximal pivot surface 19017 that is configured to rollably or movably interface with the arcuate proximal pivot surface 18223 on the first proximal mounting lug 18222 such that the first link 19010 is movable relative to proximal joint member 18210 about the first proximal pivot axis FPPA in multiple directions or in multiple proximal travel paths. For example, the first proximal saddle 19016 can move relative to the first proximal pivot axis FPPA in a first proximal travel path FPTP and a second proximal travel path SPTP. In at least one arrangement, the first proximal travel path FPTP is transverse to the second proximal travel path SPTP. See FIGS. 184 and 186-189.

The first distal end 19108 comprises a first distal saddle 19020 formed therein that is configured to be pivotally received on a corresponding first distal mounting lug 18262 formed in the proximally-facing mounting area 18260. The first distal mounting lug 18262 has an arcuate pivot surface 18263 and defines a first distal pivot axis FDPA. See FIG. 185. The first distal saddle 19020 comprises a U-shaped pivot surface 19022 that is configured to rollably or movably interface with the arcuate pivot surface 18263 on the first distal mounting lug 18262 such that the first link 19010 is movable relative to the distal proximal joint member 18250 about the first distal pivot axis FDPA in multiple directions or multiple distal travel paths. For example, the first distal saddle 19020 can move relative to the first distal pivot axis FDPA in a first distal travel path FDTP and a second distal travel path SDTP. In at least one arrangement, the first distal travel path FDTP is transverse to the second distal travel path SDTP. See FIG. 185.

The second link 19030 comprises a rigid second link body 19032 that defines a second proximal end 19034 and a second distal end 19038. The second proximal end 19034 has a second proximal saddle 19036 formed therein that is configured to be pivotally received on a corresponding second proximal mounting lug 18224 formed in the distally-facing mounting area 18220. The second proximal mounting lug 18224 has a second arcuate proximal pivot surface 18225 thereon and defines a second proximal pivot axis SPPA. See FIG. 184. The second proximal saddle 19036 comprises a second U-shaped proximal pivot surface 19037 that is configured to rollably or movably interface with the second arcuate proximal pivot surface 18225 on the second proximal mounting lug 18224 such that the second link 19030 is movable relative to proximal joint member 18210 about the second proximal pivot axis SPPA in multiple directions or multiple proximal travel paths. For example, the second proximal saddle 19036 can move relative to the second proximal pivot axis SPPA in a first proximal travel path FPTP and a second proximal travel path SPTP. In at least one arrangement, the first proximal travel path FPTP is transverse to the second proximal travel path SPTP. See FIG. 184.

The second distal end 19038 comprises a second distal saddle 19040 that is configured to be pivotally received on a corresponding second distal mounting lug 18264 formed in the proximally-facing mounting area 18260. See FIG. 185. The second distal mounting lug 18264 has a second arcuate distal pivot surface 18265 and defines a second distal pivot axis SDPA. The second distal saddle 19040 comprises a second U-shaped distal pivot surface 19042 that is configured to rollably interface with the second arcuate distal pivot surface 18265 on the second distal mounting lug 18264 such that the second link 19030 is movable relative to the distal joint member 18250 about the second distal pivot axis SDPA in multiple directions or multiple distal paths. For example, the second distal saddle 19040 can move relative to the second distal pivot axis SDPA in a first distal travel path FDTP and a second distal travel path SDTP. In at least one arrangement, the first distal travel path FDTP is transverse to the second distal travel path SDTP. See FIG. 185.

The third link 19050 comprises a rigid third link body 19052 that defines a third proximal end 19054 and a third distal end 19058. The third proximal end 19054 has a third proximal saddle 19056 formed therein that is configured to be pivotally received on a corresponding third proximal mounting lug 18226 formed in the distally-facing mounting area 18220. The third proximal mounting lug 18226 has a third arcuate proximal pivot surface 18227 and defines a third proximal pivot axis TPPA. See FIG. 184. The third proximal saddle 19056 comprises a third U-shaped proximal pivot surface 19057 that is configured to rollably or movably interface with the third arcuate proximal pivot surface 18227 on the third proximal mounting lug 18226 such that the third link 19050 is movable relative to proximal joint member 18210 about the third proximal pivot axis TPPA in multiple directions or multiple travel paths. For example, the third proximal saddle 19056 can move relative to the third proximal pivot axis TPPA in a first proximal travel path FPTP and a second proximal travel path SPTP. In at least one arrangement, the first proximal travel path FPTP is transverse to the second proximal travel path SPTP. See FIG. 184.

The third distal end 19058 comprises a third distal saddle 19060 that is configured to be pivotally received on a corresponding third distal mounting lug 18266 formed in the proximally-facing mounting area 18260. See FIG. 185. The third distal mounting lug 18266 comprises a third arcuate distal pivot surface 18267 and defines a third distal pivot axis TDPA. The third distal saddle 19060 comprises a third U-shaped distal pivot surface 19062 that is configured to rollably or movably interface with the third arcuate distal pivot surface 18267 on the third distal mounting lug 18266 such that the third link 19050 is movable relative to the distal joint member 18250 about the third distal pivot axis TDPA in multiple directions or multiple distal travel paths. For example, the third distal saddle 19060 can move relative to the third distal pivot axis TDPA in a first distal travel path FDTP and a second distal travel path SDTP. In at least one arrangement, the first distal travel path FDTP is transverse to the second distal travel path SDTP. See FIG. 185.

In the illustrated arrangement, none of the links 19010, 19030, and 19050 are directly attached to either of the proximal joint member 18210 or the distal joint member 18250. Instead, the link assembly 19000 is supported in movable pivotal engagement with the proximal joint member 18210 and the distal joint member 18250 by a cable-based articulation system 18400. In the illustrated example, the articulation joint 18200 is operably controlled by a cable control system 18400 that comprises four flexible actuator members in the form of cables 18410, 18420, 18430, and 18440 that extend through the elongate shaft assembly to operably interface with a cable control system that may be supported within the housing of the surgical instrument. The cable control system may comprise a plurality of cable support members/capstans, pulleys, etc. that are controlled by one or more corresponding motors that are controlled by a control circuit portion of the surgical instrument. The cable control system is configured to manage the tensioning (pulling) and paying out of cables at precise times during the articulation process. As can be seen in FIG. 181, the cable 18410 extends through a corresponding passage 18412 in the proximal joint member 18210 into a corresponding passage 18414 in the distal joint member 18250 and has a retainer lug (not shown) thereon to prevent it from pulling through the distal joint member 18250. The cable 18420 extends through a corresponding passage 18422 in the proximal joint member 18210 and enters a corresponding passage in the distal joint member 18250 and has a retainer lug (not shown) thereon to prevent it from pulling through the distal joint member 18250. The cable 18430 extends through a corresponding passage 18432 in the proximal joint member 18210 into a corresponding passage 18434 in the distal joint member 18250 and has a retainer lug (not shown) thereon to prevent it from pulling through the distal joint member 18250. The cable 18440 extends through a corresponding passage 18442 in the proximal joint member 18210 into a corresponding passage 18444 in the distal joint member 18250 and has a retainer lug (not shown) thereon to prevent it from pulling through the distal joint member 18250. Thus, in one sense, the cables 18410, 18420, 18430, and 18440 span the articulation joint 18200 to apply articulation motions to the distal joint member 18250.

The distal joint member 18250 is selectively articulatable in multiple directions relative to the proximal joint member 18210 by applying tension to the various cables while enabling the remaining cables to slacken. As can be seen in FIGS. 190 and 191, the link assembly 19000 facilitates articulation motions that essentially approximate a distal virtual sphere VDS that rolls relative to a virtual proximal sphere VPS. In the illustrated arrangement, the rotary drive system 18300 further comprises a central "dog bone" drive shaft 18320 that has a spherical proximal end 18322 that is received in a proximal socket 18312 in the proximal drive shaft 18310 and is movably retained therein by corresponding pins 18324. The central drive shaft 18320 further has a spherical distal end 18326 that is received within a distal socket 18332 in the distal drive shaft 18330 and is movably retained therein by corresponding pins 18328. Other flexible drive shaft arrangements (rotary and/or non-rotary) may also be employed. As can also be seen in FIG. 190, the three links 19010, 19030, and 19050 are configured with a geometry that places the distal end of each link at 180 degrees (about the longitudinal axis) from the proximal end of the link Each respective link 19010, 19030, and 19050 "reaches around" the central drive shaft 18320. Stated another way, the first link 19010 defines a first link axis FLA. The second link 19030 defines a second link axis SLA and the third link 19050 defines a third link axis TLA. In one arrangement, the links 19010, 19030, and 19050 are supported relative to each other such that the first link axis FLA, the second link axis SLA, and the third think axis TLA are transverse to each other. See FIG. 183. The specific geometric location of the lugs and saddle arrangements define a linkage 19000 that moves the distal joint member 18250 relative to the proximal joint member 18210 as if it was a ball rolling on another ball. The cables hold the links in compression so that the saddles are retained in movable engagement with their corresponding lugs in the proximal joint member 18210 and the distal joint member 18250 without being otherwise directly coupled thereto (e.g., without pins or other arrangements).

Closing an anvil requires a system that meets many requirements. The closure system needs to respond fast to the hand motions of the surgeon who is either operating the robotic system or the hand held system to which the end effector is attached. The closure system must also be capable of applying enough load on the tissue to ensure proper staple formation. It should also be easy to bail out in the event of failure while closing. These features should all be attainable within a footprint that is as small as possible to ensure adequate maneuverability within the patient.

FIGS. 192-194 illustrate a surgical end effector 20000 that comprises a closure system 20400 that may address many if not all of the foregoing challenges. In the illustrated example, the surgical end effector 20000 comprises an elongate channel 20100 that is configured to operably support a surgical staple cartridge 20300 therein. The surgical end effector 20000 further comprises an anvil 20200 that is configured to move between an open position and a closed position relative to the surgical staple cartridge 20300 to clamp tissue therebetween. As can be seen in FIGS. 194 and 195, the closure system 20400 comprises a rotary driven closure cam member 20410 that is configured to apply closure motions to the anvil 20200. In one arrangement, the closure cam member 20410 is supported on a rotatable cam shaft 20420 that has a driven gear 20422 formed thereon. The driven gear 20422 is supported in meshing engagement with a rotary closure gear 20660 that may be driven by a motor/gearbox arrangement supported in a housing of the surgical instrument to which the surgical end effector is operably attached. As can be seen in FIGS. 196 and 197, the cam shaft 20420 comprises a spiral drive groove 20424 that is configured to receive a drive pin 20412 on the closure cam member 20410. Rotation of the cam shaft 20420 in a first rotary direction will cause the closure cam member 20410 to move in the distal direction DD from a starting position (FIGS. 194 and 196) to an ending position (FIGS. 195 and 197).

In one arrangement, the anvil 20200 comprises an anvil mounting portion 20210 that comprises two mounting arms 20212 that each have a slot therein that is configured to receive a corresponding pivot pin 20216 that protrudes from a proximal end of the elongate channel 20100. See FIG. 193. The closure cam member 20410 further comprises two closure cams 20414 that correspond to the anvil mounting arms 20212 of the anvil 20200. In one arrangement, the anvil 20200 may be biased into the open position shown in FIGS. 193 and 194 by a spring (not shown). The anvil 20200 is moved to a closed position by actuating the rotary closure gear 20660 to drive the closure cam member 20410 distally from the starting position to the ending position. As the closure cam member 20410 is driven distally, the closure cams 20414 contact the corresponding mounting arms 20212 and causes the anvil 20200 to pivot to the closed position shown in FIG. 195.

FIG. 198 illustrates the surgical end effector 20000 attached to an articulation joint 20500 that employs a rotary drive assembly 20600 for transmitting rotary drive motions across the articulation joint 20500. In the illustrated example, the rotary drive assembly 20600 comprises nested universal joints that can permit the surgical end effector 20000 to roll distal to the articulation joint 20500. A two-side joint arrangement wherein each joint can angle approximately seventy degrees (one hundred forty degrees total) may be employed, for example.

In one arrangement, the articulation joint 20500 comprises a proximal joint member 20510 that may be attached to an outer tube member of an elongate shaft assembly that is coupled to or operably interfaces with a housing of a surgical instrument. In alternative arrangements, the proximal joint member 20510 may be integrally formed on a distal end of the outer tube member of the elongate shaft. As can be seen in FIGS. 198-200, the proximal joint member 20510 comprises a distally protruding upper pivot tang 20520 and a distally protruding lower pivot tang 20530. The articulation joint 20500 further comprises a distal joint member 20540 that is attached to the surgical end effector 20000. In one example, the distal joint member 20540 is attached to the proximal end of the elongate channel 20100 and includes a proximally protruding upper pivot tang 20550 and a proximally protruding lower pivot tang 20560. In the illustrated example, the distally protruding upper pivot tang 20520 is formed with a series of proximal articulation gear teeth 20522 and the proximally protruding upper pivot tang 20550 is formed with a series of distal articulation gear teeth 20552. The distally protruding lower pivot tang 20530 is formed with an arcuate proximal surface 20532 and the proximally protruding lower pivot tang 20560 is formed with an arcuate distal surface 20562. In one example, the rotary drive assembly 20600 extends through the articulation joint 20500 and serves to retain the proximal articulation gear teeth 20522 in meshing engagement with the distal articulation gear teeth 20552 to facilitate pivotal travel therebetween. In addition, in at least one arrangement, the arcuate distal surface 20562 and the arcuate proximal surface 20532 may be supported in rocking engagement with each other. Such arrangement permits the surgical end effector 20000 to articulate through a single articulation plane relative to the elongate shaft assembly upon application of articulation control motions to the surgical end effector 20000. Such articulation control motions may be applied to the surgical end effector by cables or other articulation members (not shown) that extend from control systems in the surgical instrument housing and span the articulation joint 20500 to operably interface with the surgical end effector.

Turning to FIG. 200, the rotary drive system 20600 comprises a series of nested shaft systems 20610, 20710, and 20810. As can be seen in FIG. 200, the centermost "first" shaft system 20610 comprises a first proximal shaft member 20620 that is attached to or otherwise operably interfaces with a corresponding first rotary drive system supported by the housing of the surgical instrument. For example, the first rotary drive system may comprise a corresponding motor/gear arrangement configured to rotate the first proximal shaft member 20620. The first shaft system 20610 further comprises a first central shaft 20630 that comprises a shaft body 20632 that has a first spherical proximal end 20634 that is rotatably supported in a first spherical proximal cup 20622 on the first proximal shaft member 20620. The first central shaft 20630 is movably pinned within a cavity 20624 in the first spherical proximal cup 20622 by a first proximal pin 20636 that extends through an arcuate slot 20635 in the first spherical proximal end 20634. The first central shaft 20630 further comprises a first spherical distal end 20640 that is rotatably supported in a first spherical distal cup 20652 that is attached to a first distal shaft member 20650. The first central shaft 20630 is movably pinned within a cavity 20654 in the first spherical distal cup 20652 by a first distal pin 20644 that extends through an arcuate slot 20642 in the first spherical distal end 20640. In one arrangement, for example, the first distal shaft member 20650 may be configured to apply rotary motions to the closure gear 20660 to apply rotary closure motions to the rotatable cam shaft 20420 in the manners described above. See FIGS. 194 and 195, for example. Thus, in at least one arrangement, actuation of the first rotary drive system to cause rotation of the first proximal shaft member 20620 will result in actuation of the closure system 20400 to move the anvil 20200 from an open position to a closed position.

Referring to FIGS. 200-202, the second shaft system 20710 comprises a second proximal shaft member 20720 that is attached to or otherwise operably interfaces with a corresponding second rotary drive system supported by the housing of the surgical instrument. For example, the second rotary drive system may comprise a corresponding motor/gear arrangement configured to rotate the second proximal shaft member 20720. The second shaft system 20710 further comprises a second hollow central shaft 20730 that comprises a hollow shaft body 20732 that has a second spherical proximal end 20734. In one arrangement, the second hollow central shaft 20730 may be fabricated in two segments that are welded or otherwise coupled together. The second spherical proximal end 20734 defines a second central proximal cavity 20735 that is configured to movably receive therein the first spherical proximal cup 20622 of the first proximal shaft member 20620 therein. The second spherical proximal end 20734 is configured to be rotatably supported in a second spherical proximal cup 20722 on the second proximal shaft member 20720. The second hollow central shaft 20730 is movably pinned within a cavity 20724 in the second spherical proximal cup 20722 by second proximal pin segments 20736 that extend from the second spherical proximal end 20734 to be movably received within corresponding arcuate slots 20726 in the second spherical proximal cup 20722 on the second proximal shaft member 20720. The second hollow central shaft 20730 further comprises a second spherical distal end 20740. The second spherical distal end 20740 defines a second central distal cavity 20742 that is configured to movably receive therein the first spherical distal cup 20652 of the first distal shaft member 20650 therein. The second hollow central shaft 20730 is movably pinned within a cavity 20754 in the second spherical distal cup 20752 by second distal pin segments 20746 that extend from the second spherical distal end 20740 to be movably received within corresponding arcuate slots 20756 in the second spherical distal cup 20752 on the second distal shaft member 20750.

In one arrangement, the second distal shaft member 20750 may be configured to apply rotary motions to a first rotary drive gear 20760 that is in meshing engagement with a driven gear 20762 that is attached to a rotary drive shaft 20770 that is rotatably supported in the elongate channel 20100. See FIGS. 194, 195, and 203. As can be seen in FIGS. 194, 195, and 203, the surgical end effector 20000 further comprises a firing member 20310 that is in threaded engagement with the rotary drive shaft 20770. Rotation of the rotary drive shaft 20770 in a first rotary direction will cause the firing member 20310 to move distally from a starting position (FIG. 194) through the surgical end effector 20000 to an ending position. Rotation of the rotary drive shaft 20770 in an opposite rotary motion will drive the firing member 20310 from the ending position back to the starting position. Thus, in at least one arrangement, actuation of the second rotary drive system to cause rotation of the second proximal shaft member 20720 will result in actuation of the firing member 20310 to cut and staple tissue that is clamped between the anvil 20200 and the surgical staple cartridge 20300.

Referring to FIGS. 200-202, the third shaft system 20810 comprises a third proximal shaft member 20820 that is attached to or otherwise operably interfaces with a corresponding third rotary drive system supported by the housing of the surgical instrument. For example, the third rotary drive system may comprise a corresponding motor/gear arrangement configured to rotate the third proximal shaft member 20820. The third shaft system 20810 further comprises a third hollow central shaft 20830 that comprises a hollow shaft body 20832 that has a third spherical proximal end 20834. In one arrangement, the third hollow central shaft 20830 may be fabricated in two segments that are welded or otherwise coupled together. The third spherical proximal end 20834 defines a third proximal cavity 20835 that is configured to movably receive therein the second spherical proximal cup 20722 of the second proximal shaft member 20720 therein. The third spherical proximal end 20834 is configured to be movably supported in a third proximal socket 20824 in the third proximal shaft member 20820. The third spherical proximal end 20834 is axially movable within the third proximal socket 20824 and is attached thereto by third proximal pin segments 20836 that extend from the third spherical proximal end 20834 to be movably received within corresponding axial slots 20824 in the third proximal socket 20824 on the third proximal shaft member 20820. The third central shaft 20830 further comprises a third spherical distal end 20840. The third spherical distal end 20840 defines a third central distal cavity 20842 that is configured to movably receive therein the second spherical distal cup 20752 of the second distal shaft member 20750 therein. The third spherical distal end 20840 is movably pinned within a third distal socket 20852 on a third distal shaft 20850. The third spherical distal end 20840 is axially movable within the third distal socket 20852 and is attached thereto by third distal pin segments 20846 that extend from the third spherical distal end 20840 to be movably received within corresponding axial slots 20854 in the third distal socket 20850.

In one arrangement, the third distal shaft member 20850 may be configured to apply rotary motions to the surgical end effector 20000 to rotate the surgical end effector 20000 about the shaft axis SA. In one arrangement, for example, the third distal shaft member 20850 may be directly attached to (welded) the elongate channel 20100. Thus, in at least one arrangement, actuation of the third rotary drive system to cause rotation of the third proximal shaft member 20820 will result in rotation of the third distal shaft member 20850 and the surgical end effector 20000. In the illustrated arrangement, the intermeshing gear teeth 20522 and 20552 on the upper proximal pivot tang 20520 and upper distal pivot tang 20550 force the centers of the shaft systems to stay in the same center distance when undergoing articulation. Such shaft systems are very strong and robust while maintaining a tight articulation joint while also facilitating distal roll of the surgical end effector.

Highly articulated robotic and handheld endo mechanical staplers need to generate a lot of force to clamp onto thick tissue. Moving forces through a highly articulated joint (sixty degrees and greater for example) is challenging. Many robotic and handheld motors are slow and their ability to produce sufficient torque is limited. FIGS. 204-210 illustrate a surgical end effector 21000 that can address many of not all of those challenges. As can be seen in FIG. 204, the surgical end effector 21000 comprises a first jaw 21100 that comprises an elongate channel 21110 that is configured to operably support a surgical staple cartridge 21300 therein. The surgical end effector 21000 further comprises a second jaw 21200 that comprises an anvil 21210 that is pivotally coupled to the elongate channel 21110 about a fixed pivot axis PA. The anvil 21210 is pivotable between an open position (FIG. 206) and a closed position (FIG. 205) by a rotary driven closure system 21400.

In one arrangement, the closure system 21400 comprises a closure drive shaft 21410 that is configured to be rotated by a corresponding source of rotary motion (motor, etc.) in the housing of the surgical instrument to which the surgical end effector is attached. The closure drive shaft 21410 may comprise a flexible shaft arrangement that can flex while transferring torque through an articulation joint. The closure drive shaft 21410 is attached to a rotary cam shaft 21420 that has a closure cam lobe 21422 formed thereon, the closure drive shaft 21410 and the rotary cam shaft 21420 in combination referred to herein as a "closure driver". In one arrangement, an opening bushing 21430 is movably journaled on the rotary cam shaft 21420 and is configured to engage an opening tab 21222 on an anvil mounting portion 21220 of the anvil 21210. An opening spring 21440 is positioned on the rotary cam shaft 21420 to bias the opening bushing 21430 distally into contact with the opening tab 21222 on the anvil 21210. As can be seen in FIG. 126, as the opening bushing 21430 moves distally, it contacts the opening tab 21222 which causes the anvil 21210 to pivot about the pivot axis PA to the open position (FIG. 206).

In one example, the anvil 21210 is pivoted from the open position to a closed position by rotating the rotary cam shaft 21420 from a first rotary position shown in FIG. 207 to a final rotary position shown in FIG. 209. As can be seen in FIGS. 204 and 205, the closure system 21400 further comprises a cam follower 21450 that is movably supported in the anvil mounting portion 21220 and is configured for movable engagement with the closure cam lobe 21422 on the rotary cam shaft 21420. FIGS. 206 and 207 illustrate the position of the closure cam lobe 21422 when the anvil 21210 is in the open position. When in that position, the anvil mounting portion 21220 has pivoted past the closure cam lobe 21422 such that the cam follower 21450 is not contacted by the closure cam lobe 21422. As the rotary cam shaft 21420 begins to rotate, the closure can lobe 21422 contacts the cam follower 21450 (FIG. 208) and cams the cam follower 21450 into contact with a pivot cradle 12224 in the anvil mounting portion 21220 (upward in FIG. 208) to the position shown in FIG. 209 wherein the cam follower 21452 has pivoted the anvil 21210 to the closed position (FIG. 210). As the anvil 21210 pivots to the closed position, the opening tab 21222 biases the opening bushing 21430 proximally on the rotary cam shaft 21420 against the bias of the opening spring 21440. Thus, when the rotary cam shaft 21420 is rotated in an opposite direction, the anvil opening spring 21440 biases the opening bushing 21430 distally into contact with the opening tab 21222 to pivot the anvil 21210 back to the open position.

FIG. 211 illustrates another rotary driver in the form of a rotary cam shaft 21420' that is identical to the rotary cam shaft 21420 except that a distal end 21426 of the rotary cam shaft 21420' further comprises an opening cam 21426 that is configured to engage the opening tab 21222 on the anvil 21210 to move the anvil 21210 to an open position. Thus, when the rotary cam shaft 21420' is in a first rotary position, the opening cam 21426 has cammed the anvil opening tab 21222 to pivot the anvil 21210 to the open position. See FIG. 212. To close the anvil, the rotary cam shaft 21420' is rotated in a closure direction to cause the cam lobe 21422 to cam the cam follower 21450 upward to pivot the anvil 21210 into the closed position. The anvil 21210 can then be returned to the open position by rotating the rotary cam shaft 21420' back to the first rotary position. In alternative arrangements, the opening bushing 21430 and opening spring 21440 may be used in conjunction with the rotary cam shaft 21420'.

It will be appreciated that the foregoing embodiments of the closure system 21400 facilitates the application of relatively quick closure and opening motions to the anvil 21210. In various arrangements, the cam profile(s) may be formed to establish a low mechanical advantage at the start and a relatively high mechanical advantage at the end when the anvil 21210 starts to compress tissue. Such closure system arrangement employs fewer components than many other closure system designs. This arrangement also provides additional space at the proximal end of the end effector to accommodate electronics and other mechanisms in the end effector.

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry
forming a general purpose computing device configured by
a computer program (e.g., a general purpose computer
configured by a computer program which at least partially
carries out processes and/or devices described herein, or a
microprocessor configured by a computer program which at
least partially carries out processes and/or devices described
herein), electrical circuitry forming a memory device (e.g.,
forms of random access memory), and/or electrical circuitry
forming a communications device (e.g., a modem, commu-
nications switch, or optical-electrical equipment). Those
having skill in the art will recognize that the subject matter
described herein may be implemented in an analog or digital
fashion or some combination thereof.

While several forms have been illustrated and described,
it is not the intention of Applicant to restrict or limit the
scope of the appended claims to such detail. Numerous
modifications, variations, changes, substitutions, combina-
tions, and equivalents to those forms may be implemented
and will occur to those skilled in the art without departing
from the scope of the present disclosure. Moreover, the
structure of each element associated with the described
forms can be alternatively described as a means for provid-
ing the function performed by the element. Also, where
materials are disclosed for certain components, other mate-
rials may be used. It is therefore to be understood that the
foregoing description and the appended claims are intended
to cover all such modifications, combinations, and variations
as falling within the scope of the disclosed forms. The
appended claims are intended to cover all such modifica-
tions, variations, changes, substitutions, modifications, and
equivalents.

One or more components may be referred to herein as
"configured to," "configurable to," "operable/operative to,"
"adapted/adaptable," "able to," "conformable/conformed
to," etc. Those skilled in the art will recognize that "con-
figured to" can generally encompass active-state compo-
nents and/or inactive-state components and/or standby-state
components, unless context requires otherwise.

Those skilled in the art will recognize that, in general,
terms used herein, and especially in the appended claims
(e.g., bodies of the appended claims) are generally intended
as "open" terms (e.g., the term "including" should be
interpreted as "including but not limited to," the term
"having" should be interpreted as "having at least," the term
"includes" should be interpreted as "includes but is not
limited to," etc.). It will be further understood by those
within the art that if a specific number of an introduced claim
recitation is intended, such an intent will be explicitly recited
in the claim, and in the absence of such recitation no such
intent is present. For example, as an aid to understanding,
the following appended claims may contain usage of the
introductory phrases "at least one" and "one or more" to
introduce claim recitations. However, the use of such
phrases should not be construed to imply that the introduc-
tion of a claim recitation by the indefinite articles "a" or "an"
limits any particular claim containing such introduced claim
recitation to claims containing only one such recitation, even
when the same claim includes the introductory phrases "one
or more" or "at least one" and indefinite articles such as "a"
or "an" (e.g., "a" and/or "an" should typically be interpreted
to mean "at least one" or "one or more"); the same holds true
for the use of definite articles used to introduce claim
recitations.

In addition, even if a specific number of an introduced
claim recitation is explicitly recited, those skilled in the art
will recognize that such recitation should typically be interpreted to mean at least the recited number (e.g., the bare
recitation of "two recitations," without other modifiers,
typically means at least two recitations, or two or more
recitations). Furthermore, in those instances where a con-
vention analogous to "at least one of A, B, and C, etc." is
used, in general such a construction is intended in the sense
one having skill in the art would understand the convention
(e.g., "a system having at least one of A, B, and C" would
include but not be limited to systems that have A alone, B
alone, C alone, A and B together, A and C together, B and
C together, and/or A, B, and C together, etc.). In those
instances where a convention analogous to "at least one of
A, B, or C, etc." is used, in general such a construction is
intended in the sense one having skill in the art would
understand the convention (e.g., "a system having at least
one of A, B, or C" would include but not be limited to
systems that have A alone, B alone, C alone, A and B
together, A and C together, B and C together, and/or A, B,
and C together, etc.). It will be further understood by those
within the art that typically a disjunctive word and/or phrase
presenting two or more alternative terms, whether in the
description, claims, or drawings, should be understood to
contemplate the possibilities of including one of the terms,
either of the terms, or both terms unless context dictates
otherwise. For example, the phrase "A or B" will be typi-
cally understood to include the possibilities of "A" or "B" or
"A and B."

With respect to the appended claims, those skilled in the
art will appreciate that recited operations therein may gen-
erally be performed in any order. Also, although various
operational flow diagrams are presented in a sequence(s), it
should be understood that the various operations may be
performed in other orders than those which are illustrated, or
may be performed concurrently. Examples of such alternate
orderings may include overlapping, interleaved, interrupted,
reordered, incremental, preparatory, supplemental, simulta-
neous, reverse, or other variant orderings, unless context
dictates otherwise. Furthermore, terms like "responsive to,"
"related to," or other past-tense adjectives are generally not
intended to exclude such variants, unless context dictates
otherwise.

It is worthy to note that any reference to "one aspect," "an
aspect," "an exemplification," "one exemplification," and
the like means that a particular feature, structure, or char-
acteristic described in connection with the aspect is included
in at least one aspect. Thus, appearances of the phrases "in
one aspect," "in an aspect," "in an exemplification," and "in
one exemplification" in various places throughout the speci-
fication are not necessarily all referring to the same aspect.
Furthermore, the particular features, structures or character-
istics may be combined in any suitable manner in one or
more aspects.

Any patent application, patent, non-patent publication, or
other disclosure material referred to in this specification
and/or listed in any Application Data Sheet is incorporated
by reference herein, to the extent that the incorporated
materials is not inconsistent herewith. As such, and to the
extent necessary, the disclosure as explicitly set forth herein
supersedes any conflicting material incorporated herein by
reference. Any material, or portion thereof, that is said to be
incorporated by reference herein, but which conflicts with
existing definitions, statements, or other disclosure material
set forth herein will only be incorporated to the extent that
no conflict arises between that incorporated material and the
existing disclosure material.

In summary, numerous benefits have been described
which result from employing the concepts described herein.

The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single compo-nent, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that recondi-tioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy elec-trons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exem-plary designs, the present invention may be further modified within the spirit and scope of the disclosure. This application is therefore intended to cover any variations, uses, or adap-tations of the invention using its general principles.

What is claimed is:

1. An apparatus, comprising:
(a) a shaft;
(b) an end effector operatively coupled with the shaft, wherein the end effector includes:
(i) a first jaw, and
(ii) a second jaw configured to cooperate with the first jaw to clamp and staple tissue with a plurality of staples;
(c) a firing driver actuatable to deploy staples from the end effector; and
(d) a closure driver actuatable independently of the firing driver and rotatable about a longitudinal axis of the end effector to cammingly engage at least one of the first jaw or the second jaw and thereby transition the end effector from an open position to a closed position.

2. The apparatus of claim 1, wherein at least a portion of the closure driver is housed within the end effector.

3. The apparatus of claim 1, wherein the first jaw is configured to receive a replaceable staple cartridge that houses the staples and the second jaw includes an anvil configured to form the staples, wherein the second jaw is movable relative to the first jaw between the open position and the closed position.

4. The apparatus of claim 1, wherein the closure driver is rotatable in a first direction to transition the end effector from the open position toward the closed position, wherein the closure driver is rotatable in a second direction opposite the first direction to transition the end effector from the closed position to the open position.

5. The apparatus of claim 4, wherein the second jaw is movable relative to the first jaw between the open position and the closed position, wherein the closure driver is rotat-able in the first direction to close the second jaw, wherein the closure driver is rotatable in the second direction to open the second jaw.

6. The apparatus of claim 4, wherein the closure driver includes a cam lobe and the second jaw includes a cam follower configured to cammingly engage the cam lobe to provide closure of the end effector.

7. The apparatus of claim 6, wherein the cam follower is configured to move within a cradle of the second jaw when the cam follower engages the cam lobe.

8. The apparatus of claim 4, wherein the end effector is resiliently biased toward the open position, wherein the end effector is actuatable from the closed position toward the open position via the resilient bias in response to rotation of the closure driver in the second direction.

9. The apparatus of claim 8, wherein the closure driver includes a spring and a bushing, wherein the bushing is translatable along the closure driver and is biased by the spring into contact with the at last one of the first jaw or the second jaw to thereby bias the end effector toward the open position.

10. The apparatus of claim 9, wherein the spring is configured to resiliently bias the bushing distally.

11. The apparatus of claim 1, wherein the closure driver includes a first cam and a second cam longitudinally offset from the first cam, wherein the first cam is configured to cammingly engage the at least one of the first jaw or the second jaw to thereby drive the end effector from the open position toward the closed position, wherein the second cam is configured to cammingly engage the at least one of the first jaw or the second jaw to thereby drive the end effector from the closed position toward the open position.

12. The apparatus of claim 11, wherein the second jaw is pivotably coupled with the first jaw about a pivot axis, wherein the first cam is proximal to the pivot axis and the second cam.

13. The apparatus of claim 12, wherein the closure driver is at least partially housed within the end effector, wherein each of the first cam and the second cam is proximal to the pivot axis.

14. The apparatus of claim 1, wherein the closure driver is rotatable about the longitudinal axis while remaining longitudinally fixed.

15. The apparatus of claim 1, wherein the firing driver comprises a first rotary shaft, wherein the closure driver comprises a second rotary shaft rotatable independently of the first rotary shaft and having a cam lobe configured to directly contact and thereby actuate the at least one of the first jaw or the second jaw as the second rotary shaft with the cam lobe rotates about the longitudinal axis.

16. An apparatus, comprising:
(a) a shaft;
(b) an end effector operatively coupled with the shaft, wherein the end effector includes:
(i) a first jaw, and
(ii) a second jaw configured to cooperate with the first jaw to clamp and staple tissue with a plurality of staples, wherein the second jaw is movable relative to the first jaw between an open position and a closed position; and (c) a rotary driver having a cam, wherein the rotary driver with the cam is rotatable about a longitudinal axis of the end effector in a first direction so the cam drives the second jaw toward the closed position, wherein the rotary driver is rotatable about the longitudinal axis in a second direction opposite the first direction to enable the second jaw to assume the open position.

17. The apparatus of claim 16, wherein the cam comprises a cam lobe, wherein the second jaw includes a cam follower configured to cammingly engage the cam lobe to provide closure of the second jaw relative to the first jaw.

18. The apparatus of claim 16, wherein the second jaw is resiliently biased toward the open position, wherein the second jaw is configured to move from the closed position toward the open position via the resilient bias in response to rotation of the rotary driver in the second direction.

19. The apparatus of claim 16, wherein the cam comprises a first cam, wherein the rotary driver further includes a second cam longitudinally offset from the first cam and configured to cammingly drive the second jaw from the closed position toward the open position in response to rotation of the rotary driver in the second direction.

20. An apparatus, comprising:
(a) a shaft;
(b) an end effector operatively coupled with the shaft, wherein the end effector includes:
(i) a first jaw, and
(ii) a second jaw configured to cooperate with the first jaw to clamp and staple tissue with a plurality of staples, wherein the second jaw is movable relative to the first jaw between an open position and a closed position; and
(c) a rotary driver, including:
(i) a first cam, and
(ii) a second cam longitudinally offset from the first cam,
wherein the first cam is configured to cammingly engage and thereby drive the second jaw from the open position toward the closed position in response to rotation of the rotary driver in a first direction,
wherein the second cam is configured to cammingly engage and thereby drive the second jaw from the closed position toward the open position in response to rotation of the rotary driver in a second direction opposite the first direction.

* * * * *